United States Patent
Blanc et al.

(10) Patent No.: US 11,390,604 B2
(45) Date of Patent: Jul. 19, 2022

(54) IMIDAZOLE-PYRAZOLE DERIVATIVES

(71) Applicant: Hoffmann-La Roche Inc., Little Falls, NJ (US)

(72) Inventors: Jean-Baptiste Blanc, Basel (CH); Christian Kramer, Basel (CH); Christian Lerner, Basel (CH); Matthias Nettekoven, Basel (CH); Philippe Pflieger, Basel (CH); Bernd Puellmann, Basel (CH); Thomas Ryckmans, Basel (CH); Sébastien Schmitt, Basel (CH); Min Wang, Shanghai (CN); Song Yang, Shanghai (CN); Chengang Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/811,924

(22) Filed: Mar. 6, 2020

(65) Prior Publication Data
US 2020/0290998 A1 Sep. 17, 2020

(30) Foreign Application Priority Data

Mar. 8, 2019 (WO) ................ PCT/CN2019/077533
Jan. 30, 2020 (WO) ................ PCT/CN2020/074081

(51) Int. Cl.
| | |
|---|---|
| *A61K 31/454* | (2006.01) |
| *C07D 401/14* | (2006.01) |
| *A61P 31/04* | (2006.01) |
| *C07D 403/04* | (2006.01) |
| *C07D 403/14* | (2006.01) |
| *C07D 409/14* | (2006.01) |
| *C07D 413/14* | (2006.01) |
| *C07D 417/14* | (2006.01) |
| *C07D 471/08* | (2006.01) |
| *C07D 487/04* | (2006.01) |
| *C07D 487/10* | (2006.01) |

(52) U.S. Cl.
CPC ............ *C07D 401/14* (2013.01); *A61P 31/04* (2018.01); *C07D 403/04* (2013.01); *C07D 403/14* (2013.01); *C07D 409/14* (2013.01); *C07D 413/14* (2013.01); *C07D 417/14* (2013.01); *C07D 471/08* (2013.01); *C07D 487/04* (2013.01); *C07D 487/10* (2013.01)

(58) Field of Classification Search
None
See application file for complete search history.

(56) References Cited

FOREIGN PATENT DOCUMENTS

WO 2019/016782 A1 1/2019

OTHER PUBLICATIONS

"International Preliminary Report on Patentability—PCT/EP2020/055987" pp. 1-6(dated Aug. 25, 2021).
"International Search Report—PCT/EP2020/055987" pp. 1-3 (dated Apr. 29, 2020).
"Written Opinion of the International Searching Authority—PCT/EP2020/055987" pp. 1-5 (dated Apr. 29, 2020).

*Primary Examiner* — Samantha L Shterengarts
(74) *Attorney, Agent, or Firm* — Andre T. Krammer

(57) ABSTRACT

The disclosure provides novel imidazole pyrazole derivatives having the general formula (I), and pharmaceutically acceptable salts thereof, wherein $X^1$, $R^A$ and $R^3$ to $R^7$ are as described herein:

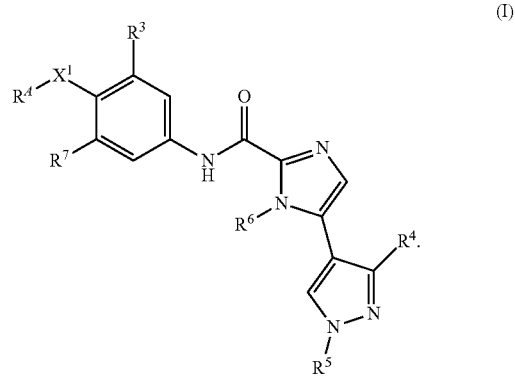

(I)

Further provided are pharmaceutical compositions including the compounds, processes of manufacturing the compounds and methods of using the compounds as medicaments, in particular methods of using the compounds as antibiotics for the treatment or prevention of bacterial infections and resulting diseases.

31 Claims, No Drawings

IMIDAZOLE-PYRAZOLE DERIVATIVES

CROSS-REFERENCE TO RELATED APPLICATIONS

This patent application claims the benefit of PCT Application No. PCT/CN2019/077533, filed Mar. 8, 2019, and PCT Application No. PCT/CN2020/074081, filed Jan. 30, 2020, each of which is incorporated herein by reference in its entirety.

FIELD OF THE INVENTION

The present invention relates to novel imidazole-pyrazole derivatives which exhibit antibacterial properties. The invention also relates to methods of using the compounds for the treatment or prevention of bacterial infections and resulting diseases, in particular for the treatment or prevention of infections with *Acinetobacter baumannii* and resulting diseases.

BACKGROUND

*Acinetobacter baumannii* is a Gram-negative, aerobic, nonfermenting bacterium recognized over the last decades as an emerging pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistence that allows its survival and spread in the nosocomial setting, making this organism a frequent cause of outbreaks of infection and an endemic, health care-associated pathogen.

Due to increasing antibiotic resistance to most if not all available therapeutic options, Multi-Drug Resistant (MDR) *A. baumannii* infections, for example, those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*.

The present invention provides novel compounds which exhibit activity against drug-susceptible as well as drug-resistant strains of *Acinetobacter baumannii*.

SUMMARY OF THE DISCLOSURE

In a first aspect, the present disclosure provides compounds of formula (I)

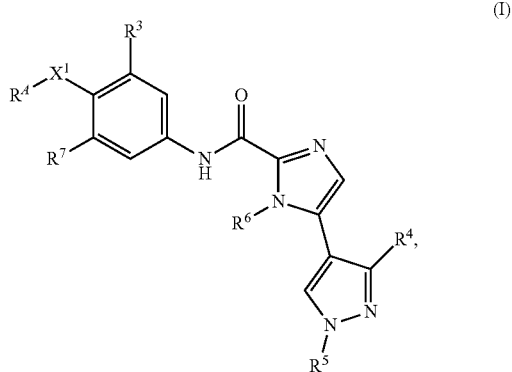

(I)

or a pharmaceutically acceptable salts thereof, wherein $R^4$ and $R^3$ to $R^7$ and $X^1$ are as defined herein.

In one aspect, the present disclosure provides a process of manufacturing the compounds of formula (I) described herein, comprising:

(i) reacting a heteroaryl bromide 5 or 15, wherein $R^1$ to $R^3$, $R^6$ and $R^7$ are as defined herein,

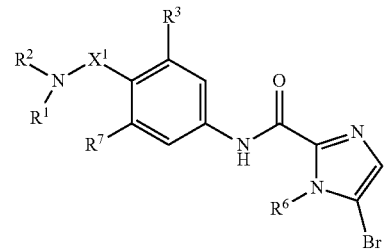

5: $X^1$ = C(O)
15: $X^1$ = SO$_2$ with a boronate, such as heteroaryl boronic acid 6b, wherein $R^4$ and $R^5$ are as defined herein,

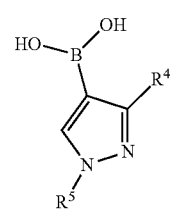

6b in the presence of a transition metal catalyst, such as 1,1'-bis(diphenylphosphino)ferrocene-palladium(II)dichloride dichloromethane complex, to afford said compound of formula (I); or (ii) reacting a carboxylic acid 12a, wherein $R^3$ to $R^7$ are as defined herein,

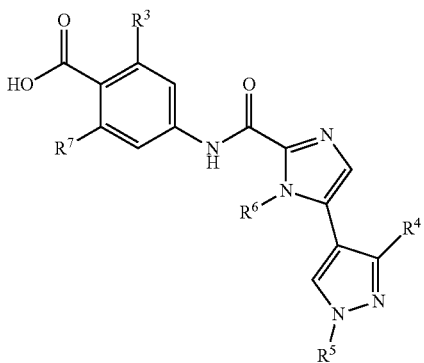

with an amine 1, wherein $R^1$ and $R^2$ are as defined herein,

in the presence of a coupling reagent (e.g., HATU or TBTU) and a base (e.g., DIPEA or triethyl amine), to afford said compound of formula (I); or
(iii) reacting an amine 7

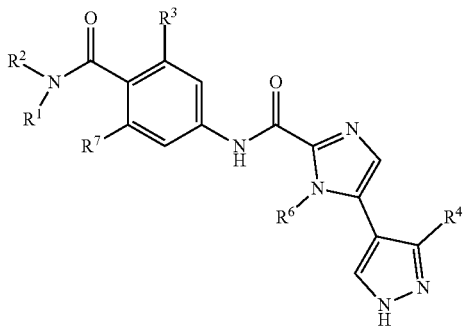

with an alkylating reagent 8, wherein X is a leaving group, such as a halide (e.g., Br, I, Cl) or a sulfonate

to afford said compound of formula (I); and
(iv) optionally converting said compound of formula (I) to a pharmaceutically acceptable salt thereof.

In a further aspect, the present disclosure provides a compound of formula (I) as described herein, when manufactured according to the processes described herein.

In a further aspect, the present disclosure provides a compound of formula (I) as described herein, or a pharmaceutically acceptable salt thereof, for use as therapeutically active substance.

In a further aspect, the present disclosure provides a pharmaceutical composition comprising a compound of formula (I) as described herein, or a pharmaceutically acceptable salt thereof, and a therapeutically inert carrier.

In a further aspect, the present disclosure provides a compound of formula (I) as described herein, or a pharmaceutically acceptable salt thereof, for use as antibiotic.

In a further aspect, the present disclosure provides a compound of formula (I) as described herein, or a pharmaceutically acceptable salt thereof, for use in the treatment or prevention of nosocomial infections and resulting diseases.

In a further aspect, the present disclosure provides a compound of formula (I) as described herein, or a pharmaceutically acceptable salt thereof, for use in the treatment or prevention of infections and resulting diseases caused by Gram-negative bacteria.

In a further aspect, the present disclosure provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present disclosure provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, which method comprises administering a compound of formula (I) as described herein, or a pharmaceutically acceptable salt thereof, to a mammal.

In a further aspect, the present disclosure provides the use of a compound of formula (I) as described herein, or a pharmaceutically acceptable salt thereof, as an antibiotic.

In a further aspect, the present disclosure provides the use of a compound of formula (I) as described herein, or a pharmaceutically acceptable salt thereof, for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present disclosure provides the use of a compound of formula (I) as described herein, or a pharmaceutically acceptable salt thereof, for the preparation of medicaments useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

DETAILED DESCRIPTION OF THE DISCLOSURE

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. An example of alkyl is methyl.

The term "alkenyl" denotes a monovalent linear or branched hydrocarbon group of 2 to 6 carbon atoms with at least one double bond ("$C_2$-$C_6$-alkenyl"), e.g. 1 or 2 double bonds. In particular embodiments, alkenyl has 2 to 4 carbon atoms with at least one double bond, e.g. 1 or 2 double bonds. Examples of alkenyl include ethenyl, propenyl, prop-2-enyl, isopropenyl, n-butenyl, iso-butenyl, allyl, and propa-1,2-dienyl. Particular alkenyl group is allyl and propa-1,2-dienyl.

The term "alkynyl" denotes a monovalent linear or branched hydrocarbon group of 2 to 6 carbon atoms with at least one triple bond ("$C_2$-$C_6$-alkynyl"). In particular embodiments, alkynyl has 2 to 4 carbon atoms with at least one triple bond. Examples of alkynyl include ethynyl, propynyl, n-butynyl or isobutynyl. An example of alkynyl is prop-2-ynyl.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some embodiments, the alkoxy group contains contains 1 to 4 carbon atoms. In still other embodiments, the alkoxy group contains 1 to 3 carbon atoms. Some non-limiting examples of alkoxy groups include methoxy, ethoxy, n-propoxy, iso-propoxy, n-butoxy, isobutoxy and tert-butoxy. An example of alkoxy is methoxy.

The term "halogen" or "halo" refers to fluoro (F), chloro (Cl), bromo (Br), or iodo (I). In some examples, the term "halogen" or "halo" refers to fluoro (F), chloro (Cl) or bromo (Br). Some examples of "halogen" or "halo" are fluoro (F) and chloro (Cl).

The term "cycloalkyl" as used herein refers to a saturated or partly unsaturated monocyclic or bicyclic hydrocarbon group of 3 to 12 ring carbon atoms ("$C_3$-$C_{12}$-cycloalkyl"). In some embodiments, the cycloalkyl group is a saturated monocyclic hydrocarbon group of 3 to 10 ring carbon atoms, in particular 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. In some examples, the cycloalkyl group is a saturated monocyclic hydrocarbon group of 3 to 6 ring carbon atoms, e.g., of 3, 4, 5 or 6 carbon atoms. Some examples of cycloalkyl include cyclopropyl, cyclobutyl, cyclopentyl, cyclohexyl, cycloheptyl, and spiro[2.3]hexan-5-yl. An example of cycloalkyl includes cyclopropyl.

The term "aminocycloalkyl" refers to a cycloalkyl group, wherein at least one of the hydrogen atoms of the cycloalkyl group has been replaced by an amino group. In some examples, "aminocycloalkyl" refers to a cycloalkyl group wherein 1, 2 or 3 hydrogen atoms of the cycloalkyl group have been replaced by an amino group. Some examples of aminocycloalkyl are aminocyclopentyl (e.g., (1R,3S)-3-aminocyclopentyl or (1R,2S)-2-aminocyclopentyl) and aminocyclobutyl (e.g., 3-aminocyclobutyl).

The term "aminoalkyl" refers to an alkyl group, wherein at least one of the hydrogen atoms of the alkyl group has been replaced by an amino group. In some examples, "aminoalkyl" refers to an alkyl group wherein 1, 2 or 3 hydrogen atoms of the alkyl group have been replaced by an amino group. Some examples of aminoalkyl are aminomethyl and 1-aminoethyl.

The term "aminoalkynyl" refers to an alkynyl group, wherein at least one of the hydrogen atoms of the alkynyl group has been replaced by an amino group. In some examples, "aminoalkynyl" refers to an alkynyl group wherein 1, 2 or 3 hydrogen atoms of the alkynyl group have been replaced by an amino group. An example of aminoalkynyl is 4-aminobut-2-ynyl.

The term "hydroxyalkynyl" refers to an alkynyl group, wherein at least one of the hydrogen atoms of the alkynyl group has been replaced by a hydroxy group. In some examples, "hydroxyalkynyl" refers to an alkynyl group wherein 1, 2 or 3 hydrogen atoms of the alkynyl group have been replaced by a hydroxy group. An example of hydroxyalkynyl is 4-hydroxybut-2-ynyl.

The term "heterocyclyl" refers to a saturated or partly unsaturated mono- or bicyclic, in some examples, monocyclic ring system of 3 to 10 ring atoms, in other examples, 3 to 8 ring atoms, wherein 1, 2, or 3 of said ring atoms are heteroatoms selected from N, O and S, the remaining ring atoms being carbon. In some examples, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, oxetan-3-yl, oxetan-2-yl, 2-oxopyrrolidin-1-yl, 2-oxopyrrolidin-3-yl, 5-oxopyrrolidin-2-yl, 5-oxopyrrolidin-3-yl, 2-oxo-1-piperidyl, 2-oxo-3-piperidyl, 2-oxo-4-piperidyl, 6-oxo-2-piperidyl, 6-oxo-3-piperidyl, 1-piperidinyl, 2-piperidinyl, 3-piperidinyl, 4-piperidinyl, morpholino, morpholin-2-yl, morpholin-3-yl, pyrrolidinyl (e.g., pyrrolidin-3-yl), piperazinyl (e.g., piperazin-1-yl), 3-azabicyclo[3.1.0]hexan-6-yl, or 2,5-diazabicyclo[2.2.1]heptan-2-yl. Some examples of heterocyclyl include piperidyl, piperazinyl, pyrrolidinyl and 3-azabicyclo[3.1.0]hexan-6-yl.

The term "aryl" refers to a monocyclic, bicyclic, or tricyclic carbocyclic ring system having a total of 6 to 14 ring members ("$C_6$-$C_{14}$-aryl"), in some examples, 6 to 12 ring members, and, in other examples, 6 to 10 ring members, and wherein at least one ring in the system is aromatic. An example of aryl is phenyl.

The term "heteroaryl" refers to a mono- or multivalent, monocyclic or bicyclic, in some examples, bicyclic ring system having a total of 5 to 14 ring members, in other examples, 5 to 12 ring members, and, in yet other examples, 5 to 10 ring members, wherein at least one ring in the system is aromatic, and at least one ring in the system contains one or more heteroatoms. In some examples, "heteroaryl" refers to a 5-10 membered heteroaryl comprising 1, 2, 3 or 4 heteroatoms independently selected from O, S and N. In other examples, "heteroaryl" refers to a 5-10 membered heteroaryl comprising 1 to 2 heteroatoms independently selected from O and N. Some examples of heteroaryl include 2-pyridyl, 3-pyridyl, 4-pyridyl, indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, 1,2-benzoxazol-7-yl, 1H-indazol-3-yl, 1H-indazol-4-yl, 1H-indazol-5-yl, 1H-indazol-6-yl, 1H-indazol-7-yl, pyrazol-1-yl, 1H-pyrazol-3-yl, 1H-pyrazol-4-yl, 1H-pyrazol-5-yl, imidazol-1-yl, 1H-imidazol-2-yl, 1H-imidazol-4-yl, 1H-imidazol-5-yl, oxazol-2-yl, oxazol-4-yl, oxazol-5-yl, thiazol-4-yl, and 1,2,4-oxadiazol-3-yl. In some examples, "heteroaryl" refers to 3-pyridyl, 4-pyridyl, 1H-pyrazol-5-yl, thiazol-4-yl, or 1,2,4-oxadiazol-3-yl.

The term "hydroxy" refers to an —OH group.

The term "amino" refers to an —NH$_2$ group.

The term "cyano" refers to a —CN (nitrile) group.

The term "oxo" refers to a double bonded oxygen (═O).

The term "carbamoyl" refers to a —C(O)NH$_2$ group.

The term "carbonyl" refers to a carbon radical having two of the four covalent bonds shared with an oxygen atom (C═O).

The term "alkoxycarbonyl" refers to a —C(O)—O-alkyl group (i.e., an alkyl ester).

The term "haloalkyl" refers to an alkyl group, wherein at least one of the hydrogen atoms of the alkyl group has been replaced by a halogen atom, for example, fluoro. In some examples, "haloalkyl" refers to an alkyl group wherein 1, 2 or 3 hydrogen atoms of the alkyl group have been replaced by a halogen atom, in other examples, fluoro. Some examples of haloalkyl are trifluoromethyl, trifluoroethyl, 2-fluoroethyl, and 2,2-difluoroethyl.

The term "haloalkoxy" refers to an alkoxy group, wherein at least one of the hydrogen atoms of the alkoxy group has been replaced by a halogen atom, for example, fluoro. In some examples, "haloalkoxy" refers to an alkoxy group wherein 1, 2 or 3 hydrogen atoms of the alkoxy group have been replaced by a halogen atom, for example, fluoro. Some examples of haloalkoxy are difluoromethoxy and trifluoromethoxy.

The term "alkoxyalkoxy" refers to an alkoxy group, wherein at least one of the hydrogen atoms of the alkoxy group has been replaced by an alkoxy group, for example, methoxy. In some examples, "alkoxyalkoxy" refers to an alkoxy group wherein 1, 2 or 3 hydrogen atoms of the alkoxy group have been replaced by an alkoxy group, for example, methoxy. An example of alkoxyalkoxy is 2-methoxyethoxy.

The term "alkoxyalkynyl" refers to an alkynyl group, wherein at least one of the hydrogen atoms of the alkynyl group has been replaced by an alkoxy group. In some examples, "alkoxyalkynyl" refers to an alkynyl group wherein 1, 2 or 3 hydrogen atoms of the alkynyl group have been replaced by an alkoxy group. An example of an alkoxyalkynyl group is 4-methoxybut-2-ynyl.

The term "hydroxyalkyl" refers to an alkyl group, wherein at least one of the hydrogen atoms of the alkyl group has been replaced by a hydroxy group. In some examples, "hydroxyalkyl" refers to an alkyl group wherein 1, 2 or 3 hydrogen atoms, for example, 1 hydrogen atom of the alkyl group have been replaced by a hydroxy group. Some examples of hydroxyalkyl are hydroxymethyl, hydroxyethyl (e.g. 2-hydroxyethyl), and 3-hydroxy-3-methyl-butyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prevention" or "prophylaxis" as used herein includes: preventing or delaying the appearance of clinical symptoms of the state, disorder or condition developing in a mammal, for example, a human, that may be afflicted with or predisposed to the state, disorder or condition but does not yet experience or display clinical or subclinical symptoms of the state, disorder or condition. In some embodiments, the term "treatment" as used herein also includes prophylaxis.

The term "mammal" as used herein includes both humans and non-humans and includes but is not limited to humans, non-human primates, canines, felines, murines, bovines, equines, and porcines. In an embodiment, the term "mammal" refers to humans.

The term "nosocomial infection" refers to a hospital-acquired infection (HAI), which is an infection that is acquired in a hospital or other health care facility. To emphasize both hospital and nonhospital settings, it is sometimes instead called a health care-associated infection (HAI or HCAI). Such an infection can be acquired in hospitals, nursing homes, rehabilitation facilities, outpatient clinics, or other clinical settings.

Compounds

In a first aspect, the present disclosure provides a compound of formula (I)

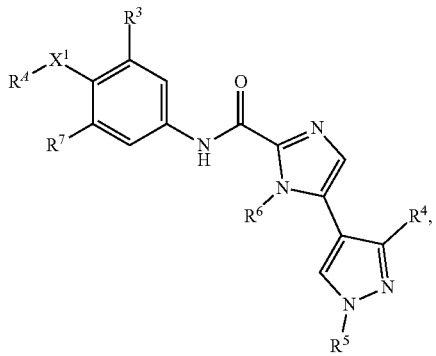

or a pharmaceutically acceptable salt thereof, wherein:

$R^4$ is $C_1$-$C_6$-alkyl or a group

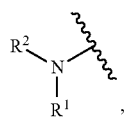

wherein:
(i) $R^1$ and $R^2$, taken together with the nitrogen atom to which they are attached, form a $C_2$-$C_9$-heterocyclic ring which is optionally substituted with one or more (1-2) $R^8$; or
(ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-, $C_1$-$C_6$-alkoxycarbonyl-NH—$C_1$-$C_6$-alkyl-, $C_1$-$C_6$-alkoxycarbonyl-$C_1$-$C_6$-alkyl-NH—$C_1$-$C_6$-alkyl- or a group

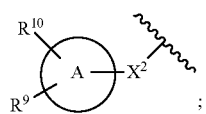

and
$R^2$ is hydrogen or $C_1$-$C_6$-alkyl;
$R^3$ and $R^7$ are each independently hydrogen, halogen or $C_1$-$C_6$-alkyl;
$R^4$ is halo-$C_1$-$C_6$-alkyl or $C_6$-$C_{14}$-aryl;
$R^5$ is hydrogen, $CF_3$, $C_1$-$C_6$-alkyl substituted with $R^{11}$ and $R^{12}$, $C_2$-$C_6$-alkenyl, halo-$C_2$-$C_6$-alkenyl, $C_2$-$C_6$-alkynyl, amino-$C_2$-$C_6$-alkynyl-, $C_1$-$C_6$-alkoxy, halo-$C_1$-$C_6$-alkoxy-$C_1$-$C_6$-alkyl, $C_1$-$C_6$-alkoxy-$C_2$-$C_6$-alkynyl-, hydroxy-$C_2$-$C_6$-alkynyl-, or a group

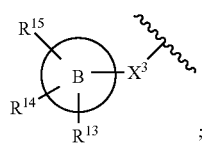

$R^6$ is $C_1$-$C_6$-alkyl;
$R^8$ is $C_1$-$C_6$-alkoxycarbonyl, amino-$C_1$-$C_6$-alkyl, $C_1$-$C_6$-alkyl-NH—, amino-$C_1$-$C_6$-alkyl-C(O)—, amino-$C_1$-$C_6$-alkyl-NH—C(O)—$C_1$-$C_6$-alkyl-, amino-$C_1$-$C_6$-alkyl-CH(OH)—, amino-$C_1$-$C_6$-alkyl-CH(NH$_2$)—C(O)—, ($C_1$-$C_6$-alkyl)$_2$N—$C_1$-$C_6$-alkyl-, ($C_1$-$C_6$-alkyl)$_2$N—$C_1$-$C_6$-alkyl-N($C_1$-$C_6$-alkyl)-, ($C_1$-$C_6$-alkyl)$_2$N—$C_1$-$C_6$-alkyl-C(O)—, $C_1$-$C_6$-alkyl-NH—$C_1$-$C_6$-alkyl-C(O)—, $C_1$-$C_6$-alkyl-NH—$C_1$-$C_6$-alkyl-NH—C(O)—, oxo, amino, halogen, or a group

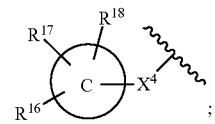

$R^9$ and $R^{10}$ are each independently hydrogen, hydroxy, amino, $C_1$-$C_6$-alkyl, $C_1$-$C_6$-alkoxy, amino-$C_1$-$C_6$-alkyl-C(O)—NH—, amino-$C_1$-$C_6$-alkyl-CH(halo-$C_1$-$C_6$-alkyl)-NH—C(O)—, amino-$C_3$-$C_{12}$-cycloalkyl-C(O)—NH— or a group

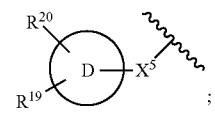

$R^{11}$ and $R^{12}$ are each independently hydrogen, halogen, hydroxy, cyano, $CF_3$, carbamoyl, halo-$C_1$-$C_6$-alkoxy-, ($C_1$-$C_6$-alkyl)$_2$N—C(O)—, $C_1$-$C_6$-alkyl-NH—C(O)—, $C_1$-$C_6$-alkoxy-, or $C_1$-$C_6$-alkoxy-$C_1$-$C_6$-alkoxy;
$R^{13}$, $R^{14}$, and $R^{15}$ are each independently hydrogen, oxo, amino, hydroxy, $C_1$-$C_6$-alkyl-NH—, ($C_1$-$C_6$-alkyl)$_2$N—, halogen, $C_3$-$C_{12}$-cycloalkyl, $C_1$-$C_6$-alkyl, halo-$C_1$-$C_6$-alkyl or hydroxy-$C_1$-$C_6$-alkyl;
$R^{16}$, $R^{17}$, and $R^{18}$ are each independently hydrogen, halogen, amino, hydroxy, amino-$C_1$-$C_6$-alkyl, $C_1$-$C_6$-alkyl-NH— or $C_1$-$C_6$-alkyl;
$R^{19}$ and $R^{20}$ are each independently hydrogen, amino, hydroxy, $C_1$-$C_6$-alkyl, amino-$C_1$-$C_6$-alkyl-, or HO—S(O)$_2$—$C_1$-$C_6$-alkyl;
A, B, C, and D are each independently $C_6$-$C_{14}$-aryl, $C_1$-$C_{13}$-heteroaryl, $C_3$-$C_{12}$-cycloalkyl, or $C_2$-$C_9$-heterocyclyl; and
$X^1$, $X^2$, $X^3$, $X^4$, and $X^5$ are each independently a covalent bond, carbonyl, $C_1$-$C_6$-alkyl, —$C_1$-$C_6$-alkyl-C(O)—, —NH—C(O)—, —C(O)—NH—, —NH—C(O)—NH—, —NH—C(O)—NH—$C_1$-$C_6$-alkyl-, —NH—C(O)—N($C_1$-$C_6$-alkyl)-$C_1$-$C_6$-alkyl-, —$C_1$-$C_6$-alkyl-NH—C(O)—NH—$C_1$-$C_6$-alkyl-, —$C_1$-$C_6$-alkyl-NH—C(O)—, —S—, —SO—, —SO$_2$— or a group

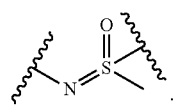

In an embodiment, the present disclosure provides a compound of formula (I) as defined herein, or a pharmaceutically acceptable salt thereof, wherein the compound of formula (I) is a compound of formula (I-I):

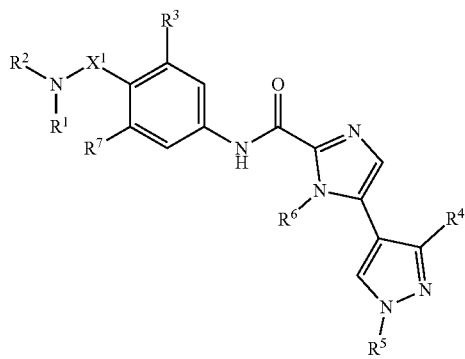

wherein $R^1$ to $R^7$ are as defined herein.

In one embodiment, the present disclosure provides a compound of formula (I-I) wherein:

(i) $R^1$ and $R^2$, taken together with the nitrogen atom to which they are attached, form a $C_2$-$C_9$-heterocyclic ring which is optionally substituted with $R^8$; or (ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-, or a group R

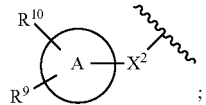

and $R^2$ is hydrogen or $C_1$-$C_6$-alkyl;

$R^3$ and $R^7$ are each independently hydrogen, halogen or $C_1$-$C_6$-alkyl;

$R^4$ is halo-$C_1$-$C_6$-alkyl or $C_6$-$C_{14}$-aryl;

$R^5$ is hydrogen, $CF_3$, $C_1$-$C_6$-alkyl substituted with $R^{11}$ and $R^{12}$, $C_2$-$C_6$-alkenyl, $C_2$-$C_6$-alkynyl, amino-$C_2$-$C_6$-alkynyl-, $C_1$-$C_6$-alkoxy-$C_2$-$C_6$-alkynyl-, hydroxy-$C_2$-$C_6$-alkynyl-, or a group

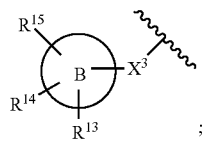

$R^6$ is $C_1$-$C_6$-alkyl;

$R^8$ is $C_1$-$C_6$-alkoxycarbonyl, amino-$C_1$-$C_6$-alkyl-C(O)—, $(C_1$-$C_6$-alkyl$)_2$N—$C_1$-$C_6$-alkyl-C(O)—, $C_1$-$C_6$-alkyl-NH—$C_1$-$C_6$-alkyl-C(O)—, $C_1$-$C_6$-alkyl-NH—$C_1$-$C_6$-alkyl-NH—C(O)—, or a group R

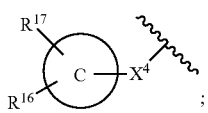

$R^9$ and $R^{10}$ are each independently hydrogen, hydroxy, amino, amino-$C_1$-$C_6$-alkyl-C(O)—NH—, or amino-$C_3$-$C_{12}$-cycloalkyl-C(O)—NH—;

$R^{11}$ and $R^{12}$ are each independently hydrogen, halogen, hydroxy, cyano, $CF_3$, carbamoyl, halo-$C_1$-$C_6$-alkoxy-, $(C_1$-$C_6$-alkyl$)_2$N—C(O)—, $C_1$-$C_6$-alkyl-NH—C(O)—, $C_1$-$C_6$-alkoxy-, or $C_1$-$C_6$-alkoxy-$C_1$-$C_6$-alkoxy;

$R^{13}$, $R^{14}$, and $R^{15}$ are each independently hydrogen, oxo, halogen, $C_3$-$C_{12}$-cycloalkyl, $C_1$-$C_6$-alkyl, or hydroxy-$C_1$-$C_6$-alkyl;

$R^{16}$ and $R^{17}$ are each independently hydrogen, amino, hydroxy, amino-$C_1$-$C_6$-alkyl, or $C_1$-$C_6$-alkyl;

A, B, and C are each independently $C_6$-$C_{14}$-aryl, $C_1$-$C_{13}$-heteroaryl, $C_3$-$C_{12}$-cycloalkyl, or $C_2$-$C_9$-heterocyclyl; and $X^1$, $X^2$, $X^3$, and $X^4$ are each independently a covalent bond, carbonyl, $C_1$-$C_6$-alkyl, —NH—C(O)—, —C(O)—NH—, —$C_1$-$C_6$-alkyl-NH—C(O)—, or $SO_2$.

In one embodiment, the present disclosure provides a compound of formula (I) as described herein, or a pharmaceutically acceptable salt thereof, wherein the compound of formula (I) is a compound of formula (I-A):

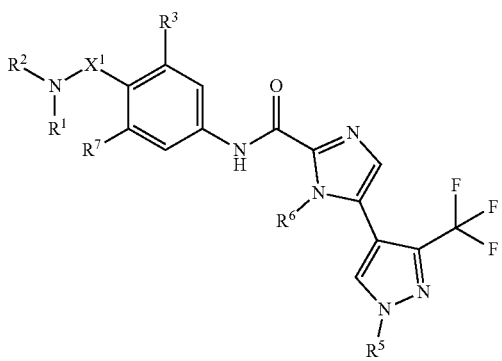

wherein $X^1$, $R^1$ to $R^3$, and $R^5$ to $R^7$ are as defined herein.

In one embodiment, the present disclosure provides a compound of formula (I) as described herein, or a pharmaceutically acceptable salt thereof, wherein the compound of formula (I) is a compound of formula (I-B):

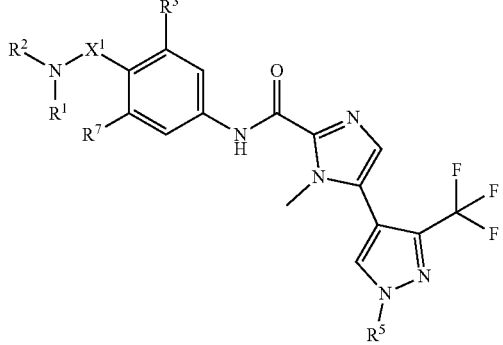

wherein $X^1$, $R^1$ to $R^3$, $R^5$, and $R^7$ are as defined herein.

In one embodiment, the present disclosure provides a compound of formula (I) as described herein, or a pharmaceutically acceptable salt thereof, wherein the compound of formula (I) is a compound of formula (I-C):

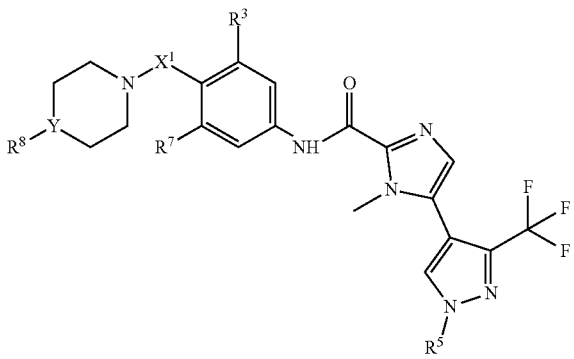

(I-C)

wherein $R^3$, $R^5$, $R^7$, $R^8$ and $X^1$ are as defined herein and Y is CH or N.

In one embodiment, the present disclosure provides a compound of formula (I) as described herein, or a pharmaceutically acceptable salt thereof, wherein the compound of formula (I) is a compound of formula (I-D):

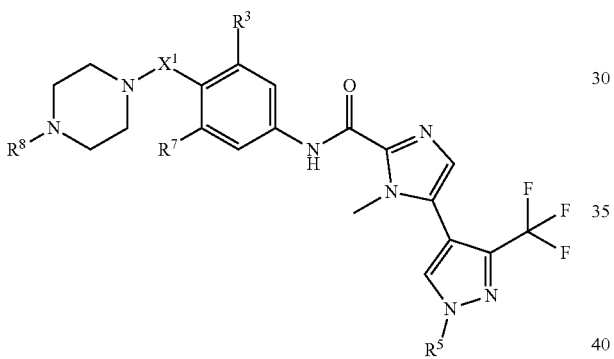

(I-D)

wherein $R^3$, $R^5$, $R^7$, $R^8$ and $X^1$ are as defined herein.

In one embodiment, the present disclosure provides a compound of formula (I) as described herein, or a pharmaceutically acceptable salt thereof, wherein the compound of formula (I) is a compound of formula (I-E):

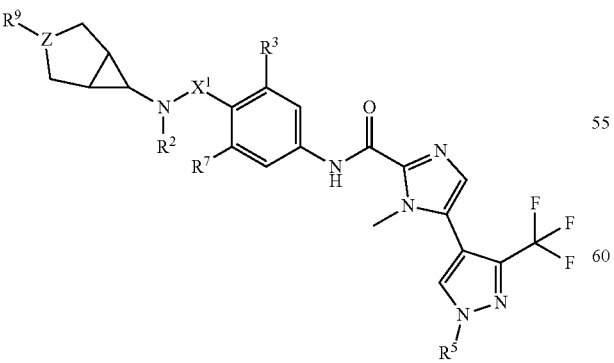

(I-E)

wherein $R^2$, $R^3$, $R^5$, $R^7$, $R^9$ and $X^1$ are as defined herein and Z is CH or N.

In one embodiment, the present disclosure provides a compound of formula (I) as described herein, or a pharmaceutically acceptable salt thereof, wherein the compound of formula (I) is a compound of formula (I-F):

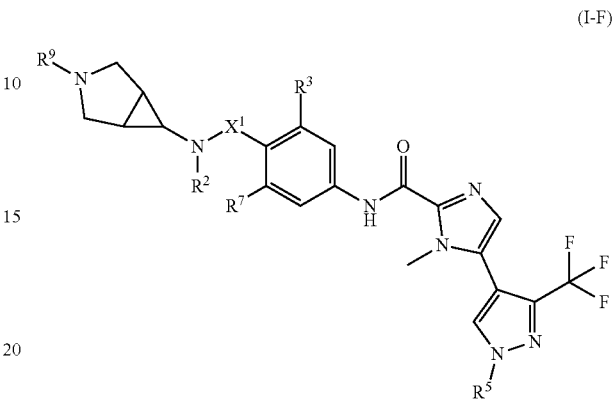

(I-F)

wherein $R^2$, $R^3$, $R^5$, $R^7$, $R^9$ and $X^1$ are as defined herein.

In an embodiment, the present disclosure provides a compound of formula (I) as described herein, or a pharmaceutically acceptable salt thereof, wherein $R^4$ is a group

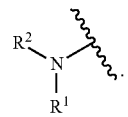

In one embodiment, the present disclosure provides a compound of formula (I) as described herein, or a pharmaceutically acceptable salt thereof, wherein:

(i) $R^1$ and $R^2$, taken together with the nitrogen atom to which they are attached, form a $C_2$-$C_9$-heterocyclic ring which is optionally substituted with one or two $R^8$; or (ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-$C_1$-$C_6$-alkoxycarbonyl-NH—$C_1$-$C_6$-alkyl-, $C_1$-$C_6$-alkoxycarbonyl-$C_1$-$C_6$-alkyl-NH—$C_1$-$C_6$-alkyl- or a group

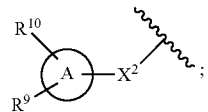

and $R^2$ is hydrogen or $C_1$-$C_6$-alkyl.

In an embodiment, the present disclosure provides a compound of formula (I) as described herein, or a pharmaceutically acceptable salt thereof, wherein:

(i) $R^1$ and $R^2$, taken together with the nitrogen atom to which they are attached, form a $C_2$-$C_9$-heterocyclic ring which is optionally substituted with one or two $R^8$; or (ii) $R^1$ is amino-$C_1$-$C_6$-alkyl-O—$C_1$-$C_6$-alkyl- or a group

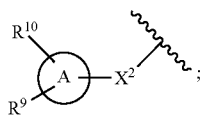

and $R^2$ is hydrogen.

In an embodiment, the present disclosure provides a compound of formula (I) as described herein, or a pharmaceutically acceptable salt thereof, wherein:
(i) $R^1$ and $R^2$, taken together with the nitrogen atom to which they are attached, form a piperazinyl or a piperidyl ring which is optionally substituted with one or two $R^8$; or
(ii) $R^1$ is 2-(2-amino-2-methyl-propoxy)ethyl or a group

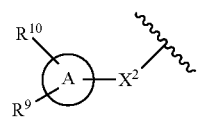

and $R^2$ is hydrogen.

In an embodiment, the present disclosure provides a compound of formula (I) as described herein, or a pharmaceutically acceptable salt thereof, wherein:
(i) $R^1$ and $R^2$, taken together with the nitrogen atom to which they are attached, form a $C_2$-$C_9$-heterocyclic ring which is optionally substituted with $R^8$; or
(ii) $R^1$ is a group

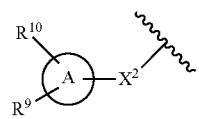

and $R^2$ is hydrogen.

In an embodiment, the present disclosure provides a compound of formula (I) as described herein, or a pharmaceutically acceptable salt thereof, wherein:
(i) $R^1$ and $R^2$, taken together with the nitrogen atom to which they are attached, form a piperazinyl ring which is optionally substituted with $R^8$; or
(ii) $R^1$ is a group

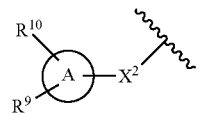

$R^9$ and $R^2$ is hydrogen.

In one embodiment, the present disclosure provides a compound of formula (I) as described herein, or a pharmaceutically acceptable salt thereof, wherein $R^3$ is halogen or $C_1$-$C_6$-alkyl.

In an embodiment, the present disclosure provides a compound of formula (I) as described herein, or a pharmaceutically acceptable salt thereof, wherein $R^3$ is chloro or ethyl.

In an embodiment, the present disclosure provides a compound of formula (I) as described herein, or a pharmaceutically acceptable salt thereof, wherein $R^3$ is halogen.

In an embodiment, the present disclosure provides a compound of formula (I) as described herein, or a pharmaceutically acceptable salt thereof, wherein $R^3$ is chloro.

In an embodiment, the present disclosure provides a compound of formula (I) as described herein, or a pharmaceutically acceptable salt thereof, wherein $R^4$ is halo-$C_1$-$C_6$-alkyl.

In an embodiment, the present disclosure provides a compound of formula (I) as described herein, or a pharmaceutically acceptable salt thereof, wherein $R^4$ is $CF_3$.

In one embodiment, the present disclosure provides a compound of formula (I) as described herein, or a pharmaceutically acceptable salt thereof, wherein $R^5$ is hydrogen, $C_1$-$C_6$-alkyl substituted with $R^{11}$ and $R^{12}$, $C_2$-$C_6$-alkenyl, $C_2$-$C_6$-alkynyl, halo-$C_2$-$C_6$-alkenyl, amino-$C_2$-$C_6$-alkynyl-, halo-$C_1$-$C_6$-alkoxy-$C_1$-$C_6$-alkyl, $C_1$-$C_6$-alkoxy-$C_2$-$C_6$-alkynyl-, hydroxy-$C_2$-$C_6$-alkynyl-, or a group

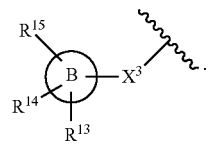

In an embodiment, the present disclosure provides a compound of formula (I) as described herein, or a pharmaceutically acceptable salt thereof, wherein $R^5$ is $C_1$-$C_6$-alkyl substituted with $R^{11}$ and $R^{12}$, $C_2$-$C_6$-alkenyl, halo-$C_2$-$C_6$-alkenyl, $C_2$-$C_6$-alkynyl, or a group

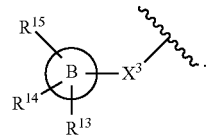

In an embodiment, the present disclosure provides a compound of formula (I) as described herein, or a pharmaceutically acceptable salt thereof, wherein $R^5$ is $C_1$-$C_6$-alkyl substituted with $R^{11}$ and $R^{12}$, allyl, vinyl, 2-fluoroallyl, 2-methylallyl, prop-2-ynyl, or a group

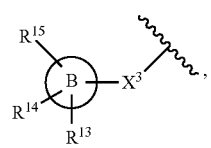

wherein said $C_1$-$C_6$-alkyl is methyl, ethyl, or isopropyl.

In one embodiment, the present disclosure provides a compound of formula (I) as described herein, or a pharmaceutically acceptable salt thereof, wherein $R^5$ is hydrogen, $C_1$-$C_6$-alkyl substituted with $R^{11}$ and $R^{12}$, $C_2$-$C_6$-alkenyl, $C_2$-$C_6$-alkynyl, amino-$C_2$-$C_6$-alkynyl-, $C_1$-$C_6$-alkoxy-$C_2$-$C_6$-alkynyl-, hydroxy-$C_2$-$C_6$-alkynyl-, or a group

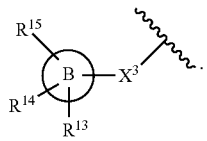

In an embodiment, the present disclosure provides a compound of formula (I-I) as described herein, or a pharmaceutically acceptable salt thereof, wherein $R^5$ is $C_1$-$C_6$-alkyl substituted with $R^{11}$ and $R^{12}$, $C_2$-$C_6$-alkenyl, $C_2$-$C_6$-alkynyl, or a group

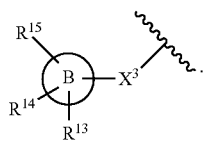

In an embodiment, the present disclosure provides a compound of formula (I) as described herein, or a pharmaceutically acceptable salt thereof, wherein $R^5$ is $C_1$-$C_6$-alkyl substituted with $R^{11}$ and $R^{12}$, allyl, prop-2-ynyl, or a group

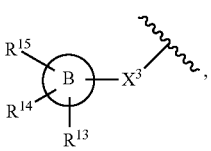

wherein said $C_1$-$C_6$-alkyl is methyl, ethyl, or isopropyl.

In an embodiment, the present disclosure provides a compound of formula (I) as described herein, or a pharmaceutically acceptable salt thereof, wherein $R^6$ is methyl.

In an embodiment, the present disclosure provides a compound of formula (I) as described herein, or a pharmaceutically acceptable salt thereof, wherein $R^7$ is hydrogen or halogen.

In an embodiment, the present disclosure provides a compound of formula (I) as described herein, or a pharmaceutically acceptable salt thereof, wherein $R^7$ is hydrogen.

In one embodiment, the present disclosure provides a compound of formula (I) as described herein, or a pharmaceutically acceptable salt thereof, wherein $R^8$ is $C_1$-$C_6$-alkoxycarbonyl, amino-$C_1$-$C_6$-alkyl, $C_1$-$C_6$-alkyl-NH—, amino-$C_1$-$C_6$-alkyl-C(O)—, amino-$C_1$-$C_6$-alkyl-NH—C(O)—$C_1$-$C_6$-alkyl-, amino-$C_1$-$C_6$-alkyl-CH(OH)—, amino-$C_1$-$C_6$-alkyl-CH(NH$_2$)—C(O)—, ($C_1$-$C_6$-alkyl)$_2$N—$C_1$-$C_6$-alkyl-, ($C_1$-$C_6$-alkyl)$_2$N—$C_1$-$C_6$-alkyl-N($C_1$-$C_6$-alkyl)-, ($C_1$-$C_6$-alkyl)$_2$N—$C_1$-$C_6$-alkyl-C(O)—, $C_1$-$C_6$-alkyl-NH—$C_1$-$C_6$-alkyl-NH—C(O)—, oxo, amino, halogen, or a group

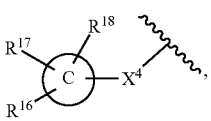

wherein $R^{16}$, $R^{17}$, $R^{18}$, C and $X^4$ are as defined herein.

In an embodiment, the present disclosure provides a compound of formula (I) as described herein, or a pharmaceutically acceptable salt thereof, wherein $R^8$ is halogen or a group

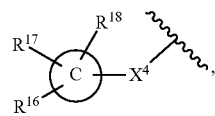

wherein $R^{16}$, $R^{17}$, $R^{18}$, C and $X^4$ are as defined herein.

In an embodiment, the present disclosure provides a compound of formula (I) as described herein, or a pharmaceutically acceptable salt thereof, wherein $R^8$ is fluoro or a group

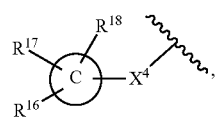

wherein $R^{16}$, $R^{17}$, $R^{18}$, C and $X^4$ are as defined herein.

In one embodiment, the present disclosure provides a compound of formula (I) as described herein, or a pharmaceutically acceptable salt thereof, wherein $R^8$ is $C_1$-$C_6$-alkoxycarbonyl, amino-$C_1$-$C_6$-alkyl-C(O)—, ($C_1$-$C_6$-alkyl)$_2$N—$C_1$-$C_6$-alkyl-C(O)—, $C_1$-$C_6$-alkyl-NH—$C_1$-$C_6$-alkyl-NH—C(O)—, or a group

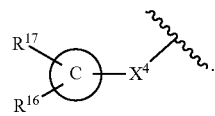

In an embodiment, the present disclosure provides a compound of formula (I) as described herein, or a pharmaceutically acceptable salt thereof, wherein $R^8$ is a group

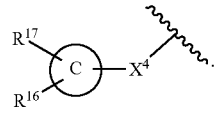

In one embodiment, the present disclosure provides a compound of formula (I) as described herein, or a pharmaceutically acceptable salt thereof, wherein $R^9$ is hydrogen, amino, hydroxy, alkyl, alkoxy, amino-$C_1$-$C_6$-alkyl-C(O)—NH— or a group

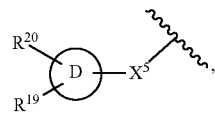

wherein $R^{19}$, $R^{20}$, $X^5$ and D are as defined herein.

In an embodiment, the present disclosure provides a compound of formula (I) as described herein, or a pharmaceutically acceptable salt thereof, wherein $R^9$ is amino or a group wherein $R^{19}$, $R^{20}$, $X^5$ and D are as defined herein.

In an embodiment, the present disclosure provides a compound of formula (I) as described herein, or a pharmaceutically acceptable salt thereof, wherein $R^9$ is amino.

In one embodiment, the present disclosure provides a compound of formula (I) as described herein, or a pharmaceutically acceptable salt thereof, wherein $R^{10}$ is hydrogen, $C_1$-$C_6$-alkyl or $C_1$-$C_6$-alkoxy.

In an embodiment, the present disclosure provides a compound of formula (I) as described herein, or a pharmaceutically acceptable salt thereof, wherein $R^{10}$ is hydrogen.

In one embodiment, the present disclosure provides a compound of formula (I) as described herein, or a pharmaceutically acceptable salt thereof, wherein $R^{11}$ is hydrogen, halogen, hydroxy, cyano, $CF_3$, carbamoyl, halo-$C_1$-$C_6$-alkoxy-, $(C_1$-$C_6$-alkyl$)_2$N—C(O)—, $C_1$-$C_6$-alkyl-NH—C(O)—, or $C_1$-$C_6$-alkoxy-$C_1$-$C_6$-alkoxy.

In an embodiment, the present disclosure provides a compound of formula (I) as described herein, or a pharmaceutically acceptable salt thereof, wherein $R^{11}$ is hydrogen, cyano, $CF_3$, or halogen.

In an embodiment, the present disclosure provides a compound of formula (I) as described herein, or a pharmaceutically acceptable salt thereof, wherein $R^{11}$ is hydrogen, cyano, $CF_3$, or fluoro.

In an embodiment, the present disclosure provides a compound of formula (I) as described herein, or a pharmaceutically acceptable salt thereof, wherein $R^{12}$ is hydrogen or halogen.

In an embodiment, the present disclosure provides a compound of formula (I) as described herein, or a pharmaceutically acceptable salt thereof, wherein $R^{12}$ is hydrogen or fluoro.

In one embodiment, the present disclosure provides a compound of formula (I) as described herein, or a pharmaceutically acceptable salt thereof, wherein $R^{13}$ is hydrogen, oxo, halogen, $C_3$-$C_{12}$-cycloalkyl, $C_1$-$C_6$-alkyl, halo-$C_1$-$C_6$-alkyl or hydroxy-$C_1$-$C_6$-alkyl. In an embodiment, the present disclosure provides a compound of formula (I) as described herein, or a pharmaceutically acceptable salt thereof, wherein $R^{13}$ is hydrogen or halogen.

In an embodiment, the present disclosure provides a compound of formula (I) as described herein, or a pharmaceutically acceptable salt thereof, wherein $R^{13}$ is hydrogen or fluoro.

In one embodiment, the present disclosure provides a compound of formula (I) as described herein, or a pharmaceutically acceptable salt thereof, wherein $R^{14}$ is hydrogen, oxo, halogen, or $C_1$-$C_6$-alkyl.

In an embodiment, the present disclosure provides a compound of formula (I) as described herein, or a pharmaceutically acceptable salt thereof, wherein $R^{14}$ is hydrogen or halogen.

In an embodiment, the present disclosure provides a compound of formula (I) as described herein, or a pharmaceutically acceptable salt thereof, wherein $R^{14}$ is hydrogen or fluoro.

In an embodiment, the present disclosure provides a compound of formula (I) as described herein, or a pharmaceutically acceptable salt thereof, wherein $R^{15}$ is hydrogen or halogen.

In an embodiment, the present disclosure provides a compound of formula (I) as described herein, or a pharmaceutically acceptable salt thereof, wherein $R^{15}$ is hydrogen.

In an embodiment, the present disclosure provides a compound of formula (I) as described herein, or a pharmaceutically acceptable salt thereof, wherein $R^{16}$ is hydrogen, amino, or hydroxy.

In one embodiment, the present disclosure provides a compound of formula (I) as described herein, or a pharmaceutically acceptable salt thereof, wherein $R^{17}$ is hydrogen, amino or $C_1$-$C_6$-alkyl.

In one embodiment, the present disclosure provides a compound of formula (I) as described herein, or a pharmaceutically acceptable salt thereof, wherein $R^{17}$ is hydrogen or $C_1$-$C_6$-alkyl.

In an embodiment, the present disclosure provides a compound of formula (I) as described herein, or a pharmaceutically acceptable salt thereof, wherein $R^{17}$ is hydrogen.

In one embodiment, the present disclosure provides a compound of formula (I) as described herein, or a pharmaceutically acceptable salt thereof, wherein $R^{18}$ is hydrogen or amino.

In an embodiment, the present disclosure provides a compound of formula (I) as described herein, or a pharmaceutically acceptable salt thereof, wherein $R^{18}$ is hydrogen.

In one embodiment, the present disclosure provides a compound of formula (I) as described herein, or a pharmaceutically acceptable salt thereof, wherein $R^{19}$ is hydrogen, amino, hydroxy, $C_1$-$C_6$-alkyl, amino-$C_1$-$C_6$-alkyl or HO—$SO_2$—$C_1$-$C_6$-alkyl.

In an embodiment, the present disclosure provides a compound of formula (I) as described herein, or a pharmaceutically acceptable salt thereof, wherein $R^{19}$ is hydrogen, amino or hydroxy.

In one embodiment, the present disclosure provides a compound of formula (I) as described herein, or a pharmaceutically acceptable salt thereof, wherein $R^{20}$ is hydrogen or hydroxy.

In an embodiment, the present disclosure provides a compound of formula (I) as described herein, or a pharmaceutically acceptable salt thereof, wherein $R^{20}$ is hydrogen.

In one embodiment, the present disclosure provides a compound of formula (I) as described herein, or a pharmaceutically acceptable salt thereof, wherein A is $C_2$-$C_9$-heterocyclyl or $C_3$-$C_{12}$-cycloalkyl.

In an embodiment, the present disclosure provides a compound of formula (I) as described herein, or a pharmaceutically acceptable salt thereof, wherein A is cyclobutyl, cyclopropyl or 3-azabicyclo[3.1.0]hexan-6-yl.

In an embodiment, the present disclosure provides a compound of formula (I) as described herein, or a pharmaceutically acceptable salt thereof, wherein A is $C_3$-$C_{12}$-cycloalkyl.

In an embodiment, the present disclosure provides a compound of formula (I) as described herein, or a pharmaceutically acceptable salt thereof, wherein A is cyclobutyl.

In one embodiment, the present disclosure provides a compound of formula (I) as described herein, or a pharmaceutically acceptable salt thereof, wherein B is $C_3$-$C_{12}$-cycloalkyl.

In an embodiment, the present disclosure provides a compound of formula (I) as described herein, or a pharmaceutically acceptable salt thereof, wherein B is cyclopropyl, cyclobutyl, or spiro[2.3]hexan-5-yl.

In one embodiment, the present disclosure provides a compound of formula (I) as described herein, or a pharmaceutically acceptable salt thereof, wherein C is $C_3$-$C_{12}$-cycloalkyl or $C_2$-$C_9$-heterocyclyl.

In an embodiment, the present disclosure provides a compound of formula (I) as described herein, or a pharmaceutically acceptable salt thereof, wherein C is cyclobutyl, cyclopentyl, 3-piperidyl, 4-piperidyl, pyrrolidin-3-yl, azetidin-3-yl, 3-azabicyclo[3.1.0]hexan-6-yl, or 2,5-diazabicyclo[2.2.1]heptan-2-yl.

In an embodiment, the present disclosure provides a compound of formula (I) as described herein, or a pharmaceutically acceptable salt thereof, wherein C is cyclobutyl, cyclopentyl, 4-piperidyl, pyrrolidin-3-yl, 3-azabicyclo[3.1.0]hexan-6-yl, or 2,5-diazabicyclo[2.2.1]heptan-2-yl.

In one embodiment, the present disclosure provides a compound of formula (I) as described herein, or a pharmaceutically acceptable salt thereof, wherein D is $C_3$-$C_{12}$-cycloalkyl or $C_2$-$C_9$-heterocyclyl.

In one embodiment, the present disclosure provides a compound of formula (I) as described herein, or a pharmaceutically acceptable salt thereof, wherein D is pyrrolidin-3-yl, 4-piperidyl or cyclobutyl.

In one embodiment, the present disclosure provides a compound of formula (I) as described herein, or a pharmaceutically acceptable salt thereof, wherein $X^1$ is —S—, a covalent bond, carbonyl, $SO_2$ or a group

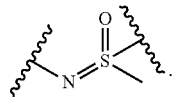

In one embodiment, the present disclosure provides a compound of formula (I) as described herein, or a pharmaceutically acceptable salt thereof, wherein $X^1$ is carbonyl or $SO_2$.

In an embodiment, the present disclosure provides a compound of formula (I) as described herein, or a pharmaceutically acceptable salt thereof, wherein $X^1$ is carbonyl.

In one embodiment, the present disclosure provides a compound of formula (I) as described herein, or a pharmaceutically acceptable salt thereof, wherein $X^2$ is a covalent bond or $C_1$-$C_6$-alkyl.

In an embodiment, the present disclosure provides a compound of formula (I) as described herein, or a pharmaceutically acceptable salt thereof, wherein $X^2$ is a covalent bond or —$CH_2$—.

In an embodiment, the present disclosure provides a compound of formula (I) as described herein, or a pharmaceutically acceptable salt thereof, wherein $X^2$ is a covalent bond.

In an embodiment, the present disclosure provides a compound of formula (I) as described herein, or a pharmaceutically acceptable salt thereof, wherein $X^3$ is a covalent bond or $C_1$-$C_6$-alkyl.

In an embodiment, the present disclosure provides a compound of formula (I) as described herein, or a pharmaceutically acceptable salt thereof, wherein $X^3$ is a covalent bond or —$CH_2$—.

In one embodiment, the present disclosure provides a compound of formula (I) as described herein, or a pharmaceutically acceptable salt thereof, wherein $X^4$ is a covalent bond, carbonyl, —NH—C(O)—, —NH—C(O)—NH—, —NH—C(O)—NH—$C_1$-$C_6$-alkyl-, —$C_1$-$C_6$-alkyl-NH—C(O)—, —$C_1$-$C_6$-alkyl-C(O)— or —$SO_2$—.

In an embodiment, the present disclosure provides a compound of formula (I) as described herein, or a pharmaceutically acceptable salt thereof, wherein $X^4$ is carbonyl, —NH—C(O)—, —NH—C(O)—NH—$C_1$-$C_6$-alkyl- or —$C_1$-$C_6$-alkyl-NH—C(O)—.

In an embodiment, the present disclosure provides a compound of formula (I) as described herein, or a pharmaceutically acceptable salt thereof, wherein $X^4$ is carbonyl, —NH—C(O)—, —NH—C(O)—NH—$CH_2$— or —$CH_2$—NH—C(O)—.

In one embodiment, the present disclosure provides a compound of formula (I) as described herein, or a pharmaceutically acceptable salt thereof, wherein $X^4$ is a covalent bond, carbonyl, —NH—C(O)—, or —$C_1$-$C_6$-alkyl-NH—C(O)—.

In an embodiment, the present disclosure provides a compound of formula (I) as described herein, or a pharmaceutically acceptable salt thereof, wherein $X^4$ is carbonyl, —NH—C(O)—, or —$C_1$-$C_6$-alkyl-NH—C(O)—.

In an embodiment, the present disclosure provides a compound of formula (I) as described herein, or a pharmaceutically acceptable salt thereof, wherein $X^4$ is carbonyl, —NH—C(O)—, or —$CH_2$—NH—C(O)—.

In one embodiment, the present disclosure provides a compound of formula (I) as described herein, or a pharmaceutically acceptable salt thereof, wherein $X^5$ is carbonyl, —C(O)—NH—, —NH—C(O)— or —NH—C(O)—NH—.

In an embodiment, the present disclosure provides a compound of formula (I) as described herein, or a pharmaceutically acceptable salt thereof, wherein $X^5$ is carbonyl or —NH—C(O)—.

In one embodiment, the present disclosure provides a compound of formula (I-I) as described herein, or a pharmaceutically acceptable salt thereof, wherein:
(i) $R^1$ and $R^2$, taken together with the nitrogen atom to which they are attached, form a $C_2$-$C_9$-heterocyclic ring which is optionally substituted with $R^8$; or
(ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-, or a group

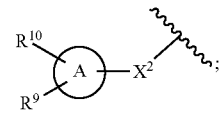

and $R^2$ is hydrogen or $C_1$-$C_6$-alkyl;

$R^3$ is halogen or $C_1$-$C_6$-alkyl;

$R^4$ is halo-$C_1$-$C_6$-alkyl or $C_6$-$C_{14}$-aryl;

$R^5$ is hydrogen, $C_1$-$C_6$-alkyl substituted with $R^{11}$ and $R^{12}$, $C_2$-$C_6$-alkenyl, $C_2$-$C_6$-alkynyl, amino-$C_2$-$C_6$-alkynyl-, $C_1$-$C_6$-alkoxy-$C_2$-$C_6$-alkynyl-, hydroxy-$C_2$-$C_6$-alkynyl-, or a group

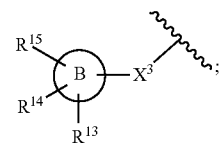

$R^6$ is $C_1$-$C_6$-alkyl;
$R^7$ is hydrogen or halogen;
$R^8$ is $C_1$-$C_6$-alkoxycarbonyl, amino-$C_1$-$C_6$-alkyl-C(O)—, ($C_1$-$C_6$-alkyl)$_2$N—$C_1$-$C_6$-alkyl-C(O)—, $C_1$-$C_6$-alkyl-NH—$C_1$-$C_6$-alkyl-NH—C(O)—, or a group

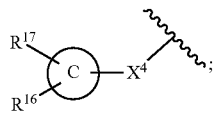

$R^9$ is hydrogen, hydroxy, amino, amino-$C_1$-$C_6$-alkyl-C(O)—NH—, or amino-$C_3$-$C_{12}$-cycloalkyl-C(O)—NH—;
$R^{10}$ is hydrogen;
$R^{11}$ is hydrogen, halogen, hydroxy, cyano, $CF_3$, carbamoyl, halo-$C_1$-$C_6$-alkoxy-, ($C_1$-$C_6$-alkyl)$_2$N—C(O)—, $C_1$-$C_6$-alkyl-NH—C(O)—, or $C_1$-$C_6$-alkoxy-$C_1$-$C_6$-alkoxy;
$R^{12}$ is hydrogen or halogen;
$R^{13}$ is hydrogen, oxo, halogen, $C_3$-$C_{12}$-cycloalkyl, $C_1$-$C_6$-alkyl, or hydroxy-$C_1$-$C_6$-alkyl;
$R^{14}$ is hydrogen, oxo, halogen, or $C_1$-$C_6$-alkyl;
$R^{15}$ is hydrogen or halogen;
$R^{16}$ is hydrogen, amino, hydroxy, amino-$C_1$-$C_6$-alkyl, or $C_1$-$C_6$-alkyl;
$R^{17}$ is hydrogen or $C_1$-$C_6$-alkyl;
A is $C_2$-$C_9$-heterocyclyl or $C_3$-$C_{12}$-cycloalkyl;
B is $C_6$-$C_{14}$-aryl, $C_1$-$C_{13}$-heteroaryl, $C_3$-$C_{12}$-cycloalkyl, or $C_2$-$C_9$-heterocyclyl;
C is $C_3$-$C_{12}$-cycloalkyl or $C_2$-$C_9$-heterocyclyl;
$X^1$ is carbonyl or $SO_2$;
$X^2$ is a covalent bond or $C_1$-$C_6$-alkyl;
$X^3$ is a covalent bond or $C_1$-$C_6$-alkyl; and
$X^4$ is a covalent bond, carbonyl, —NH—C(O)—, or —$C_1$-$C_6$-alkyl-NH—C(O)—.

In an embodiment, the present disclosure provides a compound of formula (I-I) as described herein, or a pharmaceutically acceptable salt thereof, wherein:
(i) $R^1$ and $R^2$, taken together with the nitrogen atom to which they are attached, form a $C_2$-$C_9$-heterocyclic ring which is optionally substituted with $R^8$; or
(ii) $R^1$ is a group

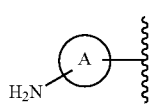

and $R^2$ is hydrogen;
$R^3$ is halogen;
$R^4$ is halo-$C_1$-$C_6$-alkyl;
$R^5$ is $C_1$-$C_6$-alkyl substituted with $R^{11}$ and $R^{12}$, $C_2$-$C_6$-alkenyl, $C_2$-$C_6$-alkynyl, or a group

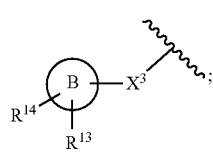

$R^6$ is $C_1$-$C_6$-alkyl;
$R^7$ is hydrogen;
$R^8$ is a group

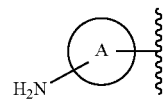

$R^{11}$ is hydrogen, cyano, $CF_3$, or halogen;
$R^{12}$, $R^{13}$, and $R^{14}$ are each independently hydrogen or halogen;
$R^{16}$ is hydrogen, amino, or hydroxy;
A and B are each independently $C_3$-$C_{12}$-cycloalkyl;
C is $C_3$-$C_{12}$-cycloalkyl or $C_2$-$C_9$-heterocyclyl;
$X^1$ is carbonyl;
$X^3$ is a covalent bond or $C_1$-$C_6$-alkyl; and
$X^4$ is carbonyl, —NH—C(O)—, or —$C_1$-$C_6$-alkyl-NH—C(O)—.

In an embodiment, the present disclosure provides a compound of formula (I-I) as described herein, or a pharmaceutically acceptable salt thereof, wherein:
(i) $R^1$ and $R^2$, taken together with the nitrogen atom to which they are attached, form a piperazinyl ring which is optionally substituted with $R^8$; or
(ii) $R^1$ is a group

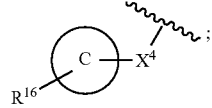

and $R^2$ is hydrogen;
$R^3$ is chloro;
$R^4$ is $CF_3$;
$R^5$ is $C_1$-$C_6$-alkyl substituted with $R^{11}$ and $R^{12}$, allyl, prop-2-ynyl, or a group

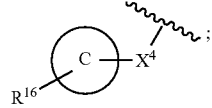

wherein said $C_1$-$C_6$-alkyl is methyl, ethyl, or isopropyl;
$R^6$ is methyl;
$R^7$ is hydrogen;
$R^8$ is a group $R^1$ is hydrogen, cyano, $CF_3$, or fluoro;
$R^{12}$, $R^{13}$, and $R^{14}$ are each independently hydrogen or fluoro;
$R^{16}$ is hydrogen, amino, or hydroxy;
A is cyclobutyl;
B is cyclopropyl, cyclobutyl, or spiro[2.3]hexan-5-yl;
C is cyclobutyl, cyclopentyl, 4-piperidyl, pyrrolidin-3-yl, 3-azabicyclo[3.1.0]hexan-6-yl, or 2,5-diazabicyclo[2.2.1]heptan-2-yl;

$X^1$ is carbonyl;
$X^3$ is a covalent bond or —$CH_2$—; and
$X^4$ is carbonyl, —NH—C(O)—, or —$CH_2$—NH—C(O)—.

In one embodiment, the present disclosure provides a compound of formula (I) as described herein, or a pharmaceutically acceptable salt thereof, wherein:
(i) $R^1$ and $R^2$, taken together with the nitrogen atom to which they are attached, form a $C_2$-$C_9$-heterocyclic ring which is optionally substituted with $R^8$; or
(ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-, or a group

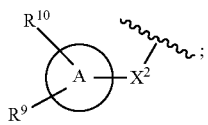

and $R^2$ is hydrogen or $C_1$-$C_6$-alkyl;
$R^8$ is $C_1$-$C_6$-alkoxycarbonyl, amino-$C_1$-$C_6$-alkyl-C(O)—, $(C_1$-$C_6$-alkyl$)_2$N—$C_1$-$C_6$-alkyl-C(O)—, $C_1$-$C_6$-alkyl-NH—$C_1$-$C_6$-alkyl-NH—C(O)—, or a group

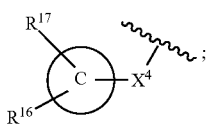

$R^9$ is hydrogen, hydroxy, amino, amino-$C_1$-$C_6$-alkyl-C(O)—NH—, or amino-$C_3$-$C_{12}$-cycloalkyl-C(O)—NH—;
$R^{10}$ is hydrogen;
$R^{16}$ is hydrogen, amino, hydroxy, amino-$C_1$-$C_6$-alkyl, or $C_1$-$C_6$-alkyl;
$R^{17}$ is hydrogen or $C_1$-$C_6$-alkyl;
A is $C_2$-$C_9$-heterocyclyl or $C_3$-$C_{12}$-cycloalkyl;
C is $C_3$-$C_{12}$-cycloalkyl or $C_2$-$C_9$-heterocyclyl;
$X^2$ is a covalent bond or $C_1$-$C_6$-alkyl; and
$X^4$ is a covalent bond, carbonyl, —NH—C(O)—, or —$C_1$-$C_6$-alkyl-NH—C(O)—.

In an embodiment, the present disclosure provides a compound of formula (I) as described herein, or a pharmaceutically acceptable salt thereof, wherein:
(i) $R^1$ and $R^2$, taken together with the nitrogen atom to which they are attached, form a $C_2$-$C_9$-heterocyclic ring which is optionally substituted with $R^8$; or
(ii) $R^1$ is a group

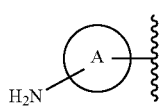

and $R^2$ is hydrogen;
$R^8$ is a group

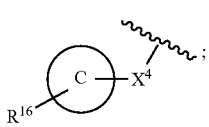

$R^{16}$ is hydrogen, amino, or hydroxy;
A is $C_3$-$C_{12}$-cycloalkyl;
C is $C_3$-$C_{12}$-cycloalkyl or $C_2$-$C_9$-heterocyclyl; and
$X^4$ is carbonyl, —NH—C(O)—, or —$C_1$-$C_6$-alkyl-NH—C(O)—.

In an embodiment, the present disclosure provides a compound of formula (I) as described herein, or a pharmaceutically acceptable salt thereof, wherein:
(i) $R^1$ and $R^2$, taken together with the nitrogen atom to which they are attached, form a piperazinyl ring which is optionally substituted with $R^8$; or
(ii) $R^1$ is a group

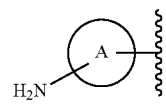

and $R^2$ is hydrogen;
$R^8$ is a group $R^{16}$

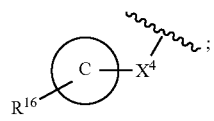

$R^{16}$ is hydrogen, amino, or hydroxy;
A is cyclobutyl;
C is cyclobutyl, cyclopentyl, 4-piperidyl, pyrrolidin-3-yl, 3-azabicyclo[3.1.0]hexan-6-yl, or 2,5-diazabicyclo[2.2.1]heptan-2-yl; and
$X^4$ is carbonyl, —NH—C(O)—, or —$CH_2$—NH—C(O)—.

In one embodiment, the present disclosure provides a compound of formula (I) as described herein, or a pharmaceutically acceptable salt thereof, wherein:
$R^5$ is hydrogen, $C_1$-$C_6$-alkyl substituted with $R^{11}$ and $R^{12}$, $C_2$-$C_6$-alkenyl, $C_2$-$C_6$-alkynyl, amino-$C_2$-$C_6$-alkynyl-, $C_1$-$C_6$-alkoxy-$C_2$-$C_6$-alkynyl-, hydroxy-$C_2$-$C_6$-alkynyl-, or a group

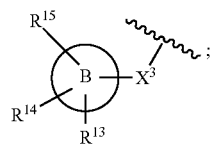

$R^{11}$ is hydrogen, halogen, hydroxy, cyano, $CF_3$, carbamoyl, halo-$C_1$-$C_6$-alkoxy-, $(C_1$-$C_6$-alkyl$)_2$N—C(O)—, $C_1$-$C_6$-alkyl-NH—C(O)—, or $C_1$-$C_6$-alkoxy-$C_1$-$C_6$-alkoxy;
$R^{12}$ is hydrogen or halogen;
$R^{13}$ is hydrogen, oxo, halogen, $C_3$-$C_{12}$-cycloalkyl, $C_1$-$C_6$-alkyl, or hydroxy-$C_1$-$C_6$-alkyl;
$R^{14}$ is hydrogen, oxo, halogen, or $C_1$-$C_6$-alkyl;
$R^{15}$ is hydrogen or halogen;
B is $C_6$-$C_{14}$-aryl, $C_1$-$C_{13}$-heteroaryl, $C_3$-$C_{12}$-cycloalkyl, or $C_2$-$C_9$-heterocyclyl; and
$X^3$ is a covalent bond or $C_1$-$C_6$-alkyl.

In an embodiment, the present disclosure provides a compound of formula (I) as described herein, or a pharmaceutically acceptable salt thereof, wherein:
$R^5$ is $C_1$-$C_6$-alkyl substituted with $R^{11}$ and $R^{12}$, $C_2$-$C_6$-alkenyl, $C_2$-$C_6$-alkynyl, or a group

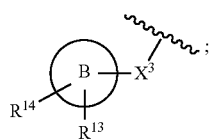

$R^{11}$ is hydrogen, cyano, $CF_3$, or halogen;
$R^{12}$, $R^{13}$, and $R^{14}$ are each independently hydrogen or halogen;
B is $C_3$-$C_{12}$-cycloalkyl; and
$X^3$ is a covalent bond or $C_1$-$C_6$-alkyl.

In an embodiment, the present disclosure provides a compound of formula (I) as described herein, or a pharmaceutically acceptable salt thereof, wherein:
$R^5$ is $C_1$-$C_6$-alkyl substituted with $R^{11}$ and $R^{12}$, allyl, prop-2-ynyl, or a group

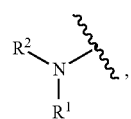

wherein said $C_1$-$C_6$-alkyl is methyl, ethyl, or isopropyl;
$R^{11}$ is hydrogen, cyano, $CF_3$, or fluoro;
$R^{12}$, $R^{13}$, and $R^{14}$ are each independently hydrogen or fluoro;
B is cyclopropyl, cyclobutyl, or spiro[2.3]hexan-5-yl; and
$X^3$ is a covalent bond or $-CH_2-$.

In one embodiment, the present disclosure provides a compound of formula (I) as described herein, or a pharmaceutically acceptable salt thereof, wherein:
$R^3$ is halogen or $C_1$-$C_6$-alkyl; and
$R^7$ is hydrogen or halogen.

In an embodiment, the present disclosure provides a compound of formula (I) as described herein, or a pharmaceutically acceptable salt thereof, wherein:
$R^3$ is halogen; and
$R^7$ is hydrogen.

In an embodiment, the present disclosure provides a compound of formula (I) as described herein, or a pharmaceutically acceptable salt thereof, wherein:
$R^3$ is chloro; and
$R^7$ is hydrogen.

In one embodiment, the present disclosure provides a compound of formula (I) as described herein, or a pharmaceutically acceptable salt thereof, wherein:
$R^4$ is $C_1$-$C_6$-alkyl or a group

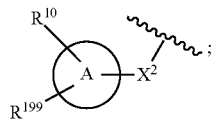

wherein:
(i) $R^1$ and $R^2$, taken together with the nitrogen atom to which they are attached, form a $C_2$-$C_9$-heterocyclic ring which is optionally substituted with one or two $R^8$; or
(ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-$C_1$-$C_6$-alkoxycarbonyl-NH—$C_1$-$C_6$-alkyl-, $C_1$-$C_6$-alkoxycarbonyl-$C_1$-$C_6$-alkyl-NH—$C_1$-$C_6$-alkyl- or a group

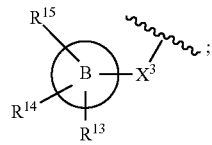

and
$R^2$ is hydrogen or $C_1$-$C_6$-alkyl;
$R^3$ is halogen or $C_1$-$C_6$-alkyl;
$R^4$ is halo-$C_1$-$C_6$-alkyl or $C_6$-$C_{14}$-aryl;
$R^5$ is hydrogen, $C_1$-$C_6$-alkyl substituted with $R^{11}$ and $R^{12}$, $C_2$-$C_6$-alkenyl, $C_2$-$C_6$-alkynyl, halo-$C_2$-$C_6$-alkenyl, amino-$C_2$-$C_6$-alkynyl-, halo-$C_1$-$C_6$-alkoxy-$C_1$-$C_6$-alkyl, $C_1$-$C_6$-alkoxy-$C_2$-$C_6$-alkynyl-, hydroxy-$C_2$-$C_6$-alkynyl-, or a group

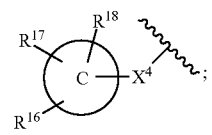

$R^6$ is $C_1$-$C_6$-alkyl;
$R^7$ is hydrogen or halogen;
$R^8$ is $C_1$-$C_6$-alkoxycarbonyl, amino-$C_1$-$C_6$-alkyl, $C_1$-$C_6$-alkyl-NH—, amino-$C_1$-$C_6$-alkyl-C(O)—, amino-$C_1$-$C_6$-alkyl-NH—C(O)—$C_1$-$C_6$-alkyl-, amino-$C_1$-$C_6$-alkyl-CH(OH)—, amino-$C_1$-$C_6$-alkyl-CH(NH$_2$)—C(O)—, ($C_1$-$C_6$-alkyl)$_2$N—$C_1$-$C_6$-alkyl-, ($C_1$-$C_6$-alkyl)$_2$N—$C_1$-$C_6$-alkyl-N($C_1$-$C_6$-alkyl)-, ($C_1$-$C_6$-alkyl)$_2$N—$C_1$-$C_6$-alkyl-C(O)—, $C_1$-$C_6$-alkyl-NH—$C_1$-$C_6$-alkyl-NH—C(O)—, oxo, amino, halogen, or a group

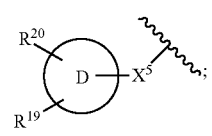

$R^9$ is hydrogen, amino, hydroxy, alkyl, alkoxy, amino-$C_1$-$C_6$-alkyl-C(O)—NH— or a group $R^{10}$ is hydrogen, $C_1$-$C_6$-alkyl or $C_1$-$C_6$-alkoxy;
$R^{11}$ is hydrogen, halogen, hydroxy, cyano, $CF_3$, carbamoyl, halo-$C_1$-$C_6$-alkoxy-, ($C_1$-$C_6$-alkyl)$_2$N—C(O)—, $C_1$-$C_6$-alkyl-NH—C(O)—, or $C_1$-$C_6$-alkoxy-$C_1$-$C_6$-alkoxy;
$R^{12}$ is hydrogen or halogen;
$R^{13}$ is hydrogen, oxo, halogen, $C_3$-$C_{12}$-cycloalkyl, $C_1$-$C_6$-alkyl, halo-$C_1$-$C_6$-alkyl or hydroxy-$C_1$-$C_6$-alkyl;
$R^{14}$ is hydrogen, oxo, halogen, or $C_1$-$C_6$-alkyl;
$R^{15}$ is hydrogen or halogen;

$R^{16}$ is hydrogen, halogen, amino, hydroxy, amino-$C_1$-$C_6$-alkyl, $C_1$-$C_6$-alkyl-NH— or $C_1$-$C_6$-alkyl;
$R^{17}$ is hydrogen, amino or $C_1$-$C_6$-alkyl;
$R^{18}$ is hydrogen or amino;
$R^{19}$ is hydrogen, amino, hydroxy, $C_1$-$C_6$-alkyl, amino-$C_1$-$C_6$-alkyl or HO—$SO_2$—$C_1$-$C_6$-alkyl;
$R^{20}$ is hydrogen or hydroxy;
A is $C_2$-$C_9$-heterocyclyl or $C_3$-$C_{12}$-cycloalkyl;
B is $C_6$-$C_{14}$-aryl, $C_1$-$C_{13}$-heteroaryl, $C_3$-$C_{12}$-cycloalkyl, or $C_2$-$C_9$-heterocyclyl;
C is $C_3$-$C_{12}$-cycloalkyl or $C_2$-$C_9$-heterocyclyl;
D is $C_3$-$C_{12}$-cycloalkyl or $C_2$-$C_9$-heterocyclyl;
$X^1$ is —S—, a covalent bond, carbonyl, $SO_2$ or a group

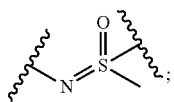 [SMILES: *N=S(*)(C)=O]

$X^2$ is a covalent bond or $C_1$-$C_6$-alkyl;
$X^3$ is a covalent bond or $C_1$-$C_6$-alkyl;
$X^4$ is a covalent bond, carbonyl, —NH—C(O)—, —NH—C(O)—NH—, —NH—C(O)—NH—$C_1$-$C_6$-alkyl-, —$C_1$-$C_6$-alkyl-NH—C(O)—, —$C_1$-$C_6$-alkyl-C(O)— or —$SO_2$—; and
$X^5$ is carbonyl, —C(O)—NH—, —NH—C(O)— or —NH—C(O)—NH—.

In an embodiment, the present disclosure provides a compound of formula (I) as described herein, or a pharmaceutically acceptable salt thereof, wherein:
$R^A$ is a group

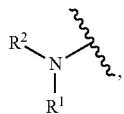

wherein:
(i) $R^1$ and $R^2$, taken together with the nitrogen atom to which they are attached, form a $C_2$-$C_9$-heterocyclic ring which is optionally substituted with one or two $R^8$; or
(ii) $R^1$ is amino-$C_1$-$C_6$-alkyl-O—$C_1$-$C_6$-alkyl- or a group

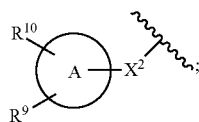

and
$R^2$ is hydrogen;
$R^3$ is halogen or $C_1$-$C_6$-alkyl;
$R^4$ is halo-$C_1$-$C_6$-alkyl;
$R^5$ is $C_1$-$C_6$-alkyl substituted with $R^{11}$ and $R^{12}$, $C_2$-$C_6$-alkenyl, halo-$C_2$-$C_6$-alkenyl, $C_2$-$C_6$-alkynyl, or a group

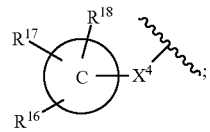

$R^6$ is $C_1$-$C_6$-alkyl;
$R^7$, $R^{10}$, $R^{15}$, $R^{17}$, $R^{18}$ and $R^{20}$ are all hydrogen;
$R^8$ is halogen or a group

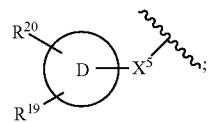

$R^9$ is amino or a group

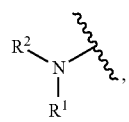

$R^{11}$ is hydrogen, cyano, $CF_3$, or halogen;
$R^{12}$, $R^{13}$, and $R^{14}$ are each independently hydrogen or halogen;
$R^{16}$ and $R^{19}$ are each independently hydrogen, amino, or hydroxy;
A, C and D are each independently $C_2$-$C_9$-heterocyclyl or $C_3$-$C_{12}$-cycloalkyl;
B is $C_3$-$C_{12}$-cycloalkyl;
$X^1$ is carbonyl;
$X^2$ and $X^3$ are each independently a covalent bond or $C_1$-$C_6$-alkyl;
$X^4$ is carbonyl, —NH—C(O)—, —NH—C(O)—NH—$C_1$-$C_6$-alkyl- or —$C_1$-$C_6$-alkyl-NH—C(O)—; and
$X^5$ is carbonyl or —NH—C(O)—.

In an embodiment, the present disclosure provides a compound of formula (I) as described herein, or a pharmaceutically acceptable salt thereof, wherein:
$R^A$ is a group $R^1$

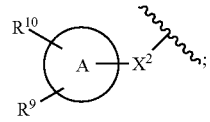

wherein:
(i) $R^1$ and $R^2$, taken together with the nitrogen atom to which they are attached, form a piperazinyl or a piperidyl ring which is optionally substituted with one or two $R^8$; or
(ii) $R^1$ is 2-(2-amino-2-methyl-propoxy)ethyl or a group

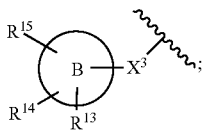

and $R^2$ is hydrogen;
$R^3$ is chloro or ethyl;
$R^4$ is $CF_3$;
$R^5$ is $C_1$-$C_6$-alkyl substituted with $R^{11}$ and $R^{12}$, allyl, prop-2-ynyl, or a group

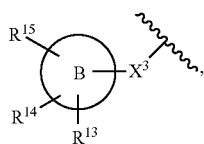

wherein said $C_1$-$C_6$-alkyl is methyl, ethyl, or isopropyl;
$R^6$ is methyl;
$R^7$, $R^{10}$, $R^{15}$, $R^{17}$, $R^{18}$ and $R^{20}$ are all hydrogen;
$R^8$ is fluoro or a group

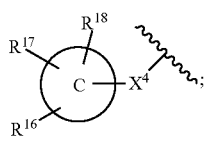

$R^9$ is amino or a group

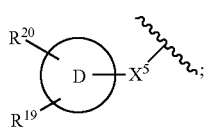

$R^{11}$ is hydrogen, cyano, $CF_3$, or fluoro;
$R^{12}$, $R^{13}$, and $R^{14}$ are each independently hydrogen or fluoro;
$R^{16}$ and $R^{19}$ are each independently hydrogen, amino, or hydroxy;
A is cyclobutyl, cyclopropyl or 3-azabicyclo[3.1.0]hexan-6-yl;
B is cyclopropyl, cyclobutyl, or spiro[2.3]hexan-5-yl;
C is cyclobutyl, cyclopentyl, 3-piperidyl, 4-piperidyl, pyrrolidin-3-yl, azetidin-3-yl, 3-azabicyclo[3.1.0]hexan-6-yl, or 2,5-diazabicyclo[2.2.1]heptan-2-yl;
D is pyrrolidin-3-yl, 4-piperidyl or cyclobutyl;
$X^1$ is carbonyl;
$X^2$ and $X^3$ are each independently a covalent bond or —$CH_2$—;
$X^4$ is carbonyl, —NH—C(O)—, —NH—C(O)—NH—$CH_2$— or —$CH_2$—NH—C(O)—; and
$X^5$ is carbonyl or —NH—C(O)—.

In one embodiment, the present disclosure provides a compound of formula (I) as described herein, or a pharmaceutically acceptable salt thereof, wherein:
$R^4$ is $C_1$-$C_6$-alkyl or a group

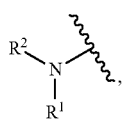

wherein:
(i) $R^1$ and $R^2$, taken together with the nitrogen atom to which they are attached, form a $C_2$-$C_9$-heterocyclic ring which is optionally substituted with one or two $R^8$; or
(ii) $R^1$ is hydrogen, $C_1$-$C_6$-alkyl, amino-$C_1$-$C_6$-alkyl-, amino-$C_1$-$C_6$-alkyl-O—$C_1$-$C_6$-alkyl-$C_1$-$C_6$-alkoxycarbonyl-NH—$C_1$-$C_6$-alkyl-, $C_1$-$C_6$-alkoxycarbonyl-$C_1$-$C_6$-alkyl-NH—$C_1$-$C_6$-alkyl- or a group

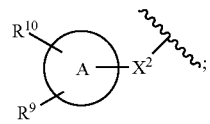

and
$R^2$ is hydrogen or $C_1$-$C_6$-alkyl;
$R^8$ is $C_1$-$C_6$-alkoxycarbonyl, amino-$C_1$-$C_6$-alkyl, $C_1$-$C_6$-alkyl-NH—, amino-$C_1$-$C_6$-alkyl-C(O)—, amino-$C_1$-$C_6$-alkyl-NH—C(O)—$C_1$-$C_6$-alkyl-, amino-$C_1$-$C_6$-alkyl-CH(OH)—, amino-$C_1$-$C_6$-alkyl-CH($NH_2$)—C(O)—, ($C_1$-$C_6$-alkyl)$_2$N—$C_1$-$C_6$-alkyl-, ($C_1$-$C_6$-alkyl)$_2$N—$C_1$-$C_6$-alkyl-N($C_1$-$C_6$-alkyl)-, ($C_1$-$C_6$-alkyl)$_2$N—$C_1$-$C_6$-alkyl-C(O)—, $C_1$-$C_6$-alkyl-NH—$C_1$-$C_6$-alkyl-NH—C(O)—, oxo, amino, halogen, or a group

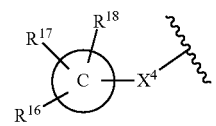

$R^9$ is hydrogen, amino, hydroxy, alkyl, alkoxy, amino-$C_1$-$C_6$-alkyl-C(O)—NH— or a group

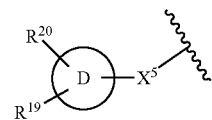

$R^{10}$ is hydrogen, $C_1$-$C_6$-alkyl or $C_1$-$C_6$-alkoxy;
$R^{16}$ is hydrogen, halogen, amino, hydroxy, amino-$C_1$-$C_6$-alkyl, $C_1$-$C_6$-alkyl-NH— or $C_1$-$C_6$-alkyl;
$R^{17}$ is hydrogen, amino or $C_1$-$C_6$-alkyl;
$R^{18}$ is hydrogen or amino;
$R^{19}$ is hydrogen, amino, hydroxy, $C_1$-$C_6$-alkyl, amino-$C_1$-$C_6$-alkyl or HO—$SO_2$—$C_1$-$C_6$-alkyl;
$R^{20}$ is hydrogen or hydroxy;
A is $C_2$-$C_9$-heterocyclyl or $C_3$-$C_{12}$-cycloalkyl;
C is $C_3$-$C_{12}$-cycloalkyl or $C_2$-$C_9$-heterocyclyl;
D is $C_3$-$C_{12}$-cycloalkyl or $C_2$-$C_9$-heterocyclyl;
$X^1$ is —S—, a covalent bond, carbonyl, $SO_2$ or a group

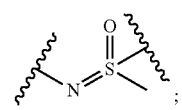 [SMILES: *N=S(*)(C)=O]

$X^2$ is a covalent bond or $C_1$-$C_6$-alkyl;
$X^4$ is a covalent bond, carbonyl, —NH—C(O)—, —NH—C(O)—NH—, —NH—C(O)—NH—$C_1$-$C_6$-alkyl-, —$C_1$-$C_6$-alkyl-NH—C(O)—, —$C_1$-$C_6$-alkyl-C(O)— or —$SO_2$—; and
$X^5$ is carbonyl, —C(O)—NH—, —NH—C(O)— or —NH—C(O)—NH—.

In an embodiment, the present disclosure provides a compound of formula (I) as described herein, or a pharmaceutically acceptable salt thereof, wherein:

$R^4$ is a group

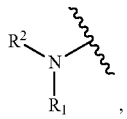

wherein:
(i) $R^1$ and $R^2$, taken together with the nitrogen atom to which they are attached, form a $C_2$-$C_9$-heterocyclic ring which is optionally substituted with one or two $R^8$; or
(ii) $R^1$ is amino-$C_1$-$C_6$-alkyl-O—$C_1$-$C_6$-alkyl- or a group

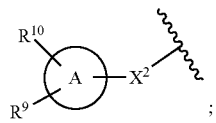

and
$R^2$ is hydrogen;
$R^{10}$, $R^{17}$, $R^{18}$ and $R^{20}$ are all hydrogen;
$R^8$ is halogen or a group

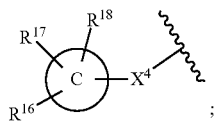

$R^9$ is amino or a group

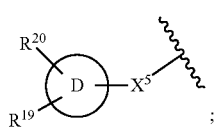

$R^{16}$ and $R^{19}$ are each independently hydrogen, amino, or hydroxy; A, C and D are each independently $C_2$-$C_9$-heterocyclyl or $C_3$-$C_{12}$-cycloalkyl;
$X^1$ is carbonyl;
$X^2$ is a covalent bond or $C_1$-$C_6$-alkyl;
$X^4$ is carbonyl, —NH—C(O)—, —NH—C(O)—NH—$C_1$-$C_6$-alkyl- or —$C_1$-$C_6$-alkyl-NH—C(O)—; and
$X^5$ is carbonyl or —NH—C(O)—.

In an embodiment, the present disclosure provides a compound of formula (I) as described herein, or a pharmaceutically acceptable salt thereof, wherein:
$R^4$ is a group

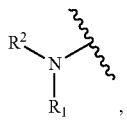

wherein:
(i) $R^1$ and $R^2$, taken together with the nitrogen atom to which they are attached, form a piperazinyl or a piperidyl ring which is optionally substituted with one or two $R^8$; or (ii) $R^1$ is 2-(2-amino-2-methyl-propoxy)ethyl or a group

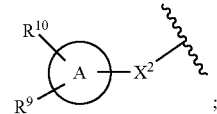

and $R^2$ is hydrogen;
$R^{10}$, $R^{17}$, $R^{18}$ and $R^{20}$ are all hydrogen;
$R^8$ is fluoro or a group

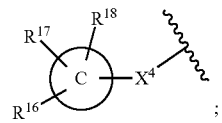

$R^9$ is amino or a group

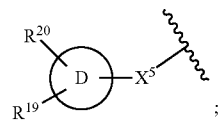

$R^{16}$ and $R^{19}$ are each independently hydrogen, amino, or hydroxy;
A is cyclobutyl, cyclopropyl or 3-azabicyclo[3.1.0]hexan-6-yl;
C is cyclobutyl, cyclopentyl, 3-piperidyl, 4-piperidyl, pyrrolidin-3-yl, azetidin-3-yl, 3-azabicyclo[3.1.0]hexan-6-yl, or 2,5-diazabicyclo[2.2.1]heptan-2-yl;
D is pyrrolidin-3-yl, 4-piperidyl or cyclobutyl;
$X^1$ is carbonyl;
$X^2$ is a covalent bond or —CH$_2$—;
$X^4$ is carbonyl, —NH—C(O)—, —NH—C(O)—NH—CH$_2$— or —CH$_2$—NH—C(O)–; and
$X^5$ is carbonyl or —NH—C(O)—.

In one embodiment, the present disclosure provides a compound of formula (I) as described herein, or a pharmaceutically acceptable salt thereof, wherein:
$R^5$ is hydrogen, $C_1$-$C_6$-alkyl substituted with $R^{11}$ and $R^{12}$, $C_2$-$C_6$-alkenyl, $C_2$-$C_6$-alkynyl, halo-$C_2$-$C_6$-alkenyl, amino-$C_2$-$C_6$-alkynyl-, halo-$C_1$-$C_6$-alkoxy-$C_1$-$C_6$-alkyl, $C_1$-$C_6$-alkoxy-$C_2$-$C_6$-alkynyl-, hydroxy-$C_2$-$C_6$-alkynyl-, or a group

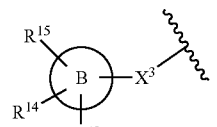

$R^{11}$ is hydrogen, halogen, hydroxy, cyano, CF$_3$, carbamoyl, halo-$C_1$-$C_6$-alkoxy-, ($C_1$-$C_6$-alkyl)$_2$N—C(O)—, $C_1$-$C_6$-alkyl-NH—C(O)—, or $C_1$-$C_6$-alkoxy-$C_1$-$C_6$-alkoxy;
$R^{12}$ is hydrogen or halogen;
$R^{13}$ is hydrogen, oxo, halogen, $C_3$-$C_{12}$-cycloalkyl, $C_1$-$C_6$-alkyl, halo-$C_1$-$C_6$-alkyl or hydroxy-$C_1$-$C_6$-alkyl;
$R^{14}$ is hydrogen, oxo, halogen, or $C_1$-$C_6$-alkyl;

$R^{15}$ is hydrogen or halogen;
B is $C_6$-$C_{14}$-aryl, $C_1$-$C_{13}$-heteroaryl, $C_3$-$C_{12}$-cycloalkyl, or $C_2$-$C_9$-heterocyclyl; and
$X^3$ is a covalent bond or $C_1$-$C_6$-alkyl.

In an embodiment, the present disclosure provides a compound of formula (I) as described herein, or a pharmaceutically acceptable salt thereof, wherein:
$R^5$ is $C_1$-$C_6$-alkyl substituted with $R^{11}$ and $R^{12}$, $C_2$-$C_6$-alkenyl, halo-$C_2$-$C_6$-alkenyl, $C_2$-$C_6$-alkynyl, or a group

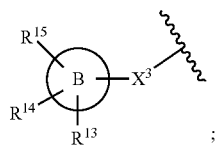

$R^{11}$ is hydrogen, cyano, $CF_3$, or halogen;
$R^{12}$, $R^{13}$, and $R^{14}$ are each independently hydrogen or halogen;
$R^{15}$ is hydrogen;
B is $C_3$-$C_{12}$-cycloalkyl; and
$X^3$ is a covalent bond or $C_1$-$C_6$-alkyl.

In an embodiment, the present disclosure provides a compound of formula (I) as described herein, or a pharmaceutically acceptable salt thereof, wherein:
$R^5$ is $C_1$-$C_6$-alkyl substituted with $R^{11}$ and $R^{12}$, allyl, prop-2-ynyl, or a group

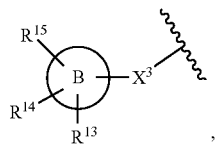

wherein said $C_1$-$C_6$-alkyl is methyl, ethyl, or isopropyl;
$R^{11}$ is hydrogen, cyano, $CF_3$, or fluoro;
$R^{12}$, $R^{13}$, and $R^{14}$ are each independently hydrogen or fluoro;
$R^{15}$ is hydrogen;
B is cyclopropyl, cyclobutyl, or spiro[2.3]hexan-5-yl; and
$X^3$ is a covalent bond or —$CH_2$—.

In an embodiment, the present disclosure provides a compound of formula (I) as described herein, or a pharmaceutically acceptable salt thereof, wherein $R^4$ is a group

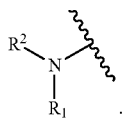

In an embodiment, the present disclosure provides a compound of formula (I) as described herein, or a pharmaceutically acceptable salt thereof, wherein:
$R^1$ is a group

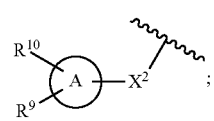

$R^9$ is a group

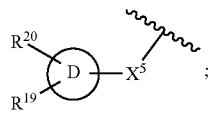

$R^{10}$ is hydrogen;
$R^{19}$ is hydroxy;
$R^{20}$ is hydrogen;
$X^2$ is a covalent bond;
$X^5$ is —NH—C(O)—;
A is $C_2$-$C_9$-heterocyclyl; and
D is $C_2$-$C_9$-heterocyclyl.

In an embodiment, the present disclosure provides a compound of formula (I) as described herein, or a pharmaceutically acceptable salt thereof, wherein:
$R^5$ is a group

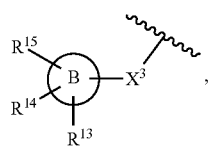

wherein:
$R^{13}$ and $R^{14}$ are both halogen;
$R^{15}$ is hydrogen;
$X^3$ is a covalent bond; and
B is $C_3$-$C_{12}$-cycloalkyl.

In an embodiment, the present disclosure provides a compound of formula (I) as described herein, or a pharmaceutically acceptable salt thereof, wherein:
$R^4$ is a group

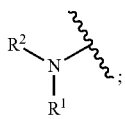

$R^1$ is a group

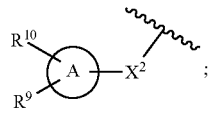

$R^2$ is hydrogen;
$R^3$ is halogen;
$R^4$ is halo-$C_1$-$C_6$-alkyl;

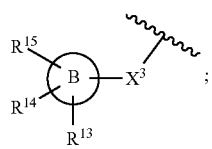

$R^5$ is a group R
$R^6$ is $C_1$-$C_6$-alkyl;
$R^7$ is hydrogen;
$R^9$ is a group

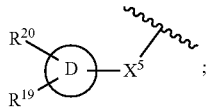

$R^{10}$ is hydrogen;
$R^{13}$ is halogen;
$R^{14}$ is halogen;
$R^{15}$ is hydrogen;
$R^{19}$ is hydroxy;
$R^{20}$ is hydrogen;
$X^1$ is carbonyl;
$X^2$ is a covalent bond;
$X^3$ is a covalent bond;
$X^5$ is —NH—C(O)—;
A is $C_2$-$C_9$-heterocyclyl;
B is $C_3$-$C_{12}$-cycloalkyl; and
D is $C_2$-$C_9$-heterocyclyl.

In an embodiment, the present disclosure provides a compound of formula (I) as described herein, or a pharmaceutically acceptable salt thereof, wherein:
$R^1$ and $R^2$, taken together with the nitrogen atom to which they are attached, form a $C_2$-$C_9$-heterocyclic ring which is substituted with one $R^8$;
$R^8$ is a group

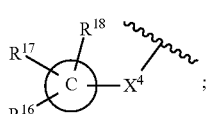

$R^{16}$, $R^{17}$ and $R^{18}$ are all hydrogen;
$X^4$ is carbonyl; and
C is $C_2$-$C_9$-heterocyclyl.

In an embodiment, the present disclosure provides a compound of formula (I) as described herein, or a pharmaceutically acceptable salt thereof, wherein $R^5$ is $C_2$-$C_6$-alkynyl.

In an embodiment, the present disclosure provides a compound of formula (I) as described herein, or a pharmaceutically acceptable salt thereof, wherein:
$R^A$ is a group

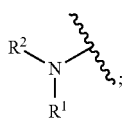

$R^1$ and $R^2$, taken together with the nitrogen atom to which they are attached, form a $C_2$-$C_9$-heterocyclic ring which is substituted with one $R^8$;
$R^3$ is halogen;
$R^4$ is halo-$C_1$-$C_6$-alkyl;
$R^5$ is $C_2$-$C_6$-alkynyl;

$R^6$ is $C_1$-$C_6$-alkyl;
$R^7$ is hydrogen;
$R^8$ is a group

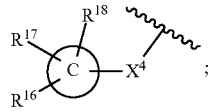

$R^{16}$, $R^{17}$ and $R^{18}$ are all hydrogen;
$X^1$ is carbonyl;
$X^4$ is carbonyl; and
C is $C_2$-$C_9$-heterocyclyl.

In one embodiment, the present disclosure provides a compound of formula (I) as described herein, or a pharmaceutically acceptable salt thereof, wherein the compound of formula (I) is selected from the compounds disclosed in Table 1.

In one embodiment, the present disclosure provides a compound of formula (I) as described herein, or a pharmaceutically acceptable salt thereof, wherein the compound of formula (I) is:
N-(azetidin-3-yl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;
4-[2-chloro-4-[[1-methyl-5-[1-prop-2-ynyl-3-(trifluoromethyl)pyrazol-4-yl]imidazole-2-carbonyl]amino]benzoyl]-N-[(3S)-pyrrolidin-3-yl]piperazine-1-carboxamide;
N-[3-chloro-4-[4-(piperidine-4-carbonyl)piperazine-1-carbonyl]phenyl]-1-methyl-5-[1-pent-2-ynyl-3-(trifluoromethyl)pyrazol-4-yl]imidazole-2-carboxamide;
4-[2-chloro-4-[[1-methyl-5-[1-prop-2-ynyl-3-(trifluoromethyl)pyrazol-4-yl]imidazole-2-carbonyl]amino]benzoyl]-N-[(3-hydroxyazetidin-3-yl)methyl]piperazine-1-carboxamide;
N-[3-chloro-4-[4-(piperidine-4-carbonyl)piperazine-1-carbonyl]phenyl]-1-methyl-5-[1-prop-2-ynyl-3-(trifluoromethyl)pyrazol-4-yl]imidazole-2-carboxamide;
N-[4-[2-(2-aminoethoxy)ethylcarbamoyl]-3-chloro-phenyl]-1-methyl-5-[1-prop-2-ynyl-3-(trifluoromethyl)pyrazol-4-yl]imidazole-2-carboxamide;
N-[3-chloro-4-[4-[(3S)-pyrrolidine-3-carbonyl]piperazine-1-carbonyl]phenyl]-1-methyl-5-[1-prop-2-ynyl-3-(trifluoromethyl)pyrazol-4-yl]imidazole-2-carboxamide;
N-[3-chloro-4-[4-[(3S,4S)-3-hydroxypiperidine-4-carbonyl]piperazine-1-carbonyl]phenyl]-1-methyl-5-[1-prop-2-ynyl-3-(trifluoromethyl)pyrazol-4-yl]imidazole-2-carboxamide;
N-[3-chloro-4-(dimethylcarbamoyl)phenyl]-1-methyl-5-[1-prop-2-ynyl-3-(trifluoromethyl)pyrazol-4-yl]imidazole-2-carboxamide;
N-[3-chloro-4-[4-(piperidine-4-carbonyl)piperazine-1-carbonyl]phenyl]-1-methyl-5-[1-propa-1,2-dienyl-3-(trifluoromethyl)pyrazol-4-yl]imidazole-2-carboxamide;
N-[3-chloro-4-[4-(4-hydroxypiperidine-4-carbonyl)piperazine-1-carbonyl]phenyl]-1-methyl-5-[1-prop-2-ynyl-3-(trifluoromethyl)pyrazol-4-yl]imidazole-2-carboxamide;
N-[4-[2-[(2R)-2-aminopropoxy]ethylcarbamoyl]-3-chloro-phenyl]-1-methyl-5-[1-prop-2-ynyl-3-(trifluoromethyl)pyrazol-4-yl]imidazole-2-carboxamide;
N-[4-[2-(2-amino-2-methyl-propoxy)ethylcarbamoyl]-3-chloro-phenyl]-1-methyl-5-[1-prop-2-ynyl-3-(trifluoromethyl)pyrazol-4-yl]imidazole-2-carboxamide;

N-[3-chloro-4-[4-[(2R)-pyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-[(2S,4R)-4-hydroxypyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(1-methylprop-2-ynyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-cyclopropyl-3-(trifluoromethyl)pyrazol-4-yl]-1-methyl-imidazole-2-carboxamide;

5-[1-but-2-ynyl-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-1-methyl-5-[1-(2,2,2-trifluoroethyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-cyclobutyl-3-(trifluoromethyl)pyrazol-4-yl]-1-methyl-imidazole-2-carboxamide;

N-[3-chloro-4-[4-(1-methylpiperidine-4-carbonyl)piperazine-1-carbonyl]phenyl]-1-methyl-5-[1-prop-2-ynyl-3-(trifluoromethyl)pyrazol-4-yl]imidazole-2-carboxamide;

5-[1-allyl-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-(2-fluoroethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(4-methoxybut-2-ynyl)-3-(trifluoromethyl)pyrazol-4-yl]-1-methyl-imidazole-2-carboxamide;

N-[4-[2-[(2S)-2-aminopropoxy]ethylcarbamoyl]-3-chloro-phenyl]-1-methyl-5-[1-prop-2-ynyl-3-(trifluoromethyl)pyrazol-4-yl]imidazole-2-carboxamide;

N-[3-chloro-4-[4-(4-hydroxypiperidine-4-carbonyl)piperazine-1-carbonyl]phenyl]-5-[1-(cyanomethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-isobutyl-3-(trifluoromethyl)pyrazol-4-yl]-1-methyl-imidazole-2-carboxamide;

N-[3-chloro-4-(methylcarbamoyl)phenyl]-1-methyl-5-[1-prop-2-ynyl-3-(trifluoromethyl)pyrazol-4-yl]imidazole-2-carboxamide;

N-[3-chloro-4-[4-(1-methylpiperidine-4-carbonyl)piperazine-1-carbonyl]phenyl]-5-[1-(cyanomethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(cyanomethyl)-3-(trifluoromethyl)pyrazol-4-yl]-1-methyl-imidazole-2-carboxamide;

N-[3-chloro-4-[4-(1-methylpiperidine-4-carbonyl)piperazine-1-carbonyl]phenyl]-1-methyl-5-[3-(trifluoromethyl)-1H-pyrazol-4-yl]imidazole-2-carboxamide;

N-[3-chloro-4-[4-(piperidine-4-carbonyl)piperazine-1-carbonyl]phenyl]-1-methyl-5-[3-(trifluoromethyl)-1H-pyrazol-4-yl]imidazole-2-carboxamide;

N-[4-(3-aminopropylcarbamoyl)-3-chloro-phenyl]-1-methyl-5-[1-prop-2-ynyl-3-(trifluoromethyl)pyrazol-4-yl]imidazole-2-carboxamide;

5-[1-(4-aminobut-2-ynyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[4-[4-(3-aminocyclobutanecarbonyl)piperazine-1-carbonyl]-3-chloro-phenyl]-1-methyl-5-[1-(3-pyridylmethyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(4-hydroxybut-2-ynyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2,2-difluoroethyl)-3-(trifluoromethyl)pyrazol-4-yl]-1-methyl-imidazole-2-carboxamide;

N-(4-carbamoyl-3-chloro-phenyl)-1-methyl-5-[1-prop-2-ynyl-3-(trifluoromethyl)pyrazol-4-yl]imidazole-2-carboxamide;

N-[3-chloro-4-[4-[(2S,4R)-4-hydroxypyrrolidine-2-carbonyl]piperazin-1-yl]sulfonyl-phenyl]-1-methyl-5-[3-(trifluoromethyl)-1H-pyrazol-4-yl]imidazole-2-carboxamide;

N-[4-[4-[(2S)-2-aminopropanoyl]piperazine-1-carbonyl]-3-chloro-phenyl]-1-methyl-5-[1-(3-pyridylmethyl)-3-(trifluoromethyl)pyrazol-4-yl]imidazole-2-carboxamide;

5-[1-(cyanomethyl)-3-(trifluoromethyl)pyrazol-4-yl]-1-methyl-N-[3-methyl-4-[4-(piperidine-4-carbonyl)piperazine-1-carbonyl]phenyl]imidazole-2-carboxamide;

N-[3-chloro-4-[[(3S)-pyrrolidin-3-yl]methylcarbamoyl]phenyl]-1-methyl-5-[1-prop-2-ynyl-3-(trifluoromethyl)pyrazol-4-yl]imidazole-2-carboxamide;

N-[3-chloro-4-[[(3S,4R)-4-hydroxypyrrolidin-3-yl]methylcarbamoyl]phenyl]-1-methyl-5-[1-prop-2-ynyl-3-(trifluoromethyl)pyrazol-4-yl]imidazole-2-carboxamide;

N-[3-chloro-4-[4-[2-(dimethylamino)acetyl]piperazin-1-yl]sulfonyl-phenyl]-1-methyl-5-[3-(trifluoromethyl)-1H-pyrazol-4-yl]imidazole-2-carboxamide;

N-[3-chloro-4-[[(3R)-pyrrolidin-3-yl]methylcarbamoyl]phenyl]-1-methyl-5-[1-prop-2-ynyl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[2-(isopropylamino)-2-oxo-ethyl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2-cyanoethyl)-3-(trifluoromethyl)pyrazol-4-yl]-1-methyl-imidazole-2-carboxamide;

tert-butyl 4-[2-chloro-4-[[1-methyl-5-[1-prop-2-ynyl-3-(trifluoromethyl)pyrazol-4-yl]imidazole-2-carbonyl]amino]benzoyl]piperazine-1-carboxylate;

5-[1-(2-amino-1-methyl-2-oxo-ethyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-(1,1-dioxothietan-3-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(2-pyrazol-1-ylethyl)-3-(trifluoromethyl)pyrazol-4-yl]imidazole-2-carboxamide;

1-methyl-N-[3-methyl-4-[4-(piperidine-4-carbonyl)piperazine-1-carbonyl]phenyl]-5-[3-(trifluoromethyl)-1H-pyrazol-4-yl]imidazole-2-carboxamide;

N-[3-chloro-4-[4-(piperidine-4-carbonyl)piperazine-1-carbonyl]phenyl]-1-methyl-5-[1-[2-(methylamino)-2-oxo-ethyl]-3-(trifluoromethyl)pyrazol-4-yl]imidazole-2-carboxamide;

N-[3-chloro-4-[4-(4-hydroxypiperidine-4-carbonyl)piperazine-1-carbonyl]phenyl]-1-methyl-5-[1-methyl-3-(trifluoromethyl)pyrazol-4-yl]imidazole-2-carboxamide;

5-[1-(2-amino-2-oxo-ethyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[2-(dimethylamino)-2-oxo-ethyl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(1-cyclopropyl-2-oxo-pyrrolidin-3-yl)-3-(trifluoromethyl)pyrazol-4-yl]-1-methyl-imidazole-2-carboxamide;

N-[3-chloro-4-[4-[(2S,4R)-4-hydroxypyrrolidine-2-carbonyl]piperazine-1-carbonyl]phenyl]-1-methyl-5-[1-methyl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[2-(2-methoxyethoxy)ethyl]-3-(trifluoromethyl)pyrazol-4-yl]-1-methyl-imidazole-2-carboxamide;

N-[4-(6-aminohexylcarbamoyl)-3-methyl-phenyl]-1-methyl-5-[3-(trifluoromethyl)-1H-pyrazol-4-yl]imidazole-2-carboxamide;

N-[3-chloro-4-(piperazine-1-carbonyl)phenyl]-1-methyl-5-[3-(trifluoromethyl)-1H-pyrazol-4-yl]imidazole-2-carboxamide;

5-[1-(3-amino-3-oxo-propyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[4-[2-(2-aminoethoxy)ethylcarbamoyl]-3-ethyl-phenyl]-1-methyl-5-[1-methyl-3-(trifluoromethyl)pyrazol-4-yl]imidazole-2-carboxamide;

N-[4-[4-[(1S,3R)-3-aminocyclopentanecarbonyl]piperazine-1-carbonyl]-3-chloro-phenyl]-1-methyl-5-[1-(3-pyridylmethyl)-3-(trifluoromethyl)pyrazol-4-yl]imidazole-2-carboxamide;

N-[4-(5-aminopentylcarbamoyl)-3-methyl-phenyl]-1-methyl-5-[3-(trifluoromethyl)-1H-pyrazol-4-yl]imidazole-2-carboxamide;

N-[3-chloro-4-[4-[rac-(1S,5R)-3-azabicyclo[3.1.0]hexane-6-carbonyl]piperazine-1-carbonyl]phenyl]-1-methyl-5-[1-prop-2-ynyl-3-(trifluoromethyl)pyrazol-4-yl]imidazole-2-carboxamide;

N-(3-aminocyclobutyl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[4-[4-[(3R)-3-aminopyrrolidine-1-carbonyl]piperazine-1-carbonyl]-3-chloro-phenyl]-1-methyl-5-[1-prop-2-ynyl-3-(trifluoromethyl)pyrazol-4-yl]imidazole-2-carboxamide;

N-[(1S,2R)-2-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[3-chloro-4-[4-[(1S,4S)-2,5-diazabicyclo[2.2.1]heptane-2-carbonyl]piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-(1,6-diazaspiro[3.3]heptane-6-carbonyl)piperazine-1-carbonyl]phenyl]-1-methyl-5-[1-prop-2-ynyl-3-(trifluoromethyl)pyrazol-4-yl]imidazole-2-carboxamide;

N-[4-[4-[(3S)-3-aminopiperidine-1-carbonyl]piperazine-1-carbonyl]-3-chloro-phenyl]-1-methyl-5-[1-prop-2-ynyl-3-(trifluoromethyl)pyrazol-4-yl]imidazole-2-carboxamide;

N-[4-[(3-aminocyclobutyl)carbamoyl]-3-chloro-phenyl]-5-[1-(cyanomethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(cyclobutylmethyl)-3-(trifluoromethyl)pyrazol-4-yl]-1-methyl-imidazole-2-carboxamide;

N-[4-[4-(4-aminopiperidine-1-carbonyl)piperazine-1-carbonyl]-3-chloro-phenyl]-1-methyl-5-[1-prop-2-ynyl-3-(trifluoromethyl)pyrazol-4-yl]imidazole-2-carboxamide;

N-[3-chloro-4-[4-(3,6-diazabicyclo[3.2.0]heptane-3-carbonyl)piperazine-1-carbonyl]phenyl]-1-methyl-5-[1-prop-2-ynyl-3-(trifluoromethyl)pyrazol-4-yl]imidazole-2-carboxamide;

N-[4-[4-[(3S)-3-aminopyrrolidine-1-carbonyl]piperazine-1-carbonyl]-3-chloro-phenyl]-1-methyl-5-[1-prop-2-ynyl-3-(trifluoromethyl)pyrazol-4-yl]imidazole-2-carboxamide;

N-[4-[4-[(2S)-2-aminopropanoyl]piperazine-1-carbonyl]-3-chloro-phenyl]-5-[1-(cyanomethyl)-3-(trifluoromethyl)pyrazol-4-yl]-1-methyl-imidazole-2-carboxamide;

4-[2-chloro-4-[[1-methyl-5-[1-prop-2-ynyl-3-(trifluoromethyl)pyrazol-4-yl]imidazole-2-carbonyl]amino]benzoyl]-N-[rac-(1S,5R)-3-azabicyclo[3.1.0]hexan-6-yl]piperazine-1-carboxamide;

N-[4-[4-[(3aS,6aS)-2,3,3a,4,6,6a-hexahydro-1H-pyrrolo[3,4-c]pyrrole-5-carbonyl]piperazine-1-carbonyl]-3-chloro-phenyl]-1-methyl-5-[1-prop-2-ynyl-3-(trifluoromethyl)pyrazol-4-yl]imidazole-2-carboxamide;

N-[4-[4-(3-amino-3-methyl-azetidine-1-carbonyl)piperazine-1-carbonyl]-3-chloro-phenyl]-1-methyl-5-[1-prop-2-ynyl-3-(trifluoromethyl)pyrazol-4-yl]imidazole-2-carboxamide;

N-(2-azaspiro[3.3]heptan-6-yl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

4-[2-chloro-4-[[1-methyl-5-[1-prop-2-ynyl-3-(trifluoromethyl)pyrazol-4-yl]imidazole-2-carbonyl]amino]benzoyl]-N-[2-(methylamino)ethyl]piperazine-1-carboxamide;

N-[3-chloro-4-[4-(piperidine-4-carbonyl)piperazine-1-carbonyl]phenyl]-1-methyl-5-[1-spiro[2.3]hexan-5-yl-3-(trifluoromethyl)pyrazol-4-yl]imidazole-2-carboxamide;

N-[3-chloro-4-[4-(piperazine-1-carbonyl)piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[(2,2-difluorocyclopropyl)methyl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(cyclopropylmethyl)-3-(trifluoromethyl)pyrazol-4-yl]-1-methyl-imidazole-2-carboxamide;

N-[(1S,3S)-3-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

4-[4-[[5-[1-allyl-3-(trifluoromethyl)pyrazol-4-yl]-1-methyl-imidazole-2-carbonyl]amino]-2-chloro-benzoyl]-N-(azetidin-3-yl)piperazine-1-carboxamide;

5-[1-allyl-3-(trifluoromethyl)pyrazol-4-yl]-N-[4-[(3-aminocyclobutyl)carbamoyl]-3-chloro-phenyl]-1-methyl-imidazole-2-carboxamide;

N-[3-chloro-4-(piperazine-1-carbonyl)phenyl]-5-[1-(cyanomethyl)-3-(trifluoromethyl)pyrazol-4-yl]-1-methyl-imidazole-2-carboxamide;

N-(azetidin-3-yl)-4-[2-chloro-4-[[5-[1-cyclobutyl-3-(trifluoromethyl)pyrazol-4-yl]-1-methyl-imidazole-2-carbonyl]amino]benzoyl]piperazine-1-carboxamide;

N-[3-chloro-4-[4-(piperidine-4-carbonyl)piperazine-1-carbonyl]phenyl]-5-[1-ethyl-3-(trifluoromethyl)pyrazol-4-yl]-1-methyl-imidazole-2-carboxamide;

4-[2-chloro-4-[[5-[1-(2,2-difluoroethyl)-3-(trifluoromethyl)pyrazol-4-yl]-1-methyl-imidazole-2-carbonyl]amino]benzoyl]-N— [(3S)-pyrrolidin-3-yl]piperazine-1-carboxamide;

N-[3-chloro-4-[4-(piperidine-4-carbonyl)piperazine-1-carbonyl]phenyl]-5-[1-[(3,3-difluorocyclobutyl)methyl]-3-(trifluoromethyl)pyrazol-4-yl]-1-methyl-imidazole-2-carboxamide;

N-[4-[4-(3-aminocyclobutanecarbonyl)piperazine-1-carbonyl]-3-chloro-phenyl]-5-[1-(2-fluoroethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[3-(trifluoromethyl)-1-(3,3,3-trifluoropropyl)pyrazol-4-yl]imidazole-2-carboxamide;

N-[3-chloro-4-[4-(piperidine-4-carbonyl)piperazine-1-carbonyl]phenyl]-5-[1-(fluoromethyl)-3-(trifluoromethyl)pyrazol-4-yl]-1-methyl-imidazole-2-carboxamide;

N-[4-[(3-aminocyclobutyl)carbamoyl]-3-chloro-phenyl]-5-[1-(cyanomethyl)-3-(trifluoromethyl)pyrazol-4-yl]-1-methyl-imidazole-2-carboxamide;

N-[4-[[3-[[(2R)-2-aminopropanoyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

4-[2-chloro-4-[[5-[1-(cyanomethyl)-3-(trifluoromethyl)pyrazol-4-yl]-1-methyl-imidazole-2-carbonyl]amino]benzoyl]-N-[(3S)-pyrrolidin-3-yl]piperazine-1-carboxamide;

N-[3-chloro-4-[4-(piperidine-4-carbonyl)piperazine-1-carbonyl]phenyl]-5-[1-(1-cyanoethyl)-3-(trifluoromethyl)pyrazol-4-yl]-1-methyl-imidazole-2-carboxamide;

N-(azetidin-3-yl)-4-[2-chloro-4-[[5-[1-(2,2-difluoroethyl)-3-(trifluoromethyl)pyrazol-4-yl]-1-methyl-imidazole-2-carbonyl]amino]benzoyl]piperazine-1-carboxamide;

N-[3-chloro-4-[4-(piperidine-4-carbonyl)piperazine-1-carbonyl]phenyl]-1-methyl-5-[1-[(3-methylthietan-3-yl)methyl]-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-isopropyl-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[2-(difluoromethoxy)ethyl]-3-(trifluoromethyl)pyrazol-4-yl]-1-methyl-imidazole-2-carboxamide;

N-(azetidin-3-yl)-4-[2-chloro-4-[[5-[1-(cyanomethyl)-3-(trifluoromethyl)pyrazol-4-yl]-1-methyl-imidazole-2-carbonyl]amino]benzoyl]piperazine-1-carboxamide;

N-[4-[(3-aminocyclobutyl)carbamoyl]-3-chloro-phenyl]-5-[1-cyclobutyl-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(difluoromethyl)-3-(trifluoromethyl)pyrazol-4-yl]-1-methyl-imidazole-2-carboxamide;

N-[3-chloro-4-(piperazine-1-carbonyl)phenyl]-5-[1-(2-fluoroethyl)-3-(trifluoromethyl)pyrazol-4-yl]-1-methyl-imidazole-2-carboxamide;

N-[3-chloro-4-[4-[(3S)-pyrrolidine-3-carbonyl]piperazine-1-carbonyl]phenyl]-1-methyl-5-[1-(3-pyridylmethyl)-3-(trifluoromethyl)pyrazol-4-yl]imidazole-2-carboxamide;

N-[4-[[3-[[(1S,3R)-3-aminocyclopentanecarbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[4-[4-(aminomethyl)-4,5-dihydrooxazol-2-yl]piperazine-1-carbonyl]-3-chloro-phenyl]-1-methyl-5-[1-(2,2,2-trifluoroethyl)-3-(trifluoromethyl)pyrazol-4-yl]imidazole-2-carboxamide;

N-[3-chloro-4-[4-(3-hydroxypiperidine-3-carbonyl)piperazine-1-carbonyl]phenyl]-1-methyl-5-[1-(3-pyridylmethyl)-3-(trifluoromethyl)pyrazol-4-yl]imidazole-2-carboxamide;

N-(azetidin-3-yl)-4-[2-chloro-4-[[1-methyl-5-[1-(2,2,2-trifluoroethyl)-3-(trifluoromethyl)pyrazol-4-yl]imidazole-2-carbonyl]amino]benzoyl]piperazine-1-carboxamide;

N-[4-[(3-aminocyclobutyl)carbamoyl]-3-chloro-phenyl]-1-methyl-5-[1-prop-2-ynyl-3-(trifluoromethyl)pyrazol-4-yl]imidazole-2-carboxamide;

N-[4-[(3-aminocyclobutyl)carbamoyl]-3-chloro-phenyl]-5-[1-cyclopropyl-3-(trifluoromethyl)pyrazol-4-yl]-1-methyl-imidazole-2-carboxamide;

N-(azetidin-3-yl)-4-[2-chloro-4-[[5-[1-(2-fluoroethyl)-3-(trifluoromethyl)pyrazol-4-yl]-1-methyl-imidazole-2-carbonyl]amino]benzoyl]piperazine-1-carboxamide;

5-[1-[1-(chloromethyl)-2-hydroxy-ethyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(cyanomethyl)-3-(trifluoromethyl)pyrazol-4-yl]-N-[3-ethyl-4-[4-(1-methylpiperidine-4-carbonyl)piperazine-1-carbonyl]phenyl]-1-methyl-imidazole-2-carboxamide;

5-[1-[2-(chloromethyl)-3-hydroxy-2-methyl-propyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[4-[4-(4-amino-4-methyl-piperidine-1-carbonyl)piperazine-1-carbonyl]-3-ethyl-phenyl]-5-[1-(cyanomethyl)-3-(trifluoromethyl)pyrazol-4-yl]-1-methyl-imidazole-2-carboxamide;

5-[1-(2,2-difluoroethyl)-3-(trifluoromethyl)pyrazol-4-yl]-N-[3-ethyl-4-[4-[(3R)-pyrrolidine-3-carbonyl]piperazine-1-carbonyl]phenyl]-1-methyl-imidazole-2-carboxamide;

N-[4-[4-[(1S,3R)-3-aminocyclopentanecarbonyl]piperazine-1-carbonyl]-3-fluoro-5-methyl-phenyl]-5-[1-(cyanomethyl)-3-(trifluoromethyl)pyrazol-4-yl]-1-methyl-imidazole-2-carboxamide;

N-[4-[4-(3-aminopiperidine-1-carbonyl)piperazine-1-carbonyl]-3-ethyl-phenyl]-5-[1-(cyanomethyl)-3-(trifluoromethyl)pyrazol-4-yl]-1-methyl-imidazole-2-carboxamide;

5-[1-(cyanomethyl)-3-(trifluoromethyl)pyrazol-4-yl]-N-[3-ethyl-4-[4-[rac-(3S,4S)-3-amino-4-methyl-piperidine-1-carbonyl]piperazine-1-carbonyl]phenyl]-1-methyl-imidazole-2-carboxamide;

N-[3-chloro-4-[4-(piperidine-4-carbonyl)piperazine-1-carbonyl]phenyl]-1-methyl-5-[1-[(5-methyl-1,2,4-oxadiazol-3-yl)methyl]-3-(trifluoromethyl)pyrazol-4-yl]imidazole-2-carboxamide;

N-[4-[4-(6-amino-2-azaspiro[3.3]heptane-2-carbonyl)piperazine-1-carbonyl]-3-ethyl-phenyl]-5-[1-(cyanomethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-(3-phenyl-1H-pyrazol-4-yl)imidazole-2-carboxamide;

N-[4-[4-(3-aminocyclobutanecarbonyl)piperazine-1-carbonyl]-3-fluoro-5-methyl-phenyl]-5-[1-(cyanomethyl)-3-(trifluoromethyl)pyrazol-4-yl]-1-methyl-imidazole-2-carboxamide;

5-[1-(cyanomethyl)-3-(trifluoromethyl)pyrazol-4-yl]-N-[3-ethyl-4-[4-(3-methylpiperazine-1-carbonyl)piperazine-1-carbonyl]phenyl]-1-methyl-imidazole-2-carboxamide;

5-[1-(cyanomethyl)-3-(trifluoromethyl)pyrazol-4-yl]-N-[4-[4-(2,5-diazabicyclo[2.2.1]heptane-2-carbonyl)piperazine-1-carbonyl]-3-ethyl-phenyl]-1-methyl-imidazole-2-carboxamide;

N-[4-[4-[3-(aminomethyl)pyrrolidine-1-carbonyl]piperazine-1-carbonyl]-3-ethyl-phenyl]-5-[1-(cyanomethyl)-3-(trifluoromethyl)pyrazol-4-yl]-1-methyl-imidazole-2-carboxamide;

N-[4-[4-[4-(aminomethyl)-4,5-dihydrooxazol-2-yl]piperazine-1-carbonyl]-3-chloro-phenyl]-5-[1-(2-fluoroethyl)-3-(trifluoromethyl)pyrazol-4-yl]-1-methyl-imidazole-2-carboxamide;

5-[1-(cyanomethyl)-3-(trifluoromethyl)pyrazol-4-yl]-N-[3-ethyl-4-[4-[(3R)-pyrrolidine-3-carbonyl]piperazine-1-carbonyl]phenyl]-1-methyl-imidazole-2-carboxamide;

5-[1-(cyanomethyl)-3-(trifluoromethyl)pyrazol-4-yl]-N-[3-ethyl-4-[4-(4-hydroxypiperidine-4-carbonyl)piperazine-1-carbonyl]phenyl]-1-methyl-imidazole-2-carboxamide;

5-[1-(2,2-difluoroethyl)-3-(trifluoromethyl)pyrazol-4-yl]-N-[3-ethyl-4-[4-(piperidine-4-carbonyl)piperazine-1-carbonyl]phenyl]-1-methyl-imidazole-2-carboxamide;

N-[4-[4-[(2S)-2-aminopropanoyl]piperazine-1-carbonyl]-3-fluoro-5-methyl-phenyl]-5-[1-(cyanomethyl)-3-(trifluoromethyl)pyrazol-4-yl]-1-methyl-imidazole-2-carboxamide;

5-[1-(cyanomethyl)-3-(trifluoromethyl)pyrazol-4-yl]-N-[3-fluoro-5-methyl-4-[4-[(3S)-pyrrolidine-3-carbonyl]piperazine-1-carbonyl]phenyl]-1-methyl-imidazole-2-carboxamide;

N-[4-[4-(azetidine-3-carbonyl)piperazine-1-carbonyl]-3-ethyl-phenyl]-5-[1-(2,2-difluoroethyl)-3-(trifluoromethyl)pyrazol-4-yl]-1-methyl-imidazole-2-carboxamide;

4-[4-[[5-[1-(2,2-difluoroethyl)-3-(trifluoromethyl)pyrazol-4-yl]-1-methyl-imidazole-2-carbonyl]amino]-2-ethyl-benzoyl]-N-[(3-hydroxyazetidin-3-yl)methyl]piperazine-1-carboxamide;

N-[3-chloro-4-[4-(piperidine-4-carbonyl)piperazine-1-carbonyl]phenyl]-5-[1-(3-hydroxy-3-methyl-butyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(1H-pyrazol-5-ylmethyl)-3-(trifluoromethyl)pyrazol-4-yl]imidazole-2-carboxamide;

5-[1-(cyanomethyl)-3-(trifluoromethyl)pyrazol-4-yl]-N-[3-ethyl-4-[4-(piperidine-4-carbonyl)piperazine-1-carbonyl]phenyl]-1-methyl-imidazole-2-carboxamide;

N-(3-azabicyclo[3.1.0]hexan-6-yl)-4-[4-[[5-[1-(cyanomethyl)-3-(trifluoromethyl)pyrazol-4-yl]-1-methyl-imidazole-2-carbonyl]amino]-2-ethyl-benzoyl]piperazine-1-carboxamide;

5-[1-(2,2-difluoroethyl)-3-(trifluoromethyl)pyrazol-4-yl]-N-[3-ethyl-4-[4-(4-hydroxypiperidine-4-carbonyl)piperazine-1-carbonyl]phenyl]-1-methyl-imidazole-2-carboxamide;

N-[3-ethyl-4-[4-(piperidine-4-carbonyl)piperazine-1-carbonyl]phenyl]-1-methyl-5-[1-(3-pyridylmethyl)-3-(trifluoromethyl)pyrazol-4-yl]imidazole-2-carboxamide;

N-[4-[4-[2-(aminomethyl)pyrrolidine-1-carbonyl]piperazine-1-carbonyl]-3-ethyl-phenyl]-5-[1-(cyanomethyl)-3-(trifluoromethyl)pyrazol-4-yl]-1-methyl-imidazole-2-carboxamide;

4-[4-[[5-[1-(cyanomethyl)-3-(trifluoromethyl)pyrazol-4-yl]-1-methyl-imidazole-2-carbonyl]amino]-2-ethyl-benzoyl]-N-[(3-hydroxyazetidin-3-yl)methyl]piperazine-1-carboxamide;

5-[1-(2,2-difluoroethyl)-3-(trifluoromethyl)pyrazol-4-yl]-N-[3-ethyl-4-[4-(1-methylpiperidine-4-carbonyl)piperazine-1-carbonyl]phenyl]-1-methyl-imidazole-2-carboxamide;

N-[3-ethyl-4-[4-(1-methylpiperidine-4-carbonyl)piperazine-1-carbonyl]phenyl]-1-methyl-5-[1-(3-pyridylmethyl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-methyl-3-(trifluoromethyl)pyrazol-4-yl]imidazole-2-carboxamide;

N-[3-ethyl-4-[4-[(3R)-pyrrolidine-3-carbonyl]piperazine-1-carbonyl]phenyl]-1-methyl-5-[1-(3-pyridylmethyl)-3-(trifluoromethyl)pyrazol-4-yl]imidazole-2-carboxamide;

N-[3-chloro-4-(piperazine-1-carbonyl)phenyl]-1-methyl-5-[1-(3-pyridylmethyl)-3-(trifluoromethyl)pyrazol-4-yl]imidazole-2-carboxamide;

4-[2-ethyl-4-[[1-methyl-5-[1-(3-pyridylmethyl)-3-(trifluoromethyl)pyrazol-4-yl]imidazole-2-carbonyl]amino]benzoyl]-N-[(3-hydroxyazetidin-3-yl)methyl]piperazine-1-carboxamide;

N-[3-ethyl-4-[4-(4-hydroxypiperidine-4-carbonyl)piperazine-1-carbonyl]phenyl]-1-methyl-5-[1-(3-pyridylmethyl)-3-(trifluoromethyl)pyrazol-4-yl]imidazole-2-carboxamide;

5-[1-[[3-chloro-1-(hydroxymethyl)-3-methyl-cyclobutyl]methyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[4-[4-(azetidine-3-carbonyl)piperazine-1-carbonyl]-3-ethyl-phenyl]-5-[1-(cyanomethyl)-3-(trifluoromethyl)pyrazol-4-yl]-1-methyl-imidazole-2-carboxamide;

N-[4-[(3-aminocyclobutyl)carbamoyl]-3-chloro-phenyl]-1-methyl-5-[1-[(2-methylthiazol-4-yl)methyl]-3-(trifluoromethyl)pyrazol-4-yl]imidazole-2-carboxamide;

5-[1-(cyanomethyl)-3-(trifluoromethyl)pyrazol-4-yl]-N-[3-fluoro-4-[4-(3-hydroxypiperidine-3-carbonyl)piperazine-1-carbonyl]-5-methyl-phenyl]-1-methyl-imidazole-2-carboxamide;

N-[3-chloro-4-[4-(3-hydroxypiperidine-3-carbonyl)piperazine-1-carbonyl]phenyl]-5-[1-(cyanomethyl)-3-(trifluoromethyl)pyrazol-4-yl]-1-methyl-imidazole-2-carboxamide;

N-[4-[4-(3-aminocyclobutanecarbonyl)piperazine-1-carbonyl]-3-chloro-phenyl]-5-[1-(cyanomethyl)-3-(trifluoromethyl)pyrazol-4-yl]-1-methyl-imidazole-2-carboxamide;

N-[4-[(4-aminocyclohexyl)carbamoyl]-3-chloro-phenyl]-1-methyl-5-[3-(trifluoromethyl)-1H-pyrazol-4-yl]imidazole-2-carboxamide;

(1R,5S)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

N-[4-[(1-aminocyclopropyl)methylcarbamoyl]-3-chloro-phenyl]-5-[1-(2,2-difluorocyclopropyl)-3-(trifluoromethyl)pyrazol-4-yl]-1-methyl-imidazole-2-carboxamide;

(1R,5S)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide;
(1R,5S)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;
rac-(1R,5S)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-rac-(3S,4S)-4-hydroxypyrrolidin-3-yl]-3-azabicyclo[3.1.0]hexane-3-carboxamide;
rac-(1S,5R)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;
N-[3-chloro-4-[[rac-(1S,5R)-3-(piperazine-1-carbonyl)-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;
N-[3-chloro-4-[[rac-(1S,5R)-3-(piperidine-4-carbonyl)-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;
N-[4-(5-aminopentylcarbamoyl)-3-chloro-phenyl]-5-[1-(2-fluoroallyl)-3-(trifluoromethyl)pyrazol-4-yl]-1-methyl-imidazole-2-carboxamide;
rac-(1S,5R)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(1R,2S)-2-aminocyclopentyl]-3-azabicyclo[3.1.0]hexane-3-carboxamide;
N-[4-(6-aminohexylcarbamoyl)-3-chloro-phenyl]-5-[1-cyclopropyl-3-(trifluoromethyl)pyrazol-4-yl]-1-methyl-imidazole-2-carboxamide;
N-(3-chloro-4-piperazin-1-ylsulfonyl-phenyl)-5-[1-(2,2-difluoroethyl)-3-(trifluoromethyl)pyrazol-4-yl]-1-methyl-imidazole-2-carboxamide;
rac-(1S,5R)-6-[[2-chloro-4-[[5-[1-(2-fluoroallyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;
rac-(1R,5S)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;
rac-(1S,5R)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3S)-pyrrolidin-3-yl]-3-azabicyclo[3.1.0]hexane-3-carboxamide;
(1R,5S)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide;
N-[4-[4-aminobutyl(methyl)carbamoyl]-3-chloro-phenyl]-5-[1-cyclopropyl-3-(trifluoromethyl)pyrazol-4-yl]-1-methyl-imidazole-2-carboxamide;
N-[4-[4-(2-aminoethyl)piperidine-1-carbonyl]-3-chloro-phenyl]-5-[1-cyclopropyl-3-(trifluoromethyl)pyrazol-4-yl]-1-methyl-imidazole-2-carboxamide;
N-[3-chloro-4-[[rac-(1S,5R)-3-[rac-(3R)-3-aminopyrrolidine-1-carbonyl]-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;
N-[4-[(6-aminospiro[3.3]heptan-2-yl)carbamoyl]-3-chloro-phenyl]-5-[1-(2,2-difluorocyclopropyl)-3-(trifluoromethyl)pyrazol-4-yl]-1-methyl-imidazole-2-carboxamide;
N-[3-chloro-4-[4-fluoro-4-[[[rac-(3S,4S)-4-hydroxypyrrolidin-3-yl]carbamoylamino]methyl]piperidine-1-carbonyl]phenyl]-5-[1-(2,2-difluorocyclopropyl)-3-(trifluoromethyl)pyrazol-4-yl]-1-methyl-imidazole-2-carboxamide;
5-[1-(cyclopropylmethyl)-3-(trifluoromethyl)pyrazol-4-yl]-N-[3-fluoro-4-[4-[rac-(1R,5S)-3-azabicyclo[3.1.0]hexane-6-carbonyl]piperazine-1-carbonyl]phenyl]-1-methyl-imidazole-2-carboxamide;
N-[4-[(3R)-3-(aminomethyl)pyrrolidine-1-carbonyl]-3-chloro-phenyl]-5-[1-cyclopropyl-3-(trifluoromethyl)pyrazol-4-yl]-1-methyl-imidazole-2-carboxamide;
N-[4-(1,2,3,3a,4,5,6,6a-octahydrocyclopenta[c]pyrrol-5-ylmethylcarbamoyl)-3-chloro-phenyl]-5-[1-(2,2-difluorocyclopropyl)-3-(trifluoromethyl)pyrazol-4-yl]-1-methyl-imidazole-2-carboxamide;
N-[4-[4-(azetidin-3-yl)piperidine-1-carbonyl]-3-chloro-phenyl]-5-[1-cyclopropyl-3-(trifluoromethyl)pyrazol-4-yl]-1-methyl-imidazole-2-carboxamide;
N-(azetidin-3-yl)-4-[2-chloro-4-[[1-methyl-5-[3-(trifluoromethyl)-1-vinyl-pyrazol-4-yl]imidazole-2-carbonyl]amino]benzoyl]piperazine-1-carboxamide;
N-[3-chloro-4-[4-[(2R,4S)-4-hydroxypyrrolidine-2-carbonyl]piperazin-1-yl]sulfonyl-phenyl]-5-[1-(2,2-difluoroethyl)-3-(trifluoromethyl)pyrazol-4-yl]-1-methyl-imidazole-2-carboxamide;
N-[4-(4-aminobutylcarbamoyl)-3-chloro-phenyl]-1-methyl-5-[1-(2-methylallyl)-3-(trifluoromethyl)pyrazol-4-yl]imidazole-2-carboxamide;
N-[4-[4-(2-aminoacetyl)piperazine-1-carbonyl]-3-chloro-phenyl]-5-[1-cyclopropyl-3-(trifluoromethyl)pyrazol-4-yl]-1-methyl-imidazole-2-carboxamide;
N-[4-[4-(aminomethyl)-4-fluoro-piperidine-1-carbonyl]-3-chloro-phenyl]-5-[1-(2,2-difluorocyclopropyl)-3-(trifluoromethyl)pyrazol-4-yl]-1-methyl-imidazole-2-carboxamide;
N-[4-[4-(2-aminoacetyl)piperazine-1-carbonyl]-3-chloro-phenyl]-5-[1-(cyclobutylmethyl)-3-(trifluoromethyl)pyrazol-4-yl]-1-methyl-imidazole-2-carboxamide;
N-[3-chloro-4-[[rac-(1S,5R)-3-(piperidine-4-carbonyl)-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;
N-(3-aminocyclobutyl)-4-[2-chloro-4-[[5-[1-(cyclopropylmethyl)-3-(trifluoromethyl)pyrazol-4-yl]-1-methyl-imidazole-2-carbonyl]amino]benzoyl]piperazine-1-carboxamide;
5-[1-(2,2-difluorocyclopropyl)-3-(trifluoromethyl)pyrazol-4-yl]-1-methyl-N-[4-(2-oxopyrrolidin-1-yl)phenyl]imidazole-2-carboxamide;
N-[4-(5-aminopentylcarbamoyl)-3-chloro-phenyl]-1-methyl-5-[1-(2-methylallyl)-3-(trifluoromethyl)pyrazol-4-yl]imidazole-2-carboxamide;
N-[4-[4-[(1R,3R)-3-aminocyclopentanecarbonyl]piperazine-1-carbonyl]-3-chloro-phenyl]-5-[1-(cyclopropylmethyl)-3-(trifluoromethyl)pyrazol-4-yl]-1-methyl-imidazole-2-carboxamide;
N-[4-[4-(aminomethyl)piperidine-1-carbonyl]-3-chloro-phenyl]-5-[1-cyclopropyl-3-(trifluoromethyl)pyrazol-4-yl]-1-methyl-imidazole-2-carboxamide;

N-[4-[4-(azetidine-3-carbonyl)piperazine-1-carbonyl]-3-chloro-phenyl]-5-[1-(cyclopropylmethyl)-3-(trifluoromethyl)pyrazol-4-yl]-1-methyl-imidazole-2-carboxamide;

N-(3-aminocyclobutyl)-6-[[2-chloro-4-[[5-[1-(2,2-difluoroethyl)-3-(trifluoromethyl)pyrazol-4-yl]-1-methyl-imidazole-2-carbonyl]amino]benzoyl]amino]-3-azabicyclo[3.1.0]hexane-3-carboxamide;

N-[4-[4-(2-aminoacetyl)piperazine-1-carbonyl]-3-chloro-phenyl]-5-[1-(cyclopropylmethyl)-3-(trifluoromethyl)pyrazol-4-yl]-1-methyl-imidazole-2-carboxamide;

N-(3-aminocyclobutyl)-4-[2-chloro-4-[[1-methyl-5-[1-spiro[2.3]hexan-5-yl-3-(trifluoromethyl)pyrazol-4-yl]imidazole-2-carbonyl]amino]benzoyl]piperazine-1-carboxamide;

N-[4-[4-[(1S,3R)-3-aminocyclopentanecarbonyl]piperazin-1-yl]sulfonyl-3-chloro-phenyl]-5-[1-(2,2-difluoroethyl)-3-(trifluoromethyl)pyrazol-4-yl]-1-methyl-imidazole-2-carboxamide;

N-[3-chloro-4-[[3-(piperidine-4-carbonyl)-3-azabicyclo[3.1.0]hexan-6-yl]carbamoyl]phenyl]-5-[1-cyclobutyl-3-(trifluoromethyl)pyrazol-4-yl]-1-methyl-imidazole-2-carboxamide;

N-[4-[2-(2-amino-2-methyl-propoxy)ethylcarbamoyl]-3-ethyl-phenyl]-5-[1-(cyanomethyl)-3-(trifluoromethyl)pyrazol-4-yl]-1-methyl-imidazole-2-carboxamide;

N-[3-chloro-4-[4-[rac-(1S,5R)-3-azabicyclo[3.1.0]hexane-6-carbonyl]piperazine-1-carbonyl]phenyl]-5-[1-cyclopropyl-3-(trifluoromethyl)pyrazol-4-yl]-1-methyl-imidazole-2-carboxamide;

N-[4-(6-amino-3-azabicyclo[3.1.0]hexane-3-carbonyl)-3-chloro-phenyl]-5-[1-(2,2-difluorocyclopropyl)-3-(trifluoromethyl)pyrazol-4-yl]-1-methyl-imidazole-2-carboxamide;

5-[1-(2,2-difluoroethyl)-3-(trifluoromethyl)pyrazol-4-yl]-N-[3-fluoro-4-[4-[rac-(1R,5S)-3-azabicyclo[3.1.0]hexane-6-carbonyl]piperazine-1-carbonyl]phenyl]-1-methyl-imidazole-2-carboxamide;

N-(azetidin-3-ylmethyl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

5-[1-allyl-3-(trifluoromethyl)pyrazol-4-yl]-N-[3-chloro-4-[[3-(piperidine-4-carbonyl)-3-azabicyclo[3.1.0]hexan-6-yl]carbamoyl]phenyl]-1-methyl-imidazole-2-carboxamide;

N-[4-[4-(3-aminoazetidine-1-carbonyl)piperazine-1-carbonyl]-3-chloro-phenyl]-5-[1-cyclopropyl-3-(trifluoromethyl)pyrazol-4-yl]-1-methyl-imidazole-2-carboxamide;

N-[4-[(3S)-3-(aminomethyl)pyrrolidine-1-carbonyl]-3-chloro-phenyl]-5-[1-cyclopropyl-3-(trifluoromethyl)pyrazol-4-yl]-1-methyl-imidazole-2-carboxamide;

N-(3-aminocyclobutyl)-4-[4-[[5-[1-(cyclopropylmethyl)-3-(trifluoromethyl)pyrazol-4-yl]-1-methyl-imidazole-2-carbonyl]amino]-2-fluoro-benzoyl]piperazine-1-carboxamide;

tert-butyl 2-[5-[[4-[[5-[1-(2,2-difluoroethyl)-3-(trifluoromethyl)pyrazol-4-yl]-1-methyl-imidazole-2-carbonyl]amino]-2-ethyl-benzoyl]amino]pentylamino]acetate;

N-[3-chloro-4-[[3-(piperidine-4-carbonyl)-3-azabicyclo[3.1.0]hexan-6-yl]carbamoyl]phenyl]-5-[1-[(2,2-difluorocyclopropyl)methyl]-3-(trifluoromethyl)pyrazol-4-yl]-1-methyl-imidazole-2-carboxamide;

N-(3-aminocyclobutyl)-4-[2-chloro-4-[[5-[1-(cyclopropylmethyl)-3-(trifluoromethyl)pyrazol-4-yl]-1-methyl-imidazole-2-carbonyl]amino]benzoyl]piperazine-1-carboxamide;

N-[4-(5-aminopentylcarbamoyl)-3-chloro-phenyl]-5-[1-cyclopropyl-3-(trifluoromethyl)pyrazol-4-yl]-1-methyl-imidazole-2-carboxamide;

N-[4-[2-(2-amino-2-methyl-propoxy)ethylcarbamoyl]-3-ethyl-phenyl]-1-methyl-5-[1-prop-2-ynyl-3-(trifluoromethyl)pyrazol-4-yl]imidazole-2-carboxamide;

N-[3-chloro-4-[[3-(piperidine-4-carbonyl)-3-azabicyclo[3.1.0]hexan-6-yl]carbamoyl]phenyl]-5-[1-(cyclobutylmethyl)-3-(trifluoromethyl)pyrazol-4-yl]-1-methyl-imidazole-2-carboxamide;

N-[3-chloro-4-[4-[(3R)-piperidine-3-carbonyl]piperazine-1-carbonyl]phenyl]-5-[1-cyclopropyl-3-(trifluoromethyl)pyrazol-4-yl]-1-methyl-imidazole-2-carboxamide;

N-[4-[4-(azetidine-3-carbonyl)piperazine-1-carbonyl]-3-chloro-phenyl]-5-[1-cyclopropyl-3-(trifluoromethyl)pyrazol-4-yl]-1-methyl-imidazole-2-carboxamide;

N-(3-aminocyclobutyl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

3-[[[2-chloro-4-[[5-[1-(2,2-difluorocyclopropyl)-3-(trifluoromethyl)pyrazol-4-yl]-1-methyl-imidazole-2-carbonyl]amino]benzoyl]amino]methyl]-N-[rac-(3S,4S)-4-hydroxypyrrolidin-3-yl]piperidine-1-carboxamide;

N-[3-chloro-4-[[3-(piperidine-4-carbonyl)-3-azabicyclo[3.1.0]hexan-6-yl]carbamoyl]phenyl]-5-[1-(cyclopropylmethyl)-3-(trifluoromethyl)pyrazol-4-yl]-1-methyl-imidazole-2-carboxamide;

N-[4-[4-(2-aminoethyl)piperazine-1-carbonyl]-3-chloro-phenyl]-5-[1-cyclopropyl-3-(trifluoromethyl)pyrazol-4-yl]-1-methyl-imidazole-2-carboxamide;

N-[3-chloro-4-[4-[(3R)-pyrrolidine-3-carbonyl]piperazine-1-carbonyl]phenyl]-5-[1-cyclopropyl-3-(trifluoromethyl)pyrazol-4-yl]-1-methyl-imidazole-2-carboxamide;

N-[4-[4-[(1R,3R)-3-aminocyclopentanecarbonyl]piperazine-1-carbonyl]-3-chloro-phenyl]-5-[1-cyclopropyl-3-(trifluoromethyl)pyrazol-4-yl]-1-methyl-imidazole-2-carboxamide;

N-[4-[4-(4-aminocyclohexanecarbonyl)piperazine-1-carbonyl]-3-chloro-phenyl]-5-[1-cyclopropyl-3-(trifluoromethyl)pyrazol-4-yl]-1-methyl-imidazole-2-carboxamide;

N-[(1R,3R)-3-aminocyclopentyl]-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

N-(azetidin-3-yl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

N-[4-[(3-aminocyclobutyl)carbamoyl]-3-chloro-phenyl]-1-methyl-5-[1-(2-methylallyl)-3-(trifluoromethyl)pyrazol-4-yl]imidazole-2-carboxamide;

N-[3-chloro-4-[[3-(piperidine-4-carbonyl)-3-azabicyclo[3.1.0]hexan-6-yl]carbamoyl]phenyl]-5-[1-(2,2-difluoroethyl)-3-(trifluoromethyl)pyrazol-4-yl]-1-methyl-imidazole-2-carboxamide;

4-[2-chloro-4-[[5-[1-cyclopropyl-3-(trifluoromethyl)pyrazol-4-yl]-1-methyl-imidazole-2-carbonyl]amino]benzoyl]-N-pyrrolidin-3-yl-piperazine-1-carboxamide;

N-(3-aminocyclobutyl)-4-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]piperidine-1-carboxamide;

N-(3-amino-3-methyl-cyclobutyl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

N-[4-[4-(2-aminoethyl)piperidine-1-carbonyl]-3-chloro-phenyl]-5-[1-ethyl-3-(trifluoromethyl)pyrazol-4-yl]-1-methyl-imidazole-2-carboxamide;

N-(3-aminocyclobutyl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

5-[1-benzyl-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[4-[2-(2-aminoethoxy)ethylcarbamoyl]-3-ethyl-phenyl]-1-methyl-5-[1-prop-2-ynyl-3-(trifluoromethyl)pyrazol-4-yl]imidazole-2-carboxamide;

N-[4-[4-[(1R,2S)-2-aminocyclopentanecarbonyl]piperazine-1-carbonyl]-3-chloro-phenyl]-5-[1-cyclopropyl-3-(trifluoromethyl)pyrazol-4-yl]-1-methyl-imidazole-2-carboxamide;

5-[1-(2,2-difluoroethyl)-3-(trifluoromethyl)pyrazol-4-yl]-1-methyl-N-(4-piperazin-1-yl sulfonylphenyl)imidazole-2-carboxamide;

N-[3-chloro-4-[[3-(piperidine-4-carbonyl)-3-azabicyclo[3.1.0]hexan-6-yl]carbamoyl]phenyl]-1-methyl-5-[1-prop-2-ynyl-3-(trifluoromethyl)pyrazol-4-yl]imidazole-2-carboxamide;

N-[3-chloro-4-[4-[2-[(3R)-pyrrolidin-3-yl]acetyl]piperazine-1-carbonyl]phenyl]-5-[1-cyclopropyl-3-(trifluoromethyl)pyrazol-4-yl]-1-methyl-imidazole-2-carboxamide;

N-[4-(5-aminopentylcarbamoyl)-3-chloro-phenyl]-5-[1-(2,2-difluorocyclopropyl)-3-(trifluoromethyl)pyrazol-4-yl]-1-methyl-imidazole-2-carboxamide;

rac-(1R,5S)—N-[1-(aminomethyl)-2-chloro-ethyl]-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-3-azabicyclo[3.1.0]hexane-3-carboxamide;

N-[3-chloro-4-(3,9-diazaspiro[5.5]undecane-3-carbonyl)phenyl]-5-[1-cyclopropyl-3-(trifluoromethyl)pyrazol-4-yl]-1-methyl-imidazole-2-carboxamide;

N-[3-chloro-4-[4-[(2R)-pyrrolidine-2-carbonyl]piperazine-1-carbonyl]phenyl]-5-[1-cyclopropyl-3-(trifluoromethyl)pyrazol-4-yl]-1-methyl-imidazole-2-carboxamide;

N-(azetidin-3-yl)-4-[2-chloro-4-[[5-[1-(2-chloroethyl)-3-(trifluoromethyl)pyrazol-4-yl]-1-methyl-imidazole-2-carbonyl]amino]benzoyl]piperazine-1-carboxamide;

N-[4-[4-(3-aminopropanoyl)piperazine-1-carbonyl]-3-chloro-phenyl]-5-[1-cyclopropyl-3-(trifluoromethyl)pyrazol-4-yl]-1-methyl-imidazole-2-carboxamide;

N-[3-chloro-4-[[3-[[(3R)-pyrrolidine-3-carbonyl]amino]cyclobutyl]carbamoyl]phenyl]-5-[1-(cyanomethyl)-3-(trifluoromethyl)pyrazol-4-yl]-1-methyl-imidazole-2-carboxamide;

N-(3-aminocyclobutyl)-4-[2-chloro-4-[[5-[1-[(2,2-difluorocyclopropyl)methyl]-3-(trifluoromethyl)pyrazol-4-yl]-1-methyl-imidazole-2-carbonyl]amino]benzoyl]piperazine-1-carboxamide;

N-[4-(3-aminopropylcarbamoyl)-3-chloro-phenyl]-1-methyl-5-[1-(2-methylallyl)-3-(trifluoromethyl)pyrazol-4-yl]imidazole-2-carboxamide;

4-[2-chloro-4-[[5-[1-cyclopropyl-3-(trifluoromethyl)pyrazol-4-yl]-1-methyl-imidazole-2-carbonyl]amino]benzoyl]-N-[3-(methylamino)cyclobutyl]piperazine-1-carboxamide;

N-[3-chloro-4-[4-[rac-(1S,5R)-3-azabicyclo[3.1.0]hexane-6-carbonyl]piperazine-1-carbonyl]phenyl]-1-methyl-5-[1-(2-methylallyl)-3-(trifluoromethyl)pyrazol-4-yl]imidazole-2-carboxamide;

N-[3-chloro-4-[4-[(2S)-2-methylpyrrolidine-2-carbonyl]piperazine-1-carbonyl]phenyl]-5-[1-cyclopropyl-3-(trifluoromethyl)pyrazol-4-yl]-1-methyl-imidazole-2-carboxamide;

N-[3-chloro-4-[[rac-(1S,5R)-3-(piperidine-4-carbonyl)-3-azabicyclo[3.1.0]hexan-6-yl]carbamoyl]phenyl]-5-[1-(3-fluorocyclobut-2-en-1-yl)-3-(trifluoromethyl)pyrazol-4-yl]-1-methyl-imidazole-2-carboxamide;

N-(3-aminocyclobutyl)-4-[2-chloro-4-[[5-[1-(cyclobutylmethyl)-3-(trifluoromethyl)pyrazol-4-yl]-1-methyl-imidazole-2-carbonyl]amino]benzoyl]piperazine-1-carboxamide;

N-[3-fluoro-4-[4-(piperidine-4-carbonyl)piperazine-1-carbonyl]phenyl]-1-methyl-5-[1-prop-2-ynyl-3-(trifluoromethyl)pyrazol-4-yl]imidazole-2-carboxamide;

N-[4-[6-[(3-aminocyclobutyl)carbamoylamino]hexyl carbamoyl]-3-chloro-phenyl]-5-[1-cyclopropyl-3-(trifluoromethyl)pyrazol-4-yl]-1-methyl-imidazole-2-carboxamide;

N-[3-bromo-4-[4-[rac-(1S,5R)-3-azabicyclo[3.1.0]hexane-6-carbonyl]piperazine-1-carbonyl]phenyl]-5-[1-ethyl-3-(trifluoromethyl)pyrazol-4-yl]-1-methyl-imidazole-2-carboxamide;

N-[3-chloro-4-[[rac-(1S,5R)-3-[4-(3-aminopropyl)piperazine-1-carbonyl]-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;

rac-(1R,5S)—N-(3-aminocyclobutyl)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-3-azabicyclo[3.1.0]hexane-3-carboxamide;

rac-(1S,5R)-6-[[2-chloro-4-[[5-[1-(cyanomethyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;

N-[(1R,3S)-3-amino-2,2-dimethyl-cyclobutyl]-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

N-[3-chloro-4-[4-(piperidine-4-carbonyl)piperazine-1-carbonyl]phenyl]-5-[1-(2,2-difluorocyclopropyl)-3-(trifluoromethyl)pyrazol-4-yl]-1-methyl-imidazole-2-carboxamide;

N-[3-chloro-4-(3,8-diazabicyclo[3.2.1]octane-8-carbonyl)phenyl]-5-[1-(2,2-difluorocyclopropyl)-3-(trifluoromethyl)pyrazol-4-yl]-1-methyl-imidazole-2-carboxamide;

N-[4-[[3-[(3-aminocyclobutanecarbonyl)amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[4-[4-(3-amino-2-hydroxy-propanoyl)piperazine-1-carbonyl]-3-chloro-phenyl]-5-[1-cyclopropyl-3-(trifluoromethyl)pyrazol-4-yl]-1-methyl-imidazole-2-carboxamide;

N-[3-chloro-4-[rac-(3aR,6aS)-2,3,3a,4,6,6a-hexahydro-1H-pyrrolo[3,4-c]pyrrole-5-carbonyl]phenyl]-5-[1-(2,2-difluorocyclopropyl)-3-(trifluoromethyl)pyrazol-4-yl]-1-methyl-imidazole-2-carboxamide;

N-(3-aminocyclobutyl)-4-[4-[[5-[1-(2,2-difluoroethyl)-3-(trifluoromethyl)pyrazol-4-yl]-1-methyl-imidazole-2-carbonyl]amino]-2-fluoro-benzoyl]piperazine-1-carboxamide;

N-[3-chloro-4-[4-[(2R)-piperidine-2-carbonyl]piperazine-1-carbonyl]phenyl]-5-[1-cyclopropyl-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-cyclopentyl-3-(trifluoromethyl)pyrazol-4-yl]-1-methyl-imidazole-2-carboxamide;

N-[4-[[3-[[(1R,3S)-3-aminocyclopentyl]carbamoylamino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[4-[4-(3-aminocyclobutanecarbonyl)piperazine-1-carbonyl]-3-chloro-phenyl]-5-[1-(cyclobutylmethyl)-3-(trifluoromethyl)pyrazol-4-yl]-1-methyl-imidazole-2-carboxamide;

N-[4-[3-(aminomethyl)piperidine-1-carbonyl]-3-chloro-phenyl]-5-[1-cyclopropyl-3-(trifluoromethyl)pyrazol-4-yl]-1-methyl-imidazole-2-carboxamide;

N-[4-[4-[(2S)-2-aminopropanoyl]piperazine-1-carbonyl]-3-chloro-phenyl]-5-[1-(cyclobutylmethyl)-3-(trifluoromethyl)pyrazol-4-yl]-1-methyl-imidazole-2-carboxamide;

4-[4-[[5-[1-(2,2-difluoroethyl)-3-(trifluoromethyl)pyrazol-4-yl]-1-methyl-imidazole-2-carbonyl]amino]phenyl]sulfonyl-N-[rac-(3R,4R)-4-hydroxypyrrolidin-3-yl]piperazine-1-carboxamide;

N-[3-chloro-4-[[rac-(3S,4S)-4-methoxypyrrolidin-3-yl]carbamoyl]phenyl]-5-[1-(2,2-difluorocyclopropyl)-3-(trifluoromethyl)pyrazol-4-yl]-1-methyl-imidazole-2-carboxamide;

N-(3-aminocyclobutyl)-4-[2-chloro-4-[[5-[1-ethyl-3-(trifluoromethyl)pyrazol-4-yl]-1-methyl-imidazole-2-carbonyl]amino]benzoyl]piperazine-1-carboxamide;

N-[4-[4-(azetidine-2-carbonyl)piperazine-1-carbonyl]-3-chloro-phenyl]-5-[1-(cyclobutylmethyl)-3-(trifluoromethyl)pyrazol-4-yl]-1-methyl-imidazole-2-carboxamide;

N-[4-[4-(2-aminoacetyl)piperazin-1-yl]sulfonylphenyl]-5-[1-(2,2-difluoroethyl)-3-(trifluoromethyl)pyrazol-4-yl]-1-methyl-imidazole-2-carboxamide;

N-[3-chloro-4-[[rac-(1S,5R)-8-azabicyclo[3.2.1]octan-3-yl]carbamoyl]phenyl]-5-[1-(2,2-difluorocyclopropyl)-3-(trifluoromethyl)pyrazol-4-yl]-1-methyl-imidazole-2-carboxamide;

N-[4-(6-aminohexylcarbamoyl)-3-bromo-phenyl]-5-[1-ethyl-3-(trifluoromethyl)pyrazol-4-yl]-1-methyl-imidazole-2-carboxamide;

N-[3-chloro-4-[4-[(2S)-2,5-diaminopentanoyl]piperazine-1-carbonyl]phenyl]-5-[1-cyclopropyl-3-(trifluoromethyl)pyrazol-4-yl]-1-methyl-imidazole-2-carboxamide;

N-[3-chloro-4-[4-(5-hydroxypiperidine-3-carbonyl)piperazine-1-carbonyl]phenyl]-5-[1-cyclopropyl-3-(trifluoromethyl)pyrazol-4-yl]-1-methyl-imidazole-2-carboxamide;

N-[4-[4-[(1R,3R)-3-aminocyclohexanecarbonyl]piperazine-1-carbonyl]-3-chloro-phenyl]-5-[1-cyclopropyl-3-(trifluoromethyl)pyrazol-4-yl]-1-methyl-imidazole-2-carboxamide;

rac-(3aR,6aS)-2-[2-chloro-4-[[5-[1-(2,2-difluorocyclopropyl)-3-(trifluoromethyl)pyrazol-4-yl]-1-methyl-imidazole-2-carbonyl]amino]benzoyl]-N-[rac-(3S,4S)-4-hydroxypyrrolidin-3-yl]-1,3,3a,4,6,6a-hexahydropyrrolo[3,4-c]pyrrole-5-carboxamide;

N-[4-[(4-aminocyclohexyl)methylcarbamoyl]-3-chloro-phenyl]-5-[1-cyclopropyl-3-(trifluoromethyl)pyrazol-4-yl]-1-methyl-imidazole-2-carboxamide;

N-[4-[4-(2-aminoethyl)piperazine-1-carbonyl]-3-chloro-phenyl]-5-[1-(2,2-difluoroethyl)-3-(trifluoromethyl)pyrazol-4-yl]-1-methyl-imidazole-2-carboxamide;

N-[4-[N-(3-aminopropyl)-S-methyl-sulfonimidoyl]-3-methyl-phenyl]-5-[1-(cyanomethyl)-3-(trifluoromethyl)pyrazol-4-yl]-1-methyl-imidazole-2-carboxamide;

N-(3-aminocyclobutyl)-4-[2-chloro-4-[[5-[1-isobutyl-3-(trifluoromethyl)pyrazol-4-yl]-1-methyl-imidazole-2-carbonyl]amino]benzoyl]piperazine-1-carboxamide;

N-(3-aminocyclobutyl)-4-[2-chloro-4-[[5-[1-[(3,3-difluorocyclobutyl)methyl]-3-(trifluoromethyl)pyrazol-4-yl]-1-methyl-imidazole-2-carbonyl]amino]benzoyl]piperazine-1-carboxamide;

N-(3-aminocyclobutyl)-4-[[2-chloro-4-[[5-[1-(2,2-difluorocyclopropyl)-3-(trifluoromethyl)pyrazol-4-yl]-1-methyl-imidazole-2-carbonyl]amino]benzoyl]-methyl-amino]piperidine-1-carboxamide;

N-[4-[4-(3-aminocyclobutanecarbonyl)piperazine-1-carbonyl]-3-chloro-phenyl]-5-[1-(cyclobutylmethyl)-3-(trifluoromethyl)pyrazol-4-yl]-1-methyl-imidazole-2-carboxamide;

N-(3-aminocyclobutyl)-4-[2-chloro-4-[[5-[1-ethyl-3-(trifluoromethyl)pyrazol-4-yl]-1-methyl-imidazole-2-carbonyl]amino]benzoyl]piperazine-1-carboxamide;

N-[3-chloro-4-[4-(4-methylpiperazine-1-carbonyl)piperazine-1-carbonyl]phenyl]-5-[1-cyclopropyl-3-(trifluoromethyl)pyrazol-4-yl]-1-methyl-imidazole-2-carboxamide;

N-[4-[4-(3-aminocyclobutanecarbonyl)piperazine-1-carbonyl]-3-chloro-phenyl]-5-[1-(2-fluoroethyl)-3-(trifluoromethyl)pyrazol-4-yl]-1-methyl-imidazole-2-carboxamide;

N-[3-chloro-4-[4-[(3S)-pyrrolidine-3-carbonyl]piperazine-1-carbonyl]phenyl]-5-[1-cyclopropyl-3-(trifluoromethyl)pyrazol-4-yl]-1-methyl-imidazole-2-carboxamide;

N-[3-chloro-4-[6-[[rac-(3S,4S)-4-hydroxypyrrolidin-3-yl]carbamoylamino]-3-azabicyclo[3.1.0]hexane-3-carbonyl]phenyl]-5-[1-(2,2-difluorocyclopropyl)-3-(trifluoromethyl)pyrazol-4-yl]-1-methyl-imidazole-2-carboxamide;

5-[1-(2,2-difluoroethyl)-3-(trifluoromethyl)pyrazol-4-yl]-N-[3-fluoro-4-[4-(piperidine-4-carbonyl)piperazine-1-carbonyl]phenyl]-1-methyl-imidazole-2-carboxamide;

N-[4-[4-(4-aminobutanoyl)piperazine-1-carbonyl]-3-chloro-phenyl]-5-[1-cyclopropyl-3-(trifluoromethyl)pyrazol-4-yl]-1-methyl-imidazole-2-carboxamide;

4-[2-chloro-4-[[5-[1-(2,2-difluoroethyl)-3-(trifluoromethyl)pyrazol-4-yl]-1-methyl-imidazole-2-carbonyl]amino]benzoyl]-N-[(3-hydroxyazetidin-3-yl)methyl]piperazine-1-carboxamide;

N-[3-chloro-4-[4-(piperidine-4-carbonyl)piperazine-1-carbonyl]phenyl]-5-[1-(cyclopentylmethyl)-3-(trifluoromethyl)pyrazol-4-yl]-1-methyl-imidazole-2-carboxamide;

N-(3-aminocyclobutyl)-4-[2-chloro-4-[[1-methyl-5-[1-(2,2,2-trifluoroethyl)-3-(trifluoromethyl)pyrazol-4-yl]imidazole-2-carbonyl]amino]benzoyl]piperazine-1-carboxamide;

N-[3-chloro-4-[[rac-(1S,5R)-3-(piperidine-4-carbonyl)-3-azabicyclo[3.1.0]hexan-6-yl]carbamoyl]phenyl]-5-[1-cyclopropyl-3-(trifluoromethyl)pyrazol-4-yl]-1-methyl-imidazole-2-carboxamide;

N-[4-[(3-aminocyclobutyl)carbamoyl]-3-chloro-phenyl]-5-[1-(3,3-difluoroallyl)-3-(trifluoromethyl)pyrazol-4-yl]-1-methyl-imidazole-2-carboxamide;

5-[1-(2,2-difluoroethyl)-3-(trifluoromethyl)pyrazol-4-yl]-1-methyl-N-(3-methyl-4-methyl sulfanyl-phenyl)imidazole-2-carboxamide;

N-[3-chloro-4-[4-[2-(4-piperidyl)acetyl]piperazine-1-carbonyl]phenyl]-5-[1-cyclopropyl-3-(trifluoromethyl)pyrazol-4-yl]-1-methyl-imidazole-2-carboxamide;

5-[[[2-chloro-4-[[5-[1-(2,2-difluorocyclopropyl)-3-(trifluoromethyl)pyrazol-4-yl]-1-methyl-imidazole-2-carbonyl]amino]benzoyl]amino]methyl]-N-[rac-(3S,4S)-4-hydroxypyrrolidin-3-yl]-3,3a,4,5,6,6a-hexahydro-1H-cyclopenta[c]pyrrole-2-carboxamide;

N-[3-chloro-4-[4-(4-hydroxypiperidine-3-carbonyl)piperazine-1-carbonyl]phenyl]-5-[1-cyclopropyl-3-(trifluoromethyl)pyrazol-4-yl]-1-methyl-imidazole-2-carboxamide;

5-[1-[(E)-but-2-enyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-[(2R,4S)-4-hydroxypyrrolidine-2-carbonyl]piperazine-1-carbonyl]phenyl]-5-[1-cyclopropyl-3-(trifluoromethyl)pyrazol-4-yl]-1-methyl-imidazole-2-carboxamide;

tert-butyl N-[4-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]butyl]carbamate;

N-[3-chloro-4-[[3-[[(3R)-pyrrolidine-3-carbonyl]amino]cyclobutyl]carbamoyl]phenyl]-5-[1-(cyanomethyl)-3-(trifluoromethyl)pyrazol-4-yl]-1-methyl-imidazole-2-carboxamide;

N-[4-[[3-[[(3R)-3-aminopyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[4-[(6-aminospiro[3.3]heptan-2-yl)carbamoyl]-3-chloro-phenyl]-5-[1-cyclopropyl-3-(trifluoromethyl)pyrazol-4-yl]-1-methyl-imidazole-2-carboxamide;

N-[3-chloro-4-[4-(3-hydroxypyrrolidine-3-carbonyl)piperazine-1-carbonyl]phenyl]-5-[1-cyclopropyl-3-(trifluoromethyl)pyrazol-4-yl]-1-methyl-imidazole-2-carboxamide;

N-[3-chloro-4-[4-(3-hydroxypiperidine-3-carbonyl)piperazine-1-carbonyl]phenyl]-5-[1-(2-fluoroethyl)-3-(trifluoromethyl)pyrazol-4-yl]-1-methyl-imidazole-2-carboxamide;

N-[4-(3-azabicyclo[3.2.0]heptan-6-ylcarbamoyl)-3-chloro-phenyl]-5-[1-(2,2-difluorocyclopropyl)-3-(trifluoromethyl)pyrazol-4-yl]-1-methyl-imidazole-2-carboxamide;

4-[2-chloro-4-[[5-[1-cyclopropyl-3-(trifluoromethyl)pyrazol-4-yl]-1-methyl-imidazole-2-carbonyl]amino]benzoyl]-N-[(4-hydroxy-4-piperidyl)methyl]piperazine-1-carboxamide;

N-[3-chloro-4-[4-[(2S,4R)-4-hydroxypyrrolidine-2-carbonyl]piperazine-1-carbonyl]phenyl]-5-[1-cyclopropyl-3-(trifluoromethyl)pyrazol-4-yl]-1-methyl-imidazole-2-carboxamide;

N-[4-[[(1S,5R)-3-[(3R)-3-aminopyrrolidine-1-carbonyl]-3-azabicyclo[3.1.0]hexan-6-yl]carbamoyl]-3-chloro-phenyl]-5-[1-cyclopropyl-3-(trifluoromethyl)pyrazol-4-yl]-1-methyl-imidazole-2-carboxamide;

N-[3-chloro-4-[4-(4-piperidyl)piperidine-1-carbonyl]phenyl]-5-[1-cyclopropyl-3-(trifluoromethyl)pyrazol-4-yl]-1-methyl-imidazole-2-carboxamide;

N-[4-[[4-[[(2S)-2-aminopropanoyl]amino]cyclohexyl]carbamoyl]-3-chloro-phenyl]-5-[1-(cyanomethyl)-3-(trifluoromethyl)pyrazol-4-yl]-1-methyl-imidazole-2-carboxamide;

N-(3-aminocyclobutyl)-4-[2-bromo-4-[[5-[1-ethyl-3-(trifluoromethyl)pyrazol-4-yl]-1-methyl-imidazole-2-carbonyl]amino]benzoyl]piperazine-1-carboxamide;

3-amino-N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]piperidine-1-carboxamide;

N-[4-[4-[(1S,3R)-3-aminocyclopentanecarbonyl]piperazine-1-carbonyl]-3-chloro-phenyl]-5-[1-(cyclobutylmethyl)-3-(trifluoromethyl)pyrazol-4-yl]-1-methyl-imidazole-2-carboxamide;

N-(3-aminocyclobutyl)-4-[2-chloro-4-[[1-methyl-5-[1-(2-methylallyl)-3-(trifluoromethyl)pyrazol-4-yl]imidazole-2-carbonyl]amino]benzoyl]piperazine-1-carboxamide;

N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]-2,5-diazabicyclo[2.2.1]heptane-2-carboxamide;

N-[3-chloro-4-[rac-(3aR,6aR)-2,3,3a,4,6,6a-hexahydro-1H-pyrrolo[3,4-c]pyrrole-5-carbonyl]phenyl]-5-[1-(2,2-difluorocyclopropyl)-3-(trifluoromethyl)pyrazol-4-yl]-1-methyl-imidazole-2-carboxamide;

N-[4-[4-(2-aminoacetyl)piperazine-1-carbonyl]-3-chloro-phenyl]-5-[1-ethyl-3-(trifluoromethyl)pyrazol-4-yl]-1-methyl-imidazole-2-carboxamide;

N-[3-chloro-4-[4-[methyl-[[rac-(3S,4S)-4-hydroxypyrrolidin-3-yl]carbamoyl]amino]butylcarbamoyl]phenyl]-5-[1-(2,2-difluorocyclopropyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-[2-(trifluoromethoxy)ethyl]-3-(trifluoromethyl)pyrazol-4-yl]imidazole-2-carboxamide;

N-(3-aminocyclobutyl)-4-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-4-methyl-piperidine-1-carboxamide;

(1S,5R)—N-[(1R,2S)-2-aminocyclopentyl]-6-[[2-chloro-4-[[5-[1-cyclopropyl-3-(trifluoromethyl)pyrazol-4-yl]-1-methyl-imidazole-2-carbonyl]amino]benzoyl]amino]-3-azabicyclo[3.1.0]hexane-3-carboxamide;

N-[3-chloro-4-[4-[(2S,4R)-4-hydroxypyrrolidine-2-carbonyl]piperazine-1-carbonyl]phenyl]-5-[1-(cyclobutylmethyl)-3-(trifluoromethyl)pyrazol-4-yl]-1-methyl-imidazole-2-carboxamide;

N-[3-chloro-4-(piperazine-1-carbonyl)phenyl]-5-[1-(2,2-difluoroethyl)-3-(trifluoromethyl)pyrazol-4-yl]-1-methyl-imidazole-2-carboxamide;

4-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]piperidine-1-carboxamide;

N-[3-chloro-4-(4-piperazin-1-ylsulfonylpiperazine-1-carbonyl)phenyl]-5-[1-cyclopropyl-3-(trifluoromethyl)pyrazol-4-yl]-1-methyl-imidazole-2-carboxamide;

N-(3-aminocyclobutyl)-1-[2-chloro-4-[[5-[1-cyclopropyl-3-(trifluoromethyl)pyrazol-4-yl]-1-methyl-imidazole-2-carbonyl]amino]benzoyl]piperidine-4-carboxamide;

N-[4-[4-(3-aminocyclobutanecarbonyl)piperazine-1-carbonyl]-3-ethyl-phenyl]-5-[1-(cyanomethyl)-3-(trifluoromethyl)pyrazol-4-yl]-1-methyl-imidazole-2-carboxamide;

N-[3-chloro-4-[(4-hydroxypyrrolidin-3-yl)carbamoyl]phenyl]-5-[1-(2,2-difluorocyclopropyl)-3-(trifluoromethyl)pyrazol-4-yl]-1-methyl-imidazole-2-carboxamide;

N-[4-[N-(3-aminopropyl)-S-methyl-sulfonimidoyl]-3-methyl-phenyl]-1-methyl-5-[1-prop-2-ynyl-3-(trifluoromethyl)pyrazol-4-yl]imidazole-2-carboxamide;

4-[2-chloro-4-[[5-[1-(cyanomethyl)-3-(trifluoromethyl)pyrazol-4-yl]-1-methyl-imidazole-2-carbonyl]amino]benzoyl]-N-[(3-hydroxyazetidin-3-yl)methyl]piperazine-1-carboxamide;

N-[3-chloro-4-[(4-methyl-4-piperidyl)carbamoyl]phenyl]-5-[1-(2,2-difluorocyclopropyl)-3-(trifluoromethyl)pyrazol-4-yl]-1-methyl-imidazole-2-carboxamide;

N-[4-(4-aminobutylcarbamoyl)-3-chloro-phenyl]-5-[1-(cyanomethyl)-3-(trifluoromethyl)pyrazol-4-yl]-1-methyl-imidazole-2-carboxamide;

N-[3-chloro-4-[[rac-(1S,5R)-8-azabicyclo[3.2.1]octan-3-yl]carbamoyl]phenyl]-5-[1-(2,2-difluorocyclopropyl)-3-(trifluoromethyl)pyrazol-4-yl]-1-methyl-imidazole-2-carboxamide;

6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3S,4S)-4-hydroxypyrrolidin-3-yl]-3-azabicyclo[3.2.0]heptane-3-carboxamide;

N-[4-[4-[(2R)-azetidine-2-carbonyl]piperazine-1-carbonyl]-3-chloro-phenyl]-5-[1-cyclopropyl-3-(trifluoromethyl)pyrazol-4-yl]-1-methyl-imidazole-2-carboxamide;

N-[4-[4-[(3R)-3-aminopyrrolidine-1-carbonyl]piperazine-1-carbonyl]-3-chloro-phenyl]-5-[1-cyclopropyl-3-(trifluoromethyl)pyrazol-4-yl]-1-methyl-imidazole-2-carboxamide;

N-[3-chloro-4-[[4-methoxy-1-[[rac-(3S,4S)-4-hydroxypyrrolidin-3-yl]carbamoyl]pyrrolidin-3-yl]carbamoyl]phenyl]-5-[1-(2,2-difluorocyclopropyl)-3-(trifluoromethyl)pyrazol-4-yl]-1-methyl-imidazole-2-carboxamide;

N-[4-[(4-aminocyclohexyl)carbamoyl]-3-chloro-phenyl]-5-[1-(cyanomethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2-cyclopropylethyl)-3-(trifluoromethyl)pyrazol-4-yl]-1-methyl-imidazole-2-carboxamide;

N-[4-[N-(3-aminopropyl)-S-methyl-sulfonimidoyl]-3-methyl-phenyl]-5-[1-(2,2-difluoroethyl)-3-(trifluoromethyl)pyrazol-4-yl]-1-methyl-imidazole-2-carboxamide;

N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]-3-methyl-piperazine-1-carboxamide;

N-[4-[4-(3-aminocyclobutanecarbonyl)piperazine-1-carbonyl]-3-chloro-phenyl]-5-[1-(cyanomethyl)-3-(trifluoromethyl)pyrazol-4-yl]-1-methyl-imidazole-2-carboxamide;

N-[4-(5-aminopentylcarbamoyl)-3-ethyl-phenyl]-5-[1-(2,2-difluoroethyl)-3-(trifluoromethyl)pyrazol-4-yl]-1-methyl-imidazole-2-carboxamide;

N-[3-chloro-4-[4-[2-(dimethylamino)ethyl-methyl-amino]piperidine-1-carbonyl]phenyl]-5-[1-cyclopropyl-3-(trifluoromethyl)pyrazol-4-yl]-1-methyl-imidazole-2-carboxamide;

N-[3-chloro-4-[4-[rac-(1R,5S)-3-azabicyclo[3.1.0]hexane-6-carbonyl]piperazine-1-carbonyl]phenyl]-5-[1-(cyclopropylmethyl)-3-(trifluoromethyl)pyrazol-4-yl]-1-methyl-imidazole-2-carboxamide;

N-[4-[[3-[[3-(aminomethyl)pyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[3-chloro-4-[4-[3-(dimethylamino)-3-methyl-butyl]piperidine-1-carbonyl]phenyl]-5-[1-ethyl-3-(trifluoromethyl)pyrazol-4-yl]-1-methyl-imidazole-2-carboxamide;

N-[4-[[3-[[2-(aminomethyl)pyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[4-[4-(4-aminopiperidine-1-carbonyl)piperazine-1-carbonyl]-3-chloro-phenyl]-5-[1-cyclopropyl-3-(trifluoromethyl)pyrazol-4-yl]-1-methyl-imidazole-2-carboxamide;

N-[3-chloro-4-[6-(piperidine-4-carbonyl)-1,6-diazaspiro[3.3]heptane-1-carbonyl]phenyl]-5-[1-(2,2-difluoroethyl)-3-(trifluoromethyl)pyrazol-4-yl]-1-methyl-imidazole-2-carboxamide;

N-[3-chloro-4-[4-[rac-(1S,5R)-3-azabicyclo[3.1.0]hexane-6-carbonyl]piperazine-1-carbonyl]phenyl]-5-[1-(2,2-difluoroethyl)-3-(trifluoromethyl)pyrazol-4-yl]-1-methyl-imidazole-2-carboxamide;

6-[[[2-chloro-4-[[5-[1-(2,2-difluorocyclopropyl)-3-(trifluoromethyl)pyrazol-4-yl]-1-methyl-imidazole-2-carbonyl]amino]benzoyl]amino]methyl]-N-[rac-(3S,4S)-4-hydroxypyrrolidin-3-yl]-3-azabicyclo[3.1.0]hexane-3-carboxamide;

N-[3-chloro-4-[4-(methylamino)piperidine-1-carbonyl]phenyl]-5-[1-cyclopropyl-3-(trifluoromethyl)pyrazol-4-yl]-1-methyl-imidazole-2-carboxamide;

N-[3-chloro-4-[(2S,4S)-4-fluoropyrrolidine-2-carbonyl]piperazine-1-carbonyl]phenyl]-5-[1-cyclopropyl-3-(trifluoromethyl)pyrazol-4-yl]-1-methyl-imidazole-2-carboxamide;

N-[3-chloro-4-[methyl(4-piperidyl)carbamoyl]phenyl]-5-[1-(2,2-difluorocyclopropyl)-3-(trifluoromethyl)pyrazol-4-yl]-1-methyl-imidazole-2-carboxamide;

N-[(1R,3R)-3-aminocyclopentyl]-4-[2-chloro-4-[[5-[1-(cyclopropylmethyl)-3-(trifluoromethyl)pyrazol-4-yl]-1-methyl-imidazole-2-carbonyl]amino]benzoyl]piperazine-1-carboxamide;

N-[3-chloro-4-[4-(4-hydroxy-1-piperidyl)piperidine-1-carbonyl]phenyl]-5-[1-cyclopropyl-3-(trifluoromethyl)pyrazol-4-yl]-1-methyl-imidazole-2-carboxamide;

N-[3-chloro-4-(piperazine-1-carbonyl)phenyl]-5-[1-(cyclobutylmethyl)-3-(trifluoromethyl)pyrazol-4-yl]-1-methyl-imidazole-2-carboxamide;

N-[4-[[4-[(3-aminocyclobutanecarbonyl)amino]cyclohexyl]carbamoyl]-3-chloro-phenyl]-5-[1-(cyanomethyl)-3-(trifluoromethyl)pyrazol-4-yl]-1-methyl-imidazole-2-carboxamide;

N-[4-[[1-[(3-aminocyclobutyl)carbamoyl]azetidin-3-yl]methylcarbamoyl]-3-chloro-phenyl]-5-[1-(cyclopropylmethyl)-3-(trifluoromethyl)pyrazol-4-yl]-1-methyl-imidazole-2-carboxamide;

N-[3-bromo-4-[4-(piperidine-4-carbonyl)piperazine-1-carbonyl]phenyl]-5-[1-ethyl-3-(trifluoromethyl)pyrazol-4-yl]-1-methyl-imidazole-2-carboxamide;

N-[4-[4-[2-(2-aminoethylamino)-2-oxo-ethyl]piperazine-1-carbonyl]-3-chloro-phenyl]-5-[1-(2,2-difluoroethyl)-3-(trifluoromethyl)pyrazol-4-yl]-1-methyl-imidazole-2-carboxamide;

rac-(1R,5S)—N-(azetidin-3-yl)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-3-azabicyclo[3.1.0]hexane-3-carboxamide;

rac-(1S,5R)-8-[2-chloro-4-[[5-[1-(2,2-difluorocyclopropyl)-3-(trifluoromethyl)pyrazol-4-yl]-1-methyl-imidazole-2-carbonyl]amino]benzoyl]-N-[rac-(3S,4S)-4-hydroxypyrrolidin-3-yl]-3,8-diazabicyclo[3.2.1]octane-3-carboxamide;

N-[4-[6-(azetidin-3-ylmethylcarbamoylamino)hexylcarbamoyl]-3-chloro-phenyl]-5-[1-cyclopropyl-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[3-(trifluoromethyl)-1-[2-(trifluoromethyl)cyclopropyl]pyrazol-4-yl]imidazole-2-carboxamide;

(1S,5R)-6-[[2-chloro-4-[[1-methyl-5-[1-prop-2-ynyl-3-(trifluoromethyl)pyrazol-4-yl]imidazole-2-carbonyl]amino]benzoyl]amino]-N-[(3R,4R)-4-hydroxypyrrolidin-3-yl]-3-azabicyclo[3.1.0]hexane-3-carboxamide;

rac-(1S,5R)-6-[[2-chloro-4-[[5-[1-[(2,2-difluorocyclopropyl)methyl]-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;

(1S,5R)-6-[[2-chloro-4-[[5-[1-(2,2-difluoroethyl)-3-(trifluoromethyl)pyrazol-4-yl]-1-methyl-imidazole-2-carbonyl]

amino]benzoyl]amino]-N-[(3R,4R)-4-hydroxypyrrolidin-3-yl]-3-azabicyclo[3.1.0]hexane-3-carboxamide;

(1S,5R)-6-[[4-[[5-[1-allyl-3-(trifluoromethyl)pyrazol-4-yl]-1-methyl-imidazole-2-carbonyl]amino]-2-chloro-benzoyl]amino]-N-[(3R,4R)-4-hydroxypyrrolidin-3-yl]-3-azabicyclo[3.1.0]hexane-3-carboxamide or (1S,5R)-6-[[2-chloro-4-[[5-[1-(cyclobutylmethyl)-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide.

In an embodiment, the present disclosure provides a compound of formula (I) as described herein, or a pharmaceutically acceptable salt thereof, wherein the compound of formula (I) is:

N-(azetidin-3-yl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

4-[2-chloro-4-[[1-methyl-5-[1-prop-2-ynyl-3-(trifluoromethyl)pyrazol-4-yl]imidazole-2-carbonyl]amino]benzoyl]-N-[(3-hydroxyazetidin-3-yl)methyl]piperazine-1-carboxamide;

N-[3-chloro-4-[4-(piperidine-4-carbonyl)piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-[(3S)-pyrrolidine-3-carbonyl]piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-cyclopropyl-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(2,2,2-trifluoroethyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(2-fluoroethyl)-3-(trifluoromethyl)pyrazol-4-yl]-1-methyl-imidazole-2-carboxamide;

N-[3-chloro-4-[4-[rac-(1S,5R)-3-azabicyclo[3.1.0]hexane-6-carbonyl]piperazine-1-carbonyl]phenyl]-1-methyl-5-[1-prop-2-ynyl-3-(trifluoromethyl)pyrazol-4-yl]imidazole-2-carboxamide;

N-(3-aminocyclobutyl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[4-[4-[(3R)-3-aminopyrrolidine-1-carbonyl]piperazine-1-carbonyl]-3-chloro-phenyl]-1-methyl-5-[1-prop-2-ynyl-3-(trifluoromethyl)pyrazol-4-yl]imidazole-2-carboxamide;

N-[(1S,2R)-2-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[3-chloro-4-[4-[(1S,4S)-2,5-diazabicyclo[2.2.1]heptane-2-carbonyl]piperazine-1-carbonyl]phenyl]-1-methyl-5-[1-prop-2-ynyl-3-(trifluoromethyl)pyrazol-4-yl]imidazole-2-carboxamide;

N-[4-[(3-aminocyclobutyl)carbamoyl]-3-chloro-phenyl]-5-[1-(cyanomethyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(cyclobutylmethyl)-3-(trifluoromethyl)pyrazol-4-yl]-1-methyl-imidazole-2-carboxamide;

N-[4-[4-[(3S)-3-aminopyrrolidine-1-carbonyl]piperazine-1-carbonyl]-3-chloro-phenyl]-1-methyl-5-[1-prop-2-ynyl-3-(trifluoromethyl)pyrazol-4-yl]imidazole-2-carboxamide;

4-[2-chloro-4-[[1-methyl-5-[1-prop-2-ynyl-3-(trifluoromethyl)pyrazol-4-yl]imidazole-2-carbonyl]amino]benzoyl]-N-[rac-(1S,5R)-3-azabicyclo[3.1.0]hexan-6-yl]piperazine-1-carboxamide;

N-[3-chloro-4-[4-(piperidine-4-carbonyl)piperazine-1-carbonyl]phenyl]-1-methyl-5-[1-spiro[2.3]hexan-5-yl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[(2,2-difluorocyclopropyl)methyl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(cyclopropylmethyl)-3-(trifluoromethyl)pyrazol-4-yl]-1-methyl-imidazole-2-carboxamide;

4-[4-[[5-[1-allyl-3-(trifluoromethyl)pyrazol-4-yl]-1-methyl-imidazole-2-carbonyl]amino]-2-chloro-benzoyl]-N-(azetidin-3-yl)piperazine-1-carboxamide;

N-[3-chloro-4-(piperazine-1-carbonyl)phenyl]-5-[1-(cyanomethyl)-3-(trifluoromethyl)pyrazol-4-yl]-1-methyl-imidazole-2-carboxamide;

N-(azetidin-3-yl)-4-[2-chloro-4-[[5-[1-cyclobutyl-3-(trifluoromethyl)pyrazol-4-yl]-1-methyl-imidazole-2-carbonyl]amino]benzoyl]piperazine-1-carboxamide;

N-[3-chloro-4-[4-(piperidine-4-carbonyl)piperazine-1-carbonyl]phenyl]-5-[1-ethyl-3-(trifluoromethyl)pyrazol-4-yl]-1-methyl-imidazole-2-carboxamide;

4-[2-chloro-4-[[5-[1-(2,2-difluoroethyl)-3-(trifluoromethyl)pyrazol-4-yl]-1-methyl-imidazole-2-carbonyl]amino]benzoyl]-N-[(3S)-pyrrolidin-3-yl]piperazine-1-carboxamide;

N-[3-chloro-4-[4-(piperidine-4-carbonyl)piperazine-1-carbonyl]phenyl]-5-[1-[(3,3-difluorocyclobutyl)methyl]-3-(trifluoromethyl)pyrazol-4-yl]-1-methyl-imidazole-2-carboxamide;

N-(azetidin-3-yl)-4-[2-chloro-4-[[5-[1-(2,2-difluoroethyl)-3-(trifluoromethyl)pyrazol-4-yl]-1-methyl-imidazole-2-carbonyl]amino]benzoyl]piperazine-1-carboxamide;

N-[3-chloro-4-[4-(piperidine-4-carbonyl)piperazine-1-carbonyl]phenyl]-5-[1-isopropyl-3-(trifluoromethyl)pyrazol-4-yl]-1-methyl-imidazole-2-carboxamide;

(1R,5S)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

N-[4-[(1-aminocyclopropyl)methylcarbamoyl]-3-chloro-phenyl]-5-[1-(2,2-difluorocyclopropyl)-3-(trifluoromethyl)pyrazol-4-yl]-1-methyl-imidazole-2-carboxamide;

(1R,5S)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide;

(1R,5S)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

rac-(1R,5S)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3S,4S)-4-hydroxypyrrolidin-3-yl]-3-azabicyclo[3.1.0]hexane-3-carboxamide;

rac-(1S,5R)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;

N-[3-chloro-4-[[rac-(1S,5R)-3-(piperidine-4-carbonyl)-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;

rac-(1S,5R)-6-[[2-chloro-4-[[5-[1-(2-fluoroallyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;

rac-(1R,5S)-6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;

(1R,5S)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide;

N-[3-chloro-4-[4-fluoro-4-[[[rac-(3S,4S)-4-hydroxypyrrolidin-3-yl]carbamoylamino]methyl]piperidine-1-carbonyl]phenyl]-5-[1-(2,2-difluorocyclopropyl)-3-(trifluoromethyl)pyrazol-4-yl]-1-methyl-imidazole-2-carboxamide;

N-(azetidin-3-yl)-4-[2-chloro-4-[[1-methyl-5-[3-(trifluoromethyl)-1-vinyl-pyrazol-4-yl]imidazole-2-carbonyl]amino]benzoyl]piperazine-1-carboxamide;

N-[3-chloro-4-[[rac-(1S,5R)-3-(piperidine-4-carbonyl)-3-azabicyclo[3.1.0]hexan-6-yl]carbamoyl]phenyl]-5-[1-(2,2-difluorocyclopropyl)-3-(trifluoromethyl)pyrazol-4-yl]-1-methyl-imidazole-2-carboxamide;

N-(3-aminocyclobutyl)-6-[[2-chloro-4-[[5-[1-(2,2-difluoroethyl)-3-(trifluoromethyl)pyrazol-4-yl]-1-methyl-imidazole-2-carbonyl]amino]benzoyl]amino]-3-azabicyclo[3.1.0]hexane-3-carboxamide;

N-[3-chloro-4-[[3-(piperidine-4-carbonyl)-3-azabicyclo[3.1.0]hexan-6-yl]carbamoyl]phenyl]-5-[1-cyclobutyl-3-(trifluoromethyl)pyrazol-4-yl]-1-methyl-imidazole-2-carboxamide;

N-[4-[2-(2-amino-2-methyl-propoxy)ethylcarbamoyl]-3-ethyl-phenyl]-5-[1-(cyanomethyl)-3-(trifluoromethyl)pyrazol-4-yl]-1-methyl-imidazole-2-carboxamide;

N-[3-chloro-4-[4-[rac-(1S,5R)-3-azabicyclo[3.1.0]hexane-6-carbonyl]piperazine-1-carbonyl]phenyl]-5-[1-cyclopropyl-3-(trifluoromethyl)pyrazol-4-yl]-1-methyl-imidazole-2-carboxamide;

N-(3-aminocyclobutyl)-4-[2-chloro-4-[[5-[1-(cyclopropylmethyl)-3-(trifluoromethyl)pyrazol-4-yl]-1-methyl-imidazole-2-carbonyl]amino]benzoyl]piperazine-1-carboxamide;

N-[3-chloro-4-[[3-(piperidine-4-carbonyl)-3-azabicyclo[3.1.0]hexan-6-yl]carbamoyl]phenyl]-5-[1-(cyclobutylmethyl)-3-(trifluoromethyl)pyrazol-4-yl]-1-methyl-imidazole-2-carboxamide;

rac-(1S,5R)-6-[[2-chloro-4-[[5-[1-(cyanomethyl)-3-(trifluoromethyl)pyrazol-4-yl]-1-methyl-imidazole-2-carbonyl]amino]benzoyl]amino]-N-[rac-(3R,4R)-4-hydroxypyrrolidin-3-yl]-3-azabicyclo[3.1.0]hexane-3-carboxamide;

N-(3-aminocyclobutyl)-4-[2-chloro-4-[[5-[1-ethyl-3-(trifluoromethyl)pyrazol-4-yl]-1-methyl-imidazole-2-carbonyl]amino]benzoyl]piperazine-1-carboxamide;

N-[3-chloro-4-[4-(3-hydroxypiperidine-3-carbonyl)piperazine-1-carbonyl]phenyl]-5-[1-(2-fluoroethyl)-3-(trifluoromethyl)pyrazol-4-yl]-1-methyl-imidazole-2-carboxamide; or N-(3-aminocyclobutyl)-4-[2-chloro-4-[[1-methyl-5-[1-(2-methylallyl)-3-(trifluoromethyl)pyrazol-4-yl]imidazole-2-carbonyl]amino]benzoyl]piperazine-1-carboxamide.

In one embodiment, the present disclosure provides pharmaceutically acceptable salts of the compounds of formula (I) as described herein, for example, pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present disclosure provides compounds according to formula (I) as described herein (i.e., as "free bases" or "free acids", respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}$H, $^{3}$H, C, $^{13}$C, $^{14}$C, $^{13}$N, $^{15}$N, $^{15}$O, $^{17}$, $^{18}$O, $^{31}$P, $^{32}$P, $^{35}$S, $^{18}$F, $^{36}$Cl, $^{123}$I, and $^{125}$I, respectively. Certain isotopically-labeled compounds of formula (I), for example, those incorporating a radioactive isotope, are useful in drug and/or substrate tissue distribution studies. The radioactive isotopes tritium, i.e. $^{3}$H, and carbon-14, i.e., $^{14}$C, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can, for example, be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present disclosure may be carried out in sequential or convergent synthetic routes. Syntheses of the compounds of the present disclosure are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 3rd Edition, Richard C. Larock. John Wiley & Sons, New York, N.Y. 2018). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Substituted aniline carboxylic acid derivatives 2 (e.g. $R^3$=Me, Cl, Et) are commercially available and can be conveniently reacted with amines 1 in presence of a coupling reagent (HATU, TBTU and the like) in presence of a solvent (DMF, dioxane, THF, and the like) in the presence of a base (DIPEA, triethyl amine, and the like) to give amide derivatives 3. The aniline can then be reacted with imidazole carboxylic acids 4 in presence of a coupling reagent (HATU, TBTU and the like) in presence of a solvent (DMF, dioxane, THF, and the like) in the presence of a base (DIPEA, triethyl amine, and the like) to give amide derivatives 5. Bromo imidazole, or alternative other halides like iodo or chloro derivatives can then be reacted with a boronate such as a boronic acid 6 or boronic ester such as pinacol ester, in a Suzuki reaction under transition metal catalysis (e.g., metal source Pd and the like) in a solvent (dioxane, THF, DMF, water and the like) in the presence of base ($Na_2CO_3$, $Cs_2CO_3$, $K_2CO_3$, $Et_3N$, DIPEA, and the like) to yield imidazole derivatives 11. The pyrazole can then be alkylated with alkylating reagents 8 (X=suitable leaving group such as a halide (e.g., Br, I, Cl) or a sulfonate) to give, after optional deprotection steps desired target compounds of general structure I. Alternatively, boronates that are already substituted on the nitrogen atom are either commercially available or can be prepared by methods known well in the art. Alternative methods can be used to connect the $R^5$ substituent, such as Chan-Lam coupling reactions using a suitable boronate derivative in the presence of copper (II) species and an amine such as pyridine, DMAP, Et3N and the like in a solvent (dioxane, THF, DMF, water and the like), in the presence of oxygen. The order of steps can be altered, such as reacting first an ester aniline derivative 9 with imidazole carboxylic acids 4 in presence of a coupling reagent (HATU, TBTU and the like) in presence of a solvent (DMF, dioxane, THF, and the like) in the presence of a base (DIPEA, triethyl amine, and the like) to give amide derivatives 10, which can then be reacted with a boronate such as a boronic acid 6 or boronic ester such as pinacol ester, in a Suzuki reaction under transition metal catalysis (e.g., metal source Pd and the like) in a solvent (dioxane, THF, DMF, water and the like) in the presence of base ($Na_2CO_3$, $Cs_2CO_3$, $K_2CO_3$, $Et_3N$, DIPEA, and the like) to yield imidazole derivatives 11. The ester can then be hydrolyzed with standard methods using base (e.g. LiOH or NaOH and the like) in the presence of water and optionally an organic solvent mixture to the corresponding acid derivative. Some esters such as tert-butyl esters can be cleaved under acidic conditions, with an acid such as TFA and the like in an organic solvent (dichloromethane and the like) to the corresponding acid derivative. The intermediate carboxylic acid is then reacted with amines 1 in presence of a coupling reagent (HATU, TBTU and the like) in presence of a solvent (DMF, dioxane, THF, and the like) in the presence of a base (DIPEA, triethyl amine, and the like) to give amide derivatives 7, which is then converted as described above to target molecules of structure I.

Alternatively, intermediates 11 can be connected as described above with the $R^5$ substituent, e.g. by alkylation, the ester converted to the corresponding carboxylic acid and then reacted with amines 1 as described above to give target molecules I. Other variations described herein include conversion of the ester of intermediates 10 to the corresponding carboxylic acid, followed by amide coupling with 1 to yield intermediate halides 5, which are then converted in a Suzuki reaction to give, after optional deprotection target molecules of general structure I.

Scheme 1
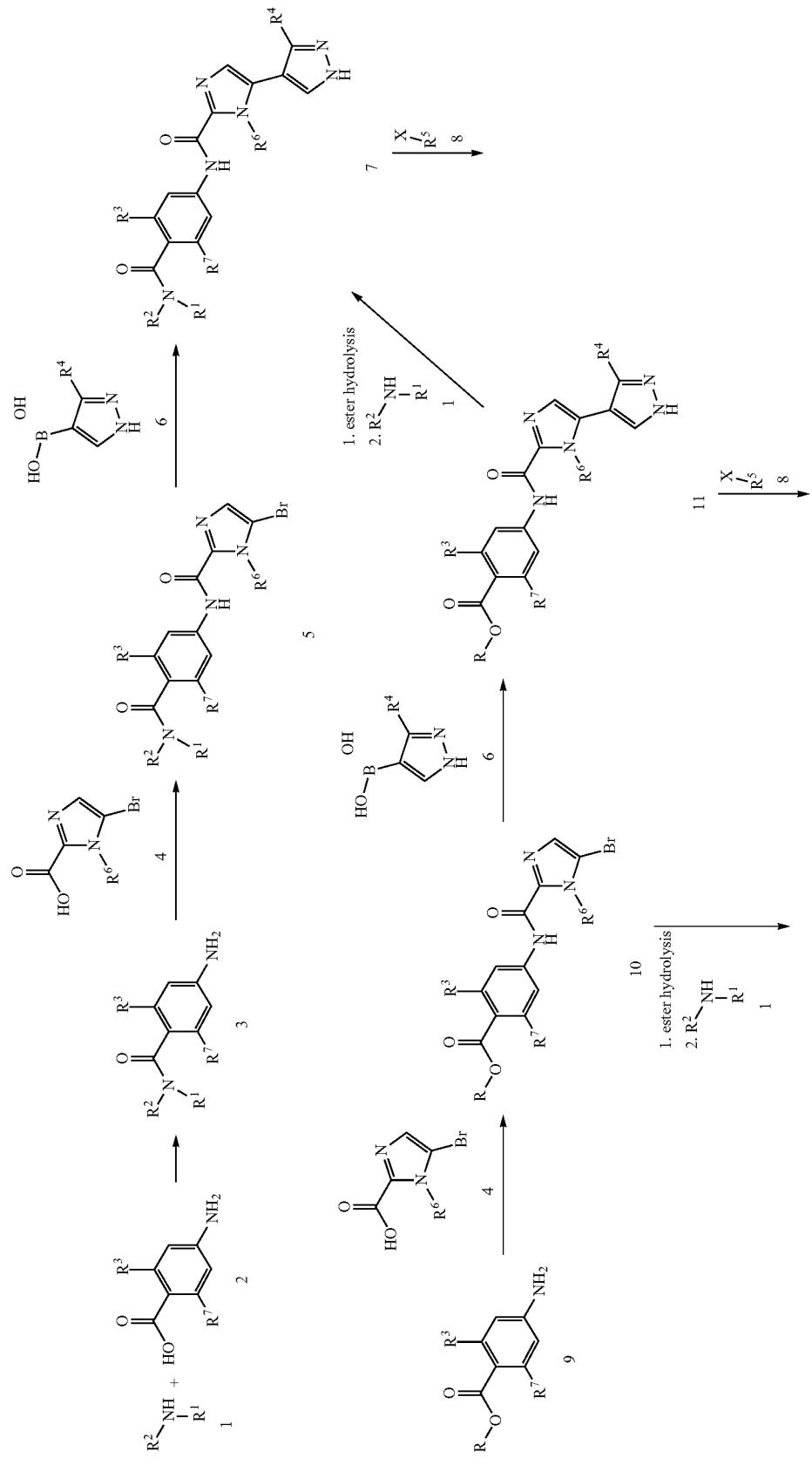

-continued
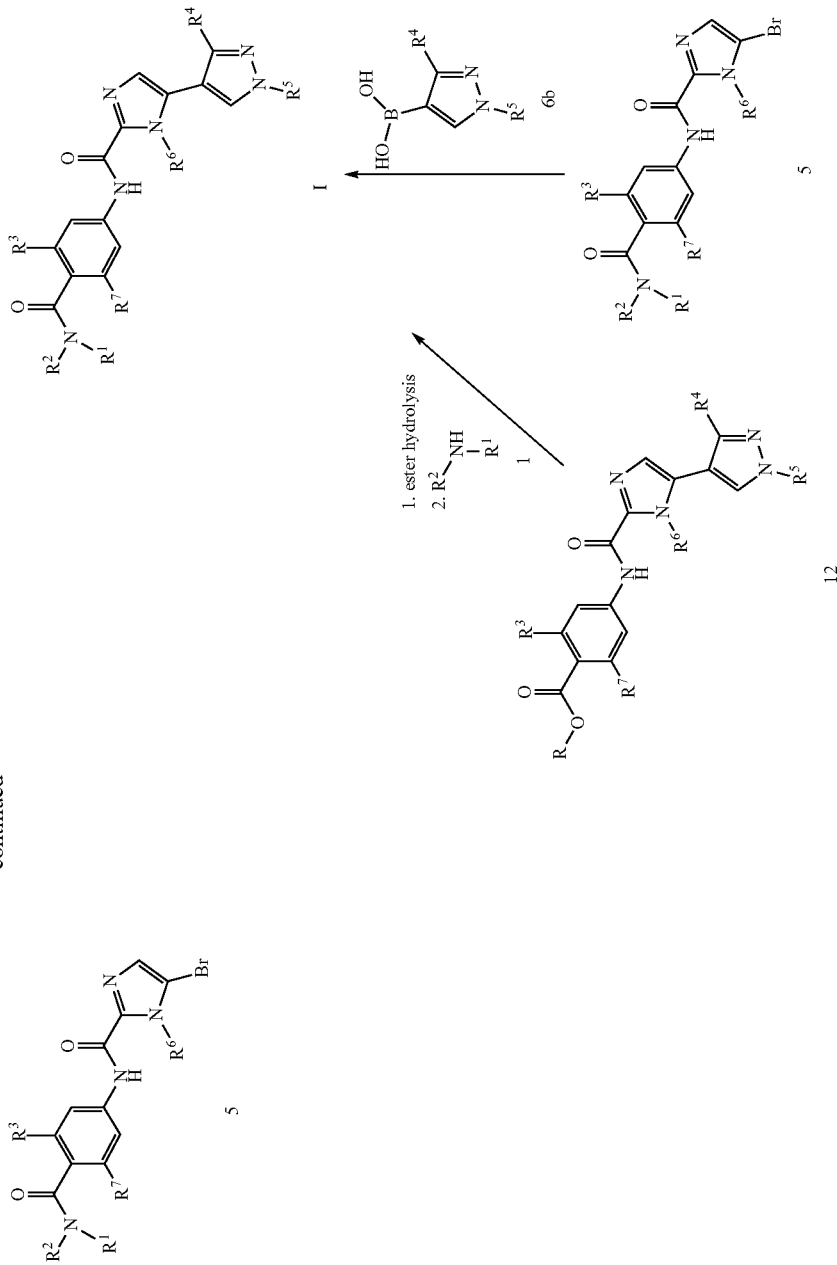

A protected linker 18 can be introduced to acids obtained from ester 11. Piperazine intermediates 7b can then be reacted further by alkylation or other C—C bond forming reactions, for example a Chan-Lam coupling reaction known well in the art to obtain intermediates 7b, that can then be deprotected to obtain intermediates 16. Intermediate 16 can be further reacted with an acid to obtain amides 17b using well known amide bond formation reaction such as using a coupling reagent (HATU, TBTU and the like) in presence of a solvent (DMF, dioxane, THF, and the like) in the presence of a base (DIPEA, triethyl amine, and the like). Alternatively, ureas 17b can be obtained by reacting intermediates 16 with an amine and a suitable reagent such as triphosgene or carbonyldiimidazole. Optional deprotection yields the desired target molecules of structure I. The order of steps may be adapted, for example pyrazole 11 substituted on the pyrazole NH first.

Scheme 1b

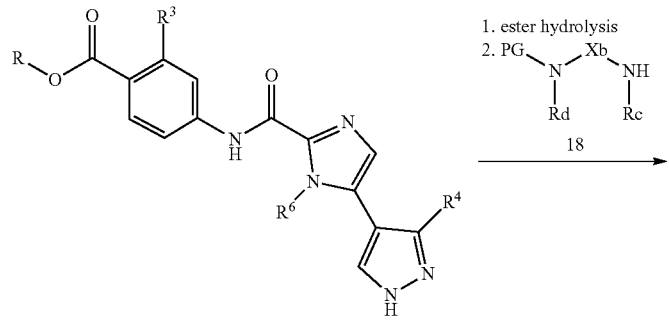

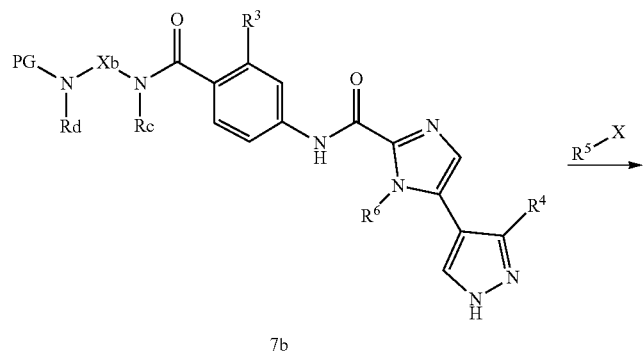

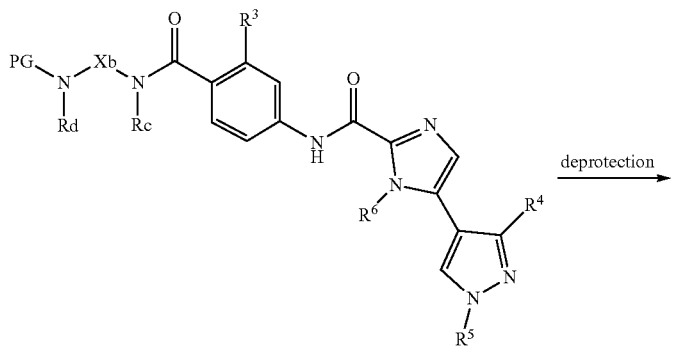

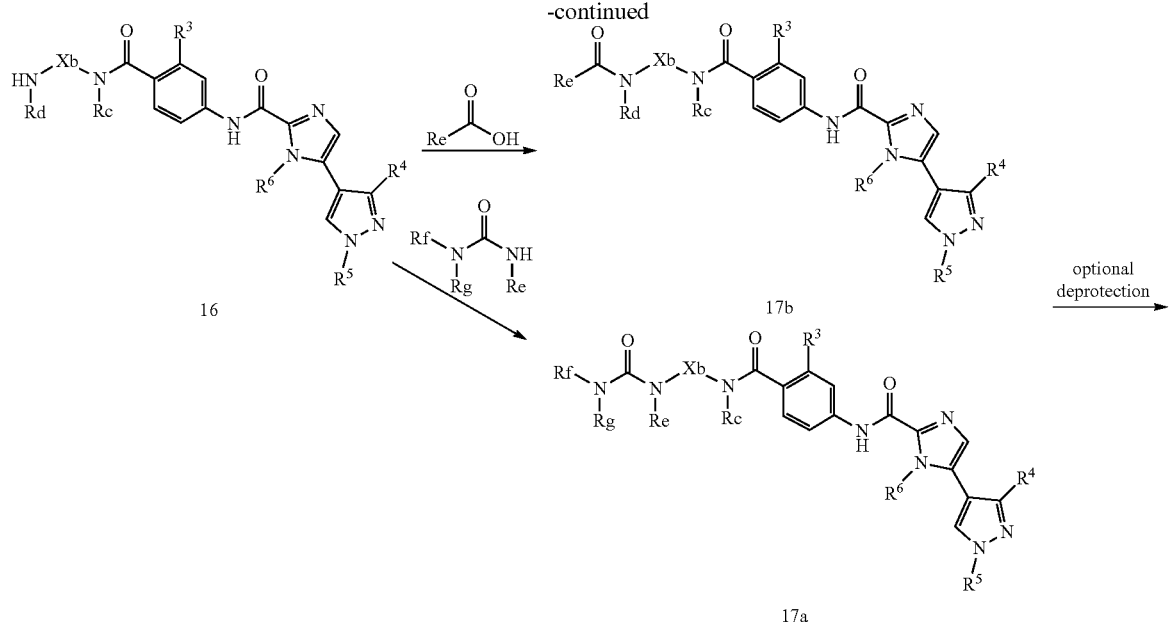

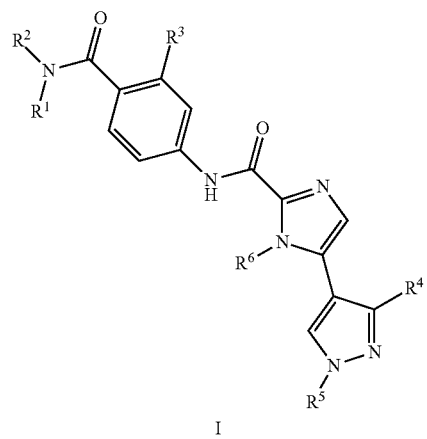

The linker $X^1$ of the structures I can be varied. For example, the amide can be varied to a sulfonamide by reacting commercially available nitro sulfonyl chlorides 13 with an amine 1 in the presence of base (such as $Et_3N$, DiPEA and the like) in a solvent (such as dichloromethane, the routes described in scheme 1, e.g. by reaction of the aniline with acid 4 in presence of a the like) in of the presence of a base (DIPEA, triethyl amine, and the like) to give amide derivatives 15, followed by reaction with boronate such as a bole nitro sulfonic acid 6 yl chlorides 13 boronic ester such as pinacol ester, in a Suzuki reaction under transition metal catalysis (e.g., metal source Pd and the like) in a solvent (dioxane, THF, DMF, water and the like) in the presence of base ($Na_2CO_3$, $Cs_2CO_3$, $K_2CO_3$, $Et_3N$, DIPEA, and the like) to yield imidazole derivatives I.

Scheme 2

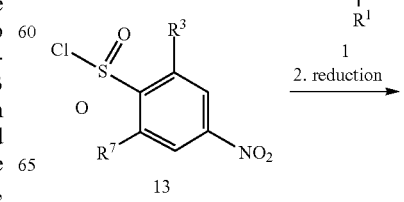

73

-continued

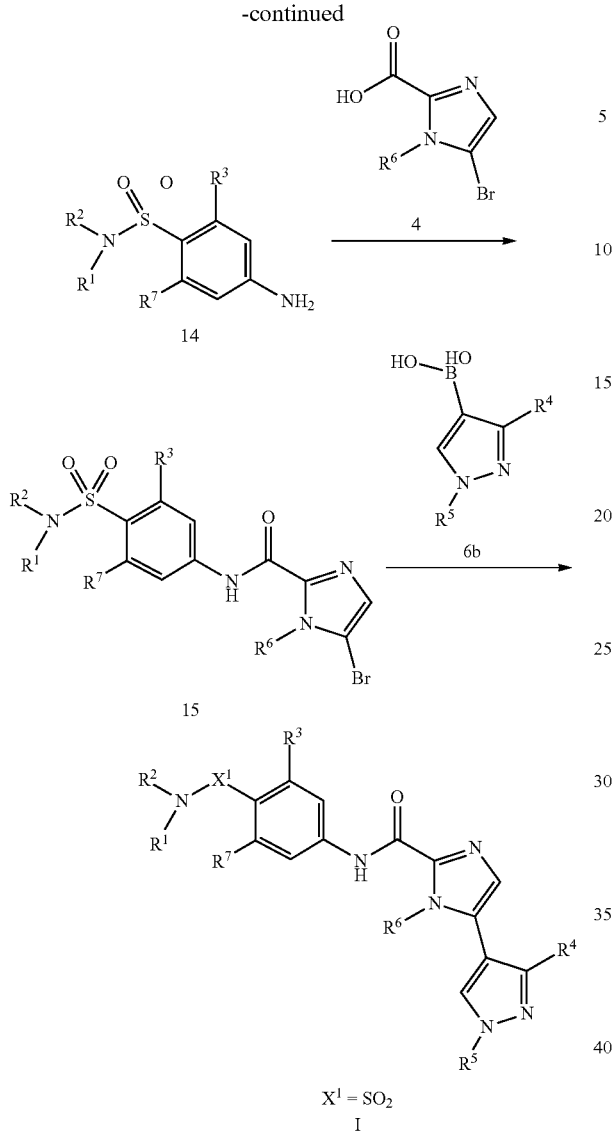

In one aspect, the present disclosure provides a process of manufacturing the compounds of formula (I) described herein, comprising:
(i) reacting a heteroaryl bromide 5 or 15, wherein R¹ to R³, R⁶ and R⁷ are as defined herein,

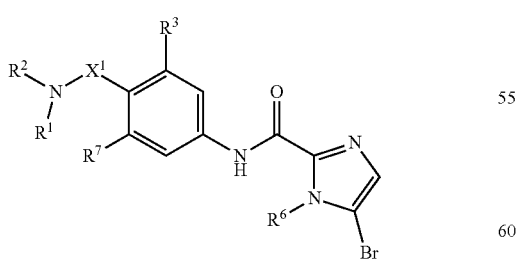

5: X¹ = C(O)
15: X¹ = SO₂ with a boronate, such as heteroaryl boronic acid 6b, wherein R⁴ and R⁵ are as defined herein,

74

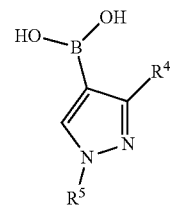

in the presence of a transition metal catalyst, such as 1,1'-bis(diphenylphosphino)ferrocene-palladium(II) dichloride dichloromethane complex, to afford said compound of formula (I); or
(ii) reacting a carboxylic acid 12a, wherein R³ to R⁷ are as defined herein,

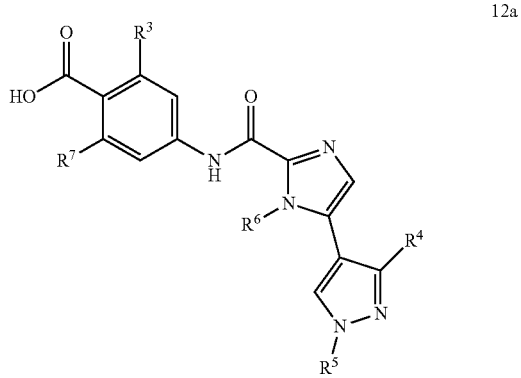

with an amine 1, wherein R¹ and R² are as defined herein,

in the presence of a coupling reagent (e.g., HATU or TBTU) and a base (e.g., DIPEA or triethyl amine), to afford said compound of formula (I); or
(iii) reacting an amine 7

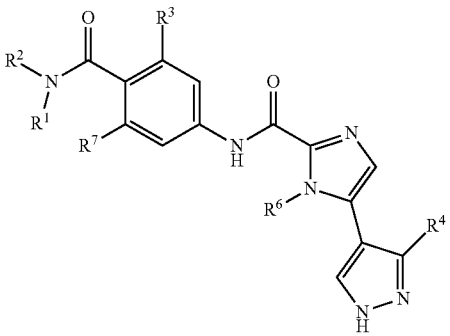

with an alkylating reagent 8, wherein X is a leaving group, such as a halide (e.g., Br, I, Cl) or a sulfonate

to afford said compound of formula (I); and
(iv) optionally converting said compound of formula (I) to a pharmaceutically acceptable salt thereof.

In a further aspect, the present disclosure provides a compound of formula (I) as described herein, or a pharmaceutically acceptable salt thereof, when manufactured according to the processes disclosed herein.

Using the Compounds of the Disclosure

As illustrated in the experimental section, the compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii*.

In some embodiments, compounds of formula (I) and their pharmaceutically acceptable salts exhibit activity as antibiotics, for example, as antibiotics against *Acinetobacter* species, more particularly as antibiotics against *Acinetobacter baumannii*, most particularly as pathogen-specific antibiotics against *Acinetobacter baumannii*.

In other embodiments, compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii*.

In yet other embodiments, compounds of the present disclosure can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In one aspect, the present disclosure provides compounds of formula (I) or their pharmaceutically acceptable salts as described herein for use as therapeutically active substances.

In a further aspect, the present disclosure provides a compound of formula (I) as described herein, or a pharmaceutically acceptable salt thereof, for use as antibiotic.

In a further aspect, the present disclosure provides a compound of formula (I) as described herein, or a pharmaceutically acceptable salt thereof, for use in the treatment or prevention of nosocomial infections and resulting diseases.

In a particular embodiment, said nosocomial infections and resulting diseases are selected from bacteremia, pneumonia, meningitis, urinary tract infection and wound infection, or a combination thereof.

In a further aspect, the present disclosure provides a compound of formula (I) as described herein, or a pharmaceutically acceptable salt thereof, for use in the treatment or prevention of infections and resulting diseases caused by Gram-negative bacteria.

In a particular embodiment, said infections and resulting diseases caused by Gram-negative bacteria are selected from bacteremia, pneumonia, meningitis, urinary tract infection and wound infection, or a combination thereof.

In a further aspect, the present disclosure provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present disclosure provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, which method comprises administering a compound of formula (I) as described herein, or a pharmaceutically acceptable salt thereof, to a mammal.

In a further aspect, the present disclosure provides the use of a compound of formula (I) as described herein, or a pharmaceutically acceptable salt thereof, as an antibiotic.

In a further aspect, the present disclosure provides the use of a compound of formula (I) as described herein, or a pharmaceutically acceptable salt thereof, for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present disclosure provides the use of a compound of formula (I) as described herein, or a pharmaceutically acceptable salt thereof, for the preparation of medicaments useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a particular embodiment, said infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, are selected from bacteremia, pneumonia, meningitis, urinary tract infection and wound infection, or a combination thereof.

In a further aspect, the present disclosure provides compounds of formula (I) or their pharmaceutically acceptable salts as defined above for use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In a further aspect, the present disclosure provides a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering a compound of formula (I) or a pharmaceutically acceptable salt thereof as defined above to a mammal.

In a further aspect, the present disclosure provides the use of compounds of formula (I) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In a further aspect, the present disclosure provides the use of compounds of formula (I) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (I) or their pharmaceutically acceptable salts as defined above.

Pharmaceutical Compositions and Administration

In one aspect, the present disclosure provides pharmaceutical compositions comprising compounds of formula (I) or their pharmaceutically acceptable salts as defined above and one or more pharmaceutically acceptable excipients. Exemplary pharmaceutical compositions are described in Examples 163, 164, 165 and 166.

In a further aspect, the present disclosure relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In some examples, compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

In some examples, the compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain, for example, preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In some examples, dosage can vary in wide limits and be fitted to the individual requirements in each particular case. In some examples, in the case of oral administration a daily dosage of about 0.1 mg to 20 mg per kg body weight, in other examples, about 0.5 mg to 4 mg per kg body weight (e.g. about 300 mg per person), divided into, in some examples, 1-3 individual doses, which can consist, for example, of the same amounts, should be appropriate. It will, however, be clear that the upper limit given herein can be exceeded when this is shown to be indicated.

Co-Administration of Compounds of Formula (I) and Other Agents

The compounds of formula (I) or pharmaceutically acceptable salts thereof, or a compound disclosed herein or a pharmaceutically acceptable salt thereof, may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with an antibiotic, in particular with an antibiotic for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

The term "co-administering" refers to either simultaneous administration, or any manner of separate sequential administration in any order, of a compound of formula (I) or a pharmaceutically acceptable salt thereof, or a compound disclosed herein or a pharmaceutically acceptable salt thereof, and a further active pharmaceutical ingredient or ingredients, including antibiotic agents. In some examples, if the administration is not simultaneous, the compounds are administered in a close time proximity to each other. Furthermore, it does not matter if the compounds are administered in the same dosage form, e.g. one compound may be administered intravenously and another compound may be administered orally.

In some embodiments, any agent that has antimicrobial activity may be co-administered. Particular examples of such agents are Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified e.g. in WO 2017072062 A1, WO 2019185572 A1 and WO 2019206853 A1, each of which is incorporated herein by reference in its entirety, and Macrolides (erythromycin).

In one aspect, the present disclosure provides a pharmaceutical composition described herein, further comprising an additional therapeutic agent.

In one aspect, the present disclosure provides a pharmaceutical combination comprising a compound of formula (I) described herein and an additional therapeutic agent.

In one embodiment, said additional therapeutic agent is an antibiotic agent.

In one embodiment, said additional therapeutic agent is an antibiotic agent that is useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In one embodiment, said additional therapeutic agent is an antibiotic agent selected from Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified in WO 2017072062 A1, WO 2019185572 A1 and WO 2019206853 A1, and Macrolides (erythromycin).

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

The following abbreviations are used in the present text:
(R)-BINAP=(R)-2,2'-bis(diphenylphosphino)-1,1'-binaphthyl, ACN=acetonitrile, aq.=aqueous, Boc=tert-butyloxycarbonyl, Boc-Glu-OtBu=Boc-L-glutamic acid 1-tert-butyl ester, Boc-Glu(OtBu)-OH=N-α-t.-Boc-L-glutamic acid γ-t.-butyl ester, Boc-Orn(Z)-OH=Nα-Boc-NS-Cbz-L-ornithine, Nα-Boc-NS-Z-L-ornithine, Nδ-Z—Na—Boc-L-ornithine, BrettPhos-Pd-G3=[(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate, CAS=chemical abstracts registration number, $Cs_2CO_3$=cesium carbonate, DCM=dichloromethane, DIAD=diisopropyl azodicarboxylate, DIPEA=ethyl diisopropylamine, DMA=N,N-dimethylacetamide, DMAP=4-(dimethyl amino)-pyridine, DMF=N,N-dimethylformamide, DMSO=dimethylsulfoxide, DMSO-d6=deuterated dimethylsulfoxide, EA=ethyl acetate, EDC=1-ethyl-3-(3-dimethylaminopropyl)carbodiimide, EDCI=1-ethyl-3-(3-dimethylaminopropyl)carbodiimide, EI=electron impact, ESI=electrospray ionization, ESI+=electrospray ionization positive (mode), ESP=electrospray ionization positive (mode), $Et_2O$=diethylether, $Et_3N$=triethylamine, EtOAc=ethyl acetate, EtOH=ethanol, FA=formic acid, Fmoc-Agp(Boc)2-OH=N-α-Fmoc-N,NÆ-γ-di-t.-butoxycarbonyl-L-diaminobutanoic acid, Fmoc-Arg(Boc)2-OH=N-α-Fmoc-N-ω,N-ωÆ-bis-t-butoxycarbonyl-L-arginine, $H_2$=hydrogen, h= hour(s), HATU=1-[bis(dimethylamino)methylene]-1H-1,2,3-triazolo[4,5-b]pyridinium-3-oxide hexafluorophosphate, HCl=hydrochloric acid, HFIP=1,1,1,3,3,3-hexafluoroisopropanol, $H_2O$=water, HOBt=1-hydroxy-1H-benzotriazole, HPLC=high performance liquid chromatography, HV=high vacuum, ISN=ion spray negative (mode), $K_2CO_3$= potassium carbonate, KI=potassium iodide, KOH=potassium hydroxide, $K_3PO_4$=potassium phosphate tribasic, LC-MS= liquid chromatography coupled with mass spectroscopy, LiOH=lithium hydroxide, MeOH=methanol, $MgSO_4$= magnesium sulphate, min=minute(s), mL=milliliter, MS=mass spectrometry, MTBE=tert.-butyl methyl ether, $N_2$=nitrogen, $Na_2CO_3$=sodium carbonate, $Na_2SO_3$=sodium sulfite, $Na_2SO_4$=sodium sulfate, $Na_2S_2O_3$=sodium thiosulfate, $NEt_3$=triethylamine, $NaHCO_3$=sodium hydrogen carbonate, NaOH=sodium hydroxide, $NH_4Cl$=ammonium chloride, $NiCl_2.6H_2O$=nickel(II)chloride hexahydrate, NMO=N-methylmorpholine N-oxide, NMP=N-methyl-2-pyrrolidone, Pd/C=palladium on activated carbon, $Pd_2(dba)_3$=tris(dibenzylideneacetone)dipalladium(0), $PdCl_2(PPh_3)_2$=bis(triphenylphosphine)palladium(II) dichloride, $Pd(dppf)Cl_2$=[1,1'-bis(diphenylphosphino)ferrocene]dichloropalladium(II), $PdCl_2(dppf)\cdot CH_2Cl_2$=[1,1'-bis(diphenylphosphino)ferrocene]dichloropalladium(II) dichloromethane complex, PE= petroleum ether, $PhI(OAc)_2$=(diacetoxyiodo)benzene, PPA= polyphosphoric acid, pTsOH=para toluenesulfonic acid, Rf=retention factor, RM=reaction mixture, RT=room temperature, $SOCl_2$=thionyl chloride, SFC=supercritical fluid chromatography, TBTU=2-(1H-Benzotriazole-1-yl)-1,1,3,3-tetramethylaminium tetrafluoroborate, $T_3P$=propylphosphonic anhydride, t-Bu-X-phos=2-di-tert-butylphosphino-2',4',6'-triisopropylbiphenyl, TEA=triethylamine, TEMPO= (2,2,6,6-tetramethylpiperidin-1-yl)oxyl, TFA=trifluoroacetic acid, THF=tetrahydrofurane, prep-TLC=preparative thin layer chromatography, UV=ultraviolet.

Example 1

N-(3-chloro-4-(4-(piperidine-4-carbonyl)piperazine-1-carbonyl)phenyl)-1-methyl-5-(3-(trifluoromethyl)-1H-pyrazol-4-yl)-1H-imidazole-2-carboxamide hydrochloride

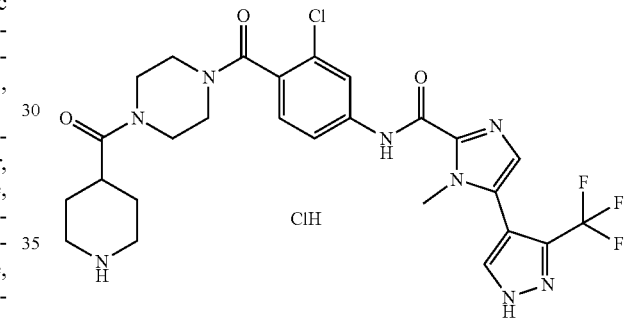

Step 1 tert-butyl 4-(4-amino-2-chloro-benzoyl)piperazine-1-carboxylate

4-Amino-2-chlorobenzoic acid (1.5 g, 8.74 mmol, Eq: 1), tert-butyl piperazine-1-carboxylate (2.44 g, 13.1 mmol, Eq: 1.50) and DIPEA (3.39 g, 4.58 ml, 26.2 mmol, Eq: 3.00) were combined with DMF (8.7 ml) to give a brown solution. HATU (4.99 g, 13.1 mmol, Eq: 1.50) was added, and the reaction mixture was stirred at room temperature overnight. Water was added to the reaction mixture and extracted with EtOAc. After drying over $Na_2SO_4$, filtration and evaporation of the volatiles the product was used in the next step without further purification.

MS (ESI, m/z): 340.2 [M+H]+

Step 2

(4-amino-2-chlorophenyl)(piperazin-1-yl)methanone dihydrochloride tert-Butyl 4-(4-amino-2-chlorobenzoyl)piperazine-1-carboxylate (2.97 g, 8.74 mmol, Eq: 1) was combined with DCM (15 ml) to give a brown solution. HCl 4M in dioxane (10.9 ml, 43.7 mmol, Eq: 5.00) was added (reaction exothermic, control with cooling bath) and the reaction mixture was stirred at RT overnight. Ether was added to reaction mixture, and the solid was filtered and dried under HV to obtain the desired product (5.47 g) as a light brown solid. MS (ESI, m/z): 240.1 [M+H]$^+$ Step 3) tert-butyl 4-(4-(4-amino-2-chlorobenzoyl) piperazine-1-carbonyl)piperidine-1-carboxylate (4-Amino-2-chlorophenyl)(piperazin-1-yl)methanone dihydrochloride (2.7 g, 8.64 mmol, Eq: 1), 1-(tert-butoxycarbonyl)piperidine-4-carboxylic acid (2.18 g, 9.5 mmol, Eq: 1.10) and DIPEA (4.47 g, 6.03 ml, 34.5 mmol, Eq: 4.00) were combined with DMF (10 ml) to give a brown solution. HATU (4.93 g, 13 mmol, Eq: 1.50) was added, and the reaction was stirred at room temperature overnight. Water was added to the reaction mixture and extracted with EtOAc. After drying over Na$_2$SO$_4$, filtration and evaporation of the volatiles, the crude product was dried and used without further purification in the next step. MS (ESI, m/z): 351.2 [M-Boc+H]$^+$ Step 4) tert-butyl 4-(4-(4-(5-bromo-1-methyl-1H-imidazole-2-carboxamido)-2-chlorobenzoyl)piperazine-1-carbonyl)piperidine-1-carboxylate tert-Butyl 4-(4-(4-amino-2-chlorobenzoyl)piperazine-1-carbonyl)piperidine-1-carboxylate (3.8 g, 8.43 mmol, Eq: 1), 5-bromo-1-methyl-1H-imidazole-2-carboxylic acid (CAS 1520621-24-2: 1.81 g, 8.85 mmol, Eq: 1.05) and DIPEA (4.36 g, 5.89 ml, 33.7 mmol, Eq: 4.00) were combined with DMF (10 ml) to give a brown solution. HATU (4.81 g, 12.6 mmol, Eq: 1.50) was added, and the reaction was stirred at RT. Water was added to the reaction mixture and extracted with AcOEt. After drying over Na$_2$SO$_4$, filtration and evaporation of the volatiles, the product was purified by flash chromatography (silica gel, 80 g, 0% to 50% MeOH in DCM) to give the title compound (4.41 g) as a light brown foam.

Step 5 tert-butyl 4-(4-(2-chloro-4-(1-methyl-5-(3-(trifluoromethyl)-1H-pyrazol-4-yl)-1H-imidazole-2-carboxamido)benzoyl)piperazine-1-carbonyl)piperidine-1-carboxylate tert-Butyl 4-(4-(4-(5-bromo-1-methyl-1H-imidazole-2-carboxamido)-2-chlorobenzoyl)piperazine-1-carbonyl)piperidine-1-carboxylate (750 mg, 1.18 mmol, Eq: 1), (3-(trifluoromethyl)-1H-pyrazol-4-yl)boronic acid (317 mg, 1.76 mmol, Eq: 1.50), Na$_2$CO$_3$ (249 mg, 2.35 mmol, Eq: 2.00) and 1,1'-bis(diphenylphosphino)ferrocene-palladium (II)dichloride dichloromethane complex (96 mg, 118 µmol, Eq: 0.10) were combined with dioxane (15 ml) and water (1.5 ml) to give an orange suspension. The reaction was stirred at 100° C. overnight. Additional (3-(trifluoromethyl)-1H-pyrazol-4-yl)boronic acid (211 mg, 1.18 mmol, Eq: 1) and 1,1'-bis(diphenylphosphino)ferrocene-palladium(II)dichloride dichloromethane complex (96 mg, 118 µmol, Eq: 0.10) were added, and the reaction mixture was heated again to 100° C. overnight. Again (3-(trifluoromethyl)-1H-pyrazol-4-yl)boronic acid (211 mg, 1.18 mmol, Eq: 1) and 1,1'-bis(diphenylphosphino)ferrocene-palladium(II)dichloride dichloromethane complex (96 mg, 118 µmol, Eq: 0.10) were added, and the reaction was stirred at 100° C. overnight. After cooling down to RT, the reaction mixture was adsorbed on Isolute-HM-N and purified by flash chromatography (silica gel, 40 g, 0% to 50% MeOH in DCM) to give the title compound (235 mg) as a brown solid. MS (ESI, m/z): 691.6 [M−H]$^-$ Step 6) N-(3-chloro-4-(4-(piperidine-4-carbonyl) piperazine-1-carbonyl)phenyl)-1-methyl-5-(3-(trifluoromethyl)-1H-pyrazol-4-yl)-1H-imidazole-2-carboxamide dihydrochloride tert-Butyl 4-(4-(2-chloro-4-(1-methyl-5-(3-(trifluoromethyl)-1H-pyrazol-4-yl)-1H-imidazole-2-carboxamido)benzoyl)piperazine-1-carbonyl)piperidine-1-carboxylate (28 mg, 40.4 µmol, Eq: 1) was combined with DCM (50 µl) to give a light brown solution. HCl 4M in dioxane (50.5 µl, 202 µmol, Eq: 5.00) was added, and the reaction was stirred at RT for 1.5 h. After removal of the volatiles, the product was lyophilized to give the title compound (25 mg) as a light brown solid.
MS (ESI, m/z): 593.2 [M+H]$^+$ Example 2

N-(3-Chloro-4-(4-(piperidine-4-carbonyl)piperazine-1-carbonyl)phenyl)-1-methyl-5-(1-(2,2,2-trifluoroethyl)-3-(trifluoromethyl)-1H-pyrazol-4-yl)-1H-imidazole-2-carboxamide Hydrochloride

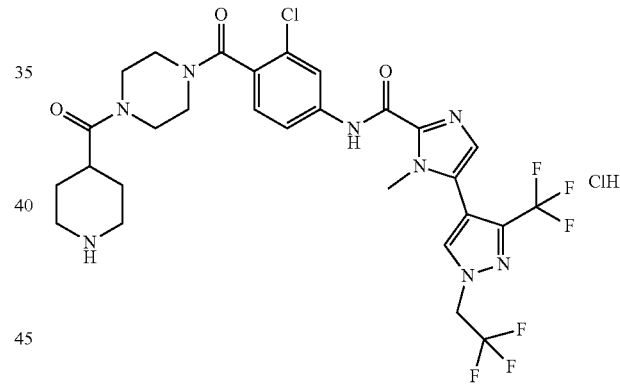

Step 1 tert-Butyl 4-[4-[2-chloro-4-[[1-methyl-5-[1-(2,2,2-trifluoroethyl)-3-(trifluoromethyl)pyrazol-4-yl]imidazole-2-carbonyl]amino]benzoyl]piperazine-1-carbonyl]piperidine-1-carboxylate tert-Butyl 4-(4-(2-chloro-4-(1-methyl-5-(3-(trifluoromethyl)-1H-pyrazol-4-yl)-1H-imidazole-2-carboxamido)benzoyl)piperazine-1-carbonyl)piperidine-1-carboxylate (50 mg, 72.1 µmol, Eq: 1) and K$_2$CO$_3$ (19.9 mg, 144 µmol, Eq: 2.00) were combined with DMF (500 µl) to give a brown suspension. 2-Bromo-1,1,1-trifluoroethane (14 mg, 86.6 µmol, Eq: 1.20) was added, and the reaction mixture was heated to 40° C. and stirred overnight. The stirring was continued at 80° C. for 1 h. and further overnight at 50° C. H$_2$O was added to the mixture and extracted with EtOAc. The combined organic layers were concentrated and the residue was purified by prep. HPLC to give the title product (21 mg). MS (ESI, m/z): 776.6 [M+H]+

Step 2

N-(3-Chloro-4-(4-(piperidine-4-carbonyl)piperazine-1-carbonyl)phenyl)-1-methyl-5-(1-(2,2,2-trifluoroethyl)-3-(trifluoromethyl)-1H-pyrazol-4-yl)-1H-imidazole-2-carboxamide hydrochloride HCl 4M in dioxane (37.5 µl, 150 µmol, Eq: 5) was added to a solution of tert-butyl 4-[4-[2-chloro-4-[[1-methyl-5-[1-(2,2,2-trifluoroethyl)-3-(trifluoromethyl)pyrazol-4-yl]imidazole-2-carbonyl]amino]benzoyl]piperazine-1-carbonyl]piperidine-1-carboxylate (21 mg) in DCM (100 l). The mixture was stirred overnight, additional HCl 4M in dioxane (7 uL) was added and the mixture was stirred again overnight. The mixture was concentrated and dried by lyophilisation to obtain the title compound (17 mg). MS (ESI, m/z): 673.6 [M−H]−

The following Examples were obtained in analogy to the procedures described above:

| Ex. | Name | Structure | ESI MS [M + H]+ | Starting Material |
|---|---|---|---|---|
| 3 | N-[3-chloro-4-[4-(piperidine-4-carbonyl)piperazine-1-carbonyl]phenyl]-1-methyl-5-[1-prop-2-ynyl-3-(trifluoromethyl)pyrazol-4-yl]imidazole-2-carboxamide hydrochloride | 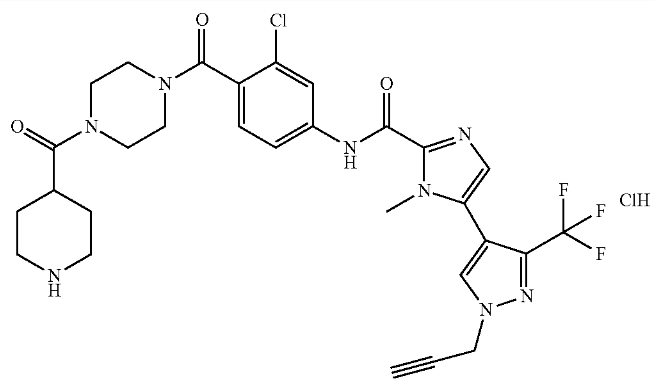 [SMILES: C#CCn1cc(-c2cnc(C(=O)Nc3ccc(C(=O)N4CCN(C(=O)C5CCNCC5)CC4)c(Cl)c3)n2C)c(C(F)(F)F)n1 ; Cl] | 629.6 (M − H)− | Propargyl bromide |
| 4 | 5-(1-(3-amino-3-oxopropyl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide | 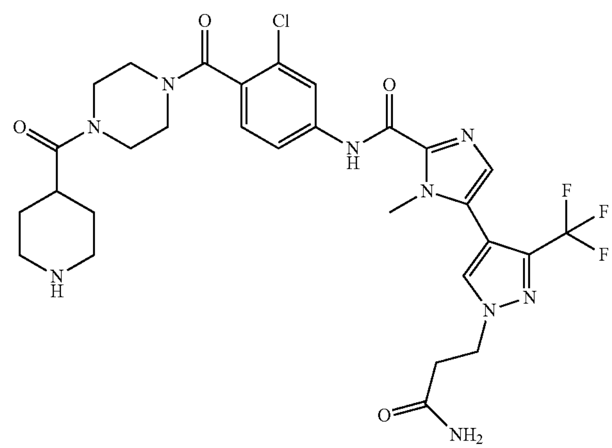 [SMILES: Cn1c(-c2cn(CCC(N)=O)nc2C(F)(F)F)cnc1C(=O)Nc1ccc(C(=O)N2CCN(C(=O)C3CCNCC3)CC2)c(Cl)c1] | 664.4 | 3-bromopropane nitrile, a mixture of Examples 4 and 5 was separated by prep HPLC |
| 5 | N-(3-chloro-4-(4-(piperidine-4-carbonyl)piperazine-1-carbonyl)phenyl)-5-(1-(2-cyanoethyl)-3-(trifluoromethyl)-1H-pyrazol-4-yl)-1-methyl-1H-imidazole-2-carboxamide separated by | 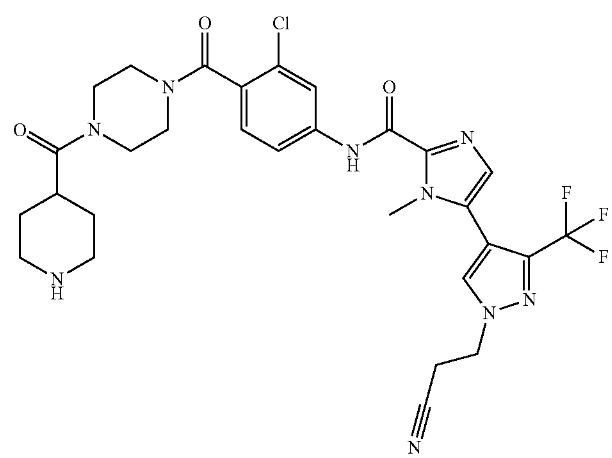 [SMILES: Cn1c(-c2cn(CCC#N)nc2C(F)(F)F)cnc1C(=O)Nc1ccc(C(=O)N2CCN(C(=O)C3CCNCC3)CC2)c(Cl)c1] | 646.4 | bromopropane nitrile, a mixture of Examples 4 and 5 was separated by prep HPLC |

-continued

| Ex. | Name | Structure | ESI MS [M + H]+ | Starting Material |
|---|---|---|---|---|
| 6 | N-(3-chloro-4-(4-(piperidine-4-carbonyl)piperazine-1-carbonyl)phenyl)-5-(1-(4-hydroxybut-2-yn-1-yl)-3-(trifluoromethyl)-1H-pyrazol-4-yl)-1-methyl-1H-imidazole-2-carboxamide hydrochloride | 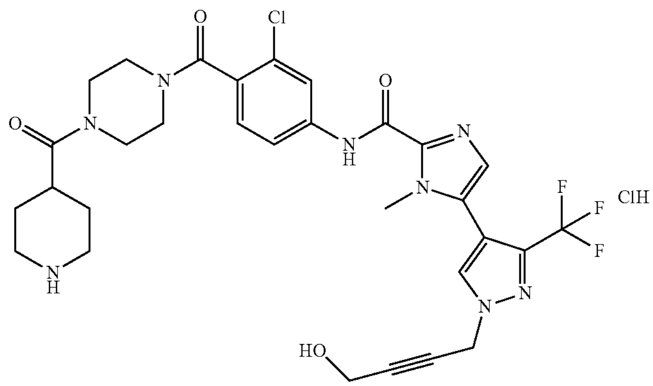 [SMILES: Cn1c(-c2cn(CC#CCO)nc2C(F)(F)F)cnc1C(=O)Nc1ccc(C(=O)N2CCN(C(=O)C3CCNCC3)CC2)c(Cl)c1 ; Cl] | 662.4 | 4-chlorobut-2-yn-1-ol |
| 7 | 5-(1-allyl-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide hydrochloride | 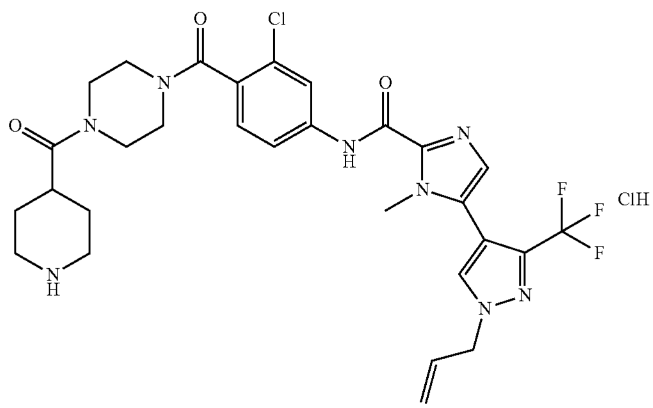 [SMILES: C=CCn1cc(-c2cnc(C(=O)Nc3ccc(C(=O)N4CCN(C(=O)C5CCNCC5)CC4)c(Cl)c3)n2C)c(C(F)(F)F)n1 ; Cl] | 634.4 | 3-bromoprop-1-ene |
| 8 | 5-(1-(but-2-yn-1-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide hydrochloride | 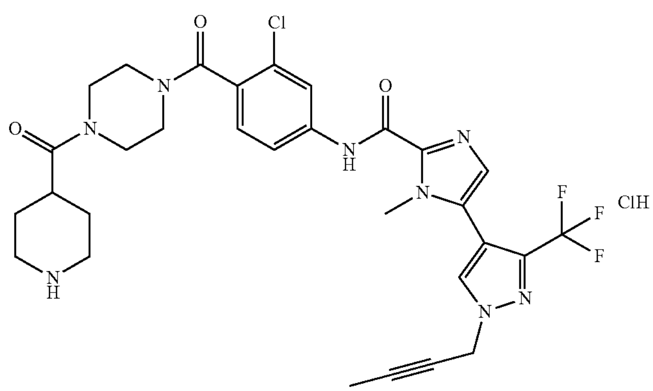 [SMILES: CC#CCn1cc(-c2cnc(C(=O)Nc3ccc(C(=O)N4CCN(C(=O)C5CCNCC5)CC4)c(Cl)c3)n2C)c(C(F)(F)F)n1 ; Cl] | 646.3 | 1-bromobut-2-yne |
| 9 | 5-(1-(but-3-yn-2-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide hydrochloride | 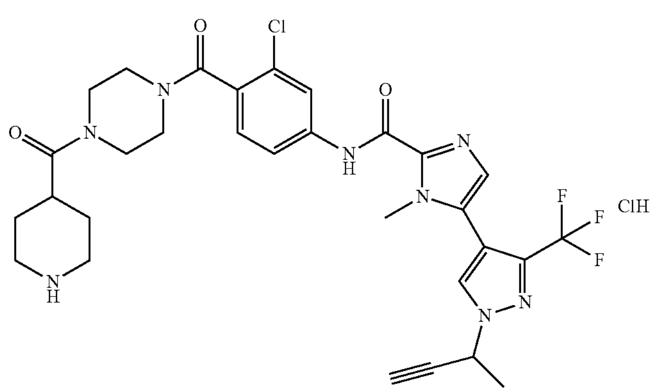 [SMILES: C#CC(C)n1cc(-c2cnc(C(=O)Nc3ccc(C(=O)N4CCN(C(=O)C5CCNCC5)CC4)c(Cl)c3)n2C)c(C(F)(F)F)n1 ; Cl] | 646.4 | 3-bromobut-1-yne |

| Ex. | Name | Structure | ESI MS [M + H]+ | Starting Material |
|---|---|---|---|---|
| 10 | N-(3-chloro-4-(4-(piperidine-4-carbonyl)piperazine-1-carbonyl)phenyl)-5-(1-cyclobutyl-3-(trifluoromethyl)-1H-pyrazol-4-yl)-1-methyl-1H-imidazole-2-carboxamide hydrochloride | 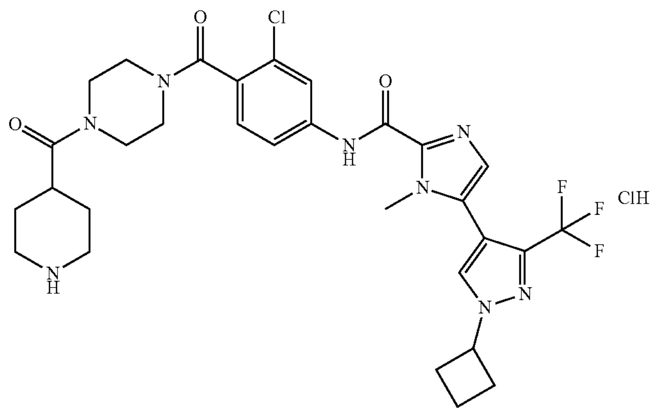 [SMILES: Cn1c(-c2cn(C3CCC3)nc2C(F)(F)F)cnc1C(=O)Nc1ccc(C(=O)N2CCN(C(=O)C3CCNCC3)CC2)c(Cl)c1 ; Cl] | 648.4 | bromocyclobutane |
| 11 | N-(3-chloro-4-(4-(piperidine-4-carbonyl)piperazine-1-carbonyl)phenyl)-5-(1-(2-fluoroethyl)-3-(trifluoromethyl)-1H-pyrazol-4-yl)-1-methyl-1H-imidazole-2-carboxamide hydrochloride | 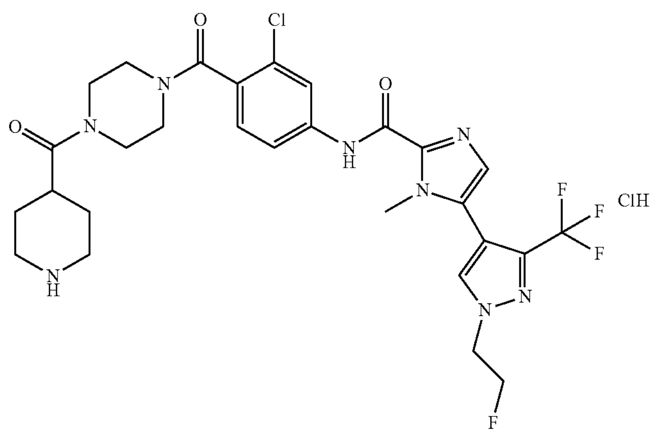 [SMILES: Cn1c(-c2cn(CCF)nc2C(F)(F)F)cnc1C(=O)Nc1ccc(C(=O)N2CCN(C(=O)C3CCNCC3)CC2)c(Cl)c1 ; Cl] | 640.4 | 1-bromo-2-fluoroethane |
| 12 | N-(3-chloro-4-(4-(piperidine-4-carbonyl)piperazine-1-carbonyl)phenyl)-5-(1-(2,2-difluoroethyl)-3-(trifluoromethyl)-1H-pyrazol-4-yl)-1-methyl-1H-imidazole-2-carboxamide hydrochloride | 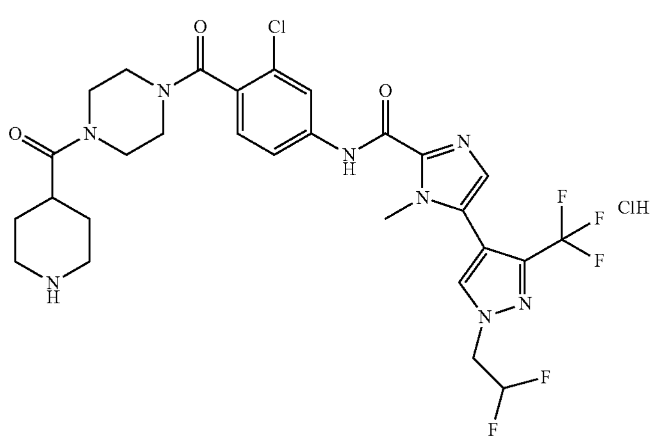 [SMILES: Cn1c(-c2cn(CC(F)F)nc2C(F)(F)F)cnc1C(=O)Nc1ccc(C(=O)N2CCN(C(=O)C3CCNCC3)CC2)c(Cl)c1 ; Cl] | 658.4 | 1-chloro-2-methylpropan-2-ol |

-continued

| Ex. | Name | Structure | ESI MS [M + H]+ | Starting Material |
|---|---|---|---|---|
| 13 | N-(3-chloro-4-(4-(1-methylpiperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide | 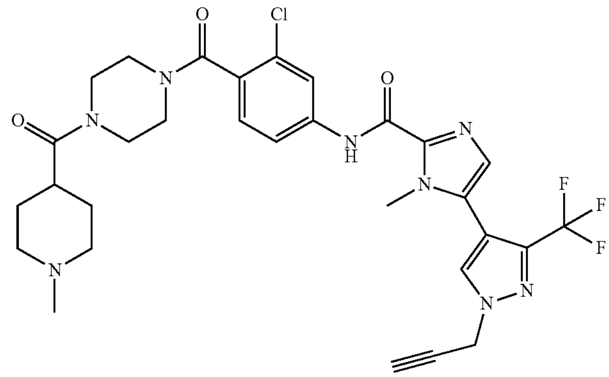 | 645.2 | Example 14 and propargyl bromide, no deprotection |
| 15 | N-(3-chloro-4-(4-(1-methylpiperidine-4-carbonyl)piperazine-1-carbonyl)phenyl)-5-(1-(cyanomethyl)-3-(trifluoromethyl)-1H-pyrazol-4-yl)-1-methyl-1H-imidazole-2-carboxamide | 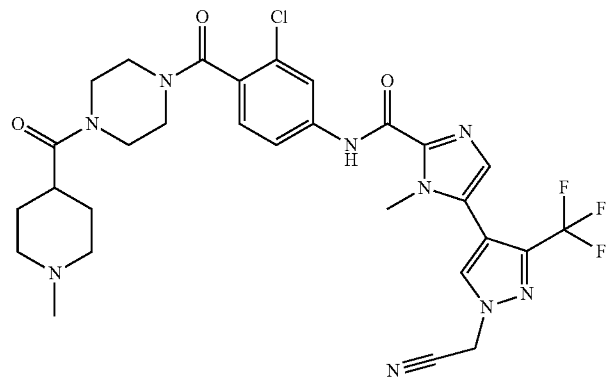 [SMILES: CN1CCC(C(=O)N2CCN(C(=O)c3ccc(NC(=O)c4ncc(-c5cn(CC#N)nc5C(F)(F)F)n4C)cc3Cl)CC2)CC1] | 646.2 | Example 14 and 2-bromoacetonitrile, no deprotection |
| 16 | N-(3-chloro-4-(4-(piperidine-4-carbonyl)piperazine-1-carbonyl)phenyl)-5-(1-(1,1-dioxidothietan-3-yl)-3-(trifluoromethyl)-1H-pyrazol-4-yl)-1-methyl-1H-imidazole-2-carboxamide | 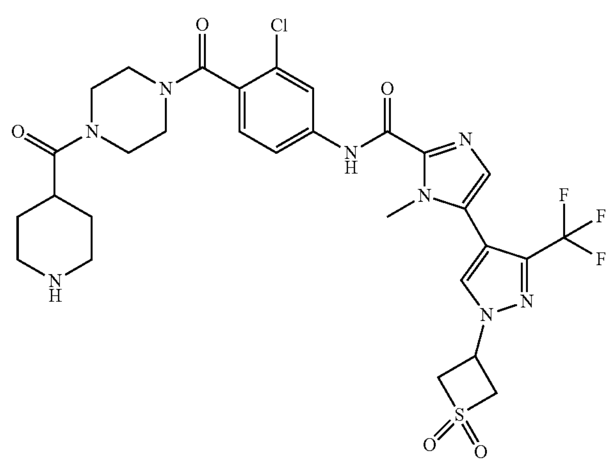 [SMILES: Cn1c(-c2cn(C3CS(=O)(=O)C3)nc2C(F)(F)F)cnc1C(=O)Nc1ccc(C(=O)N2CCN(C(=O)C3CCNCC3)CC2)c(Cl)c1] | 697.2 | 3-bromothietane 1,1-dioxide |

| Ex. | Name | Structure | ESI MS [M + H]+ | Starting Material |
|---|---|---|---|---|
| 17 | 5-(1-(4-aminobut-2-yn-1-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide dihydrochloride | 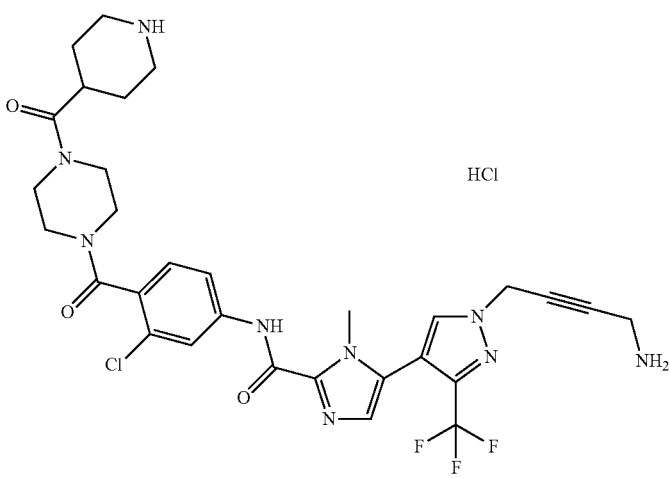 [SMILES: Cn1c(-c2cn(CC#CCN)nc2C(F)(F)F)cnc1C(=O)Nc1ccc(C(=O)N2CCN(C(=O)C3CCNCC3)CC2)c(Cl)c1 ; Cl] | 660.2 | tert-butyl (4-chlorobut-2-yn-1-yl)carbamate |
| 18 | N-(3-chloro-4-(4-(piperidine-4-carbonyl)piperazine-1-carbonyl)phenyl)-5-(1-(4-methoxybut-2-yn-1-yl)-3-(trifluoromethyl)-1H-pyrazol-4-yl)-1-methyl-1H-imidazole-2-carboxamide hydrochloride | 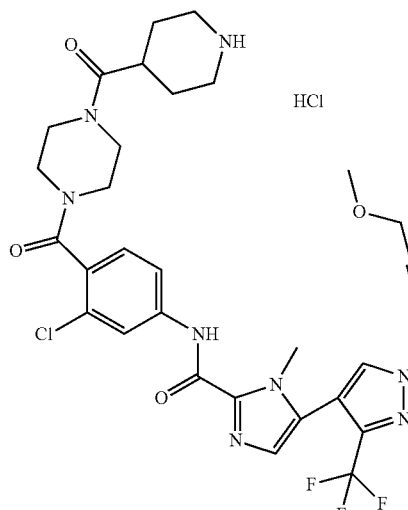 | 675.2 | 1-chloro-4-methoxybut-2-yne |
| 19 | N-(3-chloro-4-(4-(piperidine-4-carbonyl)piperazine-1-carbonyl)phenyl)-1-methyl-5-(1-(pent-2-yn-1-yl)-3-(trifluoromethyl)-1H-pyrazol-4-yl)-1H-imidazole-2-carboxamide hydrochloride | 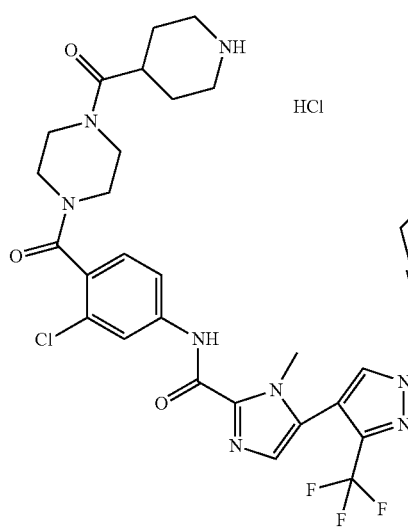 | 659.2 | 1-bromopent-2-yne |

-continued

| Ex. | Name | Structure | ESI MS [M + H]+ | Starting Material |
|---|---|---|---|---|
| 20 | 5-(1-(2-amino-2-oxoethyl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide formate | 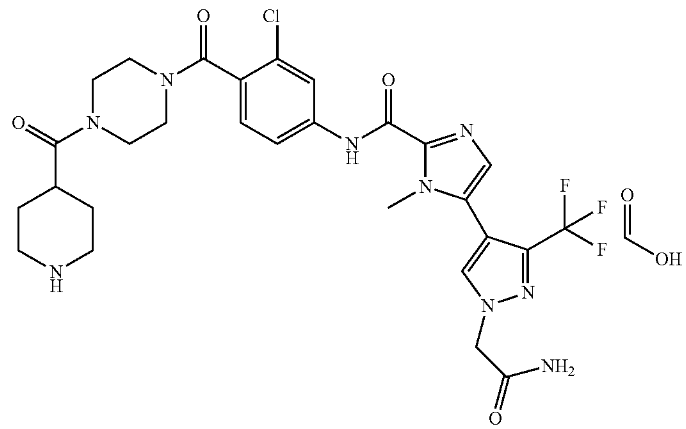 | 650.2 | 2-bromoacetamide |
| 21 | N-(3-chloro-4-(4-(piperidine-4-carbonyl)piperazine-1-carbonyl)phenyl)-5-(1-(2-(dimethylamino)-2-oxoethyl)-3-(trifluoromethyl)-1H-pyrazol-4-yl)-1-methyl-1H-imidazole-2-carboxamide formate | 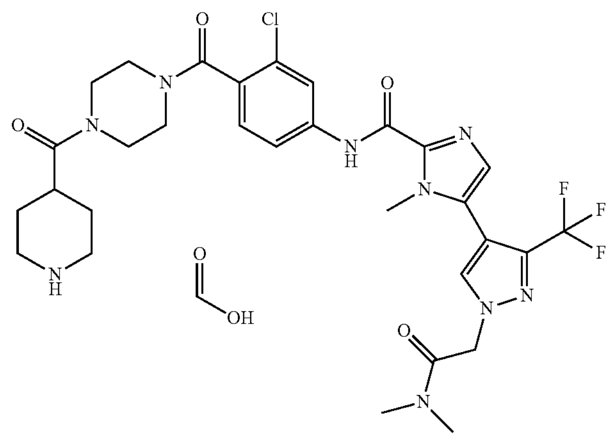 [SMILES: CN(C)C(=O)Cn1cc(-c2cnc(C(=O)Nc3ccc(C(=O)N4CCN(C(=O)C5CCNCC5)CC4)c(Cl)c3)n2C)c(C(F)(F)F)n1 ; O=CO] | 678.3 | 2-chloro-N,N-dimethylacetamide |
| 22 | 5-(1-(1-amino-1-oxopropan-2-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide formate | 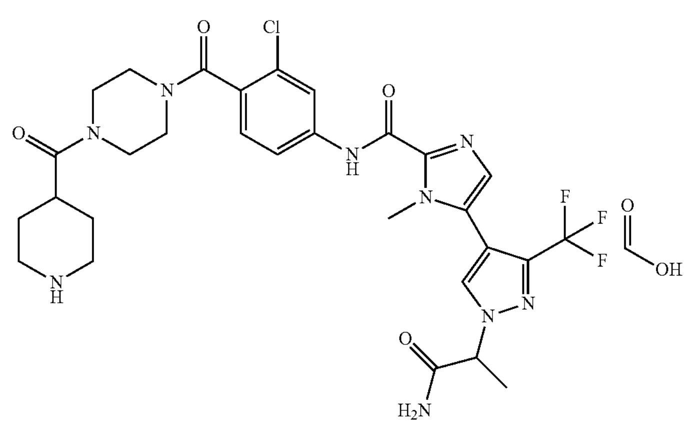 | 664.2 | 2-bromopropanamide |

| Ex. | Name | Structure | ESI MS [M + H]+ | Starting Material |
|---|---|---|---|---|
| 23 | 5-(1-(2-(1H-pyrazol-1-yl)ethyl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide formate | 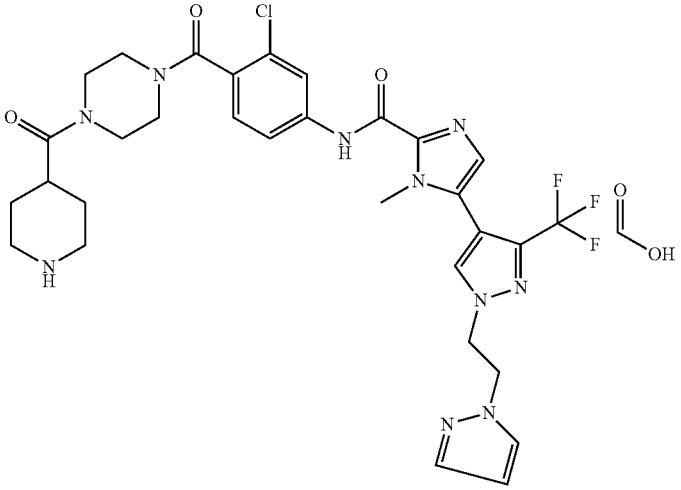 | 687.3 | 1-(2-bromoethyl)-1H-pyrazole |
| 24 | N-(3-chloro-4-(4-(piperidine-4-carbonyl)piperazine-1-carbonyl)phenyl)-5-(1-(2-(isopropylamino)-2-oxoethyl)-3-(trifluoromethyl)-1H-pyrazol-4-yl)-1-methyl-1H-imidazole-2-carboxamide formate | 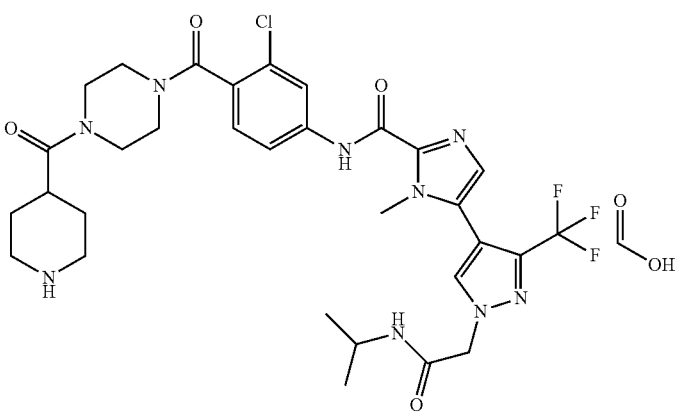 | 692.3 | 2-bromo-N-isopropyl-acetamide |
| 25 | N-(3-chloro-4-(4-(piperidine-4-carbonyl)piperazine-1-carbonyl)phenyl)-5-(1-(2-(2-methoxyethoxy)ethyl)-3-(trifluoromethyl)-1H-pyrazol-4-yl)-1-methyl-1H-imidazole-2-carboxamide | 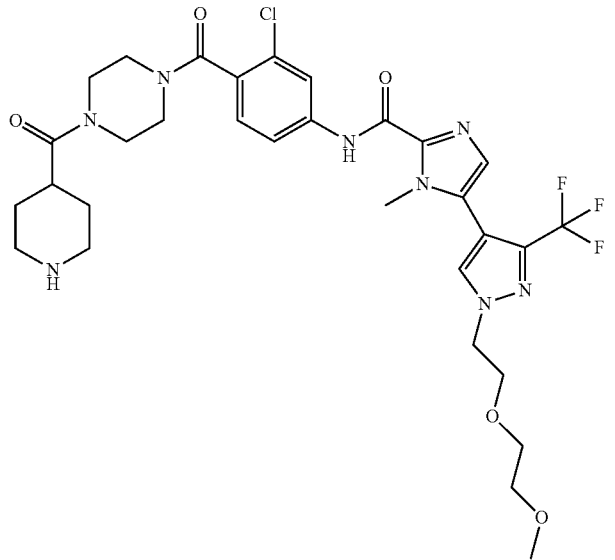 [SMILES: COCCOCCn1cc(-c2cnc(C(=O)Nc3ccc(C(=O)N4CCN(C(=O)C5CCNCC5)CC4)c(Cl)c3)n2C)c(C(F)(F)F)n1] | 695.3 | 1-bromo-2-(2-methoxyethoxy)ethane |

-continued

| Ex. | Name | Structure | ESI MS [M + H]+ | Starting Material |
|---|---|---|---|---|
| 26 | N-(3-chloro-4-(4-(piperidine-4-carbonyl)piperazine-1-carbonyl)phenyl)-5-(1-(1-cyclopropyl-2-oxopyrrolidin-3-yl)-3-(trifluoromethyl)-1H-pyrazol-4-yl)-1-methyl-1H-imidazole-2-carboxamide formate | 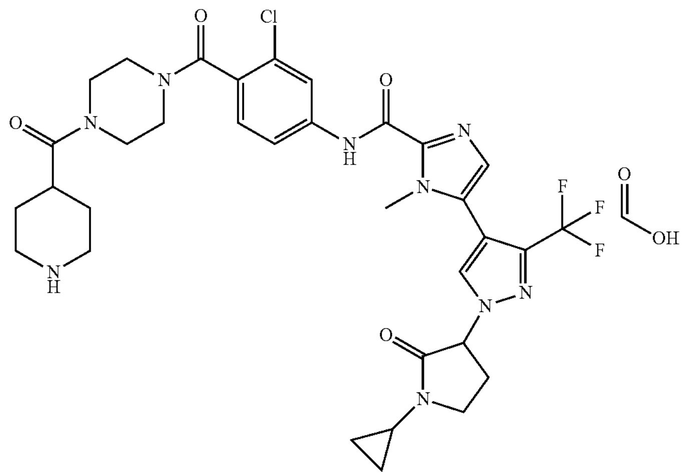 | 716.3 | 3-bromo-1-cyclopropylpyrrolidin-2-one |
| 27 | N-(3-chloro-4-(4-(piperidine-4-carbonyl)piperazine-1-carbonyl)phenyl)-5-(1-isobutyl-3-(trifluoromethyl)-1H-pyrazol-4-yl)-1-methyl-1H-imidazole-2-carboxamide | 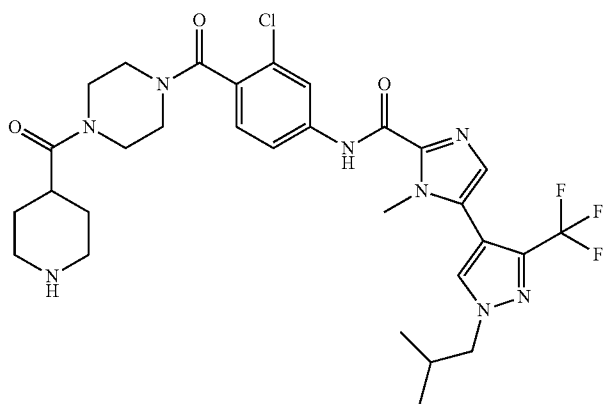 [SMILES: CC(C)Cn1cc(-c2cnc(C(=O)Nc3ccc(C(=O)N4CCN(C(=O)C5CCNCC5)CC4)c(Cl)c3)n2C)c(C(F)(F)F)n1] | 649.2 | 1-bromo-2-methylpropane |
| 28 | N-(3-chloro-4-(4-(piperidine-4-carbonyl)piperazine-1-carbonyl)phenyl)-1-methyl-5-(1-(2-(methylamino)-2-oxoethyl)-3-(trifluoromethyl)-1H-pyrazol-4-yl)-1H-imidazole-2-carboxamide formate | 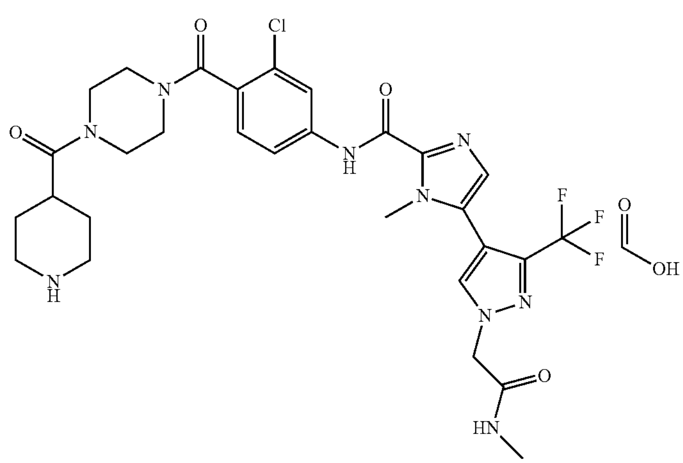 | 664.2 | 2-chloro-N-methylacetamide |

Example 29

1-Methyl-N-(3-methyl-4-(4-(piperidine-4-carbonyl)piperazine-1-carbonyl)phenyl)-5-(3-(trifluoromethyl)-1H-pyrazol-4-yl)-1H-imidazole-2-carboxamide dihydrochloride

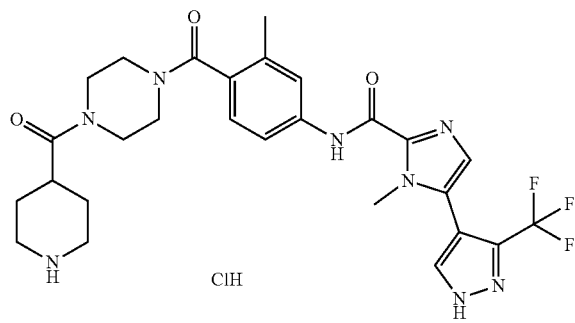 [SMILES: Cc1cc(NC(=O)c2ncc(-c3c[nH]nc3C(F)(F)F)n2C)ccc1C(=O)N1CCN(C(=O)C2CCNCC2)CC1 ; Cl]

Step 1 tert-Butyl 4-(4-(2-methyl-4-(1-methyl-5-(3-(trifluoromethyl)-1H-pyrazol-4-yl)-1H-imidazole-2-carboxamido)benzoyl)piperazine-1-carbonyl)piperidine-1-carboxylate The title compound (370 mg) was obtained as a brown solid in in analogy to Example 1, Steps 1-5 from 4-amino-2-methyl-benzoic acid. MS (ESI, m/z): 671.6 [M−H]⁻

Step 2

1-methyl-N-(3-methyl-4-(4-(piperidine-4-carbonyl)piperazine-1-carbonyl)phenyl)-5-(3-(trifluoromethyl)-1H-pyrazol-4-yl)-1H-imidazole-2-carboxamide dihydrochloride The title compound (28.8 mg) was obtained as a light brown solid in analogy to Example 1, Step 6 from tert-butyl 4-(4-(2-methyl-4-(1-methyl-5-(3-(trifluoromethyl)-1H-pyrazol-4-yl)-1H-imidazole-2-carboxamido)benzoyl)piperazine-1-carbonyl)piperidine-1-carboxylate. MS (ESI, m/z): 573.3 [M+H]⁺

Example 30

5-(1-(cyanomethyl)-3-(trifluoromethyl)-1H-pyrazol-4-yl)-1-methyl-N-(3-methyl-4-(4-(piperidine-4-carbonyl)piperazine-1-carbonyl)phenyl)-1H-imidazole-2-carboxamide

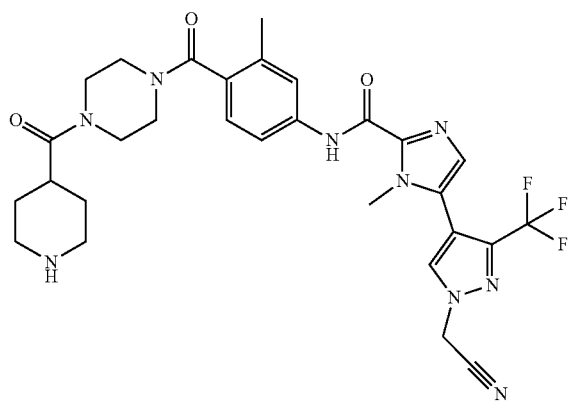 [SMILES: Cc1cc(NC(=O)c2ncc(-c3cn(CC#N)nc3C(F)(F)F)n2C)ccc1C(=O)N1CCN(C(=O)C2CCNCC2)CC1]

The title compound (43 mg) was obtained as a white solid from tert-butyl 4-(4-(2-methyl-4-(1-methyl-5-(3-(trifluoromethyl)-1H-pyrazol-4-yl)-1H-imidazole-2-carboxamido)benzoyl) piperazine-1-carbonyl)piperidine-1-carboxylate and 2-bromoacetonitrile in analogy to Example 2. The acidic reaction mixture after deprotection was poured into water, neutralized with ammonia and extracted with DCM/iPrOH 6:1 before purification with prep HPLC. MS (ESI, m/z): 612.5 [M+H]⁺

Example 31

(R)-N-(3-Chloro-4-((pyrrolidin-3-ylmethyl)carbamoyl)phenyl)-1-methyl-5-(1-(prop-2-yn-1-yl)-3-(trifluoromethyl)-1H-pyrazol-4-yl)-1H-imidazole-2-carboxamide hydrochloride

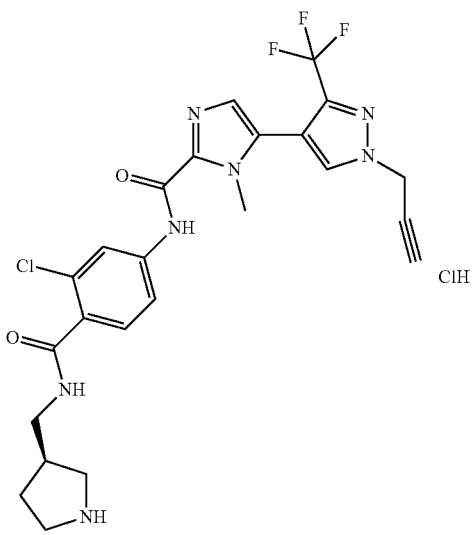 [SMILES: C#CCn1cc(-c2cnc(C(=O)Nc3ccc(C(=O)NC[C@@H]4CCNC4)c(Cl)c3)n2C)c(C(F)(F)F)n1 ; Cl]

Step 1

Methyl 4-(5-bromo-1-methyl-1H-imidazole-2-carboxamido)-2-chlorobenzoate

5-Bromo-1-methyl-1H-imidazole-2-carboxylic acid (CAS 1520621-24-2, 2.8 g, 13.7 mmol, Eq: 1), methyl 4-amino-2-chlorobenzoate (2.53 g, 13.7 mmol, Eq: 1), HATU (6.23 g, 16.4 mmol, Eq: 1.2) were dissolved in DMF (20 ml) and cooled to 0° C. DIPEA (7.06 g, 9.54 ml, 54.6 mmol, Eq: 4) was added and the reaction mixture was stirred at r.t for 3 h. The mixture was cooled to 0° C. and water was added. The mixture was filtered to obtain the desired product (4.35 g) as an off-white solid. MS (ESI, m/z): 372.2 [M+H]⁺

Step 2

Methyl 2-chloro-4-(1-methyl-5-(3-(trifluoromethyl)-1H-pyrazol-4-yl)-1H-imidazole-2-carboxamido)benzoate Methyl 4-(5-bromo-1-methyl-1H-imidazole-2-carboxamido)-2-chlorobenzoate (3.3 g, 8.86 mmol, Eq: 1), (3-(trifluoromethyl)-1H-pyrazol-4-yl)boronic acid (1.59 g, 8.86 mmol, Eq: 1) and Na₂CO₃ (2.16 g, 20.4 mmol, Eq: 2.30) were solved in in dioxane (20 ml) and water (2 ml)).

1,1'-bis(di-tert-butylphosphino)ferrocene palladium dichloride (577 mg, 886 µmol, Eq: 0.1) was added. The solution was split into 3 25 ml microwave sealed tubes, and each was heated in a microwave at 100° C. for 30 min. Additional (3-(trifluoromethyl)-1H-pyrazol-4-yl)boronic acid (797 mg, 4.43 mmol, Eq: 0.5) and 1,1'-bis(di-tert-butylphosphino)ferrocene palladium dichloride (289 mg, 443 µmol, Eq: 0.05) were individually added to the three vials. The reaction mixtures were combined, filtered over Celite and washed with MeOH. The product was purified by chromatography (silica gel, 120 g, 0% to 10% MeOH in DCM) to afford the title compound (2.85 g) as a brown solid.

MS (ESI, m/z): 428.2 [M+H]$^+$

Step 3) Intermediate 2

2-chloro-4-(1-methyl-5-(3-(trifluoromethyl)-1H-pyrazol-4-yl)-1H-imidazole-2-carboxamido)benzoic acid Methyl 2-chloro-4-(1-methyl-5-(3-(trifluoromethyl)-1H-pyrazol-4-yl)-1H-imidazole-2-carboxamido)benzoate (2.8 g, 6.55 mmol, Eq: 1) and lithium hydroxide hydrate (549 mg, 13.1 mmol, Eq: 2) were dissolved in THF (20 ml) and water (10 ml). The mixture was stirred at RT overnight. The organic solvent was evaporated in vacuo. HCl (1.0 M aq) (13.1 ml, 13.1 mmol, Eq: 2) was added adjusting the pH was to 3. The desired product (2.5 g) precipitated as a light brown solid, was filtered and washed with diethyl ether. MS (ESI, m/z): 414.2 [M+H]$^+$ The following Intermediates were prepared in analogy:

| Int. | Name | ESI MS [M + H]$^+$ | Starting Material |
|---|---|---|---|
| 1 | 2-methyl-4-(1-methyl-5-(3-(trifluoromethyl)-1H-pyrazol-4-yl)-1H-imidazole-2-carboxamido)benzoic acid | 394.2 | methyl 4-amino-2-methyl-benzoate |

Step 4) tert-Butyl (S)-3-((2-chloro-4-(1-methyl-5-(1-(prop-2-yn-1-yl)-3-(trifluoromethyl)-1H-pyrazol-4-yl)-1H-imidazole-2-carboxamido)benzamido)methyl)pyrrolidine-1-carboxylate In a 5 mL sealed tube, 2-chloro-4-(1-methyl-5-(3-(trifluoromethyl)-1H-pyrazol-4-yl)-1H-imidazole-2-carboxamido)benzoic acid (50 mg, 121 µmol, Eq: 1) and DIPEA (46.9 mg, 63.3 µl, 363 µmol, Eq: 3.00) were combined with DMF (500 µl) to give a brown suspension. HATU (59.7 mg, 157 µmol, Eq: 1.30) was added, followed, after stirring for 10 min, by addition of tert-butyl (S)-3-(aminomethyl)pyrrolidine-1-carboxylate (29 mg). The reaction mixture was stirred at RT for 2 h. Then water was added and the product extracted with DCM. After removal of the volatiles, the intermediate was used in the next step without further purification.

Step 5) (R)—N-(3-chloro-4-((pyrrolidin-3-ylmethyl)carbamoyl)phenyl)-1-methyl-5-(1-(prop-2-yn-1-yl)-3-(trifluoromethyl)-1H-pyrazol-4-yl)-1H-imidazole-2-carboxamide hydrochloride The title compound (8 mg) was obtained in analogy to Example 3 from tert-butyl (S)-3-((2-chloro-4-(1-methyl-5-(1-(prop-2-yn-1-yl)-3-(trifluoromethyl)-1H-pyrazol-4-yl)-1H-imidazole-2-carboxamido)benzamido)methyl)pyrrolidine-1-carboxylate. MS (ESI, m/z): 532.4 [M−H]$^−$ The following Examples were obtained in analogy:

| Ex. | Name | | ESI MS [M + H]$^+$ | Starting Material |
|---|---|---|---|---|
| 32 | (S)-N-(3-chloro-4-((pyrrolidin-3-ylmethyl)carbamoyl)phenyl)-1-methyl-5-(1-(prop-2-yn-1-yl)-3-(trifluoromethyl)-1H-pyrazol-4-yl)-1H-imidazole-2-carboxamide hydrochloride | 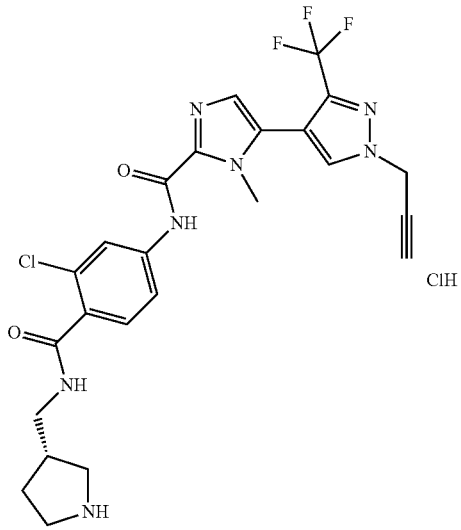 [SMILES: C#CCn1cc(-c2cnc(C(=O)Nc3ccc(C(=O)NC[C@H]4CCNC4)c(Cl)c3)n2C)c(C(F)(F)F)n1 ; Cl] | 532.4 [M − H]$^−$ | (R)-3-(aminomethyl)pyrrolidine-1-carboxylate |

| Ex. | Name | | ESI MS [M + H]+ | Starting Material |
|---|---|---|---|---|
| 33 | N-(3-chloro-4-((((3S,4R)-4-hydroxypyrrolidin-3-yl)methyl)carbamoyl)phenyl)-1-methyl-5-(1-(prop-2-yn-1-yl)-3-(trifluoromethyl)-1H-pyrazol-4-yl)-1H-imidazole-2-carboxamide hydrochloride | 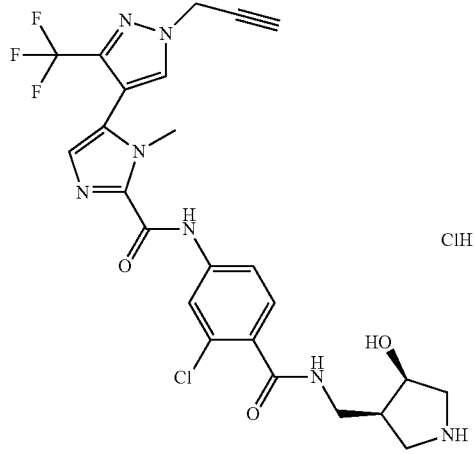 [SMILES: C#CCn1cc(-c2cnc(C(=O)Nc3ccc(C(=O)NC[C@@H]4CNC[C@@H]4O)c(Cl)c3)n2C)c(C(F)(F)F)n1 ; Cl] | 548.4 [M − H]− | tert-butyl (3R,4R)-3-(aminomethyl)-4-hydroxypyrrolidine-1-carboxylate |
| 34 | tert-butyl 4-[2-chloro-4-[[1-methyl-5-[1-prop-2-ynyl-3-(trifluoromethyl)pyrazol-4-yl]imidazole-2-carbonyl]amino]benzoyl]piperazine-1-carboxylate | 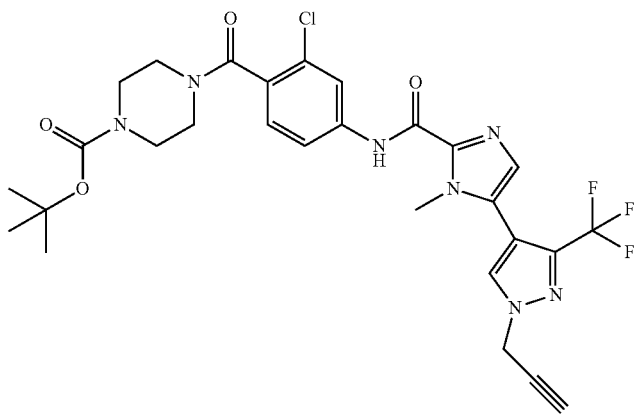 [SMILES: C#CCn1cc(-c2cnc(C(=O)Nc3ccc(C(=O)N4CCN(C(=O)OC(C)(C)C)CC4)c(Cl)c3)n2C)c(C(F)(F)F)n1] | 621.5 | tert-butyl piperazine-1-carboxylate, no deprotection step |
| 35 | N-[3-chloro-4-(piperazine-1-carbonyl)phenyl]-1-methyl-5-[3-(trifluoromethyl)-1H-pyrazol-4-yl]imidazole-2-carboxamide hydrochloride | 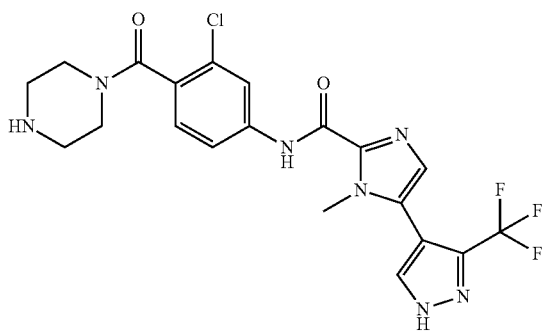 [SMILES: Cn1c(-c2c[nH]nc2C(F)(F)F)cnc1C(=O)Nc1ccc(C(=O)N2CCNCC2)c(Cl)c1] | 518.4 | tert-butyl piperazine-1-carboxylate, no alkylation step |

Example 36

N-[3-Chloro-4-[4-[(2S,4R)-4-hydroxypyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide hydrochloride

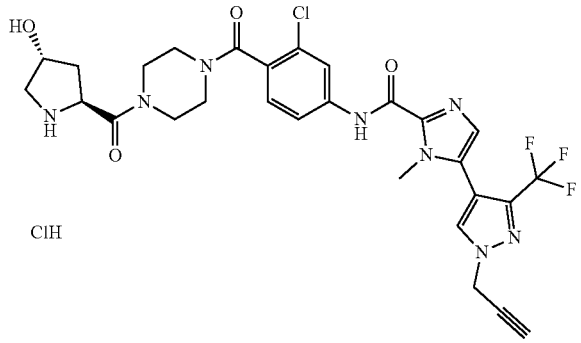 [SMILES: C#CCn1cc(-c2cnc(C(=O)Nc3ccc(C(=O)N4CCN(C(=O)[C@@H]5C[C@@H](O)CN5)CC4)c(Cl)c3)n2C)c(C(F)(F)F)n1 ; Cl]

Step 1

N-(3-Chloro-4-(piperazine-1-carbonyl)phenyl)-1-methyl-5-(1-(prop-2-yn-1-yl)-3-(trifluoromethyl)-1H-pyrazol-4-yl)-1H-imidazole-2-carboxamide 2,2,2-trifluoroacetate tert-Butyl 4-(2-chloro-4-(1-methyl-5-(1-(prop-2-yn-1-yl)-3-(trifluoromethyl)-1H-pyrazol-4-yl)-1H-imidazole-2-carboxamido)benzoyl)piperazine-1-carboxylate (Example 34, 1.15 g, 1.85 mmol, Eq: 1) was dissolved in DCM (12 ml). TFA (2.11 g, 1.43 ml, 18.5 mmol, Eq: 10) was added. The reaction mixture was stirred overnight at RT. The organic solvent was removed was in vacuo. The residue was triturated with diethyl ether. The precipitate was filtered off to afford the crude title compound (1.16 g) as an off-white solid. MS (ESI, m/z): 520.3 [M+H]$^+$

Step 2) tert-Butyl (2S,4R)-2-(4-(2-chloro-4-(1-methyl-5-(1-(prop-2-yn-1-yl)-3-(trifluoromethyl)-1H-pyrazol-4-yl)-1H-imidazole-2-carboxamido)benzoyl)piperazine-1-carbonyl)-4-hydroxypyrrolidine-1-carboxylate HATU (43.9 mg, 115 μmol, Eq: 2) was added to a mixture of N-(3-chloro-4-(piperazine-1-carbonyl)phenyl)-1-methyl-5-(1-(prop-2-yn-1-yl)-3-(trifluoromethyl)-1H-pyrazol-4-yl)-1H-imidazole-2-carboxamide 2,2,2-trifluoroacetate (30 mg), DIPEA (37.3 mg, 50.4 μl, 289 μmol, Eq: 5) and (2S,4R)-1-(tert-butoxycarbonyl)-4-hydroxypyrrolidine-2-carboxylic acid (13 mg) in DMF (400 uL). The mixture was stirred overnight and purified by prep HPLC to give the title compound (14 mg).

Step 3

N-[3-Chloro-4-[4-[(2S,4R)-4-hydroxypyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide; Hydrochloride tert-Butyl tert-butyl (2S,4R)-2-(4-(2-chloro-4-(1-methyl-5-(1-(prop-2-yn-1-yl)-3-(trifluoromethyl)-1H-pyrazol-4-yl)-1H-imidazole-2-carboxamido)benzoyl)piperazine-1-carbonyl)-4-hydroxypyrrolidine-1-carboxylate (12 mg, 16.4 μmol, Eq: 1) was combined with DCM (0.4 ml). HCl 4 M in dioxane (20.5 μl, 81.8 μmol, Eq: 5) was added. The reaction was stirred at RT for 4 h. After removal of the volatiles, the product re-dissolved in water/ACN and then was lyophilized to afford the title compound (9.1 mg) as a white solid. MS (ESI, m/z): 633.4 [M+H]$^+$ The following Examples were obtained in analogy:

| Ex. | Name | | ESI MS [M + H]$^+$ | Starting Material |
|---|---|---|---|---|
| 37 | N-[3-chloro-4-[4-[(3S)-pyrrolidine-3-carbonyl]piperazine-1-carbonyl]phenyl]-1-methyl-5-[1-prop-2-ynyl-3-(trifluoromethyl)pyrazol-4-yl]imidazole-2-carboxamide hydrochloride | 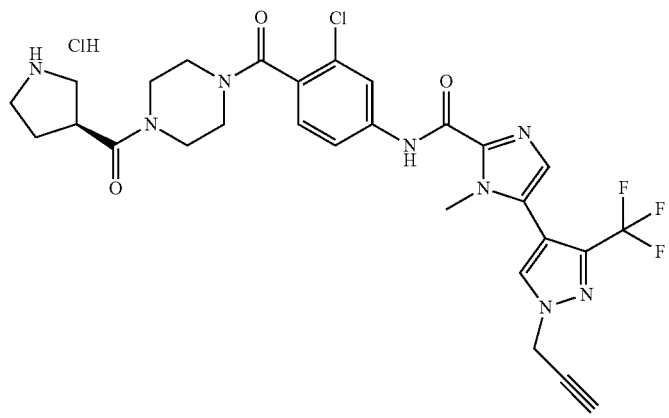 [SMILES: C#CCn1cc(-c2cnc(C(=O)Nc3ccc(C(=O)N4CCN(C(=O)[C@H]5CCNC5)CC4)c(Cl)c3)n2C)c(C(F)(F)F)n1 ; Cl] | 617.4 | (S)-1-(tert-butoxycarbonyl)pyrrolidine-3-carboxylic acid |

| Ex. | Name | | ESI MS [M + H]+ | Starting Material |
|---|---|---|---|---|
| 38 | N-[3-chloro-4-[4-[(2R)-pyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide hydrochloride | 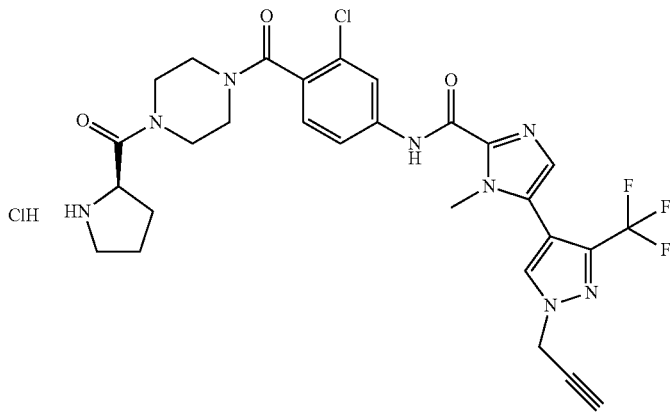 [SMILES: Cl ; C#CCn1cc(-c2cnc(C(=O)Nc3ccc(C(=O)N4CCN(C(=O)[C@H]5CCCN5)CC4)c(Cl)c3)n2C)c(C(F)(F)F)n1] | 617.4 | (tert-butoxycarbonyl)-D-proline |
| 39 | N-[3-chloro-4-[4-(4-hydroxypiperidine-4-carbonyl)piperazine-1-carbonyl]phenyl]-1-methyl-5-[1-prop-2-ynyl-3-(trifluoromethyl)pyrazol-4-yl]imidazole-2-carboxamide hydrochloride | 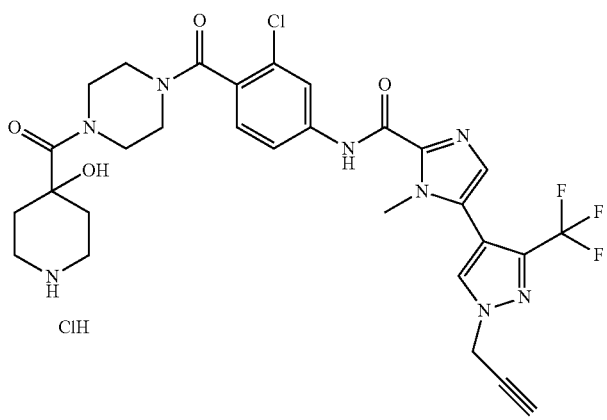 [SMILES: C#CCn1cc(-c2cnc(C(=O)Nc3ccc(C(=O)N4CCN(C(=O)C5(O)CCNCC5)CC4)c(Cl)c3)n2C)c(C(F)(F)F)n1 ; Cl] | 647.4 | 1-(tert-butoxycarbonyl)-4-hydroxypiperidine-4-carboxylic acid |
| 40 | N-(3-chloro-4-(4-((3S,4S)-3-hydroxypiperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide hydrochloride | 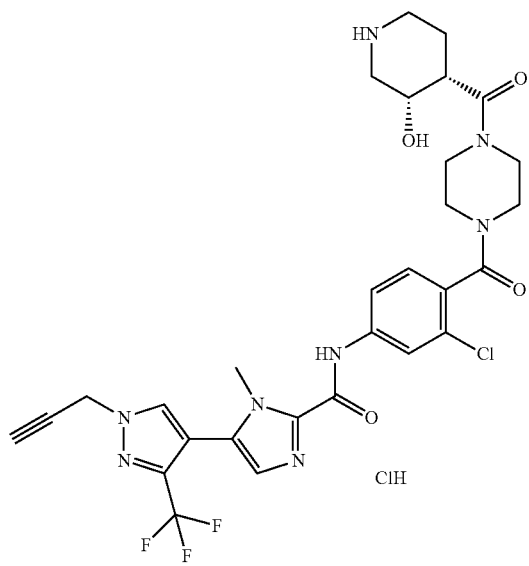 [SMILES: C#CCn1cc(-c2cnc(C(=O)Nc3ccc(C(=O)N4CCN(C(=O)[C@H]5CCNC[C@H]5O)CC4)c(Cl)c3)n2C)c(C(F)(F)F)n1 ; Cl] | 647.2 | (3R,4R)-1-(tert-butoxycarbonyl)-3-hydroxypiperidine-4-carboxylic acid |

Example 41

N-(4-Carbamoyl-3-chlorophenyl)-1-methyl-5-(1-(prop-2-yn-1-yl)-3-(trifluoromethyl)-1H-pyrazol-4-yl)-1H-imidazole-2-carboxamide

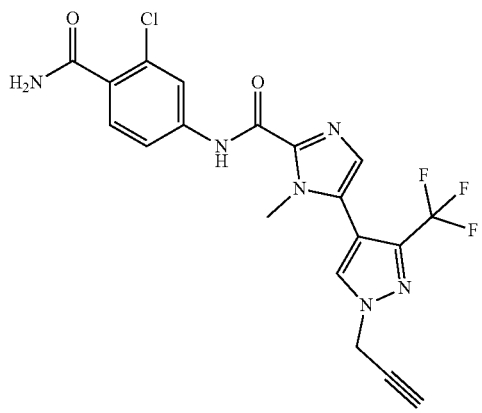 [SMILES: C#CCn1cc(-c2cnc(C(=O)Nc3ccc(C(N)=O)c(Cl)c3)n2C)c(C(F)(F)F)n1]

Step 1 tert-Butyl 2-chloro-4-(1-methyl-5-(3-(trifluoromethyl)-1H-pyrazol-4-yl)-1H-imidazole-2-carboxamido)benzoate The title compound was obtained as an orange solid in analogy to Example 31, Steps 1-2, from tert-butyl 4-amino-2-chlorobenzoate. MS (ESI, m/z): 470.4 [M+H]$^+$

Step 2 tert-butyl 2-chloro-4-(1-methyl-5-(1-(prop-2-yn-1-yl)-3-(trifluoromethyl)-1H-pyrazol-4-yl)-1H-imidazole-2-carboxamido)benzoate tert-Butyl 2-chloro-4-(1-methyl-5-(3-(trifluoromethyl)-1H-pyrazol-4-yl)-1H-imidazole-2-carboxamido)benzoate (470 mg, 1 mmol, Eq: 1) and K$_2$CO$_3$ (276 mg, 2 mmol, Eq: 2.00) were combined with DMF (5 ml) to give a white suspension. 3-Bromoprop-1-yne (119 mg, 89.1 μl, 1 mmol, Eq: 1) was added and the reaction mixture was stirred at RT for 6 h. Additional 3-bromoprop-1-yne (23.8 mg, 17.8 μl, 200 μmol, Eq: 0.2) was added and stirred for 20 min.

The reaction mixture was poured into 25 mL H$_2$O and extracted with EtOAc (3×25 mL) and washed with 25 ml NaCl (sat.). The organic layers were dried over Na$_2$SO$_4$ and concentrated in vacuo. The crude material was purified by flash chromatography (silica gel, 12 g, 0% to 100% DCM:(DCM/MeOH 9/1) to afford the title compound (382.1 mg) as an off-white solid. MS (ESI, m/z): 508.3 [M+H]$^+$

Step 3) Intermediate 3

2-Chloro-4-(1-methyl-5-(1-(prop-2-yn-1-yl)-3-(trifluoromethyl)-1H-pyrazol-4-yl)-1H-imidazole-2-carboxamido)benzoic acid trifluoroacetate tert-Butyl 2-chloro-4-(1-methyl-5-(1-(prop-2-yn-1-yl)-3-(trifluoromethyl)-1H-pyrazol-4-yl)-1H-imidazole-2-carboxamido)benzoate (330 mg, 650 μmol, Eq: 1) was dissolved in DCM (4 ml). TFA (741 mg, 501 μl, 6.5 mmol, Eq: 10) was added. The reaction mixture was stirred overnight at RT. The organic solvent was removed in vacuo. The residue was triturated in diethyl ether. The precipitate was filtered off to afford the crude title compound (260.2 mg) as an off-white solid. MS (ESI, m/z): 450.3 [M+H]$^+$

Step 4

N-(4-Carbamoyl-3-chlorophenyl)-1-methyl-5-(1-(prop-2-yn-1-yl)-3-(trifluoromethyl)-1H-pyrazol-4-yl)-1H-imidazole-2-carboxamide HATU (40 mg) was added to a mixture of 2-chloro-4-(1-methyl-5-(1-(prop-2-yn-1-yl)-3-(trifluoromethyl)-1H-pyrazol-4-yl)-1H-imidazole-2-carboxamido)benzoic acid tifluoroacetate (30 mg), DIPEA (50 uL) and 25% aq NH$_3$ (10 uL) in DMF (400 uL). The mixture was stirred for 4.5 h and then purified by prep. HPLC to afford the title compound (6 mg) as a white solid. MS (ESI, m/z): 451.2 [M+H]$^+$ The following Examples were obtained in analogy:

| Ex. | Name | Structure | ESI MS [M + H]$^+$ | Starting Material |
|---|---|---|---|---|
| 42 | N-(3-chloro-4-(dimethylcarbamoyl)phenyl)-1-methyl-5-(1-(prop-2-yn-1-yl)-3-(trifluoromethyl)-1H-pyrazol-4-yl)-1H-imidazole-2-carboxamide | 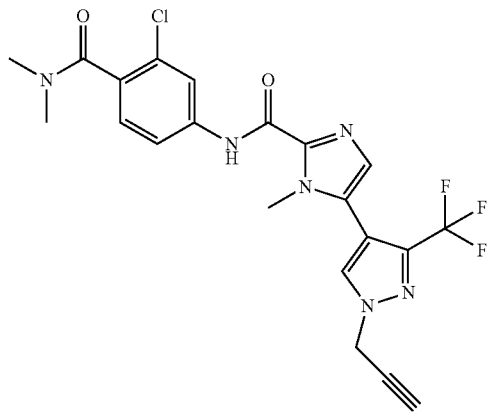 [SMILES: C#CCn1cc(-c2cnc(C(=O)Nc3ccc(C(=O)N(C)C)c(Cl)c3)n2C)c(C(F)(F)F)n1] | 479.2 | Intermediate 3 and dimethylamine |

-continued

| Ex. | Name | Structure | ESI MS [M + H]+ | Starting Material |
|---|---|---|---|---|
| 43 | N-(3-chloro-4-(methylcarbamoyl)phenyl)-1-methyl-5-(1-(prop-2-yn-1-yl)-3-(trifluoromethyl)-1H-pyrazol-4-yl)-1H-imidazole-2-carboxamide | 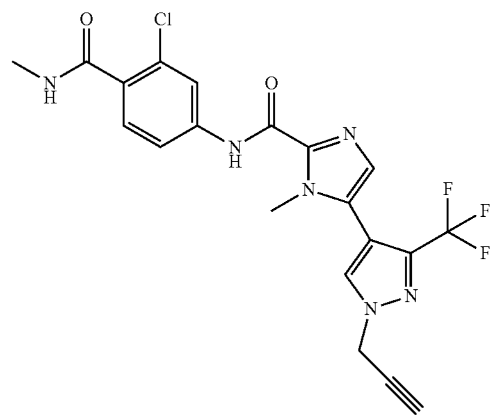 [SMILES: C#CCn1cc(-c2cnc(C(=O)Nc3ccc(C(=O)NC)c(Cl)c3)n2C)c(C(F)(F)F)n1] | 465.2 | Intermediate 3 and methylamine |
| 44 | N-(4-((3-aminopropyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide 2,2,2-trifluoroacetate | 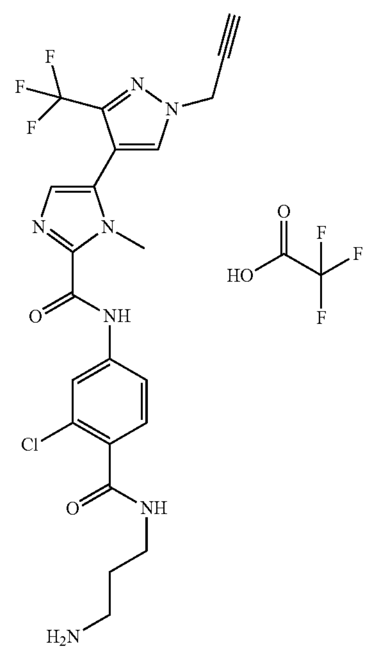 [SMILES: C#CCn1cc(-c2cnc(C(=O)Nc3ccc(C(=O)NCCCN)c(Cl)c3)n2C)c(C(F)(F)F)n1 ; O=C(O)C(F)(F)F] | 508.3 | Intermediate 3 and tert-butyl N-(3-aminopropyl)carbamate, followed by deprotection with TFA |

-continued

| Ex. | Name | Structure | ESI MS [M + H]+ | Starting Material |
|---|---|---|---|---|
| 45 | (R)-N-(4-((2-(2-aminopropoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide 2,2,2-trifluoroacetate | 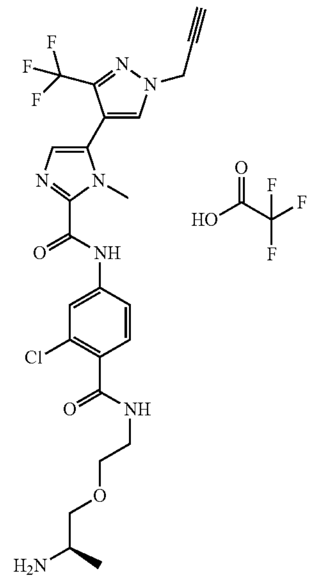 [SMILES: C#CCn1cc(-c2cnc(C(=O)Nc3ccc(C(=O)NCCOC[C@@H](C)N)c(Cl)c3)n2C)c(C(F)(F)F)n1 ; O=C(O)C(F)(F)F] | 552.3 | Intermediate 3 and tert-butyl N-[(1R)-2-(2-aminoethoxy)-1-methyl-ethyl]carbamate, followed by deprotection with TFA |
| 46 | N-(4-((2-(2-amino-2-methylpropoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide 2,2,2-trifluoroacetate | 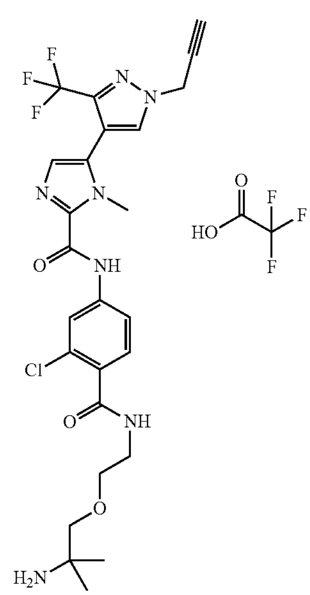 [SMILES: C#CCn1cc(-c2cnc(C(=O)Nc3ccc(C(=O)NCCOCC(C)(C)N)c(Cl)c3)n2C)c(C(F)(F)F)n1 ; O=C(O)C(F)(F)F] | 567.3 | Intermediate 3 and tert-butyl N-[2-(2-aminoethoxy)-1,1-dimethyl-ethyl]carbamate, followed by deprotection with TFA |

-continued

| Ex. | Name | Structure | ESI MS [M + H]+ | Starting Material |
|---|---|---|---|---|
| 47 | (S)-N-(4-((2-(2-aminopropoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide 2,2,2-trifluoroacetate | 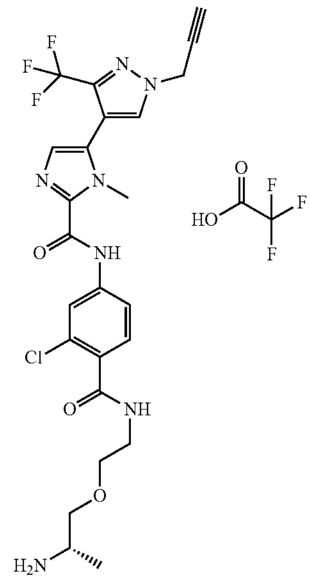 [SMILES: C#CCn1cc(-c2cnc(C(=O)Nc3ccc(C(=O)NCCOC[C@H](C)N)c(Cl)c3)n2C)c(C(F)(F)F)n1 ; O=C(O)C(F)(F)F] | 552.3 | Intermediate 3 and tert-butyl N-[(1S)-2-(2-aminoethoxy)-1-methyl-ethyl]carbamate, followed by deprotection with TFA |
| 48 | N-(4-((2-(2-aminoethoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide trifluoroacetate | 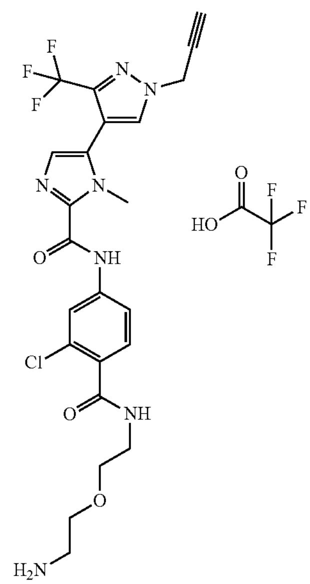 [SMILES: C#CCn1cc(-c2cnc(C(=O)Nc3ccc(C(=O)NCCOCCN)c(Cl)c3)n2C)c(C(F)(F)F)n1 ; O=C(O)C(F)(F)F] | 538.3 | Intermediate 3 and tert-butyl N-[2-(2-aminoethoxy)ethyl]carbamate, followed by TFA deprotection |
| 49 | N-(4-((6-aminohexyl)carbamoyl)-3-methylphenyl)-1-methyl-5-(3-(trifluoromethyl)-1H-pyrazol-4-yl)-1H-imidazole-2-carboxamide hydrochloride | 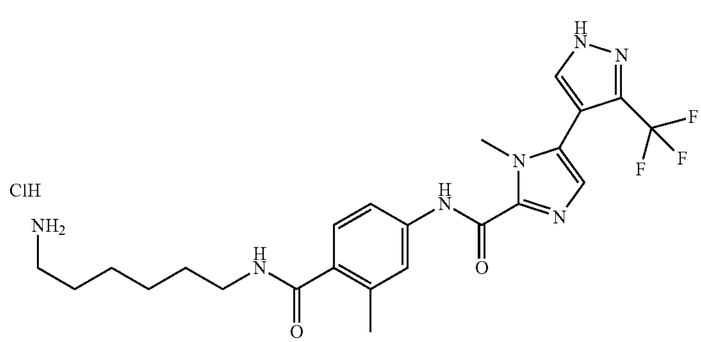 [SMILES: Cl ; Cc1cc(NC(=O)c2ncc(-c3c[nH]nc3C(F)(F)F)n2C)ccc1C(=O)NCCCCCCN] | 492.4 | Intermediate 1 and tert-butyl (6-aminohexyl)carbamate, followed by HCl deprotection |

| Ex. | Name | Structure | ESI MS [M + H]+ | Starting Material |
|---|---|---|---|---|
| 50 | N-(4-((5-aminopentyl)carbamoyl)-3-methylphenyl)-1-methyl-5-(3-(trifluoromethyl)-1H-pyrazol-4-yl)-1H-imidazole-2-carboxamide hydrochloride | 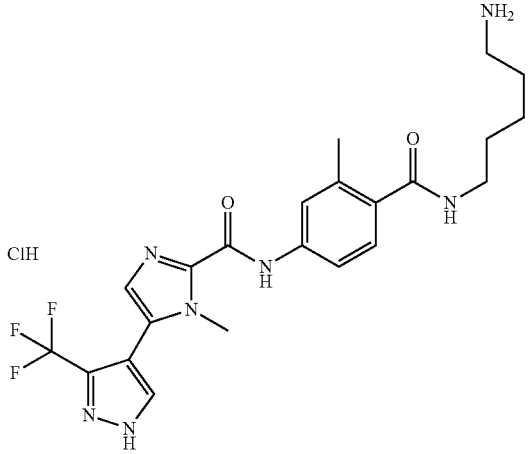 [SMILES: Cl ; Cc1cc(NC(=O)c2ncc(-c3c[nH]nc3C(F)(F)F)n2C)ccc1C(=O)NCCCCCN] | 477.4 | Intermediate 1 and tert-butyl (5-aminopentyl) carbamate, followed by HCl deprotection |
| 14 | N-[3-chloro-4-[4-(1-methylpiperidine-4-carbonyl)piperazine-1-carbonyl]phenyl]-1-methyl-5-[3-(trifluoromethyl)-1H-pyrazol-4-yl]imidazole-2-carboxamide | 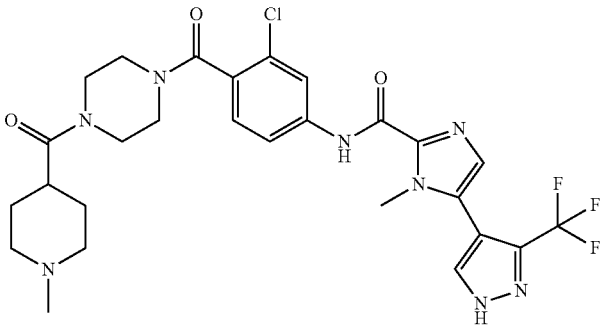 [SMILES: CN1CCC(C(=O)N2CCN(C(=O)c3ccc(NC(=O)c4ncc(-c5c[nH]nc5C(F)(F)F)n4C)cc3Cl)CC2)CC1] | 477.4 | Intermediate 2 and (1-methyl-4-piperidinyl)-1-piperazinyl-methanone (CAS 205059-44-5) |

Example 51

N-(Azetidin-3-yl)-4-(2-chloro-4-(1-methyl-5-(1-(prop-2-yn-1-yl)-3-(trifluoromethyl)-1H-pyrazol-4-yl)-1H-imidazole-2-carboxamido)benzoyl)piperazine-1-carboxamide Hydrochloride

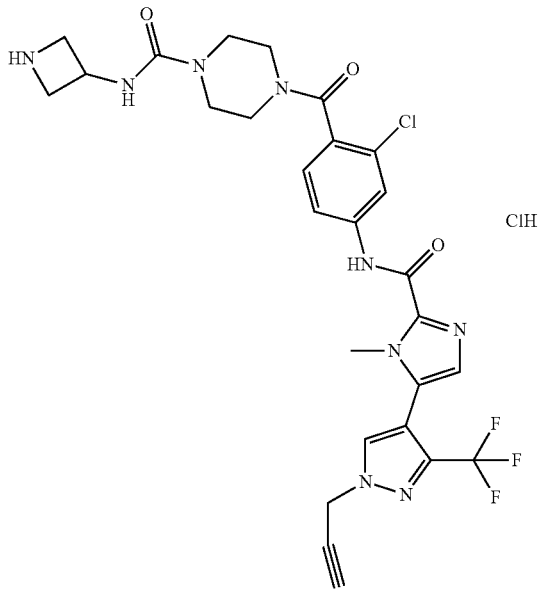 [SMILES: C#CCn1cc(-c2cnc(C(=O)Nc3ccc(C(=O)N4CCN(C(=O)NC5CNC5)CC4)c(Cl)c3)n2C)c(C(F)(F)F)n1 ; Cl]

N-(3-Chloro-4-(piperazine-1-carbonyl)phenyl)-1-methyl-5-(1-(prop-2-yn-1-yl)-3-(trifluoromethyl)-1H-pyrazol-4-yl)-1H-imidazole-2-carboxamide 2,2,2-trifluoroacetate (30 mg, 47.3 µmol, Eq: 1) was combined with DCM (0.5 ml) to give a white suspension. DIPEA (30.6 mg, 41.3 µl, 237 µmol, Eq: 5) was added, followed by triphosgene (5.62 mg, 18.9 µmol, Eq: 0.4. After stirring for 30 min at RT, tert-butyl 3-aminoazetidine-1-carboxylate (24 mg, 142 µmol, Eq: 3) was added. After stirring overnight, additional 2 Eq. DIPEA (17 ul) and tert-butyl 3-aminoazetidine-1-carboxylate (24 mg, 142 µmol, Eq: 3) were added.

The mixture was purified by preparative HPLC to give the Boc protected intermediate (34 mg), which was deprotected with 4N HCl in dioxane/DCM as described in Example 2, step 2 to give the title compound (4.6 mg) as a white solid. MS (ESI, m/z): 618.5 [M+H]$^+$ The following Examples were obtained in analogy:

| Ex. | Name | Structure | ESI MS [M + H]$^+$ | Starting Material |
|---|---|---|---|---|
| 52 | 4-(2-chloro-4-(1-methyl-5-(1-(prop-2-yn-1-yl)-3-(trifluoromethyl)-1H-pyrazol-4-yl)-1H-imidazole-2-carboxamido)benzoyl)-N-((3-hydroxyazetidin-3-yl)methyl)piperazine-1-carboxamide hydrochloride | 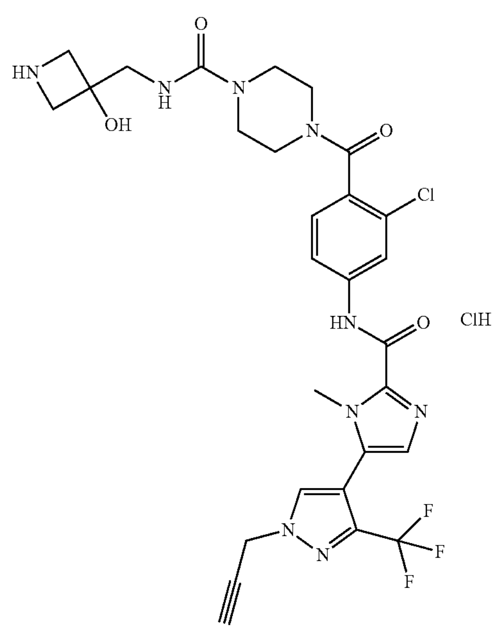 [SMILES: C#CCn1cc(-c2cnc(C(=O)Nc3ccc(C(=O)N4CCN(C(=O)NCC5(O)CNC5)CC4)c(Cl)c3)n2C)c(C(F)(F)F)n1 ; Cl] | 648.5 | tert-butyl 3-(aminomethyl)-3-hydroxy-azetidine-1-carboxylate |

| Ex. | Name | Structure | ESI MS [M + H]+ | Starting Material |
|---|---|---|---|---|
| 53 | (S)-4-(2-chloro-4-(1-methyl-5-[1-(prop-2-yn-1-yl)-3-(trifluoromethyl)-1H-pyrazol-4-yl)-1H-imidazole-2-carboxamido)benzoyl)-N-(pyrrolidin-3-yl)piperazine-1-carboxamide hydrochloride | 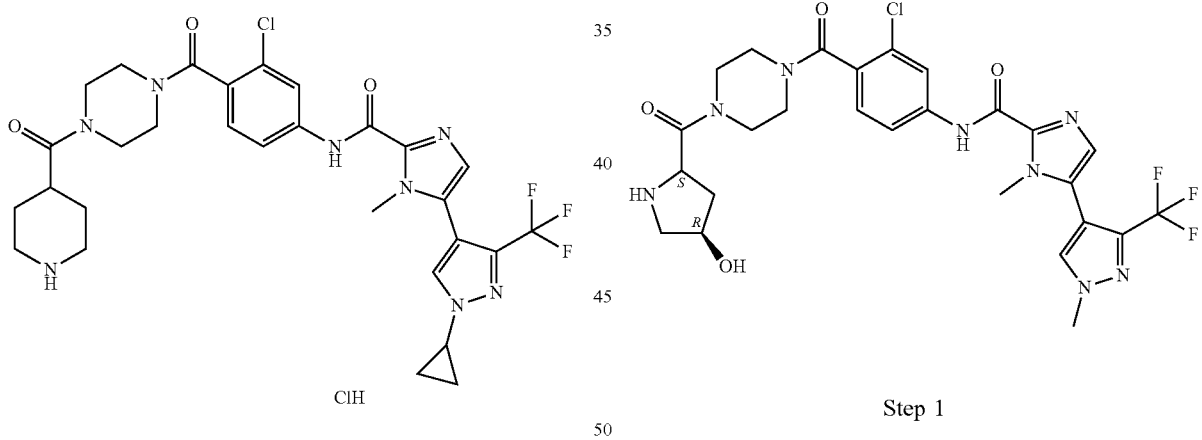 | 632.4 | tert-butyl (S)-3-amino-pyrrolidine-1-carboxylate |

Example 54

N-(3-Chloro-4-(4-(piperidine-4-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride A mixture of tert-butyl 4-(4-(2-chloro-4-(1-methyl-5-(3-(trifluoromethyl)-1H-pyrazol-4-yl)-1H-imidazole-2-carboxamido)benzoyl)piperazine-1-carbonyl)piperidine-1-carboxylate, cyclopropylboronic acid (8.67 mg, 101 µmol, Eq: 2), Na₂CO₃ (10.7 mg, 101 µmol, Eq: 2), copper (II) acetate (9.17 mg, 50.5 µmol, Eq: 1) and 2,2'-bipyridine (7.89 mg, 50.5 µmol, Eq: 1) in ClCH2CH2Cl (2.5 ml) was stirred under air at 70° C. for 3 h. The reaction mixture was poured into 3 mL DCM. 5 ml water was added and extracted with DCM (3×5 mL). The combined organic layers were dried, and concentrated. The residue was purified by prep. HPLC to give an intermediate that was deprotected with HCl in dioxane/DCM as described in Example 2, step 2 to give the title compound (22.8 mg) as a white solid. MS (ESI, m/z): 633.2 [M+H]+

Example 55

N-[3-Chloro-4-[4-[(2S,4R)-4-hydroxypyrrolidine-2-carbonyl]piperazine-1-carbonyl]phenyl]-1-methyl-5-[1-methyl-3-(trifluoromethyl)pyrazol-4-yl]imidazole-2-carboxamide

Step 1

Methyl 4-[(5-bromo-1-methyl-imidazole-2-carbonyl)amino]-2-chloro-benzoate

A mixture of 5-bromo-1-methyl-1H-imidazole-2-carboxylic acid (CAS 1520621-24-2: 800 mg, 3.9 mmol, Eq: 1), methyl 4-amino-2-chlorobenzoate (724 mg, 3.9 mmol, Eq: 1), 2-(3H-[1,2,3]triazolo[4,5-b]pyridin-3-yl)-1,1,3,3-tetramethylisouronium hexafluorophosphate(V) (1.63 g, 4.29 mmol, Eq: 1.1) and DIPEA (1.51 g, 2.04 ml, 11.7 mmol, Eq: 3) in DMF (25 mL) was stirred at room temperature for 1 h. Then the mixture was poured into water. The water phase was extracted with DCM (3×25 mL). The combined organic phases were washed with water, dried over anhydrous Na₂SO₄ and concentrated in vacuo. The residue was purified by flash column chromatography to give the title compound as a yellow solid (0.75 g). MS (ESI, m/z): 371.8 [M+H]+

Step 2

4-[(5-Bromo-1-methyl-imidazole-2-carbonyl)amino]-2-chloro-benzoic Acid

The mixture of methyl 4-(5-bromo-1-methyl-1H-imidazole-2-carboxamido)-2-chlorobenzoate (5 g, 13.4 mmol, Eq: 1) and lithium hydroxide monohydrate (1.69 g, 40.3 mmol, Eq: 3) in MeOH (30 mL), THF (15 mL) and water (10 mL) was stirred at room temperature overnight. Then the mixture was acidified with 1N HCl. The white precipitate was collected, washed with water and dried by vacuum to give the title compound as a white solid (4.5 g). MS (ESI, m/z): 357.7 [M+H]+

Step 3 tert-Butyl 4-[4-[(5-bromo-1-methyl-imidazole-2-carbonyl)amino]-2-chloro-benzoyl]piperazine-1-carboxylate At room temperature, 2,4,6-tripropyl-1,3,5,2,4,6-trioxatriphosphinane 2,4,6-trioxide (887 mg, 2.79 mmol, Eq: 2) was added a mixture of 4-(5-bromo-1-methyl-1H-imidazole-2-carboxamido)-2-chlorobenzoic acid (500 mg, 1.39 mmol, Eq: 1), tert-butyl piperazine-1-carboxylate (312 mg, 1.67 mmol, Eq: 1.2) and DIPEA (541 mg, 731 µl, 4.18 mmol, Eq: 3) in DMF (5 ml). After stirring for 2 h, the reaction mixture was poured into water. The water layer was extracted with DCM (3×10 mL). The combined organic layers were washed with water, dried over anhydrous $Na_2SO_4$ and concentrated in vacuo to give the title compound as an oil (500 mg). MS (ESI, m/z): 526.2 [M+H]+

Step 4

5-Bromo-N-[3-chloro-4-(piperazine-1-carbonyl)phenyl]-1-methyl-imidazole-2-carboxamide At room temperature, a solution of tert-butyl 4-(4-(5-bromo-1-methyl-1H-imidazole-2-carboxamido)-2-chlorobenzoyl)piperazine-1-carboxylate (750 mg, 1.42 mmol, Eq: 1) in TFA (10 mL) and $CH_2Cl_2$ (10 mL) was stirred for 2 h. Then the mixture was concentrated and water (10 mL) was added. The mixture was basified by $K_2CO_3$ to pH 8-9. The water phase was extracted with DCM (3×10 mL). The combined organic phases were washed with water, dried over anhydrous $Na_2SO_4$ and concentrated in vacuo to give the title compound (500 mg) as a yellow oil. MS (ESI, m/z): 426.2 [M+H]+

Step 5 tert-Butyl (2S,4R)-2-[4-[4-[(5-bromo-1-methyl-imidazole-2-carbonyl)amino]-2-chloro-benzoyl]piperazine-1-carbonyl]-4-hydroxy-pyrrolidine-1-carboxylate At room temperature, a mixture of (2S,4R)-1-tert-butoxycarbonyl-4-hydroxy-pyrrolidine-2-carboxylic acid (325 mg, 1.41 mmol, Eq: 1.2), 5-bromo-N-(3-chloro-4-(piperazine-1-carbonyl)phenyl)-1-methyl-1H-imidazole-2-carboxamide (500 mg, 1.17 mmol, Eq: 1), HATU (490 mg, 1.29 mmol, Eq: 1.1) and DIPEA (454 mg, 614 µl, 3.52 mmol, Eq: 3) in DMF (5 ml). was stirred for 1 h. Then the mixture was poured into water. The water layer was extracted with DCM (3×20 mL). The combined organic layers were washed with water, dried over anhydrous $Na_2SO_4$ and concentrated in vacuo to give the title compound (650 mg). The crude product was used into next step reaction without further purification. MS (ESI, m/z): 639.3 [M+H]+

Step 6 tert-Butyl (2S,4R)-2-[4-[2-chloro-4-[[1-methyl-5-[1-methyl-3-(trifluoromethyl)pyrazol-4-yl]imidazole-2-carbonyl]amino]benzoyl]piperazine-1-carbonyl]-4-hydroxy-pyrrolidine-1-carboxylate A mixture of tert-butyl (2S,4R)-2-(4-(4-(5-bromo-1-methyl-1H-imidazole-2-carboxamido)-2-chlorobenzoyl)piperazine-1-carbonyl)-4-hydroxypyrrolidine-1-carboxylate (300 mg, 469 µmol, Eq: 1), (1-methyl-3-(trifluoromethyl)-1H-pyrazol-4-yl)boronic acid (90.9 mg, 469 µmol, Eq: 1), 1,1'-bis(di-tert-butylphosphino)ferrocene palladium dichloride (30.6 mg, 46.9 µmol, Eq: 0.1) and $Na_2CO_3$ (149 mg, 1.41 mmol, Eq: 3) in 1,4-Dioxane (4 ml) and Water (0.4 ml) was irritated under microwave at 100° C. for 1 h. Then the solution was filtered and concentrated. The residue was dissolved in DCM. The organic layer was washed with water, dried over anhydrous $Na_2SO_4$ and concentrated in vacuo to give the title compound (300 mg). The crude product was used into next step reaction without further purification. MS (ESI, m/z): 709.6 [M+H]+

Step 7

N-[3-chloro-4-[4-[(2S,4R)-4-hydroxypyrrolidine-2-carbonyl]piperazine-1-carbonyl]phenyl]-1-methyl-5-[1-methyl-3-(trifluoromethyl)pyrazol-4-yl]imidazole-2-carboxamide 6N HCl (3 mL) and then 12N HCl (6 mL) were added into a solution of tert-butyl (2S,4R)-2-(4-(2-chloro-4-(1-methyl-5-(1-methyl-3-(trifluoromethyl)-1H-pyrazol-4-yl)-1H-imidazole-2-carboxamido)benzoyl)piperazine-1-carbonyl)-4-hydroxypyrrolidine-1-carboxylate (300 mg, 423 mol, Eq: 1) in THF (5 ml). and stirred for 20 mins at room temperature. Then under ice cooling, pH was neutralized using aqueous ammonia solution. The water layer was extracted with a mixture of iPrOH and DCM (1:6). The organic layer was concentrated and the residue was purified by Prep-HPLC to give the title compound (90 mg). MS (ESI, m/z): 609.43 [M+H]+

Example 56

N-[3-Chloro-4-[4-(4-hydroxypiperidine-4-carbonyl)piperazine-1-carbonyl]phenyl]-1-methyl-5-[1-methyl-3-(trifluoromethyl)pyrazol-4-yl]imidazole-2-carboxamide 2,2,2-trifluoroacetate

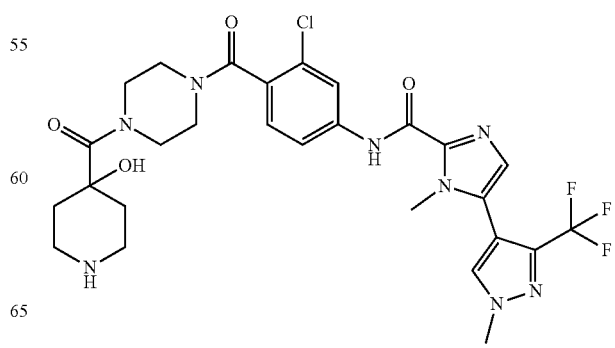

-continued

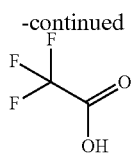

Step 1 tert-Butyl 4-[4-[4-[(5-bromo-1-methyl-imidazole-2-carbonyl)amino]-2-chloro-benzoyl]piperazine-1-carbonyl]-4-hydroxy-piperidine-1-carboxylate At room temperature, a mixture of 5-bromo-N-(3-chloro-4-(piperazine-1-carbonyl)phenyl)-1-methyl-1H-imidazole-2-carboxamide (300 mg, 703 µmol, Eq: 1), 1-(tert-butoxycarbonyl)-4-hydroxypiperidine-4-carboxylic acid (259 mg, 1.05 mmol, Eq: 1.5), 2-(3H-[1,2,3]triazolo[4,5-b]pyridin-3-yl)-1,1,3,3-tetramethylisouronium hexafluorophosphate(V) (401 mg, 1.05 mmol, Eq: 1.5) and DIPEA (454 mg, 614 µl, 3.52 mmol, Eq: 5) in DMF (5 ml) was stirred overnight. Then the mixture was poured into water. The water layer was extracted with DCM (3×20 mL). The combined organic layers were washed with brine, dried over anhydrous Na₂SO₄ and concentrated in vacuo to give the crude product (300 mg) which was used into next step reaction without further purification. MS (ESI, m/z): 653.4 [M+H]+

Step 2 tert-Butyl 4-[4-[2-chloro-4-[[1-methyl-5-[1-methyl-3-(trifluoromethyl)pyrazol-4-yl]imidazole-2-carbonyl]amino]benzoyl]piperazine-1-carbonyl]-4-hydroxy-piperidine-1-carboxylate A mixture of tert-butyl 4-(4-(4-(5-bromo-1-methyl-1H-imidazole-2-carboxamido)-2-chlorobenzoyl)piperazine-1-carbonyl)-4-hydroxypiperidine-1-carboxylate (200 mg, 306 µmol, Eq: 1), (1-methyl-3-(trifluoromethyl)-1H-pyrazol-4-yl)boronic acid (89 mg, 459 µmol, Eq: 1.5), Na₂CO₃ (97.2 mg, 917 µmol, Eq: 3) and 1,1'-bis(di-tert-butylphosphino)ferrocene palladium dichloride (19.9 mg, 30.6 µmol, Eq: 0.1) in 1,4-dioxane (4 ml) and water (0.4 ml) was irritated under microwave at 100° C. for 1 h. Then the solution was filtered and concentrated. The residue was dissolved in DCM. The organic layer was washed with water, dried over anhydrous Na₂SO₄ and concentrated in vacuo to give the crude product (200 mg) which was used into next step reaction without further purification. MS (ESI, m/z): 723.6 [M+H]+

Step 3

N-[3-chloro-4-[4-(4-hydroxypiperidine-4-carbonyl)piperazine-1-carbonyl]phenyl]-1-methyl-5-[1-methyl-3-(trifluoromethyl)pyrazol-4-yl]imidazole-2-carboxamide 2,2,2-trifluoroacetate At room temperature, a solution of tert-butyl 4-(4-(2-chloro-4-(1-methyl-5-(1-methyl-3-(trifluoromethyl)-1H-pyrazol-4-yl)-1H-imidazole-2-carboxamido)benzoyl)piperazine-1-carbonyl)-4-hydroxypiperidine-1-carboxylate (200 mg, 277 µmol, Eq: 1) in DCM (5 ml) and TFA (5 ml) was stirred for 1 h. Then the solution was poured into water and the water phase was basified by aqueous ammonia solution. The water layer was extracted with a mixture of DCM and iPrOH(6:1). The organic layer was dried over anhydrous Na₂SO₄ and concentrated. The residue was purified by Prep-HPLC to give the title compound (34 mg). MS (ESI, m/z): 623.4 [M+H]+

Example 57

N-(4-((2-(2-aminoethoxy)ethyl)carbamoyl)-3-ethylphenyl)-1-methyl-5-(1-methyl-3-(trifluoromethyl)-1H-pyrazol-4-yl)-1H-imidazole-2-carboxamide hydrochloride

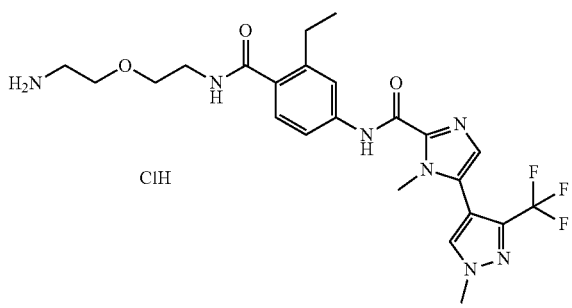 [SMILES: CCc1cc(NC(=O)c2ncc(-c3cn(C)nc3C(F)(F)F)n2C)ccc1C(=O)NCCOCCN ; Cl]

Step 1

Methyl 4-[(5-bromo-1-methyl-imidazole-2-carbonyl)amino]-2-ethyl-benzoate

To a white suspension of 5-bromo-1-methyl-1H-imidazole-2-carboxylic acid (commercially available) (935 mg, 4.56 mmol, Eq: 1) in DMF (10 mL) at room temperature were added HATU (1.91 g, 5.02 mmol, Eq: 1.1) and 1.6 mL DIPEA (2 eq). Methyl 4-amino-2-ethylbenzoate (826 mg, 4.61 mmol, Eq: 1.01) and 800 uL DIPEA (1 eq) were added and the mixture was stirred for 4 h at room temperature. The mixture was diluted with water, extracted with ethyl acetate and the combined organic layers were washed with brine/water 1:1 (3×80 mL) and dried over Na₂SO₄. The crude material was absorbed with Isolute HM-N and purified by flash chromatography on silica eluting with a gradient formed from heptane and ethyl acetate to yield after evaporation of the product containing fractions the title compound (1.057 g, 63%) as a white solid. (ESI, m/z): 366.1 [M+H]⁺.

Step 2

Methyl 2-ethyl-4-[[1-methyl-5-[1-methyl-3-(trifluoromethyl)pyrazol-4-yl]imidazole-2-carbonyl]amino]benzoate A mixture of methyl 4-(5-bromo-1-methyl-1H-imidazole-2-carboxamido)-2-ethylbenzoate (50 mg, 137 µmol, Eq: 1), 1-methyl-4-(4,4,5,5-tetramethyl-1,3,2-dioxaborolan-2-yl)-3-(trifluoromethyl)-1H-pyrazole (49 mg, 177 µmol, Eq: 1.3), [1,1'-bis(diphenylphosphino)ferrocene]dichloropalladium (II) (9.99 mg, 13.7 µmol, Eq: 0.1) and Na₂CO₃ (28.9 mg, 273 µmol, Eq: 2) in dioxane (1 mL) and water (0.1 mL) was stirred overnight at 100° C. The crude mixture was absorbed with Isolute HM-N and purified by flash column chromatography on silica eluting with a gradient formed from heptane and ethyl acetate. The product containing fractions were evaporated to yield the title compound (50.8 mg, 85%) as a waxy brown solid. (ESI, m/z): 436.3 [M+H]⁺.

Step 3

2-Ethyl-4-[[1-methyl-5-[1-methyl-3-(trifluoromethyl)pyrazol-4-yl]imidazole-2-carbonyl]amino]benzoic acid To a clear solution of methyl 2-ethyl-4-(1-methyl-5-(1-methyl-3-(trifluoromethyl)-1H-pyrazol-4-yl)-1H-imidazole-2-carboxamido)benzoate (45.8 mg, 105 µmol, Eq: 1) in THF (600 µL), water (300 µL) and MeOH (30 µL), NaOH (10.0 mg, 250 µmol, Eq: 2.38) was added and the mixture was stirred for 24 h at 70° C. The organic solvents were removed, the residue diluted with water (3 mL) and 0.1 M HCl (aq) was added dropwise until pH 5-6. The mixture was extracted with ethyl acetate (2×25 mL) and the organic layers were washed with water (2×20 mL), dried over Na$_2$SO$_4$, filtered off and evaporated to yield the title compound (41.2 mg, 93%) as off-white crystals. (ESI, m/z): 422.2 [M+H]⁺.

Step 4 tert-Butyl N-[2-[2-[[2-ethyl-4-[[1-methyl-5-[1-methyl-3-(trifluoromethyl)pyrazol-4-yl]imidazole-2-carbonyl]amino]benzoyl]amino]ethoxy]ethyl]carbamate To a solution of 2-ethyl-4-(1-methyl-5-(1-methyl-3-(trifluoromethyl)-1H-pyrazol-4-yl)-1H-imidazole-2-carboxamido)benzoic acid (20 mg, 47.5 µmol, Eq: 1) in DMF (1 mL) and NEt$_3$ (24 mg, 33.1 µl, 237 µmol, Eq: 5) at room temperature was added TBTU (17.5 mg, 54.6 mol, Eq: 1.15) and the mixture is shaken for 30 min. Tert-butyl (2-(2-aminoethoxy)ethyl)carbamate (10.7 mg, 52.2 µmol, Eq: 1.1) was added and the light brown clear mixture was shaken overnight. The mixture was acidified with formic acid (50 uL) and purified by preparative HPLC on reversed phase eluting with a gradient formed from acetonitrile, water and formic acid. The product containing fractions were evaporated to yield the title compound (23.4 mg, 81%) as colorless solid. (ESI, m/z): 608.4 [M+H]⁺.

Step 5

To a solution of tert-butyl (2-(2-(2-ethyl-4-(1-methyl-5-(1-methyl-3-(trifluoromethyl)-1H-pyrazol-4-yl)-1H-imidazole-2-carboxamido)benzamido)ethoxy)ethyl)carbamate (23 mg, 37.9 mol, Eq: 1) in DCM (2 mL) was added HCl (4 M) in dioxane (57 µl, 228 µmol, Eq: 6.02) and stirred for 16 h, evaporated and dried to yield the title compound (20.2 mg, 98%) as light brown solid. (ESI, m/z): 508.3 [M+H]⁺.

Example 58

N-(3-Chloro-4-((4-(dimethylglycyl)piperazin-1-yl)sulfonyl)phenyl)-1-methyl-5-(3-(trifluoromethyl)-1H-pyrazol-4-yl)-1H-imidazole-2-carboxamide

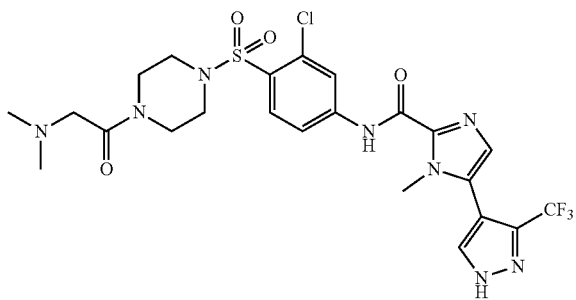 [SMILES: CN(C)CC(=O)N1CCN(S(=O)(=O)c2ccc(NC(=O)c3ncc(-c4c[nH]nc4C(F)(F)F)n3C)cc2Cl)CC1]

Step 1 tert-Butyl 4-(2-chloro-4-nitro-phenyl)sulfonylpiperazine-1-carboxylate

To a solution of tert-butyl piperazine-1-carboxylate (2.37 g, 12.7 mmol, Eq: 1.05) and N-ethyl-N-isopropylpropan-2-amine (3.14 g, 4.24 ml, 24.3 mmol, Eq: 2) in DMF (120 mL) was added 2-chloro-4-nitrobenzenesulfonyl chloride (3.109 g, 12.1 mmol, Eq: 1) in DCM (10 mL) slowly and stirred at room temperature overnight. The mixture was diluted with 10% Na$_2$CO$_3$ (150 mL) and water (150 mL). The mixture was extracted with DCM (2×150 mL) and the organic layer was dried with MgSO$_4$, filtered and evaporated. The residue was absorbed with Isolute HM-N, dried and purified by flash chromatography on silica eluting with a gradient formed from heptane and ethyl acetate. The product containing fractions were evaporated to yield the title compound (4.27 g, 87%) as orange solid. (ESI, m/z): 306.1 [M+H, –Boc]⁺.

Step 2 tert-butyl 4-(4-amino-2-chloro-phenyl)sulfonylpiperazine-1-carboxylate

A solution of tert-butyl 4-((2-chloro-4-nitrophenyl)sulfonyl)piperazine-1-carboxylate (2.51 g, 6.18 mmol, Eq: 1) in ethanol (49.2 mL) and water (16.4 mL) was heated to 80° C. and ammonium chloride (1.06 g, 19.8 mmol, Eq: 3.2) and iron (4.28 g, 76.7 mmol, Eq: 12.4) were added and stirred at 80° C. overnight. The hot reaction was filtered (over Dicalite) and the filter was washed with ethanol (3×50 mL). The filtrate was evaporated to dryness, absorbed with Isolute HM-N, dried and purified by flash chromatography on silica eluting with a gradient formed from heptane and ethyl acetate. The product containing fractions were evaporated to yield the title compound (2.3 g, 93%) as orange solid. (ESI, m/z): 276.2 [M+H, –Boc]⁺.

Step 3 tert-Butyl 4-[4-[(5-bromo-1-methyl-imidazole-2-carbonyl)amino]-2-chloro-phenyl]sulfonylpiperazine-1-carboxylate A mixture of tert-butyl 4-((4-amino-2-chlorophenyl)sulfonyl)piperazine-1-carboxylate (1.2 g, 3.19 mmol, Eq: 1)

and triethylamine (1.62 g, 2.22 ml, 16 mmol, Eq: 5) in DCM (20 mL) was treated with 5-bromo-1-methyl-1H-imidazole-2-carbonyl chloride (1.1 g, 3.69 mmol, Eq: 1.16) in DCM (10 mL). The reaction mixture was stirred for 1 h at room temperature and concentrated in vacuo. The residue was absorbed with Isolute HM-N, dried and purified by flash chromatography on silica eluting with a gradient formed from heptane/ethyl acetate. The product containing fractions were evaporated to yield the title compound (530 mg, 819 µmol, 26%) as orange solid. (ESI, m/z): 560.3 [M−H]$^-$.

Step 4 tert-Butyl 4-[2-chloro-4-[[1-methyl-5-[3-(trifluoromethyl)-1H-pyrazol-4-yl]imidazole-2-carbonyl]amino]phenyl]sulfonylpiperazine-1-carboxylate A mixture of tert-butyl 4-((4-(5-bromo-1-methyl-1H-imidazole-2-carboxamido)-2-chlorophenyl)sulfonyl)piperazine-1-carboxylate (200 mg, 355 µmol, Eq: 1), (3-(trifluoromethyl)-1H-pyrazol-4-yl)boronic acid (89.5 mg, 497 µmol, Eq: 1.4), Na$_2$CO$_3$ (75.3 mg, 711 µmol, Eq: 2.00) and 1,1'-bis(diphenylphosphino)ferrocene-palladium(II)dichloride dichloromethane complex (29 mg, 35.5 µmol, Eq: 0.10) in dioxane (3 mL) and water (300 µL) was heated to 100° C. overnight. (3-(Trifluoromethyl)-1H-pyrazol-4-yl)boronic acid (63.9 mg, 355 µmol, Eq: 1.0) and 1,1'-bis(diphenylphosphino)ferrocene-palladium(II)dichloride dichloromethane complex (29 mg, 35.5 µmol, Eq: 0.10) was added and the reaction mixture was stirred 5 h and (3-(trifluoromethyl)-1H-pyrazol-4-yl)boronic acid (63.9 mg, 355 µmol, Eq: 1.0) and 1,1'-bis(diphenylphosphino)ferrocene-palladium(II)dichloride dichloromethane complex (29 mg, 35.5 µmol, Eq: 0.10) in dioxane (3 mL) and water (300 µL) was added and heated again to 100° C. overnight. The reaction mixture was evaporated and absorbed with Isolute HM-N, dried and purified by flash chromatography on silica eluting with a gradient formed from heptane/ethyl acetate. The product containing fractions were evaporated to yield the title compound (144 mg, 207 µmol, 58%) as orange solid. (ESI, m/z): 618.4 [M+H]$^+$.

Step 5

N-(3-Chloro-4-piperazin-1-ylsulfonyl-phenyl)-1-methyl-5-[3-(trifluoromethyl)-1H-pyrazol-4-yl]imidazole-2-carboxamide A solution of tert-butyl 4-((2-chloro-4-(1-methyl-5-(3-(trifluoromethyl)-1H-pyrazol-4-yl)-1H-imidazole-2-carboxamido)phenyl)sulfonyl)piperazine-1-carboxylate (144 mg, 233 µmol, Eq: 1) in DCM (4.0 mL) and TFA (266 mg, 180 µL, 2.33 mmol, Eq: 10) was stirred for 3 h at room temperature. TFA (118 mg, 80 µL, 1.04 mmol, Eq: 5) was added and the reaction mixture was stirred for 5 h. The mixture was basified by addition of Na2CO3 aq, and then extracted with DCM (3×25 mL) and the combined organic layers were washed with Na$_2$CO$_3$ 10% aq. (2×25 mL) and brine (25 mL). The combined aqueous layers were extracted with ethyl acetate (3×25 mL) and the organic layer was washed with Na$_2$CO$_3$ 10% aq. (2×25 mL) and brine (25 mL). The combined organic layers were dried with MgSO$_4$, filtered and evaporated to afford the title compound (57 mg, 103 µmol, 44%) as orange solid. (ESI, m/z): 516.4 [M+H]$^+$.

Step 6

N-(3-Chloro-4-((4-(dimethylglycyl)piperazin-1-yl)sulfonyl)phenyl)-1-methyl-5-(3-(trifluoromethyl)-1H-pyrazol-4-yl)-1H-imidazole-2-carboxamide A mixture of dimethylglycine (6.14 mg, 59.5 µmol, Eq: 1.1), (N-(3-chloro-4-(piperazin-1-ylsulfonyl)phenyl)-1-methyl-5-(3-(trifluoromethyl)-1H-pyrazol-4-yl)-1H-imidazole-2-carboxamide (28 mg, 54.1 µmol, Eq: 1)), DIPEA (22.2 mg, 30 µl, 172 µmol, Eq: 3.18) and TBTU (19.1 mg, 59.5 µmol, Eq: 1.1) in DMF (1.5 mL) was reacted at room temperature overnight. The mixture was subjected to purification by preparative HPLC on reversed phase eluting with a gradient formed from acetonitrile, water and formic acid. The product containing fractions were evaporated to yield the title compound (5.4 mg, 99%). (ESI, m/z): 603.3 [M+H]$^+$.

Example 59

N-(3-Chloro-4-((4-((2S,4R)-4-hydroxypyrrolidine-2-carbonyl)piperazin-1-yl)sulfonyl)phenyl)-1-methyl-5-(3-(trifluoromethyl)-1H-pyrazol-4-yl)-1H-imidazole-2-carboxamide Hydrochloride

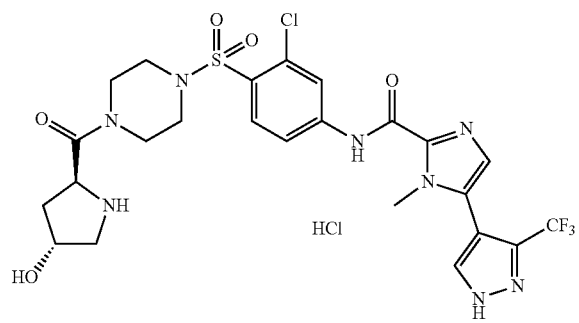 [SMILES: Cn1c(-c2c[nH]nc2C(F)(F)F)cnc1C(=O)Nc1ccc(S(=O)(=O)N2CCN(C(=O)[C@@H]3C[C@@H](O)CN3)CC2)c(Cl)c1 ; Cl]

A mixture of tert-butyl (2S,4R)-2-(4-((2-chloro-4-(1-methyl-5-(3-(trifluoromethyl)-1H-pyrazol-4-yl)-1H-imidazole-2-carboxamido)phenyl)sulfonyl)piperazine-1-carbonyl)-4-hydroxypyrrolidine-1-carboxylate (29.7 mg, 40.6 µmol, Eq: 1) and HCl 4 M in dioxane (152 µL, 609 µmol, Eq: 15) in DCM (2 mL) was stirred for 3 h at room temperature. The solvents were evaporated and the reaction mixture was dried under vacuum to yield the title compound (19.8 mg, 29.7 µmol, 73%) as light yellow solid. (ESI, m/z): 631.4 [M+H]$^+$.

Intermediate 4 tert-Butyl (1-(2-aminoethoxy)-2-methylpropan-2-yl)carbamate

Step 1: Allyl tert-butyl Carbonate

To a solution of allyl alcohol (79.84 g, 1375 mmol, 3 eq) and di-tert-butyldicarbonate (100.0 g, 458.19 mmol, 1 eq) was added 4-dimethylaminopyridine (11.2 g, 91.64 mmol, 0.200 eq) slowly. The mixture was stirred at 25° C. for 2 h. The mixture was diluted with MTBE (1000 mL), washed with brine (100 mL), dried over sodium sulfate and concentrated in vacuo. The residue was purified by silica gel chromatography eluting with petroleum ether to afford allyl tert-butyl carbonate (67 g) as a colorless oil.

$^1$H NMR (400 MHz, CHLOROFORM-d) δ=6.01-5.87 (m, 1H), 5.34 (qd, J=1.5, 17.2 Hz, 1H), 5.25 (qd, J=1.5, 10.4 Hz, 1H), 4.56 (td, J=1.3, 5.9 Hz, 2H), 1.49 (s, 9H) ppm.

Step 2: tert-Butyl N-(2-allyloxy-1,1-dimethyl-ethyl)carbamate

To a mixture of tert-butyl (1-hydroxy-2-methylpropan-2-yl)carbamate (9.0 g, 47.56 mmol, 1 eq) and allyl tert-butyl carbonate (15.05 g, 95.11 mmol, 2 eq) in THF (135 mL) was added tetrakis(triphenylphosphine)palladium(0) (2.75 g, 2.38 mmol, 0.050 eq). The resulting mixture was stirred at 80° C. for 16 h under nitrogen atmosphere. The mixture was concentrated and the residue was purified by silica gel chromatography eluting with petroleum ehter:EtOAc=30:1 to afford tert-butyl N-(2-allyloxy-1,1-dimethyl-ethyl)carbamate (8.6 g) as a light yellow oil.

$^1$H NMR (400 MHz, CHLOROFORM-d) δ=5.83 (tdd, J=5.5, 10.6, 17.2 Hz, 1H), 5.20 (qd, J=1.6, 17.2 Hz, 1H), 5.14-5.08 (m, 1H), 4.68 (br s, 1H), 3.93 (td, J=1.4, 5.5 Hz, 2H), 3.30 (s, 2H), 1.36 (s, 9H), 1.23 (s, 6H) ppm.

Step 3: tert-Butyl N-[2-(2-hydroxyethoxy)-1,1-dimethyl-ethyl]carbamate

To a solution of tert-butyl N-(2-allyloxy-1,1-dimethyl-ethyl)carbamate (14.5 g, 63.23 mmol, 1 eq) in DCM (200 mL) previously cooled to −70° C. was bubbled ozone until the mixture turned blue. The mixture was warmed to 0° C., methanol (40 mL) was added followed by sodium borohydride (4.78 g, 126.46 mmol, 2 eq). The mixture was stirred for 2 h at 0° C. The mixture was quenched with saturated aq. NH$_4$Cl and then the organic phase was separated. The mixture was dried over sodium sulfate and concentrated to give the crude product residue. The residue was purified by silica gel chromatography eluting with petroleum ether:EtOAc=20:1 to 2:1 to afford tert-butyl N-[2-(2-hydroxyethoxy)-1,1-dimethyl-ethyl]carbamate (7.5 g) as colorless oil.

Step 4: tert-Butyl N-[2-(2-azidoethoxy)-1,1-dimethyl-ethyl]carbamate

To a solution of tert-butyl N-[2-(2-hydroxyethoxy)-1,1-dimethyl-ethyl]carbamate (7.5 g, 32.15 mmol, 1 eq) and triethylamine (6.72 mL, 48.22 mmol, 1.5 eq) in DCM (90 mL) was added methanesulfonyl chloride (3.23 mL, 41.79 mmol, 1.3 eq). The resulting mixture was stirred at 5° C. for 1 h. The mixture was washed with brine (100 mL), dried over sodium sulfate and concentrated in vacuo. To a solution of the residue (10.0 g, 32.11 mmol, 1 eq) in DMF (75 mL) was added sodium azide (6.26 g, 96.34 mmol, 3 eq). The resulting mixture was stirred at 50° C. for 2.5 h. The mixture was diluted with water (320 mL), extracted with EtOAc (200 mL*2), washed with brine (150 mL), dried over sodium sulfate and concentrated to afford tert-butyl N-[2-(2-azidoethoxy)-1,1-dimethyl-ethyl]carbamate (6 g) as colorless oil, which is used directly as crude product.

Step 5: tert-Butyl N-[2-(2-aminoethoxy)-1,1-dimethyl-ethyl]carbamate

To a solution of tert-butyl N-[2-(2-azidoethoxy)-1,1-dimethyl-ethyl]carbamate (6.0 g, 23.23 mmol, 1 eq) in EtOAc (65 mL) was added 10% palladium on carbon (494.36 mg, 4.65 mmol, 0.200 eq). The resulting mixture was hydrogenated under 760 mm Hg at 30° C. for 16 h. The catalyst was removed by filtration. The filtrate was concentrated to afford tert-butyl N-[2-(2-aminoethoxy)-1,1-dimethyl-ethyl]carbamate (4.02 g) as colorless oil.

$^1$H NMR (400 MHz, CHLOROFORM-d) δ=5.00-4.55 (m, 1H), 3.54-3.48 (m, 1H), 3.42 (t, J=5.2 Hz, 1H), 3.32 (d, J=6.0 Hz, 2H), 2.79 (t, J=5.2 Hz, 1H), 2.75 (t, J=5.3 Hz, 1H), 1.36 (s, 9H), 1.22 (d, J=4.3 Hz, 6H) ppm.

Intermediate 5 tert-Butyl N-[(1S)-2-(2-aminoethoxy)-1-methyl-ethyl]carbamate

Step 1: tert-Butyl N-[(1S)-2-allyloxy-1-methyl-ethyl]carbamate

The title compound was obtained in analogy to Intermediate 4, step 2 using N-Boc-L-alaninol.

Step 2: tert-Butyl N-[(1S)-2-(2-hydroxyethoxy)-1-methyl-ethyl]carbamate

The title compound was obtained in analogy to Intermediate 4, step 3 using tert-butyl N-[(1S)-2-allyloxy-1-methyl-ethyl]carbamate.

Step 3: tert-Butyl N-[(1S)-2-(2-azidoethoxy)-1-methyl-ethyl]carbamate

The title compound was obtained in analogy to Intermediate 4, step 4 using tert-butyl N-[(1S)-2-(2-hydroxyethoxy)-1-methyl-ethyl]carbamate.

Step 4: tert-Butyl N-[(1S)-2-(2-aminoethoxy)-1-methyl-ethyl]carbamate

The title compound was obtained in analogy to Intermediate 4, step 5 using tert-butyl N-[(1S)-2-(2-azidoethoxy)-1-methyl-ethyl]carbamate.

$^1$H NMR (400 MHz, CHLOROFORM-d) δ=4.68 (br s, 1H), 3.76 (br s, 1H), 3.54-3.37 (m, 2H), 3.37-3.28 (m, 2H), 2.82-2.70 (m, 2H), 1.38 (s, 9H), 1.13-1.05 (m, 3H) ppm.

Intermediate 6 tert-Butyl N-[(1R)-2-(2-aminoethoxy)-1-methyl-ethyl]carbamate

Step 1: tert-Butyl N-[(1R)-2-allyloxy-1-methyl-ethyl]carbamate

The title compound was obtained in analogy to Intermediate 4, step 2 using N-Boc-D-alaninol.

Step 2: tert-Butyl N-[(1R)-2-(2-hydroxyethoxy)-1-methyl-ethyl]carbamate

The title compound was obtained in analogy to Intermediate 4, step 3 using tert-butyl N-[(1R)-2-allyloxy-1-methyl-ethyl]carbamate.

Step 3: tert-Butyl N-[(1R)-2-(2-azidoethoxy)-1-methyl-ethyl]carbamate

The title compound was obtained in analogy to Intermediate 4, step 4 using tert-butyl N-[(1R)-2-(2-hydroxyethoxy)-1-methyl-ethyl]carbamate.

Step 4: tert-Butyl N-[(1R)-2-(2-aminoethoxy)-1-methyl-ethyl]carbamate

The title compound was obtained in analogy to Intermediate 4, step 3 using tert-butyl N-[(1R)-2-(2-azidoethoxy)-1-methyl-ethyl]carbamate.

$^1$H NMR (400 MHz, CHLOROFORM-d) δ=4.89-4.58 (m, 1H), 3.75 (br s, 1H), 3.55-3.38 (m, 2H), 3.37-3.28 (m, 2H), 2.83-2.70 (m, 2H), 1.37 (s, 9H), 1.15-1.05 (m, 3H) ppm.

Example 60

N-[3-Chloro-4-[4-(4-hydroxypiperidine-4-carbonyl)piperazine-1-carbonyl]phenyl]-5-[1-(cyanomethyl)-3-(trifluoromethyl)pyrazol-4-yl]-1-methyl-imidazole-2-carboxamide; Formic Acid

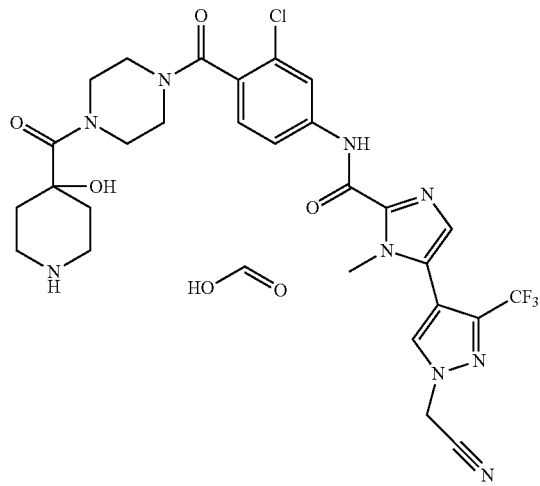 [SMILES: Cn1c(-c2cn(CC#N)nc2C(F)(F)F)cnc1C(=O)Nc1ccc(C(=O)N2CCN(C(=O)C3(O)CCNCC3)CC2)c(Cl)c1 ; O=CO]

Step 1: tert-Butyl 4-(2-chloro-4-nitro-benzoyl)piperazine-1-carboxylate

To a solution of 2-chloro-4-nitrobenzoic acid (2.0 g, 9.92 mmol, 1 eq) and O-(7-azabenzotriazol-1-yl)-N,N,N',N'-tetramethyluronium hexafluorophosphate (4.53 g, 11.91 mmol, 1.2 eq) in DMF (20 mL) was added triethylamine (1.66 mL, 11.91 mmol, 1.2 eq), after being stirred for 5 min, 1-BOC-piperazine (2.22 g, 11.91 mmol, 1.2 eq) was added. The resulting mixture was stirred at 15° C. for 15 h. The mixture was diluted with water, extracted with EtOAc, washed with brine, dried over sodium sulfate and concentrated to afford tert-butyl 4-(2-chloro-4-nitro-benzoyl)piperazine-1-carboxylate (2.5 g, 6.76 mmol, 68.13% yield), the crude product was used directly in the next step without further purification. MS (ESI, m/z): 270.1 [M+H−100]$^+$

Step 2: (2-Chloro-4-nitro-phenyl)-piperazin-1-yl-methanone

To a solution of tert-butyl 4-(2-chloro-4-nitro-benzoyl)piperazine-1-carboxylate (2.5 g, 6.76 mmol, 1 eq) in methanol (10 mL) was added 4N HCl in MeOH (10 mL). The resulting mixture was stirred at 20° C. for 1 h. The mixture was concentrated to dryness and the residue was triturated with MTBE to afford (2-chloro-4-nitro-phenyl)-piperazin-1-yl-methanone (1.6 g), used directly in the next step without further purification. White solid. MS (ESI, m/z): 270.0 [M+H]$^+$

Step 3: tert-Butyl 4-(4-(2-chloro-4-nitrobenzoyl)piperazine-1-carbonyl)-4-hydroxypiperidine-1-carboxylate To a solution of 1-tert-butoxycarbonyl-4-hydroxy-piperidine-4-carboxylic acid (0.6 g, 2.45 mmol, 1 eq) and O-(7-azabenzotriazol-1-yl)-N,N,N',N'-tetramethyluronium hexafluorophosphate (1116.18 mg, 2.94 mmol, 1.2 eq) in DMF (10 mL) was added triethylamine (0.68 mL, 4.89 mmol, 2 eq). After being stirred for 5 min, (2-chloro-4-nitro-phenyl)-piperazin-1-yl-methanone hydrochloride (0.82 g, 2.69 mmol, 1.1 eq) was added. The resulting mixture was stirred at 20° C. for 15 h. The mixture was diluted with water, extracted with EtOAC, washed with brine, dried over sodium sulfate and concentrated. The residue was purified by silica gel chromatography eluting with PE:EA=1:1 to afford tert-butyl 4-[4-(2-chloro-4-nitro-benzoyl)piperazine-1-carbonyl]-4-hydroxy-piperidine-1-carboxylate (800 mg, 1.61 mmol, 65.81% yield) as yellow solid. MS (ESI, m/z): 519.2 [M+Na]$^+$

Step 4: tert-Butyl 4-(4-(4-amino-2-chlorobenzoyl)piperazine-1-carbonyl)-4-hydroxypiperidine-1-carboxylate To a solution of nickel(II) chloride hexahydrate (143.49 mg, 0.600 mmol, 0.500 eq) and sodium borohydride (50 mg, 0.94 mmol, 0.5 eq) in THF (6.45 mL) and methanol (1.29 mL) were added tert-butyl 4-[4-(2-chloro-4-nitro-benzoyl)piperazine-1-carbonyl]-4-hydroxy-piperidine-1-carboxylate (600.0 mg, 1.21 mmol, 1 eq) in THF (2 mL) and then sodium borohydride (170 mg, 2.3 mmol, 2.5 eq). The mixture was stirred at 0° C. for 2 h. The mixture was diluted with water, extracted with EtOAc, washed with brine, dried over sodium sulfate and concentrated to afford tert-butyl 4-[4-(4-amino-2-chloro-benzoyl)piperazine-1-carbonyl]-4-hydroxy-piperidine-1-carboxylate (400 mg, 0.860 mmol, 70.95% yield) as a yellow oil, used directly in the next step.

Step 5: 5-Bromo-1-methyl-imidazole-2-carboxylic Acid

To a solution of methyl 5-bromo-1-methyl-imidazole-2-carboxylate (1.0 g, 4.57 mmol, 1 eq) in THF (20 mL) and water (1 mL) was added lithium hydroxide monohydrate (aq., 0.15 mL, 9.13 mmol, 2 eq). The resulting mixture was stirred at 25° C. for 2 h. The mixture was acidified with 1 N HCl and extracted with EtOAc, washed with brine, dried over sodium sulfate and concentrated to afford 5-bromo-1-methyl-imidazole-2-carboxylic acid (600 mg) as white solid. MS (ESI, m/z): 204.9 [M+H]$^+$

Step 6: tert-Butyl 4-(4-(4-(5-bromo-1-methyl-1H-imidazole-2-carboxamido)-2-chlorobenzoyl)piperazine-1-carbonyl)-4-hydroxypiperidine-1-carboxylate To a solution of 5-bromo-1-methyl-imidazole-2-carboxylic acid (150.0 mg, 0.730 mmol, 1 eq) and O-(7-azabenzotriazol-1-yl)-N,N,N',N'-tetramethyluronium hexafluorophosphate (417.31 mg, 1.1 mmol, 1.5 eq) in DMF (5 mL) was added triethylamine (0.15 mL, 1.1 mmol, 1.5 eq). After being stirred for 5 min, tert-butyl 4-[4-(4-amino-2-chloro-benzoyl)piperazine-1-carbonyl]-4-hydroxy-piperidine-1-carboxylate (341.66 mg, 0.730 mmol, 1 eq) was added. The resulting mixture was stirred at 25° C. for 15 h. The mixture was diluted with water, extracted with EtOAc. The organic phase was washed with brine, dried over sodium sulfate and concentrated. The residue was purified by flash column chromatography to afford tert-butyl 4-[4-[4-[(5-bromo-1-methyl-imidazole-2-carbonyl)amino]-2-chloro-benzoyl]piperazine-1-carbonyl]-4-hydroxy-piperidine-1-carboxylate (200 mg) as a white solid. MS (ESI, m/z): 539.2 [M+H−100−17]$^+$ Step 7: 2-[4-(4,4,5,5-Tetramethyl-1,3,2-dioxaborolan-2-yl)-3-(trifluoromethyl)pyrazol-1-yl]acetonitrile A mixture of 4-(4,4,5,5-tetramethyl-1,3,2-dioxaborolan-2-yl)-3-(trifluoromethyl)-1H-pyrazole (0.8 g, 3.05 mmol, 1 eq), bromoacetonitrile (0.44 g, 3.66 mmol, 1.2 eq), potassium carbonate (843.8 mg, 6.11 mmol, 2 eq) in ACN (10 mL) was stirred at 25° C. for 16 h. The mixture was filtered and concentrated to give a crude product, which was further purified with column chromatography (PE/EA=100:1 to 20:1) to afford 2-[4-(4,4,5,5-tetramethyl-1,3,2-dioxaborolan-2-yl)-3-(trifluoromethyl)pyrazol-1-yl]acetonitrile (950 mg) as a colorless oil. MS (ESI, m/z): 301.9 [M+H]$^+$ Step 8: tert-Butyl 4-[4-[2-chloro-4-[[5-[1-(cyanomethyl)-3-(trifluoromethyl)pyrazol-4-yl]-1-methyl-imidazole-2-carbonyl]amino]benzoyl]piperazine-1-carbonyl]-4-hydroxy-piperidine-1-carboxylate A mixture of tert-butyl 4-[4-[4-[(5-bromo-1-methyl-imidazole-2-carbonyl)amino]-2-chloro-benzoyl]piperazine-1-carbonyl]-4-hydroxy-piperidine-1-carboxylate (200.0 mg, 0.310 mmol, 1 eq), 2-[4-(4,4,5,5-tetramethyl-1,3,2-dioxaborolan-2-yl)-3-(trifluoromethyl)pyrazol-1-yl]acetonitrile (184.15 mg, 0.610 mmol, 2 eq), sodium carbonate (64.83 mg, 0.610 mmol, 2 eq) and [1,1′-bis(diphenylphosphino)ferrocene]dichloropalladium(II) (22.38 mg, 0.030 mmol, 0.100 eq) in 1,4-dioxane (6 mL)/water (0.600 mL) was stirred at 85° C. for 16 h. The mixture was filtered and purified with Prep-TLC (DCM/MeOH=10:1) to afford tert-butyl 4-[4-[2-chloro-4-[[5-[1-(cyanomethyl)-3-(trifluoromethyl)pyrazol-4-yl]-1-methyl-imidazole-2-carbonyl]amino]benzoyl]piperazine-1-carbonyl]-4-hydroxy-piperidine-1-carboxylate (135 mg) as a light yellow oil. MS (ESI, m/z): 748.2 [M+H]$^+$ Step 9: N-[3-Chloro-4-[4-(4-hydroxypiperidine-4-carbonyl)piperazine-1-carbonyl]phenyl]-5-[1-(cyanomethyl)-3-(trifluoromethyl)pyrazol-4-yl]-1-methyl-imidazole-2-carboxamide Formate A solution of tert-butyl 4-[4-[2-chloro-4-[[5-[1-(cyanomethyl)-3-(trifluoromethyl)pyrazol-4-yl]-1-methyl-imidazole-2-carbonyl]amino]benzoyl]piperazine-1-carbonyl]-4-hydroxy-piperidine-1-carboxylate (135.0 mg, 0.180 mmol, 1 eq) in DCM (16.51 mL) was added trifluoroacetic acid (5.0 mL, 64.9 mmol, 359.67 eq) and stirred at 25° C. for 16 h. The mixture was concentrated and purified by Prep-HPLC (FA) to afford N-[3-chloro-4-[4-(4-hydroxypiperidine-4-carbonyl)piperazine-1-carbonyl]phenyl]-5-[1-(cyanomethyl)- 3-(trifluoromethyl)pyrazol-4-yl]-1-methyl-imidazole-2-carboxamide as formate salt (18.9 mg). MS (ESI, m/z): 648.3 [M+H]$^+$ Example 61

N-[3-Chloro-4-[4-(piperidine-4-carbonyl)piperazine-1-carbonyl]phenyl]-5-[1-(cyanomethyl)-3-(trifluoromethyl)pyrazol-4-yl]-1-methyl-imidazole-2-carboxamide Formate

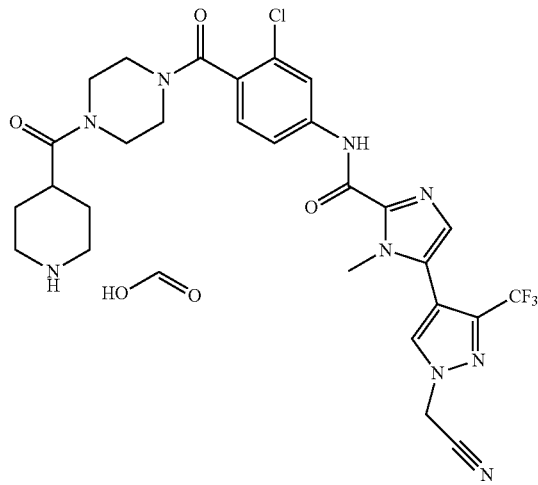

Step 1: tert-Butyl 4-[4-(2-chloro-4-nitro-benzoyl)piperazine-1-carbonyl]piperidine-1-carboxylate The title compound was obtained in analogy to Example 60, step 3 by using N-BOC-isonipecotic acid as starting material. MS (ESI, m/z): 503.0 [M+Na]$^+$ Step 2: tert-Butyl 4-[4-(4-amino-2-chloro-benzoyl)piperazine-1-carbonyl]piperidine-1-carboxylate The title compound was obtained in analogy to Example 60, step 4 by using tert-butyl 4-[4-(2-chloro-4-nitro-benzoyl)piperazine-1-carbonyl]piperidine-1-carboxylate as starting material. MS (ESI, m/z): 473.1 [M+Na]$^+$ Step 3: tert-Butyl 4-[4-[4-[(5-bromo-1-methyl-imidazole-2-carbonyl)amino]-2-chloro-benzoyl]piperazine-1-carbonyl]piperidine-1-carboxylate The title compound was obtained in analogy to Example 60, step 6 by using tert-butyl 4-[4-(4-amino-2-chloro-benzoyl)piperazine-1-carbonyl]piperidine-1-carboxylate as starting material. MS (ESI, m/z): 539.2 [M+H−100]$^+$ Step 4: tert-Butyl 4-[4-[2-chloro-4-[[5-[1-(cyanomethyl)-3-(trifluoromethyl)pyrazol-4-yl]-1-methyl-imidazole-2-carbonyl]amino]benzoyl]piperazine-1-carbonyl]piperidine-1-carboxylate The title compound was obtained in analogy to Example 60, step 8 by using tert-butyl 4-[4-[4-[(5-bromo-1-methyl-imidazole-2-carbonyl)amino]-2-chloro-benzoyl]piperazine-1-carbonyl]piperidine-1-carboxylate as starting material. MS (ESI, m/z): 732.2 [M+H]$^+$ Step 5: N-[3-Chloro-4-[4-(piperidine-4-carbonyl)piperazine-1-carbonyl]phenyl]-5-[1-(cyanomethyl)-3-(trifluoromethyl)pyrazol-4-yl]-1-methyl-imidazole-2-carboxamide formate The title compound was obtained in analogy to Example 60, step 9 by using tert-butyl 4-[4-[2-chloro-4-[[5-[1-(cyanomethyl)-3-(trifluoromethyl)pyrazol-4-yl]-1-methyl-imidazole-2-carbonyl]amino]benzoyl]piperazine-1-carbonyl]piperidine-1-carboxylate as starting material.
MS (ESI, m/z): 632.1 [M+H]+

Example 62 tert-butyl (S)-(1-(4-(2-chloro-4-(1-methyl-5-(1-(pyridin-3-ylmethyl)-3-(trifluoromethyl)-1H-pyrazol-4-yl)-1H-imidazole-2-carboxamido)benzoyl)piperazin-1-yl)-1-oxopropan-2-yl)carbamate

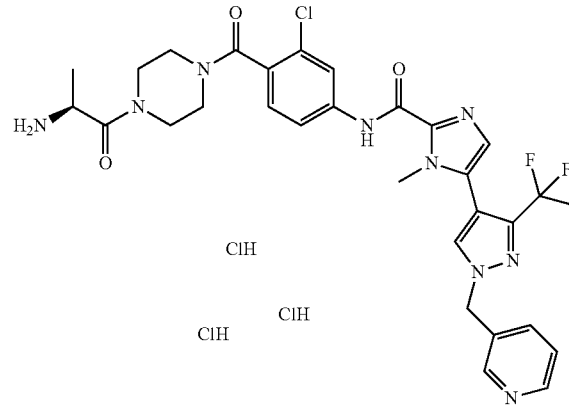

Step 1 tert-butyl 4-(4-(5-bromo-1-methyl-1H-imidazole-2-carboxamido)-2-chlorobenzoyl) piperazine-1-carboxylate 5-bromo-1-methyl-1H-imidazole-2-carboxylic acid (3.96 g, 19.3 mmol, Eq: 1), 2-(3H-[1,2,3]triazolo[4,5-b]pyridin-3-yl)-1,1,3,3-tetramethylisouronium hexafluorophosphate (V) (HATU) (11 g, 29 mmol, Eq: 1.5) and 5-bromo-1-methyl-1H-imidazole-2-carboxylic acid (2 g, 9.71 mmol, Eq: 1) were dissolved in DMF (100 ml) and cooled to 0° C. N-ethyl-N-isopropylpropan-2-amine (DIPEA) (7.49 g, 10.3 ml, 57.9 mmol, Eq: 3) was added to give a brown solution and the reaction mixture was stirred at room temperature over the weekend. Water was added to the mixture. The obtained precipitate was collected by filtration and dried with HV to provide the desired product as a beige solid (4.96 g). MS (ESI, m/z): 528.2 [M+H]+

Step 2 tert-Butyl 4-(2-chloro-4-(1-methyl-5-(3-(trifluoromethyl)-1H-pyrazol-4-yl)-1H-imidazole-2-carboxamido)benzoyl)piperazine-1-carboxylate In a 250 mL three-necked flask, tert-butyl 4-(4-(5-bromo-1-methyl-1H-imidazole-2-carboxamido)-2-chlorobenzoyl)piperazine-1-carboxylate (4.96 g, 9.42 mmol, Eq: 1), (3-(trifluoromethyl)-1H-pyrazol-4-yl)boronic acid (2.54 g, 14.1 mmol, Eq: 1.5), Na₂CO₃ (2 g, 18.8 mmol, Eq: 2.00) and 1,1'-bis(di-tert-butylphosphino)ferrocene palladium dichloride (dtbpf) (614 mg, 942 μmol, Eq: 0.10) were combined with dioxane (40 mL) and water (4 ml) to give a brown suspension. After 15 min of bubbling of Ar through the reaction mixture with Ar, it was stirred at 85° C. overnight.
(3-(Trifluoromethyl)-1H-pyrazol-4-yl)boronic acid (847 mg, 4.71 mmol, Eq: 0.5) and 1,1'-bis(di-tert-butylphosphino)ferrocene palladium dichloride (dtbpf) (614 mg, 942 μmol, Eq: 0.10) was added. The RM was stirred again at 85° C. overnight. 1,1'-Bis(di-tert-butylphosphino)ferrocene palladium dichloride (dtbpf) (307 mg, 471 μmol, Eq: 0.05) and (3-(trifluoromethyl)-1H-pyrazol-4-yl)boronic acid (847 mg, 4.71 mmol, Eq: 0.5) were added. The RM was stirred again at 85° C. overnight. Again 1,1'-bis(di-tert-butylphosphino)ferrocene palladium dichloride (dtbpf) (307 mg, 471 μmol, Eq: 0.05) and (3-(trifluoromethyl)-1H-pyrazol-4-yl)boronic acid (847 mg, 4.71 mmol, Eq: 0.5) were added two more times.
After filtration over celite, the volatiles were evaporated and the crude material was purified by flash chromatography in two batches (silica gel, 40 g, 0% to 100% EtOAC/EtOH 3/1 in heptane).
Product containing fractions were combined to yield a light brown solid as title compound (2.255 g). MS (ESI, m/z): 582.3 [M+H]+

Step 3 tert-Butyl 4-(2-chloro-4-(1-methyl-5-(1-(pyridin-3-ylmethyl)-3-(trifluoromethyl)-1H-pyrazol-4-yl)-1H-imidazole-2-carboxamido)benzoyl)piperazine-1-carboxylate Under Ar, tert-butyl 4-(2-chloro-4-(1-methyl-5-(3-(trifluoromethyl)-1H-pyrazol-4-yl)-1H-imidazole-2-carboxamido)benzoyl)piperazine-1-carboxylate (1 g, 1.72 mmol, Eq: 1) was dissolved in DMF (10 ml). Sodium bicarbonate (433 mg, 5.15 mmol, Eq: 3) and 3-(chloromethyl)pyridine hydrochloride (388 mg, 2.37 mmol, Eq: 1.38) were added and the light brown reaction mixture was stirred in the microwave at 120° C. for 2 h. The RM was filtered and the filtrate was washed with NaHCO₃ sat. solution 3x. The organic layers were combined and evaporated to result in 1.02 g dark brown sticky solid as crude product. The crude material was purified by flash chromatography (silica gel, 40 g, 0% to 40% EtOAc/EtOH (3/1) in heptane). The fractions containing product were combined and evaporated to result in 580 mg light brown solid as desired product. MS (ESI, m/z): 673.4 [M+H]+

Step 4

N-(3-Chloro-4-(piperazine-1-carbonyl)phenyl)-1-methyl-5-(1-(pyridin-3-ylmethyl)-3-(trifluoromethyl)-1H-pyrazol-4-yl)-1H-imidazole-2-carboxamide trihydrochloride Tert-Butyl 4-(2-chloro-4-(1-methyl-5-(1-(pyridin-3-ylmethyl)-3-(trifluoromethyl)-1H-pyrazol-4-yl)-1H-imidazole-2-carboxamido)benzoyl)piperazine-1-carboxylate (580 mg, 862 μmol, Eq: 1) was stirred with 4M HCl in dioxane (4.31 ml, 17.2 mmol, Eq: 20) in dioxane (5 ml) at room temperature (Rxn Molarity: 172 mM, Reaction Time: overnight). Diethyl ether (3 mL) was added and the mixture was stirred for 30 min at RT. The resulting suspension was filtered off and the solid was evaporated to dryness to result in 480 mg of an off-white solid as desired product. MS (ESI, m/z): 573.3 [M+H]+

Step 5 tert-Butyl (S)-(1-(4-(2-chloro-4-(1-methyl-5-(1-(pyridin-3-ylmethyl)-3-(trifluoromethyl)-1H-pyrazol-4-yl)-1H-imidazole-2-carboxamido)benzoyl)piperazin-1-yl)-1-oxopropan-2-yl)carbamate In a 25 mL pear-shaped flask, N-(3-chloro-4-(piperazine-1-carbonyl)phenyl)-1-methyl-5-(1-(pyridin-3-ylmethyl)-3-(trifluoromethyl)-1H-pyrazol-4-yl)-1H-imidazole-2-carboxamide trihydrochloride (30 mg, 44 µmol, Eq: 1), and rac-(tert-butoxycarbonyl)-D-alanine (12.5 mg, 65.9 µmol, Eq: 1.5) were combined with DMF (1 ml) to give a brown solution. DIEA (8.52 mg, 11.5 µl, 65.9 µmol, Eq: 1.5) was added dropwise at room temperature. The reaction mixture was stirred over the weekend at room temperature. LC/MS showed the desired product, no remaining starting material. The mixture was poured into water, partitioned with ethyl acetate. The organic phase was washed with water (3×), brine (2×), dried over magnesium sulfate and concentrated. The obtained residue was purified by flash chromatography (0-100% EtOAc/EtOH 3/1 in heptanes) to yield the desired product as an off-white waxy solid (28 mg). MS (ESI, m/z): 744.7 [M+H]+

Step 6

N-[4-[4-[(2S)-2-Aminopropanoyl]piperazine-1-carbonyl]-3-chlorophenyl]-1-methyl-5-[1-(pyridin-3-ylmethyl)-3-(trifluoromethyl)pyrazol-4-yl]imidazole-2-carboxamide trihydrochloride tert-Butyl (S)-(1-(4-(2-chloro-4-(1-methyl-5-(1-(pyridin-3-ylmethyl)-3-(trifluoromethyl)-1H-pyrazol-4-yl)-1H-imidazole-2-carboxamido)benzoyl)piperazin-1-yl)-1-oxopropan-2-yl)carbamate (28 mg, 37.6 µmol, Eq: 1) was stirred with 4M HCl in dioxane (188 µl, 753 µmol, Eq: 20) in dioxane (2 ml) at room temperature (Rxn Molarity: 18.8 mM, Reaction Time: 2 hr). Diethylether (2 mL) was added and the RM was stirred for 30 min at RT. The resulting suspension was filtered off and the solid was evaporated to dryness to result in a yellow waxy solid as desired product (24 mg). MS (ESI, m/z): 644.3 [M+H]+

The following Examples were obtained in analogy:

| Ex. | Name | Structure | ESI MS [M + H]+ | Starting Material |
|---|---|---|---|---|
| 63 | rac-N-(4-(4-((1r,3r)-3-aminocyclobutane-1-carbonyl)piperazine-1-carbonyl)-3-chlorophenyl)-1-methyl-5-(1-(pyridin-3-ylmethyl)-3-(trifluoromethyl)-1H-pyrazol-4-yl)-1H-imidazole-2-carboxamide trihydrochloride | 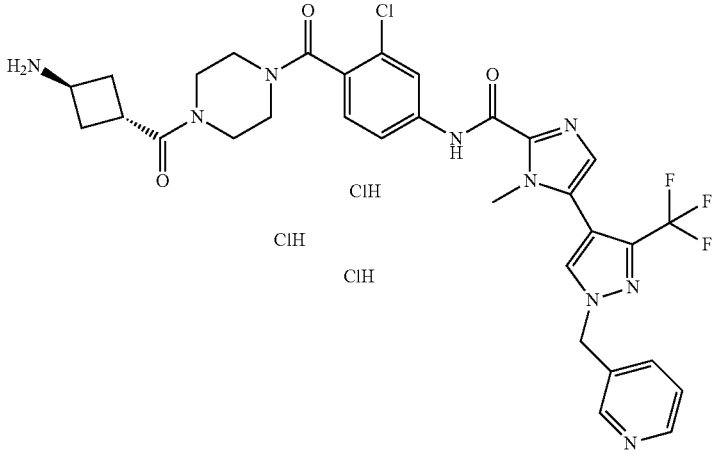 [SMILES: Cn1c(-c2cn(Cc3cccnc3)nc2C(F)(F)F)cnc1C(=O)Nc1ccc(C(=O)N2CCN(C(=O)[C@H]3C[C@H](N)C3)CC2)c(Cl)c1 ; Cl ; Cl ; Cl] | 670.3 | N-(3-chloro-4-(piperazine-1-carbonyl)phenyl)-1-methyl-5-(1-(pyridin-3-ylmethyl)-3-(trifluoromethyl)-1H-pyrazol-4-yl)-1H-imidazole-2-carboxamide trihydrochloride, then HCl deprotection |
| 64 | N-(4-(4-((1S,3R)-3-aminocyclopentane-1-carbonyl)piperazine-1-carbonyl)-3-chlorophenyl)-1-methyl-5-(1-(pyridin-3-ylmethyl)-3-(trifluoromethyl)-1H-pyrazol-4-yl)-1H-imidazole-2-carboxamide trihydrochloride | 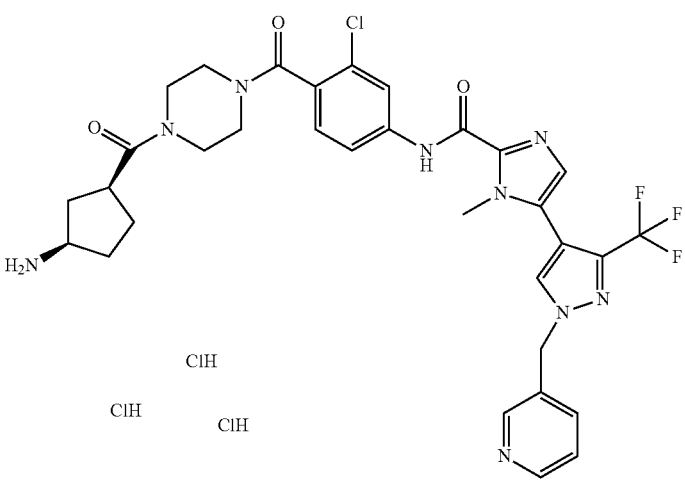 [SMILES: Cn1c(-c2cn(Cc3cccnc3)nc2C(F)(F)F)cnc1C(=O)Nc1ccc(C(=O)N2CCN(C(=O)[C@H]3CC[C@@H](N)C3)CC2)c(Cl)c1 ; Cl ; Cl ; Cl] | 684.4 | N-(3-chloro-4-(piperazine-1-carbonyl)phenyl)-1-methyl-5-(1-(pyridin-3-ylmethyl)-3-(trifluoromethyl)-1H-pyrazol-4-yl)-1H-imidazole-2-carboxamide trihydrochloride, then HCl deprotection |

Example 65

N-[3-chloro-4-[4-(piperidine-4-carbonyl)piperazine-1-carbonyl]phenyl]-1-methyl-5-[1-propa-1,2-dienyl-3-(trifluoromethyl)pyrazol-4-yl]imidazole-2-carboxamide; Hydrochloride

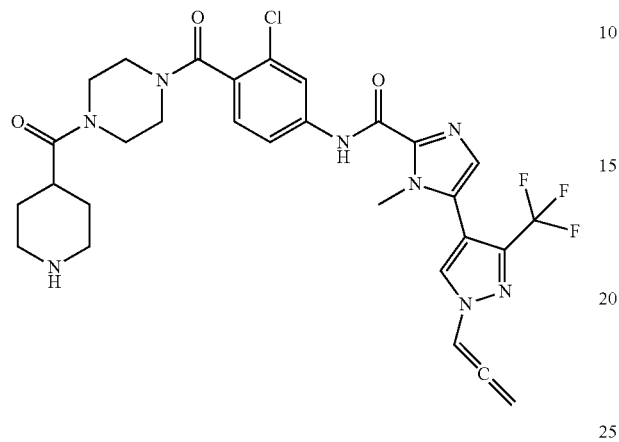

N-(3-Chloro-4-(4-(piperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide hydrochloride (Example 3, 20 mg, 30 μmol, Eq: 1) was combined with THF (200 ml) and MeOH (100 ml). Aq LiOH 1M (59.9 μl, 59.9 μmol, Eq: 2) was added and the reaction mixture was stirred at RT overnight. The non-aqueous solvent was evaporated and the product was extracted with AcOEt. After drying over $Na_2SO_4$, the combined organic layers were concentrated and dried to give the title compound (19 mg) as an off-white solid. ESI MS: 631.2 $[M+H]^+$ The following additional Examples have been prepared with the methods described above:

| Ex. | Name | Structure | ESI MS $[M + H]^+$ |
|---|---|---|---|
| 66 | N-[3-chloro-4-[4-(piperidine-4-carbonyl)piperazine-1-carbonyl]phenyl]-1-methyl-5-(3-phenyl-1H-pyrazol-4-yl)imidazole-2-carboxamide | 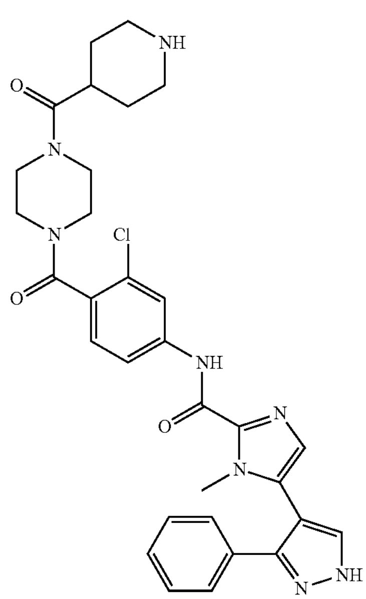 [SMILES: Cn1c(-c2c[nH]nc2-c2ccccc2)cnc1C(=O)Nc1ccc(C(=O)N2CCN(C(=O)C3CCNCC3)CC2)c(Cl)c1] | 601.2 |

| Ex. | Name | Structure | ESI MS [M + H]+ |
|---|---|---|---|
| 67 | N-[3-chloro-4-(piperazine-1-carbonyl)phenyl]-1-methyl-5-[1-(pyridin-3-ylmethyl)-3-(trifluoromethyl)pyrazol-4-yl]imidazole-2-carboxamide;hydrochloride | 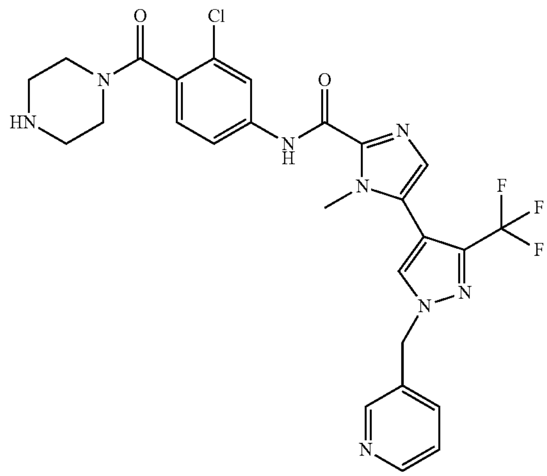 [SMILES: Cn1c(-c2cn(Cc3cccnc3)nc2C(F)(F)F)cnc1C(=O)Nc1ccc(C(=O)N2CCNCC2)c(Cl)c1] | 573.3 |
| 68 | N-[3-chloro-4-(piperazine-1-carbonyl)phenyl]-5-[1-(2-fluoroethyl)-3-(trifluoromethyl)pyrazol-4-yl]-1-methylimidazole-2-carboxamide;hydrochloride | 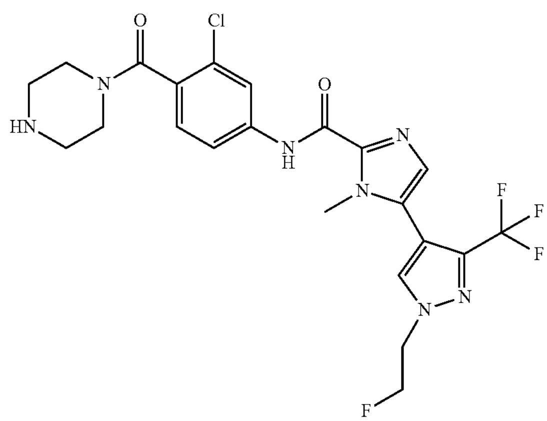 [SMILES: Cn1c(-c2cn(CCF)nc2C(F)(F)F)cnc1C(=O)Nc1ccc(C(=O)N2CCNCC2)c(Cl)c1] | 528.3 |
| 69 | N-[3-chloro-4-(piperazine-1-carbonyl)phenyl]-5-[1-(cyanomethyl)-3-(trifluoromethyl)pyrazol-4-yl]-1-methylimidazole-2-carboxamide;2,2,2-trifluoroacetic acid | 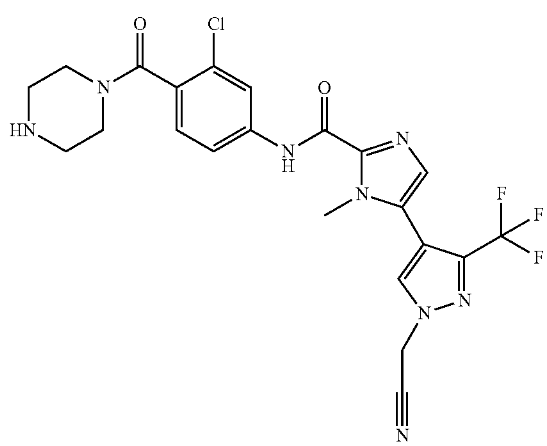 [SMILES: Cn1c(-c2cn(CC#N)nc2C(F)(F)F)cnc1C(=O)Nc1ccc(C(=O)N2CCNCC2)c(Cl)c1] | 521.2 |

-continued

| Ex. | Name | Structure | ESI MS [M + H]+ |
|---|---|---|---|
| 70 | N-[3-chloro-4-[4-[(3S)-pyrrolidine-3-carbonyl]piperazine-1-carbonyl]phenyl]-1-methyl-5-[1-(pyridin-3-ylmethyl)-3-(trifluoromethyl)pyrazol-4-yl]imidazole-2-carboxamide | 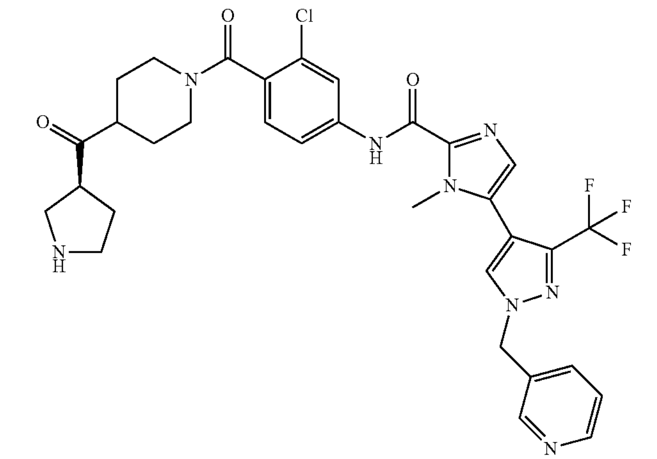 [SMILES: Cn1c(-c2cn(Cc3cccnc3)nc2C(F)(F)F)cnc1C(=O)Nc1ccc(C(=O)N2CCC(C(=O)[C@H]3CCNC3)CC2)c(Cl)c1] | 670.3 |
| 71 | N-[4-[4-[(2S)-2-aminopropanoyl]piperazine-1-carbonyl]-3-chlorophenyl]-5-[1-(cyanomethyl)-3-(trifluoromethyl)pyrazol-4-yl]-1-methylimidazole-2-carboxamide;2,2,2-trifluoroacetic acid | 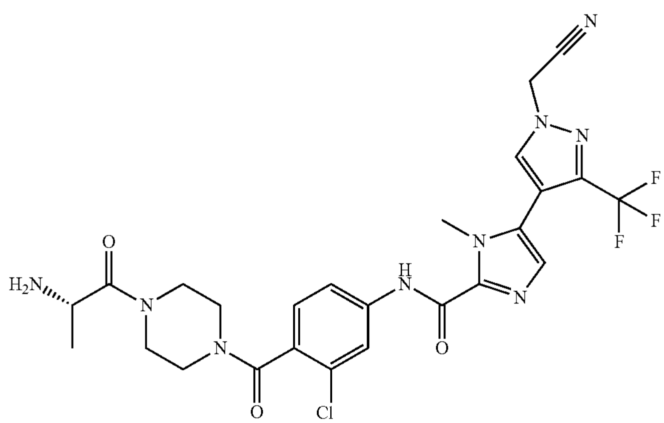 [SMILES: C[C@H](N)C(=O)N1CCN(C(=O)c2ccc(NC(=O)c3ncc(-c4cn(CC#N)nc4C(F)(F)F)n3C)cc2Cl)CC1] | 594.3 |
| 72 | N-[3-chloro-4-[4-(3-hydroxypiperidine-3-carbonyl)piperazine-1-carbonyl]phenyl]-5-[1-(cyanomethyl)-3-(trifluoromethyl)pyrazol-4-yl]-1-methylimidazole-2-carboxamide;2,2,2-trifluoroacetic acid | 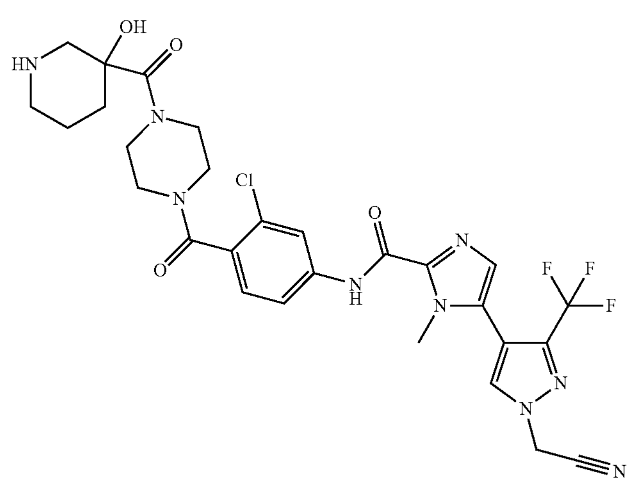 [SMILES: Cn1c(-c2cn(CC#N)nc2C(F)(F)F)cnc1C(=O)Nc1ccc(C(=O)N2CCN(C(=O)C3(O)CCCNC3)CC2)c(Cl)c1] | 648.4 |

-continued

| Ex. | Name | Structure | ESI MS [M + H]+ |
|---|---|---|---|
| 73 | N-[4-[4-(3-aminocyclobutanecarbonyl)piperazine-1-carbonyl]-3-chlorophenyl]-5-[1-(cyanomethyl)-3-(trifluoromethyl)pyrazol-4-yl]-1-methylimidazole-2-carboxamide;2,2,2-trifluoroacetic acid | AND Enantiomer | 618.5 |
| 74 | N-[4-[4-(3-aminocyclobutanecarbonyl)piperazine-1-carbonyl]-3-chlorophenyl]-5-[1-(2-fluoroethyl)-3-(trifluoromethyl)pyrazol-4-yl]-1-methylimidazole-2-carboxamide;hydrochloride | AND Enantiomer | 625.3 |
| 75 | N-[3-chloro-4-[4-(3-hydroxypiperidine-3-carbonyl)piperazine-1-carbonyl]phenyl]-1-methyl-5-[1-(pyridin-3-ylmethyl)-3-(trifluoromethyl)pyrazol-4-yl]imidazole-2-carboxamide;hydrochloride | 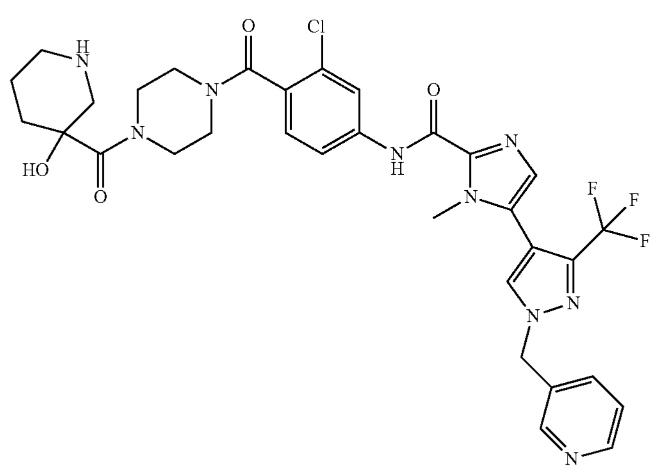 [SMILES: Cn1c(-c2cn(Cc3cccnc3)nc2C(F)(F)F)cnc1C(=O)Nc1ccc(C(=O)N2CCN(C(=O)C3(O)CCCNC3)CC2)c(Cl)c1] | 700.4 |

| Ex. | Name | Structure | ESI MS [M + H]+ |
|---|---|---|---|
| 76 | 4-[2-chloro-4-[[1-methyl-5-[1-prop-2-ynyl-3-(trifluoromethyl)pyrazol-4-yl]imidazole-2-carbonyl]amino]benzoyl]-N-[2-(methylamino)ethyl]piperazine-1-carboxamide | 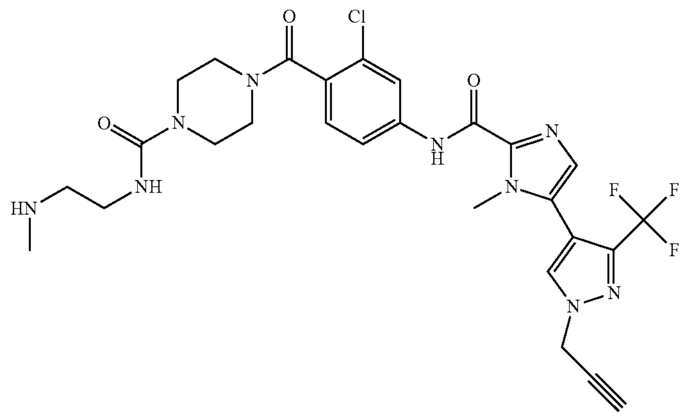 [SMILES: C#CCn1cc(-c2cnc(C(=O)Nc3ccc(C(=O)N4CCN(C(=O)NCCNC)CC4)c(Cl)c3)n2C)c(C(F)(F)F)n1] | 620.4 |
| 77 | N-[3-chloro-4-[4-(piperazine-1-carbonyl)piperazine-1-carbonyl]phenyl]-1-methyl-5-[1-prop-2-ynyl-3-(trifluoromethyl)pyrazol-4-yl]imidazole-2-carboxamide | 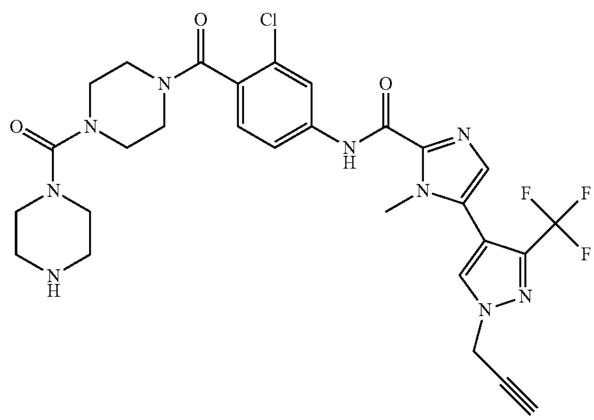 [SMILES: C#CCn1cc(-c2cnc(C(=O)Nc3ccc(C(=O)N4CCN(C(=O)N5CCNCC5)CC4)c(Cl)c3)n2C)c(C(F)(F)F)n1] | 633.6 |
| 78 | N-(3-aminocyclobutyl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide | AND Enantiomer | 633.4 |

| Ex. | Name | Structure | ESI MS [M + H]+ |
|---|---|---|---|
| 79 | N-[4-[4-[(3R)-3-aminopyrrolidine-1-carbonyl]piperazine-1-carbonyl]-3-chlorophenyl]-1-methyl-5-[1-prop-2-ynyl-3-(trifluoromethyl)pyrazol-4-yl]imidazole-2-carboxamide | 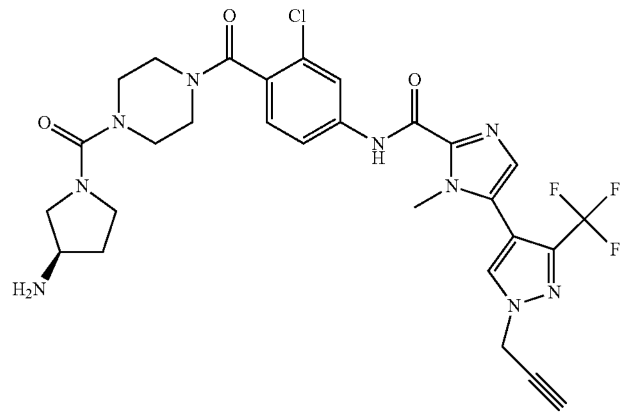 [SMILES: C#CCn1cc(-c2cnc(C(=O)Nc3ccc(C(=O)N4CCN(C(=O)N5CC[C@@H](N)C5)CC4)c(Cl)c3)n2C)c(C(F)(F)F)n1] | 633.2 |
| 80 | N-[4-[4-[(3S)-3-carbonyl]piperazine-1-carbonyl]-3-chlorophenyl]-1-methyl-5-[1-prop-2-ynyl-3-(trifluoromethyl)pyrazol-4-yl]imidazole-2-carboxamide | 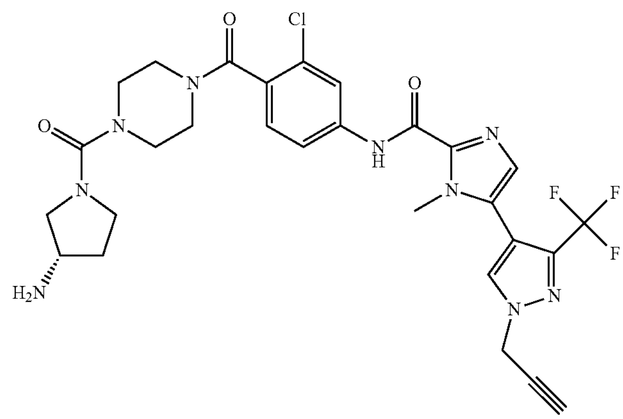 [SMILES: C#CCn1cc(-c2cnc(C(=O)Nc3ccc(C(=O)N4CCN(C(=O)N5CC[C@H](N)C5)CC4)c(Cl)c3)n2C)c(C(F)(F)F)n1] | 633.3 |
| 81 | N-[4-[4-(3-amino-3-methylazetidine-1-carbonyl)piperazine-1-carbonyl]-3-chlorophenyl]-1-methyl-5-[1-prop-2-ynyl-3-(trifluoromethyl)pyrazol-4-yl]imidazole-2-carboxamide | 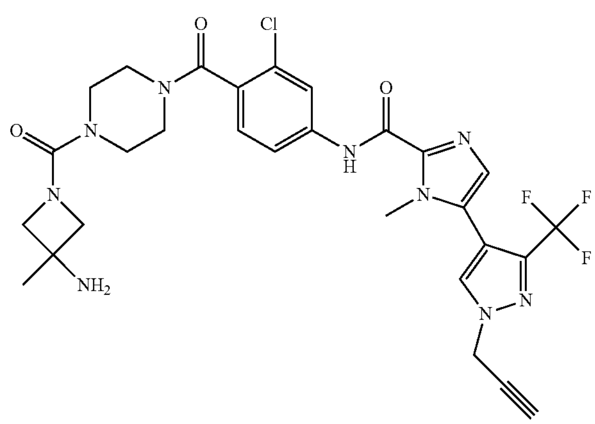 [SMILES: C#CCn1cc(-c2cnc(C(=O)Nc3ccc(C(=O)N4CCN(C(=O)N5CC(C)(N)C5)CC4)c(Cl)c3)n2C)c(C(F)(F)F)n1] | 633.4 |

| Ex. | Name | Structure | ESI MS [M + H]+ |
|---|---|---|---|
| 82 | N-[(1S,2R)-2-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide | 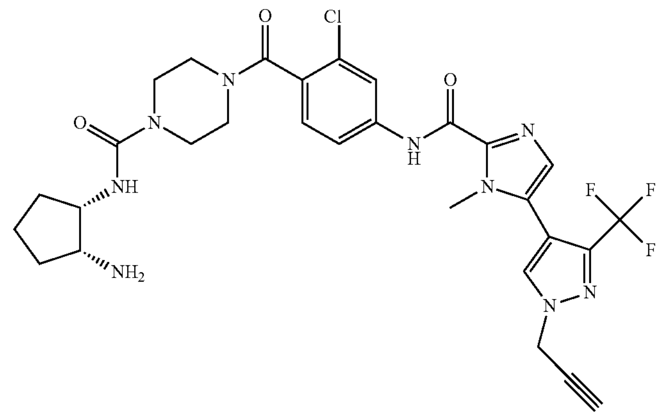 [SMILES: C#CCn1cc(-c2cnc(C(=O)Nc3ccc(C(=O)N4CCN(C(=O)N[C@H]5CCC[C@H]5N)CC4)c(Cl)c3)n2C)c(C(F)(F)F)n1] | 647.5 |
| 83 | N-[(1S,3S)-3-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide | 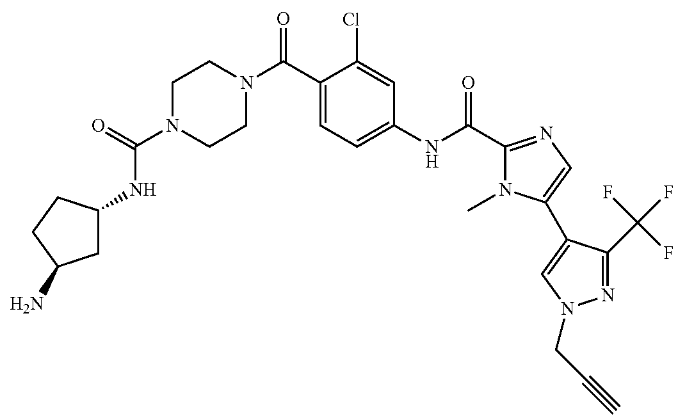 [SMILES: C#CCn1cc(-c2cnc(C(=O)Nc3ccc(C(=O)N4CCN(C(=O)N[C@H]5CC[C@H](N)C5)CC4)c(Cl)c3)n2C)c(C(F)(F)F)n1] | 647.3 |
| 84 | N-[4-[4-(4-aminopiperidine-1-carbonyl)piperazine-1-carbonyl]-3-chlorophenyl]-1-methyl-5-[1-prop-2-ynyl-3-(trifluoromethyl)pyrazol-4-yl]imidazole-2-carboxamide | 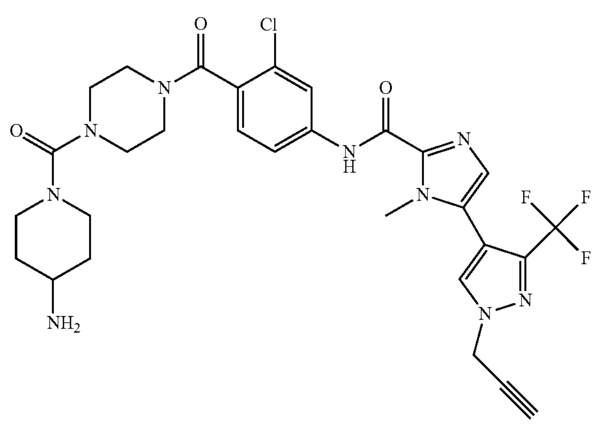 [SMILES: C#CCn1cc(-c2cnc(C(=O)Nc3ccc(C(=O)N4CCN(C(=O)N5CCC(N)CC5)CC4)c(Cl)c3)n2C)c(C(F)(F)F)n1] | 647.5 |

| Ex. | Name | Structure | ESI MS [M + H]+ |
|---|---|---|---|
| 85 | N-[4-[4-[(3S)-3-aminopiperidine-1-carbonyl]piperazine-1-carbonyl]-3-chlorophenyl]-1-methyl-5-[1-prop-2-ynyl-3-(trifluoromethyl)pyrazol-4-yl]imidazole-2-carboxamide | 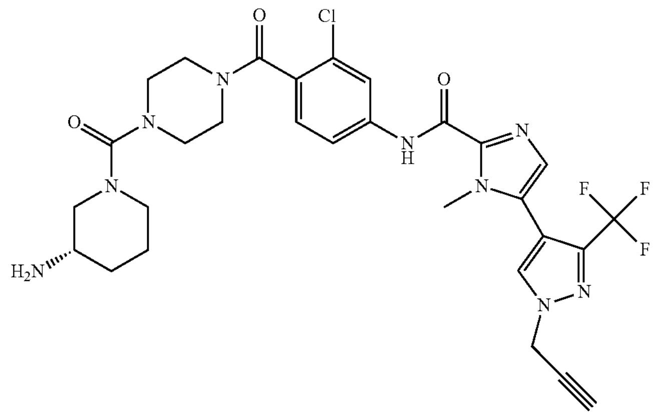 [SMILES: C#CCn1cc(-c2cnc(C(=O)Nc3ccc(C(=O)N4CCN(C(=O)N5CCC[C@H](N)C5)CC4)c(Cl)c3)n2C)c(C(F)(F)F)n1] | 647.4 |
| 86 | N-[3-chloro-4-[4-(3,6-diazabicyclo[3.2.0]heptane-3-carbonyl)piperazine-1-carbonyl]phenyl]-1-methyl-5-[1-prop-2-ynyl-3-(trifluoromethyl)pyrazol-4-yl]imidazole-2-carboxamide | 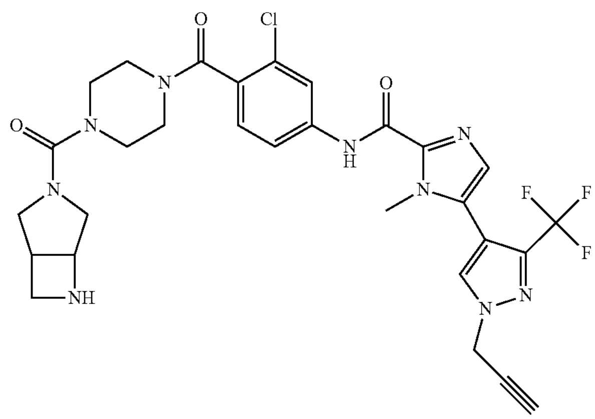 [SMILES: C#CCn1cc(-c2cnc(C(=O)Nc3ccc(C(=O)N4CCN(C(=O)N5CC6CNC6C5)CC4)c(Cl)c3)n2C)c(C(F)(F)F)n1] | 645.3 |
| 87 | 4-[2-chloro-4-[[1-methyl-5-[1-prop-2-ynyl-3-(trifluoromethyl)pyrazol-4-yl]imidazole-2-carbonyl]amino]benzoyl]-N-[rac-(1R,5S)-3-azabicyclo[3.1.0]hexan-6-yl]piperazine-1-carboxamide | AND Enantiomer | 644.6 |

-continued

| Ex. | Name | Structure | ESI MS [M + H]+ |
|---|---|---|---|
| 88 | N-[3-chloro-4-[4-[(1S,4S)-2,5-diazabicyclo[2.2.1]heptane-2-carbonyl]piperazine-1-carbonyl]phenyl]-1-methyl-5-[1-prop-2-ynyl-3-(trifluoromethyl)pyrazol-4-yl]imidazole-2-carboxamide | 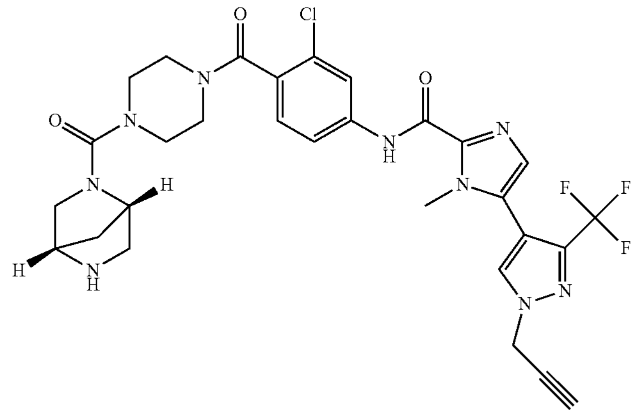 [SMILES: C#CCn1cc(-c2cnc(C(=O)Nc3ccc(C(=O)N4CCN(C(=O)N5C[C@@H]6C[C@H]5CN6)CC4)c(Cl)c3)n2C)c(C(F)(F)F)n1] | 645.4 |
| 89 | N-(2-azaspiro[3.3]heptan-6-yl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide | 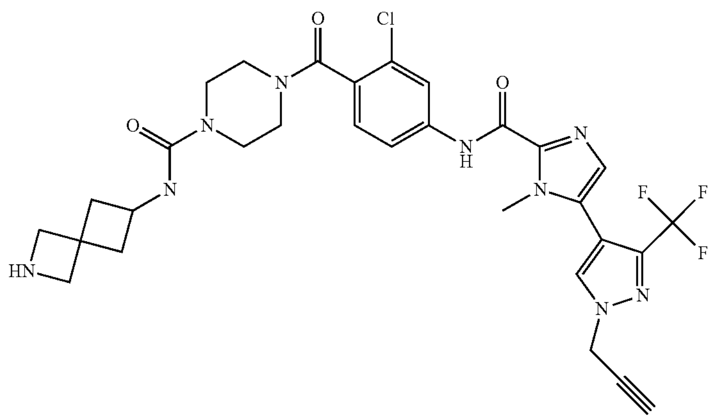 [SMILES: C#CCn1cc(-c2cnc(C(=O)Nc3ccc(C(=O)N4CCN(C(=O)NC5CC6(CNC6)C5)CC4)c(Cl)c3)n2C)c(C(F)(F)F)n1] | 659.1 |
| 90 | N-[4-[4-[(3aS,6aS)-2,3,3a,4,6,6a-hexahydro-1H-pyrrolo[3,4-c]pyrrole-5-carbonyl]piperazine-1-carbonyl]-3-chlorophenyl]-1-methyl-5-[1-prop-2-ynyl-3-(trifluoromethyl)pyrazol-4-yl]imidazole-2-carboxamide | 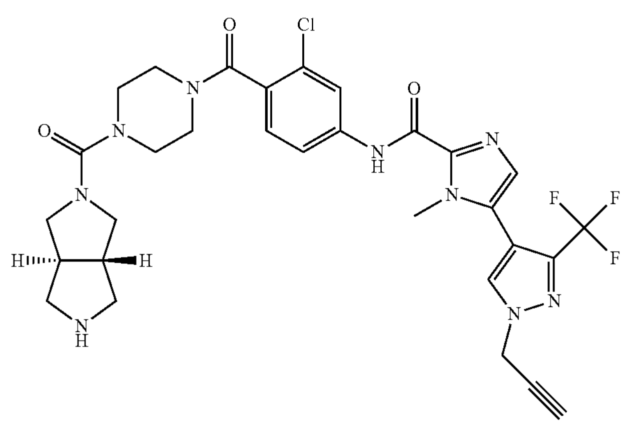 [SMILES: C#CCn1cc(-c2cnc(C(=O)Nc3ccc(C(=O)N4CCN(C(=O)N5C[C@@H]6CNC[C@H]6C5)CC4)c(Cl)c3)n2C)c(C(F)(F)F)n1] | 658.4 |

| Ex. | Name | Structure | ESI MS [M + H]+ |
|---|---|---|---|
| 91 | N-[3-chloro-4-[4-(1,6-diazaspiro[3.3]heptane-6-carbonyl)piperazine-1-carbonyl]phenyl]-1-methyl-5-[1-prop-2-ynyl-3-(trifluoromethyl)pyrazol-4-yl]imidazole-2-carboxamide | 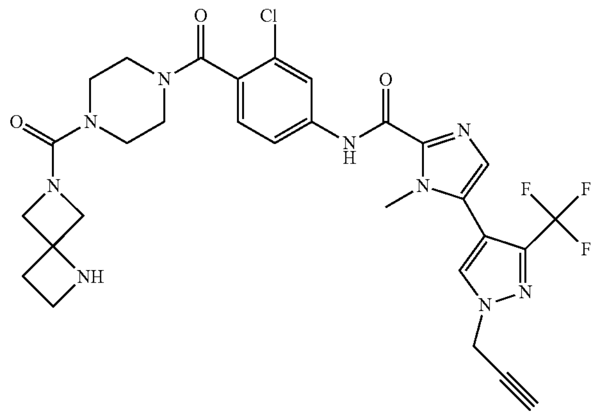 [SMILES: C#CCn1cc(-c2cnc(C(=O)Nc3ccc(C(=O)N4CCN(C(=O)N5CC6(CCN6)C5)CC4)c(Cl)c3)n2C)c(C(F)(F)F)n1] | 645.5 |
| 92 | N-[3-chloro-4-[4-[rac-(1R,5S)-3-azabicyclo[3.1.0]hexane-6-carbonyl]piperazine-1-carbonyl]phenyl]-1-methyl-5-[1-prop-2-ynyl-3-(trifluoromethyl)pyrazol-4-yl]imidazole-2-carboxamide;hydrochloride | AND Enantiomer | 629.3 |
| 93 | N-[4-[(3-aminocyclobutyl)carbamoyl]-3-chlorophenyl]-1-methyl-5-[1-prop-2-ynyl-3-(trifluoromethyl)pyrazol-4-yl]imidazole-2-carboxamide;hydrochloride | AND Enantiomer | 520.2 |

| Ex. | Name | Structure | ESI MS [M + H]+ |
|---|---|---|---|
| 94 | N-[4-[(3-aminocyclobutyl)carbamoyl]-3-chlorophenyl]-5-[1-(cyanomethyl)-3-(trifluoromethyl)pyrazol-4-yl]-1-methylimidazole-2-carboxamide;2,2,2-trifluoroacetic acid | AND Enantiomer | 521.3 |
| 95 | N-[4-[[3-[[(2R)-2-aminopropanoyl]amino]cyclobutyl]carbamoyl]-3-chlorophenyl]-5-[1-(cyanomethyl)-3-(trifluoromethyl)pyrazol-4-yl]-1-methylimidazole-2-carboxamide;2,2,2-trifluoroacetic acid | 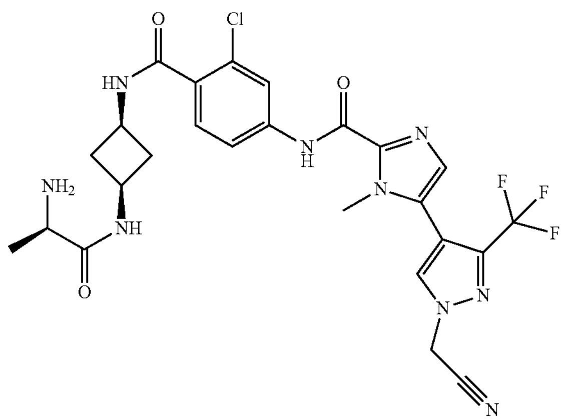 [SMILES: C[C@@H](N)C(=O)N[C@H]1C[C@@H](NC(=O)c2ccc(NC(=O)c3ncc(-c4cn(CC#N)nc4C(F)(F)F)n3C)cc2Cl)C1] | 592.4 |
| 96 | N-[4-[[3-[[(1S,3R)-3-aminocyclopentanecarbonyl]amino]cyclobutyl]carbamoyl]-3-chlorophenyl]-5-[1-(cyanomethyl)-3-(trifluoromethyl)pyrazol-4-yl]-1-methylimidazole-2-carboxamide;2,2,2-trifluoroacetic acid | 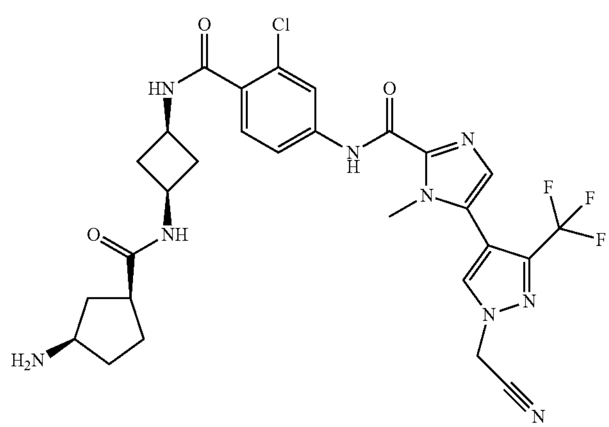 [SMILES: Cn1c(-c2cn(CC#N)nc2C(F)(F)F)cnc1C(=O)Nc1ccc(C(=O)N[C@H]2C[C@@H](NC(=O)[C@H]3CC[C@@H](N)C3)C2)c(Cl)c1] | 632.3 |

| Ex. | Name | Structure | ESI MS [M + H]+ |
|---|---|---|---|
| 97 | N-[4-[(3-aminocyclobutyl)carbamoyl]-3-chlorophenyl]-5-[1-cyclopropyl-3-(trifluoromethyl)pyrazol-4-yl]-1-methylimidazole-2-carboxamide | AND Enantiomer | 520.3 [M − H] |
| 98 | N-[3-chloro-4-[4-(piperidine-4-carbonyl)piperazine-1-carbonyl]phenyl]-1-methyl-5-[3-(trifluoromethyl)-1-(3,3,3-trifluoropropyl)pyrazol-4-yl]imidazole-2-carboxamide;hydrochloride | 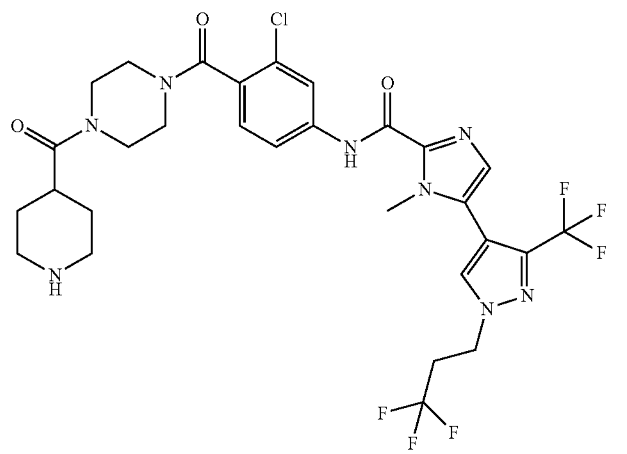 [SMILES: Cn1c(-c2cn(CCC(F)(F)F)nc2C(F)(F)F)cnc1C(=O)Nc1ccc(C(=O)N2CCN(C(=O)C3CCNCC3)CC2)c(Cl)c1] | 689.2 |
| 99 | N-[3-chloro-4-[4-(piperidine-4-carbonyl)piperazine-1-carbonyl]phenyl]-5-[1-(fluoromethyl)-3-(trifluoromethyl)pyrazol-4-yl]-1-methylimidazole-2-carboxamide;hydrochloride | 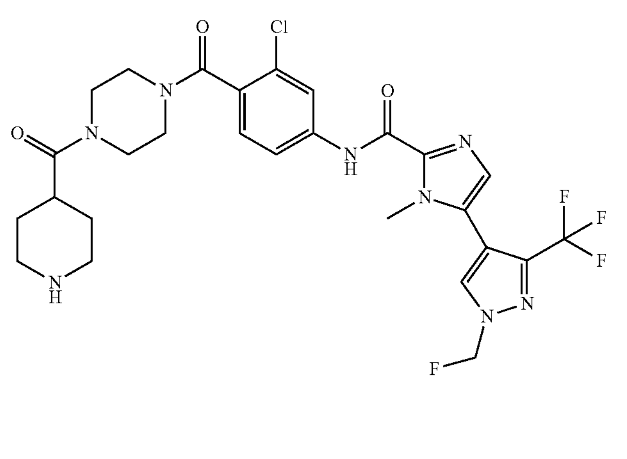 [SMILES: Cn1c(-c2cn(CF)nc2C(F)(F)F)cnc1C(=O)Nc1ccc(C(=O)N2CCN(C(=O)C3CCNCC3)CC2)c(Cl)c1] | 625.3 |

| Ex. | Name | Structure | ESI MS [M + H]+ |
|---|---|---|---|
| 100 | N-[3-chloro-4-[4-(piperidine-4-carbonyl)piperazine-1-carbonyl]phenyl]-1-methyl-5-[1-(1H-pyrazol-5-ylmethyl)-3-(trifluoromethyl)pyrazol-4-yl]imidazole-2-carboxamide | 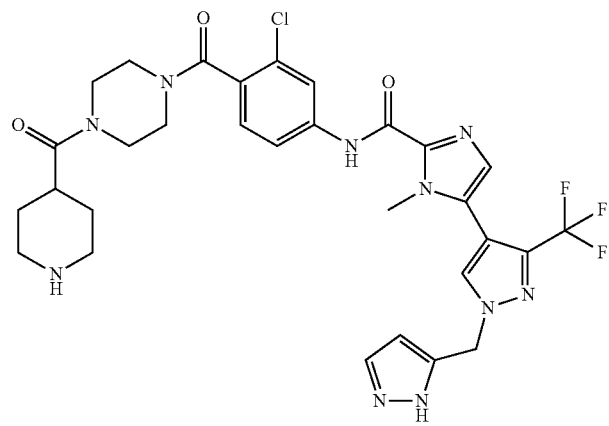 [SMILES: Cn1c(-c2cn(Cc3ccn[nH]3)nc2C(F)(F)F)cnc1C(=O)Nc1ccc(C(=O)N2CCN(C(=O)C3CCNCC3)CC2)c(Cl)c1] | 673.2 |
| 101 | 5-[1-[2-(chloromethyl)-3-hydroxy-2-methylpropyl]-3-(trifluoromethyl)pyrazol-4-yl]-N-[3-chloro-4-[4-(piperidine-4-carbonyl)piperazine-1-carbonyl]phenyl]-1-methylimidazole-2-carboxamide;formic acid | 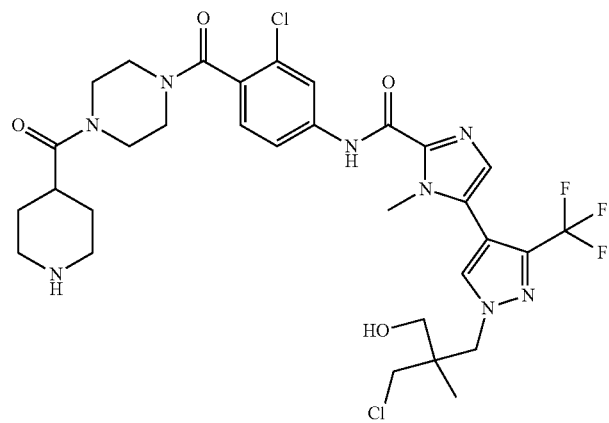 [SMILES: Cn1c(-c2cn(CC(C)(CO)CCl)nc2C(F)(F)F)cnc1C(=O)Nc1ccc(C(=O)N2CCN(C(=O)C3CCNCC3)CC2)c(Cl)c1] | 713.2 |
| 102 | N-[3-chloro-4-[4-(piperidine-4-carbonyl)piperazine-1-carbonyl]phenyl]-1-methyl-5-[1-propan-2-yl-3-(trifluoromethyl)pyrazol-4-yl]imidazole-2-carboxamide;hydrochloride | 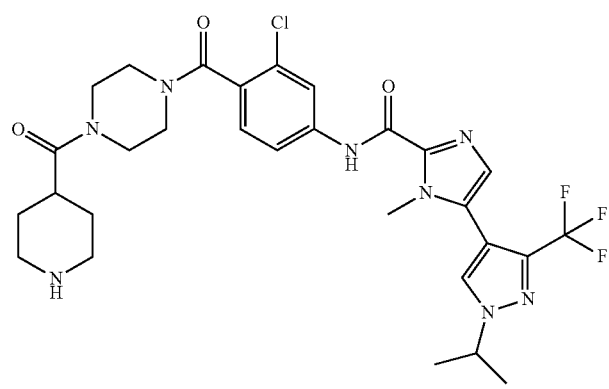 [SMILES: CC(C)n1cc(-c2cnc(C(=O)Nc3ccc(C(=O)N4CCN(C(=O)C5CCNCC5)CC4)c(Cl)c3)n2C)c(C(F)(F)F)n1] | 636.3 |

-continued

| Ex. | Name | Structure | ESI MS [M + H]+ |
|---|---|---|---|
| 103 | 5-[1-(1-chloro-3-hydroxypropan-2-yl)-3-(trifluoromethyl)pyrazol-4-yl]-N-[3-chloro-4-[4-(piperidine-4-carbonyl)piperazine-1-carbonyl]phenyl]-1-methylimidazole-2-carboxamide;hydrochloride | 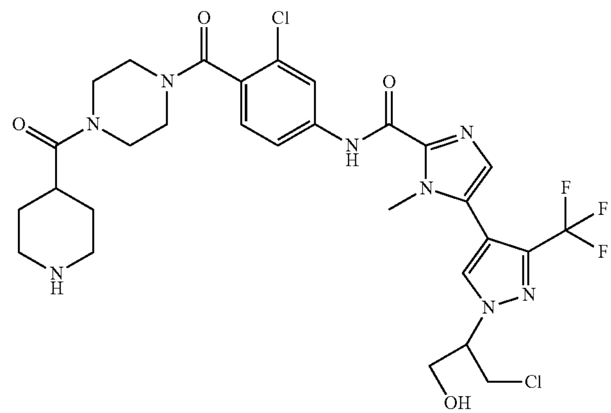 [SMILES: Cn1c(-c2cn(C(CO)CCl)nc2C(F)(F)F)cnc1C(=O)Nc1ccc(C(=O)N2CCN(C(=O)C3CCNCC3)CC2)c(Cl)c1] | 685.2 |
| 104 | N-[3-chloro-4-[4-(piperidine-4-carbonyl)piperazine-1-carbonyl]phenyl]-5-[1-(3-hydroxy-3-methylbutyl)-3-(trifluoromethyl)pyrazol-4-yl]-1-methylimidazole-2-carboxamide;hydrochloride | 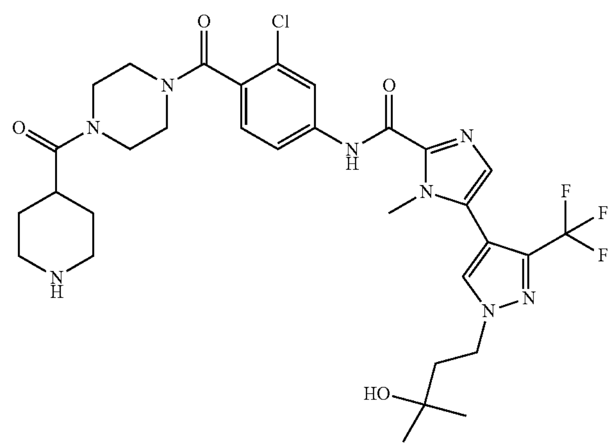 [SMILES: Cn1c(-c2cn(CCC(C)(C)O)nc2C(F)(F)F)cnc1C(=O)Nc1ccc(C(=O)N2CCN(C(=O)C3CCNCC3)CC2)c(Cl)c1] | 680.4 |
| 105 | 5-[1-[[3-chloro-1-(hydroxymethyl)-3-methylcyclobutyl]methyl]-3-(trifluoromethyl)pyrazol-4-yl]-N-[3-chloro-4-[4-(piperidine-4-carbonyl)piperazine-1-carbonyl]phenyl]-1-methylimidazole-2-carboxamide;hydrochloride | 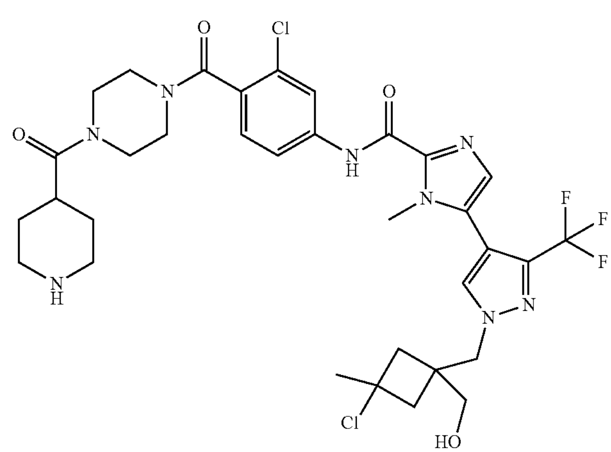 [SMILES: Cn1c(-c2cn(CC3(CO)CC(C)(Cl)C3)nc2C(F)(F)F)cnc1C(=O)Nc1ccc(C(=O)N2CCN(C(=O)C3CCNCC3)CC2)c(Cl)c1] | 739.2 |

| Ex. | Name | Structure | ESI MS [M + H]+ |
|---|---|---|---|
| 106 | N-[3-chloro-4-[4-(piperidine-4-carbonyl)piperazine-1-carbonyl]phenyl]-1-methyl-5-[1-[(5-methyl-1,2,4-oxadiazol-3-yl)methyl]-3-(trifluoromethyl)pyrazol-4-yl]imidazole-2-carboxamide;hydrochloride | 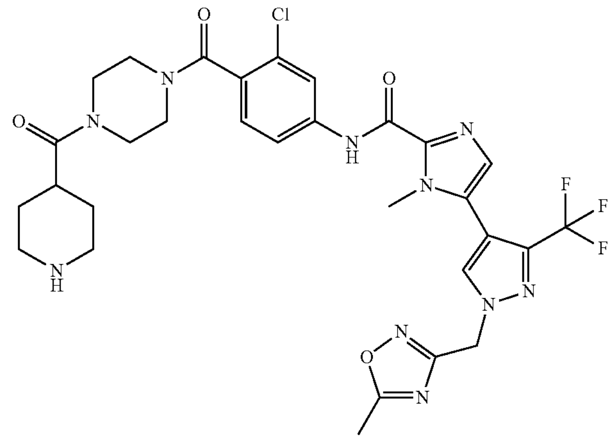 [SMILES: Cc1nc(Cn2cc(-c3cnc(C(=O)Nc4ccc(C(=O)N5CCN(C(=O)C6CCNCC6)CC5)c(Cl)c4)n3C)c(C(F)(F)F)n2)no1] | 690.3 |
| 107 | N-[3-chloro-4-[4-(piperidine-4-carbonyl)piperazine-1-carbonyl]phenyl]-1-methyl-5-[1-[(3-methylthietan-3-yl)methyl]-3-(trifluoromethyl)pyrazol-4-yl]imidazole-2-carboxamide;hydrochloride | 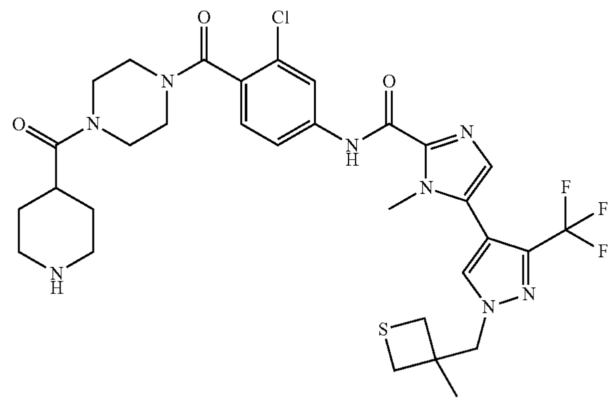 [SMILES: Cn1c(-c2cn(CC3(C)CSC3)nc2C(F)(F)F)cnc1C(=O)Nc1ccc(C(=O)N2CCN(C(=O)C3CCNCC3)CC2)c(Cl)c1] | 694.3 |
| 108 | N-[3-chloro-4-[4-(piperidine-4-carbonyl)piperazine-1-carbonyl]phenyl]-1-methyl-5-[1-spiro[2.3]hexan-5-yl-3-(trifluoromethyl)pyrazol-4-yl]imidazole-2-carboxamide;hydrochloride | 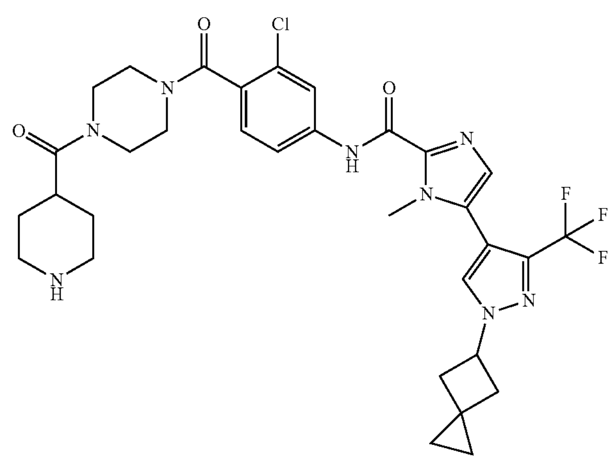 [SMILES: Cn1c(-c2cn(C3CC4(CC4)C3)nc2C(F)(F)F)cnc1C(=O)Nc1ccc(C(=O)N2CCN(C(=O)C3CCNCC3)CC2)c(Cl)c1] | 673.3 |

-continued

| Ex. | Name | Structure | ESI MS [M + H]+ |
|---|---|---|---|
| 109 | N-[3-chloro-4-[4-(piperidine-4-carbonyl)piperazine-1-carbonyl]phenyl]-5-[1-[2-(difluoromethoxy)ethyl]-3-(trifluoromethyl)pyrazol-4-yl]-1-methylimidazole-2-carboxamide;hydrochloride | 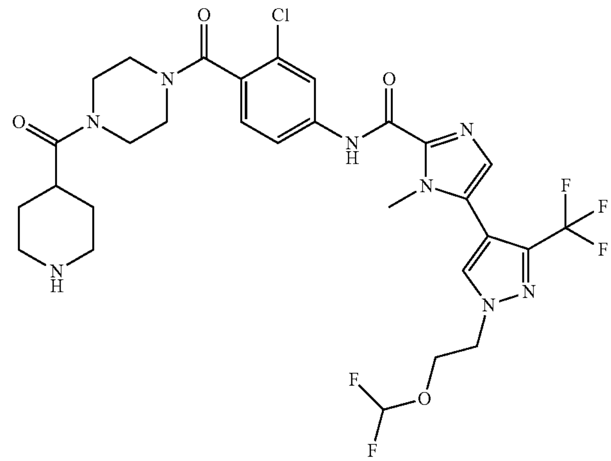 [SMILES: Cn1c(-c2cn(CCOC(F)F)nc2C(F)(F)F)cnc1C(=O)Nc1ccc(C(=O)N2CCN(C(=O)C3CCNCC3)CC2)c(Cl)c1] | 688.3 |
| 110 | N-[3-chloro-4-[4-(piperidine-4-carbonyl)piperazine-1-carbonyl]phenyl]-5-[1-[(2,2-difluorocyclopropyl)methyl]-3-(trifluoromethyl)pyrazol-4-yl]-1-methylimidazole-2-carboxamide;hydrochloride | 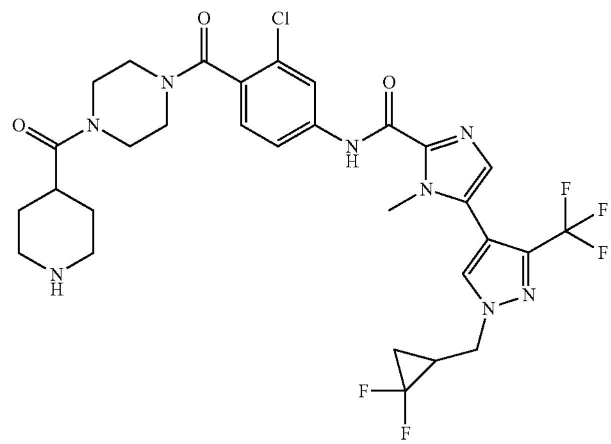 [SMILES: Cn1c(-c2cn(CC3CC3(F)F)nc2C(F)(F)F)cnc1C(=O)Nc1ccc(C(=O)N2CCN(C(=O)C3CCNCC3)CC2)c(Cl)c1] | 684.3 |
| 111 | N-[3-chloro-4-[4-(piperidine-4-carbonyl)piperazine-1-carbonyl]phenyl]-5-[1-[(3,3-difluorocyclobutyl)methyl]-3-(trifluoromethyl)pyrazol-4-yl]-1-methylimidazole-2-carboxamide;hydrochloride | 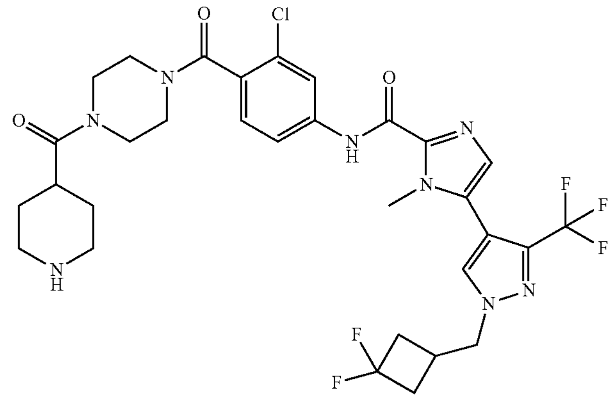 [SMILES: Cn1c(-c2cn(CC3CC(F)(F)C3)nc2C(F)(F)F)cnc1C(=O)Nc1ccc(C(=O)N2CCN(C(=O)C3CCNCC3)CC2)c(Cl)c1] | 698.4 |

-continued

| Ex. | Name | Structure | ESI MS [M + H]+ |
|---|---|---|---|
| 112 | N-[3-chloro-4-[4-(piperidine-4-carbonyl)piperazine-1-carbonyl]phenyl]-5-[1-(cyclopropylmethyl)-3-(trifluoromethyl)pyrazol-4-yl]-1-methylimidazole-2-carboxamide;hydrochloride | 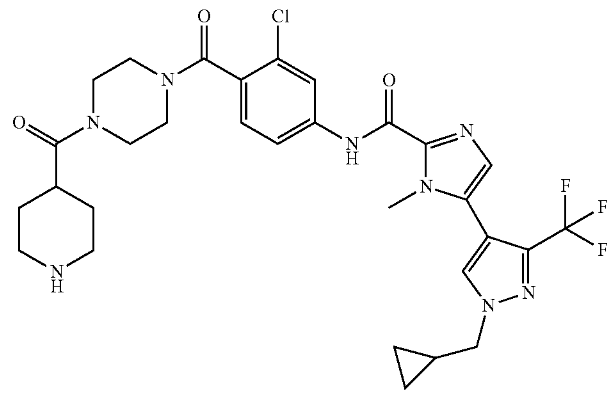 [SMILES: Cn1c(-c2cn(CC3CC3)nc2C(F)(F)F)cnc1C(=O)Nc1ccc(C(=O)N2CCN(C(=O)C3CCNCC3)CC2)c(Cl)c1] | 647.3 |
| 113 | N-[3-chloro-4-[4-(piperidine-4-carbonyl)piperazine-1-carbonyl]phenyl]-5-[1-(cyclobutylmethyl)-3-(trifluoromethyl)pyrazol-4-yl]-1-methylimidazole-2-carboxamide;hydrochloride | 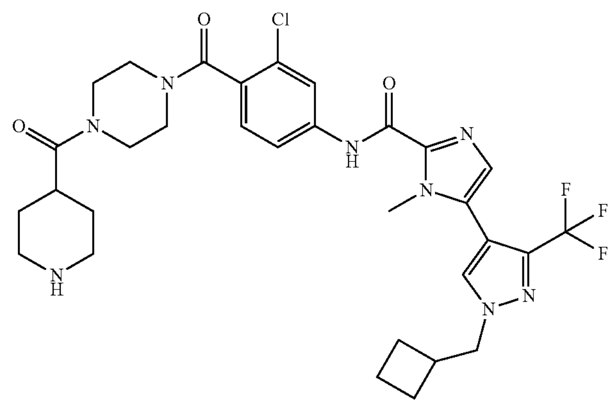 [SMILES: Cn1c(-c2cn(CC3CCC3)nc2C(F)(F)F)cnc1C(=O)Nc1ccc(C(=O)N2CCN(C(=O)C3CCNCC3)CC2)c(Cl)c1] | 662.4 |
| 114 | N-[3-chloro-4-[4-(piperidine-4-carbonyl)piperazine-1-carbonyl]phenyl]-5-[1-ethyl-3-(trifluoromethyl)pyrazol-4-yl]-1-methylimidazole-2-carboxamide;hydrochloride | 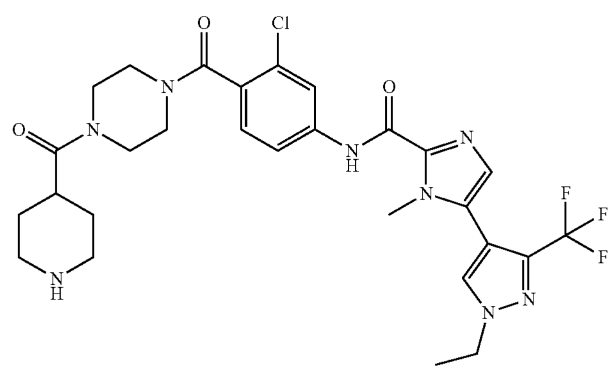 [SMILES: CCn1cc(-c2cnc(C(=O)Nc3ccc(C(=O)N4CCN(C(=O)C5CCNCC5)CC4)c(Cl)c3)n2C)c(C(F)(F)F)n1] | 622.3 |
| 115 | N-[3-chloro-4-[4-(piperidine-4-carbonyl)piperazine-1-carbonyl]phenyl]-1-methyl-5-[1-methyl-3-(trifluoromethyl)pyrazol-4-yl]imidazole-2-carboxamide;hydrochloride | 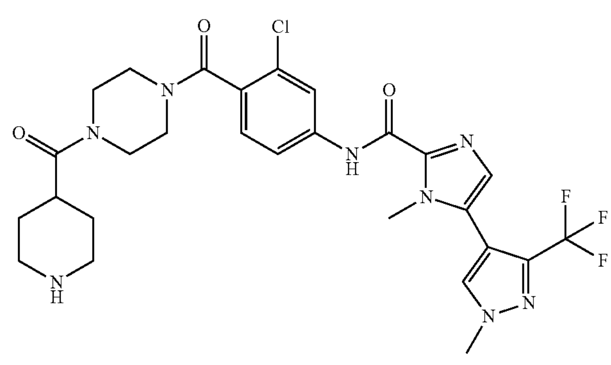 [SMILES: Cn1cc(-c2cnc(C(=O)Nc3ccc(C(=O)N4CCN(C(=O)C5CCNCC5)CC4)c(Cl)c3)n2C)c(C(F)(F)F)n1] | 608.5 |

| Ex. | Name | Structure | ESI MS [M + H]+ |
|---|---|---|---|
| 116 | N-[3-chloro-4-[4-(piperidine-4-carbonyl)piperazine-1-carbonyl]phenyl]-5-[1-(difluoromethyl)-3-(trifluoromethyl)pyrazol-4-yl]-1-methylimidazole-2-carboxamide;hydrochloride | 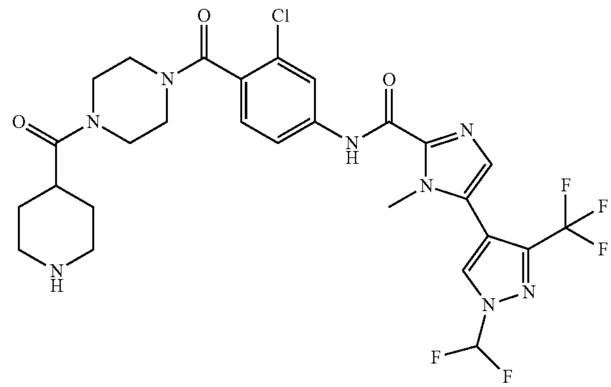 [SMILES: Cn1c(-c2cn(C(F)F)nc2C(F)(F)F)cnc1C(=O)Nc1ccc(C(=O)N2CCN(C(=O)C3CCNCC3)CC2)c(Cl)c1] | 643.2 |
| 117 | N-[3-chloro-4-[4-(piperidine-4-carbonyl)piperazine-1-carbonyl]phenyl]-5-[1-(1-cyanoethyl)-3-(trifluoromethyl)pyrazol-4-yl]-1-methylimidazole-2-carboxamide;formic acid | 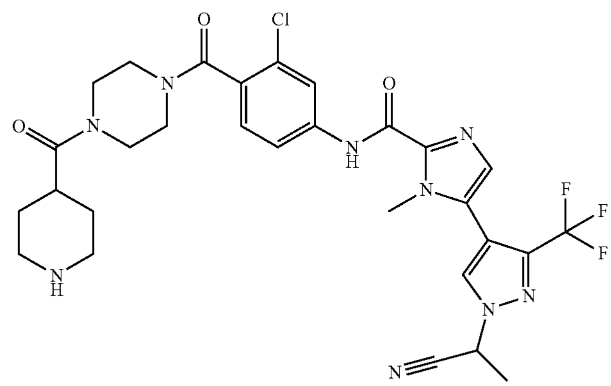 [SMILES: CC(C#N)n1cc(-c2cnc(C(=O)Nc3ccc(C(=O)N4CCN(C(=O)C5CCNCC5)CC4)c(Cl)c3)n2C)c(C(F)(F)F)n1] | 646.2 |
| 118 | N-[4-[4-(3-aminocyclobutanecarbonyl)piperazine-1-carbonyl]-3-fluoro-5-methylphenyl]-5-[1-(cyanomethyl)-3-(trifluoromethyl)pyrazol-4-yl]-1-methylimidazole-2-carboxamide | AND Enantiomer | 616.3 |

| Ex. | Name | Structure | ESI MS [M + H]+ |
|---|---|---|---|
| 119 | N-[4-[4-[(1S,3R)-3-aminocyclopentanecarbonyl]piperazine-1-carbonyl]-3-fluoro-5-methylphenyl]-5-[1-(cyanomethyl)-3-(trifluoromethyl)pyrazol-4-yl]-1-methylimidazole-2-carboxamide | 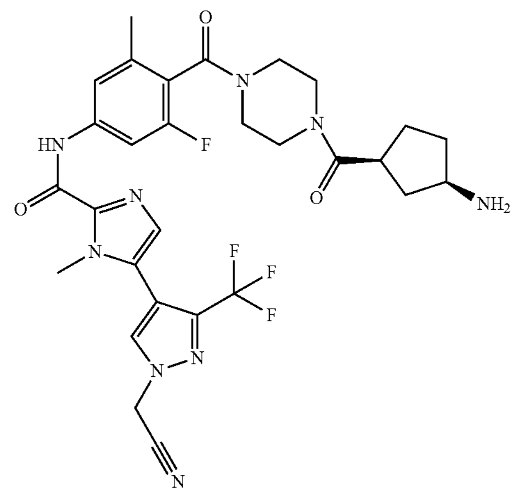 [SMILES: Cc1cc(NC(=O)c2ncc(-c3cn(CC#N)nc3C(F)(F)F)n2C)cc(F)c1C(=O)N1CCN(C(=O)[C@H]2CC[C@@H](N)C2)CC1] | 630.3 |
| 120 | 5-[1-(cyanomethyl)-3-(trifluoromethyl)pyrazol-4-yl]-N-[3-fluoro-4-[4-(3-hydroxypiperidine-3-carbonyl)piperazine-1-carbonyl]-5-methylphenyl]-1-methylimidazole-2-carboxamide | 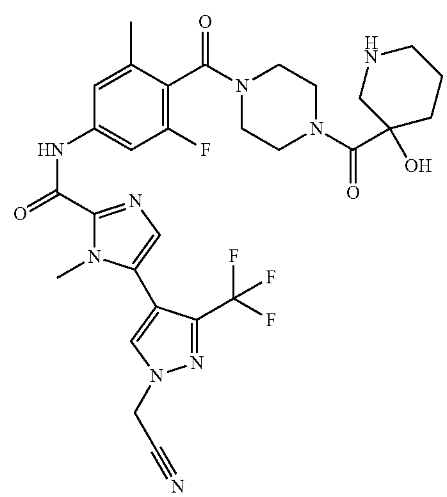 [SMILES: Cc1cc(NC(=O)c2ncc(-c3cn(CC#N)nc3C(F)(F)F)n2C)cc(F)c1C(=O)N1CCN(C(=O)C2(O)CCCNC2)CC1] | 646.3 |
| 121 | N-[4-[4-[(2S)-2-aminopropanoyl]piperazine-1-carbonyl]-3-fluoro-5-methylphenyl]-5-[1-(cyanomethyl)-3-(trifluoromethyl)pyrazol-4-yl]-1-methylimidazole-2-carboxamide | 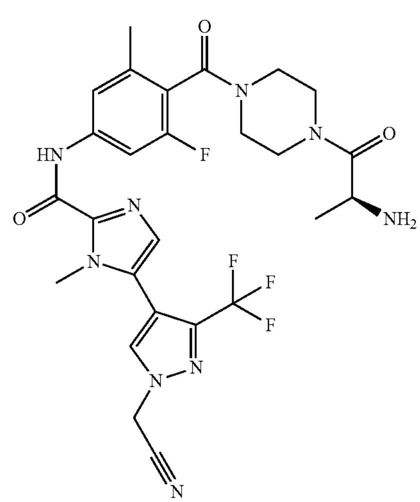 [SMILES: Cc1cc(NC(=O)c2ncc(-c3cn(CC#N)nc3C(F)(F)F)n2C)cc(F)c1C(=O)N1CCN(C(=O)[C@H](C)N)CC1] | 590.3 |

-continued

| Ex. | Name | Structure | ESI MS [M + H]+ |
|---|---|---|---|
| 122 | 5-[1-(cyanomethyl)-3-(trifluoromethyl)pyrazol-4-yl]-N-[3-fluoro-5-methyl-4-[4-[(3S)-pyrrolidine-3-carbonyl]piperazine-1-carbonyl]phenyl]-1-methylimidazole-2-carboxamide | 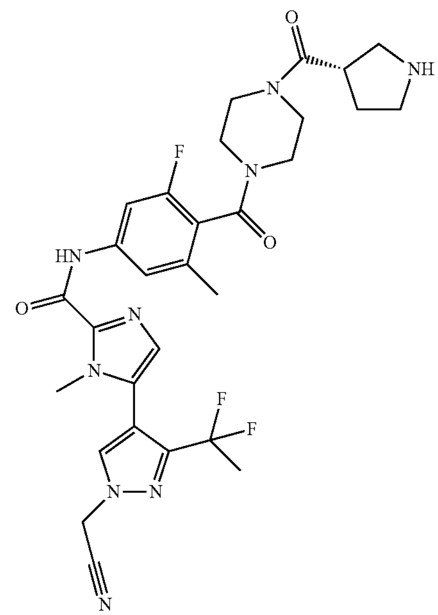 [SMILES: Cc1cc(NC(=O)c2ncc(-c3cn(CC#N)nc3C(C)(F)F)n2C)cc(F)c1C(=O)N1CCN(C(=O)[C@H]2CCNC2)CC1] | 616.3 |
| 123 | N-[4-[(4-aminocyclohexyl)carbamoyl]-3-chlorophenyl]-1-methyl-5-[3-(trifluoromethyl)-1H-pyrazol-4-yl]imidazole-2-carboxamide;2,2,2-trifluoroacetic acid | AND Enantiomer | 508.3 |
| 124 | N-[4-[(3-aminocyclobutyl)carbamoyl]-3-chlorophenyl]-1-methyl-5-[1-[(2-methyl-1,3-thiazol-4-yl)methyl]-3-(trifluoromethyl)pyrazol-4-yl]imidazole-2-carboxamide;hydrochloride | AND Enantiomer | 593.2 |

| Ex. | Name | Structure | ESI MS [M + H]+ |
|---|---|---|---|
| 125 | N-[4-[(3-aminocyclobutyl)carbamoyl]-3-chlorophenyl]-5-[1-cyclobutyl-3-(trifluoromethyl)pyrazol-4-yl]-1-methylimidazole-2-carboxamide;hydrochloride | AND Enantiomer | 536.3 |
| 126 | N-[4-[(3-aminocyclobutyl)carbamoyl]-3-chlorophenyl]-1-methyl-5-[1-prop-2-enyl-3-(trifluoromethyl)pyrazol-4-yl]imidazole-2-carboxamide;2,2,2-trifluoroacetic acid | AND Enantiomer | 522.2 |
| 127 | 5-[1-(cyanomethyl)-3-(trifluoromethyl)pyrazol-4-yl]-N-[3-ethyl-4-[4-(1-methylpiperidine-4-carbonyl)piperazine-1-carbonyl]phenyl]-1-methylimidazole-2-carboxamide;formic acid | 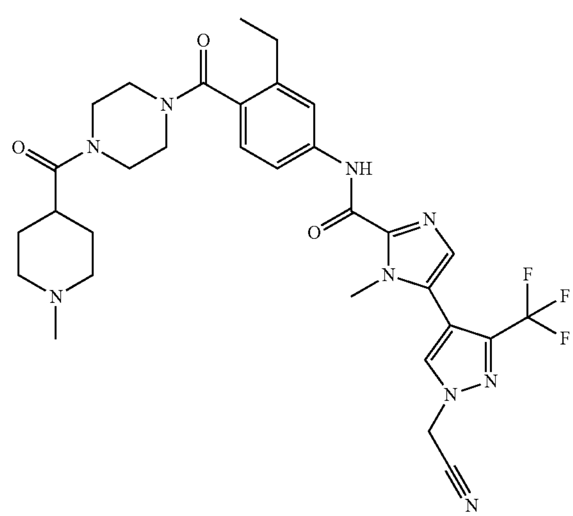 [SMILES: CCc1cc(NC(=O)c2ncc(-c3cn(CC#N)nc3C(F)(F)F)n2C)ccc1C(=O)N1CCN(C(=O)C2CCN(C)CC2)CC1] | 640.2 |

| Ex. | Name | Structure | ESI MS [M + H]+ |
|---|---|---|---|
| 128 | 5-[1-(cyanomethyl)-3-(trifluoromethyl)pyrazol-4-yl]-N-[3-ethyl-4-[4-(piperidine-4-carbonyl)piperazine-1-carbonyl]phenyl]-1-methylimidazole-2-carboxamide;formic acid | 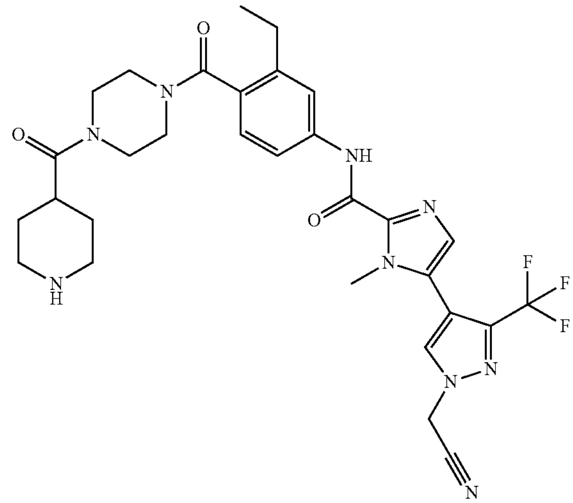 [SMILES: CCc1cc(NC(=O)c2ncc(-c3cn(CC#N)nc3C(F)(F)F)n2C)ccc1C(=O)N1CCN(C(=O)C2CCNCC2)CC1] | 626.1 |
| 129 | 5-[1-(cyanomethyl)-3-(trifluoromethyl)pyrazol-4-yl]-N-[3-ethyl-4-[4-(4-hydroxypiperidine-4-carbonyl)piperazine-1-carbonyl]phenyl]-1-methylimidazole-2-carboxamide;formic acid | 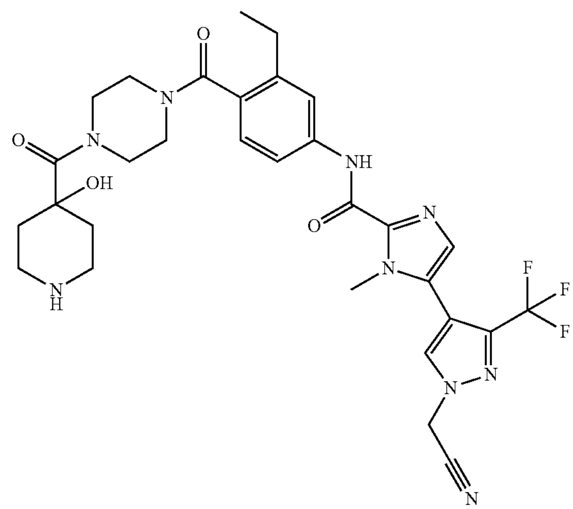 [SMILES: CCc1cc(NC(=O)c2ncc(-c3cn(CC#N)nc3C(F)(F)F)n2C)ccc1C(=O)N1CCN(C(=O)C2(O)CCNCC2)CC1] | 642.1 |
| 130 | 5-[1-(cyanomethyl)-3-(trifluoromethyl)pyrazol-4-yl]-N-[3-ethyl-4-[4-[(3R)-pyrrolidine-3-carbonyl]piperazine-1-carbonyl]phenyl]-1-methylimidazole-2-carboxamide;formic acid | 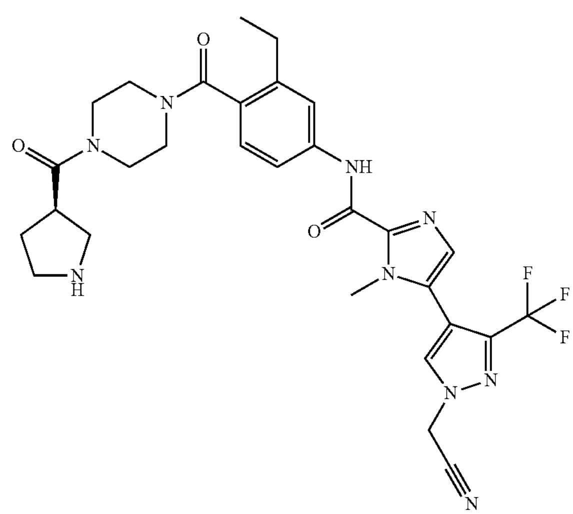 [SMILES: CCc1cc(NC(=O)c2ncc(-c3cn(CC#N)nc3C(F)(F)F)n2C)ccc1C(=O)N1CCN(C(=O)[C@@H]2CCNC2)CC1] | 612.1 |

| Ex. | Name | Structure | ESI MS [M + H]+ |
|---|---|---|---|
| 131 | N-[4-[4-(azetidine-3-carbonyl)piperazine-1-carbonyl]-3-ethylphenyl]-5-[1-(cyanomethyl)-3-(trifluoromethyl)pyrazol-4-yl]-1-methylimidazole-2-carboxamide;formic acid | 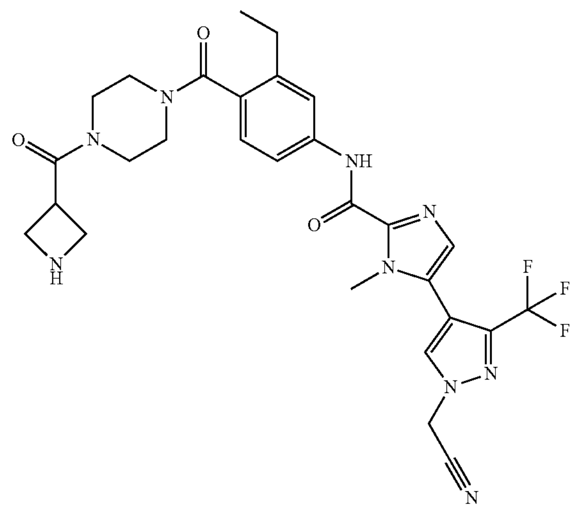 [SMILES: CCc1cc(NC(=O)c2ncc(-c3cn(CC#N)nc3C(F)(F)F)n2C)ccc1C(=O)N1CCN(C(=O)C2CNC2)CC1] | 598.3 |
| 132 | 4-[4-[[5-[1-(cyanomethyl)-3-(trifluoromethyl)pyrazol-4-yl]-1-methylimidazole-2-carbonyl]amino]-2-ethylbenzoyl]-N-[(3-hydroxyazetidin-3-yl)methyl]piperazine-1-carboxamide;formic acid | 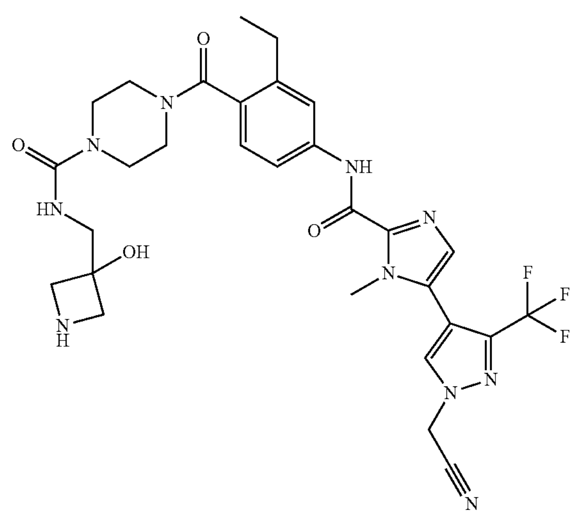 [SMILES: CCc1cc(NC(=O)c2ncc(-c3cn(CC#N)nc3C(F)(F)F)n2C)ccc1C(=O)N1CCN(C(=O)NCC2(O)CNC2)CC1] | 643.3 |
| 133 | N-[4-[4-(3-aminopiperidine-1-carbonyl)piperazine-1-carbonyl]-3-ethylphenyl]-5-[1-(cyanomethyl)-3-(trifluoromethyl)pyrazol-4-yl]-1-methylimidazole-2-carboxamide;formic acid | 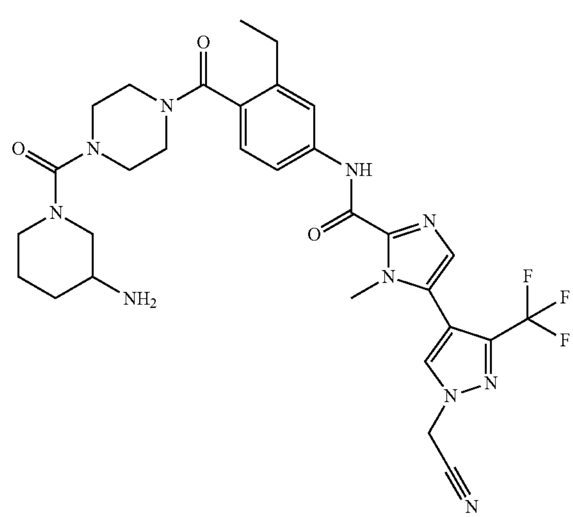 [SMILES: CCc1cc(NC(=O)c2ncc(-c3cn(CC#N)nc3C(F)(F)F)n2C)ccc1C(=O)N1CCN(C(=O)N2CCCC(N)C2)CC1] | 641.4 |

| Ex. | Name | Structure | ESI MS [M + H]+ |
|---|---|---|---|
| 134 | N-[4-[4-(6-amino-2-azaspiro[3.3]heptane-2-carbonyl)piperazine-1-carbonyl]-3-ethylphenyl]-5-[1-(cyanomethyl)-3-(trifluoromethyl)pyrazol-4-yl]-1-methylimidazole-2-carboxamide;formic acid | 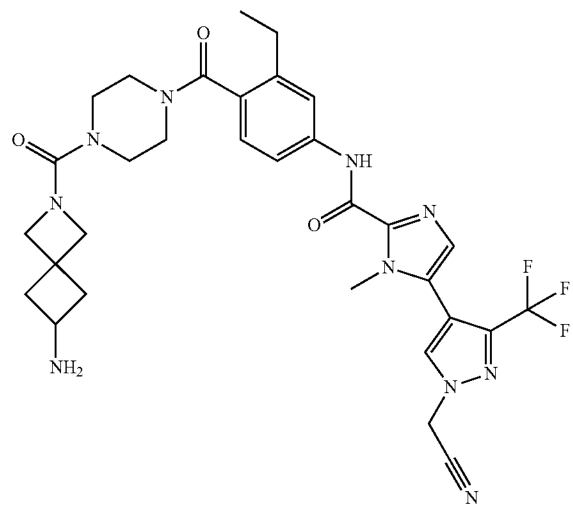 [SMILES: CCc1cc(NC(=O)c2ncc(-c3cn(CC#N)nc3C(F)(F)F)n2C)ccc1C(=O)N1CCN(C(=O)N2CC3(CC(N)C3)C2)CC1] | 653.4 |
| 135 | 5-[1-(cyanomethyl)-3-(trifluoromethyl)pyrazol-4-yl]-N-[3-ethyl-4-[4-(3-methylpiperazine-1-carbonyl)piperazine-1-carbonyl]phenyl]-1-methylimidazole-2-carboxamide;formic acid | 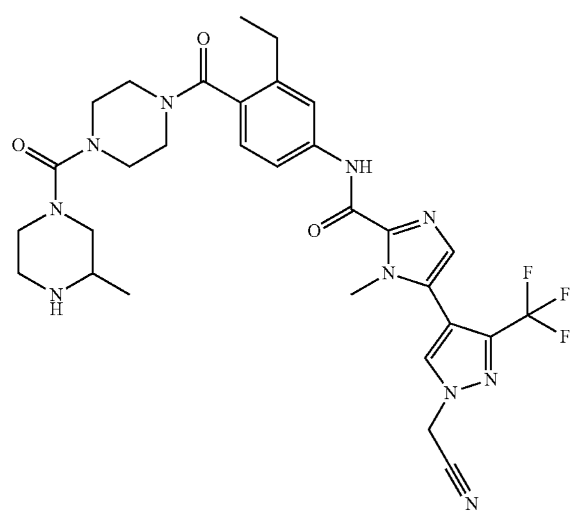 [SMILES: CCc1cc(NC(=O)c2ncc(-c3cn(CC#N)nc3C(F)(F)F)n2C)ccc1C(=O)N1CCN(C(=O)N2CCNC(C)C2)CC1] | 641.4 |
| 136 | N-[4-[4-(4-amino-4-methylpiperidine-1-carbonyl)piperazine-1-carbonyl]-3-ethylphenyl]-5-[1-(cyanomethyl)-3-(trifluoromethyl)pyrazol-4-yl]-1-methylimidazole-2-carboxamide;formic acid | 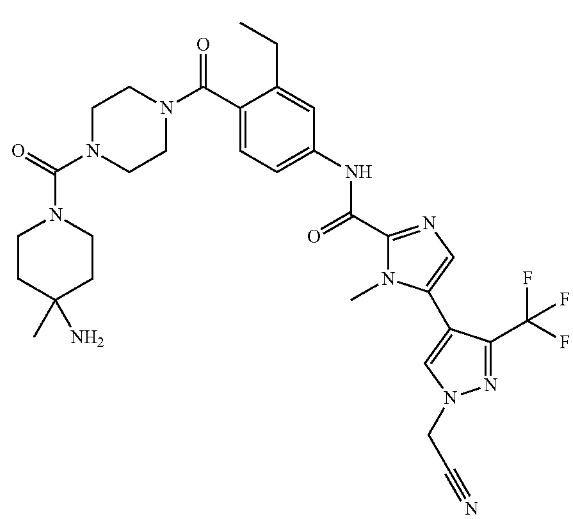 [SMILES: CCc1cc(NC(=O)c2ncc(-c3cn(CC#N)nc3C(F)(F)F)n2C)ccc1C(=O)N1CCN(C(=O)N2CCC(C)(N)CC2)CC1] | 655.4 |

-continued

| Ex. | Name | Structure | ESI MS [M + H]+ |
|---|---|---|---|
| 137 | 5-[1-(cyanomethyl)-3-(trifluoromethyl)pyrazol-4-yl]-N-[3-ethyl-4-[4-[rac-(3R,4R)-3-amino-4-methylpiperidine-1-carbonyl]piperazine-1-carbonyl]phenyl]-1-methylimidazole-2-carboxamide;formic acid | AND Enantiomer | 655.4 |
| 138 | N-[4-[4-[3-(aminomethyl)pyrrolidine-1-carbonyl]piperazine-1-carbonyl]-3-ethylphenyl]-5-[1-(cyanomethyl)-3-(trifluoromethyl)pyrazol-4-yl]-1-methylimidazole-2-carboxamide;formic acid | 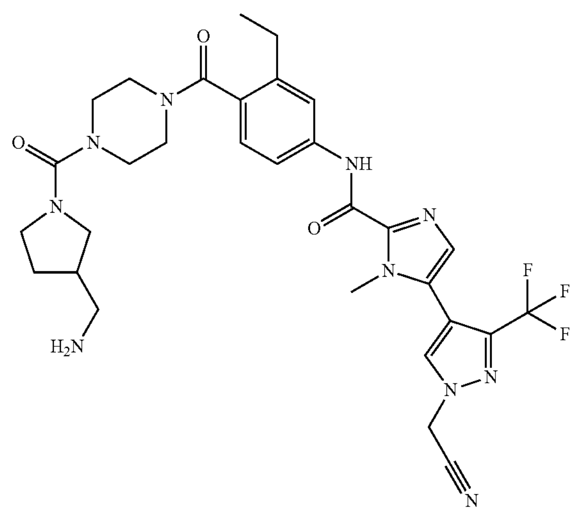 [SMILES: CCc1cc(NC(=O)c2ncc(-c3cn(CC#N)nc3C(F)(F)F)n2C)ccc1C(=O)N1CCN(C(=O)N2CCC(CN)C2)CC1] | 641.3 |
| 139 | N-[4-[4-[2-(aminomethyl)pyrrolidine-1-carbonyl]piperazine-1-carbonyl]-3-ethylphenyl]-5-[1-(cyanomethyl)-3-(trifluoromethyl)pyrazol-4-yl]-1-methylimidazole-2-carboxamide;formic acid | 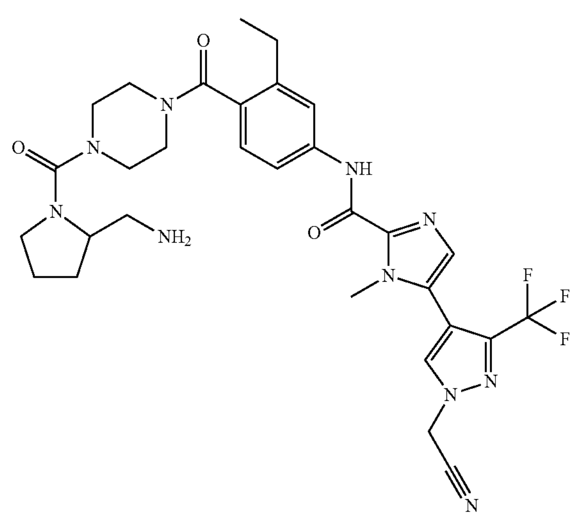 [SMILES: CCc1cc(NC(=O)c2ncc(-c3cn(CC#N)nc3C(F)(F)F)n2C)ccc1C(=O)N1CCN(C(=O)N2CCCC2CN)CC1] | 641.4 |

-continued

| Ex. | Name | Structure | ESI MS [M + H]+ |
|---|---|---|---|
| 140 | N-(3-azabicyclo[3.1.0]hexan-6-yl)-4-[4-[[5-[1-(cyanomethyl)-3-(trifluoromethyl)pyrazol-4-yl]-1-methylimidazole-2-carbonyl]amino]-2-ethylbenzoyl]piperazine-1-carboxamide;formic acid | 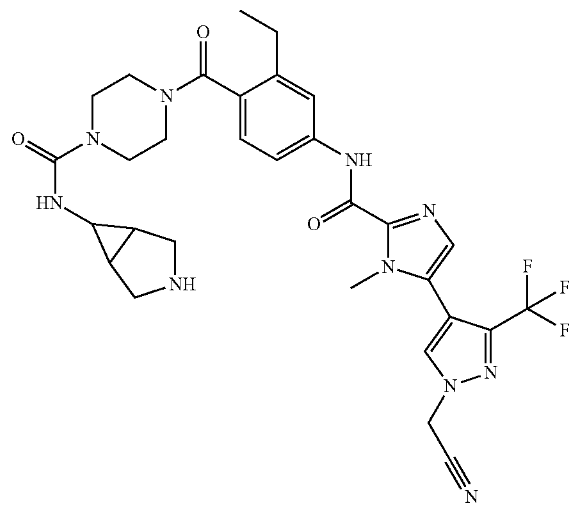 [SMILES: CCc1cc(NC(=O)c2ncc(-c3cn(CC#N)nc3C(F)(F)F)n2C)ccc1C(=O)N1CCN(C(=O)NC2C3CNCC32)CC1] | 639.3 |
| 141 | 5-[1-(cyanomethyl)-3-(trifluoromethyl)pyrazol-4-yl]-N-[4-[4-(2,5-diazabicyclo[2.2.1]heptane-2-carbonyl)piperazine-1-carbonyl]-3-ethylphenyl]-1-methylimidazole-2-carboxamide;formic acid | 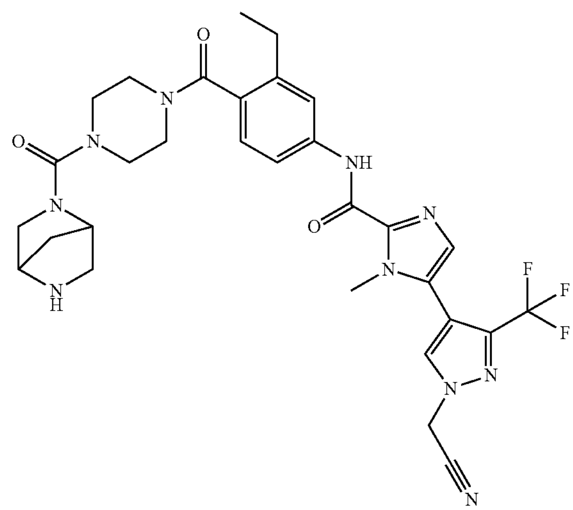 [SMILES: CCc1cc(NC(=O)c2ncc(-c3cn(CC#N)nc3C(F)(F)F)n2C)ccc1C(=O)N1CCN(C(=O)N2CC3CC2CN3)CC1] | 639.3 |
| 142 | 4-[2-chloro-4-[[5-[1-(2,2-difluoroethyl)-3-(trifluoromethyl)pyrazol-4-yl]-1-methylimidazole-2-carbonyl]amino]benzoyl]-N-[(3S)-pyrrolidin-3-yl]piperazine-1-carboxamide;formic acid | 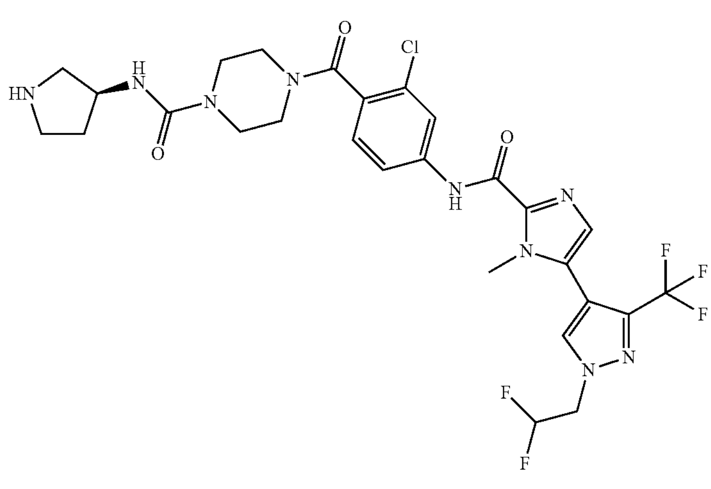 [SMILES: Cn1c(-c2cn(CC(F)F)nc2C(F)(F)F)cnc1C(=O)Nc1ccc(C(=O)N2CCN(C(=O)N[C@H]3CCNC3)CC2)c(Cl)c1] | 658.3 |

| Ex. | Name | Structure | ESI MS [M + H]+ |
|---|---|---|---|
| 143 | 4-[2-chloro-4-[[5-[1-(cyanomethyl)-3-(trifluoromethyl)pyrazol-4-yl]-1-methylimidazole-2-carbonyl]amino]benzoyl]-N-[(3S)-pyrrolidin-3-yl]piperazine-1-carboxamide;formic acid | 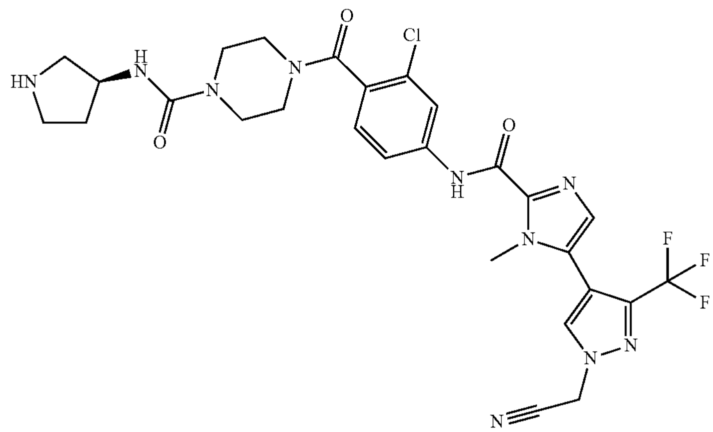 [SMILES: Cn1c(-c2cn(CC#N)nc2C(F)(F)F)cnc1C(=O)Nc1ccc(C(=O)N2CCN(C(=O)N[C@H]3CCNC3)CC2)c(Cl)c1] | 633.3 |
| 144 | N-(azetidin-3-yl)-4-[2-chloro-4-[[5-[1-(2-fluoroethyl)-3-(trifluoromethyl)pyrazol-4-yl]-1-methylimidazole-2-carbonyl]amino]benzoyl]piperazine-1-carboxamide;formic acid | 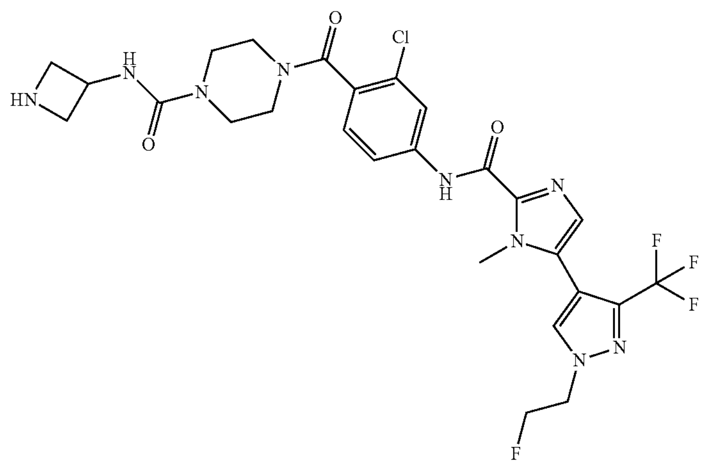 [SMILES: Cn1c(-c2cn(CCF)nc2C(F)(F)F)cnc1C(=O)Nc1ccc(C(=O)N2CCN(C(=O)NC3CNC3)CC2)c(Cl)c1] | 626.4 |
| 145 | N-[4-[4-[4-(aminomethyl)-4,5-dihydro-1,3-oxazol-2-yl]piperazine-1-carbonyl]-3-chlorophenyl]-5-[1-(2-fluoroethyl)-3-(trifluoromethyl)pyrazol-4-yl]-1-methylimidazole-2-carboxamide;formic acid | 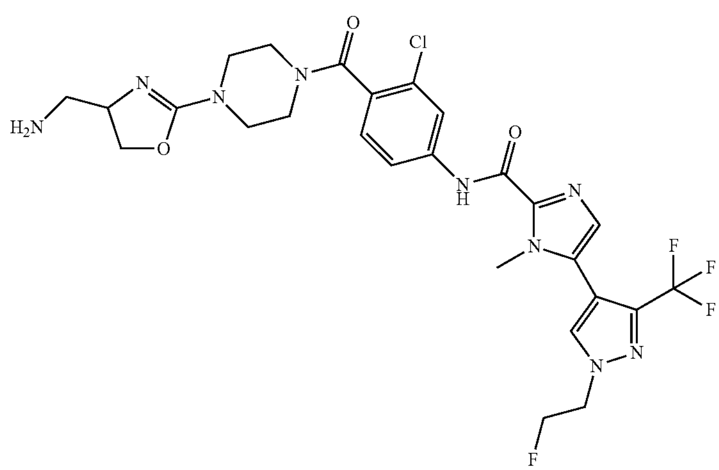 [SMILES: Cn1c(-c2cn(CCF)nc2C(F)(F)F)cnc1C(=O)Nc1ccc(C(=O)N2CCN(C3=NC(CN)CO3)CC2)c(Cl)c1] | 626.2 |

| Ex. | Name | Structure | ESI MS [M + H]+ |
|---|---|---|---|
| 146 | N-(azetidin-3-yl)-4-[2-chloro-4-[[5-[1-(2,2-difluoroethyl)-3-(trifluoromethyl)pyrazol-4-yl]-1-methylimidazole-2-carbonyl]amino]benzoyl]piperazine-1-carboxamide;formic acid | 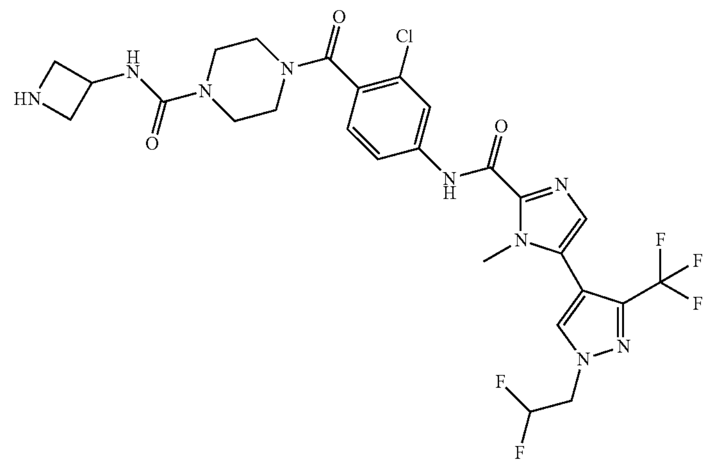 [SMILES: Cn1c(-c2cn(CC(F)F)nc2C(F)(F)F)cnc1C(=O)Nc1ccc(C(=O)N2CCN(C(=O)NC3CNC3)CC2)c(Cl)c1] | 644.2 |
| 147 | N-(azetidin-3-yl)-4-[2-chloro-4-[[1-methyl-5-[1-prop-2-enyl-3-(trifluoromethyl)pyrazol-4-yl]imidazole-2-carbonyl]amino]benzoyl]piperazine-1-carboxamide | 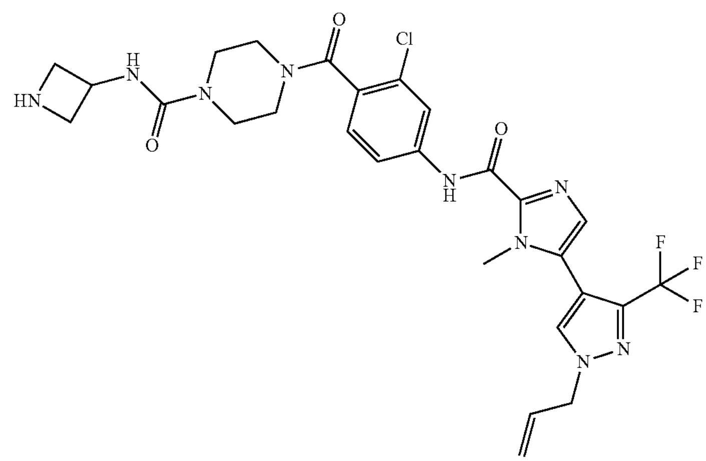 [SMILES: C=CCn1cc(-c2cnc(C(=O)Nc3ccc(C(=O)N4CCN(C(=O)NC5CNC5)CC4)c(Cl)c3)n2C)c(C(F)(F)F)n1] | 620.2 |
| 148 | N-[4-[4-[4-(aminomethyl)-4,5-dihydro-1,3-oxazol-2-yl]piperazine-1-carbonyl]-3-chlorophenyl]-1-methyl-5-[1-(2,2,2-trifluoroethyl)-3-(trifluoromethyl)pyrazol-4-yl]imidazole-2-carboxamide | 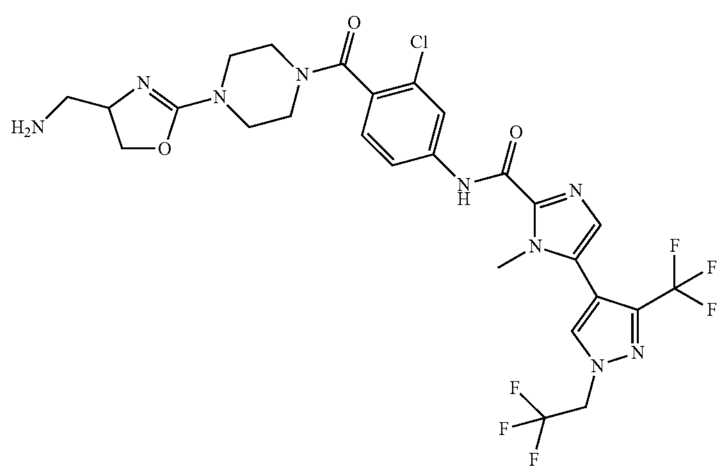 [SMILES: Cn1c(-c2cn(CC(F)(F)F)nc2C(F)(F)F)cnc1C(=O)Nc1ccc(C(=O)N2CCN(C3=NC(CN)CO3)CC2)c(Cl)c1] | 662.1 |

-continued

| Ex. | Name | Structure | ESI MS [M + H]+ |
|---|---|---|---|
| 149 | N-(azetidin-3-yl)-4-[2-chloro-4-[[1-methyl-5-[1-(2,2,2-trifluoroethyl)-3-(trifluoromethyl)pyrazol-4-yl]imidazole-2-carbonyl]amino]benzoyl]piperazine-1-carboxamide | 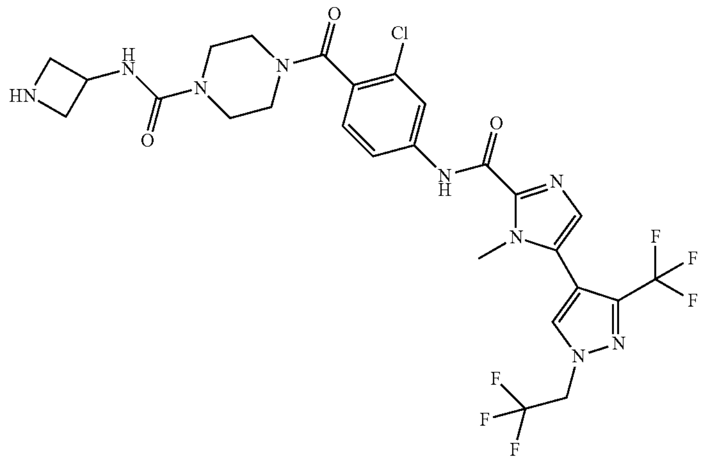 [SMILES: Cn1c(-c2cn(CC(F)(F)F)nc2C(F)(F)F)cnc1C(=O)Nc1ccc(C(=O)N2CCN(C(=O)NC3CNC3)CC2)c(Cl)c1] | 662.1 |
| 150 | N-(azetidin-3-yl)-4-[2-chloro-4-[[5-[1-cyclobutyl-3-(trifluoromethyl)pyrazol-4-yl]-1-methylimidazole-2-carbonyl]amino]benzoyl]piperazine-1-carboxamide | 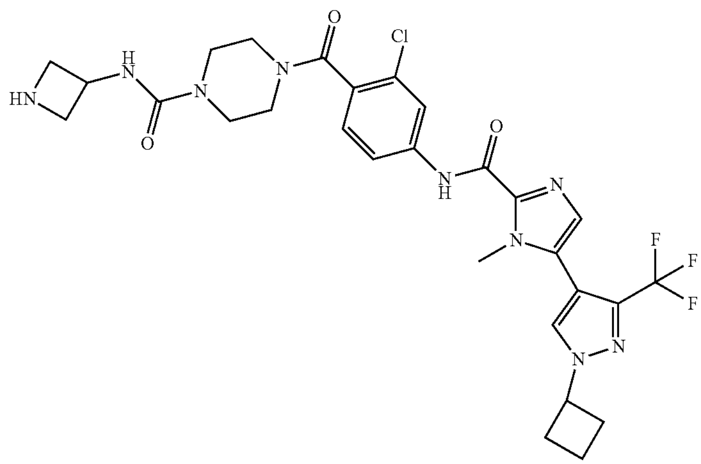 [SMILES: Cn1c(-c2cn(C3CCC3)nc2C(F)(F)F)cnc1C(=O)Nc1ccc(C(=O)N2CCN(C(=O)NC3CNC3)CC2)c(Cl)c1] | 634.2 |
| 151 | N-(azetidin-3-yl)-4-[2-chloro-4-[[5-[1-(cyanomethyl)-3-(trifluoromethyl)pyrazol-4-yl]-1-methylimidazole-2-carbonyl]amino]benzoyl]piperazine-1-carboxamide | 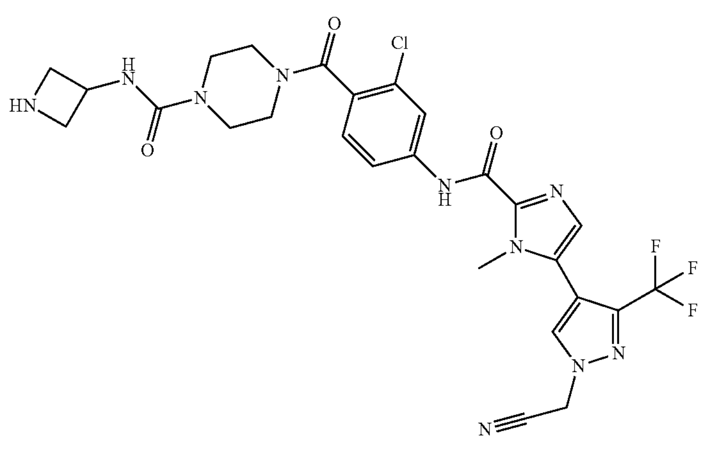 [SMILES: Cn1c(-c2cn(CC#N)nc2C(F)(F)F)cnc1C(=O)Nc1ccc(C(=O)N2CCN(C(=O)NC3CNC3)CC2)c(Cl)c1] | 619.3 |

-continued

| Ex. | Name | Structure | ESI MS [M + H]+ |
|---|---|---|---|
| 152 | 5-[1-(2,2-difluoroethyl)-3-(trifluoromethyl)pyrazol-4-yl]-N-[3-ethyl-4-[4-(1-methylpiperidine-4-carbonyl)piperazine-1-carbonyl]phenyl]-1-methylimidazole-2-carboxamide | 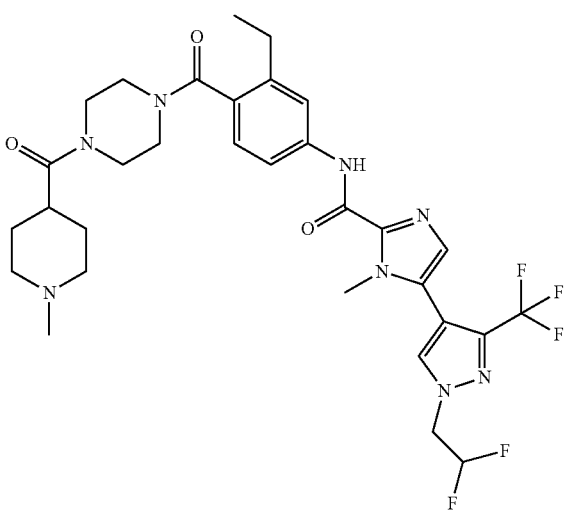 [SMILES: CCc1cc(NC(=O)c2ncc(-c3cn(CC(F)F)nc3C(F)(F)F)n2C)ccc1C(=O)N1CCN(C(=O)C2CCN(C)CC2)CC1] | 665.4 |
| 153 | N-[4-[4-(azetidine-3-carbonyl)piperazine-1-carbonyl]-3-ethylphenyl]-5-[1-(2,2-difluoroethyl)-3-(trifluoromethyl)pyrazol-4-yl]-1-methylimidazole-2-carboxamide;formic acid | 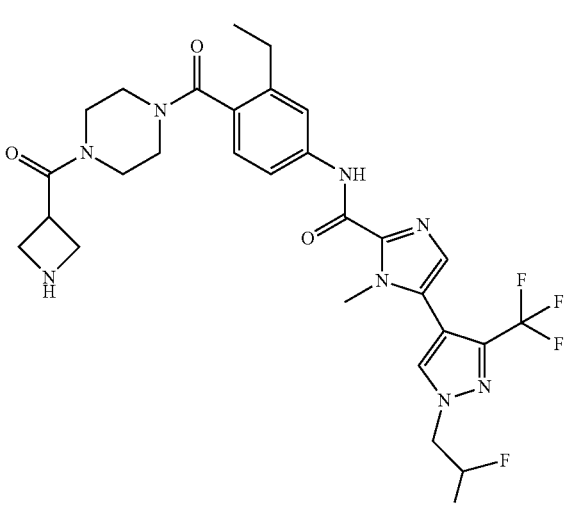 | 623.3 |
| 154 | 5-[1-(2,2-difluoroethyl)-3-(trifluoromethyl)pyrazol-4-yl]-N-[3-ethyl-4-[4-(piperidine-4-carbonyl)piperazine-1-carbonyl]phenyl]-1-methylimidazole-2-carboxamide;formic acid | 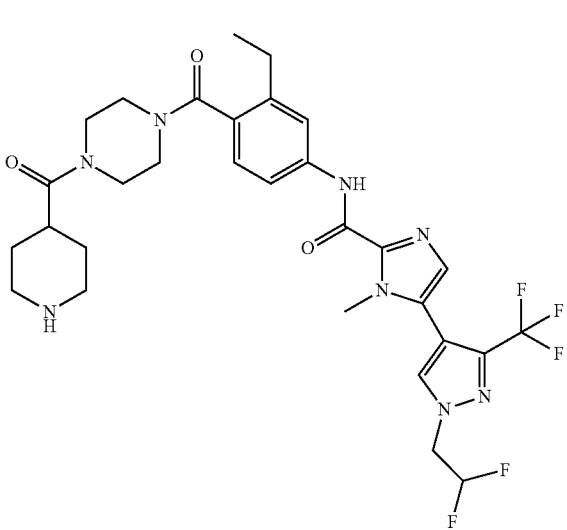 [SMILES: CCc1cc(NC(=O)c2ncc(-c3cn(CC(F)F)nc3C(F)(F)F)n2C)ccc1C(=O)N1CCN(C(=O)C2CCNCC2)CC1] | 651.4 |

| Ex. | Name | Structure | ESI MS [M + H]+ |
|---|---|---|---|
| 155 | 5-[1-(2,2-difluoroethyl)-3-(trifluoromethyl)pyrazol-4-yl]-N-[3-ethyl-4-[4-(4-hydroxypiperidine-4-carbonyl)piperazine-1-carbonyl]phenyl]-1-methylimidazole-2-carboxamide;formic acid | 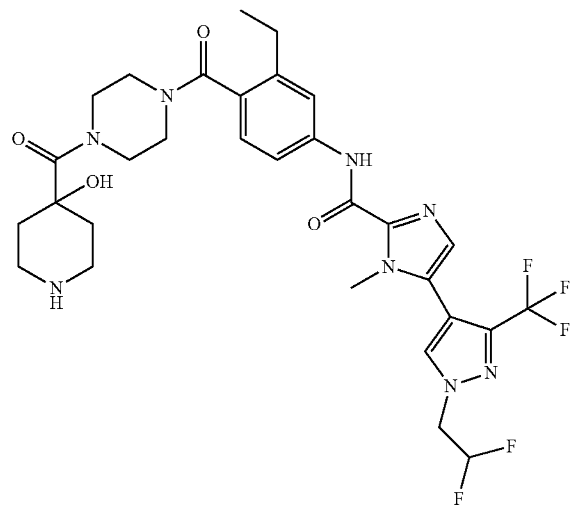 [SMILES: CCc1cc(NC(=O)c2ncc(-c3cn(CC(F)F)nc3C(F)(F)F)n2C)ccc1C(=O)N1CCN(C(=O)C2(O)CCNCC2)CC1] | 667.4 |
| 156 | 5-[1-(2,2-difluoroethyl)-3-(trifluoromethyl)pyrazol-4-yl]-N-[3-ethyl-4-[(3R)-pyrrolidine-3-carbonyl]piperazine-1-carbonyl]phenyl]-1-methylimidazole-2-carboxamide;formic acid | 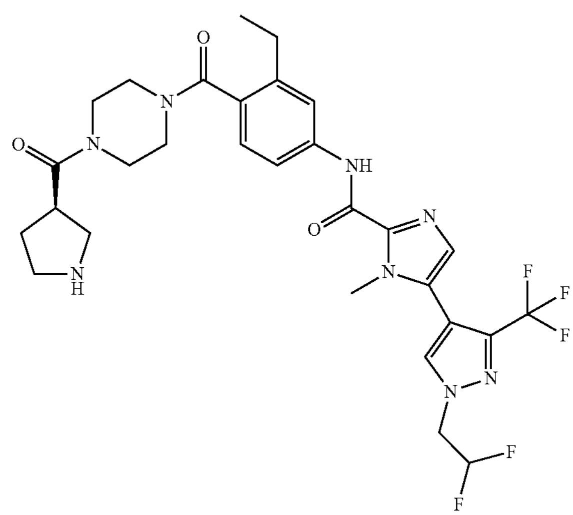 [SMILES: CCc1cc(NC(=O)c2ncc(-c3cn(CC(F)F)nc3C(F)(F)F)n2C)ccc1C(=O)N1CCN(C(=O)[C@@H]2CCNC2)CC1] | 637.4 |
| 157 | 4-[4-[[5-[1-(2,2-difluoroethyl)-3-(trifluoromethyl)pyrazol-4-yl]-1-methylimidazole-2-carbonyl]amino]-2-ethylbenzoyl]-N-[(3-hydroxyazetidin-3-yl)methyl]piperazine-1-carboxamide;formic acid | 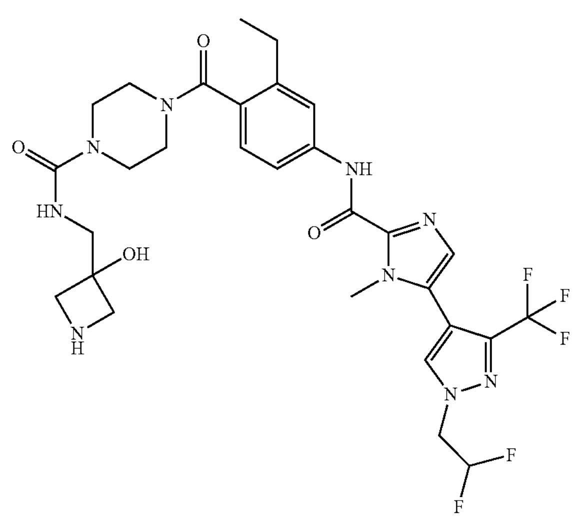 [SMILES: CCc1cc(NC(=O)c2ncc(-c3cn(CC(F)F)nc3C(F)(F)F)n2C)ccc1C(=O)N1CCN(C(=O)NCC2(O)CNC2)CC1] | 668.3 |

-continued

| Ex. | Name | Structure | ESI MS [M + H]+ |
|---|---|---|---|
| 158 | N-[3-ethyl-4-[4-(1-methylpiperidine-4-carbonyl)piperazine-1-carbonyl]phenyl]-1-methyl-5-[1-(pyridin-3-ylmethyl)-3-(trifluoromethyl)pyrazol-4-yl]imidazole-2-carboxamide;formic acid | 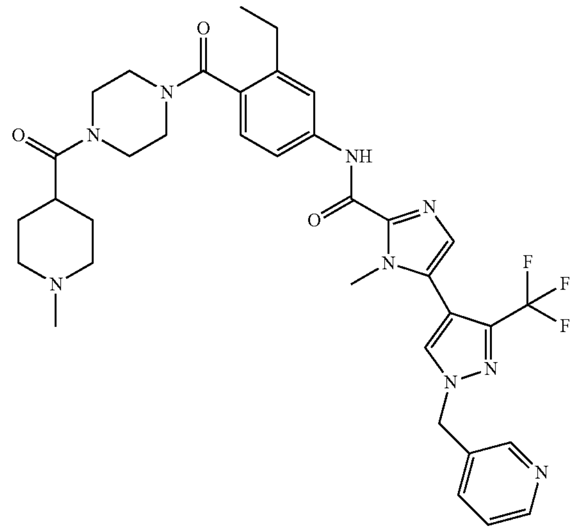 [SMILES: CCc1cc(NC(=O)c2ncc(-c3cn(Cc4cccnc4)nc3C(F)(F)F)n2C)ccc1C(=O)N1CCN(C(=O)C2CCN(C)CC2)CC1] | 692.2 |
| 159 | N-[3-ethyl-4-[4-(piperidine-4-carbonyl)piperazine-1-carbonyl]phenyl]-1-methyl-5-[1-(pyridin-3-ylmethyl)-3-(trifluoromethyl)pyrazol-4-yl]imidazole-2-carboxamide;formic acid | 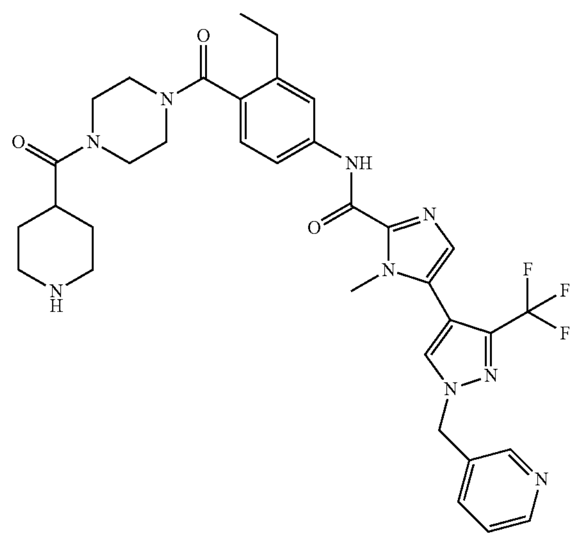 [SMILES: CCc1cc(NC(=O)c2ncc(-c3cn(Cc4cccnc4)nc3C(F)(F)F)n2C)ccc1C(=O)N1CCN(C(=O)C2CCNCC2)CC1] | 678.2 |
| 160 | N-[3-ethyl-4-[4-(4-hydroxypiperidine-4-carbonyl)piperazine-1-carbonyl]phenyl]-1-methyl-5-[1-(pyridin-3-ylmethyl)-3-(trifluoromethyl)pyrazol-4-yl]imidazole-2-carboxamide;formic acid | 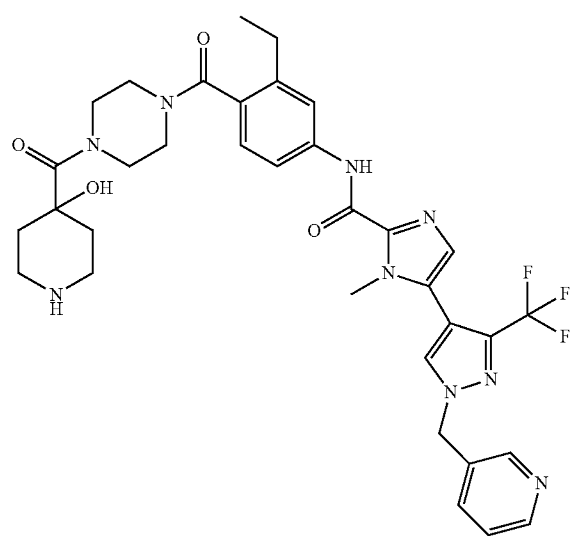 [SMILES: CCc1cc(NC(=O)c2ncc(-c3cn(Cc4cccnc4)nc3C(F)(F)F)n2C)ccc1C(=O)N1CCN(C(=O)C2(O)CCNCC2)CC1] | 694.3 |

-continued

| Ex. | Name | Structure | ESI MS [M + H]+ |
|---|---|---|---|
| 161 | N-[3-ethyl-4-[4-[(3R)-pyrrolidine-3-carbonyl]piperazine-1-carbonyl]phenyl]-1-methyl-5-[1-(pyridin-3-ylmethyl)-3-(trifluoromethyl)pyrazol-4-yl]imidazole-2-carboxamide;formic acid | 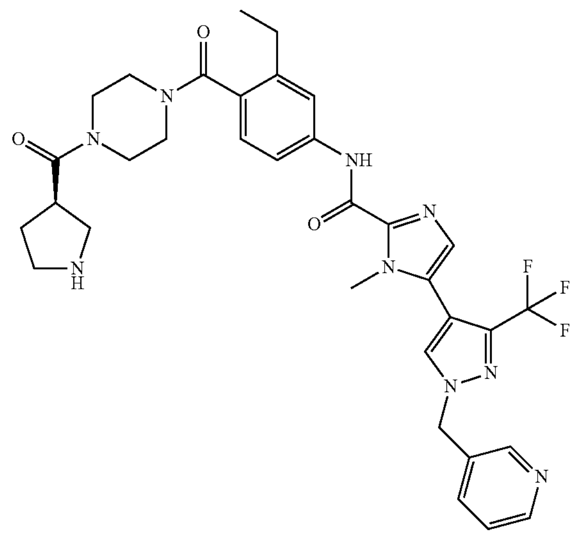 [SMILES: CCc1cc(NC(=O)c2ncc(-c3cn(Cc4cccnc4)nc3C(F)(F)F)n2C)ccc1C(=O)N1CCN(C(=O)[C@@H]2CCNC2)CC1] | 664.3 |
| 162 | 4-[2-ethyl-4-[[1-methyl-5-[1-(pyridin-3-ylmethyl)-3-(trifluoromethyl)pyrazol-4-yl]imidazole-2-carbonyl]amino]benzoyl]-N-[(3-hydroxyazetidin-3-yl)methyl]piperazine-1-carboxamide;formic acid | 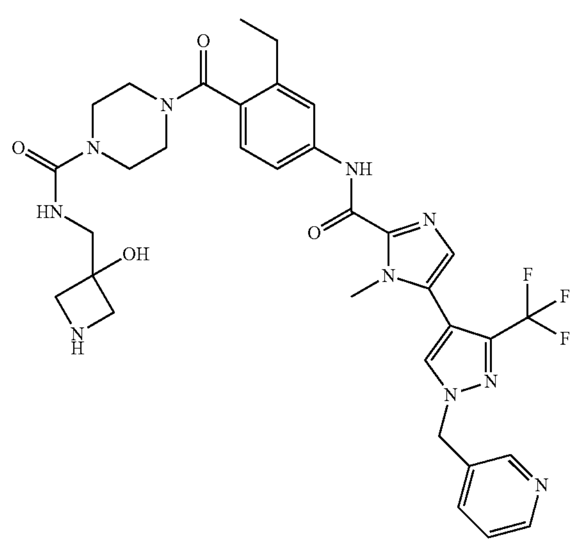 [SMILES: CCc1cc(NC(=O)c2ncc(-c3cn(Cc4cccnc4)nc3C(F)(F)F)n2C)ccc1C(=O)N1CCN(C(=O)NCC2(O)CNC2)CC1] | 695.3 |

Example 167

N-[3-chloro-4-[4-[rac-(1R,5S)-3-azabicyclo[3.1.0]hexane-6-carbonyl]piperazine-1-carbonyl]phenyl]-5-[1-cyclopropyl-3-(trifluoromethyl)pyrazol-4-yl]-1-methylimidazole-2-carboxamide; Hydrochloride

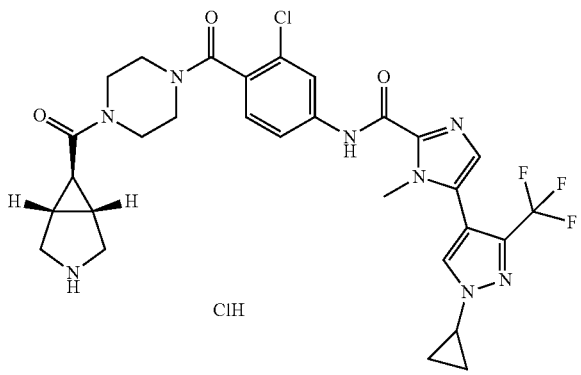 [SMILES: Cn1c(-c2cn(C3CC3)nc2C(F)(F)F)cnc1C(=O)Nc1ccc(C(=O)N2CCN(C(=O)[C@H]3[C@@H]4CNC[C@@H]43)CC2)c(Cl)c1 ; Cl]

Step 1 tert-butyl 4-(2-chloro-4-(1-methyl-5-(3-(trifluoromethyl)-1H-pyrazol-4-yl)-1H-imidazole-2-carboxamido)benzoyl)piperazine-1-carboxylate 2-Chloro-4-(1-methyl-5-(3-(trifluoromethyl)-1H-pyrazol-4-yl)-1H-imidazole-2-carboxamido)benzoic acid (Intermediate 2, 4.19 g, 8.3 mmol, Eq: 1) and tert-butyl piperazine-1-carboxylate (2.32 g, 12.5 mmol, Eq: 1.5) were combined with DMF (15 ml) to give a brown solution. DIPEA (3.22 g, 4.35 ml, 24.9 mmol, Eq: 3.0) and HATU (4.74 g, 12.5 mmol, Eq: 1.5) were added, and the reaction mixture was stirred at RT. Water was added to the reaction mixture which was then extracted with EtOAc. The organic layer was washed with an aqueous 5% LiCl solution and sat. aq. NaCl solution. After drying over $Na_2SO_4$, filtration and evaporation to dryness, the crude material was purified by flash chromatography (silica gel, 80 g, 0% to 100% DCM:MeOH; 9:1 in DCM) to give the title compound (2.29 g) as a brown foam.

MS (ESI, m/z): 582.2 [M+H]$^+$

Step 2 tert-butyl 4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxylate Cu(OAc)2 (125 mg) and 4-DMAP (252 mg) were added to tert-butyl 4-(2-chloro-4-(1-methyl-5-(3-(trifluoromethyl)-1H-pyrazol-4-yl)-1H-imidazole-2-carb oxamido)benzoyl) piperazine-1-carboxylate (400 mg, 687 µmol, Eq: 1) in dioxane (4 mL) and pyridine (67 uL). The reaction mixture was heated to 100° C. and stirred overnight under air.

The crude reaction mixture was concentrated in vacuo. The residue was taken up in 50 mL EtOAc and extracted with 1 M HCl (3×25 mL). The organic layer was dried over MgSO4 and concentrated in vacuo.

The crude material was purified by flash chromatography (silica gel, 12 g, 0% to 10% MeOH in DCM) to afford the title compound (233 mg, 363 µmol, 52.9% yield) as a yellow solid.

MS (ESI, m/z): 622.3 [M+H]$^+$

Step 3

N-(3-chloro-4-(piperazine-1-carbonyl)phenyl)-5-(1-cyclopropyl-3-(trifluoromethyl)-1H-pyrazol-4-yl)-1-methyl-1H-imidazole-2-carboxamide hydrochloride tert-Butyl 4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxylate (965 mg, 1.55 mmol, Eq: 1) was dissolved in MeOH (9 ml). HCl (4M in dioxane) (3.6 g, 3 ml, 12 mmol, Eq: 7.74) was added and stirred for 2.5 h. The crude reaction mixture was concentrated in vacuo to afford the title compound (948 mg) as an orange solid.

MS (ESI, m/z): 522.2 [M+H]$^+$

Step 4

N-[3-chloro-4-[4-[rac-(1R,5S)-3-azabicyclo[3.1.0]hexane-6-carbonyl]piperazine-1-carbonyl]phenyl]-5-[1-cyclopropyl-3-(trifluoromethyl)pyrazol-4-yl]-1-methylimidazole-2-carboxamide; Hydrochloride rac-(1R,5S,6r)-3-(tert-butoxycarbonyl)-3-azabicyclo[3.1.0]hexane-6-carboxylic acid (8.14 mg, 35.8 µmol, Eq: 1) was combined with DMF (0.5 ml) to give a brown solution. DIPEA (23.1 mg, 31.3 µl, 179 µmol, Eq: 5) and HATU (27.2 mg, 71.6 µmol, Eq: 2) were added. The reaction mixture was stirred for 15 min. N-(3-chloro-4-(piperazine-1-carbonyl)phenyl)-5-(1-cyclopropyl-3-(trifluoromethyl)-1H-pyrazol-4-yl)-1-methyl-1H-imidazole-2-carboxamide hydrochloride (20 mg, 35.8 µmol, Eq: 1) was added. The mixture was stirred overnight. The crude intermediate was purified by prep HPLC, then dissolved in MeOH (400 µl). TFA (296 mg, 200 µl, 2.6 mmol, Eq: 72.5) was added and stirred for 4 h. The reaction mixture was concentrated and lyophilized to afford the title compound (12.7 mg, 19 µmol, 53.1% yield) as a light yellow solid.

MS (ESI, m/z): 631.3 [M+H]$^+$

Example 168 rac-N-((1s,3s)-3-aminocyclobutyl)-4-(2-chloro-4-(5-(1-ethyl-3-(trifluoromethyl)-1H-pyrazol-4-yl)-1-methyl-1H-imidazole-2-carboxamido)benzoyl)piperazine-1-carboxamide Hydrochloride

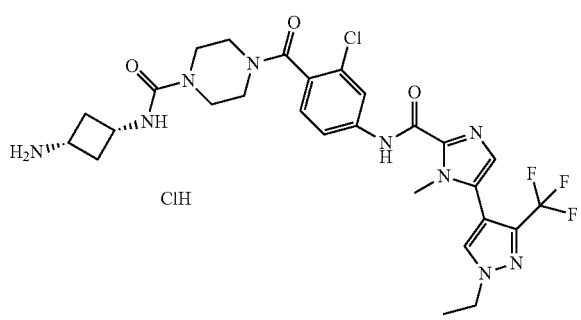 [SMILES: CCn1cc(-c2cnc(C(=O)Nc3ccc(C(=O)N4CCN(C(=O)N[C@H]5C[C@@H](N)C5)CC4)c(Cl)c3)n2C)c(C(F)(F)F)n1 ; Cl]

Step 1 rac-tert-butyl ((1s,3s)-3-(4-(4-(5-bromo-1-methyl-1H-imidazole-2-carboxamido)-2-chlorobenzoyl)piperazine-1-carboxamido)cyclobutyl)carbamate 5-Bromo-N-(3-chloro-4-(piperazine-1-carbonyl)phenyl)-1-methyl-1H-imidazole-2-carboxamide hydrochloride (Example 55 step 4, 1000 mg, 2.16 mmol, Eq: 1) was combined with DCM (10 ml) to give a light brown suspension. DIPEA (1.4 g, 1.89 ml, 10.8 mmol, Eq: 5.00) was added, then triphosgene (256 mg, 864 µmol, Eq: 0.40). After stirring for 30 min, rac-tert-butyl ((1s,3s)-3-aminocyclobutyl)carbamate (1.21 g, 6.48 mmol, Eq: 3.00) was added. The reaction mixture was concentrated, and purified by flash chromatography (silica gel, 40 g, 0% to 100% DCM:MeOH:NH4OH (100:10:1) in DCM) to give the title compound (1 g) as an off-white foam.

MS (ESI, m/z): 638.1 [M+H]+

Step 2 rac-tert-butyl ((1s,3s)-3-(4-(2-chloro-4-(1-methyl-5-(3-(trifluoromethyl)-1H-pyrazol-4-yl)-1H-imidazole-2-carboxamido)benzoyl)piperazine-1-carboxamido)cyclobutyl)carbamate A mixture of rac-tert-butyl ((1s,3s)-3-(4-(4-(5-bromo-1-methyl-1H-imidazole-2-carboxamido)-2-chlorobenzoyl)piperazine-1-carboxamido)cyclobutyl)carbamate (600 mg, 939 µmol, Eq: 1), (3-(trifluoromethyl)-1H-pyrazol-4-yl)boronic acid (203 mg, 1.13 mmol, Eq: 1.20), Na2CO3 (199 mg, 1.88 mmol, Eq: 2.00) and 1,1'-bis(di-tert-butylphosphino)ferrocene palladium dichloride (61.2 mg, 93.9 µmol, Eq: 0.10) in dioxane (2.5 ml) and water (250 µl) was heated in a microwave at 90° C. for 2 h. The reaction mixture was diluted with AcOEt, and filtered over celite. The product was purified by flash chromatography (silica gel, 40 g, 0% to 80% DCM:MeOH:NH3; 100:10:1 in DCM) to give the title compound (652 mg) as a brown viscous oil.

MS (ESI, m/z): 694.2 [M+H]+

Step 3 rac-N-((1s,3s)-3-aminocyclobutyl)-4-(2-chloro-4-(5-(1-ethyl-3-(trifluoromethyl)-1H-pyrazol-4-yl)-1-methyl-1H-imidazole-2-carboxamido)benzoyl)piperazine-1-carboxamide Hydrochloride Iodoethane (11 mg, 70 µmol, Eq: 2) was added to a mixture of rac-tert-butyl ((1s,3s)-3-(4-(2-chloro-4-(1-methyl-5-(3-(trifluoromethyl)-1H-pyrazol-4-yl)-1H-imidazole-2-carboxamido)benzoyl)piperazine-1-carboxamido)cyclobutyl)carbamate (24.3 mg, 35 µmol, Eq: 1) and K2CO3 (19.3 mg, 140 µmol, Eq: 4) in DMF (500 µl).

The mixture was stirred overnight, filtered and then purified by prep. HPLC.

Intermediate MS (ESI, m/z): 722.4 [M+H]+

The intermediate was combined with DCM (350 µl), then HCl (65.6 µl, 262 µmol, Eq: 7.5) was added. The reaction mixture was stirred for 4 h at room temperature and then kept at 4° C. in a fridge overnight. After removal of the volatiles, the product was lyophilized.

MS (ESI, m/z): 622.2 [M+H]+

Example 169 rac-N-((1s,3s)-3-aminocyclobutyl)-4-(2-chloro-4-(5-(1-(cyclopropylmethyl)-3-(trifluoromethyl)-1H-pyrazol-4-yl)-1-methyl-1H-imidazole-2-carboxamido)benzoyl)piperazine-1-carboxamide Hydrochloride

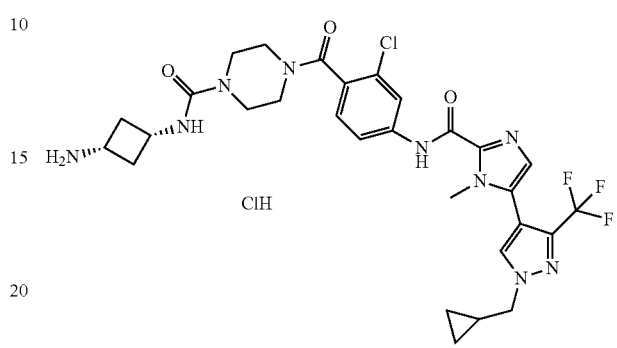

The title compound was prepared in analogy to Example 168 using (bromomethyl)cyclopropane instead of iodoethane.

MS (ESI, m/z): 649.3 [M+H]+

Example 170

N-(4-((2-(2-amino-2-methylpropoxy)ethyl)carbamoyl)-3-ethylphenyl)-5-(1-(cyanomethyl)-3-(trifluoromethyl)-1H-pyrazol-4-yl)-1-methyl-1H-imidazole-2-carboxamide

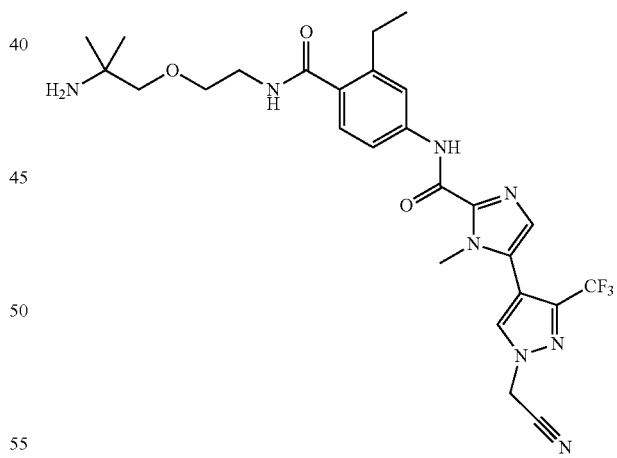

Step 1: tert-butyl N-[2-[2-[(4-amino-2-ethyl-benzoyl)amino]ethoxy]-1,1-dimethyl-ethyl]carbamate A mixture of 4-amino-2-ethyl-benzoic acid (175.0 mg, 1.06 mmol, 1 eq), N,N-diisopropylethylamine (0.37 mL, 2.12 mmol, 2 eq), O-(7-azabenzotriazol-1-yl)-N,N,N',N'-tetramethyluronium hexafluorophosphate (483.37 mg, 1.27 mmol, 1.2 eq) in DMF (7 mL) was stirred at 10° C. for 0.5 h, then tert-butyl N-[2-(2-aminoethoxy)-1,1-dimethyl-ethyl]

carbamate (Intermediate 4, 270.73 mg, 1.17 mmol, 1.1 eq) was added. The mixture was stirred at 15° C. for 16 h. The mixture was diluted with water (30 mL) and extracted with EtOAc (30 mL*2). The combined organic layers were washed with brine (20 mL*2), dried over sodium sulfate, filtered and concentrated in vacuum to give the crude product, which was purified by prep-HPLC to give the title compound (100 mg, 0.260 mmol, 25% yield) as a light yellow solid.

MS (ESI, m/z): 402.2 [M+Na]+

Step 2: tert-butyl N-[2-[2-[[2-ethyl-4-[[1-methyl-5-[3-(trifluoromethyl)-1H-pyrazol-4-yl]imidazole-2-carbonyl]amino]benzoyl]amino]ethoxy]-1,1-dimethyl-ethyl]carbamate A mixture of 1-methyl-5-[3-(trifluoromethyl)-1H-pyrazol-4-yl]imidazole-2-carboxylic acid (57.59 mg, 0.220 mmol, 1.2 eq), N,N-diisopropylethylamine (0.06 mL, 0.370 mmol, 2 eq), O-(7-azabenzotriazol-1-yl)-N,N,N',N'-tetramethyluronium hexafluorophosphate (84.16 mg, 0.220 mmol, 1.2 eq) in DMF (3 mL) was stirred at 10° C. for 0.5 h, then tert-butyl N-[2-2-[(4-amino-2-ethyl-benzoyl)amino]ethoxy]-1,1-dimethyl-ethyl]carbamate (70.0 mg, 0.180 mmol, 1 eq) was added. The mixture was stirred at 10° C. for 2 h. The mixture was diluted with water (50 mL) and extracted with EtOAc (2×50 mL). The combined organic layer was washed with brine (2×20 mL), dried over sodium sulfate, filtered and concentrated in vacuum to give the crude product, which was purified by prep-TLC (EtOAc) to give the title compound (112 mg, 0.180 mmol, 97.67% yield) as a light yellow oil.

MS (ESI, m/z): 622.4 [M+H]+

Step 3: N-[2-[2-[[4-[[5-[1-(cyanomethyl)-3-(trifluoromethyl)pyrazol-4-yl]-1-methyl-imidazole-2-carbonyl]amino]-2-ethyl-benzoyl]amino]ethoxy]-1,-dimethyl-ethyl]carbamate To a mixture of tert-butyl N-[2-[2-[[2-ethyl-4-[[1-methyl-5-[3-(trifluoromethyl)-1H-pyrazol-4-yl]imidazole-2-carbonyl]amino]benzoyl]amino]ethoxy]-1,1-dimethyl-ethyl]carbamate (85.0 mg, 0.140 mmol, 1 eq) and potassium carbonate (37.79 mg, 0.270 mmol, 2 eq) in DMF (3 mL) was added bromoacetonitrile (24.6 mg, 0.210 mmol, 1.5 eq) at 10° C., then the solution was stirred at 10° C. for 18 h. The solution was poured into water and extracted with EtOAc (50 mL*2). The combined organic layer was washed with brine (50 mL) and concentrated to give the crude product which was purified by Prep-TLC (DCM/MeOH=10/1) to afford tert-butyl N-[2-[2-[[4-[[5-[1-(cyanomethyl)-3-(trifluoromethyl)pyrazol-4-yl]-1-methyl-imidazole-2-carbonyl]amino]-2-ethyl-benzoyl]amino]ethoxy]-1,1-dimethyl-ethyl]carbamate (90 mg, 0.140 mmol, 99% yield) was light yellow oil. MS (ESI, m/z): 661.4 [M+H]+

Step 4: N-(4-((2-(2-amino-2-methylpropoxy)ethyl)carbamoyl)-3-ethylphenyl)-5-(1-(cyanomethyl)-3-(trifluoromethyl)-1H-pyrazol-4-yl)-1-methyl-1H-imidazole-2-carboxamide To a solution of tert-butyl N-[2-[2-[[4-[[5-[1-(cyanomethyl)-3-(trifluoromethyl)pyrazol-4-yl]-1-methyl-imidazole-2-carbonyl]amino]-2-ethyl-benzoyl]amino]ethoxy]-1,1-dimethyl-ethyl]carbamate (100.0 mg, 0.150 mmol, 1 eq) in DCM (5 mL) was added trifluoroacetic acid (0.5 mL, 6.49 mmol, 42.88 eq) at 10° C., the mixture was stirred at 10° C. for 16 h. The reaction mixture was concentrated in vacuum and the residue was purified by prep-HPLC (formic acid) to give product N-[4-[2-(2-amino-2-methyl-propoxy)ethylcarbamoyl]-3-ethyl-phenyl]-5-[1-(cyanomethyl)-3-(trifluoromethyl)pyrazol-4-yl]-1-methyl-imidazole-2-carboxamide (36.3 mg, 0.060 mmol, 39.54% yield, formic acid salt) as a light yellow solid. MS (ESI, m/z): 561.2 [M+H]+

Example 171

N-(azetidin-3-yl)-4-(2-chloro-4-(1-methyl-5-(3-(trifluoromethyl)-1-vinyl-1H-pyrazol-4-yl)-1H-imidazole-2-carboxamido)benzoyl)piperazine-1-carboxamide

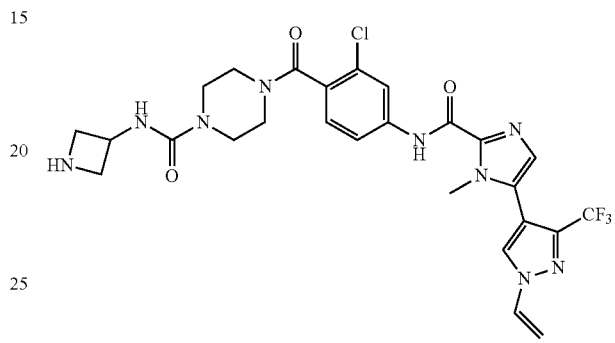

Step 1: tert-butyl 3-(4-(2-chloro-4-nitrobenzoyl)piperazine-1-carboxamido)azetidine-1-carboxylate To a solution of (2-chloro-4-nitro-phenyl)-piperazin-1-yl-methanone (500.0 mg, 1.3 mmol, 1 eq, TFA salt) (Organic Preparations and Procedures International, 1976, vol. 8, p. 85) in DMF (5 mL) was added N.N'-carbonyldiimidazole (211.29 mg, 1.3 mmol, 1 eq) and triethylamine (0.36 mL, 2.61 mmol, 2 eq) at 0° C., the mixture was stirred at 0° C. for 30 min and then 1-BOC-3-(amino)azetidine (0.09 mL, 1.3 mmol, 1 eq) was added at 0° C., the mixture was warmed to 20° C. and stirred for additional 2 h. The mixture was quenched with 10 mL of water and extracted with EtOAc (20 ml*3). The combined organic layer was washed with sat. NH4Cl aqueous solution (20 mL*3) and brine (20 mL*2), dried over Na2SO4, filtered and concentrated under reduce pressure to give a residue which was purified by silica gel (PE/EA=10/1) to give the title compound (450 mg, 0.960 mmol, 73.81% yield) as a light yellow solid.

MS (ESI, m/z): 468.3 [M+H]+

Step 2: tert-butyl 3-(4-(4-amino-2-chlorobenzoyl)piperazine-1-carboxamido)azetidine-1-carboxylate A mixture solution of NiCl2.6H2O (0.11 g, 0.480 mmol, 0.500 eq) and sodium borohydride (0.11 g, 2.89 mmol, 3 eq) in methanol (4.63 mL) was stirred at 0° C. for 30 min, and then a solution of tert-butyl 3-[[4-(2-chloro-4-nitro-benzoyl)piperazine-1-carbonyl]amino]azetidine-1-carboxylate (0.45 g, 0.960 mmol, 1 eq) and sodium borohydride (0.11 g, 2.89 mmol, 3 eq) in THF (4.63 mL) was added at 0° C., the mixture was stirred at 0° C. for additional 1.5 h. The mixture was filtered and concentrated to give the crude product tert-butyl 3-[[4-(4-amino-2-chloro-benzoyl)piperazine-1-carbonyl]amino]azetidine-1-carboxylate (240 mg, 0.550 mmol, 56.98% yield) as a white solid, used directly without purification.

MS (ESI, m/z): 438.1 [M+H]+

Step 3: 4-iodo-3-(trifluoromethyl)-1-trityl-1H-pyrazole

To a solution of 4-iodo-3-(trifluoromethyl)-1H-pyrazole (222.0 g, 847.43 mmol, 1 eq) in THF (2220 mL) was added 60% sodium hydride (37.28 g, 932.17 mmol, 1.1 eq) at 0° C., the mixture was stirred 0° C. for 0.5 h, then triphenylmethyl chloride (259.87 g, 932.17 mmol, 1.1 eq) was added. The mixture was warmed to 10° C. and stirred for 16 h. The mixture was quenched with sat. NH$_4$Cl (500 mL) and extracted with EtOAc (300 mL×2), washed with brine (700 mL), dried over sodium sulfate, filtered and concentrated in vacuum to give crude product, which was purified by silica gel column chromatography (eluting petroleum ether/EtOAc=100/1) to give 4-iodo-3-(trifluoromethyl)-1-tritylpyrazole (284 g, 563.17 mmol, 66.46% yield) as white solid. $^1$H NMR (400 MHz, CHLOROFORM-d) δ=7.42 (s, 1H), 7.34-7.37 (m, 9H), 7.09-7.12 (m, 6H) ppm.

Step 4: (3-(trifluoromethyl)-1-trityl-1H-pyrazol-4-yl)boronic Acid

To a solution of 4-iodo-3-(trifluoromethyl)-1-trityl-pyrazole (284.0 g, 563.17 mmol, 1 eq) in THF (2000 mL) was added butyllithium solution (270.32 mL, 675.8 mmol, 1.2 eq) dropwise at −70° C. under N$_2$ protection, the mixture was stirred at −70° C. for 0.5 h, then triisopropyl borate (194.94 mL, 844.75 mmol, 1.5 eq) was added dropwise to the mixture, the mixture was stirred at −70° C. for 1 h. TLC (Petroleum ether/EtOAc=5/1, R$_f$=0.2) showed the reaction was completed. Then the mixture was diluted with 300 mL of sat.NH$_4$Cl and extracted with EtOAc (300 mL×2), the combined organic layer was washed with brine (500 mL), dried over sodium sulfate, filtered and concentrated in vacuum to give the crude desired intermediate (290 g, 686.86 mmol, 73.18% yield) as light yellow oil, which was used for next step without purification.

MS (ESI, m/z): 445.2 [M+23]$^+$.

Step 5: ethyl 1-methyl-5-(3-(trifluoromethyl)-1-trityl-1H-pyrazol-4-yl)-1H-imidazole-2-carboxylate A mixture of [3-(trifluoromethyl)-1-trityl-pyrazol-4-yl] boronic acid (543.48 mg, 1.29 mmol, 1.5 eq), ethyl 5-bromo-1-methyl-imidazole-2-carboxylate (200.0 mg, 0.860 mmol, 1 eq), [1,1'-bis(diphenylphosphino)ferrocene] dichloropalladium(II) (62.79 mg, 0.090 mmol, 0.100 eq) and sodium carbonate (181.91 mg, 1.72 mmol, 2 eq) in 1,4-dioxane (5.4 mL) was stirred under N$_2$ protection at 85° C. for 16 h. LCMS showed the reaction was completed. The mixture was filtered, the filtrate was concentrated and purified by silica gel column chromatography (petroleum ether/EtOAc=3/1) to afford the title compound (330 mg, 0.620 mmol, 72.48% yield) as a light yellow oil.

MS (ESI, m/z): 531.1 [M+H]$^+$

Step 6: ethyl 1-methyl-5-(3-(trifluoromethyl)-1H-pyrazol-4-yl)-1H-imidazole-2-carboxylate A solution of ethyl 1-methyl-5-[3-(trifluoromethyl)-1-trityl-pyrazol-4-yl]imidazole-2-carboxylate (220.0 g, 331.74 mmol, 1 eq) in HCl/1,4-dioxane (4 N, 1000.0 mL, 4000 mmol, 12.06 eq) was stirred at 10° C. for 24 h. The solution was concentrated and the residue was triturated with MTBE (500 mL) to afford the title compound (38.3 g, 117.96 mmol, 35.56% yield) as white solid.

MS (ESI, m/z): 289.1 [M+H]$^+$.

Step 7: 1-methyl-5-(3-(trifluoromethyl)-1H-pyrazol-4-yl)-1H-imidazole-2-carboxylic Acid A solution of ethyl 1-methyl-5-[3-(trifluoromethyl)-1H-pyrazol-4-yl]imidazole-2-carboxylate hydrochloride (38.3 g, 117.96 mmol, 1 eq) and hydroxylithium hydrate (14.85 g, 353.88 mmol, 3 eq) in mixture solvent of THF (100 mL) and methanol (50 mL) and water (100 mL) was stirred at 5° C. for 16 h. The mixture was concentrated to remove THF and MeOH, and then acidized to pH=7 with 1 N HCl solution. A lot of white solid formed, the mixture was filtered, the filter cake was washed with water (100 mL) and dried to afford the title compound (25 g, 96.09 mmol, 81% yield) as a white solid.

MS (ESI, m/z): 261.0 [M+H]$^+$

Step 8: tert-butyl 3-(4-(2-chloro-4-(1-methyl-5-(3-(trifluoromethyl)-1H-pyrazol-4-yl)-1H-imidazole-2-carboxamido)benzoyl)piperazine-1-carboxamido)azetidine-1-carboxylate A mixture of 1-methyl-5-[3-(trifluoromethyl)-1H-pyrazol-4-yl]imidazole-2-carboxylic acid (0.7 g, 2.29 mmol, 1 eq, formic acid salt), tert-butyl 3-[[4-(4-amino-2-chlorobenzoyl)piperazine-1-carbonyl]amino]azetidine-1-carboxylate (1.0 g, 2.29 mmol, 1 eq) and N,N-diisopropylethylamine (1.19 mL, 6.86 mmol, 3 eq) in DMF (5.95 mL) was added O-(7-azabenzotriazol-1-yl)-N,N,N',N'-tetramethyluronium hexafluorophosphate (1.3 g, 3.43 mmol, 1.5 eq) at 0° C., then the solution was warmed to 30° C. and stirred for 16 h. The mixture was diluted with HCl aqueous solution (1 L, 0.5 N) and extracted with EtOAc (300 ml*3), washed with brine (500 mL*3), dried over Na$_2$SO$_4$, concentrated and purified by silica (PE/EA/MeOH=1/1/0.04) to afford the title compound (950 mg, 1.4 mmol, 61.1% yield) as a white solid.

MS (ESI, m/z): 680.1 [M+H]$^+$

Step 9: tert-butyl 3-(4-(2-chloro-4-(1-methyl-5-(3-(trifluoromethyl)-1-vinyl-1H-pyrazol-4-yl)-1H-imidazole-2-carboxamido)benzoyl)piperazine-1-carboxamido)azetidine-1-carboxylate To a mixture of 1,2-dichloroethane (4 mL) and 50% sodium hydroxide solution (58.81 mg, 0.740 mmol, 5 eq) was added tert-butyl 3-[[4-[2-chloro-4-[[1-methyl-5-[3-(trifluoromethyl)-1H-pyrazol-4-yl]imidazole-2-carbonyl]amino]benzoyl]piperazine-1-carbonyl]amino]azetidine-1-carboxylate (100.0 mg, 0.150 mmol, 1 eq) and benzyltriethylammonium chloride (3.35 mg, 0.010 mmol, 0.100 eq), the resulting mixture was then heated to 80° C. for 4 h. The mixture was diluted with DCM (20 mL), dried over sodium sulfate, filtered and concentrated in vacuum to give crude product, which was purified by prep-TLC (DCM/MeOH=10/1) to give the title compound (50 mg, 0.070 mmol, 48.16% yield) as an off-white solid. MS (ESI, m/z): 706.3 [M+H]$^+$

Step 10: N-(azetidin-3-yl)-4-(2-chloro-4-(1-methyl-5-(3-(trifluoromethyl)-1-vinyl-1H-pyrazol-4-yl)-1H-imidazole-2-carboxamido)benzoyl)piperazine-1-carboxamide A mixture of tert-butyl 3-[[4-[2-chloro-4-[[1-methyl-5-[3-(trifluoromethyl)-1-vinyl-pyrazol-4-yl]imidazole-2-carbonyl]amino]benzoyl]piperazine-1-carbonyl]amino]azetidine-1-carboxylate (50.0 mg, 0.070 mmol, 1 eq) and trifluoroacetic acid (0.01 mL, 0.070 mmol, 1 eq) in DCM (1.93 mL) was stirred at 20° C. for 4 h. The mixture was concentrated in vacuum to give the crude product, which was purified by prep-HPLC to give the title compound (11.28 mg, 0.020 mmol, 27% yield, formic acid salt) as a white solid.

MS (ESI, m/z): 606.5 [M+H]$^+$

Example 172

N-(3-chloro-4-(((1R,5S,6s)-3-(piperidine-4-carbonyl)-3-azabicyclo[3.1.0]hexan-6-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate

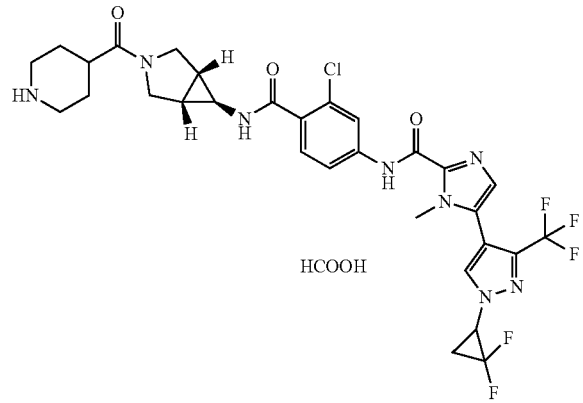 [SMILES: Cn1c(-c2cn(C3CC3(F)F)nc2C(F)(F)F)cnc1C(=O)Nc1ccc(C(=O)N[C@H]2[C@@H]3CN(C(=O)C4CCNCC4)C[C@@H]32)c(Cl)c1 ; "HCOOH"]

Step 1 tert-butyl (1R,5S,6s)-6-(2-chloro-4-(1-methyl-5-(3-(trifluoromethyl)-1H-pyrazol-4-yl)-1H-imidazole-2-carboxamido)benzamido)-3-azabicyclo[3.1.0]hexane-3-carboxylate 2-chloro-4-(1-methyl-5-(3-(trifluoromethyl)-1H-pyrazol-4-yl)-1H-imidazole-2-carboxamido)benzoic acid hydrochloride (Intermediate 2, 978 mg, 2.09 mmol, Eq: 1), tert-butyl (1R,5S,6s)-6-amino-3-azabicyclo[3.1.0]hexane-3-carboxylate (517 mg, 2.61 mmol, Eq: 1.25) and HATU (952 mg, 2.5 mmol, Eq: 1.2) were combined with DMF (15 ml) to give a light brown suspension. DIPEA (1.35 g, 1.82 ml, 10.4 mmol, Eq: 5.00) was added, and the reaction mixture was stirred at room temperature overnight. Brine was added to the reaction mixture and extracted with EtOAc. After drying over Na$_2$SO$_4$, filtration and evaporation of the volatiles, the product was purified by flash chromatography (silica gel, 50 g, 10% to 100% EtOAc in heptane) to give the title compound (984 mg) as a yellow oil. MS (ESI, m/z): 594.1 [M+H]$^+$ Step 2

Intermediate 7

N-(4-(((1R,5S,6s)-3-azabicyclo[3.1.0]hexan-6-yl)carbamoyl)-3-chlorophenyl)-1-methyl-5-(3-(trifluoromethyl)-1H-pyrazol-4-yl)-1H-imidazole-2-carboxamide hydrochloride tert-butyl (1R,5S,6s)-6-(2-chloro-4-(1-methyl-5-(3-(trifluoromethyl)-1H-pyrazol-4-yl)-1H-imidazole-2-carboxamido)benzamido)-3-azabicyclo[3.1.0]hexane-3-carboxylate (766 mg, 1.29 mmol, Eq: 1) was dissolved in DCM (20 ml) and treated with an excess of HCl 4M in dioxane (6.45 ml, 25.8 mmol, Eq: 20.00) and the reaction mixture was stirred at RT overnight. Ether was added to reaction mixture, and the solid was filtered and dried under HV to obtain the desired product (680 mg) as white powder. MS (ESI, m/z): 494.1 [M+H]$^+$ Step 3 tert-butyl 4-((1R,5S,6s)-6-(2-chloro-4-(1-methyl-5-(3-(trifluoromethyl)-1H-pyrazol-4-yl)-1H-imidazole-2-carboxamido)benzamido)-3-azabicyclo[3.1.0]hexane-3-carbonyl)piperidine-1-carboxylate N-(4-(((1R,5S,6s)-3-azabicyclo[3.1.0]hexan-6-yl)carbamoyl)-3-chlorophenyl)-1-methyl-5-(3-(trifluoromethyl)-1H-pyrazol-4-yl)-1H-imidazole-2-carboxamide hydrochloride (200 mg, 0.377 mmol, Eq: 1), 1-(tert-butoxycarbonyl)piperidine-4-carboxylic acid (CAS 84358-13-4: 112 mg, 0.49 mmol, Eq: 1.30) and TBTU (CAS 125700-67-9: 150 mg, 0.453 mmol, Eq: 1.20) were combined with DMF (10 ml). TEA (191 mg, 0.263 ml, 1.89 mmol, Eq: 5.00) was added, and the reaction was stirred at room temperature overnight. Brine was added to the reaction mixture and extracted with EtOAc. After drying over Na$_2$SO$_4$, filtration and evaporation of the volatiles, the product was purified by flash chromatography (silica gel, 20 g, 0% to 30% MeOH in EtOAc) to give the title compound (223 mg) as a white solid. MS (ESI, m/z): 705.2 [M+H]$^+$ Step 4 tert-butyl 4-((1R,5S,6s)-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carbonyl)piperidine-1-carboxylate To tert-butyl 4-((1R,5S,6s)-6-(2-chloro-4-(1-methyl-5-(3-(trifluoromethyl)-1H-pyrazol-4-yl)-1H-imidazole-2-carboxamido)benzamido)-3-azabicyclo[3.1.0]hexane-3-carbonyl)piperidine-1-carboxylate (20 mg, 0.029 mmol, Eq: 1) dissolved in 2 ml of DMF was added potassium carbonate (14 mg, 0.102 mmol, Eq: 3.50) and 2-bromo-1,1-difluorocyclopropane (CAS 51326-64-8: 11.4 mg, 0.0725 mmol, Eq: 2.5). The reaction was stirred at room temperature overnight. After filtration of the potassium carbonate and evaporation of the volatiles the product was used in the next step without further purification.

MS (ESI, m/z): 781.3 [M+H]+

Step 5

N-(3-chloro-4-(((1R,5S,6s)-3-(piperidine-4-carbonyl)-3-azabicyclo[3.1.0]hexan-6-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate tert-butyl 4-((1R,5S,6s)-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carbonyl)piperidine-1-carboxylate (23 mg, 0.029 mmol, Eq: 1) dissolved in DCM was treated with an excess of TFA (103 mg, 0.069 ml, 0.9 mmol, Eq: 30). The reaction was stirred at room temperature overnight. After evaporation of the volatiles, the residue was purified by prep. HPLC to give the title product (14 mg). MS (ESI, m/z): 681.4 [M+H]+

The following Examples were obtained in analogy:

| Ex. | Name | Structure | ESI MS [M + H]+ | Starting Material |
|---|---|---|---|---|
| 173 | N-(3-chloro-4-(((1R,5S,6s)-3-(piperidine-4-carbonyl)-3-azabicyclo[3.1.0]hexan-6-yl)carbamoyl)phenyl)-5-(1-cyclobutyl-3-(trifluoromethyl)-1H-pyrazol-4-yl)-1-methyl-1H-imidazole-2-carboxamide formate | 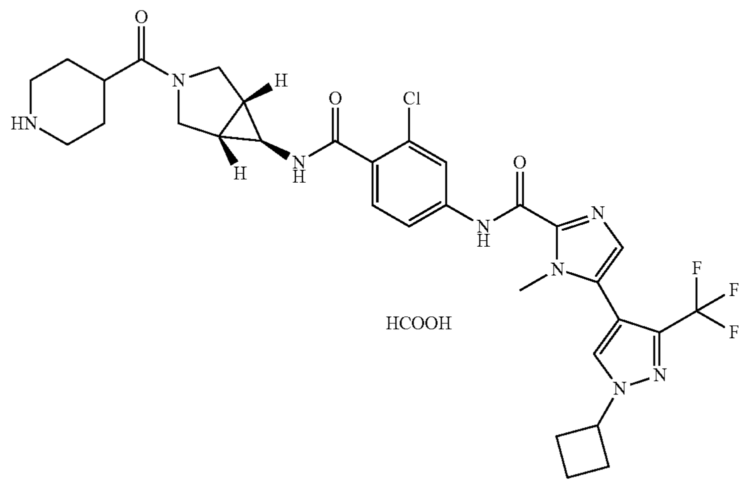 [SMILES: Cn1c(-c2cn(C3CCC3)nc2C(F)(F)F)cnc1C(=O)Nc1ccc(C(=O)N[C@H]2[C@@H]3CN(C(=O)C4CCNCC4)C[C@@H]32)c(Cl)c1 ; "HCOOH"] | 659.4 [M + H]+ | bromocyclobutane |
| 174 | N-(3-chloro-4-(((1R,5S,6s)-3-(piperidine-4-carbonyl)-3-azabicyclo[3.1.0]hexan-6-yl)carbamoyl)phenyl)-5-(1-(cyclobutylmethyl)-3-(trifluoromethyl)-1H-pyrazol-4-yl)-1-methyl-1H-imidazole-2-carboxamide formate | 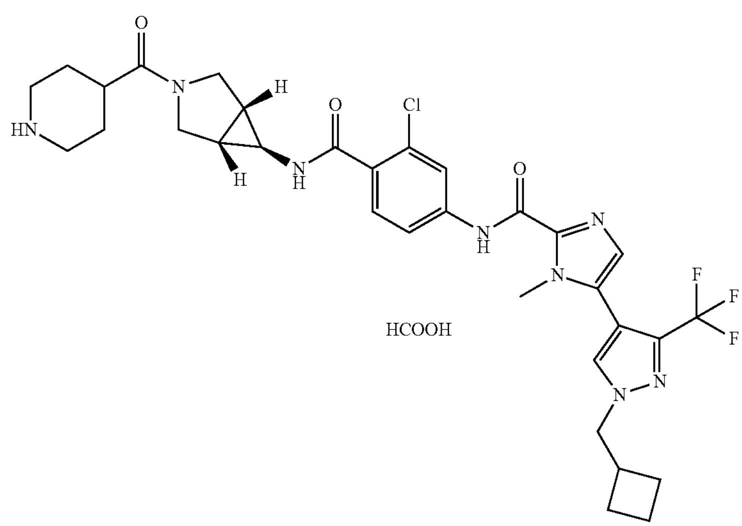 [SMILES: Cn1c(-c2cn(CC3CCC3)nc2C(F)(F)F)cnc1C(=O)Nc1ccc(C(=O)N[C@H]2[C@@H]3CN(C(=O)C4CCNCC4)C[C@@H]32)c(Cl)c1 ; "HCOOH"] | 673.4 [M + H]+ | (bromomethyl)cyclobutane |

Example 175

(1R,5S,6s)-6-(2-chloro-4-(5-(1-(cyanomethyl)-3-
(trifluoromethyl)-1H-pyrazol-4-yl)-1-methyl-1H-
imidazole-2-carboxamido)benzamido)-N-(trans-4-
hydroxypyrrolidin-3-yl)-3-azabicyclo[3.1.0]hexane-
3-carboxamide Formate

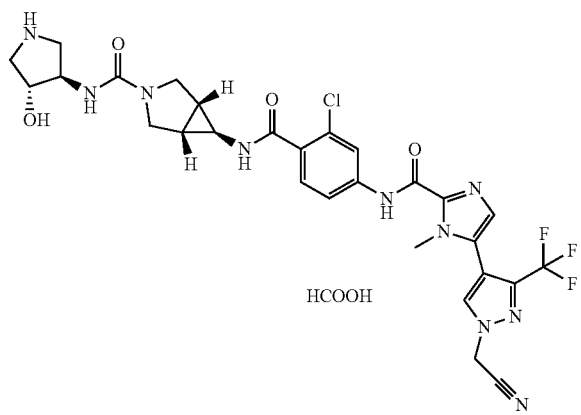 [SMILES: Cn1c(-c2cn(CC#N)nc2C(F)(F)F)cnc1C(=O)Nc1ccc(C(=O)N[C@H]2[C@@H]3CN(C(=O)N[C@@H]4CNC[C@H]4O)C[C@@H]32)c(Cl)c1 ; "HCOOH"]

Step 1 tert-butyl trans-3-((1R,5S,6s)-6-(2-chloro-4-(1-
methyl-5-(3-(trifluoromethyl)-1H-pyrazol-4-yl)-1H-
imidazole-2-carboxamido)benzamido)-3-azabicyclo
[3.1.0]hexane-3-carboxamido)-4-
hydroxypyrrolidine-1-carboxylate The title compound was prepared from intermediate 7 N-(4-(((1R,5S,6s)-3-azabicyclo[3.1.0]hexan-6-yl)carbamoyl)-3-chlorophenyl)-1-methyl-5-(3-(trifluoromethyl)-1H-pyrazol-4-yl)-1H-imidazole-2-carboxamide hydrochloride (180 mg, 0.339 mmol, Eq: 1) by combining with a 30 min pre stirred mixture of tert-butyl trans-3-amino-4-hydroxypyrrolidine-1-carboxylate (103 mg, 0.509 mmol, Eq: 1.50), CDI (CAS 530-62-1: 77.1 mg, 0.475 mmol, Eq: 1.40) and TEA (103 mg, 0.142 ml, 1.02 mmol, Eq: 3.00) in 5 ml DMF. The reaction was stirred at room temperature overnight. Water was added to the reaction mixture and extracted with EtOAc. After drying over Na$_2$SO$_4$, filtration and evaporation of the volatiles, the product was used in the next step without further purification. MS (ESI, m/z): 722.5 [M+H]$^+$

Step 2 tert-butyl trans-3-((1R,5S,6s)-6-(2-chloro-4-(5-(1-
(cyanomethyl)-3-(trifluoromethyl)-1H-pyrazol-4-yl)-
1-methyl-1H-imidazole-2-carboxamido)benzamido)-
3-azabicyclo[3.1.0]hexane-3-carboxamido)-4-
hydroxypyrrolidine-1-carboxylate tert-butyl trans-3-((1R,5S,6s)-6-(2-chloro-4-(1-methyl-5-(3-(trifluoromethyl)-1H-pyrazol-4-yl)-1H-imidazole-2-carboxamido)benzamido)-3-azabicyclo[3.1.0]hexane-3-carboxamido)-4-hydroxypyrrolidine-1-carboxylate (30 mg, 0.0415 mmol, Eq: 1) was dissolved in 1 ml of AcCN, potassium carbonate (11.5 mg, 0.125 mmol, Eq: 2.0) and 2-bromoacetonitrile (15 mg, 0.0725 mmol, Eq: 2.5) were added. The reaction was stirred 60° C. overnight. Water was added to the reaction mixture and extracted with EtOAc. After drying over Na$_2$SO$_4$, filtration and evaporation of the volatiles, the product was used in the next step without further purification MS (ESI, m/z): 761.5 [M+H]$^+$

Step 3 tert-butyl trans-3-((1R,5S,6s)-6-(2-chloro-4-(5-(1-
(cyanomethyl)-3-(trifluoromethyl)-1H-pyrazol-4-yl)-
1-methyl-1H-imidazole-2-carboxamido)benzamido)-
3-azabicyclo[3.1.0]hexane-3-carboxamido)-4-
hydroxypyrrolidine-1-carboxylate tert-butyl 4-((1R,5S,6s)-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carbonyl)piperidine-1-carboxylate (30.4 mg, 0.040 mmol, Eq: 1) dissolved in 2 ml of DCM was treated with an excess of TFA (912 mg, 0.616 ml, 8 mmol, Eq: 200). The reaction was stirred at room temperature overnight. After evaporation of the volatiles, the residue was purified by prep. HPLC to give the title product (3.7 mg). MS (ESI, m/z): 661.4 [M+H]+

Example 176

(1R,5S,6s)-6-(2-chloro-4-(5-(1-(2-fluoroallyl)-3-
(trifluoromethyl)-1H-pyrazol-4-yl)-1-methyl-1H-
imidazole-2-carboxamido)benzamido)-N-(trans-4-
hydroxypyrrolidin-3-yl)-3-azabicyclo[3.1.0]hexane-
3-carboxamide Formate

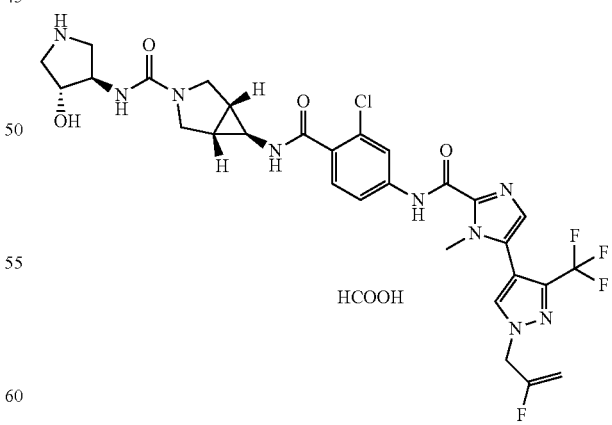

The title compound was prepared in analogy to Example 175 using 3-chloro-2-fluoroprop-1-ene with additional equimolar quantity of KI (6.9 mg, 0.0415 mmol, Eq: 1) instead of 2-bromoacetonitrile. MS (ESI, m/z): 680.5 [M+H]$^+$

Example 177

(1R,5S,6s)-N-(cis-3-aminocyclobutyl)-6-(2-chloro-4-(5-(1-(2,2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxamide

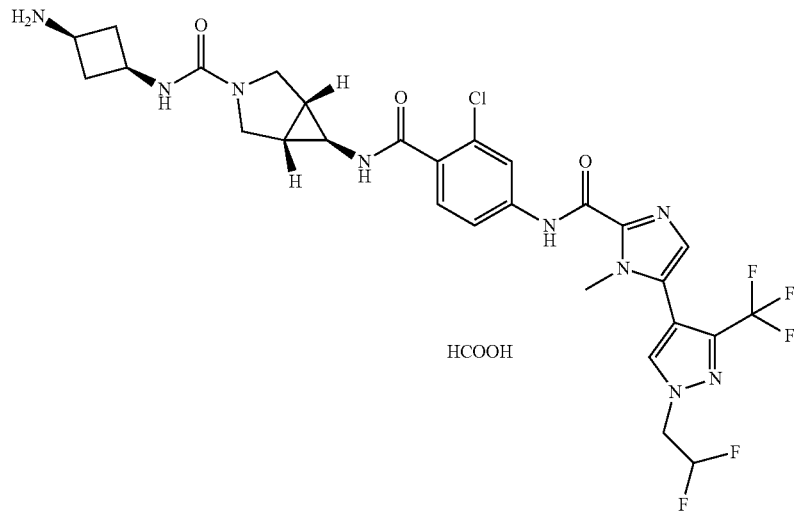 [SMILES: Cn1c(-c2cn(CC(F)F)nc2C(F)(F)F)cnc1C(=O)Nc1ccc(C(=O)N[C@H]2[C@@H]3CN(C(=O)N[C@H]4C[C@@H](N)C4)C[C@@H]32)c(Cl)c1 ; "HCOOH"]

Step 1 methyl 2-chloro-4-[[5-[1-(2,2-difluoroethyl)-3-(trifluoromethyl)pyrazol-4-yl]-1-methylimidazole-2-carbonyl]amino]benzoate To methyl 2-chloro-4-(1-methyl-5-(3-(trifluoromethyl)-1H-pyrazol-4-yl)-1H-imidazole-2-carboxamido)benzoate intermediate (954 mg, 2.23 mmol, Eq: 1) dissolved in a mix of 15 ml of AcCN and 8 ml of DMF was added potassium carbonate (616 mg, 4.46 mmol, Eq: 2.00) and 1,1-difluoro-2-iodoethane (642 mg, 3.35 mmol, Eq: 1.5). The reaction was stirred at 60° C. overnight. After filtration of the potassium carbonate and evaporation of the volatiles, the product was purified by flash chromatography (silica gel, 40 g, 10% to 100% EtOAc in heptane) to give the title compound (748 mg) as a white powder. MS (ESI, m/z): 492.0 [M+H]$^+$

Step 2

2-chloro-4-[[5-[1-(2,2-difluoroethyl)-3-(trifluoromethyl)pyrazol-4-yl]-1-methylimidazole-2-carbonyl]amino]benzoic Acid Hydrochloride The mixture of methyl 2-chloro-4-[[5-[1-(2,2-difluoroethyl)-3-(trifluoromethyl)pyrazol-4-yl]-1-methylimidazole-2-carbonyl]amino]benzoate (744 mg, 1.51 mmol, Eq: 1) and lithium hydroxide monohydrate (318 mg, 7.56 mmol, Eq: 5) in MeOH (10 mL), THF (25 mL) and water (10 mL) was stirred at room temperature overnight. Then the mixture was acidified with 1N HCl. The white precipitate was collected, washed with water and dried by vacuum to give the title compound as a white powder (587 mg). MS (ESI, m/z): 478.1 [M+H]$^+$

Step 3 tert-butyl (1R,5S,6s)-6-(2-chloro-4-(5-(1-(2,2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxylate 2-chloro-4-[[5-[1-(2,2-difluoroethyl)-3-(trifluoromethyl)pyrazol-4-yl]-1-methylimidazole-2-carbonyl]amino]benzoic acid hydrochloride (56.6 mg, 0.110 mmol, Eq: 1), tert-butyl (1R,5S,6s)-6-amino-3-azabicyclo[3.1.0]hexane-3-carboxylate (32.7 mg, 0.165 mmol, Eq: 1.50) and TBTU (CAS 125700-67-9: 47.3 mg, 0.143 mmol, Eq: 1.30) were combined with DMF (25 ml). TEA (55.7 mg, 0.0767 ml, 0.550 mmol, Eq: 5.00) was added, and the reaction was stirred at room temperature overnight. A solution of 1N KHSO$_4$ was added to the reaction mixture and extracted with EtOAc. After drying over Na$_2$SO$_4$, filtration and evaporation of the volatiles, the product was used in the next step without further purification. MS (ESI, m/z): 658.4 [M+H]$^+$

Step 4

N-(4-(((1R,5S,6s)-3-azabicyclo[3.1.0]hexan-6-yl)carbamoyl)-3-chlorophenyl)-5-(1-(2,2-difluoroethyl)-3-(trifluoromethyl)-1H-pyrazol-4-yl)-1-methyl-1H-imidazole-2-carboxamide Formate tert-butyl (1R,5S,6s)-6-(2-chloro-4-(5-(1-(2,2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxylate (72.3 mg, 0.110 mmol, Eq: 1) dissolved in DCM was treated with an excess of TFA (376 mg, 0.254 ml, 3.3 mmol, Eq: 30). The reaction was stirred at room temperature overnight. The mixture was quenched with TEA. After evaporation of the volatiles, the residue was purified by prep. HPLC to give the title product (41.1 mg). MS (ESI, m/z): 558.2 [M+H]+

Step 5 tert-butyl (cis-3-((1R,5S,6s)-6-(2-chloro-4-(5-(1-(2, 2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxamido)cyclobutyl)carbamate To N-(4-(((1R,5S,6s)-3-azabicyclo[3.1.0]hexan-6-yl)carbamoyl)-3-chlorophenyl)-5-(1-(2,2-difluoroethyl)-3-(trifluoromethyl)-1H-pyrazol-4-yl)-1-methyl-1H-imidazole-2-carboxamide formate (33.4 mg, 60 μmol, Eq: 1) was added a solution of triphogen (CAS 32315-10-9: 7.12 mg, 24 μmol, Eq: 0.40) in DCM, followed by the addition of cis tert-butyl (−3-aminocyclobutyl)carbamate (27.9 mg, 150 μmol, Eq: 2.5) and TEA (30.4 mg, 41.8 μl, 300 μmol, Eq: 5). The mixture was stirred at RT overnight. A solution of 1N KHSO₄ was added to the reaction mixture and extracted with EtOAc. After drying over Na₂SO₄, filtration and evaporation of the volatiles, the product was used in the next step without further purification.

Step 6

(1R,5S,6s)-N-(cis-3-aminocyclobutyl)-6-(2-chloro-4-(5-(1-(2,2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxamide tert-butyl (cis-3-((1R,5S,6s)-6-(2-chloro-4-(5-(1-(2,2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxamido)cyclobutyl)carbamate (23.1 mg, 30 μmol, Eq: 1) dissolved in DCM was treated with an excess of TFA (103 mg, 69 μl, 0.9 mmol, Eq: 30). The reaction was stirred at room temperature overnight. The mixture was quenched with TEA. After evaporation of the volatiles, the residue was purified by prep. HPLC to give the title product (3.4 mg). MS (ESI, m/z): 670.3 [M+H]+

Example 178

N-(4-(((1-aminocyclopropyl)methyl)carbamoyl)-3-chlorophenyl)-5-(1-(2,2-difluorocyclopropyl)-3-(trifluoromethyl)-1H-pyrazol-4-yl)-1-methyl-H-imidazole-2-carboxamide Formate

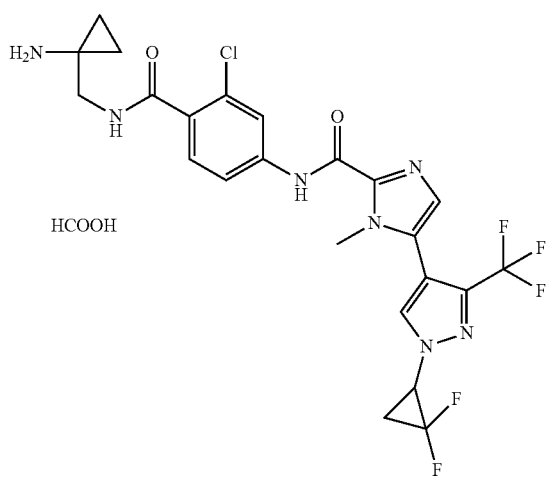 [SMILES: "HCOOH" ; Cn1c(-c2cn(C3CC3(F)F)nc2C(F)(F)F)cnc1C(=O)Nc1ccc(C(=O)NCC2(N)CC2)c(Cl)c1]

Step 1

2-chloro-4-(5-(1-(2,2-difluorocyclopropyl)-3-(trifluoromethyl)-1H-pyrazol-4-yl)-1-methyl-1H-imidazole-2-carboxamido)benzoic acid was prepared in analogy to Example 177 Step 1 using 2-bromo-1,1-difluorocyclopropane instead of 1,1-difluoro-2-iodoethane.
MS (ESI, m/z): 490.3 [M+H]+

Step 2 tert-butyl (1-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)cyclopropyl)carbamate 2-chloro-4-(5-(1-(2,2-difluorocyclopropyl)-3-(trifluoromethyl)-1H-pyrazol-4-yl)-1-methyl-1H-imidazole-2-carboxamido)benzoic acid (29.4 mg, 0.060 mmol, Eq: 1), tert-butyl (1-(aminomethyl)cyclopropyl)carbamate (17.3 mg, 0.090 mmol, Eq: 1.50) and TBTU (CAS 125700-67-9: 26.8 mg, 0.081 mmol, Eq: 1.35) were combined with DMF (2.5 ml). TEA (30.4 mg, 42 μl, 0.300 mmol, Eq: 5.00) was added, and the reaction was stirred at room temperature overnight. The residue was purified by prep. HPLC to give the title product (37 mg). MS (ESI, m/z): 602.4 [M−tBu+H]+

Step 3

N-(4-(((1-aminocyclopropyl)methyl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide Formate tert-butyl (1-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)cyclopropyl)carbamate (29.6 mg, 45 μmol, Eq: 1) dissolved in DCM was treated with an excess of TFA (128 mg, 87 μl, 1.13 mmol, Eq: 25). The reaction was stirred at room temperature overnight. The mixture was quenched with TEA. After evaporation of the volatiles, the residue was purified by prep. HPLC to give the title product (10.1 mg). MS (ESI, m/z): 558.3 [M+H]+

Example 179

N-(3-chloro-4-(4-fluoro-4-((3-(trans-4-hydroxypyrrolidin-3-yl)ureido)methyl)piperidine-1-carbonyl)phenyl)-5-(1-(2,2-difluorocyclopropyl)-3-(trifluoromethyl)-1H-pyrazol-4-yl)-1-methyl-1H-imidazole-2-carboxamide Formate

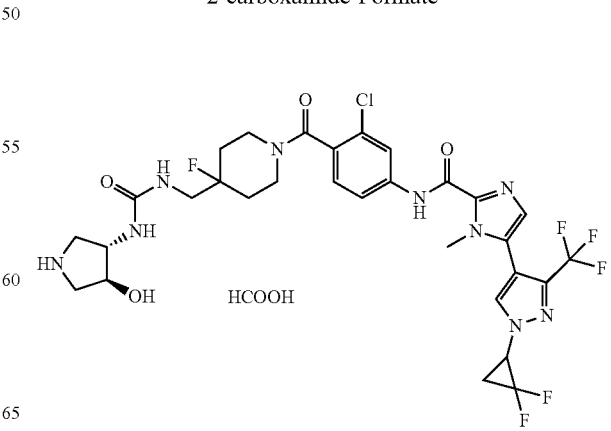

Step 1

N-[4-[4-(aminomethyl)-4-fluoro-piperidine-1-carbonyl]-3-chloro-phenyl]-5-[1-(2,2-difluorocyclopropyl)-3-(trifluoromethyl)pyrazol-4-yl]-1-methyl-imidazole-2-carboxamide was prepared in analogy to Example 178 Step 1 using tert-butyl 3-(aminomethyl)piperidine-1-carboxylate instead of tert-butyl (1-(aminomethyl)cyclopropyl)carbamate. MS (ESI, m/z): 604.3 [M+H]+

Step 2

N-(3-chloro-4-(4-fluoro-4-((3-(trans-4-hydroxypyrrolidin-3-yl)ureido)methyl)piperidine-1-carbonyl)phenyl)-5-(1-(2,2-difluorocyclopropyl)-3-(trifluoromethyl)-1H-pyrazol-4-yl)-1-methyl-1H-imidazole-2-carboxamide Formate tert-butyl trans-3-amino-4-hydroxypyrrolidine-1-carboxylate (12.6 mg, 62.5 µmol, Eq: 2.50), CDI (CAS 530-62-1: 8.9 mg, 55 µmol, Eq: 2.20) and TEA (12.6 mg, 18 µl, 0.125 mmol, Eq: 5.00) were mixed in DMF at room temperature for 20 min. N-[4-[4-(aminomethyl)-4-fluoro-piperidine-1-carbonyl]-3-chloro-phenyl]-5-[1-(2,2-difluorocyclopropyl)-3-(trifluoromethyl)pyrazol-4-yl]-1-methyl-imidazole-2-carboxamide (16.2 mg, 25 µmol, Eq: 1.00) was then added. The reaction was stirred at room temperature overnight. After evaporation of the volatiles, the product, dissolved in DCM, was treated with an excess of TFA (85 mg, 60 µl, 0.75 mmol, Eq: 30). The reaction was stirred at room temperature overnight. The mixture was quenched with TEA. After evaporation of the volatiles, the residue was purified by prep. HPLC to give the title product (1.5 mg). MS (ESI, m/z): 688.4 [M+H]+

Example 167

N-(3-aminocyclobutyl)-4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carboxamide Hydrochloride

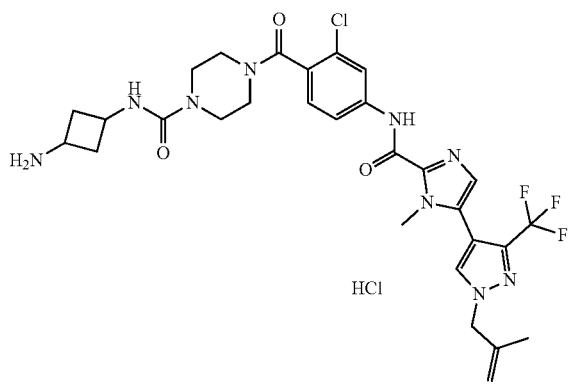 [SMILES: C=C(C)Cn1cc(-c2cnc(C(=O)Nc3ccc(C(=O)N4CCN(C(=O)NC5CC(N)C5)CC4)c(Cl)c3)n2C)c(C(F)(F)F)n1 ; Cl]

Step 1) tert-butyl 4-[2-chloro-4-[[1-methyl-5-[3-(trifluoromethyl)-1H-pyrazol-4-yl]imidazole-2-carbonyl]amino]benzoyl]piperazine-1-carboxylate A mixture of (3-(trifluoromethyl)-1H-pyrazol-4-yl)boronic acid (512 mg, 2.85 mmol, Eq: 1.5), tert-butyl 4-(4-(5-bromo-1-methyl-1H-imidazole-2-carboxamido)-2-chlorobenzoyl)piperazine-1-carboxylate (1 g, 1.9 mmol, Eq: 1), chloro[(di(1-adamantyl)-N-butylphosphine)-2-(2-aminobiphenyl)]palladium(II) (127 mg, 190 µmol, Eq: 0.1) and potassium carbonate (525 mg, 3.8 mmol, Eq: 2) in 1,4-Dioxane (17.3 ml) and Water (1.73 ml) was evacuated and filled back with argon. It was then heated by microwave at 130° C. for 30 min. LC/MS showed a ~30% progress. Additional (3-(trifluoromethyl)-1H-pyrazol-4-yl)boronic acid (341 mg, 1.9 mmol, Eq: 1) was added and the mixture was heated further at 130° C. for 30 min. LC/MS showed ~70% progress. It was heated again by microwave at 130° C. for 30 min. Little change observed. Additional (3-(trifluoromethyl)-1H-pyrazol-4-yl)boronic acid (520 mg, 2.89 mmol, Eq: 1.52) was added and the mixture was heated again at 130° C. for 30 min. LC/MS showed a complete consumption of the starting material. The mixture was diluted with ethyl acetate. The organic layer was washed with sat. NaHCO$_3$ (2×), brine, then it was dried over magnesium sulfate and concentrated. The obtained residue was purified by flash chromatography (0-100% (75:25 EtOAc: EtOH) in heptanes, 80 g SiO$_2$) to yield the title compound (740 mg, 1.27 mmol, 67% yield) as a yellow solid. MS (ESI, m/z): 582.3 [M+H]+

Step 2) tert-butyl 4-[2-chloro-4-[[1-methyl-5-[1-(2-methylallyl)-3-(trifluoromethyl)pyrazol-4-yl]imidazole-2-carbonyl]amino]benzoyl]piperazine-1-carboxylate A mixture of tert-butyl 4-(2-chloro-4-(1-methyl-5-(3-(trifluoromethyl)-1H-pyrazol-4-yl)-1H-imidazole-2-carboxamido)benzoyl)piperazine-1-carboxylate (0.3 g, 515 µmol, Eq: 1), potassium carbonate (92.6 mg, 670 µmol, Eq: 1.3) and 3-bromo-2-methylprop-1-ene (83.5 mg, 56.7 µl, 619 µmol, Eq: 1.2) was stirred at room temperature for 90 min. The mixture was diluted with ethyl acetate, washed with sat. NaHCO$_3$, then dried over magnesium sulfate and concentrated to yield crude the title compound (319 mg, 486 µmol, 94.4% yield) as a yellow sticky solid. It was used as is in the next step. MS (ESI, m/z): 636.3 [M+H]+

Step 3) N-[3-chloro-4-(piperazine-1-carbonyl)phenyl]-1-methyl-5-[1-(2-methylallyl)-3-(trifluoromethyl)pyrazol-4-yl]imidazole-2-carboxamide; Hydrochloride A mixture of 4M HCl in dioxane (2.51 ml, 10 mmol, Eq: 20) and tert-butyl 4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carboxylate (0.319 g, 502 µmol, Eq: 1) in Dioxane (3 ml) was stirred at room temperature overnight. Diethyl ether was added. The white solid was collected by filtration, washed with diethyl ether (2×), dried under reduced pressure to yield the title compound (0.26 g, 445 µmol, 88.8% yield) as a white solid. MS (ESI, m/z): 536.2

Step 4) tert-butyl (1R,5S,6r)-6-(4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carbonyl)-3-azabicyclo[3.1.0]hexane-3-carboxylate A mixture of (1R,5S,6r)-3-(tert-butoxycarbonyl)-3-azabicyclo[3.1.0]hexane-6-carboxylic acid (11.9 mg, 52.4 µmol, Eq: 1.2), N-(3-chloro-4-(piperazine-1-carbonyl)phenyl)-1- methyl-5-(1-(2-methylallyl)-3-(trifluoromethyl)-1H-pyrazol-4-yl)-1H-imidazole-2-carboxamide hydrochloride (0.025 g, 43.7 µmol, Eq: 1), HATU (19.9 mg, 52.4 µmol, Eq: 1.2) and DIEA (14.1 mg, 19.1 µl, 109 µmol, Eq: 2.5) in dry DMF (1 ml) was stirred at room temperature (Rxn Molarity: 43.7 mM) for 90 min. The mixture was diluted in ethyl acetate, washed with sat. NaHCO$_3$ (4×), then concentrated. The obtained residue was purified by flash chromatography to yield the title compound (21 mg, 27.6 µmol, 63.2% yield) as a white powder. MS (ESI, m/z): 745.4

Step 5) N-(4-(4-((1R,5S,6r)-3-azabicyclo[3.1.0] hexane-6-carbonyl)piperazine-1-carbonyl)-3-chlorophenyl)-1-methyl-5-(1-(2-methylallyl)-3-(trifluoromethyl)-1H-pyrazol-4-yl)-1H-imidazole-2-carboxamide Hydrochloride A mixture of tert-butyl (1R,5S,6r)-6-(4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carbonyl)-3-azabicyclo[3.1.0]hexane-3-carboxylate (0.021 g, 28.2 µmol, Eq: 1) and 4M HCl in dioxane (141 µl, 564 µmol, Eq: 20) in Dioxane (0.5 ml) was stirred at room temperature overnight. Diethyl ether was added. The mixture was stirred for 30 min then concentrated. The obtained residue was washed further with diethyl ether, then dried in vacuo to yield the title compound (14 mg, 20.3 µmol, 72.2% yield) as a white solid. MS (ESI, m/z): 645.4

Step 6) tert-butyl (3-(4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carboxamido)cyclobutyl)carbamate N-(3-chloro-4-(piperazine-1-carbonyl)phenyl)-1-methyl-5-(1-(2-methylallyl)-3-(trifluoromethyl)-1H-pyrazol-4-yl)-1H-imidazole-2-carboxamide hydrochloride (25 mg, 43.7 mol, Eq: 1) was dissolved in DCM (625 µl). DIPEA (28.2 mg, 38.1 µl, 218 µmol, Eq: 5) and triphosgene (5.18 mg, 17.5 µmol, Eq: 0.4) were successively added. After 5 min tert-butyl (3-aminocyclobutyl)carbamate (24.4 mg, 131 µmol, Eq: 3) was added. The reaction mixture was stirred at room temperature for 2.5 h. The mixture was quenched with sat. NaHCO$_3$, extracted with DCM. The organics was dried over magnesium sulfate and concentrated. The residue was purified by flash chromatography to yield the title compound (17 mg, 22.3 µmol, 51% yield) as a white solid. MS (ESI, m/z): 748.4

Step 7) N-(3-aminocyclobutyl)-4-(2-chloro-4-(1-methyl-5-(1-(2-methylallyl)-3-(trifluoromethyl)-1H-pyrazol-4-yl)-1H-imidazole-2-carboxamido)benzoyl) piperazine-1-carboxamide Hydrochloride A mixture of tert-butyl (3-(4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carboxamido)cyclobutyl)carbamate (0.016 g, 21.4 µmol, Eq: 1) and 4M HCl in dioxane (107 µl, 428 µmol, Eq: 20) in dioxane was stirred at room temperature overnight. Diethyl ether was added to the mixture. The evolved white solid was washed with diethyl ether twice, then dried in vacuo to yield the title compound (10 mg, 14.6 µmol, 68.3% yield) as a white solid. MS (ESI, m/z): 648.3

Example 180

N-[3-chloro-4-[4-(3-hydroxypiperidine-3-carbonyl) piperazine-1-carbonyl]phenyl]-5-[1-(2-fluoroethyl)-3-(trifluoromethyl)pyrazol-4-yl]-1-methylimidazole-2-carboxamide; Trihydrochloride

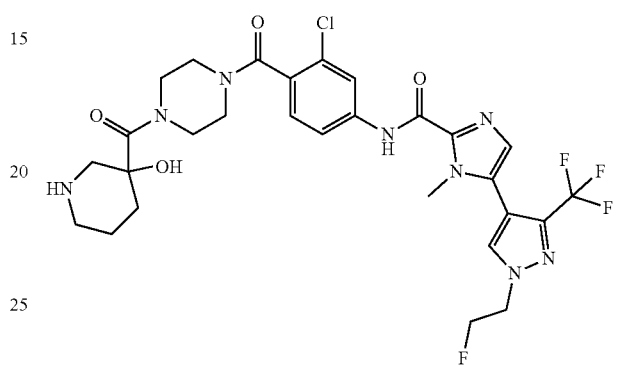

Step 1) tert-butyl 4-[2-chloro-4-[[5-[1-(2-fluoroethyl)-3-(trifluoromethyl)pyrazol-4-yl]-1-methyl-imidazole-2-carbonyl]amino]benzoyl]piperazine-1-carboxylate Under Argon, tert-butyl 4-(2-chloro-4-(1-methyl-5-(3-(trifluoromethyl)-1H-pyrazol-4-yl)-1H-imidazole-2-carboxamido)benzoyl)piperazine-1-carboxylate (Example 167 Step 1) (0.6 g, 1.03 mmol, Eq: 1) was dissolved in DMF (6 ml). Sodium bicarbonate (433 mg, 5.15 mmol, Eq: 5) and 1-bromo-2-fluoroethane (262 mg, 154 µl, 2.06 mmol, Eq: 2) were added and the dark brown reaction mixture was stirred in the microwave at 120° C. for 2 h. The reaction mixture was filtered and the filtrate was washed with NaHCO$_3$ sat. solution 3 times. The organic layers were combined and evaporated. The crude material was purified by flash chromatography to yield the title compound (200 mg, 31%) as a off white solid. MS (ESI, m/z): 628.4

Step 2) N-[3-chloro-4-(piperazine-1-carbonyl)phenyl]-5-[1-(2-fluoroethyl)-3-(trifluoromethyl)pyrazol-4-yl]-1-methyl-imidazole-2-carboxamide; Hydrochloride tert-butyl 4-(2-chloro-4-(5-(1-(2-fluoroethyl)-3-(trifluoromethyl)-1H-pyrazol-4-yl)-1-methyl-1H-imidazole-2-carboxamido)benzoyl)piperazine-1-carboxylate (200.4 mg, 319 µmol, Eq: 1) was stirred with 4M HCl in dioxane (1.6 ml, 6.38 mmol, Eq: 20) in dioxane (2 ml) at room temperature for 5 h. Diethyl ether (3 mL) was added and the reaction mixture was stirred for 30 min at room temperature. The resulting suspension was filtered off and the solid was evaporated to dryness to yield the title compound (142 mg) as off-white crystals. MS (ESI, m/z): 528.3

Step 3) tert-butyl 3-[4-[2-chloro-4-[[5-[1-(2-fluoro-ethyl)-3-(trifluoromethyl)pyrazol-4-yl]-1-methyl-imidazole-2-carbonyl]amino]benzoyl]piperazine-1-carbonyl]-3-hydroxy-piperidine-1-carboxylate N-(3-chloro-4-(piperazine-1-carbonyl)phenyl)-5-(1-(2-fluoroethyl)-3-(trifluoromethyl)-1H-pyrazol-4-yl)-1-methyl-1H-imidazole-2-carboxamide hydrochloride (24 mg, Eq: 1), 1-(tert-butoxycarbonyl)-3-hydroxypiperidine-3-carboxylic acid (28 mg, 57 µmol, Eq: 1.35) and HATU (17.3 mg, 45.6 µmol, Eq: 1.25 eq) were combined with DMF to give a yellow solution. DIEA (7.37 mg, 9.96 µl, 57 µmol, Eq: 1.5) was added. The reaction mixture was stirred overnight at room temperature. The reaction mixture was purified by prep HPLC to yield the title compound (15 mg) as a white solid.

Step 4) N-[3-chloro-4-[4-(3-hydroxypiperidine-3-carbonyl)piperazine-1-carbonyl]phenyl]-5-[1-(2-fluoroethyl)-3-(trifluoromethyl)pyrazol-4-yl]-1-methylimidazole-2-carboxamide; Hydrochloride tert-butyl 3-(4-(2-chloro-4-(5-(1-(2-fluoroethyl)-3-(trifluoromethyl)-1H-pyrazol-4-yl)-1-methyl-1H-imidazole-2-carboxamido)benzoyl)piperazine-1-carbonyl)-3-hydroxypiperidine-1-carboxylate (15 mg, 20.1 µmol, Eq: 1) was stirred with 4M HCl in dioxane (100 µl, 401 µmol, Eq: 20) in dioxane (0.5 ml) at room temperature overnight. Diethyl ether (2 mL) was added and the reaction mixture was stirred for 30 min at RT. The resulting suspension was filtered off and the obtained solid was dried to yield the title compound (12 mg, 53%) as a white waxy solid.

MS (ESI, m/z): 655.3

Intermediates A and B methyl (R)-2-chloro-4-(5-(1-(2,2-difluorocyclopropyl)-3-(trifluoromethyl)-1H-pyrazol-4-yl)-1-methyl-1H-imidazole-2-carboxamido)benzoate (A)

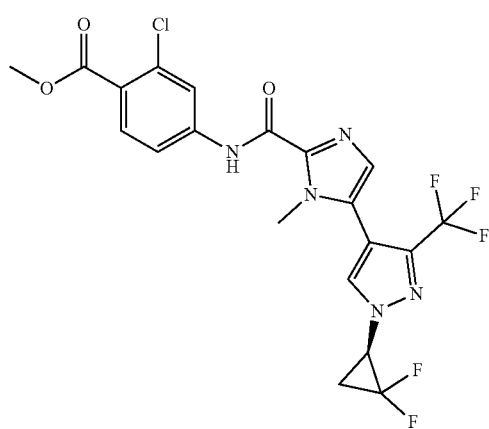 [SMILES: COC(=O)c1ccc(NC(=O)c2ncc(-c3cn([C@@H]4CC4(F)F)nc3C(F)(F)F)n2C)cc1Cl]

methyl (S)-2-chloro-4-(5-(1-(2,2-difluorocyclopropyl)-3-(trifluoromethyl)-1H-pyrazol-4-yl)-1-methyl-1H-imidazole-2-carboxamido)benzoate (B)

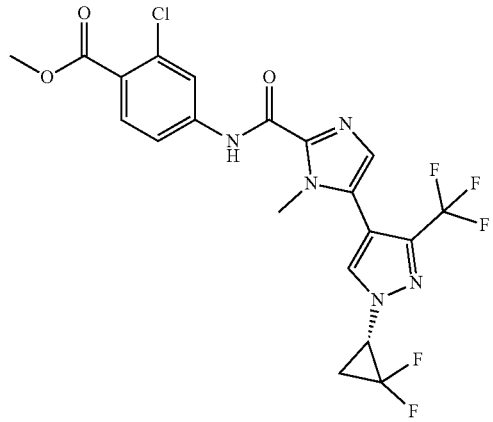 [SMILES: COC(=O)c1ccc(NC(=O)c2ncc(-c3cn([C@H]4CC4(F)F)nc3C(F)(F)F)n2C)cc1Cl]

Step 1) methyl 2-chloro-4-[[5-[1-(2,2-difluorocyclopropyl)-3-(trifluoromethyl)pyrazol-4-yl]-1-methyl-imidazole-2-carbonyl]amino]benzoate To a solution of methyl 2-chloro-4-(1-methyl-5-(3-(trifluoromethyl)-1H-pyrazol-4-yl)-1H-imidazole-2-carboxamido)benzoate (1.5 g, 3.51 mmol, Eq: 1) in DMF (10 ml) were added potassium carbonate (727 mg, 5.26 mmol, Eq: 1.5) and 2-bromo-1,1-difluorocyclopropane (771 mg, 431 µl, 4.91 mmol, Eq: 1.4). The mixture was stirred at 75° C. overnight. The reaction mixture was cooled to room temperature, diluted with ethyl acetate and washed 3 times with 5% LiCl. The organic phase was dried with MgSO$_4$, filtered and concentrated under vacuo. →1.5115 g light brown solid. The residue was purified by flash chromatography to yield the title compound (1.0335 g, 2.01 mmol, 57.3% yield) as a white solid. MS (ESI, m/z): 504.3

Step 2) methyl (R)-2-chloro-4-(5-(1-(2,2-difluorocyclopropyl)-3-(trifluoromethyl)-1H-pyrazol-4-yl)-1-methyl-1H-imidazole-2-carboxamido)benzoate (A) and methyl (S)-2-chloro-4-(5-(1-(2,2-difluorocyclopropyl)-3-(trifluoromethyl)-1H-pyrazol-4-yl)-1-methyl-1H-imidazole-2-carboxamido)benzoate (B)

methyl 2-chloro-4-[[5-[1-(2,2-difluorocyclopropyl)-3-(trifluoromethyl)pyrazol-4-yl]-1-methyl-imidazole-2-carbonyl]amino]benzoate was separated by chiral SFC to yield enantiomers A MS (ESI, m/z): 504.1 and B MS (ESI, m/z): 504.1.

Example 181

(1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide; Hydrochloride

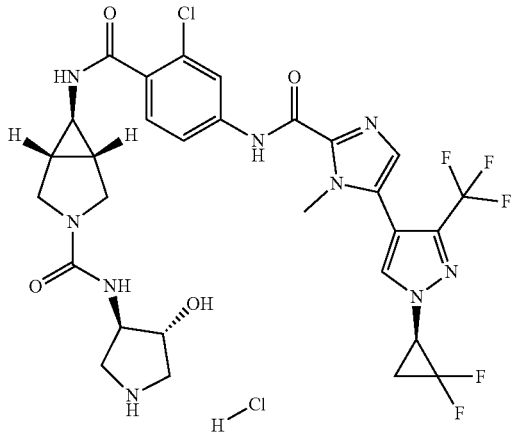 [SMILES: Cn1c(-c2cn([C@@H]3CC3(F)F)nc2C(F)(F)F)cnc1C(=O)Nc1ccc(C(=O)N[C@H]2[C@@H]3CN(C(=O)N[C@@H]4CNC[C@H]4O)C[C@@H]32)c(Cl)c1 ; Cl]

Step 1) 2-chloro-4-[[5-[1-[(1R)-2,2-difluorocyclopropyl]-3-(trifluoromethyl)pyrazol-4-yl]-1-methyl-imidazole-2-carbonyl]amino]benzoic acid Methyl (R)-2-chloro-4-(5-(1-(2,2-difluorocyclopropyl)-3-(trifluoromethyl)-1H-pyrazol-4-yl)-1-methyl-1H-imidazole-2-carboxamido)benzoate (intermediate A) was dissolved in 2-methyl-THF and MeOH. Lithium hydroxide was added. Reaction was stirred at room temperature overnight. The solvents were removed. 1.5 ml water was added. The solution was acidified with 1 M aqueous HCl. The aqueous phase was extracted with ethyl acetate, dried with magnesium sulphate and concentrated. The residue was purified by reverse phase preparative HPLC to yield the title compound (80 mg, 89.8 μmol, 76.7% yield) as a white solid. MS (ESI, m/z): 490.3

Step 2) tert-butyl (1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-3-azabicyclo[3.1.0]hexane-3-carboxylate (R)-2-chloro-4-(5-(1-(2,2-difluorocyclopropyl)-3-(trifluoromethyl)-1H-pyrazol-4-yl)-1-methyl-1H-imidazole-2-carboxamido)benzoic acid (30 mg, 61.3 μmol, Eq: 1), HATU (23.3 mg, 61.3 mol, Eq: 1) and DIEA (23.7 mg, 32.1 μl, 184 μmol, Eq: 3) were dissolved in DMF (613 μl). After ten minutes tert-butyl (1R,5S,6s)-6-amino-3-azabicyclo[3.1.0]hexane-3-carboxylate (14.6 mg, 73.5 μmol, Eq: 1.2) was added. The resulting yellow solution is stirred at room temperature for 2 hours. 10 mL of ethyl acetate were added. The organic solution was washed four times with, dried and concentrated to yield the title compound (33 mg, 80%) as a white solid. It was used as is. MS (ESI, m/z): 670.4

Step 3) N-[4-[[[(1S,5R)-3-azabicyclo[3.1.0]hexan-6-yl]carbamoyl]-3-chloro-phenyl]-5-[1-[(1R)-2,2-difluorocyclopropyl]-3-(trifluoromethyl)pyrazol-4-yl]-1-methyl-imidazole-2-carboxamide tert-butyl (1R,5S,6s)-6-(2-chloro-4-(5-(1-((R)-2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carboxylate (33 mg, 49.3 μmol, Eq: 1) was dissolved in Dioxane (246 μL), then 4M hydrochloric acid in dioxane (246 μl, 985 μmol, Eq: 20) was added. The reaction was stirred at room temperature for 30 min. 1 mL of diethyl ether was added. The mixture was then concentrated to yield the title compound as a orange waxy solid (37 mg, 80% purity, quantitative). It was used as is. MS (ESI, m/z): 570.3

Step 4) tert-butyl (3R,4R)-3-[[(1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-3-azabicyclo[3.1.0]hexane-3-carbonyl]amino]-4-hydroxy-pyrrolidine-1-carboxylate A solution of CDI (5.14 mg, 31.7 μmol, Eq: 1.3) and tert-butyl (3R,4R)-3-amino-4-hydroxypyrrolidine-1-carboxylate (6.42 mg, 31.7 μmol, Eq: 1.3) in DMF (0.5 ml was stirred for 80 min. N-(4-(((1R,5S,6s)-3-azabicyclo[3.1.0]hexan-6-yl)carbamoyl)-3-chlorophenyl)-5-(1-((R)-2,2-difluorocyclopropyl)-3-(trifluoromethyl)-1H-pyrazol-4-yl)-1-methyl-1H-imidazole-2-carboxamide hydrochloride (18.5 mg, 24.4 μmol, Eq: 1) in 250 ul DMF was added to the reaction. The resulting mixture was stirred overnight. 5 mL ethyl acetate were added. The organic phase was washed four times with water, dried with magnesium sulfate and concentrated to yield the crude title compound as a white solid (13 mg). It was used as is. MS (ESI, m/z): 798.6

Step 5) (1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide; Hydrochloride tert-butyl (3R,4R)-3-((1R,5S,6S)-6-(2-chloro-4-(5-(1-((R)-2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carboxamido)-4-hydroxypyrrolidine-1-carboxylate (13 mg, 14.5 μmol, Eq: 1) was dissolved in Dioxane (72.5 μl), then 4M HCl in dioxane (72.5 μl, 290 μmol, Eq: 20) was added. After 60 min, 0.5 mL diethyl ether was added. The suspension was evaporated. The obtained residue was purified by reverse phase preparative HPLC to yield the title compound as a white solid (4 mg, 5.34 μmol, 36.8% yield). MS (ESI, m/z): 698.5

Example 3

(1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide

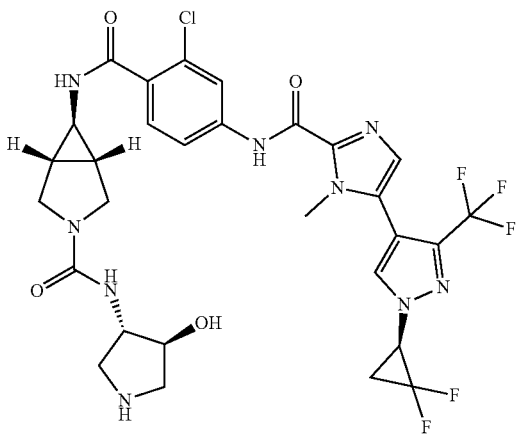 [SMILES: Cn1c(-c2cn([C@@H]3CC3(F)F)nc2C(F)(F)F)cnc1C(=O)Nc1ccc(C(=O)N[C@H]2[C@@H]3CN(C(=O)N[C@H]4CNC[C@@H]4O)C[C@@H]32)c(Cl)c1]

Step 1) tert-butyl (3S,4S)-3-[[(1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-3-azabicyclo[3.1.0]hexane-3-carbonyl]amino]-4-hydroxy-pyrrolidine-1-carboxylate tert-butyl (3S,4S)-3-amino-4-hydroxypyrrolidine-1-carboxylate (6.42 mg, 31.7 µmol, Eq: 1.3) and CDI (5.14 mg, 31.7 µmol, Eq: 1.3) were dissolved in DMF (0.5 ml). The clear solution was stirred at room temperature. After 20 minutes N-(4-(((1R,5S,6s)-3-azabicyclo[3.1.0]hexan-6-yl)carbamoyl)-3-chlorophenyl)-5-(1-((R)-2,2-difluorocyclopropyl)-3-(trifluoromethyl)-1H-pyrazol-4-yl)-1-methyl-1H-imidazole-2-carboxamide hydrochloride (18.5 mg, 24.4 µmol, Eq: 1) (Example 181 step 3) dissolved in 250 ul DMF was added. The mixture was stirred at room temperature for 90 min. 5 mL ethyl acetate were added. The organic phase was washed three times with water, dried with magnesium sulfate and concentrated to yield the crude title product as a white solid (11 mg), that was used as is. MS (ESI, m/z): 798.6

Step 2) (1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide tert-butyl (3S,4S)-3-((1R,5S,6R)-6-(2-chloro-4-(5-(1-((R)-2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carboxamido)-4-hydroxypyrrolidine-1-carboxylate (11 mg, 12.5 mol, Eq: 1) was dissolved in Dioxane (62.7 µl), then 4M HCl in dioxane (62.7 µl, 251 µmol, Eq: 20) was added. After 60 min, 0.5 mL of diethyl ether was added. The mixture was concentrated.

The residue was purified to yield the title compound (7 mg, 9.83 µmol, 78.4% yield) as a white solid. MS (ESI, m/z): 698.5

Example 182

(1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide

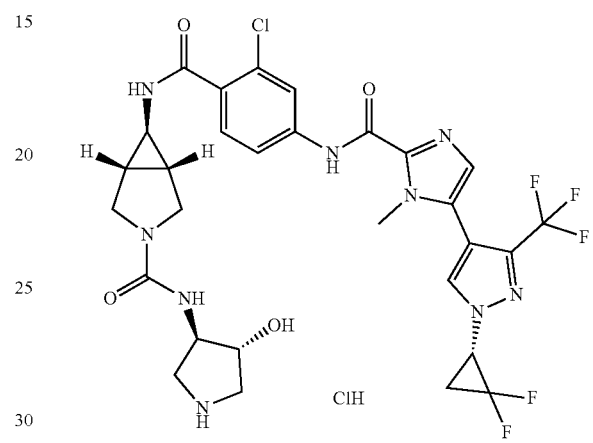

Step 1) 2-chloro-4-[[5-[1-[(1S)-2,2-difluorocyclopropyl]-3-(trifluoromethyl)pyrazol-4-yl]-1-methyl-imidazole-2-carbonyl]amino]benzoic Acid methyl (S)-2-chloro-4-(5-(1-(2,2-difluorocyclopropyl)-3-(trifluoromethyl)-1H-pyrazol-4-yl)-1-methyl-1H-imidazole-2-carboxamido)benzoate (72 mg, 143 µmol, Eq: 1) Intermediate B was dissolved in 2-Methyl-THF and MeOH. 715 uL of 1M lithium hydroxide was added. The solution was stirred overnight at room temperature. Solvents were removed in vacuo. 1.5 mL of water were added. The aqueous solution was acidified with 1M HCL to around pH 2. It was then extracted with ethyl acetate. The organic layer was dried with magnesium sulphate and concentrated to yield the crude title compound (60 mg), that was used as is. MS (ESI, m/z): 490.3

Step 2) tert-butyl (1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-3-azabicyclo[3.1.0]hexane-3-carboxylate (S)-2-chloro-4-(5-(1-(2,2-difluorocyclopropyl)-3-(trifluoromethyl)-1H-pyrazol-4-yl)-1-methyl-1H-imidazole-2-carboxamido)benzoic acid (60 mg, 123 µmol, Eq: 1), HATU (46.6 mg, 123 µmol, Eq: 1) and DIEA (47.5 mg, 64.2 µl, 368 µmol, Eq: 3) were dissolved in DMF (1.23 ml). The solution was stirred for about half an hour, then tert-butyl (1R,5S,6s)-6-amino-3-azabicyclo[3.1.0]hexane-3-carboxylate (29.1 mg, 147 µmol, Eq: 1.2) was added. The resulting yellow solution is stirred overnight. 10 mL of ethyl acetate were added. The organic phase was washed four times with water, was dried with magnesium sulfate and concentrated to yield the crude title compound as a white solid, that was used as is. (79 mg) MS (ESI, m/z): 671.5

Step 3) N-[4-[[(1S,5R)-3-azabicyclo[3.1.0]hexan-6-yl]carbamoyl]-3-chloro-phenyl]-5-[1-[(1S)-2,2-difluorocyclopropyl]-3-(trifluoromethyl)pyrazol-4-yl]-1-methyl-imidazole-2-carboxamide; Hydrochloride tert-butyl (1R,5S,6s)-6-(2-chloro-4-(5-(1-((S)-2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carboxylate (78.6 mg, 103 µmol, Eq: 1) was dissolved in Dioxane (516 µL), then 4M hydrochloric acid in dioxane (516 µL, 2.06 mmol, Eq: 20) was added. The yellow solution was stirred for about 2 hours at room temperature. The product precipitated as an orange solid. The suspension was evaporated to yield the crude title compound, that was used as is. (70 mg)

Step 4) tert-butyl (3R,4R)-3-[[(1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-3-azabicyclo[3.1.0]hexane-3-carbonyl]amino]-4-hydroxy-pyrrolidine-1-carboxylate tert-butyl (3R,4R)-3-amino-4-hydroxypyrrolidine-1-carboxylate (13.5 mg, 66.8 µmol, Eq: 1.3) and CDI (10.8 mg, 66.8 µmol, Eq: 1.3) were dissolved in DMF (1 ml). After 1 h, N-(4-(((1R,5S,6s)-3-azabicyclo[3.1.0]hexan-6-yl)carbamoyl)-3-chlorophenyl)-5-(1-((S)-2,2-difluorocyclopropyl)-3-(trifluoromethyl)-1H-pyrazol-4-yl)-1-methyl-1H-imidazole-2-carboxamide hydrochloride (35 mg, 51.4 µmol, Eq: 1), dissolved in 250 ul DMF, was added. The resulting reaction mixture was stirred at room temperature overnight. 10 mL of ethyl acetate were added. The organic phase was washed three times with water (added a bit brine for better separation), dried with magnesium sulfate and concentrated. The residue was purified by flash chromatography to yield the title compound as an off-white solid (5 mg). MS (ESI, m/z): 798.5

Step 5) (1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide tert-butyl (3R,4R)-3-((1R,5S,6S)-6-(2-chloro-4-(5-(1-((S)-2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carboxamido)-4-hydroxypyrrolidine-1-carboxylate (5 mg, 5.7 µmol, Eq: 1) was dissolved in 1,4-Dioxane (100 µl). 4M hydrogen chloride in dioxane (28.5 µl, 114 µmol, Eq: 20) was added. After 60 min, diethyl ether was added (0.5 mL). The precipitate was dried in vacuo to yield the title compound (2 mg, 2.59 µmol, 45.4% yield) as a white solid. MS (ESI, m/z): 698.5

Example 183

(1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide; Hydrochloride

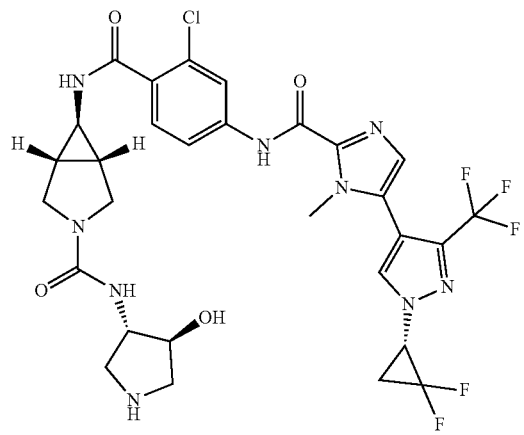 [SMILES: Cn1c(-c2cn([C@H]3CC3(F)F)nc2C(F)(F)F)cnc1C(=O)Nc1ccc(C(=O)N[C@H]2[C@@H]3CN(C(=O)N[C@H]4CNC[C@@H]4O)C[C@@H]32)c(Cl)c1]

Step 1) tert-butyl (3S,4S)-3-[[(1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-3-azabicyclo[3.1.0]hexane-3-carbonyl]amino]-4-hydroxy-pyrrolidine-1-carboxylate tert-butyl (3S,4S)-3-amino-4-hydroxypyrrolidine-1-carboxylate (13.5 mg, 66.8 µmol, Eq: 1.3) and CDI (10.8 mg, 66.8 µmol, Eq: 1.3) were dissolved in DMF (1 ml). The mixture was stirred for 25 min, then N-(4-(((1R,5S,6s)-3-azabicyclo[3.1.0]hexan-6-yl)carbamoyl)-3-chlorophenyl)-5-(1-((S)-2,2-difluorocyclopropyl)-3-(trifluoromethyl)-1H-pyrazol-4-yl)-1-methyl-1H-imidazole-2-carboxamide hydrochloride (35 mg, 51.4 µmol, Eq: 1) (Example 182 step 3), dissolved in 250 ul DMF, was added. The reaction mixture was stirred at room temperature overnight. 10 mL of ethyl acetate were added. The organic phase was washed three times with water (added a bit brine for better separation), dried with magnesium sulfate and concentrated. The residue was purified by to yield the title compound as a white solid (24 mg, 53%). MS (ESI, m/z): 798.5

Step 2) (1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide; Hydrochloride tert-butyl (3S,4S)-3-((1R,5S,6R)-6-(2-chloro-4-(5-(1-((S)-2,2-difluorocyclopropyl)-3-(trifluoromethyl)-1H-pyrazol-4-yl)-1-methyl-1H-imidazole-2-carboxamido)benzamido)-3-azabicyclo[3.1.0]hexane-3-carboxamido)-4-hydroxypyrrolidine-1-carboxylate (24 mg, 27.4 mol, Eq: 1) was dissolved in 1,4-Dioxane (137 µL). 4M hydrogen chloride in dioxane (137 µL, 547 µmol, Eq: 20) was added. After 90 min, diethyl ether was added (0.5 mL The solvents were evaporated to yield the title compound (18 mg, 24.3 µmol, 88.7% yield) as a white solid. MS (ESI, m/z): 698.5

The following additional Examples have been prepared with the methods described above:

| Example | Name | Structure | ESI MS [M + H]+ |
|---|---|---|---|
| 184 | N-(3-chloro-4-(((1R,5S,6s)-3-(piperazine-1-carbonyl)-3-azabicyclo[3.1.0]hexan-6-yl)carbamoyl)phenyl)-5-(1-(2,2-difluorocyclopropyl)-3-(trifluoromethyl)-1H-pyrazol-4-yl)-1-methyl-1H-imidazole-2-carboxamide | 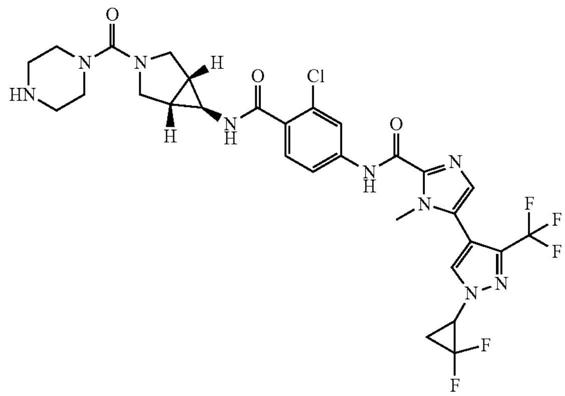 [SMILES: Cn1c(-c2cn(C3CC3(F)F)nc2C(F)(F)F)cnc1C(=O)Nc1ccc(C(=O)N[C@H]2[C@@H]3CN(C(=O)N4CCNCC4)C[C@@H]32)c(Cl)c1] | 682.5 |
| 185 | N-(4-((5-aminopentyl)carbamoyl)-3-chlorophenyl)-5-(1-(2-fluoroallyl)-3-(trifluoromethyl)-1H-pyrazol-4-yl)-1-methyl-1H-imidazole-2-carboxamide hydrochloride | 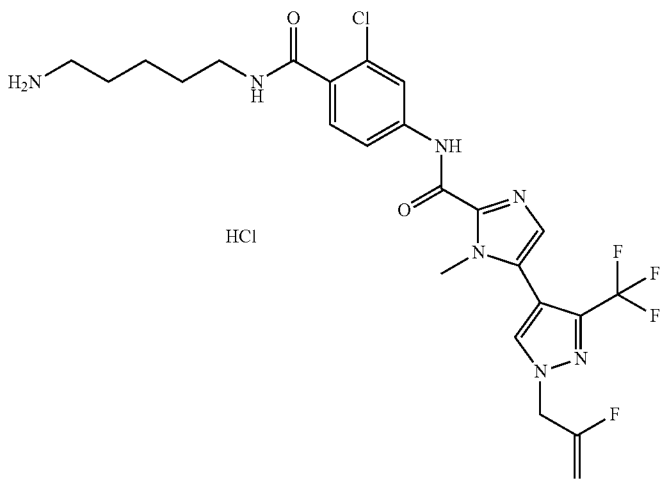 [SMILES: C=C(F)Cn1cc(-c2cnc(C(=O)Nc3ccc(C(=O)NCCCCCN)c(Cl)c3)n2C)c(C(F)(F)F)n1 ; Cl] | 556.2 |
| 186 | cis-N-[(1R,2S)-2-aminocyclopentyl]-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-3-azabicyclo[3.1.0]hexane-3-carboxamide, formate salt | AND Enantiomer | 696.3 |

| Example | Name | Structure | ESI MS [M + H]+ |
|---|---|---|---|
| 187 | N-(4-((6-aminohexyl)carbamoyl)-3-chlorophenyl)-5-(1-cyclopropyl-3-(trifluoromethyl)-1H-pyrazol-4-yl)-1-methyl-1H-imidazole-2-carboxamide hydrochloride | 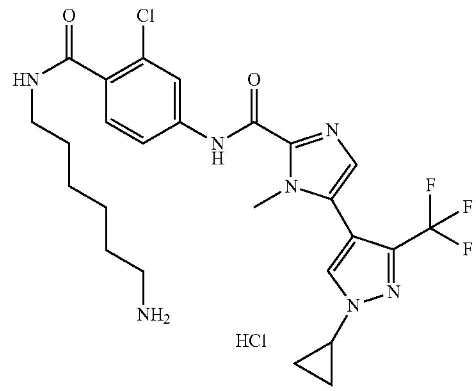 [SMILES: Cn1c(-c2cn(C3CC3)nc2C(F)(F)F)cnc1C(=O)Nc1ccc(C(=O)NCCCCCCN)c(Cl)c1 ; Cl] | 552.2 |
| 188 | N-(3-chloro-4-(piperazin-1-ylsulfonyl)phenyl)-5-(1-(2,2-difluoroethyl)-3-(trifluoromethyl)-1H-pyrazol-4-yl)-1-methyl-1H-imidazole-2-carboxamide hydrochloride | 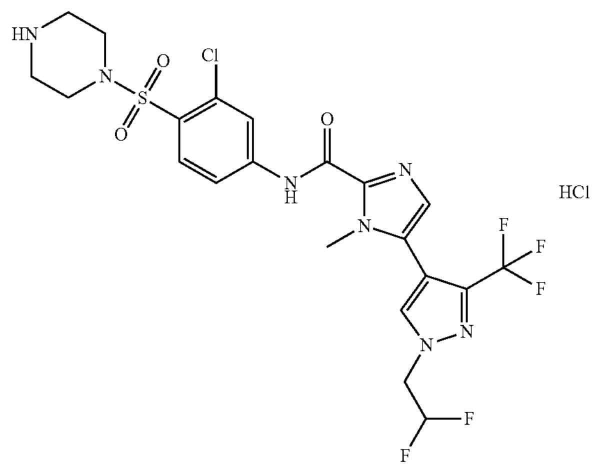 [SMILES: Cn1c(-c2cn(CC(F)F)nc2C(F)(F)F)cnc1C(=O)Nc1ccc(S(=O)(=O)N2CCNCC2)c(Cl)c1 ; Cl] | 582.2 |
| 189 | 6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3S)-pyrrolidin-3-yl]-3-azabicyclo[3.1.0]hexane-3-carboxamide,6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-N-[rac-(3R)-pyrrolidin-3-yl]-3-azabicyclo[3.1.0]hexane-3-carboxamide;formic acid | AND Enantiomer | 682.3 |

-continued

| Example | Name | Structure | ESI MS [M + H]+ |
|---|---|---|---|
| 190 | N-(4-((4-aminobutyl)(methyl)carbamoyl)-3-chlorophenyl)-5-(1-cyclopropyl-3-(trifluoromethyl)-1H-pyrazol-4-yl)-1-methyl-1H-imidazole-2-carboxamide hydrochloride | 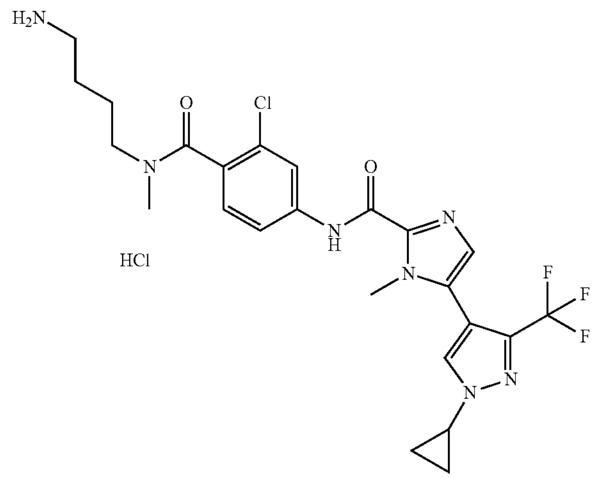 [SMILES: CN(CCCCN)C(=O)c1ccc(NC(=O)c2ncc(-c3cn(C4CC4)nc3C(F)(F)F)n2C)cc1Cl ; Cl] | 538.2 |
| 191 | N-(4-(4-(2-aminoethyl)piperidine-1-carbonyl)-3-chlorophenyl)-5-(1-cyclopropyl-3-(trifluoromethyl)-1H-pyrazol-4-yl)-1-methyl-1H-imidazole-2-carboxamide formate | 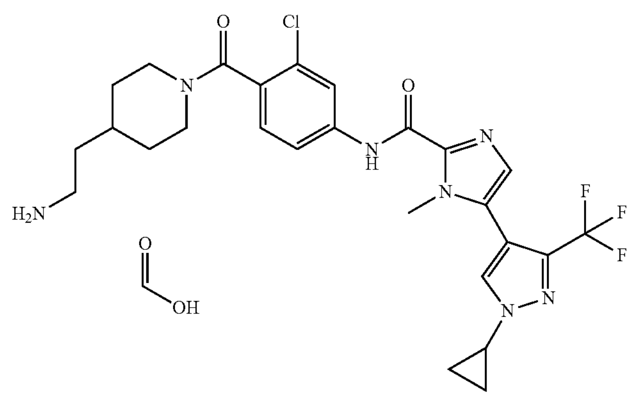 [SMILES: Cn1c(-c2cn(C3CC3)nc2C(F)(F)F)cnc1C(=O)Nc1ccc(C(=O)N2CCC(CCN)CC2)c(Cl)c1 ; O=CO] | 564.4 |
| 192 | N-[4-[[cis-3-[(3R)-3-aminopyrrolidine-1-carbonyl]-3-azabicyclo[3.1.0]hexan-6-yl]carbamoyl]-3-chlorophenyl]-5-[1-(2,2-difluorocyclopropyl)-3-(trifluoromethyl)pyrazol-4-yl]-1-methylimidazole-2-carboxamide, formate salt | AND Enantiomer | 682.3 |

| Example | Name | Structure | ESI MS [M + H]+ |
|---|---|---|---|
| 193 | N-(4-((6-aminospiro[3.3]heptan-2-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 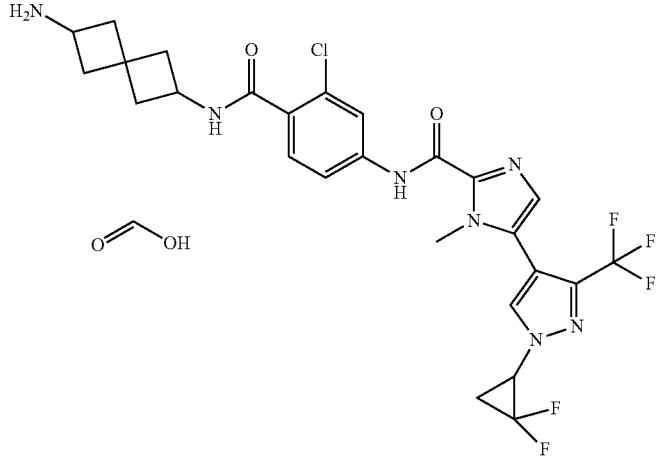 [SMILES: Cn1c(-c2cn(C3CC3(F)F)nc2C(F)(F)F)cnc1C(=O)Nc1ccc(C(=O)NC2CC3(CC(N)C3)C2)c(Cl)c1 ; O=CO] | 598.3 |
| 194 | rac-N-(4-(4-((1R,5S,6r)-3-azabicyclo[3.1.0]hexane-6-carbonyl)piperazine-1-carbonyl)-3-fluorophenyl)-5-(1-(cyclopropylmethyl)-3-(trifluoromethyl)-1H-pyrazol-4-yl)-1-methyl-1H-imidazole-2-carboxamide hydrochloride | 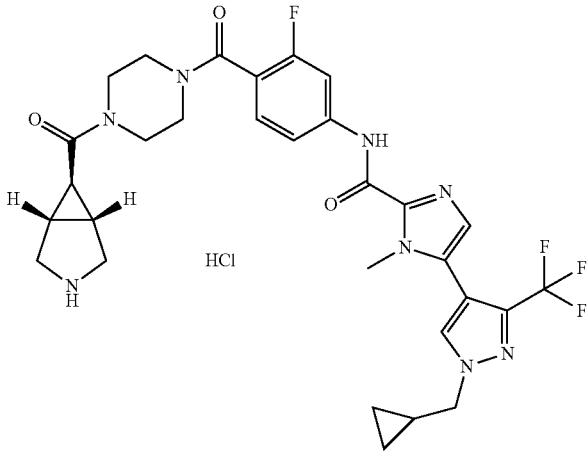 [SMILES: Cn1c(-c2cn(CC3CC3)nc2C(F)(F)F)cnc1C(=O)Nc1ccc(C(=O)N2CCN(C(=O)[C@H]3[C@@H]4CNC[C@@H]43)CC2)c(F)c1 ; Cl] | 629.3 |
| 195 | (R)-N-(4-(3-(aminomethyl)pyrrolidine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 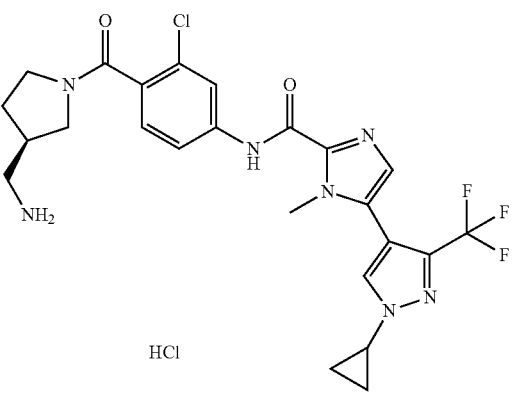 [SMILES: Cn1c(-c2cn(C3CC3)nc2C(F)(F)F)cnc1C(=O)Nc1ccc(C(=O)N2CC[C@H](CN)C2)c(Cl)c1 ; Cl] | 536.3 |

| Example | Name | Structure | ESI MS [M + H]+ |
|---|---|---|---|
| 196 | N-(3-chloro-4-(((octahydrocyclopenta[c]pyrrol-5-yl)methyl)carbamoyl)phenyl)-5-(1-(2,2-difluorocyclopropyl)-3-(trifluoromethyl)-1H-pyrazol-4-yl)-1-methyl-1H-imidazole-2-carboxamide formate | 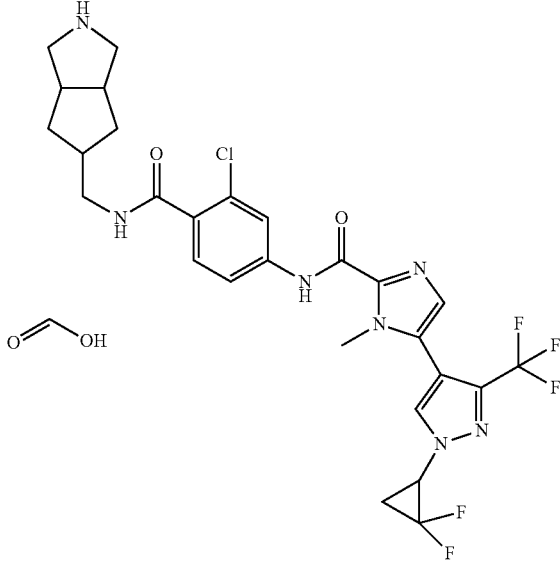 [SMILES: O=CO ; Cn1c(-c2cn(C3CC3(F)F)nc2C(F)(F)F)cnc1C(=O)Nc1ccc(C(=O)NCC2CC3CNCC3C2)c(Cl)c1] | 612.3 |
| 197 | N-(4-(4-(azetidin-3-yl)piperidine-1-carbonyl)-3-chlorophenyl)-5-(1-cyclopropyl-3-(trifluoromethyl)-1H-pyrazol-4-yl)-1-methyl-1H-imidazole-2-carboxamide formate | 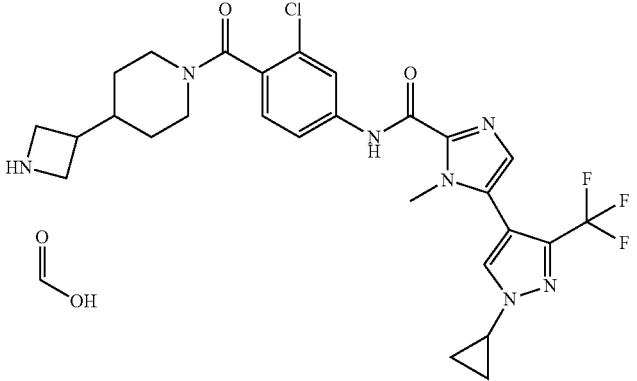 [SMILES: Cn1c(-c2cn(C3CC3)nc2C(F)(F)F)cnc1C(=O)Nc1ccc(C(=O)N2CCC(C3CNC3)CC2)c(Cl)c1 ; O=CO] | 576.2 |
| 198 | N-(3-chloro-4-((4-((2R,4S)-4-hydroxypyrrolidine-2-carbonyl)piperazin-1-yl)sulfonyl)phenyl)-5-(1-(2,2-difluoroethyl)-3-(trifluoromethyl)-1H-pyrazol-4-yl)-1-methyl-1H-imidazole-2-carboxamide hydrochloride | 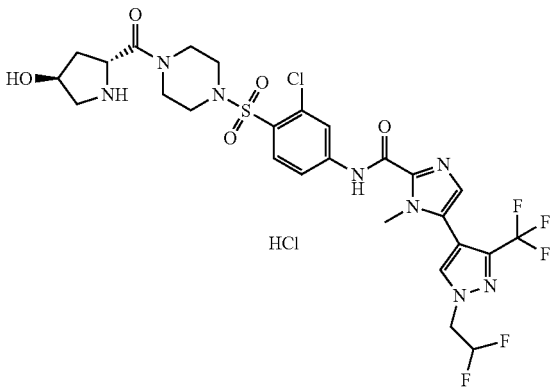 [SMILES: Cn1c(-c2cn(CC(F)F)nc2C(F)(F)F)cnc1C(=O)Nc1ccc(S(=O)(=O)N2CCN(C(=O)[C@H]3C[C@H](O)CN3)CC2)c(Cl)c1 ; Cl] | 693.4 |

-continued

| Example | Name | Structure | ESI MS [M + H]+ |
|---|---|---|---|
| 199 | N-(4-((4-aminobutyl)carbamoyl)-3-chlorophenyl)-1-methyl-5-(1-(2-methylallyl)-3-(trifluoromethyl)-1H-pyrazol-4-yl)-1H-imidazole-2-carboxamide tris(2,2,2-trifluoroacetate) | 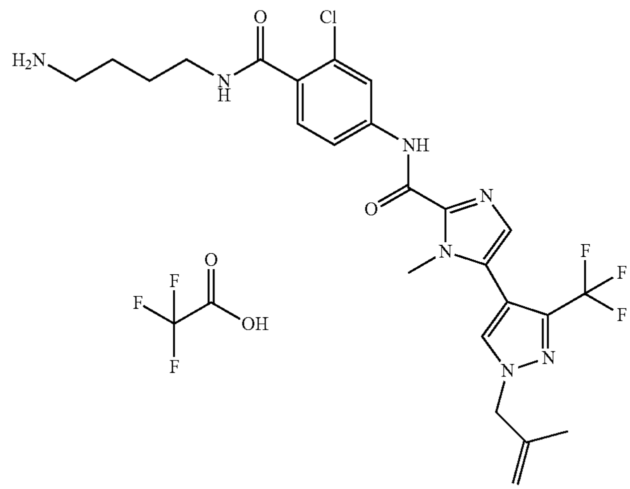 [SMILES: C=C(C)Cn1cc(-c2cnc(C(=O)Nc3ccc(C(=O)NCCCCN)c(Cl)c3)n2C)c(C(F)(F)F)n1 ; O=C(O)C(F)(F)F] | 538.3 |
| 200 | N-(3-chloro-4-(4-glycylpiperazine-1-carbonyl)phenyl)-5-(1-cyclopropyl-3-(trifluoromethyl)-1H-pyrazol-4-yl)-1-methyl-1H-imidazole-2-carboxamide hydrochloride | 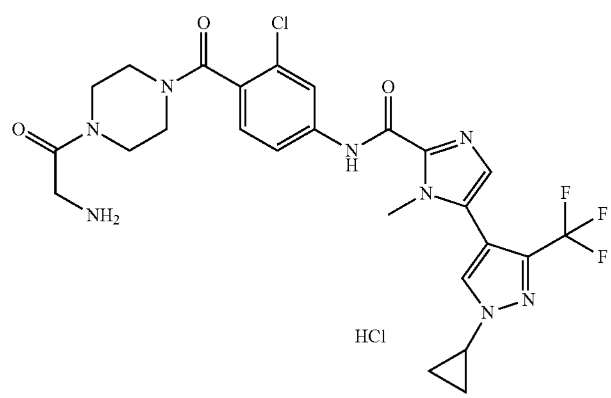 [SMILES: Cn1c(-c2cn(C3CC3)nc2C(F)(F)F)cnc1C(=O)Nc1ccc(C(=O)N2CCN(C(=O)CN)CC2)c(Cl)c1 ; Cl] | 579.3 |
| 201 | N-(4-(4-(aminomethyl)-4-fluoropiperidine-1-carbonyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 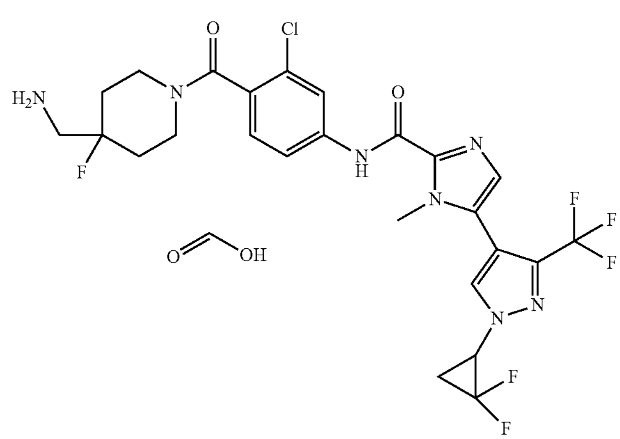 [SMILES: Cn1c(-c2cn(C3CC3(F)F)nc2C(F)(F)F)cnc1C(=O)Nc1ccc(C(=O)N2CCC(F)(CN)CC2)c(Cl)c1 ; O=CO] | 604.3 |

| Example | Name | Structure | ESI MS [M + H]+ |
|---|---|---|---|
| 202 | N-(3-chloro-4-(4-glycylpiperazine-1-carbonyl)phenyl)-5-(1-(cyclobutylmethyl)-3-(trifluoromethyl)-1H-pyrazol-4-yl)-1-methyl-1H-imidazole-2-carboxamide hydrochloride | 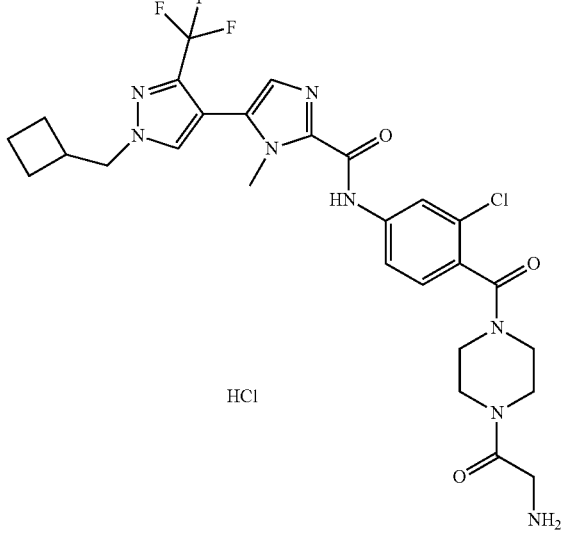 | 607.3 |
| 203 | rac-N-((1s,3s)-3-aminocyclobutyl)-4-(2-chloro-4-(5-(1-(cyclopropylmethyl)-3-(trifluoromethyl)-1H-pyrazol-4-yl)-1-methyl-1H-imidazole-2-carboxamido)benzoyl)piperazine-1-carboxamide | 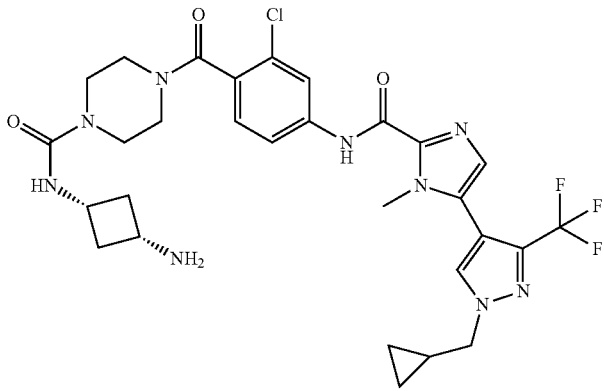 [SMILES: Cn1c(-c2cn(CC3CC3)nc2C(F)(F)F)cnc1C(=O)Nc1ccc(C(=O)N2CCN(C(=O)N[C@H]3C[C@@H](N)C3)CC2)c(Cl)c1] | 648.2 |
| 204 | 5-(1-(2,2-difluorocyclopropyl)-3-(trifluoromethyl)-1H-pyrazol-4-yl)-1-methyl-N-(4-(2-oxopyrrolidin-1-yl)phenyl)-1H-imidazole-2-carboxamide | 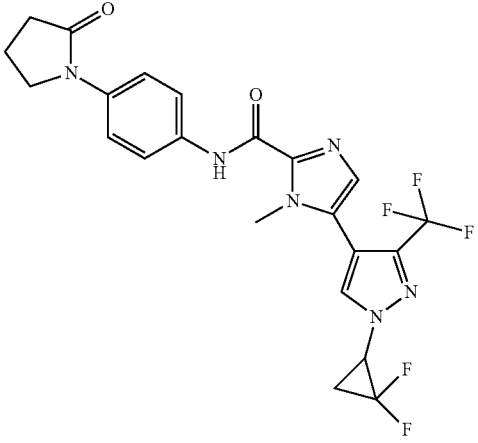 [SMILES: Cn1c(-c2cn(C3CC3(F)F)nc2C(F)(F)F)cnc1C(=O)Nc1ccc(N2CCCC2=O)cc1] | 495.3 |

| Example | Name | Structure | ESI MS [M + H]+ |
|---|---|---|---|
| 205 | N-(4-((5-aminopentyl)carbamoyl)-3-chlorophenyl)-1-methyl-5-(1-(2-methylallyl)-3-(trifluoromethyl)-1H-pyrazol-4-yl)-1H-imidazole-2-carboxamide hydrochloride | 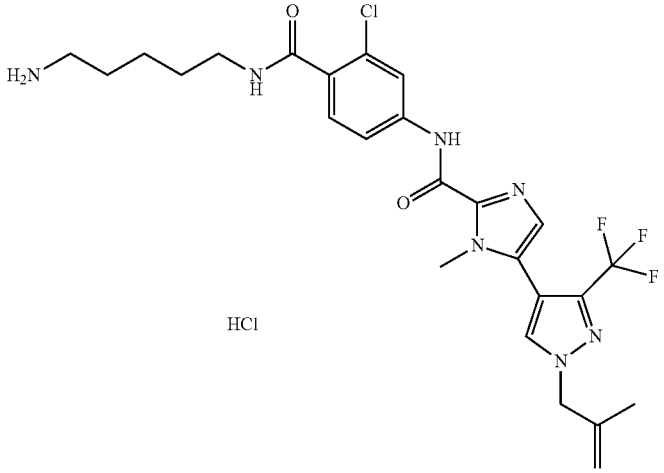 [SMILES: C=C(C)Cn1cc(-c2cnc(C(=O)Nc3ccc(C(=O)NCCCCCN)c(Cl)c3)n2C)c(C(F)(F)F)n1 ; Cl] | 552.2 |
| 206 | N-(4-(4-((1R,3R)-3-aminocyclopentane-1-carbonyl)piperazine-1-carbonyl)-3-chlorophenyl)-5-(1-(cyclopropylmethyl)-3-(trifluoromethyl)-1H-pyrazol-4-yl)-1-methyl-1H-imidazole-2-carboxamide | 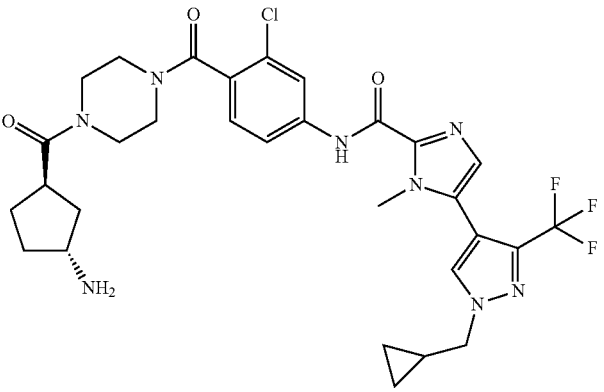 [SMILES: Cn1c(-c2cn(CC3CC3)nc2C(F)(F)F)cnc1C(=O)Nc1ccc(C(=O)N2CCN(C(=O)[C@@H]3CC[C@@H](N)C3)CC2)c(Cl)c1] | 647.2 |
| 207 | N-(4-(4-(aminomethyl)piperidine-1-carbonyl)-3-chlorophenyl)-5-(1-cyclopropyl-3-(trifluoromethyl)-1H-pyrazol-4-yl)-1-methyl-1H-imidazole-2-carboxamide formate | 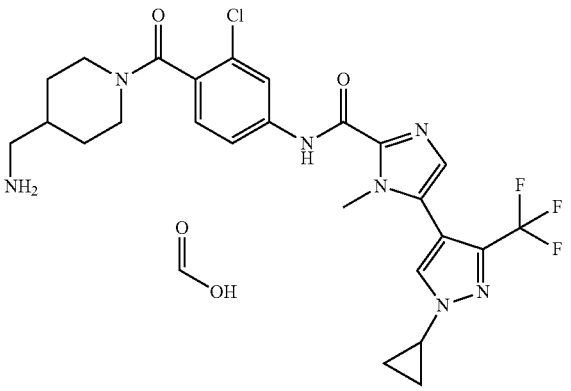 [SMILES: Cn1c(-c2cn(C3CC3)nc2C(F)(F)F)cnc1C(=O)Nc1ccc(C(=O)N2CCC(CN)CC2)c(Cl)c1 ; O=CO] | 550.2 |

| Example | Name | Structure | ESI MS [M + H]+ |
|---|---|---|---|
| 208 | N-(4-(4-(azetidine-3-carbonyl)piperazine-1-carbonyl)-3-chlorophenyl)-5-(1-(cyclopropylmethyl)-3-(trifluoromethyl)-1H-pyrazol-4-yl)-1-methyl-1H-imidazole-2-carboxamide | 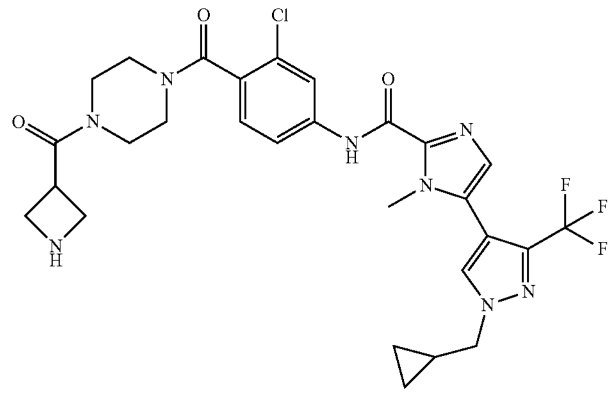 [SMILES: Cn1c(-c2cn(CC3CC3)nc2C(F)(F)F)cnc1C(=O)Nc1ccc(C(=O)N2CCN(C(=O)C3CNC3)CC2)c(Cl)c1] | 619.2 |
| 209 | N-(3-chloro-4-(4-glycylpiperazine-1-carbonyl)phenyl)-5-(1-(cyclopropylmethyl)-3-(trifluoromethyl)-1H-pyrazol-4-yl)-1-methyl-1H-imidazole-2-carboxamide | 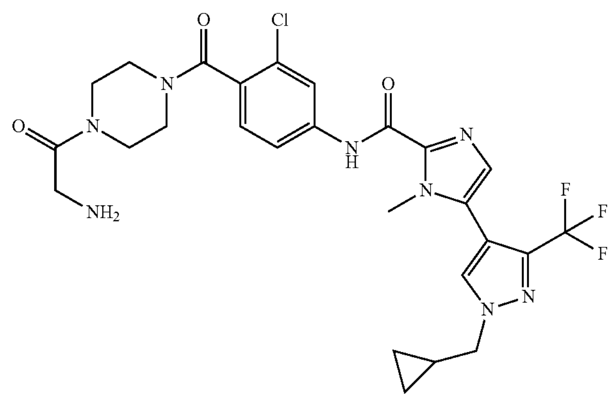 [SMILES: Cn1c(-c2cn(CC3CC3)nc2C(F)(F)F)cnc1C(=O)Nc1ccc(C(=O)N2CCN(C(=O)CN)CC2)c(Cl)c1] | 593.2 |
| 210 | rac-N-((1s,3s)-3-aminocyclobutyl)-4-(2-chloro-4-(1-methyl-5-(1-(spiro[2.3]hexan-5-yl)-3-(trifluoromethyl)-1H-pyrazol-4-yl)-1H-imidazole-2-carboxamido)benzoyl)piperazine-1-carboxamide hydrochloride | 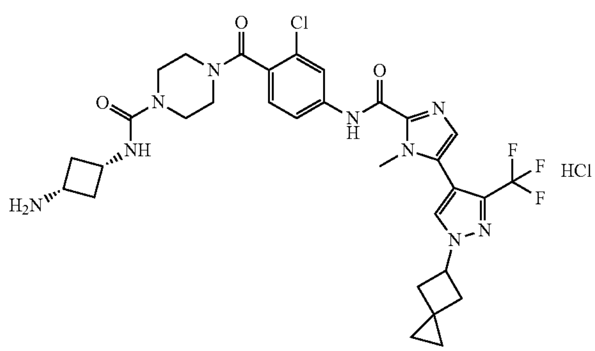 [SMILES: Cn1c(-c2cn(C3CC4(CC4)C3)nc2C(F)(F)F)cnc1C(=O)Nc1ccc(C(=O)N2CCN(C(=O)N[C@H]3C[C@@H](N)C3)CC2)c(Cl)c1 ; Cl] | 675.4 |
| 211 | N-(4-((4-((1S,3R)-3-aminocyclopentane-1-carbonyl)piperazin-1-yl)sulfonyl)-3-chlorophenyl)-5-(1-(2,2-difluoroethyl)-3-(trifluoromethyl)-1H-pyrazol-4-yl)-1-methyl-1H-imidazole-2-carboxamide hydrochloride | 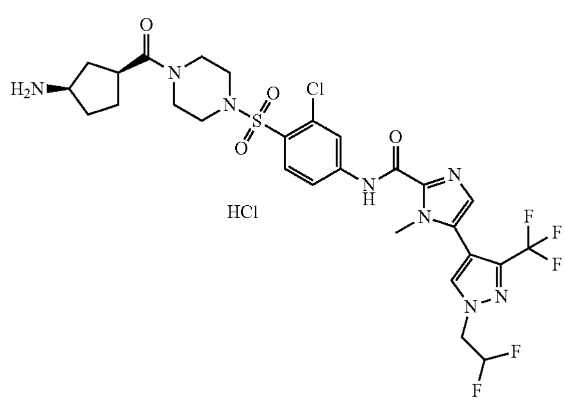 [SMILES: Cn1c(-c2cn(CC(F)F)nc2C(F)(F)F)cnc1C(=O)Nc1ccc(S(=O)(=O)N2CCN(C(=O)[C@H]3CC[C@@H](N)C3)CC2)c(Cl)c1 ; Cl] | 691.4 [M − H]− |

| Example | Name | Structure | ESI MS [M + H]+ |
|---|---|---|---|
| 212 | N-(4-(6-amino-3-azabicyclo[3.1.0]hexane-3-carbonyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 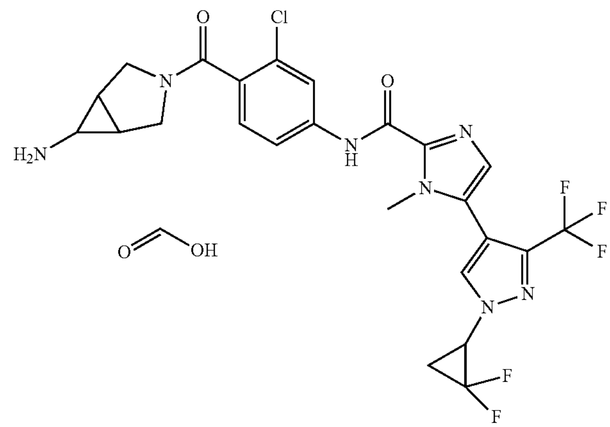 [SMILES: Cn1c(-c2cn(C3CC3(F)F)nc2C(F)(F)F)cnc1C(=O)Nc1ccc(C(=O)N2CC3C(N)C3C2)c(Cl)c1 ; O=CO] | 570.3 |
| 213 | rac-N-(4-(4-((1R,5S,6r)-3-azabicyclo[3.1.0]hexane-6-carbonyl)piperazine-1-carbonyl)-3-fluorophenyl)-5-(1-(2,2-difluoroethyl)-3-(trifluoromethyl)-1H-pyrazol-4-yl)-1-methyl-1H-imidazole-2-carboxamide | 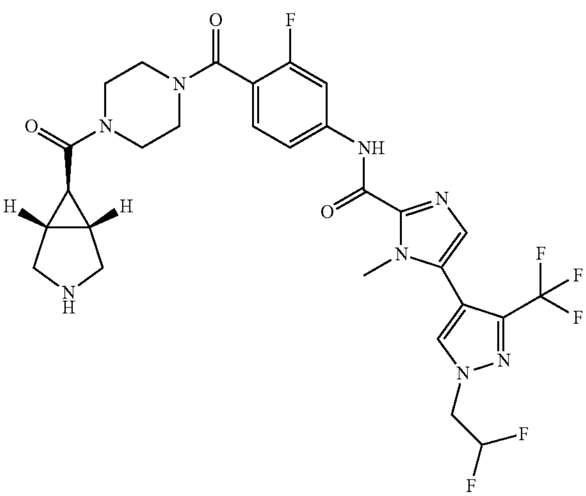 [SMILES: Cn1c(-c2cn(CC(F)F)nc2C(F)(F)F)cnc1C(=O)Nc1ccc(C(=O)N2CCN(C(=O)[C@H]3[C@@H]4CNC[C@@H]43)CC2)c(F)c1] | 639.3 |
| 214 | N-(azetidin-3-ylmethyl)-4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxamide formate | 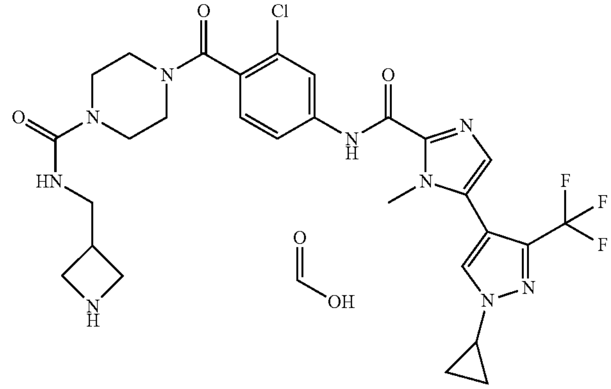 [SMILES: Cn1c(-c2cn(C3CC3)nc2C(F)(F)F)cnc1C(=O)Nc1ccc(C(=O)N2CCN(C(=O)NCC3CNC3)CC2)c(Cl)c1 ; O=CO] | 634.3 |

| Example | Name | Structure | ESI MS [M + H]+ |
|---|---|---|---|
| 215 | 5-(1-allyl-3-(trifluoromethyl)-1H-pyrazol-4-yl)-N-(3-chloro-4-((3-(piperidine-4-carbonyl)-3-azabicyclo[3.1.0]hexan-6-yl)carbamoyl)phenyl)-1-methyl-1H-imidazole-2-carboxamide formate | 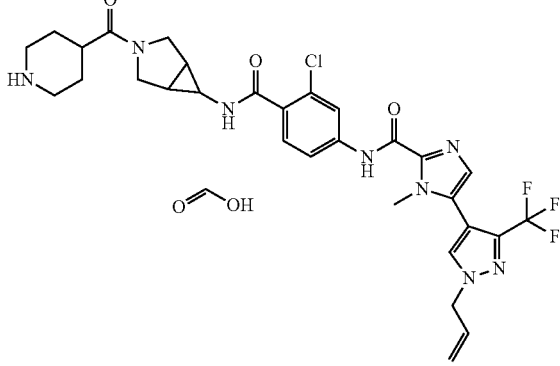 | 645.3 |
| 216 | N-(4-(4-(3-aminoazetidine-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide formate | 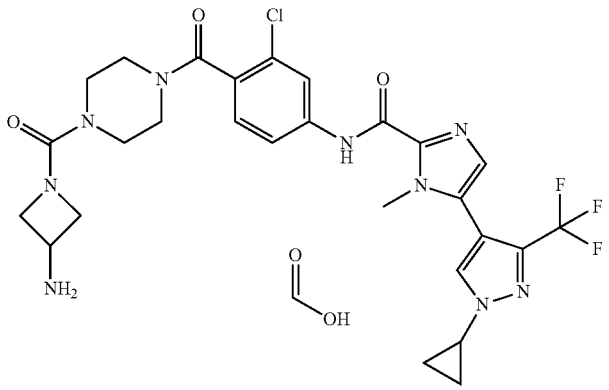 [SMILES: Cn1c(-c2cn(C3CC3)nc2C(F)(F)F)cnc1C(=O)Nc1ccc(C(=O)N2CCN(C(=O)N3CC(N)C3)CC2)c(Cl)c1 ; O=CO] | 620.3 |
| 217 | (S)-N-(4-(3-(aminomethyl)pyrrolidine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 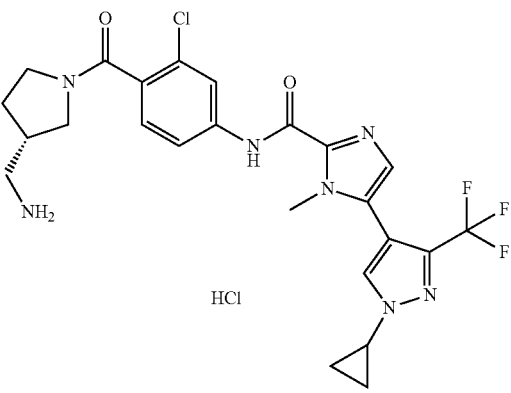 [SMILES: Cn1c(-c2cn(C3CC3)nc2C(F)(F)F)cnc1C(=O)Nc1ccc(C(=O)N2CC[C@@H](CN)C2)c(Cl)c1 ; Cl] | 536.2 |
| 218 | N-((1s,3s)-3-aminocyclobutyl)-4-(4-(5-(1-(cyclopropylmethyl)-3-(trifluoromethyl)-1H-pyrazol-4-yl)-1-methyl-1H-imidazole-2-carboxamido)-2-fluorobenzoyl)piperazine-1-carboxamide; hydrochloride | 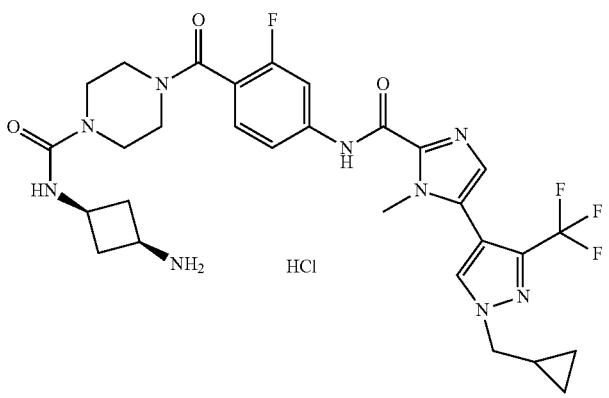 [SMILES: Cn1c(-c2cn(CC3CC3)nc2C(F)(F)F)cnc1C(=O)Nc1ccc(C(=O)N2CCN(C(=O)N[C@H]3C[C@@H](N)C3)CC2)c(F)c1 ; Cl] | 632.3 |

| Example | Name | Structure | ESI MS [M + H]+ |
|---|---|---|---|
| 219 | tert-butyl (5-(4-(5-(1-(2,2-difluoroethyl)-3-(trifluoromethyl)-1H-pyrazol-4-yl)-1-methyl-1H-imidazole-2-carboxamido)-2-ethylbenzamido)pentyl)glycinate | 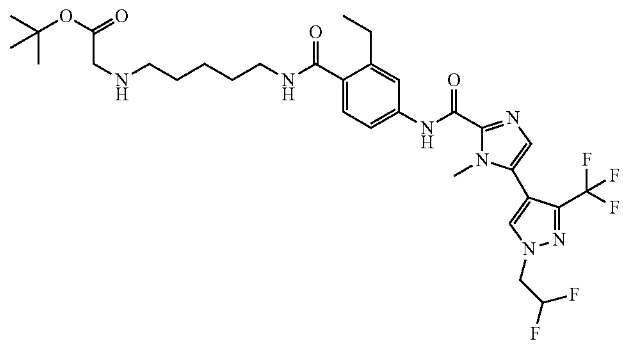 [SMILES: CCc1cc(NC(=O)c2ncc(-c3cn(CC(F)F)nc3C(F)(F)F)n2C)ccc1C(=O)NCCCCCNCC(=O)OC(C)(C)C] | 670.5 |
| 220 | N-(3-chloro-4-((3-(piperidine-4-carbonyl)-3-azabicyclo[3.1.0]hexan-6-yl)carbamoyl)phenyl)-5-(1-((2,2-difluorocyclopropyl)methyl)-3-(trifluoromethyl)-1H-pyrazol-4-yl)-1-methyl-1H-imidazole-2-carboxamide formate | 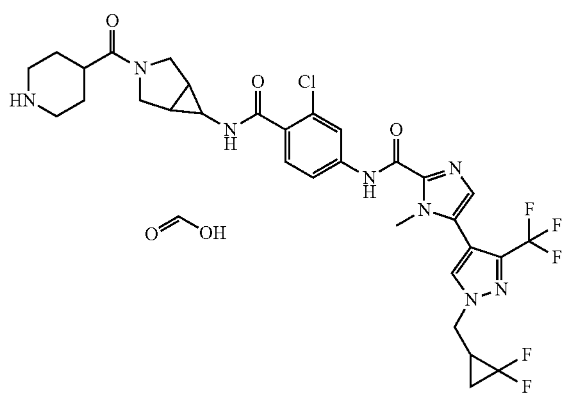 [SMILES: Cn1c(-c2cn(CC3CC3(F)F)nc2C(F)(F)F)cnc1C(=O)Nc1ccc(C(=O)NC2C3CN(C(=O)C4CCNCC4)CC32)c(Cl)c1 ; O=CO] | 695.4 |
| 221 | N-(4-((5-aminopentyl)carbamoyl)-3-chlorophenyl)-5-(1-cyclopropyl-3-(trifluoromethyl)-1H-pyrazol-4-yl)-1-methyl-1H-imidazole-2-carboxamide hydrochloride | 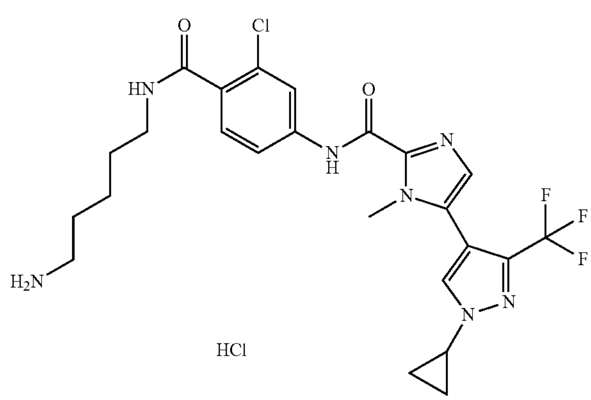 [SMILES: Cn1c(-c2cn(C3CC3)nc2C(F)(F)F)cnc1C(=O)Nc1ccc(C(=O)NCCCCCN)c(Cl)c1 ; Cl] | 538.2 |

| Example | Name | Structure | ESI MS [M + H]+ |
|---|---|---|---|
| 222 | N-[4-[2-(2-amino-2-methyl-propoxy)ethylcarbamoyl]-3-ethyl-phenyl]-1-methyl-5-[1-prop-2-ynyl-3-(trifluoromethyl)pyrazol-4-yl]imidazole-2-carboxamide; formic acid | 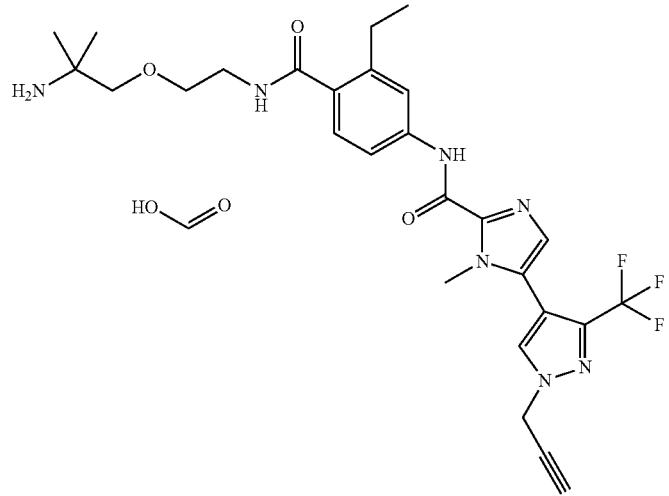 [SMILES: C#CCn1cc(-c2cnc(C(=O)Nc3ccc(C(=O)NCCOCC(C)(C)N)c(CC)c3)n2C)c(C(F)(F)F)n1 ; O=CO] | 560.1 |
| 223 | (R)-N-(3-chloro-4-(4-(piperidine-3-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 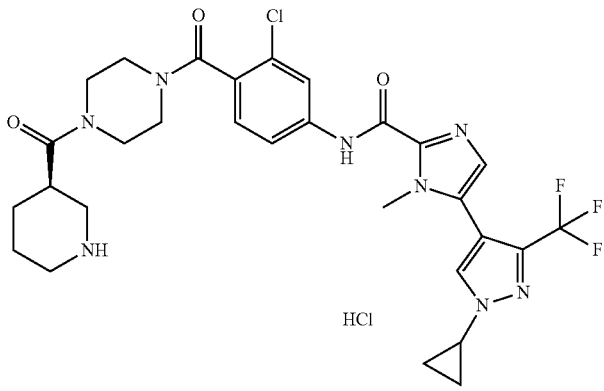 [SMILES: Cn1c(-c2cn(C3CC3)nc2C(F)(F)F)cnc1C(=O)Nc1ccc(C(=O)N2CCN(C(=O)[C@@H]3CCCNC3)CC2)c(Cl)c1 ; Cl] | 633.3 |
| 224 | N-(4-(4-(azetidine-3-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 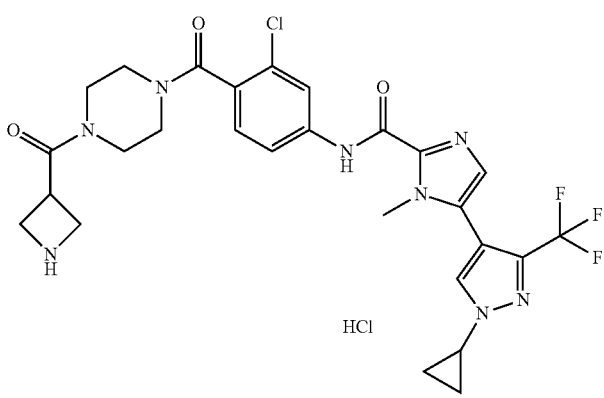 [SMILES: Cn1c(-c2cn(C3CC3)nc2C(F)(F)F)cnc1C(=O)Nc1ccc(C(=O)N2CCN(C(=O)C3CNC3)CC2)c(Cl)c1 ; Cl] | 605.4 |

| Example | Name | Structure | ESI MS [M + H]+ |
|---|---|---|---|
| 225 | N-(3-aminocyclobutyl)-4-[2-chloro-4-[[5-[1-cyclopropyl-3-(trifluoromethyl)pyrazol-4-yl]-1-methylimidazole-2-carbonyl]amino]benzoyl]piperazine-1-carboxamide;formic acid | 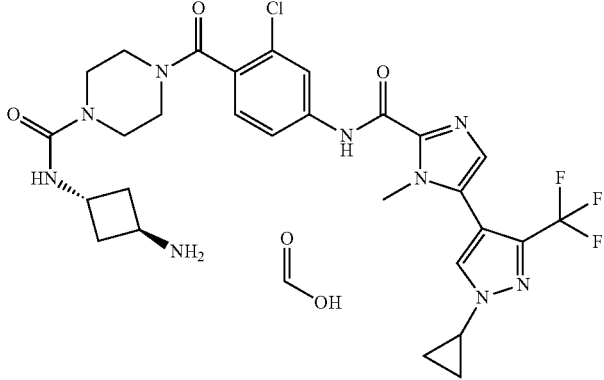 [SMILES: Cn1c(-c2cn(C3CC3)nc2C(F)(F)F)cnc1C(=O)Nc1ccc(C(=O)N2CCN(C(=O)N[C@H]3C[C@H](N)C3)CC2)c(Cl)c1 ; O=CO] | 634.3 |
| 226 | rac-3-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)-N-((3S,4S)-4-hydroxypyrrolidin-3-yl)piperidine-1-carboxamide formate | AND Enantiomer<br>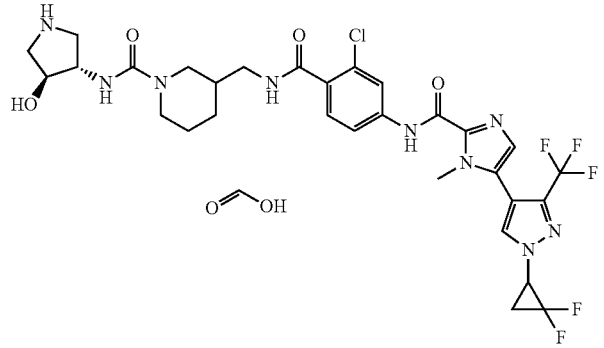 | 714.5 |
| 227 | N-(3-chloro-4-((3-(piperidine-4-carbonyl)-3-azabicyclo[3.1.0]hexan-6-yl)carbamoyl)phenyl)-5-(1-(cyclopropylmethyl)-3-(trifluoromethyl)-1H-pyrazol-4-yl)-1-methyl-1H-imidazole-2-carboxamide formate | 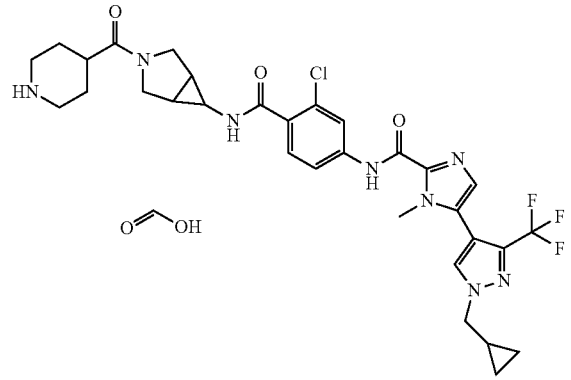 [SMILES: Cn1c(-c2cn(CC3CC3)nc2C(F)(F)F)cnc1C(=O)Nc1ccc(C(=O)NC2C3CN(C(=O)C4CCNCC4)CC32)c(Cl)c1 ; O=CO] | 659.4 |
| 228 | N-(4-(4-(2-aminoethyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide formate | 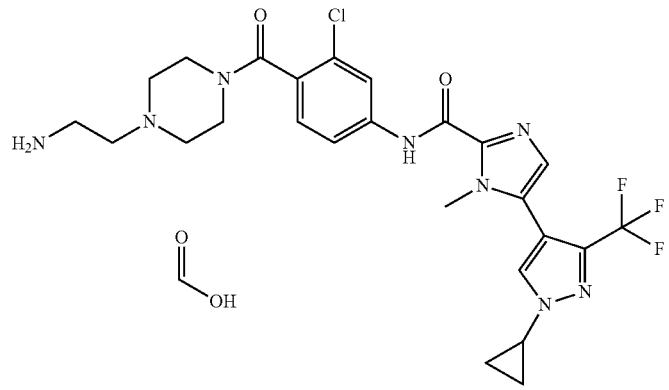 [SMILES: Cn1c(-c2cn(C3CC3)nc2C(F)(F)F)cnc1C(=O)Nc1ccc(C(=O)N2CCN(CCN)CC2)c(Cl)c1 ; O=CO] | 565.2 |

-continued

| Example | Name | Structure | ESI MS [M + H]+ |
|---|---|---|---|
| 229 | (R)-N-(3-chloro-4-(4-(pyrrolidine-3-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 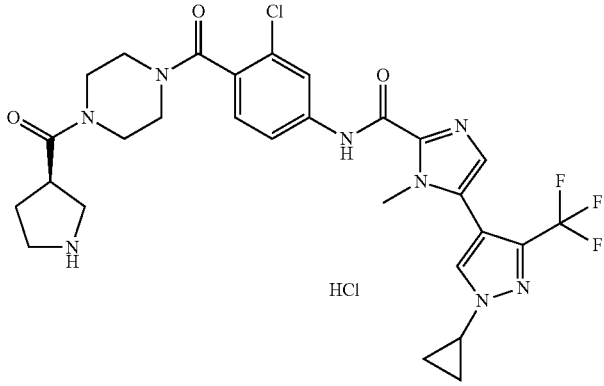 [SMILES: Cn1c(-c2cn(C3CC3)nc2C(F)(F)F)cnc1C(=O)Nc1ccc(C(=O)N2CCN(C(=O)[C@@H]3CCNC3)CC2)c(Cl)c1 ; Cl] | 619.4 |
| 230 | N-(4-(4-((1R,3R)-3-aminocyclopentane-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 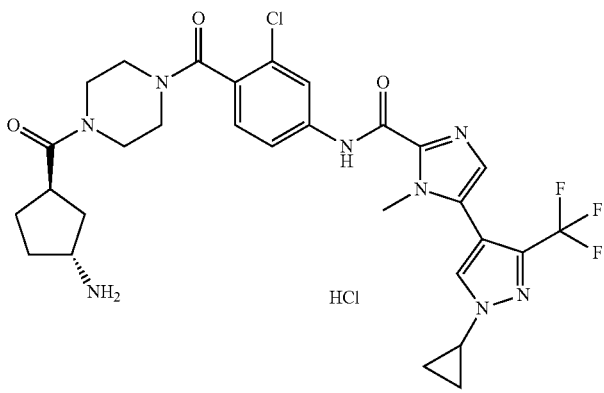 [SMILES: Cn1c(-c2cn(C3CC3)nc2C(F)(F)F)cnc1C(=O)Nc1ccc(C(=O)N2CCN(C(=O)[C@@H]3CC[C@@H](N)C3)CC2)c(Cl)c1 ; Cl] | 633.5 |
| 231 | N-[4-[4-(4-aminocyclohexanecarbonyl)piperazine-1-carbonyl]-3-chlorophenyl]-5-[1-cyclopropyl-3-(trifluoromethyl)pyrazol-4-yl]-1-methylimidazole-2-carboxamide;hydrochloride | 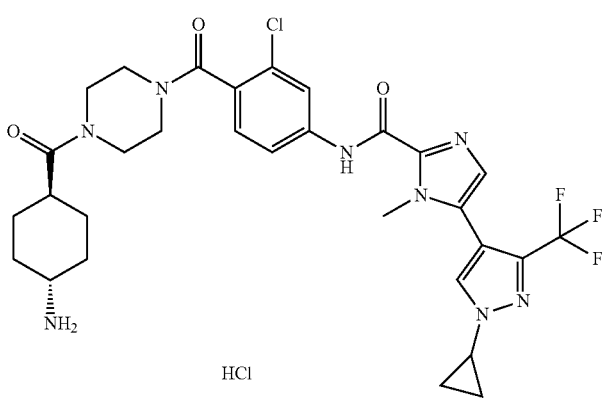 [SMILES: Cn1c(-c2cn(C3CC3)nc2C(F)(F)F)cnc1C(=O)Nc1ccc(C(=O)N2CCN(C(=O)[C@H]3CC[C@H](N)CC3)CC2)c(Cl)c1 ; Cl] | 647.4 |
| 232 | N-((1R,3R)-3-aminocyclopentyl)-4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxamide formate | 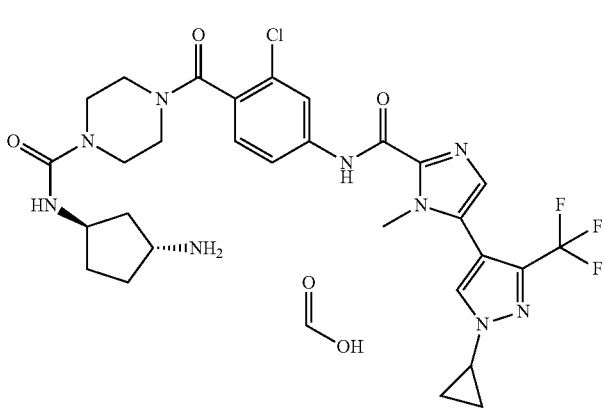 [SMILES: Cn1c(-c2cn(C3CC3)nc2C(F)(F)F)cnc1C(=O)Nc1ccc(C(=O)N2CCN(C(=O)N[C@@H]3CC[C@@H](N)C3)CC2)c(Cl)c1 ; O=CO] | 648.3 |

| Example | Name | Structure | ESI MS [M + H]+ |
|---|---|---|---|
| 233 | N-(azetidin-3-yl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide; formic acid | 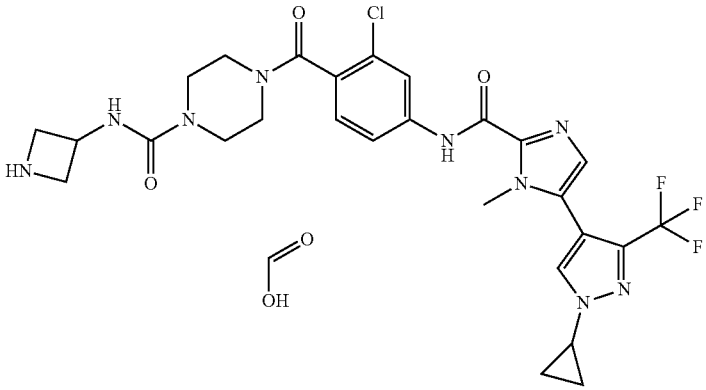 [SMILES: Cn1c(-c2cn(C3CC3)nc2C(F)(F)F)cnc1C(=O)Nc1ccc(C(=O)N2CCN(C(=O)NC3CNC3)CC2)c(Cl)c1 ; O=CO] | 620.1 |
| 234 | rac-N-(4-(((1s,3s)-3-aminocyclobutyl)carbamoyl)-3-chlorophenyl)-1-methyl-5-(1-(2-methylallyl)-3-(trifluoromethyl)-1H-pyrazol-4-yl)-1H-imidazole-2-carboxamide hydrochloride | 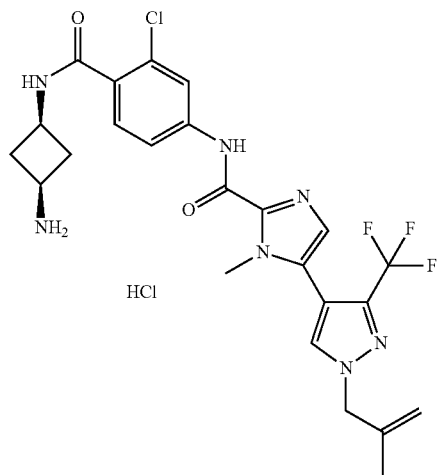 [SMILES: C=C(C)Cn1cc(-c2cnc(C(=O)Nc3ccc(C(=O)N[C@H]4C[C@@H](N)C4)c(Cl)c3)n2C)c(C(F)(F)F)n1 ; Cl] | 536.2 |
| 235 | N-(3-chloro-4-((3-(piperidine-4-carbonyl)-3-azabicyclo[3.1.0]hexan-6-yl)carbamoyl)phenyl)-5-(1-(2,2-difluoroethyl)-3-(trifluoromethyl)-1H-pyrazol-4-yl)-1-methyl-1H-imidazole-2-carboxamide formate | 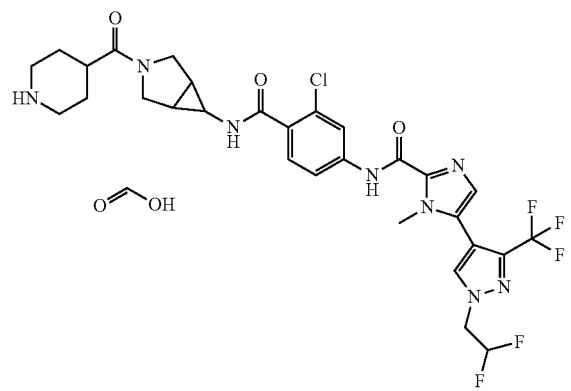 [SMILES: Cn1c(-c2cn(CC(F)F)nc2C(F)(F)F)cnc1C(=O)Nc1ccc(C(=O)NC2C3CN(C(=O)C4CCNCC4)CC32)c(Cl)c1 ; O=CO] | 669.3 |

| Example | Name | Structure | ESI MS [M + H]+ |
|---|---|---|---|
| 236 | 4-[2-chloro-4-[[5-[1-cyclopropyl-3-(trifluoromethyl)pyrazol-4-yl]-1-methylimidazole-2-carbonyl]amino]benzoyl]-N-pyrrolidin-3-ylpiperazine-1-carboxamide;formic acid | 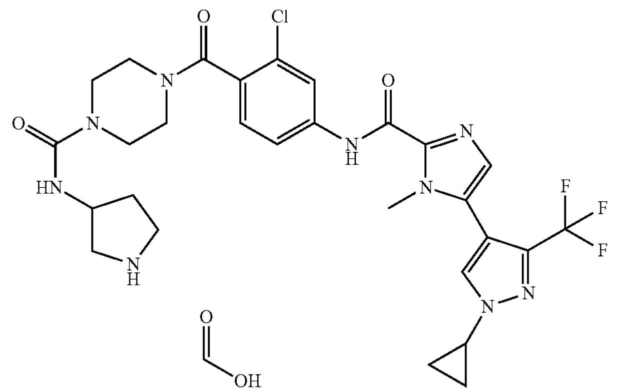 [SMILES: Cn1c(-c2cn(C3CC3)nc2C(F)(F)F)cnc1C(=O)Nc1ccc(C(=O)N2CCN(C(=O)NC3CCNC3)CC2)c(Cl)c1 ; O=CO] | 634.3 |
| 237 | rac-N-((1s,3s)-3-aminocyclobutyl)-4-(2-chloro-4-(5-(1-(2,2-difluorocyclopropyl)-3-(trifluoromethyl)-1H-pyrazol-4-yl)-1-methyl-1H-imidazole-2-carboxamido)benzamido)piperidine-1-carboxamide formate | 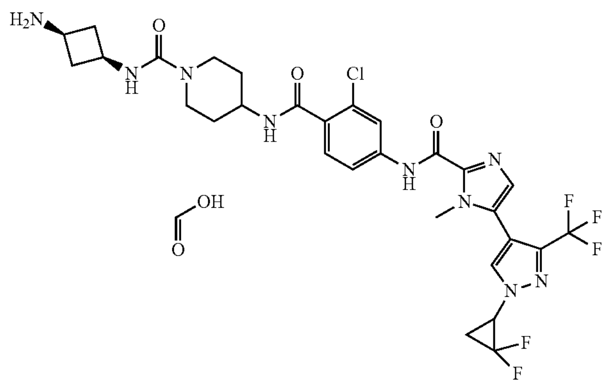 [SMILES: Cn1c(-c2cn(C3CC3(F)F)nc2C(F)(F)F)cnc1C(=O)Nc1ccc(C(=O)NC2CCN(C(=O)N[C@H]3C[C@@H](N)C3)CC2)c(Cl)c1 ; O=CO] | 684.5 |
| 238 | N-(3-amino-3-methylcyclobutyl)-4-[2-chloro-4-[[5-[1-cyclopropyl-3-(trifluoromethyl)pyrazol-4-yl]-1-methylimidazole-2-carbonyl]amino]benzoyl]piperazine-1-carboxamide;formic acid | 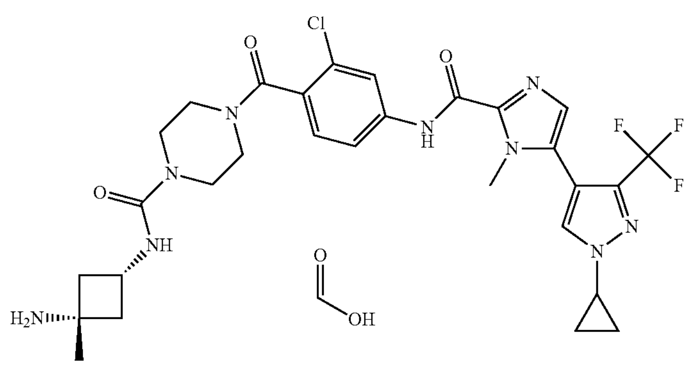 [SMILES: Cn1c(-c2cn(C3CC3)nc2C(F)(F)F)cnc1C(=O)Nc1ccc(C(=O)N2CCN(C(=O)N[C@H]3C[C@@](C)(N)C3)CC2)c(Cl)c1 ; O=CO] | 695.5 |
| 239 | N-(4-(4-(2-aminoethyl)piperidine-1-carbonyl)-3-chlorophenyl)-5-(1-ethyl-3-(trifluoromethyl)-1H-pyrazol-4-yl)-1-methyl-1H-imidazole-2-carboxamide hydrochloride | 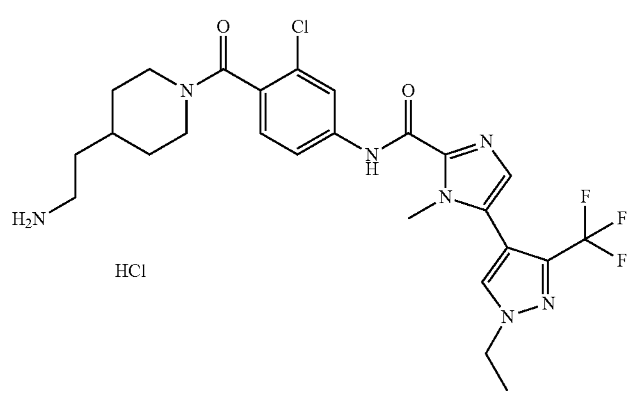 [SMILES: CCn1cc(-c2cnc(C(=O)Nc3ccc(C(=O)N4CCC(CCN)CC4)c(Cl)c3)n2C)c(C(F)(F)F)n1 ; Cl] | 552.3 |

| Example | Name | Structure | ESI MS [M + H]+ |
|---|---|---|---|
| 240 | rac-N-((1s,3s)-3-aminocyclobutyl)-4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxamide formate | 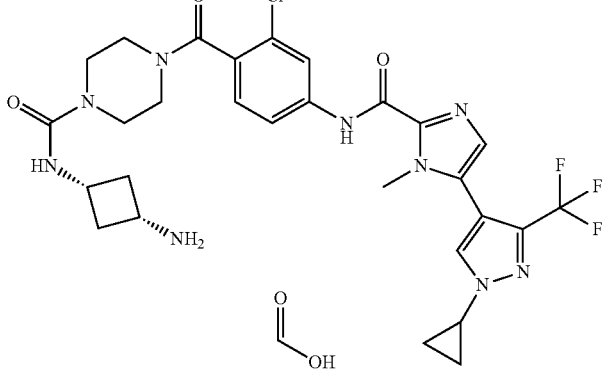 | 634.3 |
| 241 | 5-(1-benzyl-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide hydrochloride | 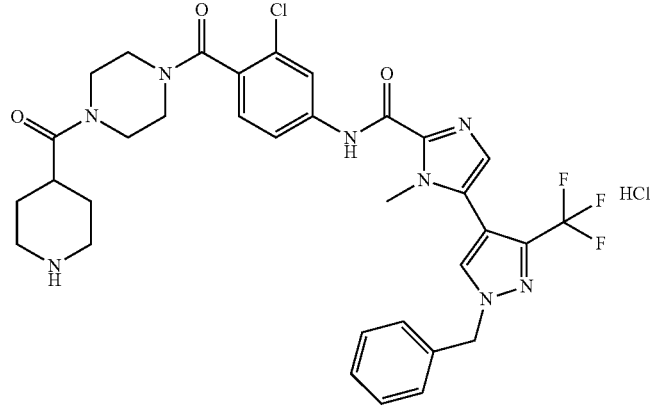 [SMILES: Cn1c(-c2cn(Cc3ccccc3)nc2C(F)(F)F)cnc1C(=O)Nc1ccc(C(=O)N2CCN(C(=O)C3CCNCC3)CC2)c(Cl)c1 ; Cl] | 683.2 |
| 242 | N-[4-[2-(2-aminoethoxy)ethylcarbamoyl]-3-ethyl-phenyl]-1-methyl-5-[1-prop-2-ynyl-3-(trifluoromethyl)pyrazol-4-yl]imidazole-2-carboxamide; formic acid | 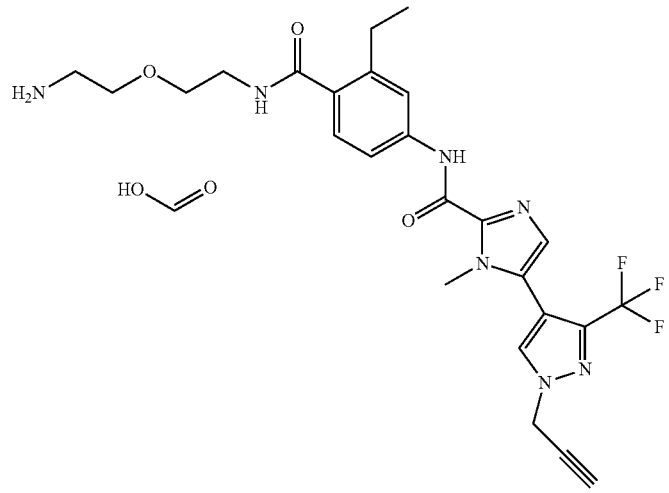 [SMILES: C#CCn1cc(-c2cnc(C(=O)Nc3ccc(C(=O)NCCOCCN)c(CC)c3)n2C)c(C(F)(F)F)n1 ; O=CO] | 532.1 |

| Example | Name | Structure | ESI MS [M + H]+ |
|---|---|---|---|
| 243 | N-(4-(4-((1R,2S)-2-aminocyclopentane-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 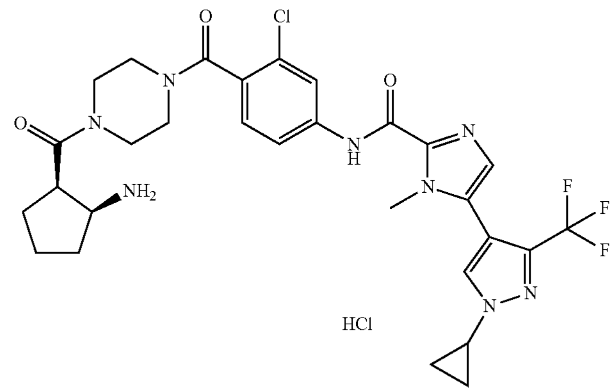 [SMILES: Cn1c(-c2cn(C3CC3)nc2C(F)(F)F)cnc1C(=O)Nc1ccc(C(=O)N2CCN(C(=O)[C@@H]3CCC[C@@H]3N)CC2)c(Cl)c1 ; Cl] | 633.4 |
| 244 | 5-(1-(2,2-difluoroethyl)-3-(trifluoromethyl)-1H-pyrazol-4-yl)-1-methyl-N-(4-(piperazin-1-ylsulfonyl)phenyl)-1H-imidazole-2-carboxamide hydrochloride | 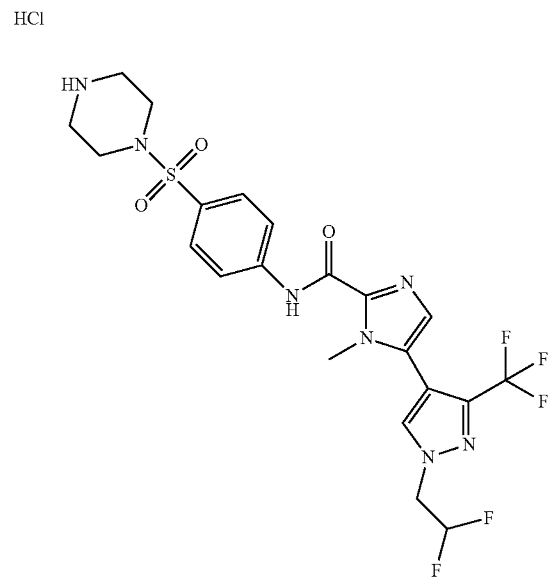 [SMILES: Cl ; Cn1c(-c2cn(CC(F)F)nc2C(F)(F)F)cnc1C(=O)Nc1ccc(S(=O)(=O)N2CCNCC2)cc1] | 546.4 |
| 245 | N-(3-chloro-4-((3-(piperidine-4-carbonyl)-3-azabicyclo[3.1.0]hexan-6-yl)carbamoyl)phenyl)-1-methyl-5-(1-(prop-2-yn-1-yl)-3-(trifluoromethyl)-1H-pyrazol-4-yl)-1H-imidazole-2-carboxamide formate | 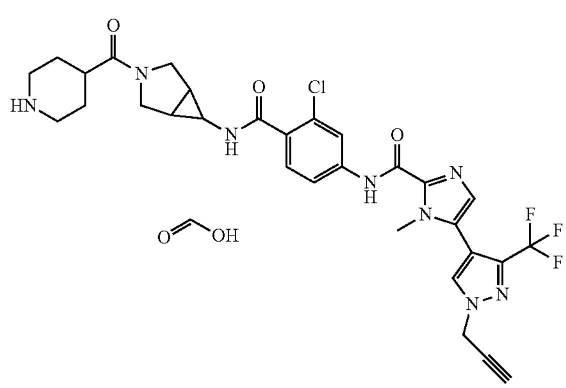 [SMILES: C#CCn1cc(-c2cnc(C(=O)Nc3ccc(C(=O)NC4C5CN(C(=O)C6CCNCC6)CC54)c(Cl)c3)n2C)c(C(F)(F)F)n1 ; O=CO] | 643.3 |

-continued

| Example | Name | Structure | ESI MS [M + H]+ |
|---|---|---|---|
| 246 | (R)-N-(3-chloro-4-(4-(2-(pyrrolidin-3-yl)acetyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 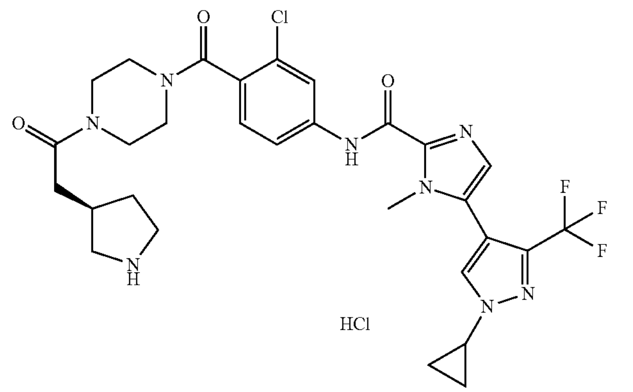 [SMILES: Cn1c(-c2cn(C3CC3)nc2C(F)(F)F)cnc1C(=O)Nc1ccc(C(=O)N2CCN(C(=O)C[C@H]3CCNC3)CC2)c(Cl)c1 ; Cl] | 633.4 |
| 247 | N-(4-((5-aminopentyl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide | 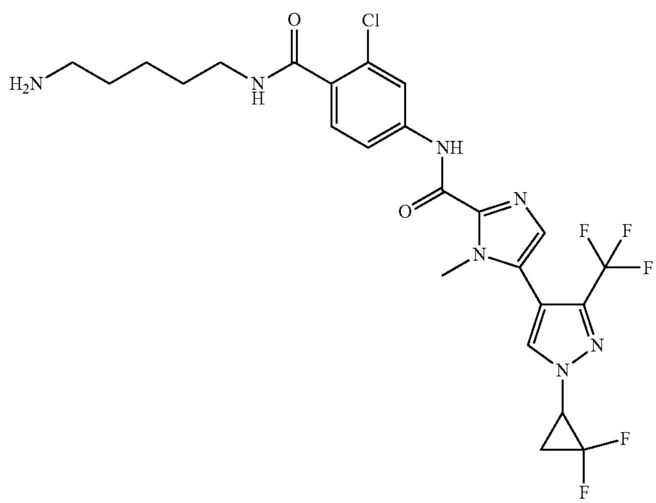 [SMILES: Cn1c(-c2cn(C3CC3(F)F)nc2C(F)(F)F)cnc1C(=O)Nc1ccc(C(=O)NCCCCCN)c(Cl)c1] | 574.3 |
| 248 | cis-N-(1-amino-3-chloropropan-2-yl)-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-3-azabicyclo[3.1.0]hexane-3-carboxamide, formate salt | 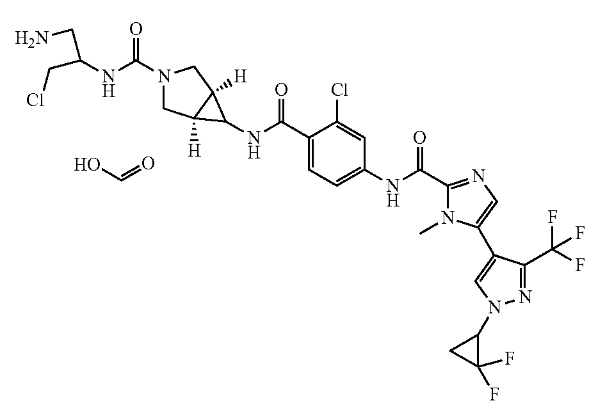 [SMILES: Cn1c(-c2cn(C3CC3(F)F)nc2C(F)(F)F)cnc1C(=O)Nc1ccc(C(=O)NC2[C@H]3CN(C(=O)NC(CN)CCl)C[C@@H]23)c(Cl)c1 ; O=CO] | 704.4 |

-continued

| Example | Name | Structure | ESI MS [M + H]+ |
|---|---|---|---|
| 249 | N-(3-chloro-4-(3,9-diazaspiro[5.5]undecane-3-carbonyl)phenyl)-5-(1-cyclopropyl-3-(trifluoromethyl)-1H-pyrazol-4-yl)-1-methyl-1H-imidazole-2-carboxamide hydrochloride | 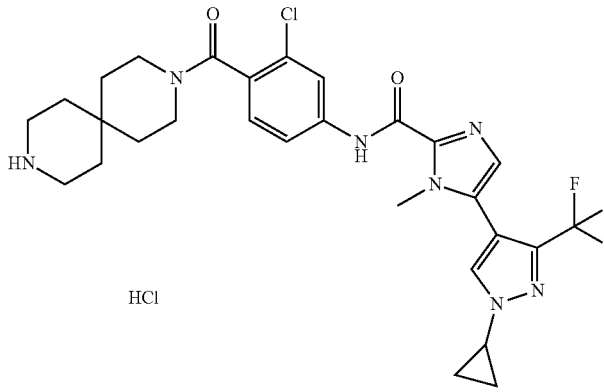 | 590.3 |
| 250 | (R)-N-(3-chloro-4-(4-prolylpiperazine-1-carbonyl)phenyl)-5-(1-cyclopropyl-3-(trifluoromethyl)-1H-pyrazol-4-yl)-1-methyl-1H-imidazole-2-carboxamide hydrochloride | 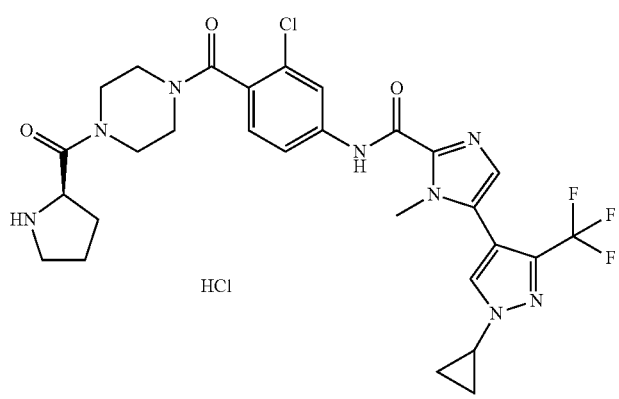 [SMILES: Cn1c(-c2cn(C3CC3)nc2C(F)(F)F)cnc1C(=O)Nc1ccc(C(=O)N2CCN(C(=O)[C@H]3CCCN3)CC2)c(Cl)c1 ; Cl] | 619.4 |
| 251 | N-(azetidin-3-yl)-4-[2-chloro-4-[[5-[1-(2-chloroethyl)-3-(trifluoromethyl)pyrazol-4-yl]-1-methyl-imidazole-2-carbonyl]amino]benzoyl]piperazine-1-carboxamide | 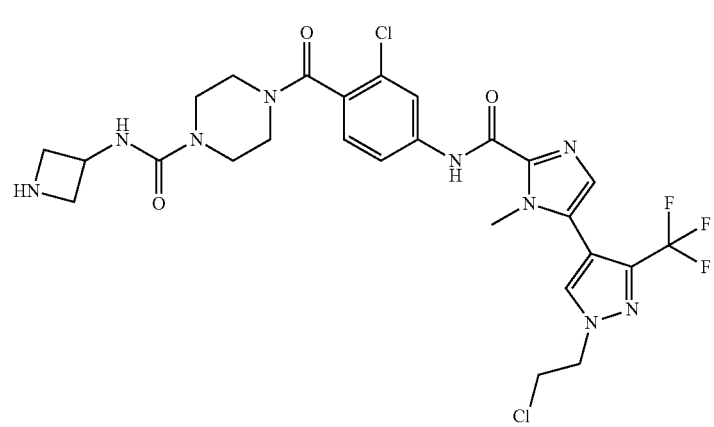 [SMILES: Cn1c(-c2cn(CCCl)nc2C(F)(F)F)cnc1C(=O)Nc1ccc(C(=O)N2CCN(C(=O)NC3CNC3)CC2)c(Cl)c1] | 642.2 |
| 252 | N-(4-(4-(3-aminopropanoyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 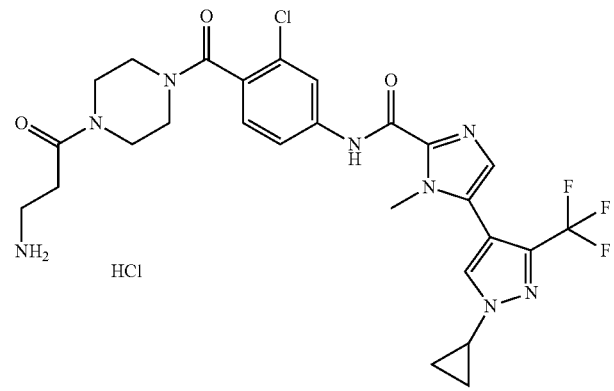 [SMILES: Cn1c(-c2cn(C3CC3)nc2C(F)(F)F)cnc1C(=O)Nc1ccc(C(=O)N2CCN(C(=O)CCN)CC2)c(Cl)c1 ; Cl] | 593.2 |

-continued

| Example | Name | Structure | ESI MS [M + H]+ |
|---|---|---|---|
| 253 | N-[3-chloro-4-[[3-[[(3R)-pyrrolidine-3-carbonyl]amino]cyclobutyl]carbamoyl]phenyl]-5-[1-(cyanomethyl)-3-(trifluoromethyl)pyrazol-4-yl]-1-methyl-imidazole-2-carboxamide; formic acid | 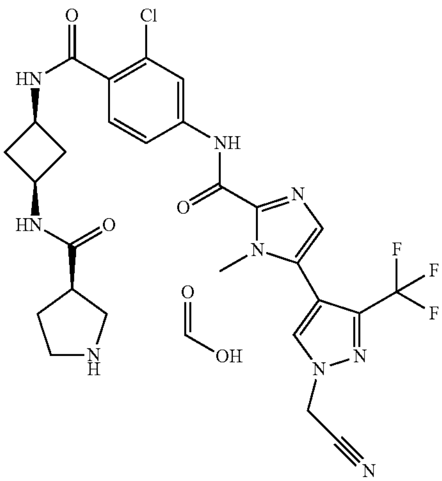 | 618.2 |
| 254 | rac-N-((1s,3s)-3-aminocyclobutyl)-4-(2-chloro-4-(5-(1-((2,2-difluorocyclopropyl)methyl)-3-(trifluoromethyl)-1H-pyrazol-4-yl)-1-methyl-1H-imidazole-2-carboxamido)benzoyl)piperazine-1-carboxamide hydrochloride | 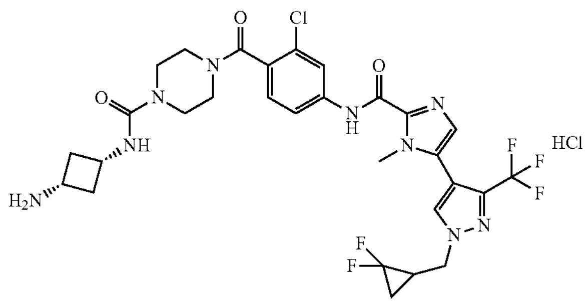 [SMILES: Cn1c(-c2cn(CC3CC3(F)F)nc2C(F)(F)F)cnc1C(=O)Nc1ccc(C(=O)N2CCN(C(=O)N[C@H]3C[C@@H](N)C3)CC2)c(Cl)c1 ; Cl] | 685.3 |
| 255 | N-(4-((3-aminopropyl)carbamoyl)-3-chlorophenyl)-1-methyl-5-(1-(2-methylallyl)-3-(trifluoromethyl)-1H-pyrazol-4-yl)-1H-imidazole-2-carboxamide tris(2,2,2-trifluoroacetate) | 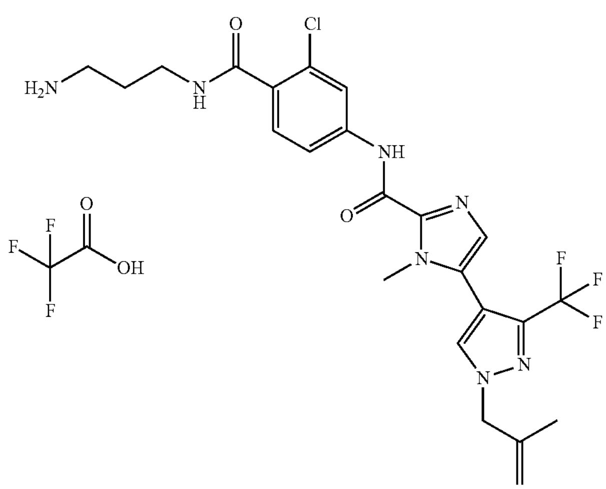 [SMILES: O=C(O)C(F)(F)F ; C=C(C)Cn1cc(-c2cnc(C(=O)Nc3ccc(C(=O)NCCCN)c(Cl)c3)n2C)c(C(F)(F)F)n1] | 524.3 |

| Example | Name | Structure | ESI MS [M + H]+ |
|---|---|---|---|
| 256 | rac-4-(2-chloro-4-(5-(1-cyclopropyl-3-(trifluoromethyl)-1H-pyrazol-4-yl)-1-methyl-1H-imidazole-2-carboxamido)benzoyl)-N-((1s,3s)-3-(methylamino)cyclobutyl)piperazine-1-carboxamide formate | 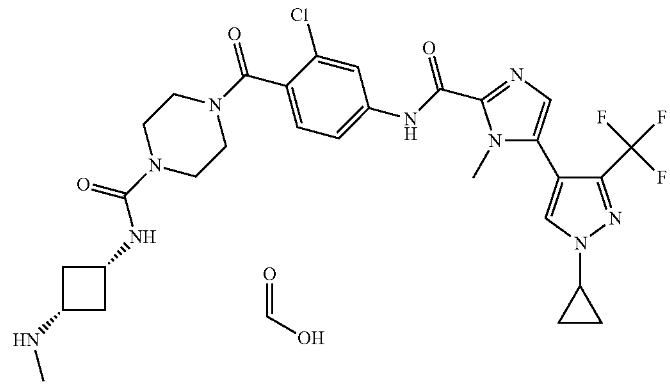 [SMILES: CN[C@H]1C[C@@H](NC(=O)N2CCN(C(=O)c3ccc(NC(=O)c4ncc(-c5cn(C6CC6)nc5C(F)(F)F)n4C)cc3Cl)CC2)C1 ; O=CO] | 695.3 |
| 257 | rac-N-(4-(4-((1R,5S,6r)-3-azabicyclo[3.1.0]hexane-6-carbonyl)piperazine-1-carbonyl)-3-chlorophenyl)-1-methyl-5-(1-(2-methylallyl)-3-(trifluoromethyl)-1H-pyrazol-4-yl)-1H-imidazole-2-carboxamide hydrochloride | 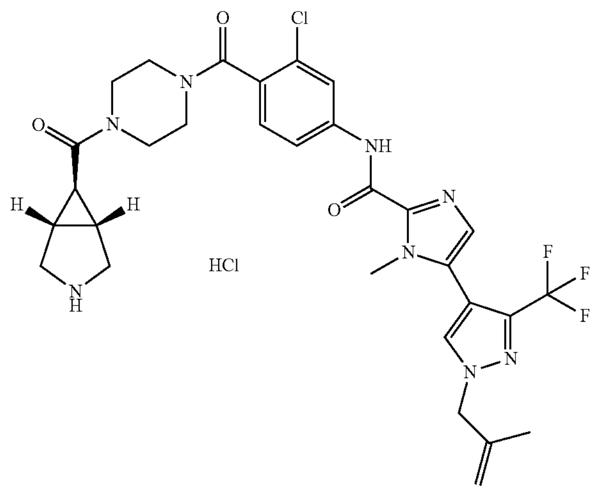 [SMILES: C=C(C)Cn1cc(-c2cnc(C(=O)Nc3ccc(C(=O)N4CCN(C(=O)[C@H]5[C@@H]6CNC[C@@H]65)CC4)c(Cl)c3)n2C)c(C(F)(F)F)n1 ; Cl] | 645.4 |
| 258 | (S)-N-(3-chloro-4-(4-(2-methylpyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 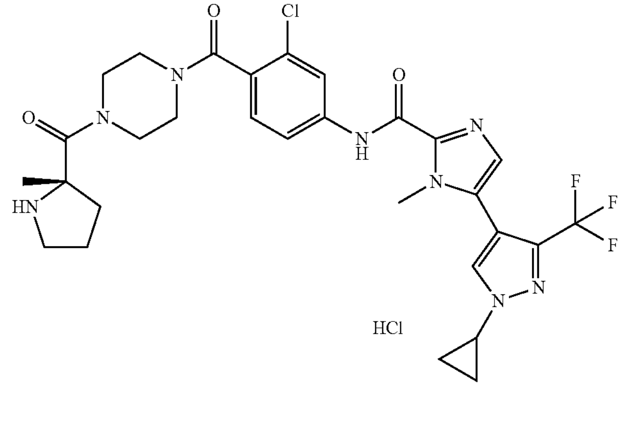 [SMILES: Cn1c(-c2cn(C3CC3)nc2C(F)(F)F)cnc1C(=O)Nc1ccc(C(=O)N2CCN(C(=O)[C@]3(C)CCCN3)CC2)c(Cl)c1 ; Cl] | 633.4 |

| Example | Name | Structure | ESI MS [M + H]+ |
|---|---|---|---|
| 259 | N-(3-chloro-4-(((exo)-3-(piperidine-4-carbonyl)-3 azabicyclo[3.1.0]hexan-6-yl)carbamoyl)phenyl)-5-(1-(3-fluorocyclobut-2-en-1-yl)-3-(trifluoromethyl)-1H-pyrazol-4-yl)-1-methyl-1H-imidazole-2-carboxamide formate | 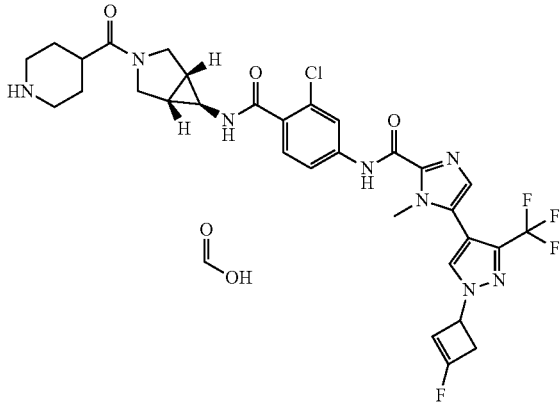 [SMILES: Cn1c(-c2cn(C3C=C(F)C3)nc2C(F)(F)F)cnc1C(=O)Nc1ccc(C(=O)N[C@H]2[C@@H]3CN(C(=O)C4CCNCC4)C[C@@H]32)c(Cl)c1 ; O=CO] | 673.4 [M − H]− |
| 260 | rac-N-((1s,3s)-3-aminocyclobutyl)-4-(2-chloro-4-(5-(1-(cyclobutylmethyl)-3-(trifluoromethyl)-1H-pyrazol-4-yl)-1-methyl-1H-imidazole-2-carboxamido)benzoyl)piperazine-1-carboxamide hydrochloride | 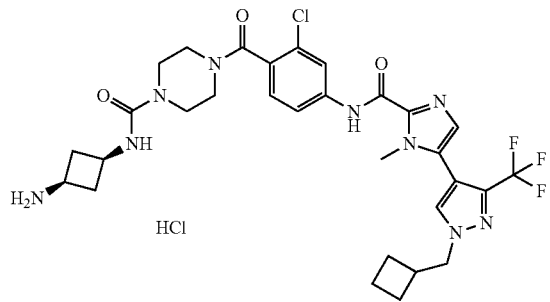 [SMILES: Cn1c(-c2cn(CC3CCC3)nc2C(F)(F)F)cnc1C(=O)Nc1ccc(C(=O)N2CCN(C(=O)N[C@H]3C[C@@H](N)C3)CC2)c(Cl)c1 ; Cl] | 662.3 |
| 261 | N-(3-fluoro-4-(4-(piperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide | 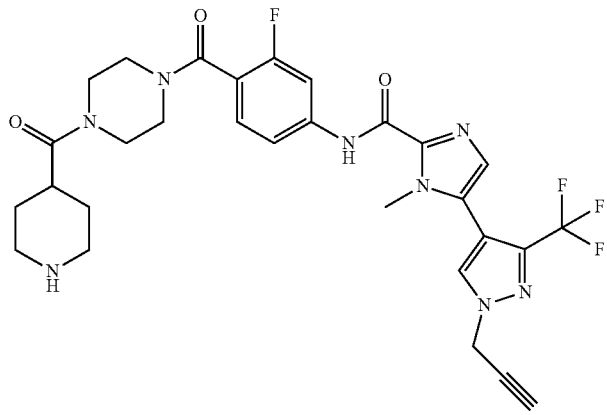 [SMILES: C#CCn1cc(-c2cnc(C(=O)Nc3ccc(C(=O)N4CCN(C(=O)C5CCNCC5)CC4)c(F)c3)n2C)c(C(F)(F)F)n1] | 615.3 |
| 262 | N-[4-[6-[(3-aminocyclobutyl)carbamoyl-amino]hexylcarbamoyl]-3-chlorophenyl]-5-[1-cyclopropyl-3-(trifluoromethyl)pyrazol-4-yl]-1-methylimidazole-2-carboxamide;formic acid | 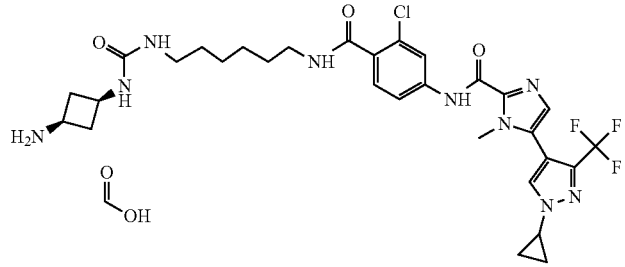 [SMILES: Cn1c(-c2cn(C3CC3)nc2C(F)(F)F)cnc1C(=O)Nc1ccc(C(=O)NCCCCCCNC(=O)N[C@H]2C[C@@H](N)C2)c(Cl)c1 ; O=CO] | 664.3 |

| Example | Name | Structure | ESI MS [M + H]+ |
|---|---|---|---|
| 263 | N-[3-bromo-4-[4-[rac-(1R,5S)-3-azabicyclo[3.1.0]hexane-6-carbonyl]piperazine-1-carbonyl]phenyl]-5-[1-ethyl-3-(trifluoromethyl)pyrazol-4-yl]-1-methylimidazole-2-carboxamide;hydrochloride | 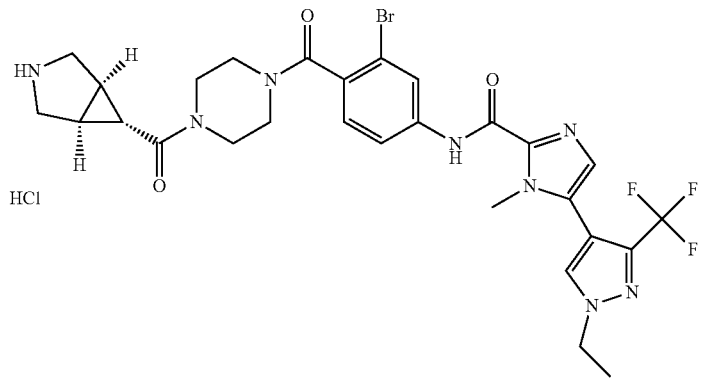 [SMILES: Cl ; CCn1cc(-c2cnc(C(=O)Nc3ccc(C(=O)N4CCN(C(=O)[C@H]5[C@@H]6CNC[C@@H]65)CC4)c(Br)c3)n2C)c(C(F)(F)F)n1] | 664.3 |
| 264 | N-(4-(((1R,5S,6s)-3-(4-(3-aminopropyl)piperazine-1-carbonyl)-3-azabicyclo[3.1.0]hexan-6-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide | 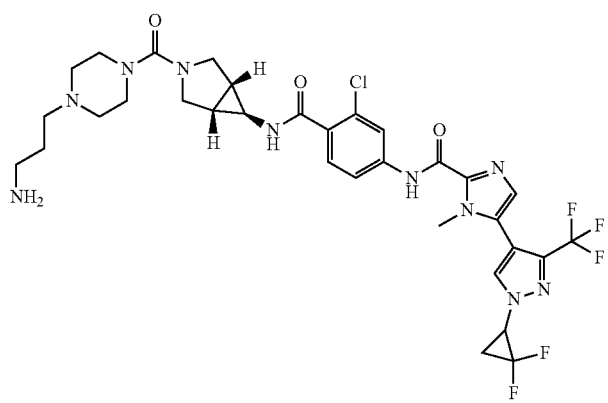 [SMILES: Cn1c(-c2cn(C3CC3(F)F)nc2C(F)(F)F)cnc1C(=O)Nc1ccc(C(=O)N[C@H]2[C@@H]3CN(C(=O)N4CCN(CCCN)CC4)C[C@@H]32)c(Cl)c1] | 739.2 |
| 265 | cis-N-(3-aminocyclobutyl)-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-3-azabicyclo[3.1.0]hexane-3-carboxamide, formate salt | 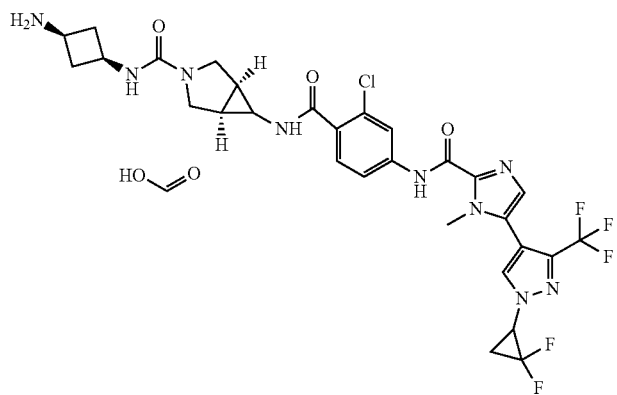 | 682.3 |
| 266 | N-[(1R,3S)-3-amino-2,2-dimethylcyclobutyl]-4-[2-chloro-4-[[5-[1-cyclopropyl-3-(trifluoromethyl)pyrazol-4-yl]-1-methylimidazole-2-carbonyl]amino]benzoyl]piperazine-1-carboxamide;formic acid | 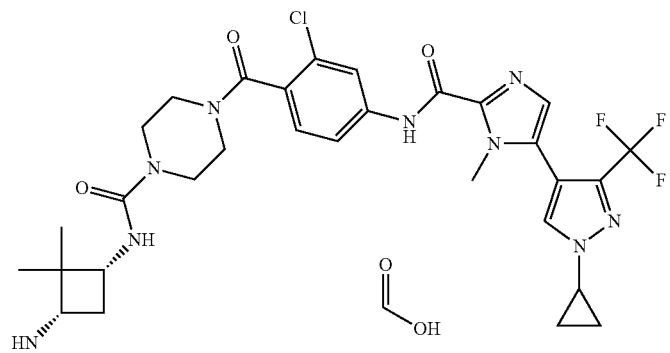 [SMILES: Cn1c(-c2cn(C3CC3)nc2C(F)(F)F)cnc1C(=O)Nc1ccc(C(=O)N2CCN(C(=O)N[C@@H]3C[C@H](N)C3(C)C)CC2)c(Cl)c1 ; O=CO] | 709.5 |

| Example | Name | Structure | ESI MS [M + H]+ |
|---|---|---|---|
| 267 | N-(3-chloro-4-(4-(piperidine-4-carbonyl)piperazine-1-carbonyl)phenyl)-5-(1-(2,2-difluorocyclopropyl)-3-(trifluoromethyl)-1H-pyrazol-4-yl)-1-methyl-1H-imidazole-2-carboxamide formate | 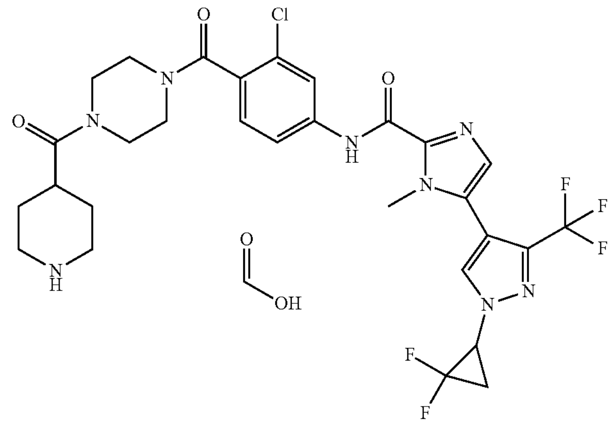 [SMILES: Cn1c(-c2cn(C3CC3(F)F)nc2C(F)(F)F)cnc1C(=O)Nc1ccc(C(=O)N2CCN(C(=O)C3CCNCC3)CC2)c(Cl)c1 ; O=CO] | 669.3 |
| 268 | N-(4-(3,8-diazabicyclo[3.2.1]octane-8-carbonyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 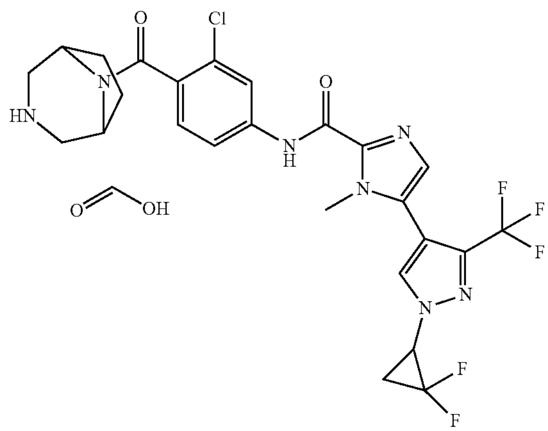 | 584.3 |
| 269 | N-[4-[[3-[(3-aminocyclobutanecarbonyl)amino]cyclobutyl]carbamoyl]-3-chloro-phenyl]-5-[1-(cyanomethyl)-3-(trifluoromethyl)pyrazol-4-yl]-1-methyl-imidazole-2-carboxamide; formic acid | 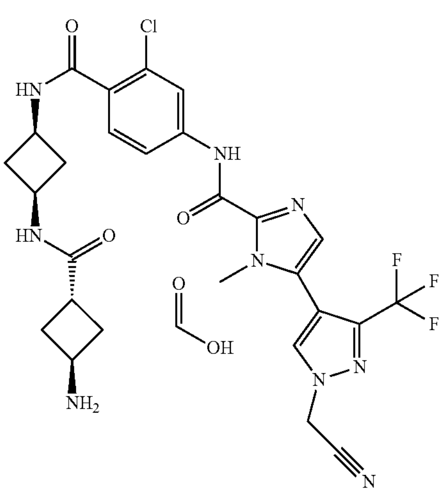 | 618.2 |

| Example | Name | Structure | ESI MS [M + H]+ |
|---|---|---|---|
| 270 | N-[4-[4-(3-amino-2-hydroxypropanoyl)piperazine-1-carbonyl]-3-chlorophenyl]-5-[1-cyclopropyl-3-(trifluoromethyl)pyrazol-4-yl]-1-methylimidazole-2-carboxamide;hydrochloride | 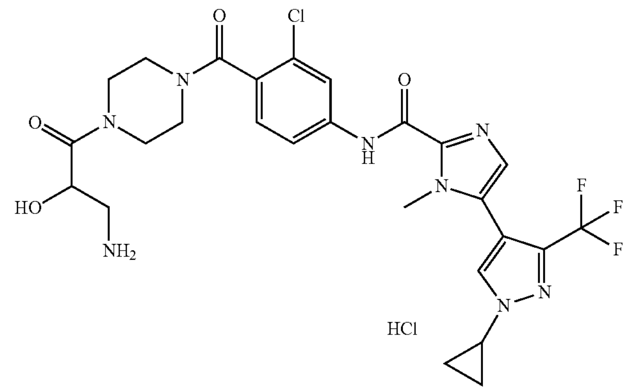 [SMILES: Cn1c(-c2cn(C3CC3)nc2C(F)(F)F)cnc1C(=O)Nc1ccc(C(=O)N2CCN(C(=O)C(O)CN)CC2)c(Cl)c1 ; Cl] | 609.3 |
| 271 | rac-N-(3-chloro-4-((3aR,6aS)-octahydropyrrolo[3,4-c]pyrrole-2-carbonyl)phenyl)-5-(1-(2,2-difluorocyclopropyl)-3-(trifluoromethyl)-1H-pyrazol-4-yl)-1-methyl-1H-imidazole-2-carboxamide formate | 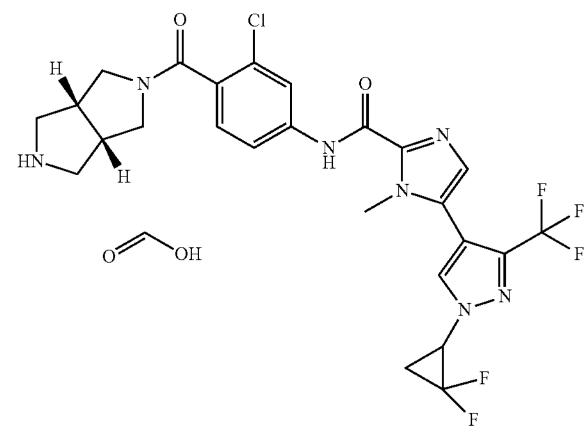 [SMILES: Cn1c(-c2cn(C3CC3(F)F)nc2C(F)(F)F)cnc1C(=O)Nc1ccc(C(=O)N2C[C@H]3CNC[C@H]3C2)c(Cl)c1 ; O=CO] | 584.3 |
| 272 | rac-N-((1s,3s)-3-aminocyclobutyl)-4-(4-(5-(1-(2,2-difluoroethyl)-3-(trifluoromethyl)-1H-pyrazol-4-yl)-1-methyl-1H-imidazole-2-carboxamido)-2-fluorobenzoyl)piperazine-1-carboxamide | 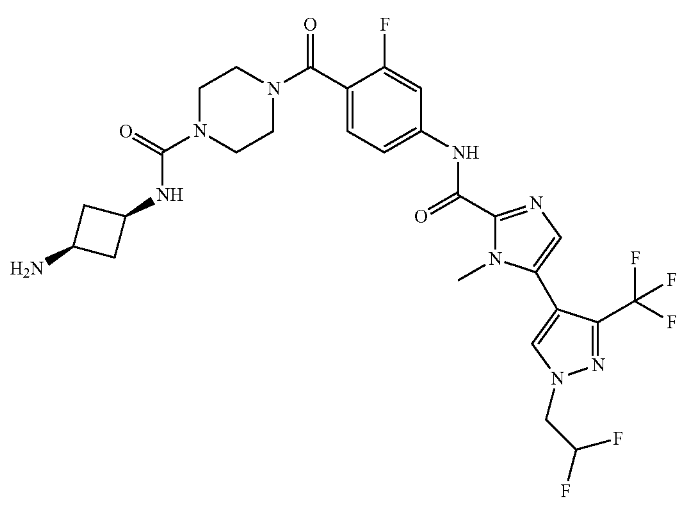 [SMILES: Cn1c(-c2cn(CC(F)F)nc2C(F)(F)F)cnc1C(=O)Nc1ccc(C(=O)N2CCN(C(=O)N[C@H]3C[C@@H](N)C3)CC2)c(F)c1] | 642.3 |

-continued

| Example | Name | Structure | ESI MS [M + H]+ |
|---|---|---|---|
| 273 | (R)-N-(3-chloro-4-(4-(piperidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 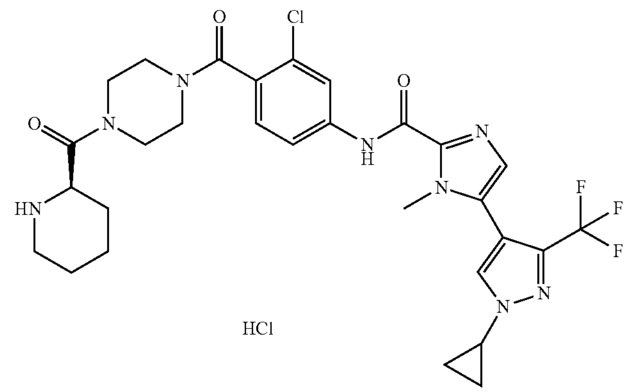 [SMILES: Cn1c(-c2cn(C3CC3)nc2C(F)(F)F)cnc1C(=O)Nc1ccc(C(=O)N2CCN(C(=O)[C@H]3CCCCN3)CC2)c(Cl)c1 ; Cl] | 633.4 |
| 274 | N-(3-chloro-4-(4-(piperidine-4-carbonyl)piperazine-1-carbonyl)phenyl)-5-(1-cyclopentyl-3-(trifluoromethyl)-1H-pyrazol-4-yl)-1-methyl-1H-imidazole-2-carboxamide hydrochloride | 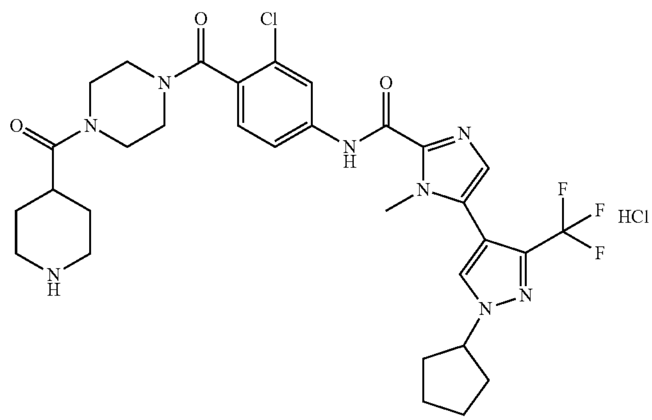 [SMILES: Cn1c(-c2cn(C3CCCC3)nc2C(F)(F)F)cnc1C(=O)Nc1ccc(C(=O)N2CCN(C(=O)C3CCNCC3)CC2)c(Cl)c1 ; Cl] | 661.3 |
| 275 | N-[4-[[3-[[[(1R,3S)-3-aminocyclopentyl]carbamoylamino]cyclobutyl]carbamoyl]-3-chloro-phenyl]-5-[1-(cyanomethyl)-3-(trifluoromethyl)pyrazol-4-yl]-1-methyl-imidazole-2-carboxamide; formic acid | 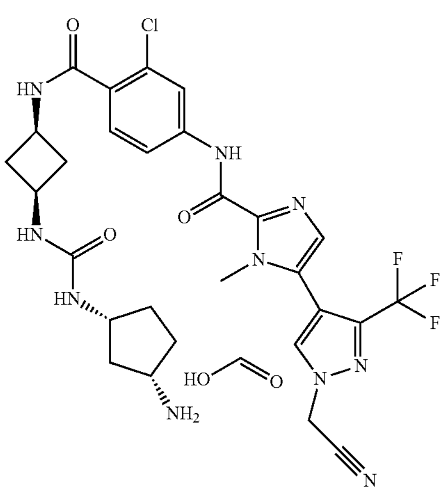 | 646.9 |

| Example | Name | Structure | ESI MS [M + H]+ |
|---|---|---|---|
| 276 | rac-N-(4-(4-((1r,3r)-3-aminocyclobutane-1-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide hydrochloride | 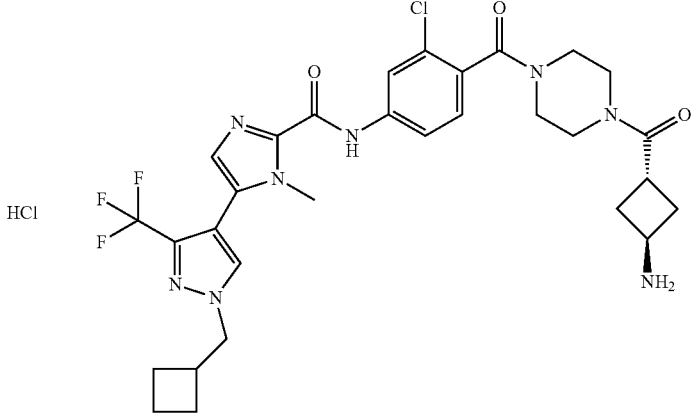 [SMILES: Cl ; Cn1c(-c2cn(CC3CCC3)nc2C(F)(F)F)cnc1C(=O)Nc1ccc(C(=O)N2CCN(C(=O)[C@H]3C[C@H](N)C3)CC2)c(Cl)c1] | 647.4 |
| 277 | N-[4-[3-(aminomethyl)piperidine-1-carbonyl]-3-chlorophenyl]-5-[1-cyclopropyl-3-(trifluoromethyl)pyrazol-4-yl]-1-methylimidazole-2-carboxamide;hydrochloride | 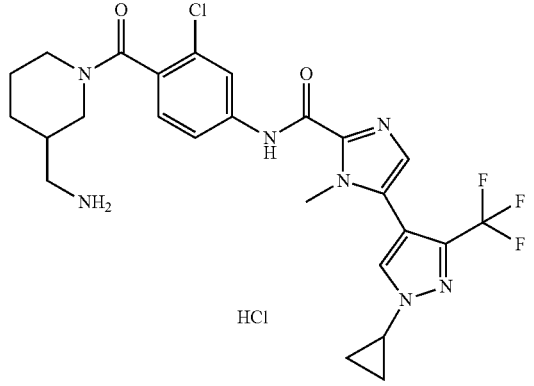 [SMILES: Cn1c(-c2cn(C3CC3)nc2C(F)(F)F)cnc1C(=O)Nc1ccc(C(=O)N2CCCC(CN)C2)c(Cl)c1 ; Cl] | 550.2 |
| 278 | N-(4-(4-(L-alanyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide hydrochloride | 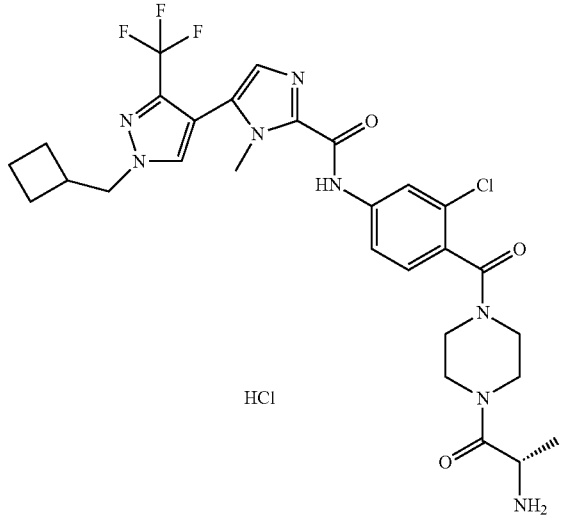 [SMILES: C[C@H](N)C(=O)N1CCN(C(=O)c2ccc(NC(=O)c3ncc(-c4cn(CC5CCC5)nc4C(F)(F)F)n3C)cc2Cl)CC1 ; Cl] | 621.3 |

-continued

| Example | Name | Structure | ESI MS [M + H]+ |
|---|---|---|---|
| 279 | rac-4-((4-(5-(1-(2,2-difluoroethyl)-3-(trifluoromethyl)-1H-pyrazol-4-yl)-1-methyl-1H-imidazole-2-carboxamido)phenyl)sulfonyl)-N-((3R,4R)-4-hydroxypyrrolidin-3-yl)piperazine-1-carboxamide formate | AND Enantiomer | 676.4 |
| 280 | N-(3-chloro-4-((trans-4-methoxypyrrolidin-3-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate | AND Enantiomer | 588.3 |
| 281 | N-(4-(4-(azetidine-2-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide hydrochloride | HCl | 633.3 |

-continued

| Example | Name | Structure | ESI MS [M + H]+ |
|---|---|---|---|
| 282 | 5-(1-(2,2-difluoroethyl)-3-(trifluoromethyl)-1H-pyrazol-4-yl)-N-(4-((4-glycylpiperazin-1-yl)sulfonyl)phenyl)-1-methyl-1H-imidazole-2-carboxamide formate | 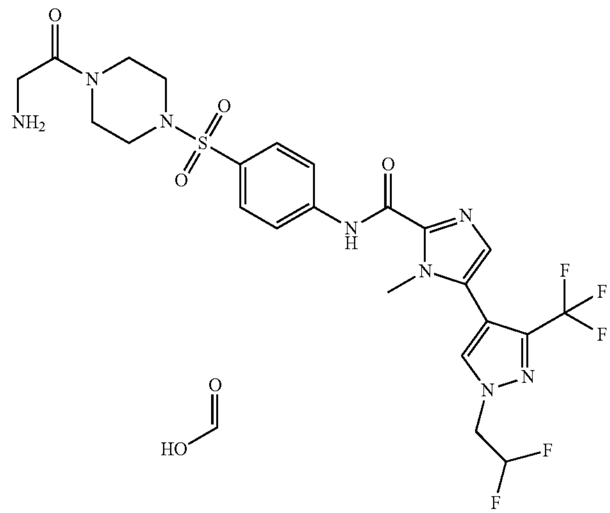 [SMILES: Cn1c(-c2cn(CC(F)F)nc2C(F)(F)F)cnc1C(=O)Nc1ccc(S(=O)(=O)N2CCN(C(=O)CN)CC2)cc1 ; O=CO] | 605.4 |
| 283 | rac-N-(4-(((1R,3s,5S)-8-azabicyclo[3.2.1]octan-3-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 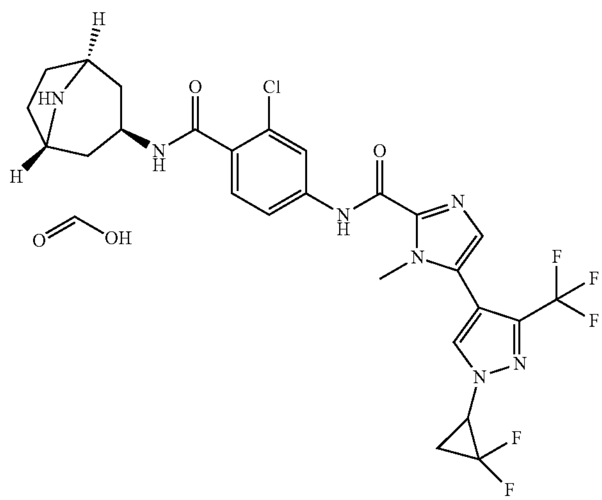 | 598.3 |
| 284 | N-(4-((6-aminohexyl)carbamoyl)-3-bromophenyl)-5-(1-ethyl-3-(trifluoromethyl)-1H-pyrazol-4-yl)-1-methyl-1H-imidazole-2-carboxamide hydrochloride | 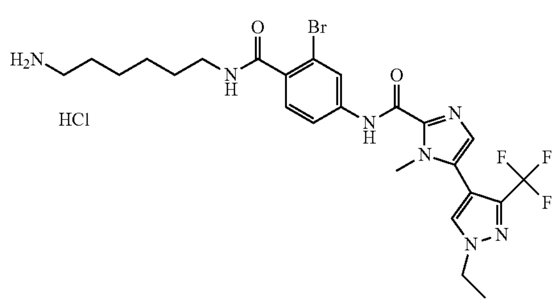 [SMILES: CCn1cc(-c2cnc(C(=O)Nc3ccc(C(=O)NCCCCCCN)c(Br)c3)n2C)c(C(F)(F)F)n1 ; Cl] | 585.2 |

-continued

| Example | Name | Structure | ESI MS [M + H]+ |
|---|---|---|---|
| 285 | (S)-N-(3-chloro-4-(4-(2,5-diaminopentanoyl)piperazine-1-carbonyl)phenyl)-5-(1-cyclopropyl-3-(trifluoromethyl)-1H-pyrazol-4-yl)-1-methyl-1H-imidazole-2-carboxamide dihydrochloride | 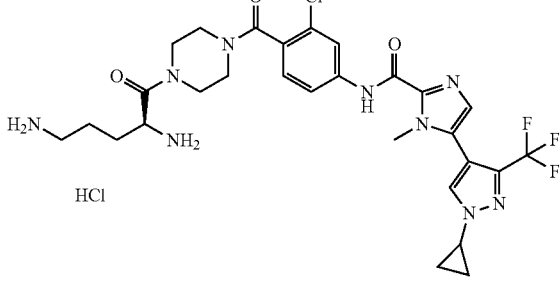 | [M + H] |
| 286 | N-[3-chloro-4-[4-(5-hydroxypiperidine-3-carbonyl)piperazine-1-carbonyl]phenyl]-5-[1-cyclopropyl-3-(trifluoromethyl)pyrazol-4-yl]-1-methylimidazole-2-carboxamide;hydrochloride | 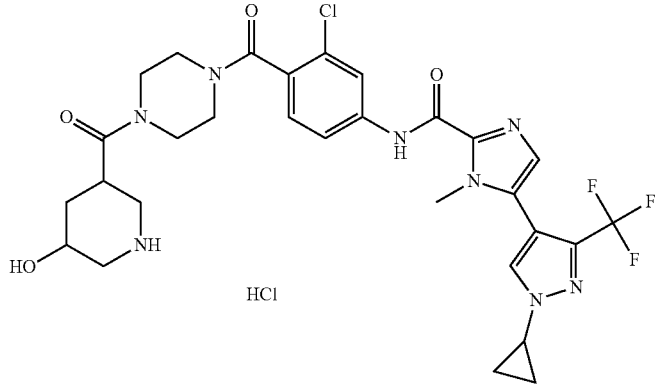 [SMILES: Cn1c(-c2cn(C3CC3)nc2C(F)(F)F)cnc1C(=O)Nc1ccc(C(=O)N2CCN(C(=O)C3CNCC(O)C3)CC2)c(Cl)c1 ; Cl] | 649.3 |
| 287 | N-(4-(4-((1R,3R)-3-aminocyclohexane-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 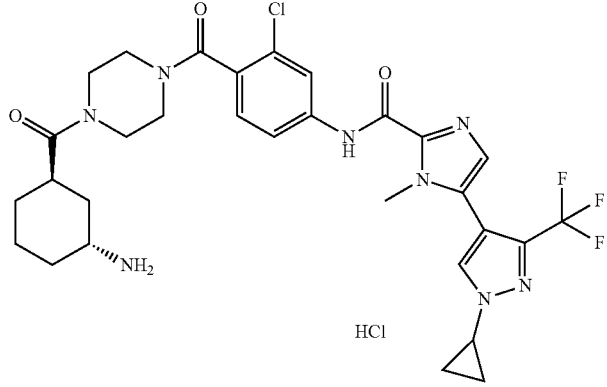 [SMILES: Cn1c(-c2cn(C3CC3)nc2C(F)(F)F)cnc1C(=O)Nc1ccc(C(=O)N2CCN(C(=O)[C@@H]3CCC[C@@H](N)C3)CC2)c(Cl)c1 ; Cl] | 647.4 |

| Example | Name | Structure | ESI MS [M + H]+ |
|---|---|---|---|
| 288 | rac-(3aR,6aS)-5-(2-chloro-4-(5-(1-(2,2-difluorocyclopropyl)-3-(trifluoromethyl)-1H-pyrazol-4-yl)-1-methyl-1H-imidazole-2-carboxamido)benzoyl)-N-((3R,4R)-4-hydroxypyrrolidin-3-yl)hexahydropyrrolo[3,4-c]pyrrole-2(1H)-carboxamide formate | 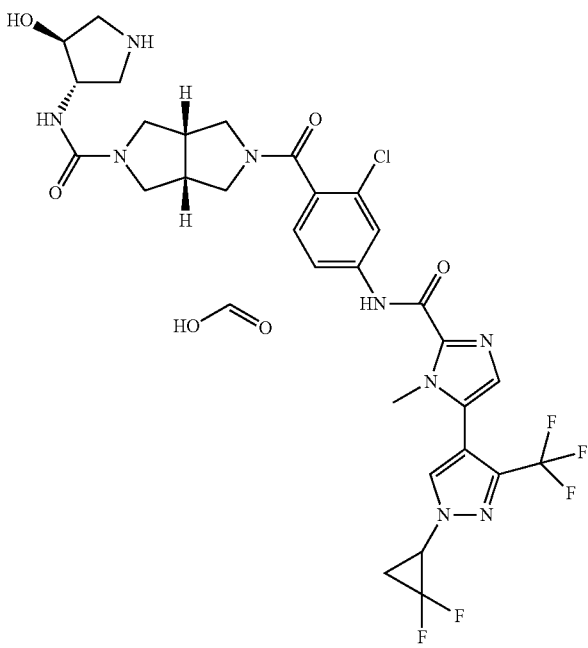 AND Enantiomer | 688.4 |
| 289 | rac-N-(4-((((1r,4r)-4-aminocyclohexyl)methyl)carbamoyl)-3-chlorophenyl)-5-(1-cyclopropyl-3-(trifluoromethyl)-1H-pyrazol-4-yl)-1-methyl-1H-imidazole-2-carboxamide hydrochloride | 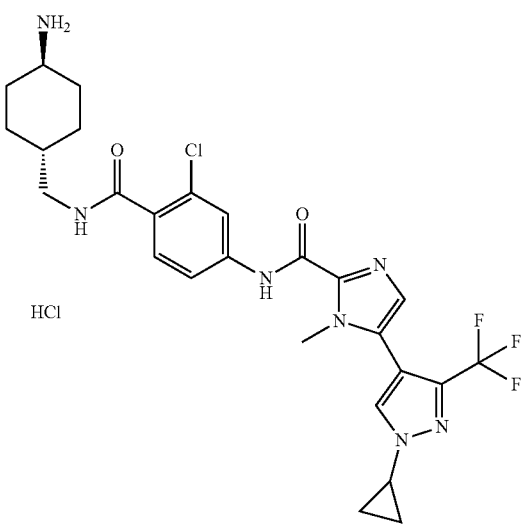 [SMILES: Cn1c(-c2cn(C3CC3)nc2C(F)(F)F)cnc1C(=O)Nc1ccc(C(=O)NC[C@H]2CC[C@H](N)CC2)c(Cl)c1 ; Cl] | 564.3 |
| 290 | N-(4-(4-(2-aminoethyl)piperazine-1-carbonyl)-3-chlorophenyl)-5-(1-(2,2-difluoroethyl)-3-(trifluoromethyl)-1H-pyrazol-4-yl)-1-methyl-1H-imidazole-2-carboxamide formate | 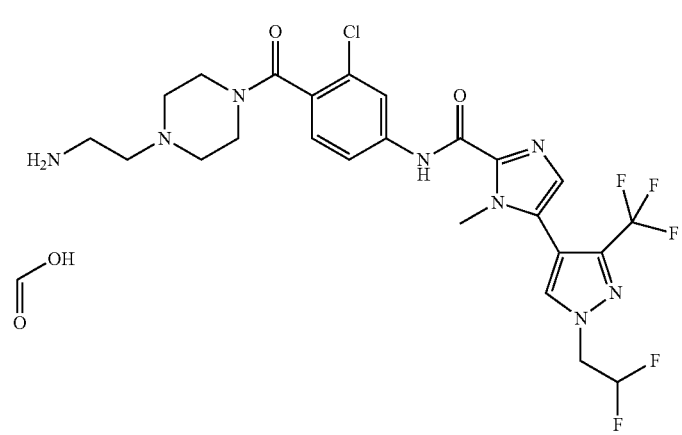 [SMILES: O=CO ; Cn1c(-c2cn(CC(F)F)nc2C(F)(F)F)cnc1C(=O)Nc1ccc(C(=O)N2CCN(CCN)CC2)c(Cl)c1] | 589.2 |

-continued

| Example | Name | Structure | ESI MS [M + H]+ |
|---|---|---|---|
| 291 | N-[4-[N-(3-aminopropyl)-S-methyl-sulfonimidoyl]-3-methyl-phenyl]-5-[1-(cyanomethyl)-3-(trifluoromethyl)pyrazol-4-yl]-1-methyl-imidazole-2-carboxamide; formic acid | 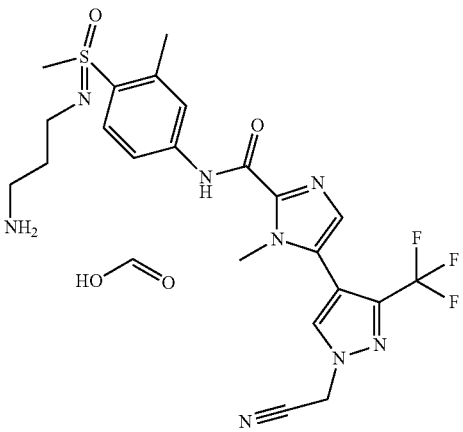 [SMILES: Cc1cc(NC(=O)c2ncc(-c3cn(CC#N)nc3C(F)(F)F)n2C)ccc1S(C)(=O)=NCCCN ; O=CO] | 523.3 |
| 292 | rac-N-((1s,3s)-3-aminocyclobutyl)-4-(2-chloro-4-(5-(1-isobutyl-3-(trifluoromethyl)-1H-pyrazol-4-yl)-1-methyl-1H-imidazole-2-carboxamido)benzoyl)piperazine-1-carboxamide hydrochloride | 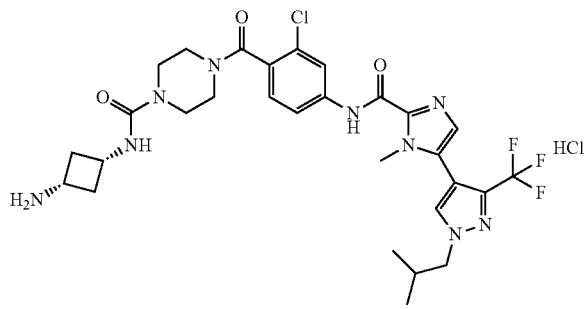 [SMILES: CC(C)Cn1cc(-c2cnc(C(=O)Nc3ccc(C(=O)N4CCN(C(=O)N[C@H]5C[C@@H](N)C5)CC4)c(Cl)c3)n2C)c(C(F)(F)F)n1 ; Cl] | 651.3 |
| 293 | rac-N-((1s,3s)-3-aminocyclobutyl)-4-(2-chloro-4-(5-(1-((3,3-difluorocyclobutypmethyl)-3-(trifluoromethyl)-1H-pyrazol-4-yl)-1-methyl-1H-imidazole-2-carboxamido)benzoyl)piperazine-1-carboxamide hydrochloride | 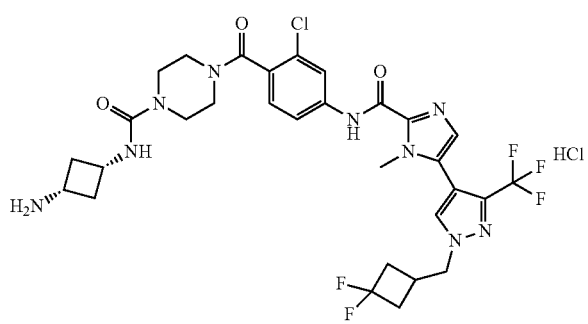 [SMILES: Cn1c(-c2cn(CC3CC(F)(F)C3)nc2C(F)(F)F)cnc1C(=O)Nc1ccc(C(=O)N2CCN(C(=O)N[C@H]3C[C@@H](N)C3)CC2)c(Cl)c1 ; Cl] | 699.3 |
| 294 | rac-N-((1s,3s)-3-aminocyclobutyl)-4-(2-chloro-4-(5-(1-(2,2-difluorocyclopropyl)-3-(trifluoromethyl)-1H-pyrazol-4-yl)-1-methyl-1H-imidazole-2-carboxamido)-N-methylbenzamido)piperidine-1-carboxamide formate | 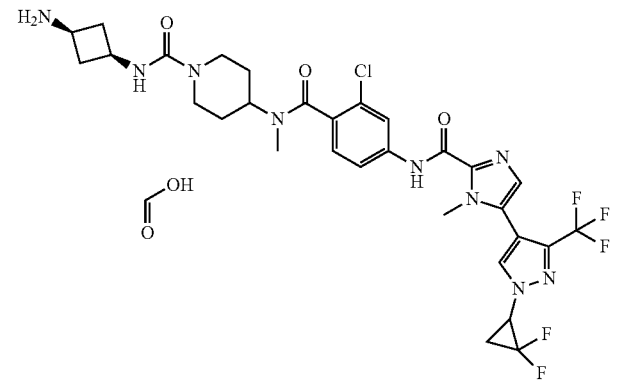 [SMILES: CN(C(=O)c1ccc(NC(=O)c2ncc(-c3cn(C4CC4(F)F)nc3C(F)(F)F)n2C)cc1Cl)C1CCN(C(=O)N[C@H]2C[C@@H](N)C2)CC1 ; O=CO] | 698.5 |

-continued

| Example | Name | Structure | ESI MS [M + H]+ |
|---|---|---|---|
| 295 | rac-N-(4-(4-((1s,3s)-3-aminocyclobutane-1-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide hydrochloride | 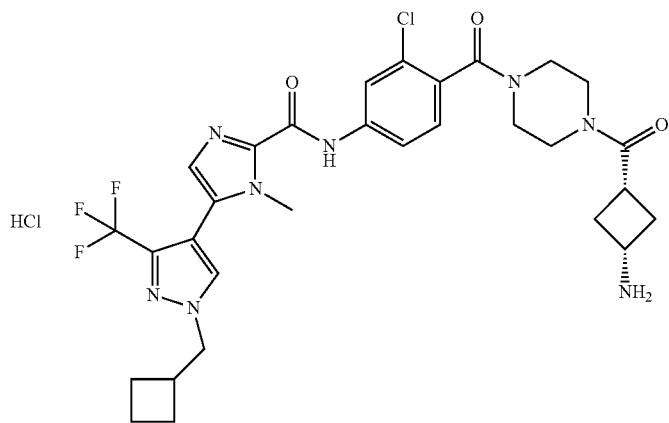 [SMILES: Cl ; Cn1c(-c2cn(CC3CCC3)nc2C(F)(F)F)cnc1C(=O)Nc1ccc(C(=O)N2CCN(C(=O)[C@H]3C[C@@H](N)C3)CC2)c(Cl)c1] | 647.3 |
| 296 | N-(3-aminocyclobutyl)-4-[2-chloro-4-[[5-[1-ethyl-3-(trifluoromethyl)pyrazol-4-yl]-1-methylimidazole-2-carbonyl]amino]benzoyl]piperazine-1-carboxamide;formic acid | 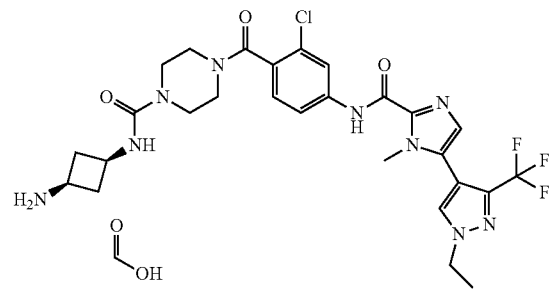 | 622.3 |
| 297 | N-(3-chloro-4-(4-(4-methylpiperazine-1-carbonyl)piperazine-1-carbonyl)phenyl)-5-(1-cyclopropyl-3-(trifluoromethyl)-1H-pyrazol-4-yl)-1-methyl-1H-imidazole-2-carboxamide | 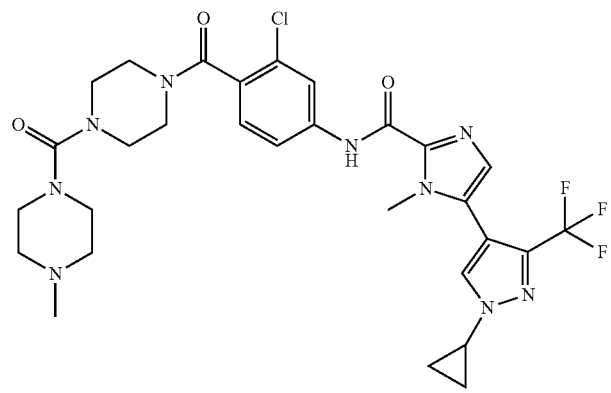 [SMILES: CN1CCN(C(=O)N2CCN(C(=O)c3ccc(NC(=O)c4ncc(-c5cn(C6CC6)nc5C(F)(F)F)n4C)cc3Cl)CC2)CC1] | 648.3 |
| 298 | N-[4-[4-(3-aminocyclobutanecarbonyl)piperazine-1-carbonyl]-3-chlorophenyl]-5-[1-(2-fluoroethyl)-3-(trifluoromethyl)pyrazol-4-yl]-1-methylimidazole-2-carboxamide;trihydrochloride | 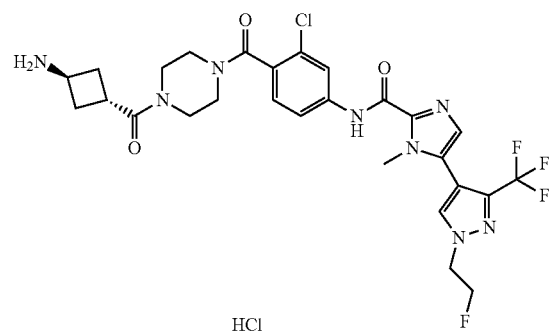 [SMILES: Cn1c(-c2cn(CCF)nc2C(F)(F)F)cnc1C(=O)Nc1ccc(C(=O)N2CCN(C(=O)[C@H]3C[C@H](N)C3)CC2)c(Cl)c1 ; Cl] | 625.3 |

| Example | Name | Structure | ESI MS [M + H]+ |
|---|---|---|---|
| 299 | (S)-N-(3-chloro-4-(4-(pyrrolidine-3-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 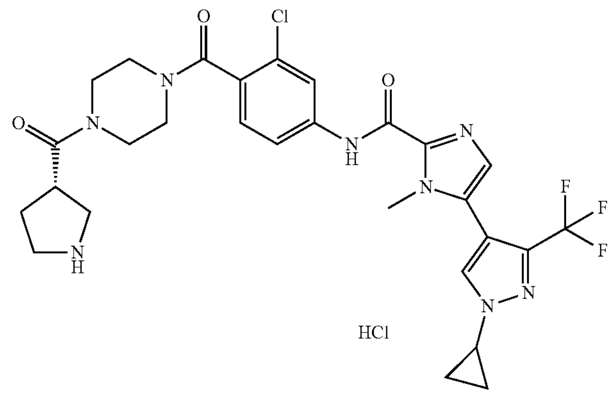 [SMILES: Cn1c(-c2cn(C3CC3)nc2C(F)(F)F)cnc1C(=O)Nc1ccc(C(=O)N2CCN(C(=O)[C@H]3CCNC3)CC2)c(Cl)c1 ; Cl] | 619.3 |
| 300 | rac-N-(3-chloro-4-(6-(3-((3R,4R)-4-hydroxypyrrolidin-3-yl)ureido)-3-azabicyclo[3.1.0]hexane-3-carbonyl)phenyl)-5-(1-(2,2-difluorocyclopropyl)-3-(trifluoromethyl)-1H-pyrazol-4-yl)-1-methyl-1H-imidazole-2-carboxamide formate | 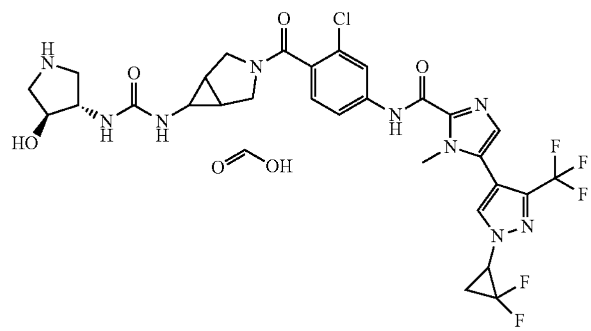 | 688.4 |
| 301 | 5-(1-(2,2-difluoroethyl)-3-(trifluoromethyl)-1H-pyrazol-4-yl)-N-(3-fluoro-4-(4-(piperidine-4-carbonyl)piperazine-1-carbonyl)phenyl)-1-methyl-1H-imidazole-2-carboxamide | 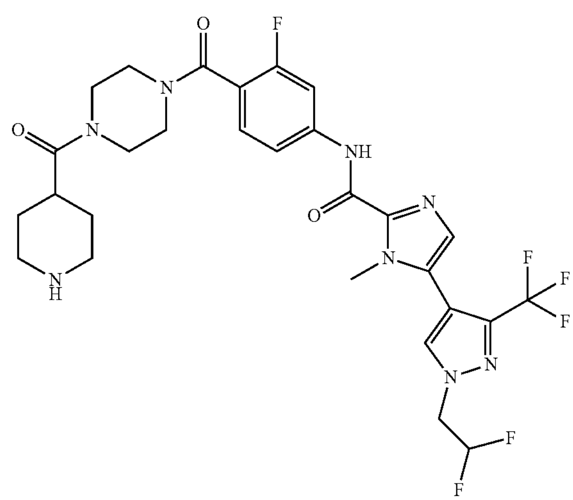 [SMILES: Cn1c(-c2cn(CC(F)F)nc2C(F)(F)F)cnc1C(=O)Nc1ccc(C(=O)N2CCN(C(=O)C3CCNCC3)CC2)c(F)c1] | 641.3 |

| Example | Name | Structure | ESI MS [M + H]+ |
|---|---|---|---|
| 302 | N-(4-(4-(4-aminobutanoyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 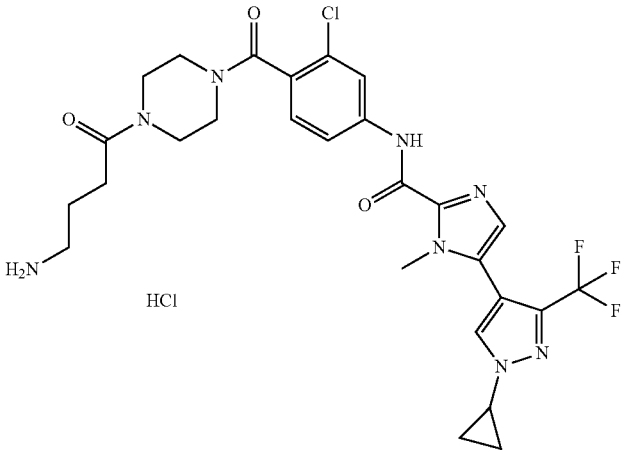 [SMILES: Cn1c(-c2cn(C3CC3)nc2C(F)(F)F)cnc1C(=O)Nc1ccc(C(=O)N2CCN(C(=O)CCCN)CC2)c(Cl)c1 ; Cl] | 607.3 |
| 303 | 4-[2-chloro-4-[[5-[1-(2,2-difluoroethyl)-3-(trifluoromethyl)pyrazol-4-yl]-1-methyl-imidazole-2-carbonyl]amino]benzoyl]-N-[(3-hydroxyazetidin-3-yl)methyl]piperazine-1-carboxamide; formic acid | 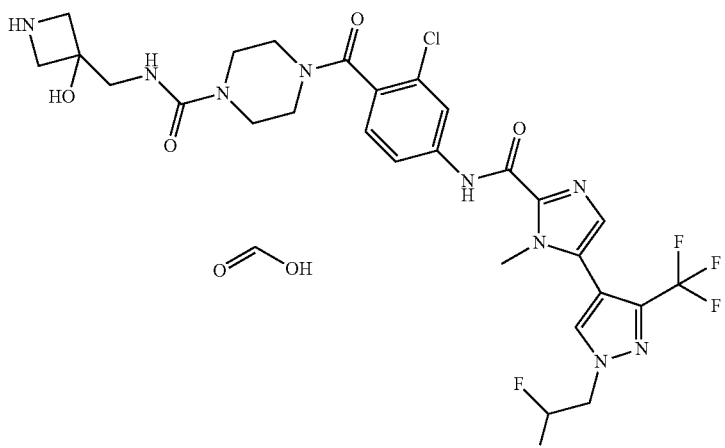 | 673.9 |
| 304 | N-(3-chloro-4-(4-(piperidine-4-carbonyl)piperazine-1-carbonyl)phenyl)-5-(1-(cyclopentylmethyl)-3-(trifluoromethyl)-1H-pyrazol-4-yl)-1-methyl-1H-imidazole-2-carboxamide hydrochloride | 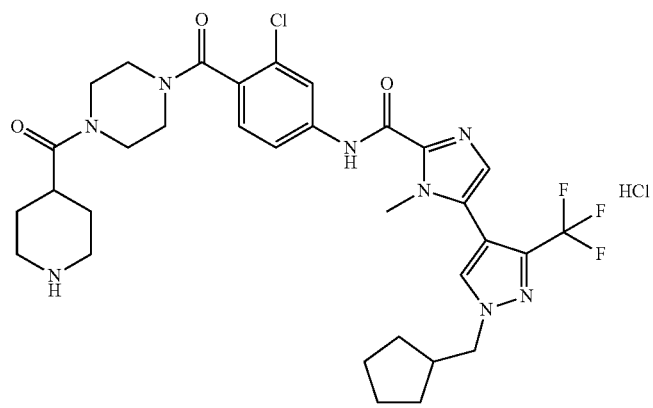 [SMILES: Cn1c(-c2cn(CC3CCCC3)nc2C(F)(F)F)cnc1C(=O)Nc1ccc(C(=O)N2CCN(C(=O)C3CCNCC3)CC2)c(Cl)c1 ; Cl] | 675.3 |

| Example | Name | Structure | ESI MS [M + H]+ |
|---|---|---|---|
| 305 | rac-N-((1s,3s)-3-aminocyclobutyl)-4-(2-chloro-4-(1-methyl-5-(1-(2,2,2-trifluoroethyl)-3-(trifluoromethyl)-1H-pyrazol-4-yl)-1H-imidazole-2-carboxamido)benzoyl)piperazine-1-carboxamide hydrochloride | 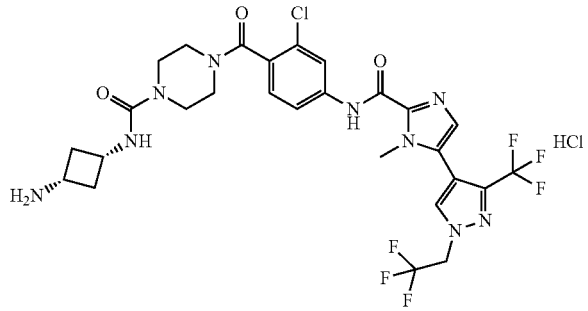 [SMILES: Cn1c(-c2cn(CC(F)(F)F)nc2C(F)(F)F)cnc1C(=O)Nc1ccc(C(=O)N2CCN(C(=O)N[C@H]3C[C@@H](N)C3)CC2)c(Cl)c1 ; Cl] | 676.2 |
| 306 | N-(3-chloro-4-((exo-3-(piperidine-4-carbonyl)-3-azabicyclo[3.1.0]hexan-6-yl)carbamoyl)phenyl)-5-(1-cyclopropyl-3-(trifluoromethyl)-1H-pyrazol-4-yl)-1-methyl-1H-imidazole-2-carboxamide | 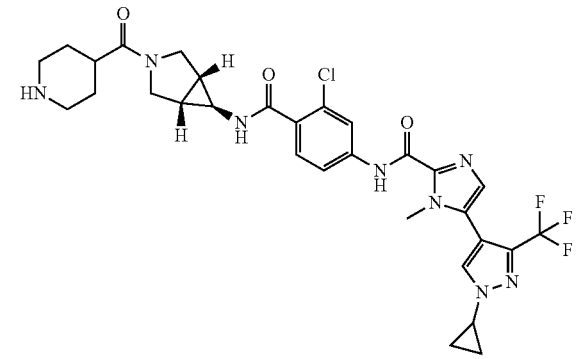 [SMILES: Cn1c(-c2cn(C3CC3)nc2C(F)(F)F)cnc1C(=O)Nc1ccc(C(=O)N[C@H]2[C@@H]3CN(C(=O)C4CCNCC4)C[C@@H]32)c(Cl)c1] | 645.2 |
| 307 | rac-N-(4-(((1s,3s)-3-aminocyclobutyl)carbamoyl)-3-chlorophenyl)-5-(1-(3,3-difluoroallyl)-3-(trifluoromethyl)-1H-pyrazol-4-yl)-1-methyl-1H-imidazole-2-carboxamide 2,2,2-trifluoroacetate | 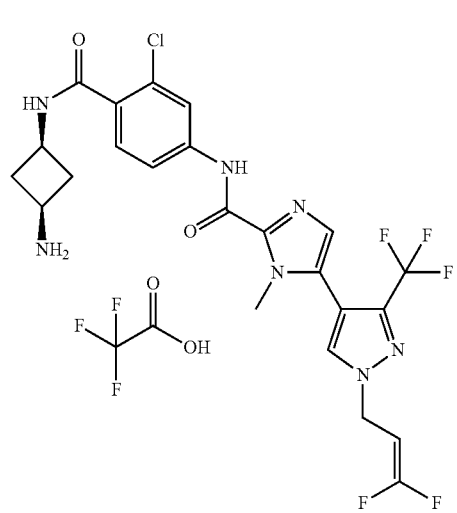 [SMILES: Cn1c(-c2cn(CC=C(F)F)nc2C(F)(F)F)cnc1C(=O)Nc1ccc(C(=O)N[C@H]2C[C@@H](N)C2)c(Cl)c1 ; O=C(O)C(F)(F)F] | 558.2 |

-continued

| Example | Name | Structure | ESI MS [M + H]+ |
|---|---|---|---|
| 308 | 5-[1-(2,2-difluoroethyl)-3-(trifluoromethyl)pyrazol-4-yl]-1-methyl-N-(3-methyl-4-methylsulfanyl-phenyl)imidazole-2-carboxamide | 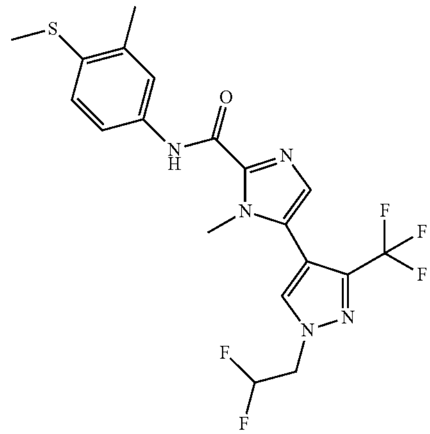 [SMILES: CSc1ccc(NC(=O)c2ncc(-c3cn(CC(F)F)nc3C(F)(F)F)n2C)cc1C] | 460.1 |
| 309 | N-(3-chloro-4-(4-(2-(piperidin-4-yl)acetyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 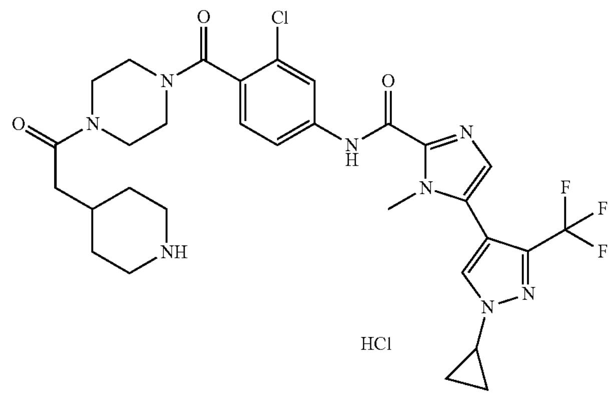 [SMILES: Cn1c(-c2cn(C3CC3)nc2C(F)(F)F)cnc1C(=O)Nc1ccc(C(=O)N2CCN(C(=O)CC3CCNCC3)CC2)c(Cl)c1 ; Cl] | 647.4 |
| 310 | rac-5-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)-N-((3R,4R)-4-hydroxypyrrolidin-3-yl)hexahydrocyclopenta[c]pyrrole-2(1H)-carboxamide formate | AND Enantiomer | 688.4 |

-continued

| Example | Name | Structure | ESI MS [M + H]+ |
|---|---|---|---|
| 311 | N-[3-chloro-4-[4-(4-hydroxypiperidine-3-carbonyl)piperazine-1-carbonyl]phenyl]-5-[1-cyclopropyl-3-(trifluoromethyl)pyrazol-4-yl]-1-methylimidazole-2-carboxamide;hydrochloride | 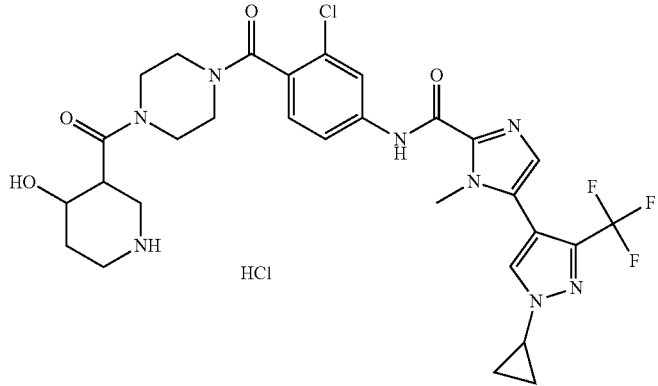 [SMILES: Cn1c(-c2cn(C3CC3)nc2C(F)(F)F)cnc1C(=O)Nc1ccc(C(=O)N2CCN(C(=O)C3CNCCC3O)CC2)c(Cl)c1 ; Cl] | 649.3 |
| 312 | (E)-5-(1-(but-2-en-1-yl)-3-(trifluoromethyl)-1H-pyrazol-4-yl)-N-(3-chloro-4-(piperidine-4-carbonyl)piperazine-1-carbonyl)phenyl)-1-methyl-1H-imidazole-2-carboxamide hydrochloride | 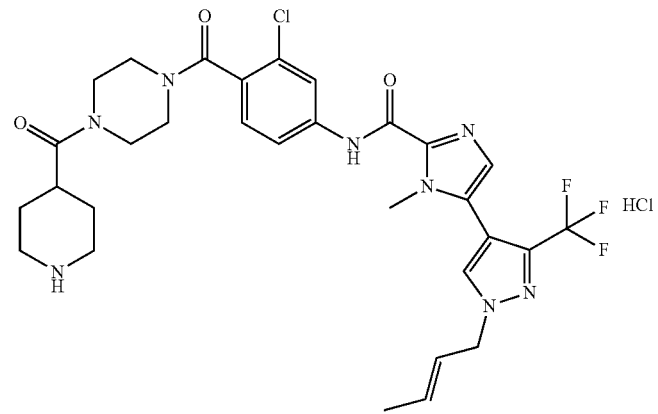 [SMILES: C/C=C/Cn1cc(-c2cnc(C(=O)Nc3ccc(C(=O)N4CCN(C(=O)C5CCNCC5)CC4)c(Cl)c3)n2C)c(C(F)(F)F)n1 ; Cl] | 647.2 |
| 313 | N-(3-chloro-4-(4-((2R,4S)-4-hydroxypyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 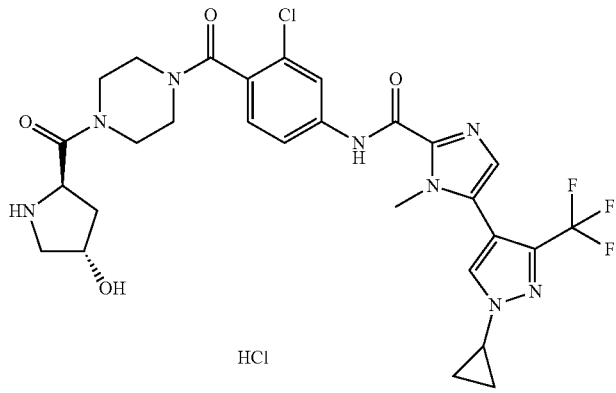 [SMILES: Cn1c(-c2cn(C3CC3)nc2C(F)(F)F)cnc1C(=O)Nc1ccc(C(=O)N2CCN(C(=O)[C@H]3C[C@H](O)CN3)CC2)c(Cl)c1 ; Cl] | 635.3 |
| 314 | tert-butyl (4-(2-chloro-4-(5-(1-(2,2-difluorocyclopropyl)-3-(trifluoromethyl)-1H-pyrazol-4-yl)-1-methyl-1H-imidazole-2-carboxamido)benzamido)butyl) carbamate | 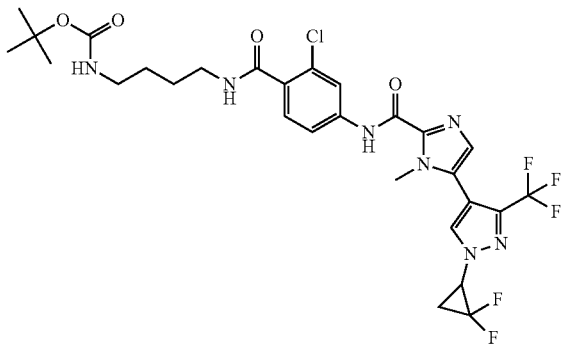 [SMILES: Cn1c(-c2cn(C3CC3(F)F)nc2C(F)(F)F)cnc1C(=O)Nc1ccc(C(=O)NCCCCNC(=O)OC(C)(C)C)c(Cl)c1] | 658.6 |

-continued

| Example | Name | Structure | ESI MS [M + H]+ |
|---|---|---|---|
| 315 | N-[3-chloro-4-[[3-[[(3R)-pyrrolidine-3-carbonyl]amino]cyclobutyl]carbamoyl]phenyl]-5-[1-(cyanomethyl)-3-(trifluoromethyl)pyrazol-4-yl]-1-methylimidazole-2-carboxamide;formic acid | 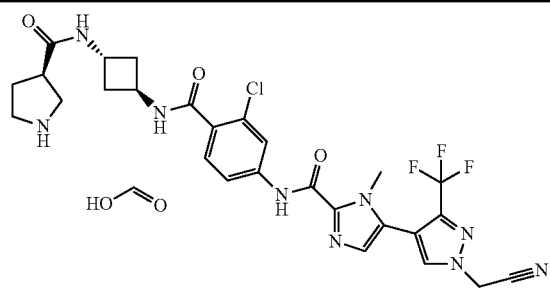 | 618.2 |
| 316 | N-[4-[[3-[[(3R)-3-aminopyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide; formic acid | 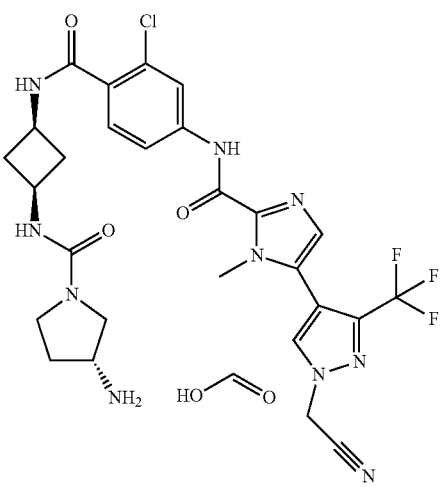 | 632.9 |
| 317 | N-(4-((6-aminospiro[3.3]heptan-2-yl)carbamoyl)-3-chlorophenyl)-5-(1-cyclopropyl-3-(trifluoromethyl)-1H-pyrazol-4-yl)-1-methyl-1H-imidazole-2-carboxamide hydrochloride | 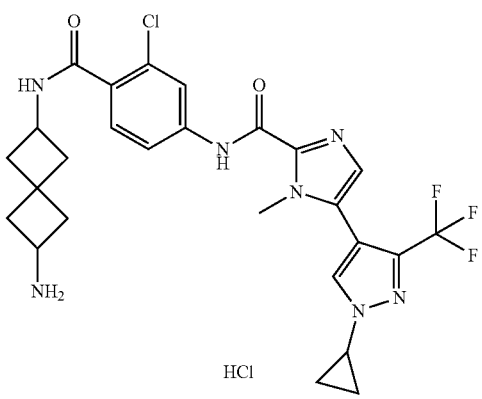 [SMILES: Cn1c(-c2cn(C3CC3)nc2C(F)(F)F)cnc1C(=O)Nc1ccc(C(=O)NC2CC3(CC(N)C3)C2)c(Cl)c1 ; Cl] | 562.2 |
| 318 | N-[3-chloro-4-[4-(3-hydroxypyrrolidine-3-carbonyl)piperazine-1-carbonyl]phenyl]-5-[1-cyclopropyl-3-(trifluoromethyl)pyrazol-4-yl]-1-methylimidazole-2-carboxamide;hydrochloride | 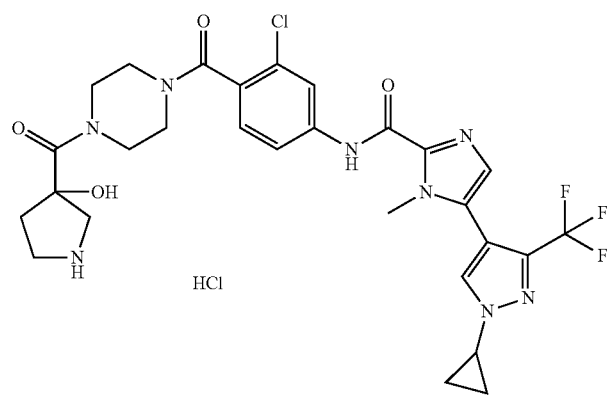 [SMILES: Cn1c(-c2cn(C3CC3)nc2C(F)(F)F)cnc1C(=O)Nc1ccc(C(=O)N2CCN(C(=O)C3(O)CCNC3)CC2)c(Cl)c1 ; Cl] | 635.3 |

| Example | Name | Structure | ESI MS [M + H]+ |
|---|---|---|---|
| 319 | N-(4-((3-azabicyclo[3.2.0]heptan-6-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 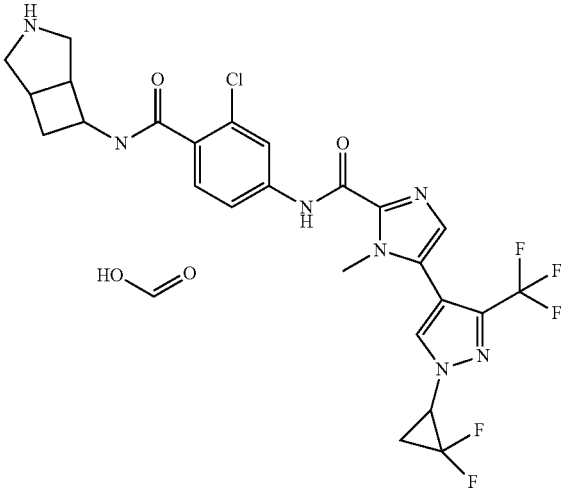 [SMILES: Cn1c(-c2cn(C3CC3(F)F)nc2C(F)(F)F)cnc1C(=O)Nc1ccc(C(=O)NC2CC3CNCC32)c(Cl)c1 ; O=CO] | 584.3 |
| 320 | 4-(2-chloro-4-(5-(1-cyclopropyl-3-(trifluoromethyl)-1H-pyrazol-4-yl)-1-methyl-1H-imidazole-2-carboxamido)benzoyl)-N-((4-hydroxypiperidin-4-yl)methyl)piperazine-1-carboxamide formate | 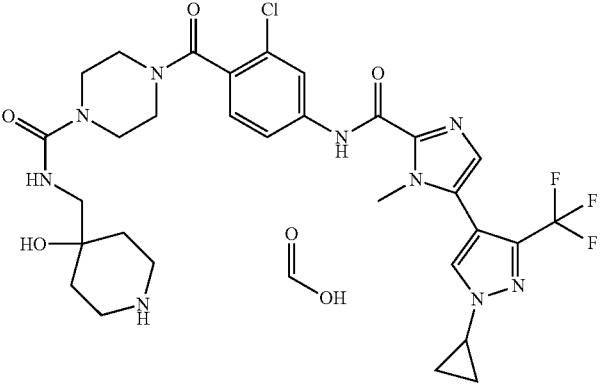 [SMILES: Cn1c(-c2cn(C3CC3)nc2C(F)(F)F)cnc1C(=O)Nc1ccc(C(=O)N2CCN(C(=O)NCC3(O)CCNCC3)CC2)c(Cl)c1 ; O=CO] | 678.3 |
| 321 | N-(3-chloro-4-(4-((2S,4R)-4-hydroxypyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 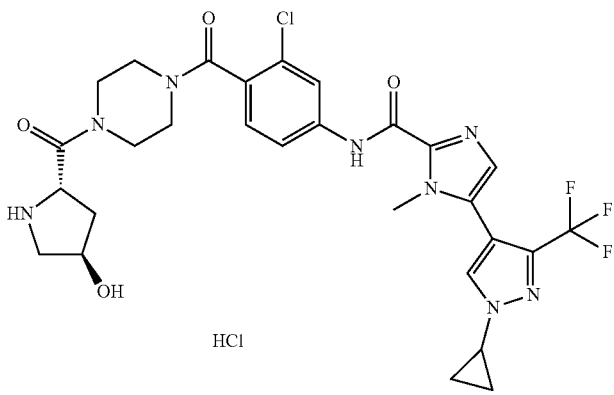 [SMILES: Cn1c(-c2cn(C3CC3)nc2C(F)(F)F)cnc1C(=O)Nc1ccc(C(=O)N2CCN(C(=O)[C@@H]3C[C@@H](O)CN3)CC2)c(Cl)c1 ; Cl] | 635.4 |

-continued

| Example | Name | Structure | ESI MS [M + H]+ |
|---|---|---|---|
| 322 | N-(4-((exo-3-((R)-3-aminopyrrolidine-1-carbonyl)-3-azabicyclo[3.1.0]hexan-6-yl)carbamoyl)-3-chlorophenyl)-5-(1-cyclopropyl-3-(trifluoromethyl)-1H-pyrazol-4-yl)-1-methyl-1H-imidazole-2-carboxamide formate | 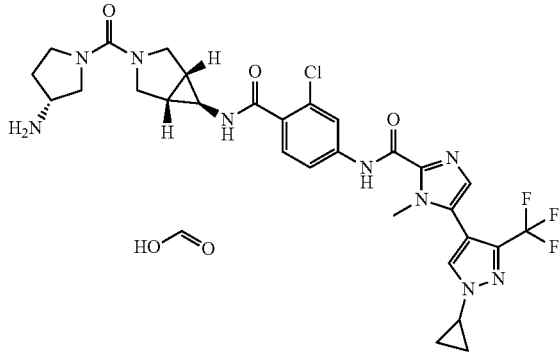 [SMILES: Cn1c(-c2cn(C3CC3)nc2C(F)(F)F)cnc1C(=O)Nc1ccc(C(=O)N[C@H]2[C@@H]3CN(C(=O)N4CC[C@@H](N)C4)C[C@@H]32)c(Cl)c1 ; O=CO] | 646.4 |
| 323 | N-(4-([4,4'-bipiperidine]-1-carbonyl)-3-chlorophenyl)-5-(1-cyclopropyl-3-(trifluoromethyl)-1H-pyrazol-4-yl)-1-methyl-1H-imidazole-2-carboxamide formate | 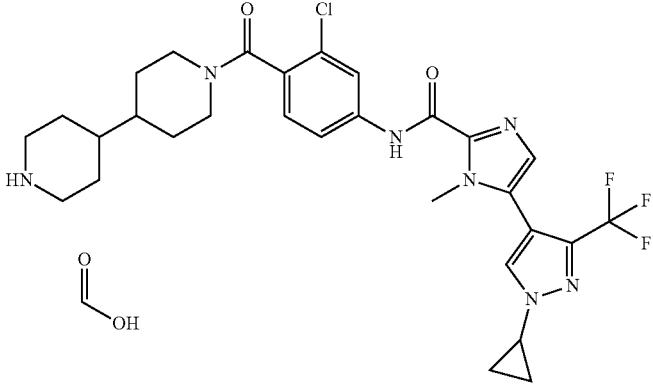 [SMILES: Cn1c(-c2cn(C3CC3)nc2C(F)(F)F)cnc1C(=O)Nc1ccc(C(=O)N2CCC(C3CCNCC3)CC2)c(Cl)c1 ; O=CO] | 604.3 |
| 324 | N-[4-[[4-[[(2S)-2-aminopropanoyl]amino]cyclohexyl]carbamoyl]-3-chlorophenyl]-5-[1-(cyanomethyl)-3-(trifluoromethyl)pyrazol-4-yl]-1-methylimidazole-2-carboxamide;2,2,2-trifluoroacetic acid | 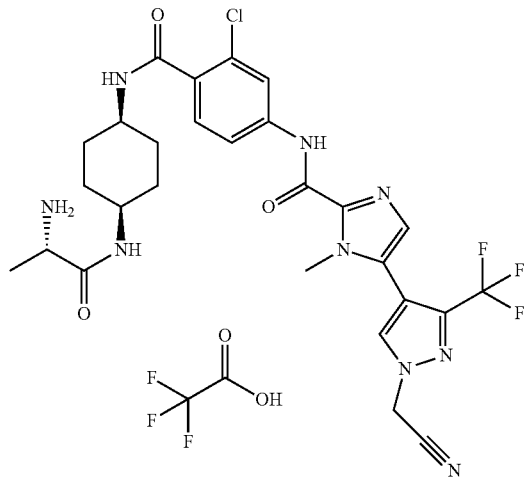 [SMILES: C[C@H](N)C(=O)N[C@H]1CC[C@@H](NC(=O)c2ccc(NC(=O)c3ncc(-c4cn(CC#N)nc4C(F)(F)F)n3C)cc2Cl)CC1 ; O=C(O)C(F)(F)F] | 620.3 |

-continued

| Example | Name | Structure | ESI MS [M + H]+ |
|---|---|---|---|
| 325 | rac-N-((is,3s)-3-aminocyclobutyl)-4-(2-bromo-4-(5-(1-ethyl-3-(trifluoromethyl)-1H-pyrazol-4-yl)-1-methyl-1H-imidazole-2-carboxamido)benzoyl)piperazine-1-carboxamidee formate | 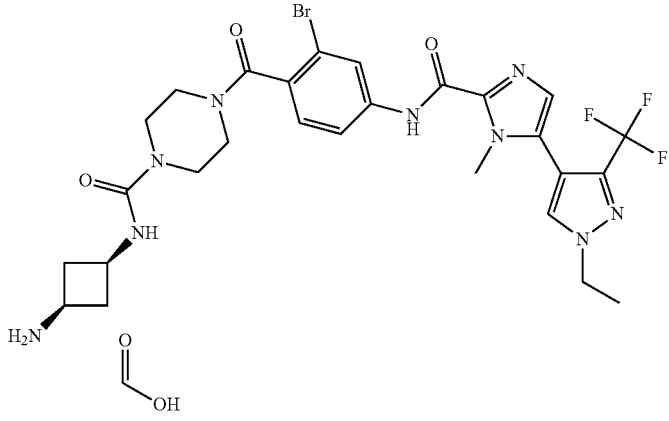 | 668.2 |
| 326 | 3-amino-N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]piperidine-1-carboxamide; formic acid | 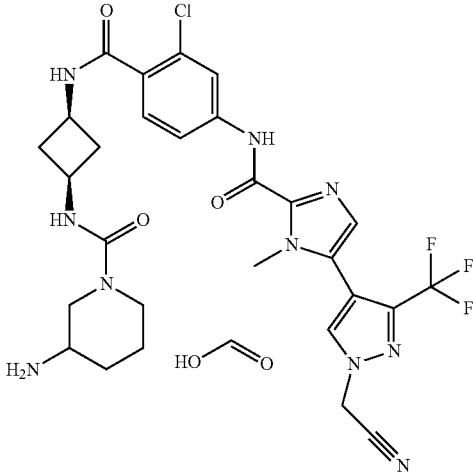 | 647.2 |
| 327 | N-(4-(4-((1S,3R)-3-aminocyclopentane-1-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide hydrochloride | HCl 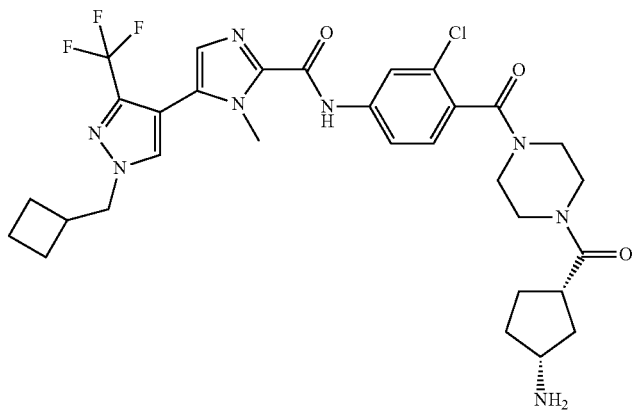 | 661.4 |

| Example | Name | Structure | ESI MS [M + H]+ |
|---|---|---|---|
| 328 | N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]-2,5-diazabicyclo[2.2.1]heptane-2-carboxamide; formic acid | 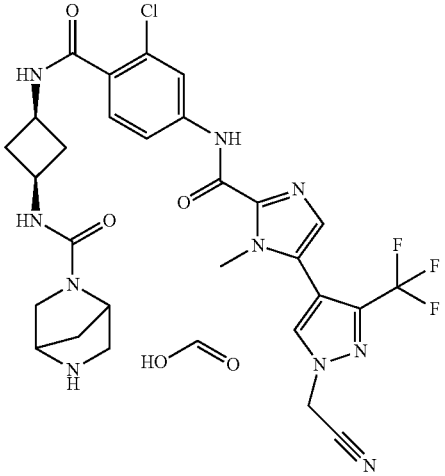 | 645.1 |
| 329 | rac-N-(3-chloro-4-((3aR,6aR)-octahydropyrrolo[3,4-c]pyrrole-2-carbonyl)phenyl)-5-(1-(2,2-difluorocyclopropyl)-3-(trifluoromethyl)-1H-pyrazol-4-yl)-1-methyl-1H-imidazole-2-carboxamide formate | AND Enantiomer 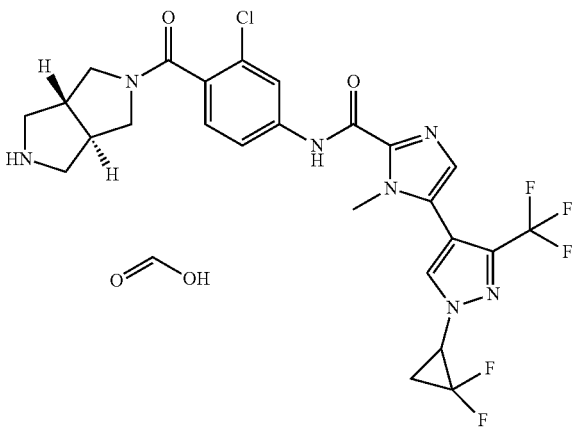 | 584.3 |
| 330 | N-[4-[4-(2-aminoacetyl)piperazine-1-carbonyl]-3-chlorophenyl]-5-[1-ethyl-3-(trifluoromethyl)pyrazol-4-yl]-1-methylimidazole-2-carboxamide;hydrochloride | 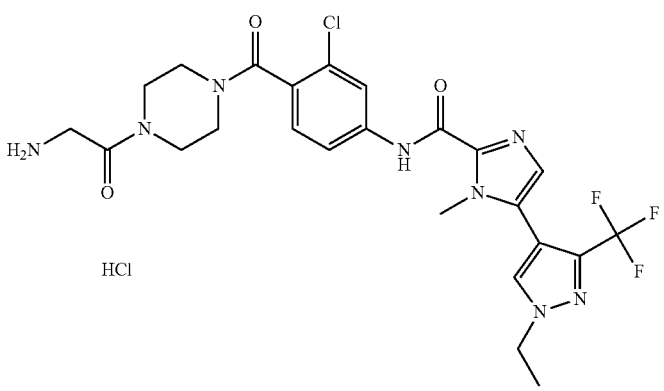 [SMILES: CCn1cc(-c2cnc(C(=O)Nc3ccc(C(=O)N4CCN(C(=O)CN)CC4)c(Cl)c3)n2C)c(C(F)(F)F)n1 ; Cl] | 567.2 |

| Example | Name | Structure | ESI MS [M + H]+ |
|---|---|---|---|
| 331 | rac-N-(3-chloro-4-((4-(3-((3S,4S)-4-hydroxypyrrolidin-3-yl)-1-methylureido)butyl)carbamoyl)phenyl)-5-(1-(2,2-difluorocyclopropyl)-3-(trifluoromethyl)-1H-pyrazol-4-yl)-1-methyl-1H-imidazole-2-carboxamide formate | AND Enantiomer | 702.5 |
| 332 | N-(3-chloro-4-(4-(piperidine-4-carbonyl)piperazine-1-carbonyl)phenyl)-1-methyl-5-(1-(2-(trifluoromethoxy)ethyl)-3-(trifluoromethyl)-1H-pyrazol-4-yl)-1H-imidazole-2-carboxamide hydrochloride | 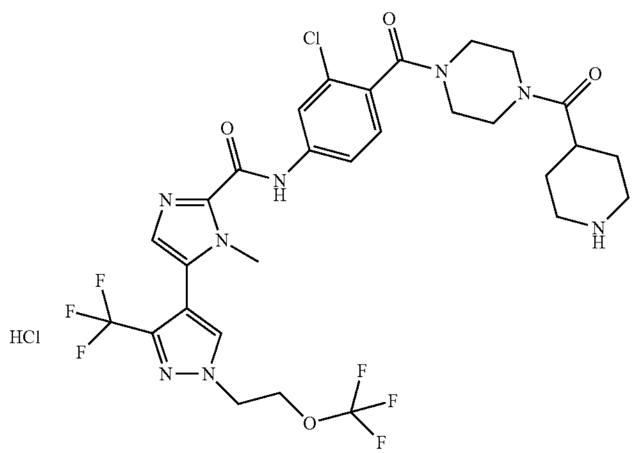 [SMILES: Cl ; Cn1c(-c2cn(CCOC(F)(F)F)nc2C(F)(F)F)cnc1C(=O)Nc1ccc(C(=O)N2CCN(C(=O)C3CCNCC3)CC2)c(Cl)c1] | 705.2 |
| 333 | rac-N-((1s,3s)-3-aminocyclobutyl)-4-(2-chloro-4-(5-(1-(2,2-difluorocyclopropyl)-3-(trifluoromethyl)-1H-pyrazol-4-yl)-1-methyl-1H-imidazole-2-carboxamido)benzamido)-4-methylpiperidine-1-carboxamide formate | 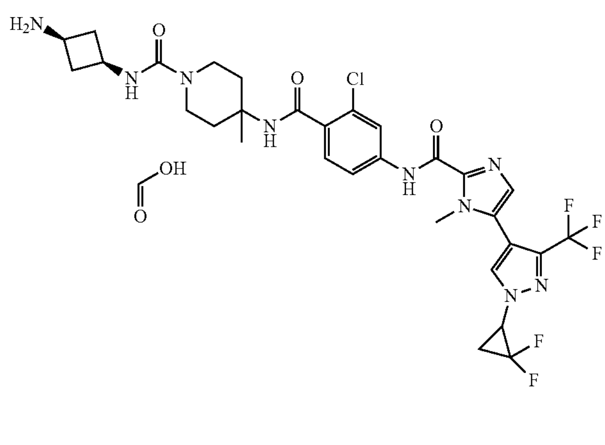 [SMILES: Cn1c(-c2cn(C3CC3(F)F)nc2C(F)(F)F)cnc1C(=O)Nc1ccc(C(=O)NC2(C)CCN(C(=O)N[C@H]3C[C@@H](N)C3)CC2)c(Cl)c1 ; O=CO] | 698.5 |

| Example | Name | Structure | ESI MS [M + H]+ |
|---|---|---|---|
| 334 | exo-N-((1R,2S)-2-aminocyclopentyl)-6-(2-chloro-4-(5-(1-cyclopropyl-3-(trifluoromethyl)-1H-pyrazol-4-yl)-1-methyl-1H-imidazole-2-carboxamido)benzamido)-3-azabicyclo[3.1.0]hexane-3-carboxamide formate | 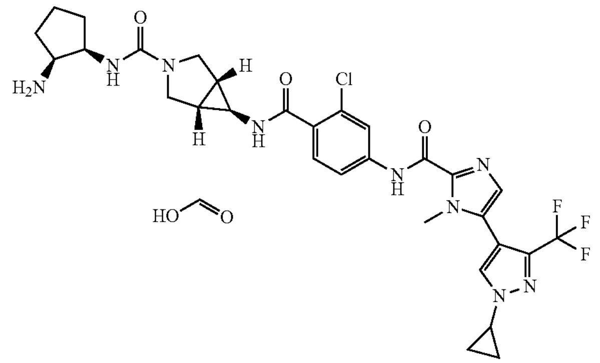 [SMILES: Cn1c(-c2cn(C3CC3)nc2C(F)(F)F)cnc1C(=O)Nc1ccc(C(=O)N[C@H]2[C@@H]3CN(C(=O)N[C@@H]4CCC[C@@H]4N)C[C@@H]32)c(Cl)c1 ; O=CO] | 660.5 |
| 335 | N-(3-chloro-4-(4-((2S,4R)-4-hydroxypyrrolidine-2-carbonyl)piperazine-1-carbonyl)phenyl)-5-(1-(cyclobutylmethyl)-3-(trifluoromethyl)-1H-pyrazol-4-yl)-1-methyl-1H-imidazole-2-carboxamide bis(2,2,2-trifluoroacetate) | 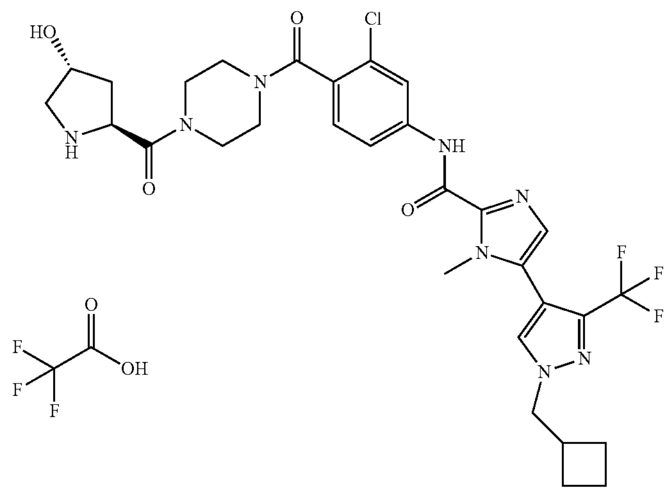 [SMILES: O=C(O)C(F)(F)F ; Cn1c(-c2cn(CC3CCC3)nc2C(F)(F)F)cnc1C(=O)Nc1ccc(C(=O)N2CCN(C(=O)[C@@H]3C[C@@H](O)CN3)CC2)c(Cl)c1] | 663.3 |
| 336 | N-(3-chloro-4-(piperazine-1-carbonyl)phenyl)-5-(1-(2,2-difluoroethyl)-3-(trifluoromethyl)-1H-pyrazol-4-yl)-1-methyl-1H-imidazole-2-carboxamide formate | 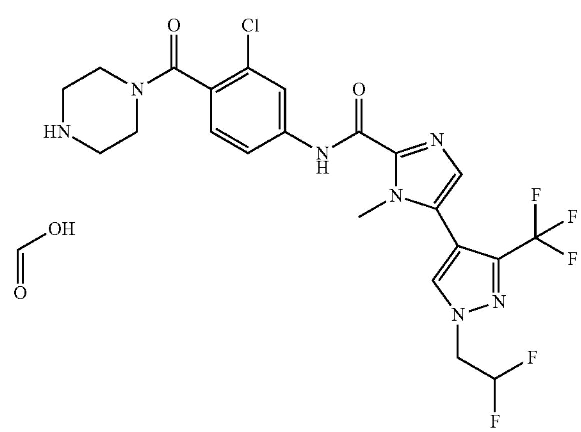 [SMILES: O=CO ; Cn1c(-c2cn(CC(F)F)nc2C(F)(F)F)cnc1C(=O)Nc1ccc(C(=O)N2CCNCC2)c(Cl)c1] | 546.2 |

| Example | Name | Structure | ESI MS [M + H]+ |
|---|---|---|---|
| 337 | 4-(2-chloro-4-(5-(1-(2,2-difluorocyclopropyl)-3-(trifluoromethyl)-1H-pyrazol-4-yl)-1-methyl-1H-imidazole-2-carboxamido)benzamido)-N-(trans-4-hydroxypyrrolidin-3-yl)piperidine-1-carboxamide | AND Enantiomer 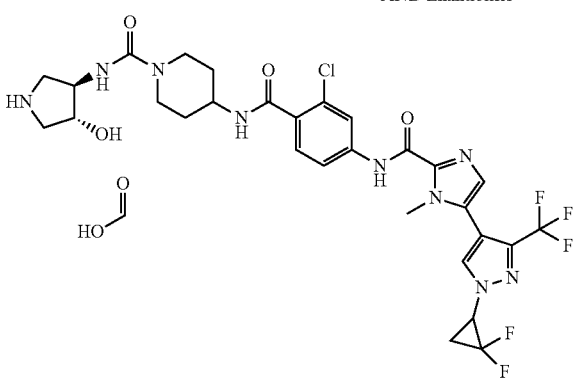 | 700.5 |
| 338 | N-(3-chloro-4-(4-(piperazin-1-ylsulfonyl)piperazine-1-carbonyl)phenyl)-5-(1-cyclopropyl-3-(trifluoromethyl)-1H-pyrazol-4-yl)-1-methyl-1H-imidazole-2-carboxamide formate | 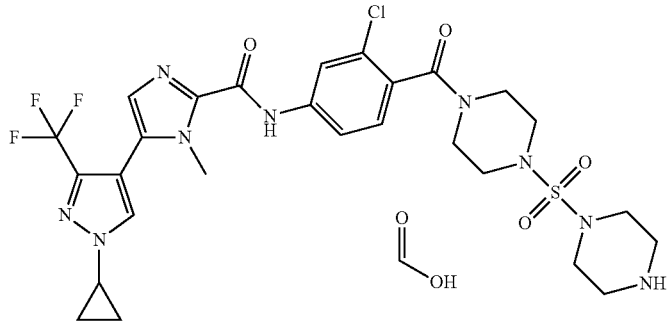 [SMILES: Cn1c(-c2cn(C3CC3)nc2C(F)(F)F)cnc1C(=O)Nc1ccc(C(=O)N2CCN(S(=O)(=O)N3CCNCC3)CC2)c(Cl)c1 ; O=CO] | 670.3 |
| 339 | N-(3-aminocyclobutyl)-1-[2-chloro-4-[[5-[1-cyclopropyl-3-(trifluoromethyl)pyrazol-4-yl]-1-methyl-imidazole-2-carbonyl]amino]benzoyl]piperidine-4-carboxamide; formic acid | 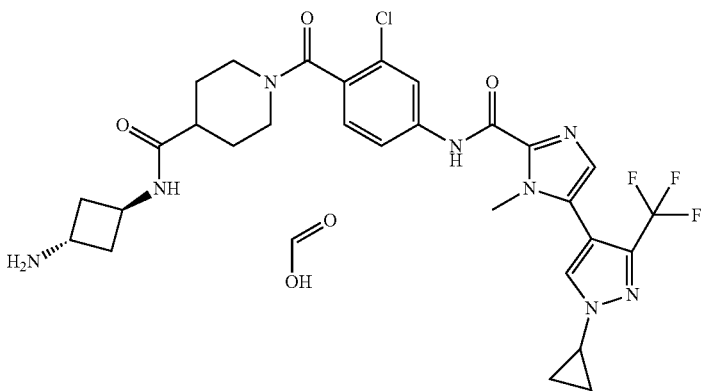 [SMILES: Cn1c(-c2cn(C3CC3)nc2C(F)(F)F)cnc1C(=O)Nc1ccc(C(=O)N2CCC(C(=O)N[C@H]3C[C@H](N)C3)CC2)c(Cl)c1 ; O=CO] | 633.2 |

-continued

| Example | Name | Structure | ESI MS [M + H]+ |
|---|---|---|---|
| 340 | N-[4-[4-(3-aminocyclobutanecarbonyl)piperazine-1-carbonyl]-3-ethyl-phenyl]-5-[1-(cyanomethyl)-3-(trifluoromethyl)pyrazol-4-yl]-1-methyl-imidazole-2-carboxamide; formic acid | 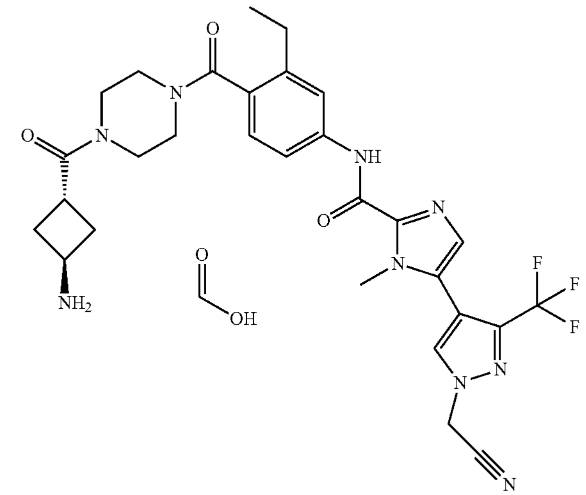 [SMILES: CCc1cc(NC(=O)c2ncc(-c3cn(CC#N)nc3C(F)(F)F)n2C)ccc1C(=O)N1CCN(C(=O)[C@H]2C[C@H](N)C2)CC1 ; O=CO] | 612.3 |
| 341 | N-(3-chloro-4-((4-hydroxypyrrolidin-3-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate | 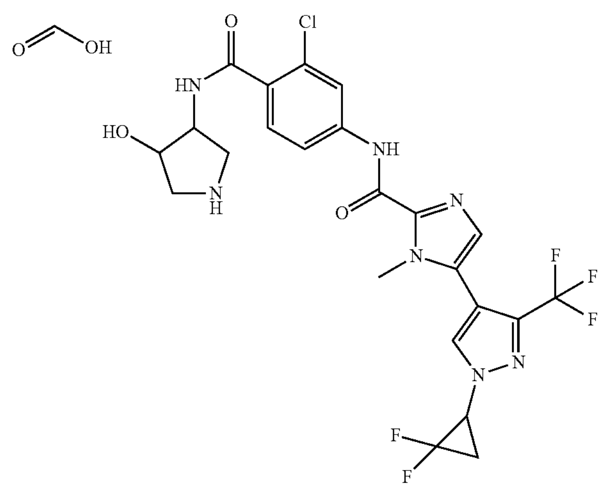 [SMILES: O=CO ; Cn1c(-c2cn(C3CC3(F)F)nc2C(F)(F)F)cnc1C(=O)Nc1ccc(C(=O)NC2CNCC2O)c(Cl)c1] | 574.3 |
| 342 | N-[4-[N-(3-aminopropyl)-S-methyl-sulfonimidoyl]-3-methyl-phenyl]-1-methyl-5-[1-prop-2-ynyl-3-(trifluoromethyl)pyrazol-4-yl]imidazole-2-carboxamide; formic acid | 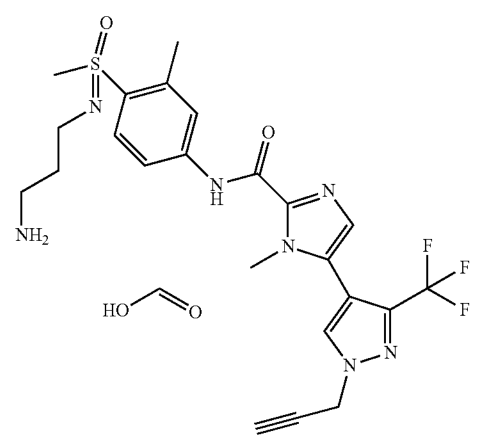 [SMILES: C#CCn1cc(-c2cnc(C(=O)Nc3ccc(S(C)(=O)=NCCCN)c(C)c3)n2C)c(C(F)(F)F)n1 ; O=CO] | 522.3 |

-continued

| Example | Name | Structure | ESI MS [M + H]+ |
|---|---|---|---|
| 343 | 4-[2-chloro-4-[[5-[1-(cyanomethyl)-3-(trifluoromethyl)pyrazol-4-yl]-1-methyl-imidazole-2-carbonyl]amino]benzoyl]-N-[(3-hydroxyazetidin-3-yl)methyl]piperazine-1-carboxamide; formic acid | 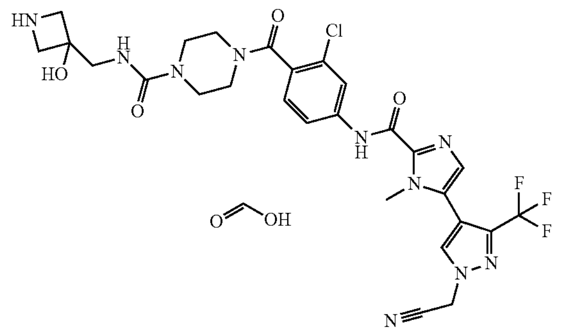 [SMILES: Cn1c(-c2cn(CC#N)nc2C(F)(F)F)cnc1C(=O)Nc1ccc(C(=O)N2CCN(C(=O)NCC3(O)CNC3)CC2)c(Cl)c1 ; O=CO] | 648.9 |
| 344 | N-(3-chloro-4-((4-methylpiperidin-4-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate | 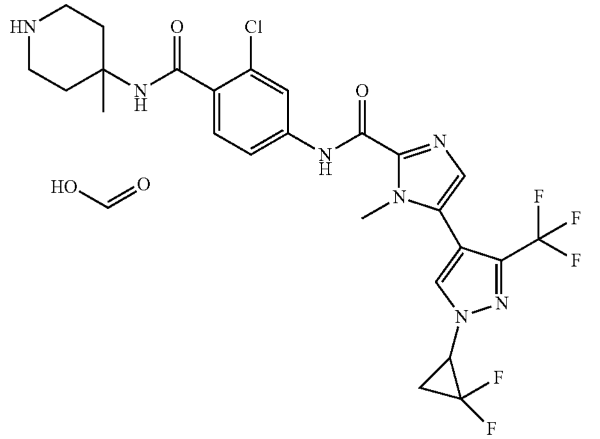 [SMILES: Cn1c(-c2cn(C3CC3(F)F)nc2C(F)(F)F)cnc1C(=O)Nc1ccc(C(=O)NC2(C)CCNCC2)c(Cl)c1 ; O=CO] | 586.3 |
| 345 | N-(4-((4-aminobutyl)carbamoyl)-3-chlorophenyl)-5-(1-(cyanomethyl)-3-(trifluoromethyl)-1H-pyrazol-4-yl)-1-methyl-1H-imidazole-2-carboxamide tris(2,2,2-trifluoroacetate) | 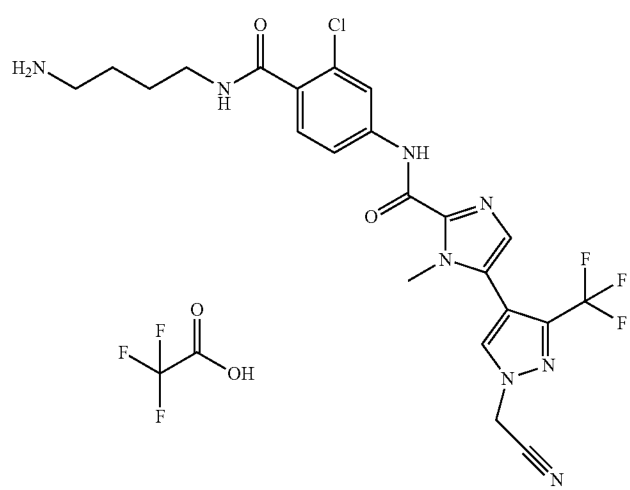 [SMILES: Cn1c(-c2cn(CC#N)nc2C(F)(F)F)cnc1C(=O)Nc1ccc(C(=O)NCCCCN)c(Cl)c1 ; O=C(O)C(F)(F)F] | 523.2 |

| Example | Name | Structure | ESI MS [M + H]+ |
|---|---|---|---|
| 346 | rac-N-(4-(((1R,3r,5S)-8-azabicyclo[3.2.1]octan-3-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide formate | 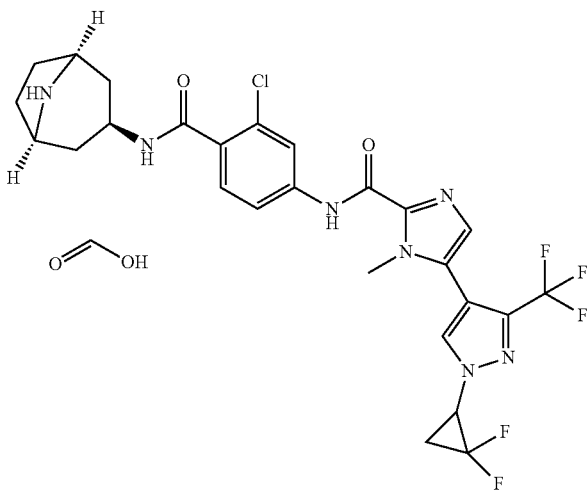 [SMILES: Cn1c(-c2cn(C3CC3(F)F)nc2C(F)(F)F)cnc1C(=O)Nc1ccc(C(=O)N[C@H]2C[C@H]3CC[C@@H](C2)N3)c(Cl)c1 ; O=CO] | 598.3 |
| 347 | rac-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-N-((3S,4S)-4-hydroxypyrrolidin-3-yl)-3-azabicyclo[3.2.0]heptane-3-carboxamide formate | AND Enantiomer<br>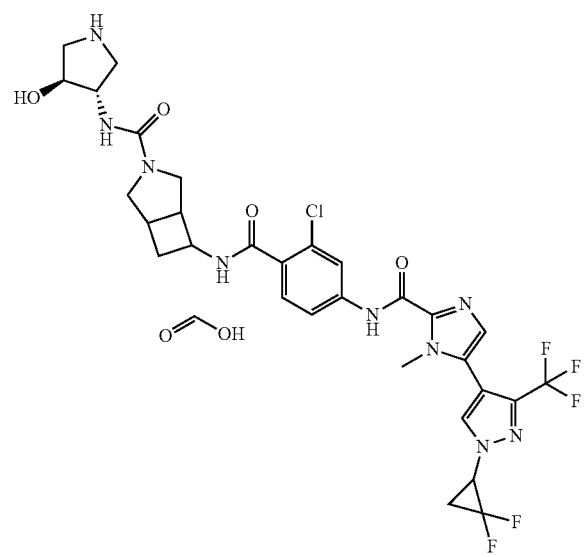 | 712.4 |
| 348 | (R)-N-(4-(4-(azetidine-2-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide hydrochloride | 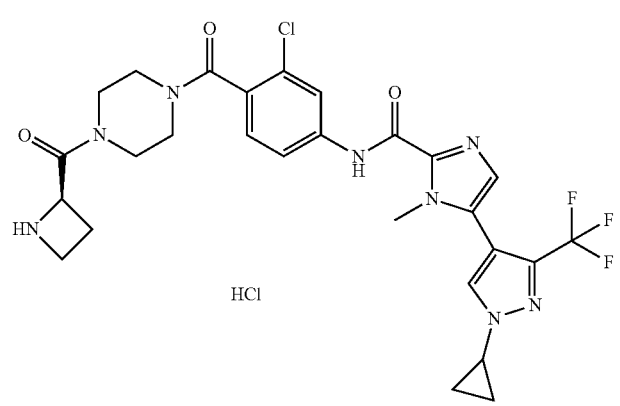 [SMILES: Cn1c(-c2cn(C3CC3)nc2C(F)(F)F)cnc1C(=O)Nc1ccc(C(=O)N2CCN(C(=O)[C@H]3CCN3)CC2)c(Cl)c1 ; Cl] | 605.4 |

-continued

| Example | Name | Structure | ESI MS [M + H]+ |
|---|---|---|---|
| 349 | (R)-N-(4-(4-(3-aminopyrrolidine-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide formate | 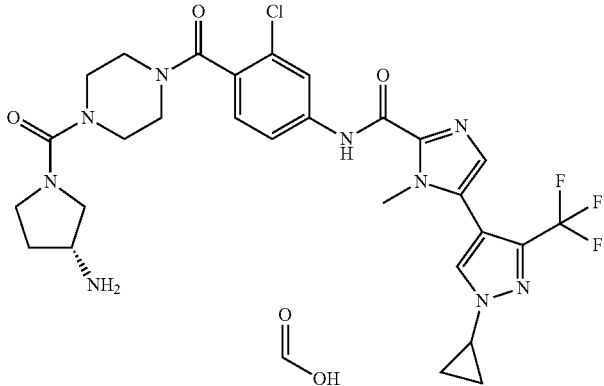 [SMILES: Cn1c(-c2cn(C3CC3)nc2C(F)(F)F)cnc1C(=O)Nc1ccc(C(=O)N2CCN(C(=O)N3CC[C@@H](N)C3)CC2)c(Cl)c1 ; O=CO] | 634.3 |
| 350 | rac-N-(3-chloro-4-(((trans-1-(((3R,4R)-4-hydroxypyrrolidin-3-yl)carbamoyl)-4-methoxypyrrolidin-3-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate | AND Enantiomer<br />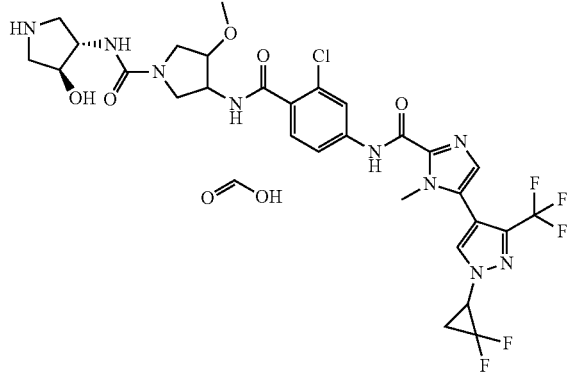 | 688.4 |
| 351 | N-[4-[(4-aminocyclohexyl)carbamoyl]-3-chlorophenyl]-5-[1-(cyanomethyl)-3-(trifluoromethyl)pyrazol-4-yl]-1-methylimidazole-2-carboxamide;2,2,2-trifluoroacetic acid | 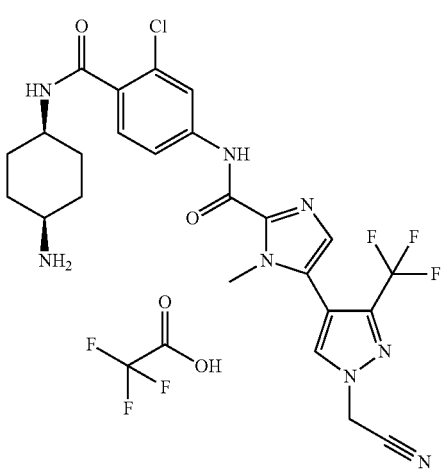 [SMILES: Cn1c(-c2cn(CC#N)nc2C(F)(F)F)cnc1C(=O)Nc1ccc(C(=O)N[C@H]2CC[C@@H](N)CC2)c(Cl)c1 ; O=C(O)C(F)(F)F] | 549.3 |

-continued

| Example | Name | Structure | ESI MS [M + H]+ |
|---|---|---|---|
| 352 | N-(3-chloro-4-(4-(piperidine-4-carbonyl)piperazine-1-carbonyl)phenyl)-5-(1-(2-cyclopropylethyl)-3-(trifluoromethyl)-1H-pyrazol-4-yl)-1-methyl-1H-imidazole-2-carboxamide hydrochloride | 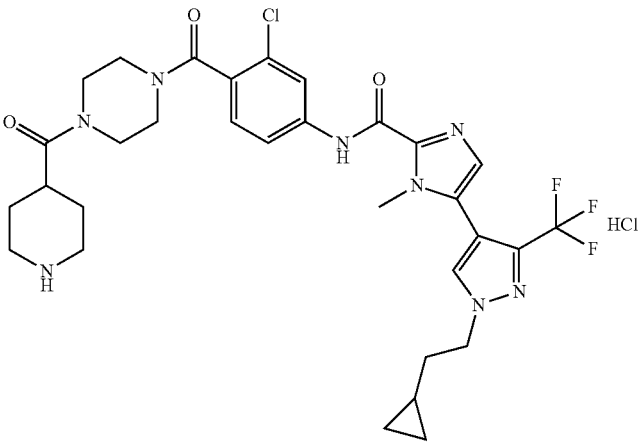 [SMILES: Cn1c(-c2cn(CCC3CC3)nc2C(F)(F)F)cnc1C(=O)Nc1ccc(C(=O)N2CCN(C(=O)C3CCNCC3)CC2)c(Cl)c1 ; Cl] | 661.3 |
| 353 | N-[4-[N-(3-aminopropyl)-S-methyl-sulfonimidoyl]-3-methyl-phenyl]-5-[1-(2,2-difluoroethyl)-3-(trifluoromethyl)pyrazol-4-yl]-1-methyl-imidazole-2-carboxamide; formic acid | 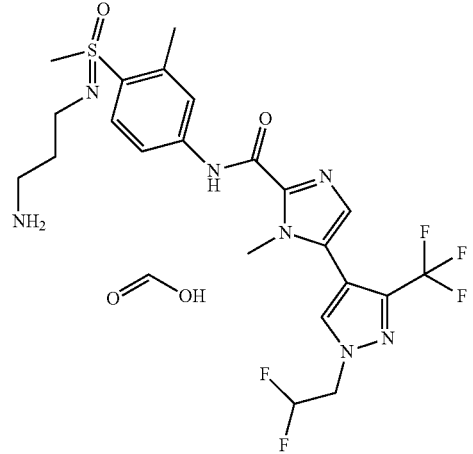 [SMILES: Cc1cc(NC(=O)c2ncc(-c3cn(CC(F)F)nc3C(F)(F)F)n2C)ccc1S(C)(=O)=NCCCN ; O=CO] | 548.2 |
| 354 | N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]-3-methyl-piperazine-1-carboxamide; formic acid | 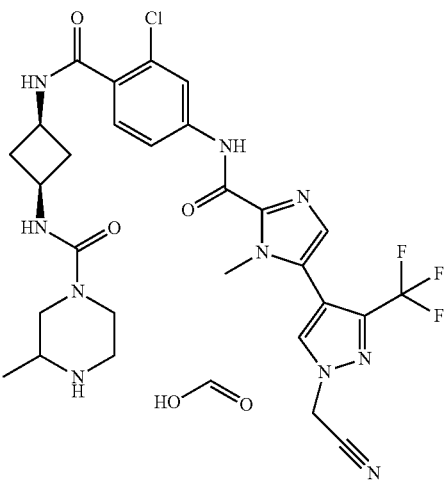 [SMILES: CC1CN(C(=O)N[C@H]2C[C@@H](NC(=O)c3ccc(NC(=O)c4ncc(-c5cn(CC#N)nc5C(F)(F)F)n4C)cc3Cl)C2)CCN1 ; O=CO] | 647.2 |

-continued

| Example | Name | Structure | ESI MS [M + H]+ |
|---|---|---|---|
| 355 | N-[4-[4-(3-aminocyclobutanecarbonyl)piperazine-1-carbonyl]-3-chlorophenyl]-5-[1-(cyanomethyl)-3-(trifluoromethyl)pyrazol-4-yl]-1-methylimidazole-2-carboxamide;trihydrochloride | 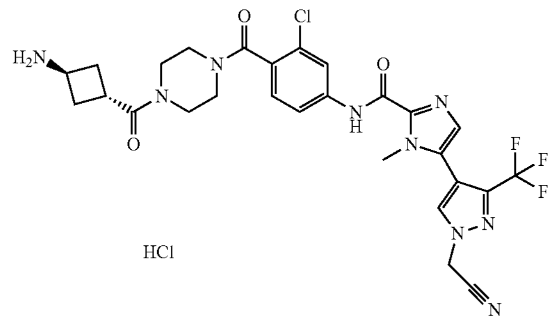 [SMILES: Cn1c(-c2cn(CC#N)nc2C(F)(F)F)cnc1C(=O)Nc1ccc(C(=O)N2CCN(C(=O)[C@H]3C[C@H](N)C3)CC2)c(Cl)c1 ; Cl] | 618.3 |
| 356 | N-(4-((5-aminopentyl)carbamoyl)-3-ethylphenyl)-5-(1-(2,2-difluoroethyl)-3-(trifluoromethyl)-1H-pyrazol-4-yl)-1-methyl-1H-imidazole-2-carboxamide hydrochloride | 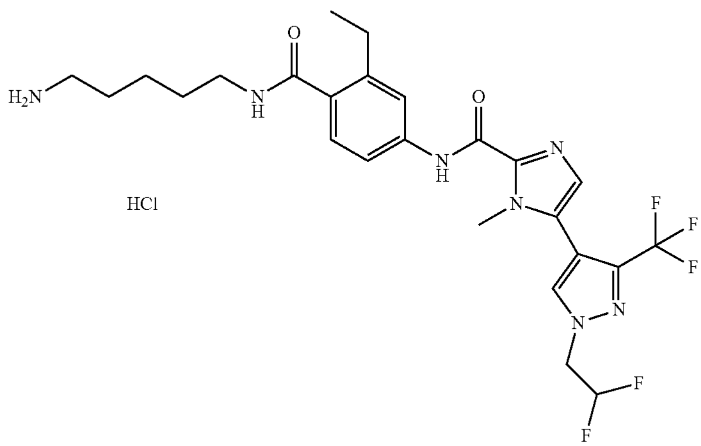 [SMILES: CCc1cc(NC(=O)c2ncc(-c3cn(CC(F)F)nc3C(F)(F)F)n2C)ccc1C(=O)NCCCCCN ; Cl] | 556.4 |
| 357 | N-(3-chloro-4-(4-((2-(dimethylamino)ethyl)(methyl)amino)piperidine-1-carbonyl)phenyl)-5-(1-cyclopropyl-3-(trifluoromethyl)-1H-pyrazol-4-yl)-1-methyl-1H-imidazole-2-carboxamide | 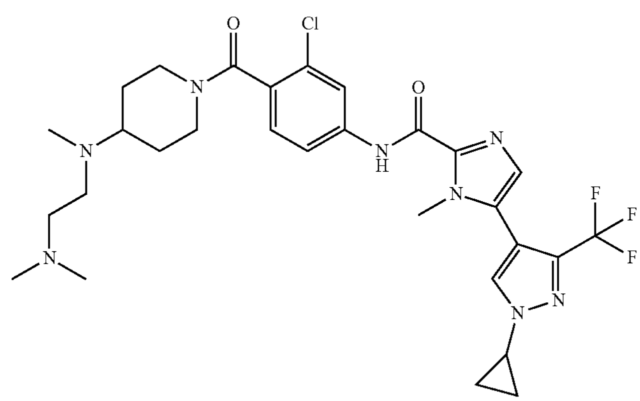 [SMILES: CN(C)CCN(C)C1CCN(C(=O)c2ccc(NC(=O)c3ncc(-c4cn(C5CC5)nc4C(F)(F)F)n3C)cc2Cl)CC1] | 621.3 |
| 358 | rac-N-(4-(4-((1R,5S)-3-azabicyclo[3.1.0]hexane-6-carbonyl)piperazine-1-carbonyl)-3-chlorophenyl)-5-(1-(cyclopropylmethyl)-3-(trifluoromethyl)-1H-pyrazol-4-yl)-1-methyl-1H-imidazole-2-carboxamide hydrochloride | 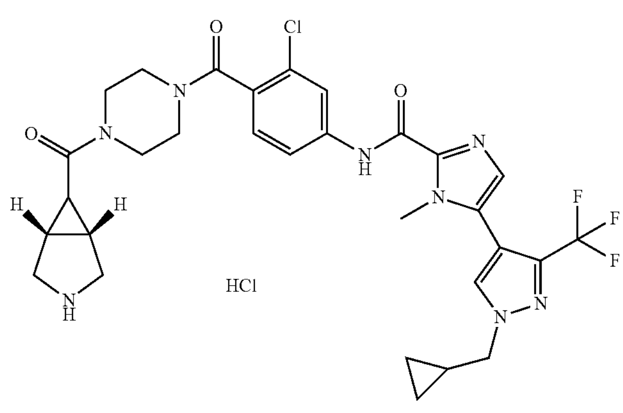 [SMILES: Cn1c(-c2cn(CC3CC3)nc2C(F)(F)F)cnc1C(=O)Nc1ccc(C(=O)N2CCN(C(=O)C3[C@H]4CNC[C@@H]34)CC2)c(Cl)c1 ; Cl] | 645.2 |

| Example | Name | Structure | ESI MS [M + H]+ |
|---|---|---|---|
| 359 | N-[4-[[3-[[3-(aminomethyl)pyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide; formic acid | 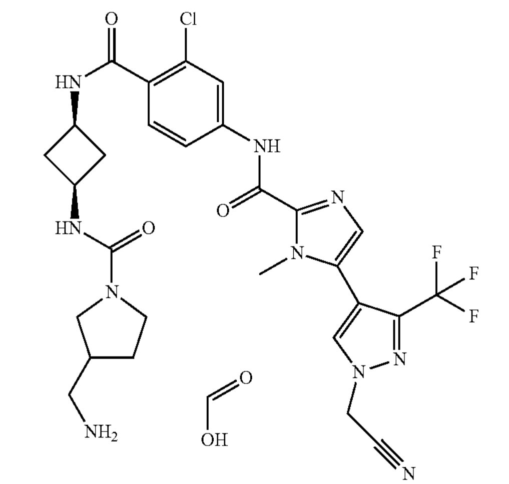 [SMILES: Cn1c(-c2cn(CC#N)nc2C(F)(F)F)cnc1C(=O)Nc1ccc(C(=O)N[C@H]2C[C@@H](NC(=O)N3CCC(CN)C3)C2)c(Cl)c1 ; O=CO] | 647.1 |
| 360 | N-(3-chloro-4-(4-(3-(dimethylamino)-3-methylbutyl)piperidine-1-carbonyl)phenyl)-5-(1-ethyl-3-(trifluoromethyl)-1H-pyrazol-4-yl)-1-methyl-1H-imidazole-2-carboxamide | 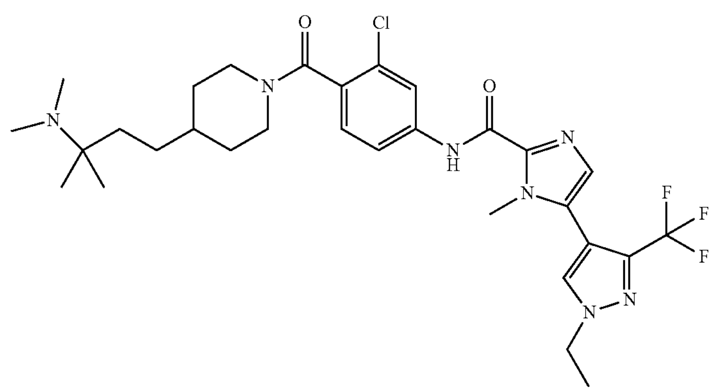 [SMILES: CCn1cc(-c2cnc(C(=O)Nc3ccc(C(=O)N4CCC(CCC(C)(C)N(C)C)CC4)c(Cl)c3)n2C)c(C(F)(F)F)n1] | 622.3 |
| 361 | N-[4-[[3-[[2-(aminomethyl)pyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide; formic acid | 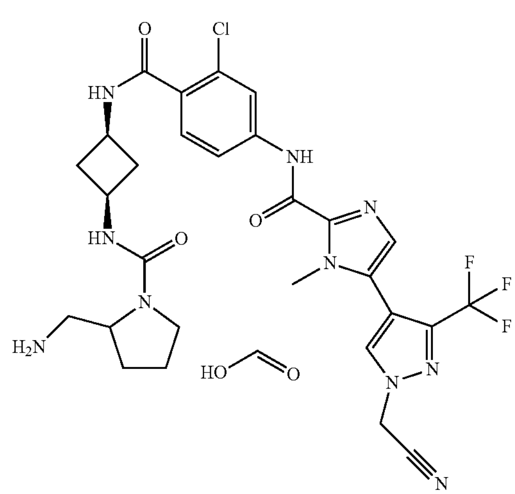 | 646.9 |

-continued

| Example | Name | Structure | ESI MS [M + H]+ |
|---|---|---|---|
| 362 | N-(4-(4-(4-aminopiperidine-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide formate | 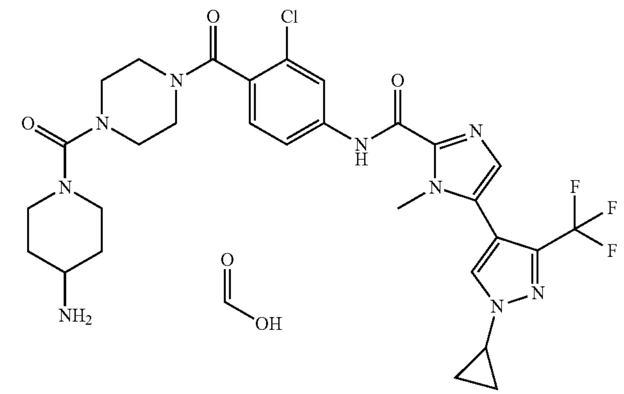 [SMILES: Cn1c(-c2cn(C3CC3)nc2C(F)(F)F)cnc1C(=O)Nc1ccc(C(=O)N2CCN(C(=O)N3CCC(N)CC3)CC2)c(Cl)c1 ; O=CO] | 648.3 |
| 363 | N-(3-chloro-4-(6-(piperidine-4-carbonyl)-1,6-diazaspiro[3.3]heptane-1-carbonyl)phenyl)-5-(1-(2,2-difluoroethyl)-3-(trifluoromethyl)-1H-pyrazol-4-yl)-1-methyl-1H-imidazole-2-carboxamide formate | 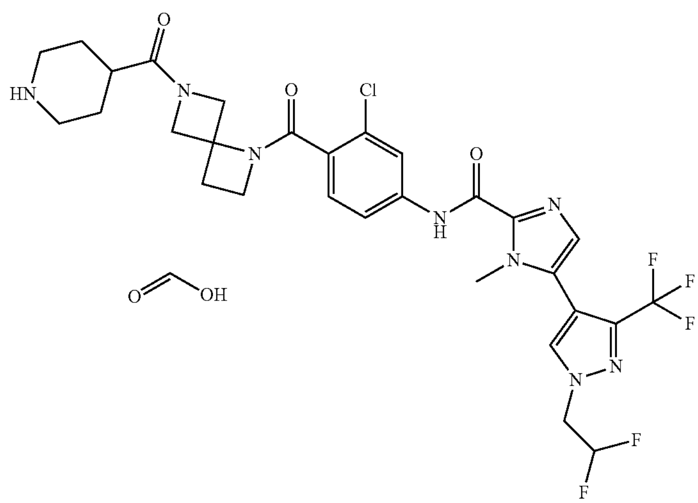 [SMILES: Cn1c(-c2cn(CC(F)F)nc2C(F)(F)F)cnc1C(=O)Nc1ccc(C(=O)N2CCC23CN(C(=O)C2CCNCC2)C3)c(Cl)c1 ; O=CO] | 669.3 |
| 364 | N-(4-(4-((1R,5S,6r)-3-azabicyclo[3.1.0]hexane-6-carbonyl)piperazine-1-carbonyl)-3-chlorophenyl)-5-(1-(2,2-difluoroethyl)-3-(difluoromethyl)-1H-pyrazol-4-yl)-1-methyl-1H-imidazole-2-carboxamide formate | 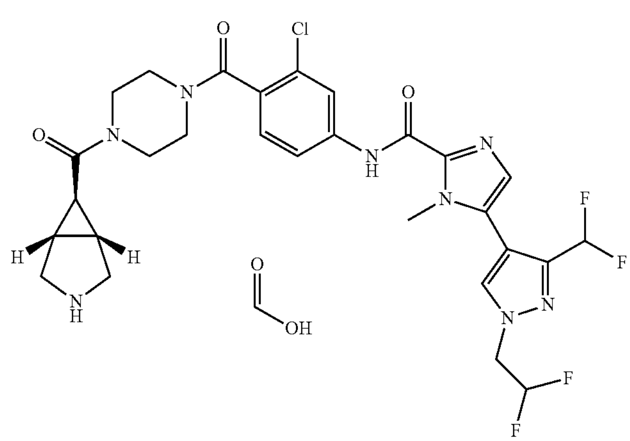 [SMILES: Cn1c(-c2cn(CC(F)F)nc2C(F)F)cnc1C(=O)Nc1ccc(C(=O)N2CCN(C(=O)[C@H]3[C@@H]4CNC[C@@H]43)CC2)c(Cl)c1 ; O=CO] | 637.3 |

| Example | Name | Structure | ESI MS [M + H]+ |
|---|---|---|---|
| 365 | rac-6-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)-N-((3S,4S)-4-hydroxypyrrolidin-3-yl)-3-azabicyclo[3.1.0]hexane-3-carboxamide formate | AND Enantiomer 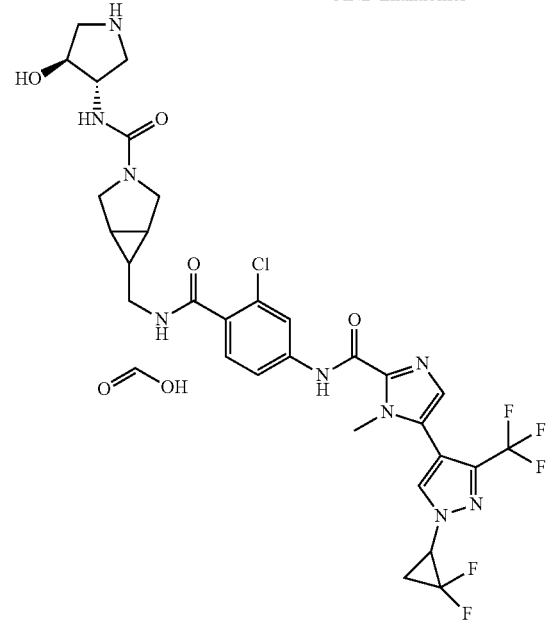 | 712.4 |
| 366 | N-(3-chloro-4-(4-(methylamino)piperidine-1-carbonyl)phenyl)-5-(1-cyclopropyl-3-(trifluoromethyl)-1H-pyrazol-4-yl)-1-methyl-1H-imidazole-2-carboxamide formate | 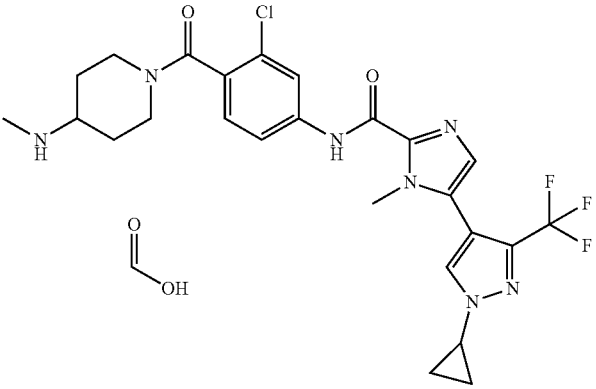 [SMILES: CNC1CCN(C(=O)c2ccc(NC(=O)c3ncc(-c4cn(C5CC5)nc4C(F)(F)F)n3C)cc2Cl)CC1 ; O=CO] | 550.3 |
| 367 | N-(3-chloro-4-(4-((2S,4S)-4-fluoropyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide hydrochloride | 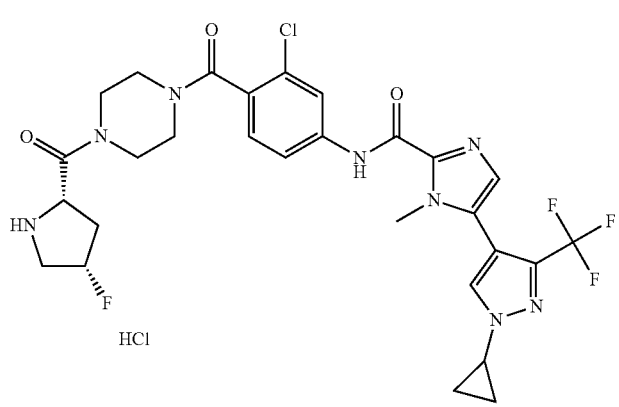 [SMILES: Cn1c(-c2cn(C3CC3)nc2C(F)(F)F)cnc1C(=O)Nc1ccc(C(=O)N2CCN(C(=O)[C@@H]3C[C@H](F)CN3)CC2)c(Cl)c1 ; Cl] | 637.3 |

| Example | Name | Structure | ESI MS [M + H]+ |
|---|---|---|---|
| 368 | N-(3-chloro-4-(methyl(piperidin-4-yl)carbamoyl)phenyl)-5-(1-(2,2-difluorocyclopropyl)-3-(trifluoromethyl)-1H-pyrazol-4-yl)-1-methyl-1H-imidazole-2-carboxamide formate | 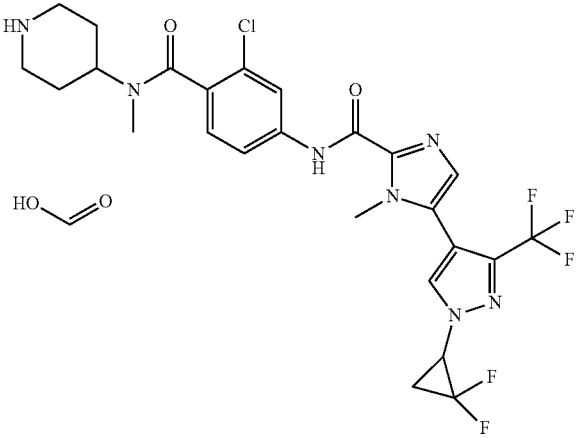 [SMILES: CN(C(=O)c1ccc(NC(=O)c2ncc(-c3cn(C4CC4(F)F)nc3C(F)(F)F)n2C)cc1Cl)C1CCNCC1 ; O=CO] | 586.3 |
| 369 | N-((1R,3R)-3-aminocyclopentyl)-4-(2-chloro-4-(5-(1-(cyclopropylmethyl)-3-(trifluoromethyl)-1H-pyrazol-4-yl)-1-methyl-1H-imidazole-2-carboxamido)benzoyl)piperazine-1-carboxamide | 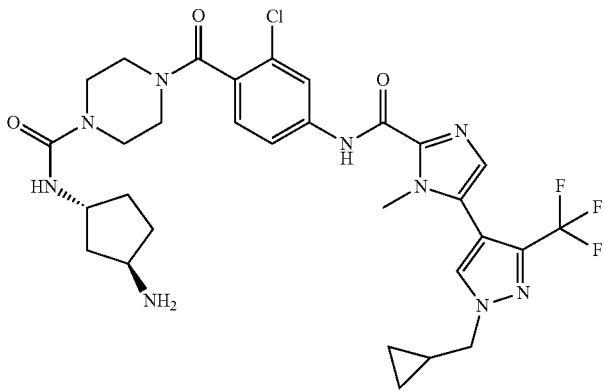 [SMILES: Cn1c(-c2cn(CC3CC3)nc2C(F)(F)F)cnc1C(=O)Nc1ccc(C(=O)N2CCN(C(=O)N[C@@H]3CC[C@@H](N)C3)CC2)c(Cl)c1] | 662.3 |
| 370 | N-(3-chloro-4-(4-hydroxy-bipiperidine]-1'-carbonyl)phenyl)-5-(1-cyclopropyl-3-(trifluoromethyl)-1H-pyrazol-4-yl)-1-methyl-1H-imidazole-2-carboxamide | 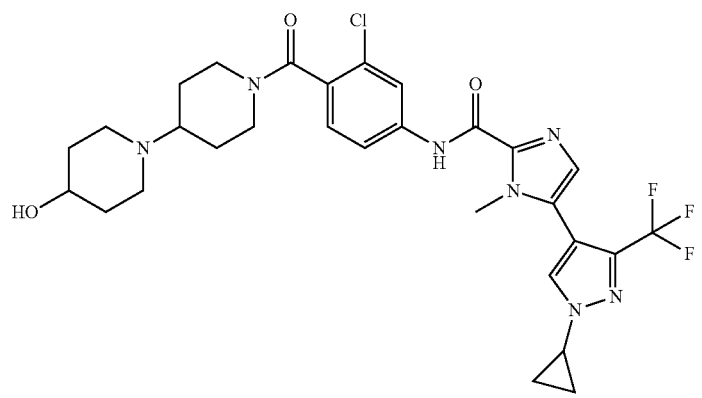 [SMILES: Cn1c(-c2cn(C3CC3)nc2C(F)(F)F)cnc1C(=O)Nc1ccc(C(=O)N2CCC(N3CCC(O)CC3)CC2)c(Cl)c1] | 620.4 |

| Example | Name | Structure | ESI MS [M + H]+ |
|---|---|---|---|
| 371 | N-(3-chloro-4-(piperazine-1-carbonyl)phenyl)-5-(1-(cyclobutylmethyl)-3-(trifluoromethyl)-1H-pyrazol-4-yl)-1-methyl-1H-imidazole-2-carboxamide dihydrochloride | 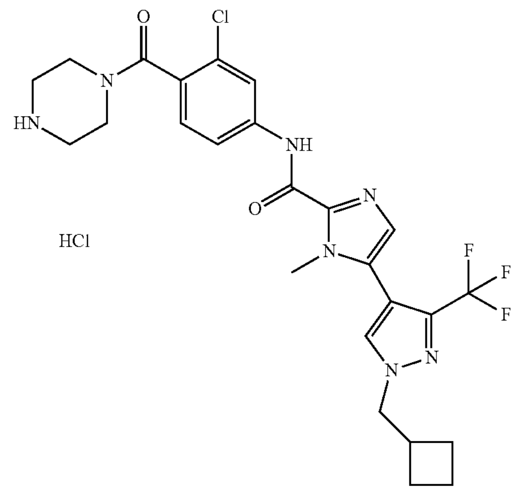 [SMILES: Cn1c(-c2cn(CC3CCC3)nc2C(F)(F)F)cnc1C(=O)Nc1ccc(C(=O)N2CCNCC2)c(Cl)c1 ; Cl] | 550.3 |
| 372 | rac-N-(4-(((1S,4s)-4-((1r,3R)-3-aminocyclobutane-1-carboxamido)cyclohexyl)carbamoyl)-3-chlorophenyl)-5-(1-(cyanomethyl)-3-(trifluoromethyl)-1H-pyrazol-4-yl)-1-methyl-1H-imidazole-2-carboxamide 2,2,2-trifluoroacetate | 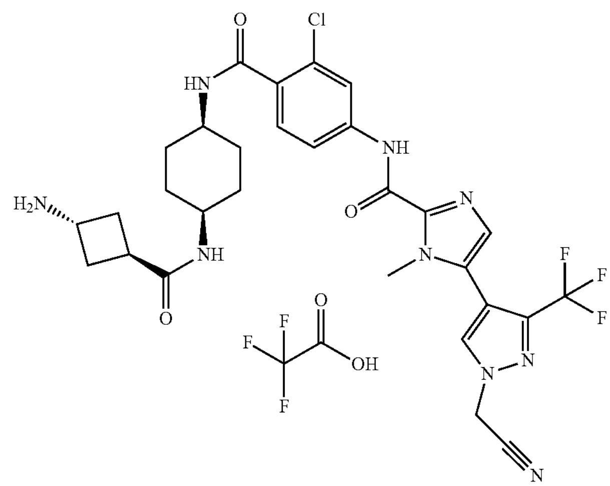 [SMILES: Cn1c(-c2cn(CC#N)nc2C(F)(F)F)cnc1C(=O)Nc1ccc(C(=O)N[C@H]2CC[C@@H](NC(=O)[C@H]3C[C@H](N)C3)CC2)c(Cl)c1 ; O=C(O)C(F)(F)F] | 646.3 |
| 373 | rac-N-(4-(((1-(((1s,3s)-3-aminocyclobutyl)carbamoyl)azetidin-3-yl)methyl)carbamoyl)-3-chlorophenyl)-5-(1-(cyclopropylmethyl)-3-(trifluoromethyl)-1H-pyrazol-4-yl)-1-methyl-1H-imidazole-2-carboxamide formate | 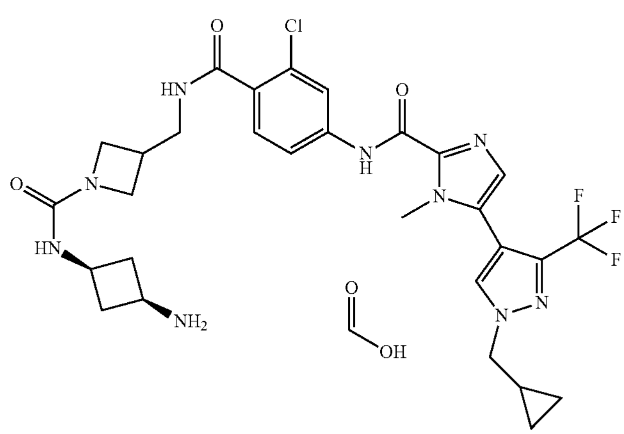 [SMILES: Cn1c(-c2cn(CC3CC3)nc2C(F)(F)F)cnc1C(=O)Nc1ccc(C(=O)NCC2CN(C(=O)N[C@H]3C[C@@H](N)C3)C2)c(Cl)c1 ; O=CO] | 648.2 |

-continued

| Example | Name | Structure | ESI MS [M + H]+ |
|---|---|---|---|
| 374 | N-(3-bromo-4-(4-(piperidine-4-carbonyl)piperazine-1-carbonyl)phenyl)-5-(1-ethyl-3-(trifluoromethyl)-1H-pyrazol-4-yl)-1-methyl-1H-imidazole-2-carboxamide hydrochloride | 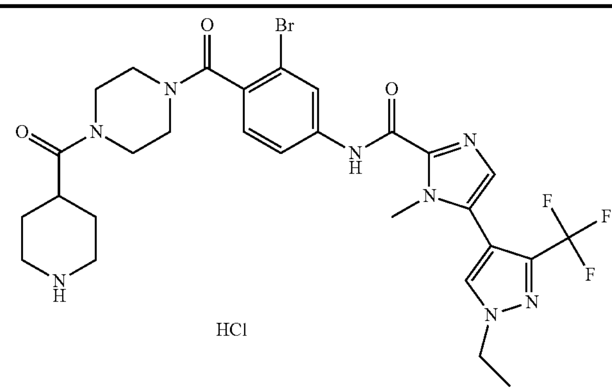 | 665.5 |
| 375 | N-(4-(4-(2-((2-aminoethyl)amino)-2-oxoethyl)piperazine-1-carbonyl)-3-chlorophenyl)-5-(1-(2,2-difluoroethyl)-3-(trifluoromethyl)-1H-pyrazol-4-yl)-1-methyl-1H-imidazole-2-carboxamide formate | 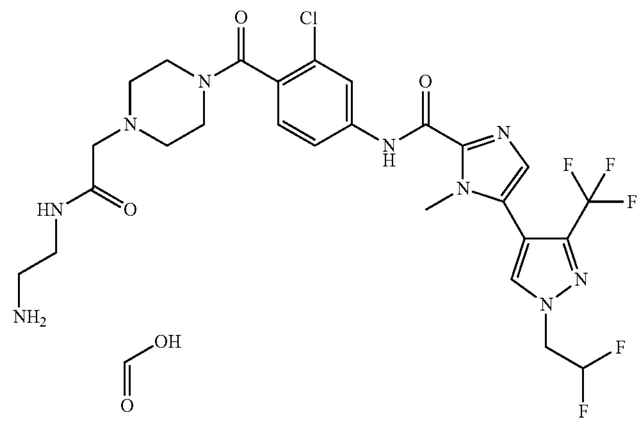 [SMILES: Cn1c(-c2cn(CC(F)F)nc2C(F)(F)F)cnc1C(=O)Nc1ccc(C(=O)N2CCN(CC(=O)NCCN)CC2)c(Cl)c1 ; O=CO] | 646.3 |
| 377 | formic acid;rac-(1S,5R)-8-[2-chloro-4-[[5-[1-(2,2-difluorocyclopropyl)-3-(trifluoromethyl)pyrazol-4-yl]-1-methyl-imidazole-2-carbonyl]amino]benzoyl]-N-[rac-(3S,4S)-4-hydroxypyrrolidin-3-yl]-3,8-diazabicyclo[3.2.1]octane-3-carboxamide | AND Enantiomer | 688.4 |
| 378 | N-[4-[6-(azetidin-3-ylmethylcarbamoylamino)hexylcarbamoyl]-3-chlorophenyl]-5-[1-cyclopropyl-3-(trifluoromethyl)pyrazol-4-yl]-1-methylimidazole-2-carboxamide;formic acid | 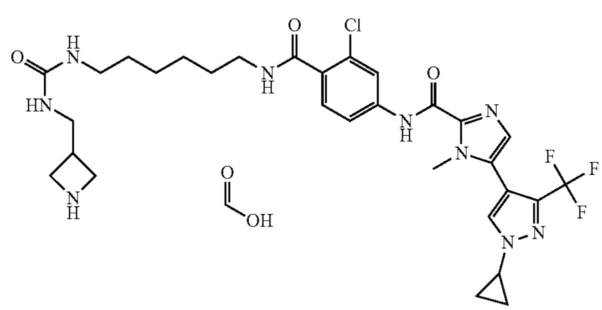 [SMILES: Cn1c(-c2cn(C3CC3)nc2C(F)(F)F)cnc1C(=O)Nc1ccc(C(=O)NCCCCCCNC(=O)NCC2CNC2)c(Cl)c1 ; O=CO] | 664.3 |

| Example | Name | Structure | ESI MS [M + H]+ |
|---|---|---|---|
| 379 | N-(3-chloro-4-(4-(piperidine-4-carbonyl)piperazine-1-carbonyl)phenyl)-1-methyl-5-(3-(trifluoromethyl)-1-(2-(trifluoromethyl)cyclopropyl)-1H-pyrazol-4-yl)-1H-imidazole-2-carboxamide formate | 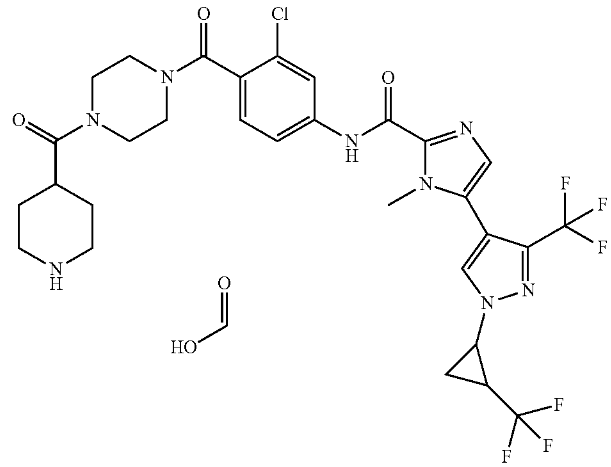 [SMILES: Cn1c(-c2cn(C3CC3C(F)(F)F)nc2C(F)(F)F)cnc1C(=O)Nc1ccc(C(=O)N2CCN(C(=O)C3CCNCC3)CC2)c(Cl)c1 ; O=CO] | 701.3 |
| 380 | (1R,5S,6R)-6-(2-chloro-4-(5-(1-((R)-2,2-difluorocyclopropyl)-3-(trifluoromethyl)-1H-pyrazol-4-yl)-1-methyl-1H-imidazole-2-carboxamido)benzamido)-N-((3S,4S)-4-hydroxypyrrolidin-3-yl)-3-azabicyclo[3.1.0]hexane-3-carboxamide | 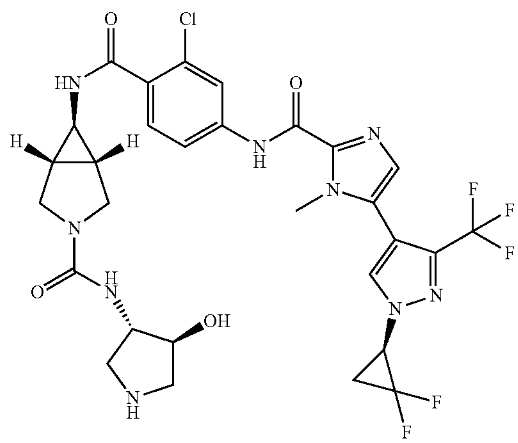 [SMILES: Cn1c(-c2cn([C@@H]3CC3(F)F)nc2C(F)(F)F)cnc1C(=O)Nc1ccc(C(=O)N[C@H]2[C@@H]3CN(C(=O)N[C@H]4CNC[C@@H]4O)C[C@@H]32)c(Cl)c1] | 698.3 |
| 381 | exo-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-N-((3S,4S)-4-hydroxypyrrolidin-3-yl)-3-azabicyclo[3.1.0]hexane-3-carboxamide formate | AND Enantiomer | 698.5 |

-continued

| Example | Name | Structure | ESI MS [M + H]+ |
|---|---|---|---|
| 382 | exo-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-N-[trans-4-hydroxypyrrolidin-azabicyclo[3.1.0]hexane-3-carboxamide, formate salt | AND Enantiomer | 698.4 |
| 383 | N-[3-chloro-4-[4-[rac-(1R,5S)-3-azabicyclo[3.1.0]hexane-6-carbonyl]piperazine-1-carbonyl]phenyl]-5-[1-cyclopropyl-3-(trifluoromethyl)pyrazol-4-yl]-1-methylimidazole-2-carboxamide;hydrochloride | 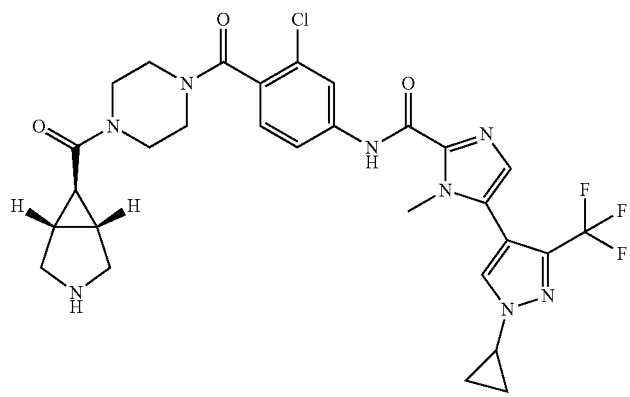 [SMILES: Cn1c(-c2cn(C3CC3)nc2C(F)(F)F)cnc1C(=O)Nc1ccc(C(=O)N2CCN(C(=O)[C@H]3[C@@H]4CNC[C@@H]43)CC2)c(Cl)c1] | 631.3 |
| 384 | (1R,5S,6s)-6-(2-chloro-4-(1-methyl-5-(1-(prop-2-yn-1-yl)-3-(trifluoromethyl)-1H-pyrazol-4-yl)-1H-imidazole-2-carboxamido)benzamido)-N-((3R,4R)-4-hydroxypyrrolidin-3-yl)-3-azabicyclo[3.1.0]hexane-3-carboxamide formate | 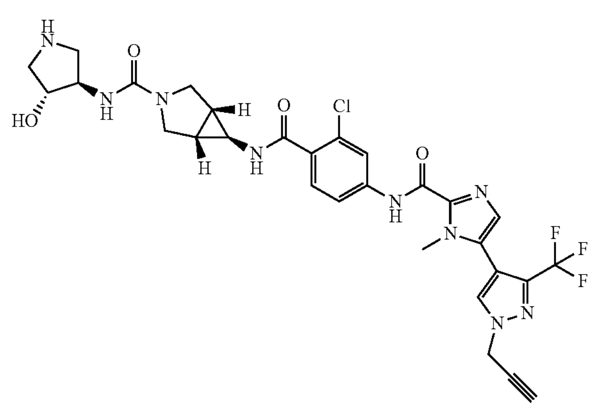 [SMILES: C#CCn1cc(-c2cnc(C(=O)Nc3ccc(C(=O)N[C@H]4[C@@H]5CN(C(=O)N[C@@H]6CNC[C@H]6O)C[C@@H]54)c(Cl)c3)n2C)c(C(F)(F)F)n1] | 660.3 |

-continued

| Example | Name | Structure | ESI MS [M + H]+ |
|---|---|---|---|
| 385 | rac-(1R,5S,6s)-6-(2-chloro-4-(5-(1-((2,2-difluorocyclopropyl)methyl)-3-(trifluoromethyl)-1H-pyrazol-4-yl)-1-methyl-1H-imidazole-2-carboxamido)benzamido)-N-((3S,4S)-4-hydroxypyrrolidin-3-yl)-3-azabicyclo[3.1.0]hexane-3-carboxamide formate | AND Enantiomer 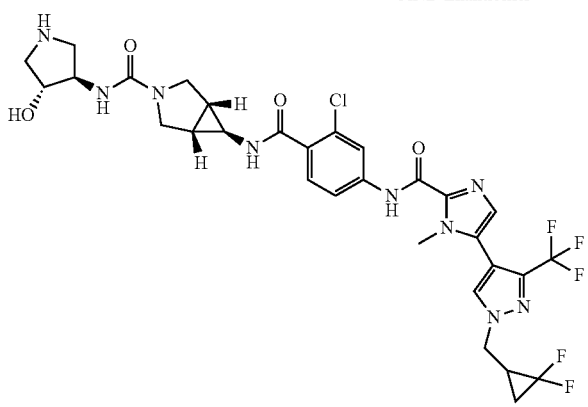 | 712.3 |
| 386 | (1R,5S,6s)-6-(2-chloro-4-(5-(1-(2,2-difluoroethyl)-3-(trifluoromethyl)-1H-pyrazol-4-yl)-1-methyl-1H-imidazole-2-carboxamido)benzamido)-N-((3R,4R)-4-hydroxypyrrolidin-3-yl)-3-azabicyclo[3.1.0]hexane-3-carboxamide formate | 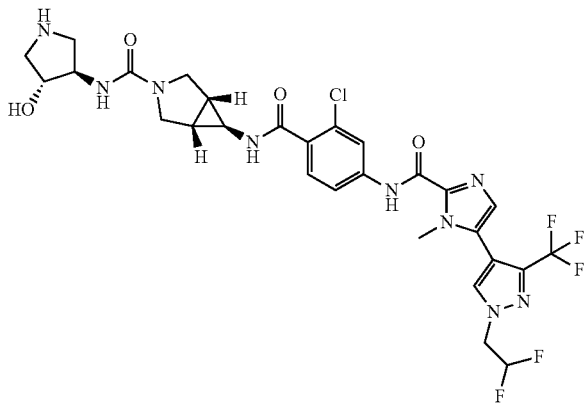 [SMILES: Cn1c(-c2cn(CC(F)F)nc2C(F)(F)F)cnc1C(=O)Nc1ccc(C(=O)N[C@H]2[C@@H]3CN(C(=O)N[C@@H]4CNC[C@H]4O)C[C@@H]32)c(Cl)c1] | 686.3 |
| 387 | (1R,5S,6s)-6-(4-(5-(1-allyl-3-(trifluoromethyl)-1H-pyrazol-4-yl)-1-methyl-1H-imidazole-2-carboxamido)-2-chlorobenzamido)-N-((3R,4R)-4-hydroxypyrrolidin-3-yl)-3-azabicyclo[3.1.0]hexane-3-carboxamide formate | 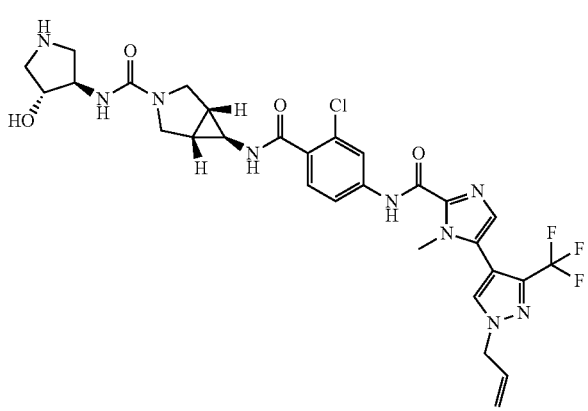 [SMILES: C=CCn1cc(-c2cnc(C(=O)Nc3ccc(C(=O)N[C@H]4[C@@H]5CN(C(=O)N[C@@H]6CNC[C@H]6O)C[C@@H]54)c(Cl)c3)n2C)c(C(F)(F)F)n1] | 662.3 |

| Example | Name | Structure | ESI MS [M + H]+ |
|---|---|---|---|
| 388 | (1R,5S,6s)-6-(2-chloro-4-(5-(1-(cyclobutylmethyl)-3-(trifluoromethyl)-1H-pyrazol-4-yl)-1-methyl-1H-imidazole-2-carboxamido)benzamido)-N-((3R,4R)-4-hydroxypyrrolidin-3-yl)-3-azabicyclo[3.1.0]hexane-3-carboxamide formate | 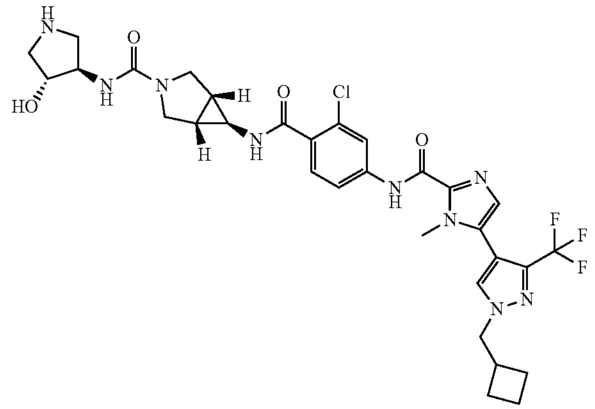 [SMILES: Cn1c(-c2cn(CC3CCC3)nc2C(F)(F)F)cnc1C(=O)Nc1ccc(C(=O)N[C@H]2[C@@H]3CN(C(=O)N[C@@H]4CNC[C@H]4O)C[C@@H]32)c(Cl)c1] | 390.3 |

Assay Procedures

Antimicrobial Susceptibility Testing:

90% Growth Inhibitory Concentration (IC90) Determination

The in vitro antimicrobial activity of the compounds was determined according to the following procedure:

The assay used a 10-points Iso-Sensitest broth medium to measure quantitatively the in vitro activity of the compounds against *Acinetobacter baumannii* ATCC 17961.

Stock compounds in DMSO were serially twofold diluted (e.g. range from 50 to 0.097 µM final concentration) in 384 wells microtiter plates and inoculated with 49 µl the bacterial suspension in Iso-Sensitest medium to have a final cell concentration of ~$5 \times 10^{(5)}$ CFU/ml in a final volume/well of 50 ul/well. Microtiter plates were incubated at 35±2° C.

Bacterial cell growth was determined with the measurement of optical density at X=600 nm each 20 minutes over a time course of 16 h. Growth inhibition was calculated during the logarithmic growth of the bacterial cells with determination of the concentration inhibiting 50% (IC50) and 90% (IC90) of the growth.

Table 1 provides the 90% growth inhibitory concentrations (IC90) in micromoles per liter of the compounds of present disclosure obtained against the strain *Acinetobacter baumannii* ATCC 17961.

Particular compounds of the present disclosure exhibit an IC90 (*Acinetobacter baumannii* ATCC 17961)≤25 µmol/l.

More particular compounds of the present disclosure exhibit an IC90 (*Acinetobacter baumannii* ATCC 17961)≤5 µmol/l.

Most particular compounds of the present disclosure exhibit an IC90 (*Acinetobacter baumannii* ATCC 17961)≤1 µmol/l.

TABLE 1

| Example | ATCC 17961 IC90 [µM] |
|---|---|
| 1 | 0.525 |
| 2 | 0.399 |
| 3 | 0.249 |
| 4 | 4.064 |
| 5 | 1.039 |
| 6 | 0.676 |
| 7 | 0.358 |
| 8 | 0.327 |
| 9 | 0.32 |
| 10 | 0.339 |
| 11 | 0.466 |
| 12 | 0.7 |
| 13 | 0.335 |
| 14 | 0.516 |
| 15 | 0.558 |
| 16 | 1.359 |
| 17 | 0.607 |
| 18 | 0.419 |
| 19 | 0.172 |
| 20 | 1.659 |
| 21 | 1.868 |
| 22 | 1.288 |
| 23 | 1.419 |
| 24 | 0.981 |
| 25 | 2.014 |
| 26 | 1.908 |
| 27 | 0.531 |
| 28 | 1.494 |
| 29 | 1.454 |
| 30 | 0.867 |
| 31 | 0.962 |
| 32 | 0.896 |
| 33 | 0.925 |
| 34 | 1.058 |
| 35 | 3.697 |
| 36 | 0.286 |
| 37 | 0.233 |
| 38 | 0.275 |
| 39 | 0.257 |
| 40 | 0.241 |
| 41 | 0.801 |
| 42 | 0.241 |
| 43 | 0.478 |
| 44 | 0.556 |
| 45 | 0.262 |
| 46 | 0.263 |
| 47 | 0.428 |
| 48 | 0.231 |
| 49 | 2.827 |
| 50 | 4.682 |
| 51 | 0.122 |
| 52 | 0.192 |

TABLE 1-continued

| Example | ATCC 17961 IC90 [μM] |
|---|---|
| 53 | 0.161 |
| 54 | 0.335 |
| 55 | 1.945 |
| 56 | 1.509 |
| 57 | 4.148 |
| 58 | 0.952 |
| 59 | 0.823 |
| 60 | 0.468 |
| 61 | 0.506 |
| 62 | 0.834 |
| 63 | 0.517 |
| 64 | 4.665 |
| 65 | 0.26 |
| 66 | 0.825 |
| 67 | 1.441 |
| 68 | 0.489 |
| 69 | 0.309 |
| 70 | 0.497 |
| 71 | 0.216 |
| 72 | 2.26 |
| 73 | 2.552 |
| 74 | 0.347 |
| 75 | 0.542 |
| 76 | 0.247 |
| 77 | 0.257 |
| 78 | 0.109 |
| 79 | 0.131 |
| 80 | 0.212 |
| 81 | 0.227 |
| 82 | 0.16 |
| 83 | 0.288 |
| 84 | 0.191 |
| 85 | 0.17 |
| 86 | 0.203 |
| 87 | 0.216 |
| 88 | 0.17 |
| 89 | 0.235 |
| 90 | 0.218 |
| 91 | 0.17 |
| 92 | 0.103 |
| 93 | 0.557 |
| 94 | 0.176 |
| 95 | 0.422 |
| 96 | 0.498 |
| 97 | 0.595 |
| 98 | 0.362 |
| 99 | 0.403 |
| 100 | 1.031 |
| 101 | 0.733 |
| 102 | 0.448 |
| 103 | 0.678 |
| 104 | 1.023 |
| 105 | 1.613 |
| 106 | 0.848 |
| 107 | 0.444 |
| 108 | 0.248 |
| 109 | 0.473 |
| 110 | 0.26 |
| 111 | 0.344 |
| 112 | 0.274 |
| 113 | 0.187 |
| 114 | 0.339 |
| 115 | 1.247 |
| 116 | 0.487 |
| 117 | 0.427 |
| 118 | 0.884 |
| 119 | 0.769 |
| 120 | 2.254 |
| 121 | 0.97 |
| 122 | 0.978 |
| 123 | 3.839 |
| 124 | 1.798 |
| 125 | 0.48 |
| 126 | 0.293 |
| 127 | 0.681 |
| 128 | 1.036 |
| 129 | 0.949 |
| 130 | 0.947 |
| 131 | 1.703 |
| 132 | 1.168 |
| 133 | 0.775 |
| 134 | 0.86 |
| 135 | 0.885 |
| 136 | 0.741 |
| 137 | 0.845 |
| 138 | 0.888 |
| 139 | 1.159 |
| 140 | 1.05 |
| 141 | 0.887 |
| 142 | 0.343 |
| 143 | 0.426 |
| 144 | 0.621 |
| 145 | 0.928 |
| 146 | 0.434 |
| 147 | 0.289 |
| 148 | 0.524 |
| 149 | 0.55 |
| 150 | 0.324 |
| 151 | 0.475 |
| 152 | 1.171 |
| 153 | 1.003 |
| 154 | 0.955 |
| 155 | 1.145 |
| 156 | 0.758 |
| 157 | 1.003 |
| 158 | 1.203 |
| 159 | 1.155 |
| 160 | 1.503 |
| 161 | 1.285 |
| 162 | 1.474 |
| 167 | 0.419 |
| 168 | 0.347 |
| 169 | 0.245 |
| 170 | 0.234 |
| 171 | 0.207 |
| 172 | 0.146 |
| 173 | 0.234 |
| 174 | 0.25 |
| 175 | 0.33 |
| 176 | 0.155 |
| 177 | 0.229 |
| 178 | 0.086 |
| 179 | 0.192 |
| 180 | 0.397 |
| 181 | 0.064 |
| 182 | 0.11 |
| 183 | 0.17 |
| 184 | 0.136 |
| 185 | 0.148 |
| 186 | 0.15 |
| 187 | 0.151 |
| 188 | 0.152 |
| 189 | 0.167 |
| 190 | 0.173 |
| 191 | 0.176 |
| 192 | 0.18 |
| 193 | 0.188 |
| 194 | 0.193 |
| 195 | 0.202 |
| 196 | 0.202 |
| 197 | 0.202 |
| 198 | 0.207 |
| 199 | 0.213 |
| 200 | 0.215 |
| 201 | 0.216 |
| 202 | 0.216 |
| 203 | 0.222 |
| 204 | 0.223 |
| 205 | 0.224 |
| 206 | 0.224 |

TABLE 1-continued

| Example | ATCC 17961 IC90 [μM] |
|---|---|
| 207 | 0.226 |
| 208 | 0.226 |
| 209 | 0.23 |
| 210 | 0.231 |
| 211 | 0.231 |
| 212 | 0.235 |
| 213 | 0.24 |
| 214 | 0.241 |
| 215 | 0.243 |
| 216 | 0.243 |
| 217 | 0.244 |
| 218 | 0.244 |
| 219 | 0.245 |
| 220 | 0.245 |
| 221 | 0.246 |
| 222 | 0.25 |
| 223 | 0.252 |
| 224 | 0.256 |
| 225 | 0.256 |
| 226 | 0.259 |
| 227 | 0.262 |
| 228 | 0.263 |
| 229 | 0.263 |
| 230 | 0.266 |
| 231 | 0.267 |
| 232 | 0.267 |
| 233 | 0.267 |
| 234 | 0.268 |
| 235 | 0.268 |
| 236 | 0.27 |
| 237 | 0.271 |
| 238 | 0.273 |
| 239 | 0.273 |
| 240 | 0.274 |
| 241 | 0.281 |
| 242 | 0.283 |
| 243 | 0.286 |
| 244 | 0.287 |
| 245 | 0.288 |
| 246 | 0.293 |
| 247 | 0.295 |
| 248 | 0.297 |
| 249 | 0.3 |
| 250 | 0.302 |
| 251 | 0.306 |
| 252 | 0.308 |
| 253 | 0.309 |
| 254 | 0.311 |
| 255 | 0.312 |
| 256 | 0.313 |
| 257 | 0.313 |
| 258 | 0.314 |
| 259 | 0.314 |
| 260 | 0.314 |
| 261 | 0.323 |
| 262 | 0.323 |
| 263 | 0.325 |
| 264 | 0.325 |
| 265 | 0.328 |
| 266 | 0.33 |
| 267 | 0.332 |
| 268 | 0.332 |
| 269 | 0.333 |
| 270 | 0.333 |
| 271 | 0.335 |
| 272 | 0.335 |
| 273 | 0.336 |
| 274 | 0.338 |
| 275 | 0.341 |
| 276 | 0.343 |
| 277 | 0.343 |
| 278 | 0.344 |
| 279 | 0.344 |
| 280 | 0.345 |
| 281 | 0.348 |
| 282 | 0.348 |
| 283 | 0.348 |
| 284 | 0.35 |
| 285 | 0.351 |
| 286 | 0.351 |
| 287 | 0.352 |
| 288 | 0.354 |
| 289 | 0.354 |
| 290 | 0.358 |
| 291 | 0.359 |
| 292 | 0.361 |
| 293 | 0.363 |
| 294 | 0.363 |
| 295 | 0.364 |
| 296 | 0.364 |
| 297 | 0.365 |
| 298 | 0.365 |
| 299 | 0.366 |
| 300 | 0.367 |
| 301 | 0.369 |
| 302 | 0.37 |
| 303 | 0.371 |
| 304 | 0.371 |
| 305 | 0.373 |
| 306 | 0.374 |
| 307 | 0.375 |
| 308 | 0.377 |
| 309 | 0.378 |
| 310 | 0.379 |
| 311 | 0.382 |
| 312 | 0.385 |
| 313 | 0.386 |
| 314 | 0.388 |
| 315 | 0.39 |
| 316 | 0.392 |
| 317 | 0.393 |
| 318 | 0.396 |
| 319 | 0.398 |
| 320 | 0.403 |
| 321 | 0.403 |
| 322 | 0.407 |
| 323 | 0.407 |
| 324 | 0.408 |
| 325 | 0.411 |
| 326 | 0.411 |
| 327 | 0.414 |
| 328 | 0.42 |
| 329 | 0.42 |
| 330 | 0.421 |
| 331 | 0.422 |
| 332 | 0.422 |
| 333 | 0.422 |
| 334 | 0.423 |
| 335 | 0.426 |
| 336 | 0.426 |
| 337 | 0.426 |
| 338 | 0.427 |
| 339 | 0.427 |
| 340 | 0.428 |
| 341 | 0.43 |
| 342 | 0.442 |
| 343 | 0.442 |
| 344 | 0.443 |
| 345 | 0.444 |
| 346 | 0.446 |
| 347 | 0.446 |
| 348 | 0.447 |
| 349 | 0.449 |
| 350 | 0.45 |
| 351 | 0.453 |
| 352 | 0.458 |
| 353 | 0.462 |
| 354 | 0.463 |
| 355 | 0.464 |
| 356 | 0.466 |

TABLE 1-continued

| Example | ATCC 17961 IC90 [μM] |
|---|---|
| 357 | 0.466 |
| 358 | 0.467 |
| 359 | 0.467 |
| 360 | 0.474 |
| 361 | 0.479 |
| 362 | 0.48 |
| 363 | 0.481 |
| 364 | 0.482 |
| 365 | 0.483 |
| 366 | 0.483 |
| 367 | 0.484 |
| 368 | 0.484 |
| 369 | 0.485 |
| 370 | 0.485 |
| 371 | 0.485 |
| 372 | 0.486 |
| 373 | 0.494 |
| 374 | 0.495 |
| 375 | 0.495 |
| 376 | 0.496 |
| 377 | 0.497 |
| 378 | 0.497 |
| 379 | 0.499 |
| 380 | 0.104 |
| 381 | 0.123 |
| 382 | 0.127 |
| 383 | 0.234 |
| 384 | 0.064 |
| 385 | 0.1 |
| 386 | 0.11 |
| 387 | 0.13 |
| 388 | 0.17 |

Example 163

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 164

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 165

A compound of formula (I) can be used in a manner known per se as the active ingredient for the production of an infusion solution of the following composition:

| | |
|---|---|
| Active ingredient | 100 mg |
| Lactic acid 90% | 100 mg |
| NaOH q.s. or HCl q.s. for adjustment to pH 4.0 | |
| Sodium chloride q.s. or glucose q.s. for adjustment of the osmolality to 290 mOsm/kg | |
| Water for injection (WFI) | ad 100 ml |

Example 166

A compound of formula (I) can be used in a manner known per se as the active ingredient for the production of an infusion solution of the following composition:

| | |
|---|---|
| Active ingredient | 100 mg |
| Hydroxypropyl-beta-cyclodextrin | 10 g |
| NaOH q.s. or HCl q.s. for adjustment to pH 7.4 | |
| Sodium chloride q.s. or glucose q.s. for adjustment of the osmolality to 290 mOsm/kg | |
| Water for injection (WFI) | ad 100 ml |

The invention claimed is:

1. A compound of formula (I)

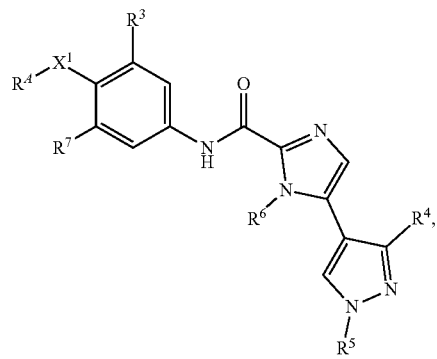

or a pharmaceutically acceptable salt thereof, wherein:
$R^A$ is $C_1$-$C_6$-alkyl or a group

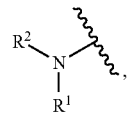

wherein:
(i) $R^1$ and $R^2$, taken together with the nitrogen atom to which they are attached, form a $C_2$-$C_9$-heterocyclic ring which is optionally substituted with one or more (1-2) $R^8$; or
(ii) $R^1$ is hydrogen, $C_1$-$C_6$-alkyl, amino-$C_1$-$C_6$-alkyl, amino-$C_1$-$C_6$-alkyl-O—$C_1$-$C_6$-alkyl, $C_1$-$C_6$-alkoxycarbonyl-NH—$C_1$-$C_6$-alkyl-, $C_1$-$C_6$-alkoxycarbonyl-$C_1$-$C_6$-alkyl-NH—$C_1$-$C_6$-alkyl- or a group

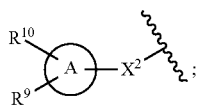

and

R² is hydrogen or $C_1$-$C_6$-alkyl;

R³ and IC are each independently hydrogen, halogen or $C_1$-$C_6$-alkyl;

R⁴ is halo-$C_1$-$C_6$-alkyl or $C_6$-$C_{14}$-aryl;

R⁵ is hydrogen, $CF_3$, $C_1$-$C_6$-alkyl substituted with R¹¹ and R¹², $C_2$-$C_6$-alkenyl, halo-$C_2$-$C_6$-alkenyl, $C_2$-$C_6$-alkynyl, amino-$C_2$-$C_6$-alkynyl-, $C_1$-$C_6$-alkoxy, halo-$C_1$-$C_6$-alkoxy-$C_1$-$C_6$-alkyl, $C_1$-$C_6$-alkoxy-$C_2$-$C_6$-alkynyl-, hydroxy-$C_2$-$C_6$-alkynyl-, or a group

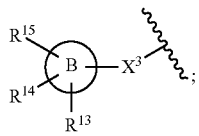

R⁶ is $C_1$-$C_6$-alkyl;

R⁸ is $C_1$-$C_6$-alkoxycarbonyl, amino-$C_1$-$C_6$-alkyl, $C_1$-$C_6$-alkyl-NH—, amino-$C_1$-$C_6$-alkyl-C(O)—, amino-$C_1$-$C_6$-alkyl-NH—C(O)—$C_1$-$C_6$-alkyl-, amino-$C_1$-$C_6$-alkyl-CH(OH)—, amino-$C_1$-$C_6$-alkyl-CH($NH_2$)—C(O)—, ($C_1$-$C_6$-alkyl)$_2$N—$C_1$-$C_6$-alkyl-, ($C_1$-$C_6$-alkyl)$_2$N—$C_1$-$C_6$-alkyl-N($C_1$-$C_6$-alkyl)-, ($C_1$-$C_6$-alkyl)$_2$N—$C_1$-$C_6$-alkyl-C(O)—, $C_1$-$C_6$-alkyl-NH—$C_1$-$C_6$-alkyl-C(O)—, $C_1$-$C_6$-alkyl-NH—$C_1$-$C_6$-alkyl-NH—C(O)—, oxo, amino, halogen, or a group

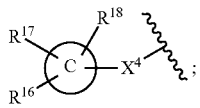

R⁹ and R¹⁰ are each independently hydrogen, hydroxy, amino, $C_1$-$C_6$-alkyl, $C_1$-$C_6$-alkoxy, amino-$C_1$-$C_6$-alkyl-C(O)—NH—, amino-$C_1$-$C_6$-alkyl-CH(halo-$C_1$-$C_6$-alkyl)-NH—C(O)—, amino-$C_3$-$C_{12}$-cycloalkyl-C(O)—NH— or a group

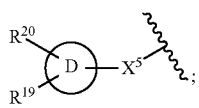

R¹¹ and R¹² are each independently hydrogen, halogen, hydroxy, cyano, $CF_3$, carbamoyl, halo-$C_1$-$C_6$-alkoxy-, ($C_1$-$C_6$-alkyl)$_2$N—C(O)—, $C_1$-$C_6$-alkyl-NH—C(O)—, $C_1$-$C_6$-alkoxy-, or $C_1$-$C_6$-alkoxy-$C_1$-$C_6$-alkoxy;

R¹³, R¹⁴, and R¹⁵ are each independently hydrogen, oxo, amino, hydroxy, $C_1$-$C_6$-alkyl-NH—, ($C_1$-$C_6$-alkyl)$_2$N—, halogen, $C_3$-$C_{12}$-cycloalkyl, $C_1$-$C_6$-alkyl, halo-$C_1$-$C_6$-alkyl or hydroxy-$C_1$-$C_6$-alkyl;

R¹⁶, R¹⁷ and R¹⁸ are each independently hydrogen, halogen, amino, hydroxy, amino-$C_1$-$C_6$-alkyl, $C_1$-$C_6$-alkyl-NH— or $C_1$-$C_6$-alkyl;

R¹⁹ and R²⁰ are each independently hydrogen, amino, hydroxy, $C_1$-$C_6$-alkyl, amino-$C_1$-$C_6$-alkyl-, or HO—S(O)$_2$-$C_1$-$C_6$-alkyl;

A, B, C, and D are each independently $C_6$-$C_{14}$-aryl, $C_1$-$C_{13}$-heteroaryl, $C_3$-$C_{12}$-cycloalkyl, or $C_2$-$C_9$-heterocyclyl; and X¹, X², X³, X⁴, and X⁵ are each independently a covalent bond, carbonyl, $C_1$-$C_6$-alkyl, —$C_1$-$C_6$-alkyl-C(O)—, —NH—C(O)—, —C(O)—NH—, —NH—C(O)—NH—, —NH—C(O)—NH—$C_1$-$C_6$-alkyl-, —NH—C(O)—N($C_1$-$C_6$-alkyl)-$C_1$-$C_6$-alkyl-, —$C_1$-$C_6$-alkyl-NH—C(O)—NH—$C_1$-$C_6$-alkyl-, —$C_1$-$C_6$-alkyl-NH—C(O)—, —S—, —SO—, —$SO_2$— or a group

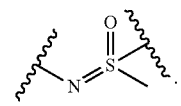

2. The compound of formula (I) according to claim 1, or a pharmaceutically acceptable salt thereof, wherein the compound of formula (I) is a compound of formula (I-I)

(I-1)

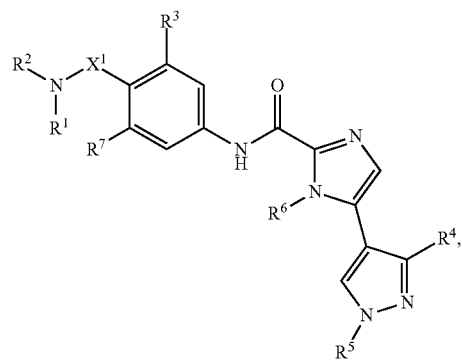

wherein:

(i) R¹ and R², taken together with the nitrogen atom to which they are attached, form a $C_2$-$C_9$-heterocyclic ring which is optionally substituted with R⁸; or (ii) R¹ is hydrogen, $C_1$-$C_6$-alkyl, amino-$C_1$-$C_6$-alkyl-, amino-$C_1$-$C_6$-alkyl-O—$C_1$-$C_6$-alkyl-, or a group

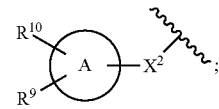

and

R² is hydrogen or $C_1$-$C_6$-alkyl;

R³ and R⁷ are each independently hydrogen, halogen or $C_1$-$C_6$-alkyl;

R⁴ is halo-$C_1$-$C_6$-alkyl or $C_6$-$C_{14}$-aryl;

R⁵ is hydrogen, $CF_3$, $C_1$-$C_6$-alkyl substituted with R¹¹ and R¹², $C_2$-$C_6$-alkenyl, $C_2$-$C_6$-alkynyl, amino-$C_2$-$C_6$-alkynyl-, $C_1$-$C_6$-alkoxy-$C_2$-$C_6$-alkynyl-, hydroxy-$C_2$-$C_6$-alkynyl-, or a group

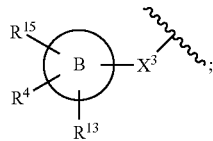

$R^6$ is $C_1$-$C_6$-alkyl;

$R^8$ is $C_1$-$C_6$-alkoxycarbonyl, $(C_1$-$C_6$-alkyl$)_2$N—$C_1$-$C_6$-alkyl-C(O)—, $C_1$-$C_6$-alkyl-NH—$C_1$-$C_6$-alkyl-C(O)—, $C_1$-$C_6$-alkyl-NH—$C_1$-$C_6$-alkyl-NH—C(O)—, or a group

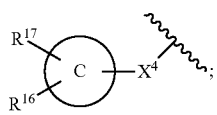

$R^9$ and $R^{10}$ are each independently hydrogen, hydroxy, amino, amino-$C_1$-$C_6$-alkyl-C(O)—NH—, or amino-$C_3$-$C_{12}$-cycloalkyl-C(O)—NH—;

$R^{11}$ and $R^{12}$ are each independently hydrogen, halogen, hydroxy, cyano, $CF_3$, carbamoyl, halo-$C_1$-$C_6$-alkoxy-, $(C_1$-$C_6$-alkyl$)_2$N—C(O)—, $C_1$-$C_6$-alkyl-NH—C(O)—, $C_1$-$C_6$-alkoxy-, or $C_1$-$C_6$-alkoxy-$C_1$-$C_6$-alkoxy;

$R^{13}$, $R^{14}$, and $R^{15}$ are each independently hydrogen, oxo, halogen, $C_3$-$C_{12}$-cycloalkyl, $C_1$-$C_6$-alkyl, or hydroxy-$C_1$-$C_6$-alkyl;

$R^{16}$ and $R^{17}$ are each independently hydrogen, amino, hydroxy, amino-$C_1$-$C_6$-alkyl, or $C_1$-$C_6$-alkyl;

A, B, and C are each independently $C_6$-$C_{14}$-aryl, $C_1$-$C_{13}$-heteroaryl, $C_3$-$C_{12}$-cycloalkyl, or $C_2$-$C_9$-heterocyclyl; and $X^1$, $X^2$, $X^3$, and $X^4$ are each independently a covalent bond, carbonyl, $C_1$-$C_6$-alkyl, C(O)—, —C(O)—NH—, —$C_1$-$C_6$-alkyl-NH—C(O)—, or $SO_2$.

3. The compound of formula (I) according to claim 1, or a pharmaceutically acceptable salt thereof, wherein:

(i) $R^1$ and $R^2$, taken together with the nitrogen atom to which they are attached, form a piperazinyl or a piperidyl ring which is optionally substituted with one or two $R^8$; or (ii) $R^1$ is 2-(2-amino-2-methyl-propoxy)ethyl or a group

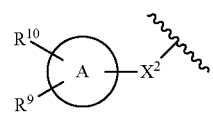

and $R^2$ is hydrogen.

4. The compound of formula (I) according to claim 1, or a pharmaceutically acceptable salt thereof, wherein $R^3$ is chloro.

5. The compound of formula (I) according to claim 1, or a pharmaceutically acceptable salt thereof, wherein $R^4$ is $CF_3$.

6. The compound of formula (I) according to claim 1, or a pharmaceutically acceptable salt thereof, wherein $R^5$ is $C_1$-$C_6$-alkyl substituted with $R^{11}$ and $R^{12}$, allyl, vinyl, 2-fluoroallyl, 2-methylallyl, prop-2-ynyl, or a group

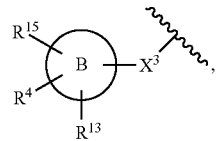

wherein said $C_1$-$C_6$-alkyl is methyl, ethyl, or isopropyl.

7. The compound of formula (I) according to claim 1, or a pharmaceutically acceptable salt thereof, wherein $R^6$ is methyl.

8. The compound of formula (I) according to claim 1, or a pharmaceutically acceptable salt thereof, wherein $R^7$ is hydrogen.

9. The compound of formula (I) according to claim 1, or a pharmaceutically acceptable salt thereof, wherein $R^8$ is $C_1$-$C_6$-alkoxycarbonyl, amino-$C_1$-$C_6$-alkyl, $C_1$-$C_6$-alkyl-NH—, amino-$C_1$-$C_6$-alkyl-C(O)—, amino-$C_1$-$C_6$-alkyl-CH(OH)—, amino-$C_1$-$C_6$-alkyl-CH($NH_2$)—C(O)—, $(C_1$-$C_6$-alkyl$)_2$N—$C_1$-$C_6$-alkyl-, $(C_1$-$C_6$-alkyl$)_2$N—$C_1$-$C_6$-alkyl-N($C_1$-$C_6$-alkyl), $(C_1$-$C_6$-alkyl$)_2$N—$C_1$-$C_6$-alkyl-C(O)—, $C_1$-$C_6$-alkyl-NH—$C_1$-$C_6$-alkyl-NH—C(O)—, oxo, amino, halogen, or a group

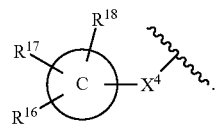

10. The compound of formula (I) according to claim 1, or a pharmaceutically acceptable salt thereof, wherein $R^9$ is hydrogen, amino, hydroxy, alkyl, alkoxy, amino-$C_1$-$C_6$-alkyl-C(O)—NH— or a group

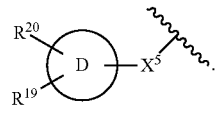

11. The compound of formula (I) according to claim 1, or a pharmaceutically acceptable salt thereof, wherein $R^{10}$ is hydrogen, $C_1$-$C_6$-alkyl or $C_1$-$C_6$-alkoxy.

12. The compound of formula (I) according to claim 1, or a pharmaceutically acceptable salt thereof, wherein $R^{11}$ is hydrogen, halogen, hydroxy, cyano, $CF_3$, carbamoyl, halo-$C_1$-$C_6$-alkoxy-, $(C_1$-$C_6$-alkyl$)_2$N—C(O)—, $C_1$-$C_6$-alkyl-NH—C(O)—, or $C_1$-$C_6$-alkoxy-$C_1$-$C_6$-alkoxy.

13. The compound of formula (I) according to claim 1, or a pharmaceutically acceptable salt thereof, wherein $R^{12}$ is hydrogen or halogen.

14. The compound of formula (I) according to claim 1, or a pharmaceutically acceptable salt thereof, wherein $R^{13}$ is hydrogen, oxo, halogen, $C_3$-$C_{12}$-cycloalkyl, $C_1$-$C_6$-alkyl, halo-$C_1$-$C_6$-alkyl or hydroxy-$C_1$-$C_6$-alkyl.

15. The compound of formula (I) according to claim 1, or a pharmaceutically acceptable salt thereof, wherein $R^{14}$ is hydrogen, oxo, halogen, or $C_1$-$C_6$-alkyl.

16. The compound of formula (I) according to claim 1, or a pharmaceutically acceptable salt thereof, wherein $R^{15}$ is hydrogen or halogen.

17. The compound of formula (I) according to claim 1, or a pharmaceutically acceptable salt thereof, wherein $R^{16}$ is hydrogen, amino, or hydroxy.

18. The compound of formula (I) according to claim 1, or a pharmaceutically acceptable salt thereof, wherein $R^{17}$ is hydrogen, amino or $C_1$-$C_6$-alkyl.

19. The compound of formula (I) according to claim 1, or a pharmaceutically acceptable salt thereof, wherein $R^{18}$ is hydrogen or amino.

20. The compound of formula (I) according to claim 1, or a pharmaceutically acceptable salt thereof, wherein $R^{19}$ is hydrogen, amino, hydroxy, $C_1$-$C_6$-alkyl, amino-$C_1$-$C_6$-alkyl or HO—$SO_2$-$C_1$-$C_6$-alkyl.

21. The compound of formula (I) according claim 1, or a pharmaceutically acceptable salt thereof, wherein $R^{20}$ is hydrogen or hydroxy.

22. The compound of formula (I) according to claim 1, or a pharmaceutically acceptable salt thereof, wherein A is $C_2$-$C_9$-heterocyclyl or $C_3$-$C_{12}$-cycloalkyl.

23. The compound of formula (I) according to claim 1, or a pharmaceutically acceptable salt thereof, wherein A is cyclobutyl, cyclopropyl or 3-azabicyclo[3.1.0]hexan-6-yl.

24. The compound of formula (I) according to claim 1, or a pharmaceutically acceptable salt thereof, wherein $X^1$ is —S—, a covalent bond, carbonyl, $SO_2$ or a group

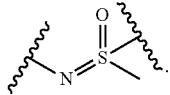 [SMILES: *N=S(*)(C)=O]

25. The compound of formula (I) according to claim 24, or a pharmaceutically acceptable salt thereof, wherein $X^1$ is carbonyl.

26. The compound of formula (I) according to claim 1, or a pharmaceutically acceptable salt thereof, wherein $X^2$ is a covalent bond or $C_1$-$C_6$-alkyl.

27. The compound of formula (I) according to claim 1, or a pharmaceutically acceptable salt thereof, wherein the compound of formula (I) is selected from the group consisting of:
N-(3-chloro-4-(4-(piperidine-4-carbonyl)piperazine-1-carbonyl)phenyl)-1-methyl-5-(3-(trifluoromethyl)-1H-pyrazol-4-yl)-1H-imidazole-2-carboxamide;
N-(3-Chloro-4-(4-(piperidine-4-carbonyl)piperazine-1-carbonyl)phenyl)-1-methyl-5-(1-(2,2,2-trifluoroethyl)-3-(trifluoromethyl)-1H-pyrazol-4-yl)-1H-imidazole-2-carboxamide;
N-[3-chloro-4-[4-(piperidine-4-carbonyl)piperazine-1-carbonyl]phenyl]-1-methyl-5-[1-prop-2-ynyl-3-(trifluoromethyl)pyrazol-4-yl]imidazole-2-carboxamide;
5-(1-(3-amino-3-oxopropyl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
N-(3-chloro-4-(4-(piperidine-4-carbonyl)piperazine-1-carbonyl)phenyl)-5-(1-(2-cyanoethyl)-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-5-(1-(4-hydroxybut-2-yn-1-yl)-3-(trifluoromethyl)-1H-pyrazol-4-yl)-1-methyl-1H-imidazole-2-carboxamide;
5-(1-allyl-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
5-(1-(but-2-yn-1-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
5-(1-(but-3-yn-2-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
N-(3-chloro-4-(4-(piperidine-4-carbonyl)piperazine-1-carbonyl)phenyl)-5-(1-cyclobutyl-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-5-(1-(2-fluoroethyl)-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-5-(1-(2,2-difluoroethyl)-3-(trifluoromethyl)-1H-pyrazol-4-yl)-1-methyl-1H-imidazole-2-carboxamide;
N-(3-chloro-4-(4-(1-methylpiperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide;
N-[3-chloro-4-[4-(1-methylpiperidine-4-carbonyl)piperazine-1-carbonyl]phenyl]-1-methyl-5-[3-(trifluoromethyl)-1H-pyrazol-4-yl]imidazole-2-carboxamide;
N-(3-chloro-4-(4-(1-methylpiperidine-4-carbonyl)piperazine-1-carbonyl)phenyl)-5-(1-(cyanomethyl)-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-5-(1-(1,1-dioxidothietan-3-yl)-3-(trifluoromethyl)-1H-pyrazol-4-yl)-1-methyl-1H-imidazole-2-carboxamide;
5-(1-(4-aminobut-2-yn-1-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
N-(3-chloro-4-(4-(piperidine-4-carbonyl)piperazine-1-carbonyl)phenyl)-5-(1-(4-methoxybut-2-yn-1-yl)-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-1-methyl-5-(1-(pent-2-yn-1-yl)-3-(trifluoromethyl)-1H-pyrazol-4-yl)-1H-imidazole-2-carboxamide;
5-(1-(2-amino-2-oxoethyl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
N-(3-chloro-4-(4-(piperidine-4-carbonyl)piperazine-1-carbonyl)phenyl)-5-(1-(2-(dimethylamino)-2-oxoethyl)-3-(trifluoromethyl)-1H-pyrazol-4-yl)-1-methyl-1H-imidazole-2-carboxamide;
5-(1-(1-amino-1-oxopropan-2-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
5-(1-(2-(1H-pyrazol-1-yl)ethyl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;
N-(3-chloro-4-(4-(piperidine-4-carbonyl)piperazine-1-carbonyl)phenyl)-5-(1-(2-(isopropylamino)-2-oxoethyl)-3-(trifluoromethyl)-1H-pyrazol-4-yl)-1-methyl-1H-imidazole-2-carboxamide;

N-(3-chloro-4-(4-(piperidine-4-carbonyl)piperazine-1-carbonyl)phenyl)-5-(1-(2-(2-methoxyethoxy)ethyl)-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-5-(1-(1-cyclopropyl-2-oxopyrrolidin-3-yl)-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-5-(1-isobutyl-3-(trifluoromethyl)-1H-pyrazol-4-yl)-1-methyl-1H-imidazole-2-carboxamide;
N-(3-chloro-4-(4-(piperidine-4-carbonyl)piperazine-1-carbonyl)phenyl)-1-methyl-5-(1-(2-(methylamino)-2-oxoethyl)-3-(trifluoromethyl)-1H-pyrazol-4-yl)-1H-imidazole-2-carboxamide;
1-Methyl-N-(3-methyl-4-(4-(piperidine-4-carbonyl)piperazine-1-carbonyl)phenyl)-5-(3-(trifluoromethyl)-1H-pyrazol-4-yl)-1H-imidazole-2-carboxamide;
5-(1-(cyanomethyl)-3-(trifluoromethyl)-1H-pyrazol-4-yl)-1-methyl-N-(3-methyl-4-(4-(piperidine-4-carbonyl)piperazine-1-carbonyl)phenyl)-1H-imidazole-2-carboxamide;
(R)—N-(3-Chloro-4-((pyrrolidin-3-ylmethyl)carbamoyl)phenyl)-1-methyl-5-(1-(prop-2-yn-1-yl)-3-(trifluoromethyl)-1H-pyrazol-4-yl)-1H-imidazole-2-carboxamide;
(S)—N-(3-chloro-4-((pyrrolidin-3-ylmethyl)carbamoyl)phenyl)-1-methyl-5-(1-(prop-2-yn-1-yl)-3-(trifluoromethyl)-1H-pyrazol-4-yl)-1H-imidazole-2-carboxamide;
N-(3-chloro-4-((((3 S,4R)-4-hydroxypyrrolidin-3-yl)methyl)carbamoyl)phenyl)-1-methyl-5-(1-(prop-2-yn-1-yl)-3-(trifluoromethyl)-1H-pyrazol-4-yl)-1H-imidazole-2-carboxamide;
tert-butyl 4-[2-chloro-4-[[1-methyl-5-[1-prop-2-ynyl-3-(trifluoromethyl)pyrazol-4-yl]imidazole-2-carbonyl]amino]benzoyl]piperazine-1-carboxylate;
N-[3-chloro-4-(piperazine-1-carbonyl)phenyl]-1-methyl-5-[3-(trifluoromethyl)-1H-pyrazol-4-yl]imidazole-2-carboxamide;
N-[3-Chloro-4-[(2S,4R)-4-hydroxypyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide;
N-[3-chloro-4-[4-[(3 S)-pyrrolidine-3-carbonyl]piperazine-1-carbonyl]phenyl]-1-methyl-5-[1-prop-2-ynyl-3-(trifluoromethyl)pyrazol-4-yl]imidazole-2-carboxamide;
N-[3-chloro-4-[4-[(2R)-pyrrolidine-2-carbonyl]piperazine-1-carbonyl]phenyl]-1-methyl-5-[1-prop-2-ynyl-3-(trifluoromethyl)pyrazol-4-yl]imidazole-2-carboxamide;
N-[3-chloro-4-[4-(4-hydroxypiperidine-4-carbonyl)piperazine-1-carbonyl]phenyl]-1-methyl-5-[1-prop-2-ynyl-3-(trifluoromethyl)pyrazol-4-yl]imidazole-2-carboxamide;
N-(3-chloro-4-(4-((3 S,4 S)-3-hydroxypiperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide;
N-(4-Carbamoyl-3-chlorophenyl)-1-methyl-5-(1-(prop-2-yn-1-yl)-3-(trifluoromethyl)-1H-pyrazol-4-yl)-1H-imidazole-2-carboxamide;
N-(3-chloro-4-(dimethylcarbamoyl)phenyl)-1-methyl-5-(1-(prop-2-yn-1-yl)-3-(trifluoromethyl)-1H-pyrazol-4-yl)-1H-imidazole-2-carboxamide;
N-(3-chloro-4-(methylcarbamoyl)phenyl)-1-methyl-5-(1-(prop-2-yn-1-yl)-3-(trifluoromethyl)-1H-pyrazol-4-yl)-1H-imidazole-2-carboxamide;
N-(4-((3-aminopropyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide;
(R)—N-(4-((2-(2-aminopropoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide;
N-(4-((2-(2-amino-2-methylpropoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide;
(S)—N-(4-((2-(2-aminopropoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide;
N-(4-((2-(2-aminoethoxy)ethyl)carbamoyl)-3-chlorophenyl)-1-methyl-5-(1-(prop-2-yn-1-yl)-3-(trifluoromethyl)-1H-pyrazol-4-yl)-1H-imidazole-2-carboxamide;
N-(4-((6-aminohexyl)carbamoyl)-3-methylphenyl)-1-methyl-5-(3-(trifluoromethyl)-1H-pyrazol-4-yl)-1H-imidazole-2-carboxamide;
N-(4-((5-aminopentyl)carbamoyl)-3-methylphenyl)-1-methyl-5-(3-(trifluoromethyl)-1H-pyrazol-4-yl)-1H-imidazole-2-carboxamide;
N-(Azetidin-3-yl)-4-(2-chloro-4-(1-methyl-5-(1-(prop-2-yn-1-yl)-3-(trifluoromethyl)-1H-pyrazol-4-yl)-1H-imidazole-2-carboxamido)benzoyl)piperazine-1-carboxamide;
4-(2-chloro-4-(1-methyl-5-(1-(prop-2-yn-1-yl)-3-(trifluoromethyl)-1H-pyrazol-4-yl)-1H-imidazole-2-carboxamido)benzoyl)-N-((3-hydroxyazetidin-3-yl)methyl)piperazine-1-carboxamide;
(S)-4-(2-chloro-4-(1-methyl-5-(1-(prop-2-yn-1-yl)-3-(trifluoromethyl)-1H-pyrazol-4-yl)-1H-imidazole-2-carboxamido)benzoyl)-N-(pyrrolidin-3-yl)piperazine-1-carboxamide;
N-(3-Chloro-4-(4-(piperidine-4-carbonyl)piperazine-1-carbonyl)phenyl)-5-(1-cyclopropyl-3-(trifluoromethyl)-1H-pyrazol-4-yl)-1-methyl-1H-imidazole-2-carboxamide;
N-[3-Chloro-4-[4-[(2S,4R)-4-hydroxypyrrolidine-2-carbonyl]piperazine-1-carbonyl]phenyl]-1-methyl-5-[1-methyl-3-(trifluoromethyl)pyrazol-4-yl]imidazole-2-carboxamide;
N-[3-Chloro-4-[4-(4-hydroxypiperidine-4-carbonyl)piperazine-1-carbonyl]phenyl]-1-methyl-5-[1-methyl-3-(trifluoromethyl)pyrazol-4-yl]imidazole-2-carboxamide;
N-(4-((2-(2-aminoethoxy)ethyl)carbamoyl)-3-ethylphenyl)-1-methyl-5-(1-methyl-3-(trifluoromethyl)-1H-pyrazol-4-yl)-1H-imidazole-2-carboxamide;
N-(3-Chloro-4-((4-(dimethylglycyl)piperazin-1-yl)sulfonyl)phenyl)-1-methyl-5-(3-(trifluoromethyl)-1H-pyrazol-4-yl)-1H-imidazole-2-carboxamide;
N-(3-Chloro-4-((4-((2S,4R)-4-hydroxypyrrolidine-2-carbonyl)piperazin-1-yl)sulfonyl)phenyl)-1-methyl-5-(3-(trifluoromethyl)-1H-pyrazol-4-yl)-1H-imidazole-2-carboxamide;
N-[3-Chloro-4-[4-(4-hydroxypiperidine-4-carbonyl)piperazine-1-carbonyl]phenyl]-5-[1-(cyanomethyl)-3-(trifluoromethyl)pyrazol-4-yl]-1-methyl-imidazole-2-carboxamide;

N-[3-Chloro-4-[4-(piperidine-4-carbonyl)piperazine-1-carbonyl]phenyl]-5-[1-(cyanomethyl)-3-(trifluoromethyl)pyrazol-4-yl]-1-methyl-imidazole-2-carboxamide;

N-[4-[4-[(2S)-2-Aminopropanoyl]piperazine-1-carbonyl]-3-chlorophenyl]-1-methyl-5-[1-(pyridin-3-ylmethyl)-3-(trifluoromethyl)pyrazol-4-yl]imidazole-2-carboxamide;

rac-N-(4-(4-((1r,3r)-3-aminocyclobutane-1-carbonyl)piperazine-1-carbonyl)-3-chlorophenyl)-1-methyl-5-(1-(pyridin-3-ylmethyl)-3-(trifluoromethyl)-1H-pyrazol-4-yl)-1H-imidazole-2-carboxamide;

N-(4-(4-((1S,3R)-3-aminocyclopentane-1-carbonyl)piperazine-1-carbonyl)-3-chlorophenyl)-1-methyl-5-(1-(pyridin-3-ylmethyl)-3-(trifluoromethyl)-1H-pyrazol-4-yl)-1H-imidazole-2-carboxamide;

N-[3-chloro-4-[4-(piperidine-4-carbonyl)piperazine-1-carbonyl]phenyl]-1-methyl-5-[1-propa-1,2-dienyl-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-(3-phenyl-1H-pyrazol-4-yl)imidazole-2-carboxamide;

N-[3-chloro-4-(piperazine-1-carbonyl)phenyl]-1-methyl-5-[1-(pyridin-3-ylmethyl)-3-(trifluoromethyl)pyrazol-4-yl]imidazole-2-carboxamide;

N-[3-chloro-4-(piperazine-1-carbonyl)phenyl]-5-[1-(2-fluoroethyl)-3-(trifluoromethyl)pyrazol-4-yl]-1-methylimidazole-2-carboxamide;

N-[3-chloro-4-(piperazine-1-carbonyl)phenyl]-5-[1-(cyanomethyl)-3-(trifluoromethyl)pyrazol-4-yl]-1-methyl-imidazole-2-carboxamide;

N-[3-chloro-4-[4-[(3S)-pyrrolidine-3-carbonyl]piperazine-1-carbonyl]phenyl]-1-methyl-5-[1-(pyridin-3-ylmethyl)-3-(trifluoromethyl)pyrazol-4-yl]imidazole-2-carboxamide;

N-[4-[4-[(2S)-2-aminopropanoyl]piperazine-1-carbonyl]-3-chlorophenyl]-5-[1-(cyanomethyl)-3-(trifluoromethyl)pyrazol-4-yl]-1-methylimidazole-2-carboxamide;

N-[3-chloro-4-[4-(3-hydroxypiperidine-3-carbonyl)piperazine-1-carbonyl]phenyl]-5-[1-(cyanomethyl)-3-(trifluoromethyl)pyrazol-4-yl]-1-methylimidazole-2-carboxamide;

N-[4-[4-(3-aminocyclobutanecarbonyl)piperazine-1-carbonyl]-3-chlorophenyl]-5-[1-(cyanomethyl)-3-(trifluoromethyl)pyrazol-4-yl]-1-methylimidazole-2-carboxamide;

N-[4-[4-(3-aminocyclobutanecarbonyl)piperazine-1-carbonyl]-3-chlorophenyl]-5-[1-(2-fluoroethyl)-3-(trifluoromethyl)pyrazol-4-yl]-1-methylimidazole-2-carboxamide;

N-[3-chloro-4-[4-(3-hydroxypiperidine-3-carbonyl)piperazine-1-carbonyl]phenyl]-1-methyl-5-[1-(pyridin-3-ylmethyl)-3-(trifluoromethyl)pyrazol-4-yl]imidazole-2-carboxamide;

4-[2-chloro-4-[[1-methyl-5-[1-prop-2-ynyl-3-(trifluoromethyl)pyrazol-4-yl]imidazole-2-carbonyl]amino]benzoyl]-N-[2-(methylamino)ethyl]piperazine-1-carboxamide;

N-[3-chloro-4-[4-(piperazine-1-carbonyl)piperazine-1-carbonyl]phenyl]-1-methyl-5-[1-prop-2-ynyl-3-(trifluoromethyl)pyrazol-4-yl]imidazole-2-carboxamide;

N-(3-aminocyclobutyl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[4-[4-[(3R)-3-aminopyrrolidine-1-carbonyl]piperazine-1-carbonyl]-3-chlorophenyl]-1-methyl-5-[1-prop-2-ynyl-3-(trifluoromethyl)pyrazol-4-yl]imidazole-2-carboxamide;

N-[4-[4-[(3S)-3-aminopyrrolidine-1-carbonyl]piperazine-1-carbonyl]-3-chlorophenyl]-1-methyl-5-[1-prop-2-ynyl-3-(trifluoromethyl)pyrazol-4-yl]imidazole-2-carboxamide;

N-[4-[4-(3-amino-3-methylazetidine-1-carbonyl)piperazine-1-carbonyl]-3-chlorophenyl]-1-methyl-5-[1-prop-2-ynyl-3-(trifluoromethyl)pyrazol-4-yl]imidazole-2-carboxamide;

N-[(1S,2R)-2-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[(1S,3S)-3-aminocyclopentyl]-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[4-[4-(4-aminopiperidine-1-carbonyl)piperazine-1-carbonyl]-3-chlorophenyl]-1-methyl-5-[1-prop-2-ynyl-3-(trifluoromethyl)pyrazol-4-yl]imidazole-2-carboxamide;

N-[4-[4-[(3S)-3-aminopiperidine-1-carbonyl]piperazine-1-carbonyl]-3-chlorophenyl]-1-methyl-5-[1-prop-2-ynyl-3-(trifluoromethyl)pyrazol-4-yl]imidazole-2-carboxamide;

N-[3-chloro-4-[4-(3,6-diazabicyclo[3.2.0]heptane-3-carbonyl)piperazine-1-carbonyl]phenyl]-1-methyl-5-[1-prop-2-ynyl-3-(trifluoromethyl)pyrazol-4-yl]imidazole-2-carboxamide;

4-[2-chloro-4-[[1-methyl-5-[1-prop-2-ynyl-3-(trifluoromethyl)pyrazol-4-yl]imidazole-2-carbonyl]amino]benzoyl]-N-[rac-(1R,5S)-3-azabicyclo[3.1.0]hexan-6-yl]piperazine-1-carboxamide;

N-[3-chloro-4-[4-[(1S,4S)-2,5-diazabicyclo[2.2.1]heptane-2-carbonyl]piperazine-1-carbonyl]phenyl]-1-methyl-5-[1-prop-2-ynyl-3-(trifluoromethyl)pyrazol-4-yl]imidazole-2-carboxamide;

N-(2-azaspiro[3.3]heptan-6-yl)-4-[2-chloro-4-[[1-methyl-5-[1-prop-2-ynyl-3-(trifluoromethyl)pyrazol-4-yl]imidazole-2-carbonyl]amino]benzoyl]piperazine-1-carboxamide;

N-[4-[4-[(3aS,6aS)-2,3,3a,4,6,6a-hexahydro-1H-pyrrolo[3,4-c]pyrrole-5-carbonyl]piperazine-1-carbonyl]-3-chlorophenyl]-1-methyl-5-[1-prop-2-ynyl-3-(trifluoromethyl)pyrazol-4-yl]imidazole-2-carboxamide;

N-[3-chloro-4-[4-(1,6-diazaspiro[3.3]heptane-6-carbonyl)piperazine-1-carbonyl]phenyl]-1-methyl-5-[1-prop-2-ynyl-3-(trifluoromethyl)pyrazol-4-yl]imidazole-2-carboxamide;

N-[3-chloro-4-[4-[rac-(1R,5S)-3-azabicyclo[3.1.0]hexane-6-carbonyl]piperazine-1-carbonyl]phenyl]-1-methyl-5-[1-prop-2-ynyl-3-(trifluoromethyl)pyrazol-4-yl]imidazole-2-carboxamide;

N-[4-[(3-aminocyclobutyl)carbamoyl]-3-chlorophenyl]-1-methyl-5-[1-prop-2-ynyl-3-(trifluoromethyl)pyrazol-4-yl]imidazole-2-carboxamide;

N-[4-[(3-aminocyclobutyl)carbamoyl]-3-chlorophenyl]-5-[1-(cyanomethyl)-3-(trifluoromethyl)pyrazol-4-yl]-1-methylimidazole-2-carboxamide;

N-[4-[[3-[[(2R)-2-aminopropanoyl]amino]cyclobutyl]carbamoyl]-3-chlorophenyl]-5-[1-(cyanomethyl)-3-(trifluoromethyl)pyrazol-4-yl]-1-methylimidazole-2-carboxamide;

N-[4-[[3-[[(1S,3R)-3-aminocyclopentanecarbonyl]amino]cyclobutyl]carbamoyl]-3-chlorophenyl]-5-[1-(cyanomethyl)-3-(trifluoromethyl)pyrazol-4-yl]-1-methylimidazole-2-carboxamide;

N-[4-[(3-aminocyclobutyl)carbamoyl]-3-chlorophenyl]-5-[1-cyclopropyl-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-1-methyl-5-[3-(trifluoromethyl)-1-(3,3,3-trifluoropropyl)pyrazol-4-yl]imidazole-2-carboxamide;

N-[3-chloro-4-[4-(piperidine-4-carbonyl)piperazine-1-carbonyl]phenyl]-5-[1-(fluoromethyl)-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-1-methyl-5-[1-(1H-pyrazol-5-ylmethyl)-3-(trifluoromethyl)pyrazol-4-yl]imidazole-2-carboxamide;

5-[1-[2-(chloromethyl)-3-hydroxy-2-methylpropyl]-3-(trifluoromethyl)pyrazol-4-yl]-N-[3-chloro-4-[4-(piperidine-4-carbonyl)piperazine-1-carbonyl]phenyl]-1-methylimidazole-2-carboxamide;

N-[3-chloro-4-[4-(piperidine-4-carbonyl)piperazine-1-carbonyl]phenyl]-1-methyl-5-[1-propan-2-yl-3-(trifluoromethyl)pyrazol-4-yl]imidazole-2-carboxamide;

5-[1-(1-chloro-3-hydroxypropan-2-yl)-3-(trifluoromethyl)pyrazol-4-yl]-N-[3-chloro-4-[4-(piperidine-4-carbonyl)piperazine-1-carbonyl]phenyl]-1-methylimidazole-2-carboxamide;

N-[3-chloro-4-[4-(piperidine-4-carbonyl)piperazine-1-carbonyl]phenyl]-5-[1-(3-hydroxy-3-methylbutyl)-3-(trifluoromethyl)pyrazol-4-yl]-1-methylimidazole-2-carboxamide;

5-[1-[[3-chloro-1-(hydroxymethyl)-3-methylcyclobutyl]methyl]-3-(trifluoromethyl)pyrazol-4-yl]-N-[3-chloro-4-[4-(piperidine-4-carbonyl)piperazine-1-carbonyl]phenyl]-1-methylimidazole-2-carboxamide;

N-[3-chloro-4-[4-(piperidine-4-carbonyl)piperazine-1-carbonyl]phenyl]-1-methyl-5-[1-[(5-methyl-1,2,4-oxadiazol-3-yl)methyl]-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-[(3-methylthietan-3-yl)methyl]-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-spiro[2.3]hexan-5-yl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[2-(difluoromethoxy)ethyl]-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-5-[1-[(2,2-difluorocyclopropyl)methyl]-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-5-[1-[(3,3-difluorocyclobutyl)methyl]-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-5-[1-(cyclopropylmethyl)-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-5-[1-(cyclobutylmethyl)-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-5-[1-ethyl-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-1-methyl-5-[1-methyl-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(difluoromethyl)-3-(trifluoromethyl)pyrazol-4-yl]-1-methylimidazole-2-carboxamide;

N-[3-chloro-4-[4-(piperidine-4-carbonyl)piperazine-1-carbonyl]phenyl]-5-[1-(1-cyanoethyl)-3-(trifluoromethyl)pyrazol-4-yl]-1-methylimidazole-2-carboxamide;

N-[4-[4-(3-aminocyclobutanecarbonyl)piperazine-1-carbonyl]-3-fluoro-5-methylphenyl]-5-[1-(cyanomethyl)-3-(trifluoromethyl)pyrazol-4-yl]-1-methylimidazole-2-carboxamide;

N-[4-[4-[(1S,3R)-3-aminocyclopentanecarbonyl]piperazine-1-carbonyl]-3-fluoro-5-methylphenyl]-5-[1-(cyanomethyl)-3-(trifluoromethyl)pyrazol-4-yl]-1-methylimidazole-2-carboxamide;

5-[1-(cyanomethyl)-3-(trifluoromethyl)pyrazol-4-yl]-N-[3-fluoro-4-[4-(3-hydroxypiperidine-3-carbonyl)piperazine-1-carbonyl]-5-methylphenyl]-1-methylimidazole-2-carboxamide;

N-[4-[4-[(2 S)-2-aminopropanoyl]piperazine-1-carbonyl]-3-fluoro-5-methylphenyl]-5-[1-(cyanomethyl)-3-(trifluoromethyl)pyrazol-4-yl]-1-methylimidazole-2-carboxamide;

5-[1-(cyanomethyl)-3-(trifluoromethyl)pyrazol-4-yl]-N-[3-fluoro-5-methyl-4-[4-[(3 S)-pyrrolidine-3-carbonyl]piperazine-1-carbonyl]phenyl]-1-methylimidazole-2-carboxamide;

N-[4-[(4-aminocyclohexyl)carbamoyl]-3-chlorophenyl]-1-methyl-5-[3-(trifluoromethyl)-1H-pyrazol-4-yl]imidazole-2-carboxamide;

N-[4-[(3-aminocyclobutyl)carbamoyl]-3-chlorophenyl]-1-methyl-5-[1-[(2-methyl-1,3-thiazol-4-yl)methyl]-3-(trifluoromethyl)pyrazol-4-yl]imidazole-2-carboxamide;

N-[4-[(3-aminocyclobutyl)carbamoyl]-3-chlorophenyl]-5-[1-cyclobutyl-3-(trifluoromethyl)pyrazol-4-yl]-1-methylimidazole-2-carboxamide;

N-[4-[(3-aminocyclobutyl)carbamoyl]-3-chlorophenyl]-1-methyl-5-[1-prop-2-enyl-3-(trifluoromethyl)pyrazol-4-yl]imidazole-2-carboxamide;

5-[1-(cyanomethyl)-3-(trifluoromethyl)pyrazol-4-yl]-N-[3-ethyl-4-[4-(1-methylpiperidine-4-carbonyl)piperazine-1-carbonyl]phenyl]-1-methylimidazole-2-carboxamide;

5-[1-(cyanomethyl)-3-(trifluoromethyl)pyrazol-4-yl]-N-[3-ethyl-4-[4-(piperidine-4-carbonyl)piperazine-1-carbonyl]phenyl]-1-methylimidazole-2-carboxamide;

5-[1-(cyanomethyl)-3-(trifluoromethyl)pyrazol-4-yl]-N-[3-ethyl-4-[4-(4-hydroxypiperidine-4-carbonyl)piperazine-1-carbonyl]phenyl]-1-methylimidazole-2-carboxamide;

5-[1-(cyanomethyl)-3-(trifluoromethyl)pyrazol-4-yl]-N-[3-ethyl-4-[4-[(3R)-pyrrolidine-3-carbonyl]piperazine-1-carbonyl]phenyl]-1-methylimidazole-2-carboxamide;

N-[4-[4-(azetidine-3-carbonyl)piperazine-1-carbonyl]-3-ethylphenyl]-5-[1-(cyanomethyl)-3-(trifluoromethyl)pyrazol-4-yl]-1-methylimidazole-2-carboxamide;

4-[4-[[5-[1-(cyanomethyl)-3-(trifluoromethyl)pyrazol-4-yl]-1-methylimidazole-2-carbonyl]amino]-2-ethylbenzoyl]-N-[(3-hydroxyazetidin-3-yl)methyl]piperazine-1-carboxamide;

N-[4-[4-(3-aminopiperidine-1-carbonyl)piperazine-1-carbonyl]-3-ethylphenyl]-5-[1-(cyanomethyl)-3-(trifluoromethyl)pyrazol-4-yl]-1-methylimidazole-2-carboxamide;

N-[4-[4-(6-amino-2-azaspiro[3.3]heptane-2-carbonyl)piperazine-1-carbonyl]-3-ethylphenyl]-5-[1-(cyanomethyl)-3-(trifluoromethyl)pyrazol-4-yl]-1-methylimidazole-2-carboxamide;

5-[1-(cyanomethyl)-3-(trifluoromethyl)pyrazol-4-yl]-N-[3-ethyl-4-[4-(3-methylpiperazine-1-carbonyl)piperazine-1-carbonyl]phenyl]-1-methylimidazole-2-carboxamide;

N-[4-[4-(4-amino-4-methylpiperidine-1-carbonyl)piperazine-1-carbonyl]-3-ethylphenyl]-5-[1-(cyanomethyl)-3-(trifluoromethyl)pyrazol-4-yl]-1-methylimidazole-2-carboxamide;

5-[1-(cyanomethyl)-3-(trifluoromethyl)pyrazol-4-yl]-N-[3-ethyl-4-[4-[rac-(3R,4R)-3-amino-4-methylpiperidine-1-carbonyl]piperazine-1-carbonyl]phenyl]-1-methylimidazole-2-carboxamide;

N-[4-[4-[3-(aminomethyl)pyrrolidine-1-carbonyl]piperazine-1-carbonyl]-3-ethylphenyl]-5-[1-(cyanomethyl)-3-(trifluoromethyl)pyrazol-4-yl]-1-methylimidazole-2-carboxamide;

N-[4-[4-[2-(aminomethyl)pyrrolidine-1-carbonyl]piperazine-1-carbonyl]-3-ethylphenyl]-5-[1-(cyanomethyl)-3-(trifluoromethyl)pyrazol-4-yl]-1-methylimidazole-2-carboxamide;

N-(3-azabicyclo[3.1.0]hexan-6-yl)-4-[4-[[5-[1-(cyanomethyl)-3-(trifluoromethyl)pyrazol-4-yl]-1-methylimidazole-2-carbonyl]amino]-2-ethylbenzoyl]piperazine-1-carboxamide;

5-[1-(cyanomethyl)-3-(trifluoromethyl)pyrazol-4-yl]-N-[4-[4-(2,5-diazabicyclo[2.2.1]heptane-2-carbonyl)piperazine-1-carbonyl]-3-ethylphenyl]-1-methylimidazole-2-carboxamide;

4-[2-chloro-4-[[5-[1-(2,2-difluoroethyl)-3-(trifluoromethyl)pyrazol-4-yl]-1-methylimidazole-2-carbonyl]amino]benzoyl]-N-[(3 S)-pyrrolidin-3-yl]piperazine-1-carboxamide;

4-[2-chloro-4-[[5-[1-(cyanomethyl)-3-(trifluoromethyl)pyrazol-4-yl]-1-methylimidazole-2-carbonyl]amino]benzoyl]-N-[(3 S)-pyrrolidin-3-yl]piperazine-1-carboxamide;

N-(azetidin-3-yl)-4-[2-chloro-4-[[5-[1-(2-fluoroethyl)-3-(trifluoromethyl)pyrazol-4-yl]-1-methylimidazole-2-carbonyl]amino]benzoyl]piperazine-1-carboxamide;

N-[4-[4-[4-(aminomethyl)-4,5-dihydro-1,3-oxazol-2-yl]piperazine-1-carbonyl]-3-chlorophenyl]-5-[1-(2-fluoroethyl)-3-(trifluoromethyl)pyrazol-4-yl]-1-methylimidazole-2-carboxamide;

N-(azetidin-3-yl)-4-[2-chloro-4-[[5-[1-(2,2-difluoroethyl)-3-(trifluoromethyl)pyrazol-4-yl]-1-methylimidazole-2-carbonyl]amino]benzoyl]piperazine-1-carboxamide;

N-(azetidin-3-yl)-4-[2-chloro-4-[[1-methyl-5-[1-prop-2-enyl-3-(trifluoromethyl)pyrazol-4-yl]imidazole-2-carbonyl]amino]benzoyl]piperazine-1-carboxamide;

N-[4-[4-[4-(aminomethyl)-4,5-dihydro-1,3-oxazol-2-yl]piperazine-1-carbonyl]-3-chlorophenyl]-1-methyl-5-[1-(2,2,2-trifluoroethyl)-3-(trifluoromethyl)pyrazol-4-yl]imidazole-2-carboxamide;

N-(azetidin-3-yl)-4-[2-chloro-4-[[1-methyl-5-[1-(2,2,2-trifluoroethyl)-3-(trifluoromethyl)pyrazol-4-yl]imidazole-2-carbonyl]amino]benzoyl]piperazine-1-carboxamide;

N-(azetidin-3-yl)-4-[2-chloro-4-[[5-[1-cyclobutyl-3-(trifluoromethyl)pyrazol-4-yl]-1-methylimidazole-2-carbonyl]amino]benzoyl]piperazine-1-carboxamide;

N-(azetidin-3-yl)-4-[2-chloro-4-[[5-[1-(cyanomethyl)-3-(trifluoromethyl)pyrazol-4-yl]-1-methylimidazole-2-carbonyl]amino]benzoyl]piperazine-1-carboxamide;

5-[1-(2,2-difluoroethyl)-3-(trifluoromethyl)pyrazol-4-yl]-N-[3-ethyl-4-[4-(1-methylpiperidine-4-carbonyl)piperazine-1-carbonyl]phenyl]-1-methylimidazole-2-carboxamide;

N-[4-[4-(azetidine-3-carbonyl)piperazine-1-carbonyl]-3-ethylphenyl]-5-[1-(2,2-difluoroethyl)-3-(trifluoromethyl)pyrazol-4-yl]-1-methylimidazole-2-carboxamide;

5-[1-(2,2-difluoroethyl)-3-(trifluoromethyl)pyrazol-4-yl]-N-[3-ethyl-4-[4-(piperidine-4-carbonyl)piperazine-1-carbonyl]phenyl]-1-methylimidazole-2-carboxamide;

5-[1-(2,2-difluoroethyl)-3-(trifluoromethyl)pyrazol-4-yl]-N-[3-ethyl-4-[4-(4-hydroxypiperidine-4-carbonyl)piperazine-1-carbonyl]phenyl]-1-methylimidazole-2-carboxamide;

5-[1-(2,2-difluoroethyl)-3-(trifluoromethyl)pyrazol-4-yl]-N-[3-ethyl-4 [(3R)-pyrrolidine-3-carbonylbpiperazine-1-carbonyl]phenyl]-1-methylimidazole-2-carboxamide;

4-[4-[[5-[1-(2,2-difluoroethyl)-3-(trifluoromethyl)pyrazol-4-yl]-1-methylimidazole-2-carbonyl]amino]-2-ethylbenzoyl]-N-[(3-hydroxyazetidin-3-yl)methyl]piperazine-1-carboxamide;

N-[3-ethyl-4-[4-(1-methylpiperidine-4-carbonyl)piperazine-1-carbonyl]phenyl]-1-methyl-5-[1-(pyridin-3-ylmethyl)-3-(trifluoromethyl)pyrazol-4-yl]imidazole-2-carboxamide;

N-[3-ethyl-4-[4-(piperidine-4-carbonyl)piperazine-1-carbonyl]phenyl]-1-methyl-5-[1-(pyridin-3-ylmethyl)-3-(trifluoromethyl)pyrazol-4-yl]imidazole-2-carboxamide;

N-[3-ethyl-4-[4-(4-hydroxypiperidine-4-carbonyl)piperazine-1-carbonyl]phenyl]-1-methyl-5-[1-(pyridin-3-ylmethyl)-3-(trifluoromethyl)pyrazol-4-yl]imidazole-2-carboxamide;

N-[3-ethyl-4-[4-[(3R)-pyrrolidine-3-carbonyl]piperazine-1-carbonyl]phenyl]-1-methyl-5-[1-(pyridin-3-ylmethyl)-3-(trifluoromethyl)pyrazol-4-yl]imidazole-2-carboxamide;

4-[2-ethyl-4-[[1-methyl-5-[1-(pyridin-3-ylmethyl)-3-(trifluoromethyl)pyrazol-4-yl]imidazole-2-carbonyl]amino]benzoyl]-N-[(3-hydroxyazetidin-3-yl)methyl]piperazine-1-carboxamide;

N-(3-aminocyclobutyl)-4-(2-chloro-4-(1-methyl-5-(1-(2-methylallyl)-3-(trifluoromethyl)-1H-pyrazol-4-yl)-1H-imidazole-2-carboxamido)benzoyl)piperazine-1-carboxamide;

rac-N-((1s,3 s)-3-aminocyclobutyl)-4-(2-chloro-4-(5-(1-ethyl-3-(trifluoromethyl)-1H-pyrazol-4-yl)-1-methyl-1H-imidazole-2-carboxamido)benzoyl)piperazine-1-carboxamide;

rac-N-((1s,3 s)-3-aminocyclobutyl)-4-(2-chloro-4-(5-(1-(cyclopropylmethyl)-3-(trifluoromethyl)-1H-pyrazol-4-yl)-1-methyl-1H-imidazole-2-carboxamido)benzoyl)piperazine-1-carboxamide;

N-(4-((2-(2-amino-2-methylpropoxy)ethyl)carbamoyl)-3-ethylphenyl)-5-(1-(cyanomethyl)-3-(trifluoromethyl)-1H-pyrazol-4-yl)-1-methyl-1H-imidazole-2-carboxamide;

N-(azetidin-3-yl)-4-(2-chloro-4-(1-methyl-5-(3-(trifluoromethyl)-1-vinyl-1H-pyrazol-4-yl)-1H-imidazole-2-carboxamido)benzoyl)piperazine-1-carboxamide;

N-(3-chloro-4-(((1R,5 S,6s)-3-(piperidine-4-carbonyl)-3-azabicyclo[3.1.0]hexan-6-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-(3-chloro-4-(((1R,5 S,6s)-3-(piperidine-4-carbonyl)-3-azabicyclo[3.1.0]hexan-6-yl)carbamoyl)phenyl)-5-(1-cyclobutyl-3-(trifluoromethyl)-1H-pyrazol-4-yl)-1-methyl-1H-imidazole-2-carboxamide;

N-(3-chloro-4-(((1R,5 S,6s)-3-(piperidine-4-carbonyl)-3-azabicyclo[3.1.0]hexan-6-yl)carbamoyl)phenyl)-5-(1-(cyclobutylmethyl)-3-(trifluoromethyl)-1H-pyrazol-4-yl)-1-methyl-1H-imidazole-2-carboxamide;

(1R,5 S,6 s)-6-(2-chloro-4-(5-(1-(cyanomethyl)-3-(trifluoromethyl)-1H-pyrazol-4-yl)-1-methyl-1H-imidazole-2-carboxamido)benzamido)-N-(trans-4-hydroxypyrrolidin-3-yl)-3-azabicyclo[3.1.0]hexane-3-carboxamide;

(1R,5 S,6 s)-6-(2-chloro-4-(5-(1-(2-fluoroallyl)-3-(trifluoromethyl)-1H-pyrazol-4-yl)-1-methyl-1H-imidazole-2-carboxamido)benzamido)-N-(trans-4-hydroxypyrrolidin-3-yl)-3-azabicyclo[3.1.0]hexane-3-carboxamide;

(1R,5 S,6s)-N-(cis-3-aminocyclobutyl)-6-(2-chloro-4-(5-(1-(2,2-difluoroethyl)-3-(trifluoromethyl)-1H-pyrazol-4-yl)-1-methyl-1H-imidazole-2-carboxamido)benzamido)-3-azabicyclo[3.1.0]hexane-3-carboxamide;

N-(4-(((1-aminocyclopropyl)methyl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

N-(3-chloro-4-(4-fluoro-4-((3-(trans-4-hydroxypyrrolidin-3-yl)ureido)methyl)piperidine-1-carbonyl)phenyl)-5-(1-(2,2-difluorocyclopropyl)-3-(trifluoromethyl)-1H-pyrazol-4-yl)-1-methyl-1H-imidazole-2-carboxamide;

N-[3-chloro-4-[4-(3-hydroxypiperidine-3-carbonyl)piperazine-1-carbonyl]phenyl]-5-[1-(2-fluoroethyl)-3-(trifluoromethyl)pyrazol-4-yl]-1-methylimidazole-2-carboxamide;

(1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

(1S,5R)-6-[[2-chloro-4-[[5-[1-[(1R)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide;

(1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

(1S,5R)-6-[[2-chloro-4-[[5-[1-[(1S)-2,2-difluorocyclopropyl]-3-(trifluoromethyl)pyrazol-4-yl]-1-methyl-imidazole-2-carbonyl]amino]benzoyl]amino]-N-[(3S,4S)-4-hydroxypyrrolidin-3-yl]-3-azabicyclo[3.1.0]hexane-3-carboxamide;

N-(3-chloro-4-(((1R,5 S,6s)-3-(piperazine-1-carbonyl)-3-azabicyclo[3.1.0]hexan-6-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-(4-((5-aminopentyl)carbamoyl)-3-chlorophenyl)-5-(1-(2-fluoroallyl)-3-(trifluoromethyl)-1H-pyrazol-4-yl)-1-methyl-1H-imidazole-2-carboxamide;

cis-N-[(1R,2S)-2-aminocyclopentyl]-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-3-azabicyclo[3.1.0]hexane-3-carboxamide;

N-(4-((6-aminohexyl)carbamoyl)-3-chlorophenyl)-5-(1-cyclopropyl-3-(trifluoromethyl)-1H-pyrazol-4-yl)-1-methyl-1H-imidazole-2-carboxamide;

N-(3-chloro-4-(piperazin-1-ylsulfonyl)phenyl)-5-(1-(2,2-difluoroethyl)-3-(trifluoromethyl)-1H-pyrazol-4-yl)-1-methyl-1H-imidazole-2-carboxamide;

6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3 S)-pyrrolidin-3-yl]-3-azabicyclo[3.1.0]hexane-3-carboxamide;

6-[[2-chloro-4-[[5-[1-(2,2-difluorocyclopropyl)-3-(trifluoromethyl)pyrazol-4-yl]-1-methyl-imidazole-2-carbonyl]amino]benzoyl]amino]-N-[rac-(3R)-pyrrolidin-3-yl]-3-azabicyclo[3.1.0]hexane-3-carboxamide;

N-(4-((4-aminobutyl)(methyl)carbamoyl)-3-chlorophenyl)-5-(1-cyclopropyl-3-(trifluoromethyl)-1H-pyrazol-4-yl)-1-methyl-1H-imidazole-2-carboxamide;

N-(4-(4-(2-aminoethyl)piperidine-1-carbonyl)-3-chlorophenyl)-5-(1-cyclopropyl-3-(trifluoromethyl)-1H-pyrazol-4-yl)-1-methyl-1H-imidazole-2-carboxamide;

N-[4-[[cis-3-[(3R)-3-aminopyrrolidine-1-carbonyl]-3-azabicyclo[3.1.0]hexan-6-yl]carbamoyl]-3-chlorophenyl]-5-[1-(2,2-difluorocyclopropyl)-3-(trifluoromethyl)pyrazol-4-yl]-1-methylimidazole-2-carboxamide;

N-(4-((6-aminospiro[3.3]heptan-2-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

rac-N-(4-(4-((1R,5-azabicyclo[3.1.0]hexane-6-carbonyl)piperazine-1-carbonyl)-3-fluorophenyl)-5-(1-(cyclopropylmethyl)-3-(trifluoromethyl)-1H-pyrazol-4-yl)-1-methyl-1H-imidazole-2-carboxamide;

(R)—N-(4-(3-(aminomethyl)pyrrolidine-1-carbonyl)-3-chlorophenyl)-5-(1-cyclopropyl-3-(trifluoromethyl)-1H-pyrazol-4-yl)-1-methyl-1H-imidazole-2-carboxamide;

N-(3-chloro-4-((((octahydrocyclopenta[c]pyrrol-5-yl)methyl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-(4-(4-(azetidin-3-yl)piperidine-1-carbonyl)-3-chlorophenyl)-5-(1-cyclopropyl-3-(trifluoromethyl)-1H-pyrazol-4-yl)-1-methyl-1H-imidazole-2-carboxamide;

N-(3-chloro-4-((4-((2R,4 S)-4-hydroxypyrrolidine-2-carbonyl)piperazin-1-yl)sulfonyl)phenyl)-5-(1-(2,2-difluoroethyl)-3-(trifluoromethyl)-1H-pyrazol-4-yl)-1-methyl-1H-imidazole-2-carboxamide;

N-(4-((4-aminobutyl)carbamoyl)-3-chlorophenyl)-1-methyl-5-(1-(2-methylallyl)-3-(trifluoromethyl)-1H-pyrazol-4-yl)-1H-imidazole-2-carboxamide;

N-(3-chloro-4-(4-glycylpiperazine-1-carbonyl)phenyl)-5-(1-cyclopropyl-3-(trifluoromethyl)-1H-pyrazol-4-yl)-1-methyl-1H-imidazole-2-carboxamide;

N-(4-(4-(aminomethyl)-4-fluoropiperidine-1-carbonyl)-3-chlorophenyl)-5-(1-(2,2-difluorocyclopropyl)-3-(trifluoromethyl)-1H-pyrazol-4-yl)-1-methyl-1H-imidazole-2-carboxamide;

N-(3-chloro-4-(4-glycylpiperazine-1-carbonyl)phenyl)-5-(1-(cyclobutylmethyl)-3-(trifluoromethyl)-1H-pyrazol-4-yl)-1-methyl-1H-imidazole-2-carboxamide;

rac-N-((1s,3 s)-3-aminocyclobutyl)-4-(2-chloro-4-(5-(1-(cyclopropylmethyl)-3-(trifluoromethyl)-1H-pyrazol-4-yl)-1-methyl-1H-imidazole-2-carboxamido)benzoyl)piperazine-1-carboxamide;

5-(1-(2,2-difluorocyclopropyl)-3-(trifluoromethyl)-1H-pyrazol-4-yl)-1-methyl-N-(4-(2-oxopyrrolidin-1-yl)phenyl)-1H-imidazole-2-carboxamide;

N-(4-((5-aminopentyl)carbamoyl)-3-chlorophenyl)-1-methyl-5-(1-(2-methylallyl)-3-(trifluoromethyl)-1H-pyrazol-4-yl)-1H-imidazole-2-carboxamide;

N-(4-(4-((1R,3R)-3-aminocyclopentane-1-carbonyl)piperazine-1-carbonyl)-3-chlorophenyl)-5-(1-(cyclopropylmethyl)-3-(trifluoromethyl)-1H-pyrazol-4-yl)-1-methyl-1H-imidazole-2-carboxamide;

N-(4-(4-(aminomethyl)piperidine-1-carbonyl)-3-chlorophenyl)-5-(1-cyclopropyl-3-(trifluoromethyl)-1H-pyrazol-4-yl)-1-methyl-1H-imidazole-2-carboxamide;

N-(4-(4-(azetidine-3-carbonyl)piperazine-1-carbonyl)-3-chlorophenyl)-5-(1-(cyclopropylmethyl)-3-(trifluoromethyl)-1H-pyrazol-4-yl)-1-methyl-1H-imidazole-2-carboxamide;

N-(3-chloro-4-(4-glycylpiperazine-1-carbonyl)phenyl)-5-(1-(cyclopropylmethyl)-3-(trifluoromethyl)-1H-pyrazol-4-yl)-1-methyl-1H-imidazole-2-carboxamide;

rac-N-((1s,3s)-3-aminocyclobutyl)-4-(2-chloro-4-(1-methyl-5-(1-(spiro[2.3]hexan-5-yl)-3-(trifluoromethyl)-1H-pyrazol-4-yl)-1H-imidazole-2-carboxamido)benzoyl)piperazine-1-carboxamide;

N-(4-((4-((1S,3R)-3-aminocyclopentane-1-carbonyl)piperazin-1-yl)sulfonyl)-3-chlorophenyl)-5-(1-(2,2-difluoroethyl)-3-(trifluoromethyl)-1H-pyrazol-4-yl)-1-methyl-1H-imidazole-2-carboxamide;

N-(4-(6-amino-3-azabicyclo[3.1.0]hexane-3-carbonyl)-3-chlorophenyl)-5-(1-(2,2-difluorocyclopropyl)-3-(trifluoromethyl)-1H-pyrazol-4-yl)-1-methyl-1H-imidazole-2-carboxamide;

rac-N-(4-(4-((1R,5S,6r)-3-azabicyclo[3.1.0]hexane-6-carbonyl)piperazine-1-carbonyl)-3-fluorophenyl)-5-(1-(2,2-difluoroethyl)-3-(trifluoromethyl)-1H-pyrazol-4-yl)-1-methyl-1H-imidazole-2-carboxamide;

N-(azetidin-3-ylmethyl)-4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxamide;

5-(1-allyl-3-(trifluoromethyl)-1H-pyrazol-4-yl)-N-(3-chloro-4-((3-(piperidine-4-carbonyl)-3-azabicyclo[3.1.0]hexan-6-yl)carbamoyl)phenyl)-1-methyl-1H-imidazole-2-carboxamide;

N-(4-(4-(3-aminoazetidine-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

(S)—N-(4-(3-(aminomethyl)pyrrolidine-1-carbonyl)-3-chlorophenyl)-5-(1-cyclopropyl-3-(trifluoromethyl)-1H-pyrazol-4-yl)-1-methyl-1H-imidazole-2-carboxamide;

N-((1s,3 s)-3-aminocyclobutyl)-4-(4-(5-(1-(cyclopropylmethyl)-3-(trifluoromethyl)-1H-pyrazol-4-yl)-1-methyl-1H-imidazole-2-carboxamido)-2-fluorobenzoyl)piperazine-1-carboxamide;

tert-butyl (5-(4-(5-(1-(2,2-difluoroethyl)-3-(trifluoromethyl)-1H-pyrazol-4-yl)-1-methyl-1H-imidazole-2-carboxamido)-2-ethylbenzamido)pentyl)glycinate;

N-(3-chloro-4-((3-(piperidine-4-carbonyl)-3-azabicyclo[3.1.0]hexan-6-yl)carbamoyl)phenyl)-5-(1-((2,2-difluorocyclopropyl)methyl)-3-(trifluoromethyl)-1H-pyrazol-4-yl)-1-methyl-1H-imidazole-2-carboxamide;

N-(4-((5-aminopentyl)carbamoyl)-3-chlorophenyl)-5-(1-cyclopropyl-3-(trifluoromethyl)-1H-pyrazol-4-yl)-1-methyl-1H-imidazole-2-carboxamide;

N-[4-[2-(2-amino-2-methyl-propoxy)ethylcarbamoyl]-3-ethyl-phenyl]-1-methyl-5-[1-prop-2-ynyl-3-(trifluoromethyl)pyrazol-4-yl]imidazole-2-carboxamide;

(R)—N-(3-chloro-4-(4-(piperidine-3-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(4-(4-(azetidine-3-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

N-(3-aminocyclobutyl)-4-[2-chloro-4-[[5-[1-cyclopropyl-3-(trifluoromethyl)pyrazol-4-yl]-1-methylimidazole-2-carbonyl]amino]benzoyl]piperazine-1-carboxamide;

rac-3-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)-N-((3S,4S)-4-hydroxypyrrolidin-3-yl)piperidine-1-carboxamide;

N-(3-chloro-4-((3-(piperidine-4-carbonyl)-3-azabicyclo[3.1.0]hexan-6-yl)carbamoyl)phenyl)-5-(1-(cyclopropylmethyl)-3-(trifluoromethyl)-1H-pyrazol-4-yl)-1-methyl-1H-imidazole-2-carboxamide;

N-(4-(4-(2-aminoethyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

(R)—N-(3-chloro-4-(4-(pyrrolidine-3-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(4-(4-((1R,3R)-3-aminocyclopentane-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

N-[4-[4-(4-aminocyclohexanecarbonyl)piperazine-1-carbonyl]-3-chlorophenyl]-5-[1-cyclopropyl-3-(trifluoromethyl)pyrazol-4-yl]-1-methylimidazole-2-carboxamide;

N-((1R,3R)-3-aminocyclopentyl)-4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxamide;

N-(azetidin-3-yl)-4-[2-chloro-4-[[5-[1-cyclopropyl-3-(trifluoromethyl)pyrazol-4-yl]-1-methyl-imidazole-2-carbonyl]amino]benzoyl]piperazine-1-carboxamide;

rac-N-(4-(((1s,3 s)-3-aminocyclobutyl)carbamoyl)-3-chlorophenyl)-1-methyl-5-(1-(2-methylallyl)-3-(trifluoromethyl)-1H-pyrazol-4-yl)-1H-imidazole-2-carboxamide;

N-(3-chloro-4-((3-(piperidine-4-carbonyl)-3-azabicyclo[3.1.0]hexan-6-yl)carbamoyl)phenyl)-5-(1-(2,2-difluoroethyl)-3-(trifluoromethyl)-1H-pyrazol-4-yl)-1-methyl-1H-imidazole-2-carboxamide;

4-[2-chloro-4-[[5-[1-cyclopropyl-3-(trifluoromethyl)pyrazol-4-yl]-1-methylimidazole-2-carbonyl]amino]benzoyl]-N-pyrrolidin-3-ylpiperazine-1-carboxamide;

rac-N-((1s,3 s)-3-aminocyclobutyl)-4-(2-chloro-4-(5-(1-(2,2-difluorocyclopropyl)-3-(trifluoromethyl)-1H-pyrazol-4-yl)-1-methyl-1H-imidazole-2-carboxamido)benzamido)piperidine-1-carboxamide;

N-(3-amino-3-methylcyclobutyl)-4-[2-chloro-4-[[5-[1-cyclopropyl-3-(trifluoromethyl)pyrazol-4-yl]-1-methylimidazole-2-carbonyl]amino]benzoyl]piperazine-1-carboxamide;

N-(4-(4-(2-aminoethyl)piperidine-1-carbonyl)-3-chlorophenyl)-5-(1-ethyl-3-(trifluoromethyl)-1H-pyrazol-4-yl)-1-methyl-1H-imidazole-2-carboxamide;

rac-N-((1s,3 s)-3-aminocyclobutyl)-4-(2-chloro-4-(5-(1-cyclopropyl-3-(trifluoromethyl)-1H-pyrazol-4-yl)-1-methyl-1H-imidazole-2-carboxamido)benzoyl)piperazine-1-carboxamide;

5-(1-benzyl-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;

N-[4-[2-(2-aminoethoxy)ethyl carbamoyl]-3-ethyl-phenyl]-1-methyl-5-[1-prop-2-ynyl-3-(trifluoromethyl)pyrazol-4-yl]imidazole-2-carboxamide;

N-(4-(4-((1R,2 S)-2-aminocyclopentane-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

5-(1-(2,2-difluoroethyl)-3-(trifluoromethyl)-1H-pyrazol-4-yl)-1-methyl-N-(4-(piperazin-1-ylsulfonyl)phenyl)-1H-imidazole-2-carboxamide;

N-(3-chloro-4-((3-(piperidine-4-carbonyl)-3-azabicyclo[3.1.0]hexan-6-yl)carbamoyl)phenyl)-1-methyl-5-(1-(prop-2-yn-1-yl)-3-(trifluoromethyl)-1H-pyrazol-4-yl)-1H-imidazole-2-carboxamide;

(R)—N-(3-chloro-4-(4-(2-(pyrrolidin-3-yl)acetyl)piperazine-1-carbonyl)phenyl)-5-(1-cyclopropyl-3-(trifluoromethyl)-1H-pyrazol-4-yl)-1-methyl-1H-imidazole-2-carboxamide;

N-(4-((5-aminopentyl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

cis-N-(1-amino-3-chloropropan-2-yl)-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-3-azabicyclo[3.1.0]hexane-3-carboxamide;

N-(3-chloro-4-(3,9-diazaspiro[5.5]undecane-3-carbonyl)phenyl)-5-(1-cyclopropyl-3-(trifluoromethyl)-1H-pyrazol-4-yl)-1-methyl-1H-imidazole-2-carboxamide;

(R)—N-(3-chloro-4-(4-prolylpiperazine-1-carbonyl)phenyl)-5-(1-cyclopropyl-3-(trifluoromethyl)-1H-pyrazol-4-yl)-1-methyl-1H-imidazole-2-carboxamide;

N-(azetidin-3-yl)-4-[2-chloro-4-[[5-[1-(2-chloroethyl)-3-(trifluoromethyl)pyrazol-4-yl]-1-methyl-imidazole-2-carbonyl]amino]benzoyl]piperazine-1-carboxamide;

N-(4-(4-(3-aminopropanoyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

N-[3-chloro-4-[[3-[[(3R)-pyrrolidine-3-carbonyl]amino]cyclobutyl]carbamoyl]phenyl]-5-[1-(cyanomethyl)-3-(trifluoromethyl)pyrazol-4-yl]-1-methyl-imidazole-2-carboxamide;

rac-N-((1s,3s)-3-aminocyclobutyl)-4-(2-chloro-4-(5-(1-((2,2-difluorocyclopropyl)methyl)-3-(trifluoromethyl)-1H-pyrazol-4-yl)-1-methyl-1H-imidazole-2-carboxamido)benzoyl)piperazine-1-carboxamide;

N-(4-((3-aminopropyl)carbamoyl)-3-chlorophenyl)-1-methyl-5-(1-(2-methylallyl)-3-(trifluoromethyl)-1H-pyrazol-4-yl)-1H-imidazole-2-carboxamide;

rac-4-(2-chloro-4-(5-(1-cyclopropyl-3-(trifluoromethyl)-1H-pyrazol-4-yl)-1-methyl-1H-imidazole-2-carboxamido)benzoyl)-N-((1s,3 s)-3-(methylamino)cyclobutyl)piperazine-1-carboxamide;

rac-N-(4-(4-((1R,5-azabicyclo[3.1.0]hexane-6-carbonyl)piperazine-1-carbonyl)-3-chlorophenyl)-1-methyl-5-(1-(2-methylallyl)-3-(trifluoromethyl)-1H-pyrazol-4-yl)-1H-imidazole-2-carboxamide;

(S)—N-(3-chloro-4-(4-(2-methylpyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(3-chloro-4-(((exo)-3-(piperidine-4-carbonyl)-3-azabicyclo[3.1.0]hexan-6-yl)carbamoyl)phenyl)-5-(1-(3-fluorocyclobut-2-en-1-yl)-3-(trifluoromethyl)-1H-pyrazol-4-yl)-1-methyl-1H-imidazole-2-carboxamide;

rac-N-((1s,3 s)-3-aminocyclobutyl)-4-(2-chloro-4-(5-(1-(cyclobutylmethyl)-3-(trifluoromethyl)-1H-pyrazol-4-yl)-1-methyl-1H-imidazole-2-carboxamido)benzoyl)piperazine-1-carboxamide;

N-(3-fluoro-4-(4-(piperidine-4-carbonyl)piperazine-1-carbonyl)phenyl)-1-methyl-5-(1-(prop-2-yn-1-yl)-3-(trifluoromethyl)-1H-pyrazol-4-yl)-1H-imidazole-2-carboxamide;

N-[4-[6-[(3-aminocyclobutyl)carbamoyl amino]hexylcarbamoyl]-3-chlorophenyl]-5-[1-cyclopropyl-3-(trifluoromethyl)pyrazol-4-yl]-1-methylimidazole-2-carboxamide;

N-[3-bromo-4-[4-[rac-(1R,5 S)-3-azabicyclo[3.1.0]hexane-6-carbonyl]piperazine-1-carbonyl]phenyl]-5-[1-ethyl-3-(trifluoromethyl)pyrazol-4-yl]-1-methylimidazole-2-carboxamide;

N-(4-(((1R,5 S,6s)-3-(4-(3-aminopropyl)piperazine-1-carbonyl)-3-azabicyclo[3.1.0]hexan-6-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

cis-N-(3-aminocyclobutyl)-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-3-azabicyclo[3.1.0]hexane-3-carboxamide;

N-[(1R,3 S)-3-amino-2,2-dimethylcyclobutyl]-4-[2-chloro-4-[[5-[1-cyclopropyl-3-(trifluoromethyl)pyrazol-4-yl]-1-methylimidazole-2-carbonyl]amino]benzoyl]piperazine-1-carboxamide;

N-(3-chloro-4-(4-(piperidine-4-carbonyl)piperazine-1-carbonyl)phenyl)-5-(1-(2,2-difluorocyclopropyl)-3-(trifluoromethyl)-1H-pyrazol-4-yl)-1-methyl-1H-imidazole-2-carboxamide;

N-(4-(3,8-diazabicyclo[3.2.1]octane-8-carbonyl)-3-chlorophenyl)-5-(1-(2,2-difluorocyclopropyl)-3-(trifluoromethyl)-1H-pyrazol-4-yl)-1-methyl-1H-imidazole-2-carboxamide;

N-[4-[[3-[(3-aminocyclobutanecarbonyl)amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-[4-[4-(3-amino-2-hydroxypropanoyl)piperazine-1-carbonyl]-3-chlorophenyl]-5-[1-cyclopropyl-3-(trifluoromethyl)pyrazol-4-yl]-1-methylimidazole-2-carboxamide;

rac-N-(3-chloro-4-((3aR,6aS)-octahydropyrrolo[3,4-c]pyrrole-2-carbonyl)phenyl)-5-(1-(2,2-difluorocyclopropyl)-3-(trifluoromethyl)-1H-pyrazol-4-yl)-1-methyl-1H-imidazole-2-carboxamide;

rac-N-((1s,3 s)-3-aminocyclobutyl)-4-(4-(5-(1-(2,2-difluoroethyl)-3-(trifluoromethyl)-1H-pyrazol-4-yl)-1-methyl-1H-imidazole-2-carboxamido)-2-fluorobenzoyl)piperazine-1-carboxamide;

(R)—N-(3-chloro-4-(4-(piperidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(3-chloro-4-(4-(piperidine-4-carbonyl)piperazine-1-carbonyl)phenyl)-5-(1-cyclopentyl-3-(trifluoromethyl)-1H-pyrazol-4-yl)-1-methyl-1H-imidazole-2-carboxamide;

N-[4-[[3-[[(1R,3 S)-3-aminocyclopentyl]carbamoylamino]cyclobutyl]carbamoyl]-3-chloro-phenyl]-5-[1-(cyanomethyl)-3-(trifluoromethyl)pyrazol-4-yl]-1-methyl-imidazole-2-carboxamide;

rac-N-(4-(4-((1 r,3 r)-3-aminocyclobutane-1-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide;

N-[4-[3-(aminomethyl)piperidine-1-carbonyl]-3-chlorophenyl]-5-[1-cyclopropyl-3-(trifluoromethyl)pyrazol-4-yl]-1-methylimidazole-2-carboxamide;

N-(4-(4-(L-alanyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide;

rac-4-((4-(5-(1-(2,2-difluoroethyl)-3-(trifluoromethyl)-1H-pyrazol-4-yl)-1-methyl-1H-imidazole-2-carboxamido)phenyl)sulfonyl)-N-((3R,4R)-4-hydroxypyrrolidin-3-yl)piperazine-1-carboxamide;

N-(3-chloro-4-((trans-4-methoxypyrrolidin-3-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-(4-(4-(azetidine-2-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide;

5-(1-(2,2-difluoroethyl)-3-(trifluoromethyl)-1H-pyrazol-4-yl)-N-(4-((4-glycylpiperazin-1-yl)sulfonyl)phenyl)-1-methyl-1H-imidazole-2-carboxamide;

rac-N-(4-(((1R,3 s,5 S)-8-azabicyclo[3.2.1]octan-3-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

N-(4-(((6-aminohexyl)carbamoyl)-3-bromophenyl)-5-(1-ethyl-3-(trifluoromethyl)-1H-pyrazol-4-yl)-1-methyl-1H-imidazole-2-carboxamide;

(S)—N-(3-chloro-4-(4-(2,5-diaminopentanoyl)piperazine-1-carbonyl)phenyl)-5-(1-cyclopropyl-3-(trifluoromethyl)-1H-pyrazol-4-yl)-1-methyl-1H-imidazole-2-carboxamide;

N-[3-chloro-4-[4-(5-hydroxypiperidine-3-carbonyl)piperazine-1-carbonyl]phenyl]-5-[1-cyclopropyl-3-(trifluoromethyl)pyrazol-4-yl]-1-methylimidazole-2-carboxamide;

N-(4-(4-((1R,3R)-3-aminocyclohexane-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

rac-(3aR,6aS)-5-(2-chloro-4-(5-(1-(2,2-difluorocyclopropyl)-3-(trifluoromethyl)-1H-pyrazol-4-yl)-1-methyl-1H-imidazole-2-carboxamido)benzoyl)-N-((3R,4R)-4-hydroxypyrrolidin-3-yl)hexahydropyrrolo[3,4-c]pyrrole-2(1H)-carboxamide;

rac-N-(4-((((1r,4r)-4-aminocyclohexyl)methyl)carbamoyl)-3-chlorophenyl)-5-(1-cyclopropyl-3-(trifluoromethyl)-1H-pyrazol-4-yl)-1-methyl-1H-imidazole-2-carboxamide;

N-(4-(4-(2-aminoethyl)piperazine-1-carbonyl)-3-chlorophenyl)-5-(1-(2,2-difluoroethyl)-3-(trifluoromethyl)-1H-pyrazol-4-yl)-1-methyl-1H-imidazole-2-carboxamide;

N-[4-[N-(3-aminopropyl)-S-methyl-sulfonimidoyl]-3-methyl-phenyl]-5-[1-(cyanomethyl)-3-(trifluoromethyl)pyrazol-4-yl]-1-methyl-imidazole-2-carboxamide;

rac-N-((1s,3 s)-3-aminocyclobutyl)-4-(2-chloro-4-(5-(1-isobutyl-3-(trifluoromethyl)-1H-pyrazol-4-yl)-1-methyl-1H-imidazole-2-carboxamido)benzoyl)piperazine-1-carboxamide;

rac-N-((1s,3 s)-3-aminocyclobutyl)-4-(2-chloro-4-(5-(1-((3,3-difluorocyclobutyl)methyl)-3-(trifluoromethyl)-1H-pyrazol-4-yl)-1-methyl-1H-imidazole-2-carboxamido)benzoyl)piperazine-1-carboxamide;

rac-N-((1s,3 s)-3-aminocyclobutyl)-4-(2-chloro-4-(5-(1-(2,2-difluorocyclopropyl)-3-(trifluoromethyl)-1H-pyrazol-4-yl)-1-methyl-1H-imidazole-2-carboxamido)-N-methylbenzamido)piperidine-1-carboxamide;

rac-N-(4-(4-((1s,3 s)-3-aminocyclobutane-1-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide;

N-(3-aminocyclobutyl)-4-[2-chloro-4-[[5-[1-ethyl-3-(trifluoromethyl)pyrazol-4-yl]-1-methylimidazole-2-carbonyl]amino]benzoyl]piperazine-1-carboxamide;

N-(3-chloro-4-(4-(4-methylpiperazine-1-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-[4-[4-(3-aminocyclobutanecarbonyl)piperazine-1-carbonyl]-3-chlorophenyl]-5-[1-(2-fluoroethyl)-3-(trifluoromethyl)pyrazol-4-yl]-1-methylimidazole-2-carboxamide;

(S)—N-(3-chloro-4-(4-(pyrrolidine-3-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

rac-N-(3-chloro-4-(6-(3-((3R,4R)-4-hydroxypyrrolidin-3-yl)ureido)-3-azabicyclo[3.1.0]hexane-3-carbonyl)phenyl)-5-(1-(2,2-difluorocyclopropyl)-3-(trifluoromethyl)-1H-pyrazol-4-yl)-1-methyl-1H-imidazole-2-carboxamide;

5-(1-(2,2-difluoroethyl)-3-(trifluoromethyl)-1H-pyrazol-4-yl)-N-(3-fluoro-4-(4-(piperidine-4-carbonyl)piperazine-1-carbonyl)phenyl)-1-methyl-1H-imidazole-2-carboxamide;

N-(4-(4-(4-aminobutanoyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

4-[2-chloro-4-[[5-[1-(2,2-difluoroethyl)-3-(trifluoromethyl)pyrazol-4-yl]-1-methyl-imidazole-2-carbonyl]amino]benzoyl]-N-[(3-hydroxyazetidin-3-yl)methyl]piperazine-1-carboxamide;

N-(3-chloro-4-(4-(piperidine-4-carbonyl)piperazine-1-carbonyl)phenyl)-5-(1-(cyclopentylmethyl)-3-(trifluoromethyl)-1H-pyrazol-4-yl)-1-methyl-1H-imidazole-2-carboxamide;

rac-N-((1s,3 s)-3-aminocyclobutyl)-4-(2-chloro-4-(1-methyl-5-(1-(2,2,2-trifluoroethyl)-3-(trifluoromethyl)-1H-pyrazol-4-yl)-1H-imidazole-2-carboxamido)benzoyl)piperazine-1-carboxamide;

N-(3-chloro-4-((exo-3-(piperidine-4-carbonyl)-3-azabicyclo[3.1.0]hexan-6-yl)carbamoyl)phenyl)-5-(1-cyclopropyl-3-(trifluoromethyl)-1H-pyrazol-4-yl)-1-methyl-1H-imidazole-2-carboxamide;

rac-N-(4-(((1s,3 s)-3-aminocyclobutyl)carbamoyl)-3-chlorophenyl)-5-(1-(3,3-difluoroallyl)-3-(trifluoromethyl)-1H-pyrazol-4-yl)-1-methyl-1H-imidazole-2-carboxamide;

5-[1-(2,2-difluoroethyl)-3-(trifluoromethyl)pyrazol-4-yl]-1-methyl-N-(3-methyl-4-methyl sulfanyl-phenyl)imidazole-2-carboxamide;

N-(3-chloro-4-(4-(2-(piperidin-4-yl)acetyl)piperazine-1-carbonyl)phenyl)-5-(1-cyclopropyl-3-(trifluoromethyl)-1H-pyrazol-4-yl)-1-methyl-1H-imidazole-2-carboxamide;

rac-5-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)-N-((3R,4R)-4-hydroxypyrrolidin-3-yl)hexahydrocyclopenta[c]pyrrole-2(1H)-carboxamide;

N-[3-chloro-4-[4-(4-hydroxypiperidine-3-carbonyl)piperazine-1-carbonyl]phenyl]-5-[1-cyclopropyl-3-(trifluoromethyl)pyrazol-4-yl]-1-methylimidazole-2-carboxamide;

(E)-5-(1-(but-2-en-1-yl)-3-(trifluoromethyl)-1H-pyrazol-4-yl)-N-(3-chloro-4-(4-(piperidine-4-carbonyl)piperazine-1-carbonyl)phenyl)-1-methyl-1H-imidazole-2-carboxamide;

N-(3-chloro-4-(4-((2R,4 S)-4-hydroxypyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

tert-butyl (4-(2-chloro-4-(5-(1-(2,2-difluorocyclopropyl)-3-(trifluoromethyl)-1H-pyrazol-4-yl)-1-methyl-1H-imidazole-2-carboxamido)benzamido)butyl)carbamate;

N-[3-chloro-4-[[3-[[(3R)-pyrrolidine-3-carbonyl]amino]cyclobutyl]carbamoyl]phenyl]-5-[1-(cyanomethyl)-3-(trifluoromethyl)pyrazol-4-yl]-1-methylimidazole-2-carboxamide;

N-[4-[[3-[[(3R)-3-aminopyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-(4-(((6-aminospiro[3.3]heptan-2-yl)carbamoyl)-3-chlorophenyl)-5-(1-cyclopropyl-3-(trifluoromethyl)-1H-pyrazol-4-yl)-1-methyl-1H-imidazole-2-carboxamide;

N-[3-chloro-4-[4-(3-hydroxypyrrolidine-3-carbonyl)piperazine-1-carbonyl]phenyl]-5-[1-cyclopropyl-3-(trifluoromethyl)pyrazol-4-yl]-1-methylimidazole-2-carboxamide;

N-(4-((3-azabicyclo[3.2.0]heptan-6-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

4-(2-chloro-4-(5-(1-cyclopropyl-3-(trifluoromethyl)-1H-pyrazol-4-yl)-1-methyl-1H-imidazole-2-carboxamido)benzoyl)-N-((4-hydroxypiperidin-4-yl)methyl)piperazine-1-carboxamide;

N-(3-chloro-4-(4-((2S,4R)-4-hydroxypyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(4-((exo-3-((R)-3-aminopyrrolidine-1-carbonyl)-3-azabicyclo[3.1.0]hexan-6-yl)carbamoyl)-3-chlorophenyl)-5-(1-cyclopropyl-3-(trifluoromethyl)-1H-pyrazol-4-yl)-1-methyl-1H-imidazole-2-carboxamide;

N-(4-([4,4'-bipiperidine]-1-carbonyl)-3-chlorophenyl)-5-(1-cyclopropyl-3-(trifluoromethyl)-1H-pyrazol-4-yl)-1-methyl-1H-imidazole-2-carboxamide;

N-[4-[[4-[[(2S)-2-aminopropanoyl]amino]cyclohexyl]carbamoyl]-3-chlorophenyl]-5-[1-(cyanomethyl)-3-(trifluoromethyl)pyrazol-4-yl]-1-methylimidazole-2-carboxamide;

rac-N-((1s,3 s)-3-aminocyclobutyl)-4-(2-bromo-4-(5-(1-ethyl-3-(trifluoromethyl)-1H-pyrazol-4-yl)-1-methyl-1H-imidazole-2-carboxamido)benzoyl)piperazine-1-carboxamide;

3-amino-N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]piperidine-1-carboxamide;

N-(4-(4-((1S,3R)-3-aminocyclopentane-1-carbonyl)piperazine-1-carbonyl)-3-chlorophenyl)-5-(1-(cyclobutylmethyl)-3-(trifluoromethyl)-1H-pyrazol-4-yl)-1-methyl-1H-imidazole-2-carboxamide;

N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]-2,5-diazabicyclo[2.2.1]heptane-2-carboxamide;

rac-N-(3-chloro-4-((3aR,6aR)-octahydropyrrolo[3,4-c]pyrrole-2-carbonyl)phenyl)-5-(1-(2,2-difluorocyclopropyl)-3-(trifluoromethyl)-1H-pyrazol-4-yl)-1-methyl-1H-imidazole-2-carboxamide;

N-[4-[4-(2-aminoacetyl)piperazine-1-carbonyl]-3-chlorophenyl]-5-[1-ethyl-3-(trifluoromethyl)pyrazol-4-yl]-1-methylimidazole-2-carboxamide;

rac-N-(3-chloro-4-((4-(3-(((3 S,4 S)-4-hydroxypyrrolidin-3-yl)-1-methylureido)butyl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-(3-chloro-4-(4-(piperidine-4-carbonyl)piperazine-1-carbonyl)phenyl)-1-methyl-5-(1-(2-(trifluoromethoxy)ethyl)-3-(trifluoromethyl)-1H-pyrazol-4-yl)-1H-imidazole-2-carboxamide;

rac-N-((1s,3 s)-3-aminocyclobutyl)-4-(2-chloro-4-(5-(1-(2,2-difluorocyclopropyl)-3-(trifluoromethyl)-1H-pyrazol-4-yl)-1-methyl-1H-imidazole-2-carboxamido)benzamido)-4-methylpiperidine-1-carboxamide;

exo-N-((1R,2 S)-2-aminocyclopentyl)-6-(2-chloro-4-(5-(1-cyclopropyl-3-(trifluoromethyl)-1H-pyrazol-4-yl)-1-methyl-1H-imidazole-2-carboxamido)benzamido)-3-azabicyclo[3.1.0]hexane-3-carboxamide;

N-(3-chloro-4-(4-((2S,4R)-4-hydroxypyrrolidine-2-carbonyl)piperazine-1-carbonyl)phenyl)-5-(1-(cyclobutylmethyl)-3-(trifluoromethyl)-1H-pyrazol-4-yl)-1-methyl-1H-imidazole-2-carboxamide;

N-(3-chloro-4-(piperazine-1-carbonyl)phenyl)-5-(1-(2,2-difluoroethyl)-3-(trifluoromethyl)-1H-pyrazol-4-yl)-1-methyl-1H-imidazole-2-carboxamide;

4-(2-chloro-4-(5-(1-(2,2-difluorocyclopropyl)-3-(trifluoromethyl)-1H-pyrazol-4-yl)-1-methyl-1H-imidazole- 2-carboxamido)benzamido)-N-(trans-4-hydroxypyrrolidin-3-yl)piperidine-1-carboxamide;

N-(3-chloro-4-(4-(piperazin-1-ylsulfonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(3-aminocyclobutyl)-1-[2-chloro-4-[[5-[1-cyclopropyl-3-(trifluoromethyl)pyrazol-4-yl]-1-methyl-imidazole-2-carbonyl]amino]benzoyl]piperidine-4-carboxamide;

N-[4-[4-(3-aminocyclobutanecarbonyl)piperazine-1-carbonyl]-3-ethyl-phenyl]-5-[1-(cyanomethyl)-3-(trifluoromethyl)pyrazol-4-yl]-1-methyl-imidazole-2-carboxamide;

N-(3-chloro-4-((4-hydroxypyrrolidin-3-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-[4-[N-(3-aminopropyl)-S-methyl-sulfonimidoyl]-3-methyl-phenyl]-1-methyl-5-[1-prop-2-ynyl-3-(trifluoromethyl)pyrazol-4-yl]imidazole-2-carboxamide;

4-[2-chloro-4-[[5-[1-(cyanomethyl)-3-(trifluoromethyl)pyrazol-4-yl]-1-methyl-imidazole-2-carbonyl]amino]benzoyl]-N-[(3-hydroxyazetidin-3-yl)methyl]piperazine-1-carboxamide;

N-(3-chloro-4-((4-methylpiperidin-4-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-(4-((4-aminobutyl)carbamoyl)-3-chlorophenyl)-5-(1-(cyanomethyl)-3-(trifluoromethyl)-1H-pyrazol-4-yl)-1-methyl-1H-imidazole-2-carboxamide;

rac-N-(4-(((1R,3r,5 S)-8-azabicyclo[3.2.1]octan-3-yl)carbamoyl)-3-chlorophenyl)-5-(1-(2,2-difluorocyclopropyl)-3-(trifluoromethyl)-1H-pyrazol-4-yl)-1-methyl-1H-imidazole-2-carboxamide;

rac-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-N-((3 S,4S)-4-hydroxypyrrolidin-3-yl)-3-azabicyclo[3.2.0]heptane-3-carboxamide;

(R)—N-(4-(4-(azetidine-2-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

(R)—N-(4-(4-(3-aminopyrrolidine-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

rac-N-(3-chloro-4-((trans-1-(((3R,4R)-4-hydroxypyrrolidin-3-yl)carbamoyl)-4-methoxypyrrolidin-3-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-[4-[(4-aminocyclohexyl)carbamoyl]-3-chlorophenyl]-5-[1-(cyanomethyl)-3-(trifluoromethyl)pyrazol-4-yl]-1-methylimidazole-2-carboxamide;

N-(3-chloro-4-(4-(piperidine-4-carbonyl)piperazine-1-carbonyl)phenyl)-5-(1-(2-cyclopropyl ethyl)-3-(trifluoromethyl)-1H-pyrazol-4-yl)-1-methyl-1H-imidazole-2-carboxamide;

N-[4-[N-(3-aminopropyl)-S-methyl-sulfonimidoyl]-3-methyl-phenyl]-5-[1-(2,2-difluoroethyl)-3-(trifluoromethyl)pyrazol-4-yl]-1-methyl-imidazole-2-carboxamide;

N-[3-[[2-chloro-4-[[5-[1-(cyanomethyl)-3-(trifluoromethyl)pyrazol-4-yl]-1-methyl-imidazole-2-carbonyl]amino]benzoyl]amino]cyclobutyl]-3-methyl-piperazine-1-carboxamide;

N-[4-[4-(3-aminocyclobutanecarbonyl)piperazine-1-carbonyl]-3-chlorophenyl]-5-[1-(cyanomethyl)-3-(trifluoromethyl)pyrazol-4-yl]-1-methylimidazole-2-carboxamide;

N-(4-((5-aminopentyl)carbamoyl)-3-ethylphenyl)-5-(1-(2,2-difluoroethyl)-3-(trifluoromethyl)-1H-pyrazol-4-yl)-1-methyl-1H-imidazole-2-carboxamide;

N-(3-chloro-4-(4-((2-(dimethylamino)ethyl)(methyl)amino)piperidine-1-carbonyl)phenyl)-5-(1-cyclopropyl-3-(trifluoromethyl)-1H-pyrazol-4-yl)-1-methyl-1H-imidazole-2-carboxamide;

rac-N-(4-(4-((1R,5 S)-3-azabicyclo[3.1.0]hexane-6-carbonyl)piperazine-1-carbonyl)-3-chlorophenyl)-5-(1-(cyclopropylmethyl)-3-(trifluoromethyl)-1H-pyrazol-4-yl)-1-methyl-1H-imidazole-2-carboxamide;

N-[4-[[3-[[3-(aminomethyl)pyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-(3-chloro-4-(4-(3-(dimethylamino)-3-methylbutyl)piperidine-1-carbonyl)phenyl)-5-(1-ethyl-3-(trifluoromethyl)-1H-pyrazol-4-yl)-1-methyl-1H-imidazole-2-carboxamide;

N-[4-[[3-[[2-(aminomethyl)pyrrolidine-1-carbonyl]amino]cyclobutyl]carbamoyl]-3-chloro-phenyl]-5-[1-(cyanomethyl)-3-(trifluoromethyl)pyrazol-4-yl]-1-methyl-imidazole-2-carboxamide;

N-(4-(4-(4-aminopiperidine-1-carbonyl)piperazine-1-carbonyl)-3-chlorophenyl)-5-(1-cyclopropyl-3-(trifluoromethyl)-1H-pyrazol-4-yl)-1-methyl-1H-imidazole-2-carboxamide;

N-(3-chloro-4-(6-(piperidine-4-carbonyl)-1,6-diazaspiro[3.3]heptane-1-carbonyl)phenyl)-5-(1-(2,2-difluoroethyl)-3-(trifluoromethyl)-1H-pyrazol-4-yl)-1-methyl-1H-imidazole-2-carboxamide;

N-(4-(4-((1R,5-azabicyclo[3.1.0]hexane-6-carbonyl)piperazine-1-carbonyl)-3-chlorophenyl)-5-(1-(2,2-difluoroethyl)-3-(difluoromethyl)-1H-pyrazol-4-yl)-1-methyl-1H-imidazole-2-carboxamide;

rac-6-((2-chloro-4-(5-(1-(2,2-difluorocyclopropyl)-3-(trifluoromethyl)-1H-pyrazol-4-yl)-1-methyl-1H-imidazole-2-carboxamido)benzamido)methyl)-N-((3S,4 S)-4-hydroxypyrrolidin-3-yl)-3-azabicyclo[3.1.0]hexane-3-carboxamide;

N-(3-chloro-4-(4-(methylamino)piperidine-1-carbonyl)phenyl)-5-(1-cyclopropyl-3-(trifluoromethyl)-1H-pyrazol-4-yl)-1-methyl-1H-imidazole-2-carboxamide;

N-(3-chloro-4-(4-((2S,4 S)-4-fluoropyrrolidine-2-carbonyl)piperazine-1-carbonyl)phenyl)-5-(1-cyclopropyl-3-(trifluoromethyl)-1H-pyrazol-4-yl)-1-methyl-1H-imidazole-2-carboxamide;

N-(3-chloro-4-(methyl(piperidin-4-yl)carbamoyl)phenyl)-5-(1-(2,2-difluorocyclopropyl)-3-(trifluoromethyl)-1H-pyrazol-4-yl)-1-methyl-1H-imidazole-2-carboxamide;

N-((1R,3R)-3-aminocyclopentyl)-4-(2-chloro-4-(5-(1-(cyclopropylmethyl)-3-(trifluoromethyl)-1H-pyrazol-4-yl)-1-methyl-1H-imidazole-2-carboxamido)benzoyl)piperazine-1-carboxamide;

N-(3-chloro-4-(4-hydroxy-[1,4'-bipiperidine]-1'-carbonyl)phenyl)-5-(1-cyclopropyl-3-(trifluoromethyl)-1H-pyrazol-4-yl)-1-methyl-1H-imidazole-2-carboxamide;

N-(3-chloro-4-(piperazine-1-carbonyl)phenyl)-5-(1-(cyclobutylmethyl)-3-(trifluoromethyl)-1H-pyrazol-4-yl)-1-methyl-1H-imidazole-2-carboxamide;

rac-N-(4-(((1S,4s)-4-((1 r, 3R)-3-aminocyclobutane-1-carboxamido)cyclohexyl)carbamoyl)-3-chlorophenyl)-5-(1-(cyanomethyl)-3-(trifluoromethyl)-1H-pyrazol-4-yl)-1-methyl-1H-imidazole-2-carboxamide;

rac-N-(4-(((1-(((1s,3 s)-3-aminocyclobutyl)carbamoyl)azetidin-3-yl)methyl)carbamoyl)-3-chlorophenyl)-5-(1-(cyclopropylmethyl)-3-(trifluoromethyl)-1H-pyrazol-4-yl)-1-methyl-1H-imidazole-2-carboxamide;

N-(3-bromo-4-(4-(piperidine-4-carbonyl)piperazine-1-carbonyl)phenyl)-5-(1-ethyl-3-(trifluoromethyl)-1H-pyrazol-4-yl)-1-methyl-1H-imidazole-2-carboxamide;

N-(4-(4-(2-((2-aminoethyl)amino)-2-oxoethyl)piperazine-1-carbonyl)-3-chlorophenyl)-5-(1-(2,2-difluoroethyl)-3-(trifluoromethyl)-1H-pyrazol-4-yl)-1-methyl-1H-imidazole-2-carboxamide;

rac-(1 S, 5R)-8-[2-chloro-4-[[5-[1-(2,2-difluorocyclopropyl)-3-(trifluoromethyl)pyrazol-4-yl]-1-methyl-imidazole-2-carbonyl]amino]benzoyl]-N-[rac-(3 S,4 S)-4-hydroxypyrrolidin-3-yl]-3,8-diazabicyclo[3.2.1]octane-3-carboxamide;

N-[4-[6-(azetidin-3-ylmethyl carbamoyl amino)hexyl carbamoyl]-3-chlorophenyl]-5-[1-cyclopropyl-3-(trifluoromethyl)pyrazol-4-yl]-1-methylimidazole-2-carboxamide;

N-(3-chloro-4-(4-(piperidine-4-carbonyl)piperazine-1-carbonyl)phenyl)-1-methyl-5-(3-(trifluoromethyl)-1-(2-(trifluoromethyl)cyclopropyl)-1H-pyrazol-4-yl)-1H-imidazole-2-carboxamide;

(1R,5 S,6R)-6-(2-chloro-4-(5-(1-((R)-2,2-difluorocyclopropyl)-3-(trifluoromethyl)-1H-pyrazol-4-yl)-1-methyl-1H-imidazole-2-carboxamido)benzamido)-N-((3 S,4 S)-4-hydroxypyrrolidin-3-yl)-3-azabicyclo[3.1.0]hexane-3-carboxamide;

exo-6-(2-chloro-4-(5-(1-(2,2-difluorocyclopropyl)-3-(trifluoromethyl)-1H-pyrazol-4-yl)-1-methyl-1H-imidazole-2-carboxamido)benzamido)-N-((3 S,4 S)-4-hydroxypyrrolidin-3-yl)-3-azabicyclo[3.1.0]hexane-3-carboxamide;

exo-6-[[2-chloro-4-[[5-[1-(2,2-difluorocyclopropyl)-3-(trifluoromethyl)pyrazol-4-yl]-1-methylimidazole-2-carbonyl]amino]benzoyl]amino]-N-[trans-4-hydroxypyrrolidin-3-yl]-3-azabicyclo[3.1.0]hexane-3-carboxamide;

N-[3-chloro-4-[4-[rac-(1R,5S)-3-azabicyclo[3.1.0]hexane-6-carbonyl]piperazine-1-carbonyl]phenyl]-5-[1-cyclopropyl-3-(trifluoromethyl)pyrazol-4-yl]-1-methylimidazole-2-carboxamide;

(1R,5 S,6s)-6-(2-chloro-4-(1-methyl-5-(1-(prop-2-yn-1-yl)-3-(trifluoromethyl)-1H-pyrazol-4-yl)-1H-imidazole-2-carboxamido)benzamido)-N-((3R,4R)-4-hydroxypyrrolidin-3-yl)-3-azabicyclo[3.1.0]hexane-3-carboxamide;

rac-(1R,5S,6s)-6-(2-chloro-4-(5-(1-(2,2-difluorocyclopropyl)methyl)-3-(trifluoromethyl)-1H-pyrazol-4-yl)-1-methyl-1H-imidazole-2-carboxamido)benzamido)-N-((3S,4S)-4-hydroxypyrrolidin-3-yl)-3-azabicyclo[3.1.0]hexane-3-carboxamide;

(1R,5S,6s)-6-(2-chloro-4-(5-(1-(2,2-difluoroethyl)-3-(trifluoromethyl)-1H-pyrazol-4-yl)-1-methyl-1H-imidazole-2-carboxamido)benzamido)-N-((3R,4R)-4-hydroxypyrrolidin-3-yl)-3-azabicyclo[3.1.0]hexane-3-carboxamide;

(1R,5S,6s)-6-(4-(5-(1-allyl-3-(trifluoromethyl)-1H-pyrazol-4-yl)-1-methyl-1H-imidazole-2-carboxamido)-2-chlorobenzamido)-N-((3R,4R)-4-hydroxypyrrolidin-3-yl)-3-azabicyclo[3.1.0]hexane-3-carboxamide; and (1R,5S,6s)-6-(2-chloro-4-(5-(1-(cyclobutylmethyl)-3-(trifluoromethyl)-1H-pyrazol-4-yl)-1-methyl-1H-imidazole-2-carboxamido)benzamido)-N-((3R,4R)-4-hydroxypyrrolidin-3-yl)-3-azabicyclo[3.1.0]hexane-3-carboxamide.

28. A pharmaceutical composition comprising a compound of formula (I) according to claim 1, or a pharmaceutically acceptable salt thereof, and a therapeutically inert carrier.

29. A process of manufacturing the compounds of formula (I) according to claim 1, the process comprising:
(i) reacting a heteroaryl bromide 5 or 15, wherein $R^1$ to $R^3$, $R^6$ and $R^7$ are as defined herein,

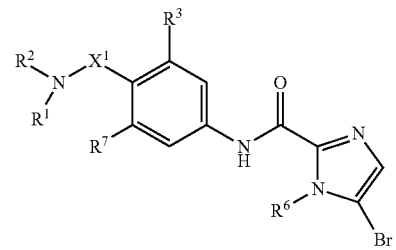

5: $X^1$ = C(O)
15: $X^1$ = SO$_2$ with a boronate, such as heteroaryl boronic acid 6b, wherein $R^4$ and $R^5$ are as defined herein,

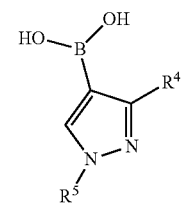

in the presence of a transition metal catalyst to afford said compound of formula (I); or (ii) reacting a carboxylic acid 12a, wherein $R^3$ to $R^7$ are as defined herein,

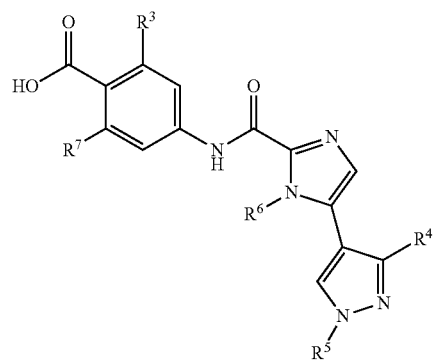

with an amine 1, wherein $R^1$ and $R^2$ are as defined herein,

in the presence of a coupling reagent and a base to afford said compound of formula (I); or (iii) reacting an amine 7

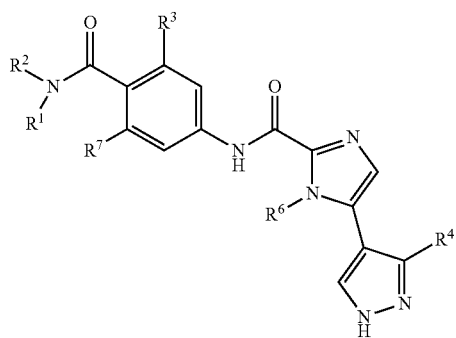

with an alkylating reagent 8, wherein X is a leaving group,

to afford said compound of formula (I); and (iv) optionally converting said compound of formula (I) to a pharmaceutically acceptable salt thereof.

30. The process according to claim 27, wherein:
the transition metal catalyst is a 1,1'-bis(diphenylphosphino)ferrocene-palladium(II)dichloride dichloromethane complex;
the coupling reagent is HATU or TBTU;
the base is DIPEA or triethyl amine; and
the leaving group is a halide or a sulfonate.

31. A method for the treatment of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, the method comprising administering a compound of formula (I) according to claim 1, or a pharmaceutically acceptable salt thereof, to a mammal in need thereof.

* * * * *